US012746291B2

(12) United States Patent
Ellis et al.

(10) Patent No.: US 12,746,291 B2
(45) Date of Patent: Sep. 29, 2026

(54) METHODS OF LOADING EXTRACELLULAR VESICLES

(71) Applicant: LONZA SALES AG, Basel (CH)

(72) Inventors: Kimberly Ellis, Cambridge, MA (US); Aaron Noyes, Cambridge, MA (US); Andrew Wood, Cambridge, MA (US)

(73) Assignee: LONZA SALES AG, Basel (CH)

( * ) Notice: Subject to any disclaimer, the term of this patent is extended or adjusted under 35 U.S.C. 154(b) by 176 days.

(21) Appl. No.: 18/546,134

(22) PCT Filed: Feb. 17, 2022

(86) PCT No.: PCT/US2022/016825
§ 371 (c)(1),
(2) Date: Aug. 11, 2023

(87) PCT Pub. No.: WO2022/178147
PCT Pub. Date: Aug. 25, 2022

(65) Prior Publication Data

US 2025/0127919 A1 Apr. 24, 2025

Related U.S. Application Data

(60) Provisional application No. 63/150,497, filed on Feb. 17, 2021.

(51) Int. Cl.

| | |
|---|---|
| ***A61K 47/69*** | (2017.01) |
| ***A61K 9/50*** | (2006.01) |
| ***A61K 31/7105*** | (2006.01) |
| ***A61K 47/54*** | (2017.01) |
| ***A61K 47/60*** | (2017.01) |

(52) U.S. Cl.
CPC ........ *A61K 47/6911* (2017.08); *A61K 9/5015* (2013.01); *A61K 9/5068* (2013.01); *A61K 9/5089* (2013.01); *A61K 31/7105* (2013.01); *A61K 47/542* (2017.08); *A61K 47/543* (2017.08); *A61K 47/548* (2017.08); *A61K 47/554* (2017.08); *A61K 47/60* (2017.08)

(58) Field of Classification Search
CPC ............ A61K 47/6911; A61K 31/7105; A61K 47/543
See application file for complete search history.

(56) References Cited

U.S. PATENT DOCUMENTS

| | | | | |
|---|---|---|---|---|
| 4,683,195 | A | 7/1987 | Mullis et al. | |
| 10,195,290 | B1 | 2/2019 | Dooley et al. | |
| 10,561,740 | B2 | 2/2020 | Dooley et al. | |
| 2019/0151456 | A1 | 5/2019 | Mcconnell et al. | |
| 2019/0175506 | A1* | 6/2019 | Noyes | A61K 9/1278 |
| 2020/0347112 | A1 | 11/2020 | Mcconnell et al. | |

FOREIGN PATENT DOCUMENTS

| | | | | |
|---|---|---|---|---|
| WO | 2019/040920 A1 | 2/2019 | | |
| WO | 2019/099942 A1 | 5/2019 | | |
| WO | 2019/246591 A1 | 12/2019 | | |
| WO | 2020/101740 A1 | 5/2020 | | |
| WO | 2020/191361 A1 | 9/2020 | | |
| WO | 2020/191369 A1 | 9/2020 | | |
| WO | 2020/191377 A1 | 9/2020 | | |
| WO | WO-2020191361 A2 * | 9/2020 | | A61K 39/00 |

OTHER PUBLICATIONS

Besse, B., et al., "Dendritic cell-derived exosomes as maintenance immunotherapy after first line chemotherapy in NSCLC," *Oncoimmunology* 5(4):e1071008 (2015).
Dobeli, H., et al., "Role of the carboxy-terminal sequence on the biological activity of human immune interferon (IFN-γ)," *J. Biotechnology* 7(3):199-216 (1988).
Dosio, F. et al., "Immunotoxins and anticancer drug conjugate assemblies: the role of the linkage between components," *Toxins (Basel)* 3(7):848-883 (2011).
Gayle, R. B., et al., "Identification of regions in interleukin-1 alpha important for activity," *J. Biol. Chem.* 268(29):22105-22111 (1993).
Kuypers, F. A., et al., "Survival of rabbit and horse erythrocytes in vivo after changing the fatty acyl composition of their phosphatidylcholine," *Biochim Biophys Acta* 819(2):170-178 (1985).
Oudshoorn, M. H., et al., "Synthesis and characterization of hyperbranched polyglycerol hydrogels," *Biomaterials* 27(32):5471-5479 (2006).
Papapetrou, E. P., et al., "Genetic modification of hematopoietic stem cells with nonviral systems: past progress and future prospects," *Gene Therapy* 12 Suppl: S118-S130 (2005).

(Continued)

*Primary Examiner* — Andrew S Rosenthal

(74) *Attorney, Agent, or Firm* — MEDLER FERRO WOODHOUSE & MILLS PLLC

(57) ABSTRACT

The present disclosure relates to methods of loading an EV with a payload. In some aspects, the payload and the EV are mixed at a specific loading condition (e.g., at the disclosed salt concentrations, loading temperature, loading duration, payload feed concentration, and/or EV feed concentration), such that the amount of the payload that is associated with the exterior surface of the EV is increased. Also provided herein are methods for producing the extracellular vesicles and methods for using the extracellular vesicles to treat diseases or disorders.

20 Claims, 8 Drawing Sheets

Figure 1A:
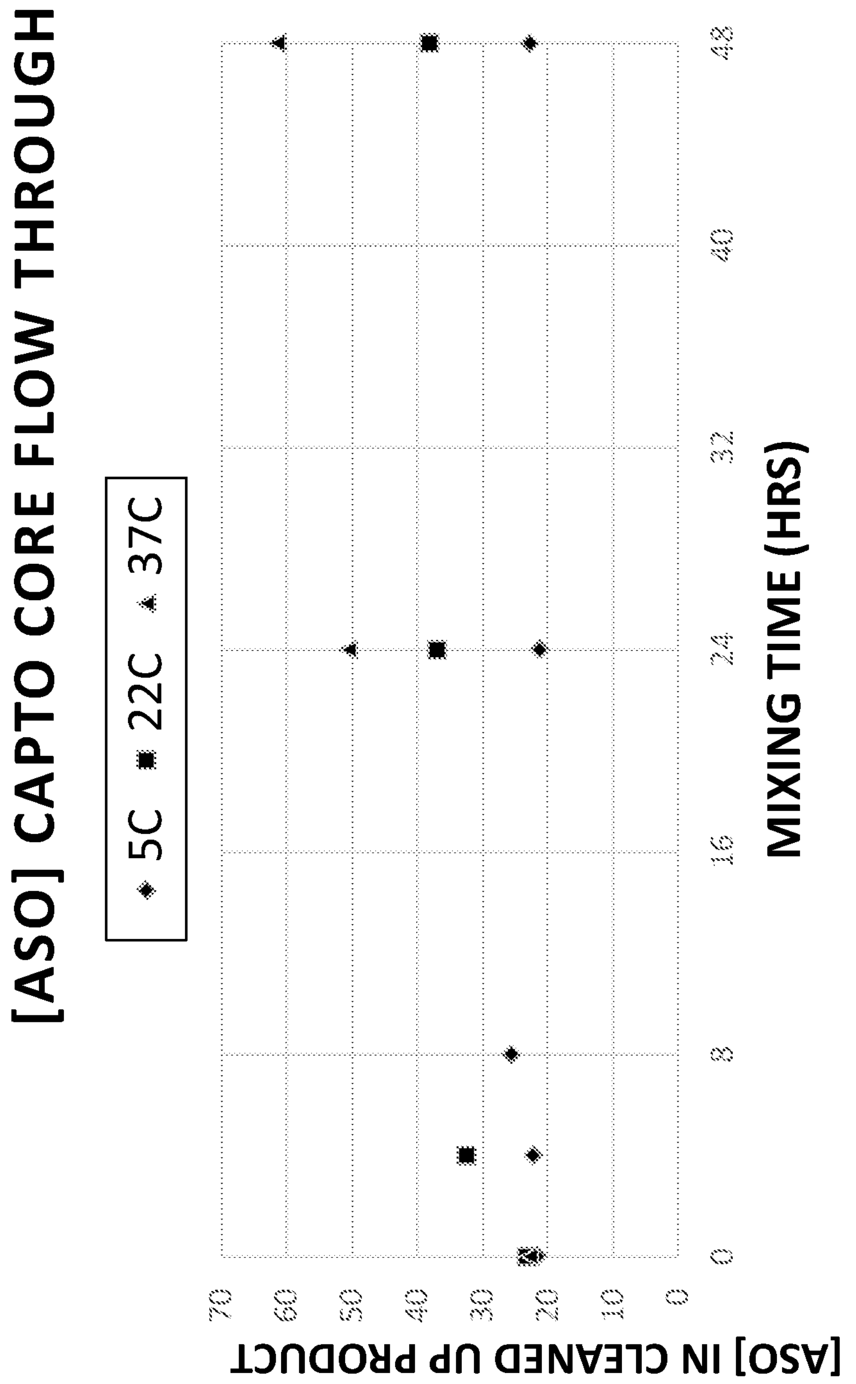

Specification includes a Sequence Listing.

(56) References Cited

OTHER PUBLICATIONS

Ron, D., et al., "Expression of biologically active recombinant keratinocyte growth factor. Structure/function analysis of amino-terminal truncation mutants," *J. Biol. Chem.* 268(4):2984-2988 (1993).
Senti, G., et al., "Intralymphatic allergen administration renders specific immunotherapy faster and safer: a randomized controlled trial," *Proc Natl Acad Sci USA.* 105(46):17908-17912 (2008).
Wilms, D., et al., "Hyperbranched polyglycerols: from the controlled synthesis of biocompatible polyether polyols to multipurpose applications," *Acc. Chem. Res.* 43(1):129-141 (2010).

* cited by examiner (Chol4)

Molecular Weight =755.98
Molecular Formula =C40H70NO10P (Chol2)

Molecular Weight =682.91
Molecular Formula =C37H65NO8P

Fig. 3A

| Description | Sequence | SEQ ID NO |
|---|---|---|
| ASO-STAT6 | GAAAGGTTCCGTCGG | 41 |
| ASO-STAT6 | GGCTAGTAACGTACTG | 42 |
| ASO-STAT6 | GAAAGGTTCCGTCGGGC | 43 |
| ASO-STAT6 | CTGAGTCGCTGAAGCGG | 44 |
| ASO-STAT6 | CGCTCACACCGCTTGATCTT | 45 |
| ASO-STAT6 | AGAAGAAGGCTAGTAACGTA | 46 |
| ASO-STAT6 | GAGAAAGGTTCCGTCGGGCT | 47 |
| ASO-STAT6 | GCAAGATCCCGGATTCGGTC | 48 |
| ASO-STAT6 | GTGCGTGTGCGCGCTGCAGG | 49 |
| ASO-STAT6 | GCCCTTGTACTTTTGCATAG | 50 |

Fig. 3B

| Descriptio n | Sequence | SEQ ID NO |
|---|---|---|
| ASO-KRAS | CCATCAGCTCCAAC | 51 |
| ASO-KRAS | GCCATCAGCTCCAA | 52 |
| ASO-KRAS | CGCCATCAGCTCCA | 53 |
| ASO-KRAS | CCATCAGCTCCAACT | 54 |
| ASO-KRAS | GCCATCAGCTCCAAC | 55 |
| ASO-KRAS | CGCCATCAGCTCCAA | 56 |
| ASO-KRAS | CCATCAGCTCCAACTA | 57 |
| ASO-KRAS | GCCATCAGCTCCAACT | 58 |
| ASO-KRAS | CGCCATCAGCTCCAAC | 59 |
| ASO-KRAS | ACGCCATCAGCTCCAA | 60 |
| ASO-KRAS | GCCTACGCCATCAGCTC | 61 |

Fig. 3C

| Description | Sequence | SEQ ID NO |
|---|---|---|
| ASO-NRAS | GGATTGTCAGTGCGC | 62 |
| ASO-NRAS | ATTCGGTACTGGCGT | 63 |
| ASO-NRAS | GGATTGTCAGTGCGCTTTTC | 64 |
| ASO-NRAS | GACTTGCTATTATTGATGGC | 65 |
| ASO-NRAS | TACTCGCTTAATCTGCTCCC | 66 |
| ASO-NRAS | ATCAACTGTCCTTGTTGGCA | 67 |
| ASO-NRAS | GCGTATTTCTCTTACCAGTG | 68 |
| ASO-NRAS | GTTTTTTCATTCGGTACTGG | 69 |
| ASO-NRAS | AACAGGGAGTAACAAGAGGT | 70 |
| ASO-NRAS | CAGTTGCTACTTTAGAGCTC | 71 |

Fig. 3D

| Description | Sequence | SEQ ID NO |
|---|---|---|
| ASO-PMP22 | CAAACAGCGTAACCCCT | 72 |
| ASO-PMP22 | AGCACCGCGACGTGGAGGAC | 73 |
| ASO-PMP22 | TGGACAGACTGCAGCCATTC | 74 |
| ASO-PMP22 | GTAAAACCTGCCCCCCTTGG | 75 |
| ASO-PMP22 | CTCATTCGCGTTTCCGCAAG | 76 |
| ASO-PMP22 | CTTTAAGGCTCAACACGAGG | 77 |
| ASO-PMP22 | TTGGGGTTTCTACCCACACT | 78 |
| ASO-PMP22 | CACCTGTAAGGGCAAGTATG | 79 |
| ASO-PMP22 | TCCAGTGAGTTGTTTAGATG | 80 |
| ASO-PMP22 | TCACGGTCCCAAGGAGTCTA | 81 |

Fig. 3E

| Description | Sequence | SEQ ID NO |
|---|---|---|
| ASO-CEBPb | GCTCGTGGTCGCCGA | 82 |
| ASO-CEBPb | CGTAGTCGTCGGAGA | 83 |
| ASO-CEBPb | TCGTGGTCGCCGATGC | 84 |
| ASO-CEBPb | TCGCGCCGGATCTTGT | 85 |
| ASO-CEBPb | CGCTCGTGGTCGCCGAT | 86 |
| ASO-CEBPb | CCGTAGTCGTCGGAGAA | 87 |
| ASO-CEBPb | TGCCCCCGTAGTCGTCG | 88 |
| ASO-CEBPb | CGGATCTTGTACTCGTC | 89 |
| ASO-CEBPb | TAAGCGCGCAGCGCGTACGG | 90 |
| ASO-CEBPb | CGCGCCGGATCTTGTACTCG | 91 |

Fig. 3F

| Description | Sequence | SEQ ID NO |
|---|---|---|
| ASO-STAT3 | ATTTGTTGACGGGTC | 92 |
| ASO-STAT3 | CGACAATACTTTCCG | 93 |
| ASO-STAT3 | GAACTGGACGCCGGTC | 94 |
| ASO-STAT3 | CACAATTGGCTCGGCC | 95 |
| ASO-STAT3 | CGTAGATTGTGCTGATAGAG | 96 |
| ASO-STAT3 | GCCACAATCCGGGCAATCTC | 97 |
| ASO-STAT3 | AGTTTTCTAGCCGATCTAGG | 98 |
| ASO-STAT3 | CGACAATACTTTCCGAATGC | 99 |
| ASO-STAT3 | AGGTAGGCGCCTCAGTCGTA | 100 |
| ASO-STAT3 | CAGGTAGGCGCCTCAGTCGT | 101 |

Fig. 3G

| Description | Sequence | SEQ ID NO |
|---|---|---|
| ASO-NLRP3 | CTCCGAGAGTGTTGCCTCGC | 102 |
| ASO-NLRP3 | GTAAAGGTGCGTGAGATTCT | 103 |
| ASO-NLRP3 | GTCGAAGCAGCACTCATGCG | 104 |
| ASO-NLRP3 | AGTCCATGGCCCTTTGCACG | 105 |
| ASO-NLRP3 | GCAGTGTGACGTGAGGTTGC | 106 |
| ASO-NLRP3 | CGAGAGTGTTGCCTCGCAGG | 107 |
| ASO-NLRP3 | ATCGCAGCGAAGATCCACAC | 108 |
| ASO-NLRP3 | ATCTTAATGGGACTCACGGG | 109 |
| ASO-NLRP3 | GATCTCCACATGCCGAGGAT | 110 |
| ASO-NLRP3 | TCCGAGAGTGTTGCCTCGCA | 111 |
| ASO-NLRP3 | TGGTTGCTGCTGAGGACCAA | 112 |

SEQUENCE LISTING

```
<160> NUMBER OF SEQ ID NOS: 112

<210> SEQ ID NO 1

<400> SEQUENCE: 1

000


<210> SEQ ID NO 2
<211> LENGTH: 16010
<212> TYPE: DNA
<213> ORGANISM: Artificial Sequence
<220> FEATURE:
<223> OTHER INFORMATION: STAT6 pre-mRNA transcript

<400> SEQUENCE: 2

agagctccag ggagggacct gggtagaagg agaagccgga aacagcgggc tggggcagcc     60

actgcttaca ctgaagaggg aggacgggag aggagtgtgt gtgtgtgtgt gtgtgtgtgt    120

gtgtatgtat gtgtgtgctt tatcttattt ttctttttgg tggtggtggt ggaagggggg    180

aggtgctagc agggccagcc ttgaactcgc tggacagagc tacagaccta tggggcctgg    240

aagtgcccgc tgagaaaggg agaagacagc agaggggttg ccgaggtgag gggttgcctc    300

cgaggtgggt gcgggggcct ctatgagtgc atgggggtgg attcgtgggg ggagctctcg    360

ggatcctccc ctggctgggt ggatggtccc caagagatgg tttcagctag tgttggtggc    420

tggtggcact gggttttagc agtttcgaac tcctggagga atctgggagg gtccaggcct    480

cagtactccc ctcccccatg ggtcacgttt tcacagcctc accccctgcac ccccagggcc    540
```

-continued

```
atggaaagtc agggaaagga ggtgaaggag tgcccctctg ccctgagtcg ggggaagtgg    600
ccgcccctcc ctggaaggtt gatgccagag ggcagtggat ccttgttaaa cccctatcct    660
gccctccact aaaggttcct gttcaagggt gtggctgggg cgtgagcaag ccccagatgt    720
agacctcatg gtggcccaga cgagggggaa tttccccctc aaaactgctc cacgcttggc    780
tgctgtagac gctgagattt cccagcggcg gcgccgagtt aaccctcctc gtgctgaact    840
ggctccacct ccccgcctgc ccccaccgcc acattcacgc attgggcaac tcagagaagc    900
tgttttaact ttcgatcctg tggtcccaca atcagaggac tcgggcagat aggggttgag    960
ataagcgagt ttaggccacc aagcgggcgg acgaggatcc cagaccttgc gcttcccttc   1020
tgagtttggg aggtaacact ggccccgccc ctcacgccgt ggctcctccc tcccttcccc   1080
ttcaaggggc tgaagacaaa aggtgcccct gtcctggtca agccaatcga cccagccttg   1140
ttatgggttg gggtggggag aaatgtgtcc tcctgatggc tggggaagaa gaggggttgg   1200
atatttctag ccagggccat gccaggaggc tggtcactct gcaaggggat gcagaggaaa   1260
gcggtgccca ctcactccag aggacctttc tctcttgggc tagagaaagg cctattggag   1320
gaacctgagc aggaggggta aggattctgc cttgaggaga aaagagctgg ggtaagtggg   1380
cactggagga aagaggggca tgaaggtctt ggagcagaaa cgtccagaga agggacctct   1440
ccattttcca tccctctgag aggcctggga gaggtgagag gctgaacgtg caacaggagg   1500
acttggggtt actgggtttg gggagacctg gggagttgtc atcccatcct ctccctcatc   1560
tctgggagag ggatattatg agaaacgtga actgagaggc cctgggaaa ccactggtta    1620
cccagtcctc cctgaacctg gaaatgggga tgcaaccccc tcttctactt ccctgtcccc   1680
tcctctcctt tctacctgtt ttcgtctctc atctttgcct tctagccctc cagcttcctc   1740
tctcttctag gctctttcct cctagcttac taaacccgcc ttttttccag tctcttccat   1800
cctcttcctt agttctctct actttccttt tccacctctc ctccttcaag tctcctccca   1860
ccttcccccca cttcttagga tgatcagatt tgcccctgga agggatccta acaacacagt   1920
gcgatggtta atccccactc agattcaaag cctgctttcc aaactcactt actgagtggc   1980
cttgggcaga gtagagaaac tccttaagcc tcagtttctt catctataaa atgggatatt   2040
atatatttta aaaagtgtcg tgaggcctga aggagataat acactgagtg taatgcctca   2100
tacacagtaa gtgcttaaca aatagtagct gttattactc tcccatcctc ttcatcatct   2160
agccttgtgg ttttcatttt tattttattt catttattta tttatttatt ttgaggcaga   2220
gtctctctct gtcgcccagg ctggagtgca gtggctcgat ctctgctcac tgcaagctcc   2280
gccccccagg ttcacgccat tctgtcacct cagcctcccc agtagctggg actacaggcg   2340
ctcgccacca cgccctgcta attttgtttt tgtattttta gtagagatgg ggtttcactg   2400
tgttagccag gatggtcttg atctcctgac ctcgtgatct gcccgcctcg gcctcccaaa   2460
gcgctgggat tacaggcatg agccactgcg cctggccgag ccttgtggtt ttcaaattat   2520
ctcatggagt cctagaattt tgagaggttt gtctagggat gcctttggcg tcaggaggtg   2580
gggagaggga agtagaagca gtcgagtttc aggctttcca tgcttgcttt caacagggca   2640
tcttcggttt cgtacctttt atgtaattga gattccacag attaaaagct gacattgcct   2700
accgctttaa aaagtttgga aagttttcca ctcatctaac actcatattt tatagatgag   2760
aagatcgaag cccacaaagg gaaggctctt tgcccacaga accagagcca ggtctagagc   2820
tgcaactaaa tcctctgcca ctctaagaga gctctcgctc tactgccctg tctccctttg   2880
cctccccatc cctctggcta cagctcagct cttcccaccc ctgtgtctat cactgaagga   2940
```

-continued

```
gttaccccca tctcaggcat tgactcagga tgcccctggt ttaaggtggt ctggccatga   3000
gtggtggtgg ggacggtccc taggagggct atctatggga ggtccctggc tgccccagga   3060
gataggccaa gtttcttggg caccccctcag agtggcctta tttttctcct ccaggcaacc   3120
tccaagtccc agatcatgtc tctgtggggt ctggtctcca agatgccccc agaaaaagtg   3180
cagcggctct atgtcgactt tccccaacac ctgcggcatc ttctgggtga ctggctggag   3240
agccagccct ggtgagtcct ggctgctccc tgctggtccc ccaagtcttc cctaactcat   3300
cttccttctc cttagatttt tctcccctca cccatggatt cagaacttga gacctgttat   3360
tccatgtgta gtgacctaga tttagcaggg agtctgtgcc ccatcaagac caggctatga   3420
atgttgacag atggagaccc catctcttag gaggctgagc cgaagaggag gggggtttgg   3480
gctgggacaa aggcacttct cataacagct agaagactgg gaaacaaggc gcatgggtga   3540
aagctacaga gggcctagat ggagaataag gagcgagaaa ggaactgctg agcttttggc   3600
tgtggggtaa agggtcagga gagctgagga agccctggcc tgaggtagcc tcatcctgat   3660
cttcctgcag ggagttcctg gtcggctccg acgccttctg ctgcaacttg gctagtgccc   3720
tactttcaga cactgtccag caccttcagg cctcggtggg agagcagggg gaggggagca   3780
ccatcttgca acacatcagc acccttgagg tggggcagga ggggagggga caaggctggg   3840
tggggctgag gttgaactgg gttgagcatt gggccctgga agaaaattgg ttggatgctg   3900
gaagcaaatt ggtgttcctg tggttaactg ctagctagca ggcaaattag attttaaaag   3960
catgcaaatg cacaaaaact tctggagtct acagttgtgc ttccttatag tatatgtgtg   4020
aatgcaggcc tggggattgg agggattgaa ggacatgggt aagagcaaag ctcactgttt   4080
accaccctca tttctgtaga gcatatatca gagggacccc ctgaagctgg tggccacttt   4140
cagacaaata cttcaaggag agaaaaaagc tgttatggaa caggtattgt gatattccac   4200
ctcccacccc aactcaatcc cctgagactt tggcctgagc catgacaaac tagaaagaat   4260
ttgaacctca gtaaaggctc agtgttctag gcccaggaat gaccaaagga ggttcctagg   4320
gtcagagtga accccaagtc aagctcaggg aatctttcta tgagggactg aaggtaagag   4380
gccggggaga acagagcaag ggataaggag ctgattctgc taggagcaag gtcttatctc   4440
cacgatattc caaaaggtca ggaagaactg ccaaagggga gaggggaaca agaaaacgct   4500
atctgcagag cagagagtgg aggccaggta tagagggatg agcagagtgt ttcacttctt   4560
ggcatctgtc cttcctgtgt agttccgcca cttgccaatg cctttccact ggaagcagga   4620
agaactcaag tttaagacag gcttgcggag gctgcagcac cgagtagggg agatccacct   4680
tctccgagaa gccctgcaga agggggctga ggctggccaa ggtgggggcc agggtggttc   4740
tggggagtgt gtaggagtgg ttgcctcttg gatctcaacc ttatctgaac ctctaatctg   4800
tctgcaccct tgatttctgc ccccaaccct cagtgtctct gcacagcttg atagaaactc   4860
ctgctaatgg gactgggcca agtgaggtga gtaatgggct gacaggtgga gaccttggtc   4920
aaagtgcagc tggagggatg gaagctagac ctcagaaaga cacaggctga agtagggcaa   4980
gggaatgcca gaggagtgag aaaaagagcc gtatcccagg agctgggtgt ggaggcagcg   5040
tgaggccctg gctcaggccc ctctctgccc ataggccctg gccatgctac tgcaggagac   5100
cactggagag ctagaggcag ccaaagccct agtgctgaag aggatccaga tttggaaacg   5160
gcagcagcag ctggcaggga atggcgcacc gtttgaggag agcctggccc cactccagga   5220
gaggttgggc tagggctgat ggggaagagg gggcaagctg gggtgggca gctgaccctg   5280
```

-continued

```
ctgaaggccc tacaggtgag agaaagaagc caggcgggag ggccttggag tggaccaaga   5340
tgcataaaag ccagttccag cggggctgtg cacactgtcg ttcaggtcgc atcctgtaca   5400
agtgggccta gtggaggggc acaagcgggg actcatccaa cccaggcttc tctcctcaag   5460
ccccatgcct agaggaatag gagggctttt ccatttggtt tattgggtgg gaacactttc   5520
caatttgcca caaagcactg taagtggtgg cagttgtcct gggtgcaaga gccgtcgggg   5580
gagaggcagc tgggtttcca caggggggtgt aggcactgag aatgaacctc ccacccagac   5640
cctaggccaa cagatcacag aacccccttc agcccaggtg ccttgcagcc acacccacta   5700
cccaccccac ttctccacac atgatagcct ttctccctgg gtatagggga agggggtctg   5760
ggccggagca agcagcctta atcctgtgcc ccctgaccac tgtcctggcc ccaggtgtga   5820
aagcctggtg gacatttatt cccagctaca gcaggaggta ggggcggctg gtggggagct   5880
tgagcccaag acccgggcat cgctgactgg ccggctggat gaagtcctga gaaccctcgt   5940
caccaggtat tccccgggag ctcccagtct ggcctagaac agacctcggg aagaaaagaa   6000
gggggctaga gctgtgggga gggcaccagc agggacctag cccccaactc cccttgtgtc   6060
ctcctcactc ccagttgctt cctggtggag aagcagcccc cccaggtact gaagactcag   6120
accaagttcc aggctggagt tcgattcctg ttgggcttga ggttcctggg ggccccagcc   6180
aagcctccgc tggtcagggc cgacatggtg acagagaagc aggcgcggga gctgagtgtg   6240
cctcagggtc ctggggctgg agcgtaagct gggattggac ctggggttgg agaagggctg   6300
ttagggtgat ggaggcagcc tggagggctg gcactgaaaa gagcaaggga tggggaggga   6360
gggccatggg atgtggagac cctgaatggt caaggcagag gaaagggagg gacccattta   6420
gggctggaat ggggtggggg catcatgatt tggccaagat ggggactcct cccttaagaa   6480
cccaaacaga gacatggaga tttagggctg gtgacagtgg gtagtctaca ctcacccatg   6540
cactcgccac acctgacgac agtgagatga gctcgttcac actctgacct cccctggcag   6600
agaaagcact ggagaaatca tcaacaacac tgtgcccttg gagaacagca ttcctgggaa   6660
ctgctgctct gccctgttca agaacctggt gaggggcttt ggggtgcagt gagggggggca   6720
ccactaggag actgtgggac tctccttgga gaggatgtca ggaagcccag gaggagcggt   6780
ctctgtcctc atgacctcgc ccttgctctc cctcacccca cccacagctt ctcaagaaga   6840
tcaagcggtg tgagcggaag ggcactgagt ctgtcacaga ggagaagtgc gctgtgctct   6900
tctctgccag cttcacactt ggccccggca aactccccat ccagctccag gtgaaccgtg   6960
gcccagccct gccccaatct gggaccccga gtcctcctcc aatgccacac acaagggccc   7020
tggaccctca cctcttgtga ctgccccata ccccatgtgt ctgggattca tgcacactgg   7080
ggcccgggtg agtgggggtg agcaagagca tggagtgcac agggcaggga atggtagtgg   7140
atagcagcaa acacttcgga agcacttcct atagaccagg gcactctatt aaatgataca   7200
tacgcacatg cgtgccagca cacacacgtc tggttttcac aataacatta tgaggtaggc   7260
agtattatca gcctcatttt atagataagg acattgagac agagagttta agtagtttgt   7320
cccagtcaca cagctaagtg ttggagctgg tatttgaaac ctggaggtct ggttccatag   7380
cgatgactaa taaccacttc tctacggtga ggccctgatt gagcttcaga acgcatttaa   7440
taacatggca tgagcttttt gattatgatg tgtgagtcca ataacttctc tgagtgctca   7500
gagccagtcc cctgaggaaa cttcttgctt cactaagaaa cccctgtccg gctgggcatg   7560
gtggctcaag cctgtaatcc cagcactttg ggaggccgag gtgggtagat cacaaggtca   7620
ggagttcaag accagcctgg ccaatatggt gaaaccccgt ctccactaaa aatacaaaaa   7680
```

-continued

```
ttagctgggc gtggtggtgc aggcctgtag tcccagctgc tcgggaggct aagcaggaga   7740
atcgcttgaa cccaggaggc ggaggttgca gtgagccaag attgcgccac tgcccttcag   7800
cctgggcgac agagcaagac tatgtctcaa aaacaaaaca aaacaactca gcactttggg   7860
aggccaaggt aggaggatcg cttgagcctg caagtttaag accagcctgg gctacatagg   7920
gagatccaat ctctacaaaa aataaaaaat tggccgggca tggtggctca cgcctgtaat   7980
cccagcactt tgggaggcca aggcgggcgg atcatgaggt caggaaatcg agaccatcct   8040
ggctaacacg gtgaaacctc gtatctacta aaaatacaaa aaattagcca ggcatggtgg   8100
cgggcgcctg agtcccagct actcgggagg ctgaagcagg agaatggcgt gaacctggga   8160
gggagagctt gcagtgagcc aagatcgcgc cactgcactc cagcctgagt gacagagcga   8220
gactctgtct caaaaataaa taaataaata attagctgga ttaggtggta catttctgta   8280
gttccagcta ttcaggaggc tgaggtggaa ggatcacttg agccctgaag gctgaggctg   8340
cagtgagctg agattgcact actgcactcc agcctgggca acagagtgag atactatcta   8400
aaaaaaaaaa aaaaaaaaaa aaaaaaaaaa aaaaaaaaaa aaaaaaaagg aaagaaagaa   8460
agaaaagaaa cccctgtcct caccctcttc aggccctgtc tctgcccctg gtggtcatcg   8520
tccatggcaa ccaagacaac aatgccaaag ccactatcct gtgggacaat gccttctctg   8580
agatggtgag gaaagtcctg gagttggagg gaacaggggc agggtgggtt ctaacatggg   8640
cagtggtgca ggcctgctga tggggtggtg ggcatgttta aatgggtgtg accttaacac   8700
tttctcatgg gcctgctttc gtgcttctga cctcttttca ccccagtctt aacaactatc   8760
aggccacagc actgtaacct agaaaaaaca gcatgtttgt gagcgatatc aggggctgtg   8820
gaggggtagg ccacaggcag gtgggaggga tgaaggccgg cccgaggaat aacaagacgg   8880
tagcctgcag tgctctcttc ttccccctttc tccccaggac cgcgtgccct ttgtggtggc   8940
tgagcgggtg ccctgggaga agatgtgtga aactctgaac ctgaagttca tggctgaggt   9000
ggggaccaac cgggggctgc tcccagagca cttcctcttc ctggcccaga agatcttcaa   9060
tgacaacagc ctcagtatgg aggccttcca gcaccgttct gtgtcctggt cgcagttcaa   9120
caaggtcatt ctcctgccct ttggacctcc cacccccaag ctcttcatcc ctggggcact   9180
cagggcctgc tcagcctcca tgcagggacc ttccactgga ttctccacag tgccccctca   9240
ggtcctttag gaaggcctgt catggaccag ggaggaaaaa ccccaggcct gggggttggc   9300
tctggagatg cgttctctga catccctgag gttttggtct gggggccatc tgtccttcct   9360
ctttaccagt gacttgcatg actcacccag gttgtgtgta aacagagctc tgattcaaag   9420
tgactttgac ctgttggaaa aatagttcct ggccgggcac agcggctcat gcctgtaatc   9480
ccagtctttg acatgccggg gtgggtggat cacctgaggt caggagtttg agaccagcct   9540
ggccaacatg gtgaaactcc atctctacta aaaatacaaa aattagccag ttgcggtggc   9600
acatgcctgt aatcccagct acatgggagg ctgacgcagg agaattgctt gaacccagga   9660
ggtggaggtt gcagtgagct gagatcatac cactgcactc aagcctgggt gacagagcaa   9720
gactctgtct caaaaaaaaa aaaaaaaaaa ggccaggcat ggtggttcat gcctgtaatc   9780
ccagcacttt gggaggccga gacggataga tcacctgagg tcaggagttc gagaccagcc   9840
tggccaacat ggcaaaaccc cgtctctact aaaaacaaaa aaatagccag gagtggtcgt   9900
ttgcgtctgt aatcccagct actcggctga ggcaggaggt gaacccagga ggtagaggct   9960
gcagggaaga tgaaaccatt gcactccagc ctgggcaaga ctctgtatca aaaaaaaaaa  10020
```

-continued

```
aaaaaaaggc taggtgtggt ggctcacacc tgtaatccca gcactttggg aggctgaggc  10080
gggcggatca caaggtcaag agatcgagac catcctgacc aacatggtga aaccccgtct  10140
ctactaaaaa tacaaaaatt acctgggcat ggtggcgcat gcctgtagtc ccaactactc  10200
gggaggctga ggcaggagaa tcacttgaac ctgggaggca gaggttgcag cgagccaaga  10260
ttgtgccact gcactccagc ctgccaacag aatgagattc tgtctaaaaa aaaaaagaaa  10320
gaaagaaaga aagaaaaaga attcctgttg caaaaactga acaaaatccc acagggacat  10380
gtgcagtaat accagctacc acgtgttgac agcttatatg ccaggcgctg tgcttaacac  10440
cttatgtatg ttatctcact taatcctccc aacatctctt tgaggtagat actattatta  10500
tccccatttt acagatgagg aatctgatgc tcagagggtt atgtagtttg ttcaagttcc  10560
caaagcaggt gagtgccatg gctaggagag aaccacatat ttctgactct tgctctttta  10620
ttttatgtta tattatgtta ttttatgttt tggttttttt ttcttttctt tctttctttc  10680
tttctttctt tctttctttc tttctttctt tctctttctt tctttctttc tttctttctt  10740
tctttctttc tttctttctt tctttctttc tttctctttc tctttctctc tttttctttc  10800
ttttgtgtga gacagaatct ttaaagagaa gaaagaaatg ctcatgtgac cagagggtgt  10860
gttagctaaa gggagcaaga cagtcacacc cagcaggtta ccttcctttg ggcgtcacct  10920
ctgccacacc tccttaggga gagggtgtag catagtagtt aagaggggct ccagggccag  10980
aatgcctggg tttaaatcct agctctgcct cttaccagct atgtagacct gggcaagtca  11040
ttcgacgttt ttggacttcc atttcttcat ctgtaagatg gaattattat aatccctact  11100
tccatagcct ggtaaagagc aaataaatat atggaaaggc ttgaaatagt ggctggcacg  11160
tgtaagcatt aggattggtc gttgtcattg atggagtctc aggttcggtc tgatcctcag  11220
ccctgtgatt ctgtcgtgag ggcactcaca gctcactgcc tgccctaaac aggctccagc  11280
tctggccctc cctcggctca cacctttccc cctctccccc taggagatcc tgctgggccg  11340
tggcttcacc ttttggcagt ggtttgatgg tgtcctggac ctcaccaaac gctgtctccg  11400
gagctactgg tctgaccggt gagtccccac cctgggtagt ctgagcagcc atacaccagt  11460
cacctccata ctcactgccc atgccccatc ctctccttca tcccggccag gctgatcatt  11520
ggcttcatca gcaaacagta cgttactagc cttcttctca atgagcccga cggaaccttt  11580
ctcctccgct tcagcgactc agagattggg ggcatcacca ttgcccatgt catccggggc  11640
caggatggtg aggccacccc agccagtcct ctgtctctgt gcctgtgccc tctggggttt  11700
cttctgggaa tgaaatgtcc tgaccttcct gatgccgatc ctgatcttca ggaagttctt  11760
ccagcttctc ttcttccttc tgtggtctaa atgttcacct tctcactgtg agctctgtgg  11820
gaacggagac tagtgggtct ctctccctca ggagccccac cctaggtcct ctctcccttg  11880
ccttggtgga gtgagaacag gtcttatggt aggggttggg gaaggggaag aaagtccgga  11940
cagagggatc tcagggtctc cttcctacca taggctctcc acagatagag aacatccagc  12000
cattctctgc caaagacctg tccattcgct cactgggggga ccgaatccgg gatcttgctc  12060
agctcaaaaa tctctatccc aagaagccca aggatgaggc tttccggagc cactacaagc  12120
gtgagctgga actggcagct ctgattcctt cctgtcaccc acttcctccc tgctccccgc  12180
tgccctcctc tccctgcccg cgtgtcatcc tgatgtcact ccctatttca tagctgtgct  12240
tctcttactt ccccatgatc catgcccacc ttttccacct cccttcctcc ctaaccccag  12300
agcactccat ggctgtcttt tccttctcac aacagctgaa cagatgggta aggatggcag  12360
gggttatgtc ccagctacca tcaagatgac cgtggaaagg tgagtgtggt ggtatggaca  12420
```

gtgggtaggt caggggctta gtgcttatct gcaggaagga ggggtggcat caacccttgg 12480
tcagtcacat gtacctcctt ccctcctcca gggaccaacc acttcctacc ccagagctcc 12540
agatgcctac catggtgcct tcttatgacc ttggaatggc cctgattcc tccatgagca 12600
tgcagcttgg cccagatatg gtgtaaggag ctggaaagac aggaatggga gtggtctgtg 12660
cagatgggct aatcttagca tgggcagctg ggagagctgg cactgggggc tgaacaggga 12720
atcttccttt ccatgagagg gacacctgtt caaaagcagg gtgtggtggt gtccaggaga 12780
agggctggca tcagggggtc tgttttcttt ccccaggccc caggtgtacc caccacactc 12840
tcactccatc cccccgtatc aaggcctctc cccagaagaa tcagtcaacg tgttgtcagc 12900
cttccaggag taagtgaaaa acctcatggg gataccatcc cactctaagg gggtgggcat 12960
ttgaattgtt agaagaggct cttctgtgag aaaggagcag caaatgctaa cagcctgtct 13020
tcttctcttc tgtccactct aatgaggggg tagtagttaa gatctggact gcctaggttt 13080
gaattctagc tccaccactt actggtttgg ggcaaattac ttagcctttg gtgccttatc 13140
tgcacaatgg gggataataa tgctaataat aataacctac ctcactgcat tattgtggag 13200
attaaatgag ttcataacac ttaaaaagct gagcatagtg catggctcat agcaaaagct 13260
gtgtaagtcc agtcgtggat cacttaatga aggagcattt tctgtctttg gcagtttcat 13320
aattatgcga ataccattga gtataattac acaaacctag atggtataga ctactataca 13380
ctgaggctat attgtgtagc ctattgatcc tagctttaaa cccgagcagc atgatactgt 13440
tctgaatagt ataaggaaat agtaacataa tggtaaatat ttgtgtgata ggaattttca 13500
gcttgattat aatttttttt ttttgagaca gggtctcact cactggagtg cagtggtgcg 13560
atcttagctc cctgcaacct ccgcctcttg ggctcgagca atcctcctgc tgtagtgcac 13620
cacgacactc ggctaattct tttttaagat ttttctgcag acaaggtctc acttactgcc 13680
caagctggtc tcaaactcct gggcttaagt gatcctccca cctcggcctc ccaaagcgtt 13740
aggattacag gcgtgagtca ctctgcctgg ccttgattat aatcttatgg gaccactgtg 13800
gtctgtagtt gacagaaatg tcgttaatgt ggtgcatgac tgttattatt attttctgtc 13860
ctgcccctga gagccactgt cacttctctg ctgtattggt ttttgtttac tcatctgttt 13920
tggccttgaa atggcctaga cattttttctt cccgaagtat gacactcggg tgcttattaa 13980
cttagtcaag acacaacatc tcccttccca gaaggtgagg cgggagtgag gacttgggga 14040
cttaagaact accaaagttc agagtccaaa gaaacattag aaattggcta atccaccccc 14100
ataacacgca cattttacag atgagaagac tgagctcaga gcatagaaat agcttgccca 14160
ggccatgact aagtcaggat aaggagctgg agcttgtttc ctcactcagt ggtcctgact 14220
ttgcaccact ctgcatttgc ctagcctgcc ttcctctaac tgtgctctcc ctacttccag 14280
gcctcacctg cagatgcccc ccagcctggg ccagatgagc ctgccctttg accagcctca 14340
cccccagtga gtgacaaagc ccctcctgac cccatgtgcc tcttctttcc tggccttgcc 14400
ccgctctcct tatttccatt gctggttcct ggcaggggcc tgctgccgtg ccagcctcag 14460
gagcatgctg tgtccagccc tgaccccctg ctctgctcag atgtgaccat ggtggaagac 14520
agctgcctga gccagccagt gacagcgttt cctcagggca cttggtgagt ggcagcttgg 14580
gagtggaggc tgggtggcat ctaggggagt gggcgccatg cctactccac tgcttctccc 14640
atctccttgc aggattggtg aagacatatt ccctcctctg ctgcctccca ctgaacagga 14700
cctcactaag cttctcctgg aggggcaagg ggagtcgggg ggagggtcct tgggggcaca 14760

```
gcccctcctg cagccctccc actatgggca atctgggatc tcaatgtccc acatggacct  14820

aagggccaac cccagttggt gatcccagct ggagggagaa cccaaagaga cagctcttct  14880

actaccccca cagacctgct ctggacactt gctcatgccc tgccaagcag cagatgggga  14940

gggtgccctc ctatccccac ctactcctgg gtcaggagga aaagactaac aggagaatgc  15000

acagtgggtg gagccaatcc actccttcct ttctatcatt cccctgccca cctccttcca  15060

gcactgactg gaagggaagt tcaggctctg agacacaccc caacatgcct gcacctgcag  15120

cgcgcacacg cacgcacaca cacatacaga gctctctgag ggtgatgggg ctgagcagga  15180

ggggggctgg gtaagagcac aggttagggc atggaaggct tctccgccca ttctgaccca  15240

gggcctagga cggataggca ggaacataca gacacattta cactagaggc cagggataga  15300

ggatattggg tctcagccct aggggaatgg gaagcagctc aagggaccct gggtgggagc  15360

ataggagggg tctggacatg tggttactag tacaggtttt gccctgatta aaaaatctcc  15420

caaagcccca aattcctgtt agccaggtgg aggcttctga tacgtgtatg agactatgca  15480

aaagtacaag ggctgagatt cttcgtgtat agctgtgtga acgtgtatgt acctaggata  15540

tgttaaatgt atagctggca ccttagttgc atgaccacat agaacatgtg tctatctgct  15600

tttgcctacg tgacaacaca aatttgggag ggtgagacac tgcacagaag acagcagcaa  15660

gtgtgctggc ctctctgaca tatgctaacc cccaaatact ctgaatttgg agtctgactg  15720

tgcccaagtg ggtccaagtg gctgtgacat ctacgtatgg ctccacacct ccaatgctgc  15780

ctgggagcca gggtgagagt ctgggtccag gcctggccat gtggccctcc agtgtatgag  15840

agggccctgc ctgctgcatc ttttctgttg ccccatccac cgccagcttc ccttcactcc  15900

cctatcccat tctccctctc aaggcagggg tcatagatcc taagccataa aataaatttt  15960

attccaaaat aacaaaataa ataatctact gtacacaatc tgaaaagaaa             16010
```

```
<210> SEQ ID NO 3
<211> LENGTH: 847
<212> TYPE: PRT
<213> ORGANISM: Artificial Sequence
<220> FEATURE:
<223> OTHER INFORMATION: STAT6 Amino Acid

<400> SEQUENCE: 3

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
            20                  25                  30

Trp Leu Glu Ser Gln Pro Trp Glu Phe Leu Val Gly Ser Asp Ala Phe
        35                  40                  45

Cys Cys Asn Leu Ala Ser Ala Leu Leu Ser Asp Thr Val Gln His Leu
    50                  55                  60

Gln Ala Ser Val Gly Glu Gln Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Arg Gln Ile Leu Gln Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Lys Thr Gly Leu Arg Arg Leu Gln His Arg Val Gly Glu Ile
    130                 135                 140
```

-continued

```
His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
    290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
        355                 360                 365

Lys Arg Cys Glu Arg Lys Gly Thr Glu Ser Val Thr Glu Glu Lys Cys
    370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
        435                 440                 445

Glu Lys Met Cys Glu Thr Leu Asn Leu Lys Phe Met Ala Glu Val Gly
    450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
        515                 520                 525

Leu Arg Ser Tyr Trp Ser Asp Arg Leu Ile Ile Gly Phe Ile Ser Lys
    530                 535                 540

Gln Tyr Val Thr Ser Leu Leu Leu Asn Glu Pro Asp Gly Thr Phe Leu
545                 550                 555                 560

Leu Arg Phe Ser Asp Ser Glu Ile Gly Gly Ile Thr Ile Ala His Val
```

-continued

```
                565                 570                 575

Ile Arg Gly Gln Asp Gly Ser Pro Gln Ile Glu Asn Ile Gln Pro Phe
            580                 585                 590

Ser Ala Lys Asp Leu Ser Ile Arg Ser Leu Gly Asp Arg Ile Arg Asp
        595                 600                 605

Leu Ala Gln Leu Lys Asn Leu Tyr Pro Lys Lys Pro Lys Asp Glu Ala
    610                 615                 620

Phe Arg Ser His Tyr Lys Pro Glu Gln Met Gly Lys Asp Gly Arg Gly
625                 630                 635                 640

Tyr Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
            660                 665                 670

Gly Met Ala Pro Asp Ser Ser Met Ser Met Gln Leu Gly Pro Asp Met
        675                 680                 685

Val Pro Gln Val Tyr Pro Pro His Ser His Ser Ile Pro Pro Tyr Gln
    690                 695                 700

Gly Leu Ser Pro Glu Glu Ser Val Asn Val Leu Ser Ala Phe Gln Glu
705                 710                 715                 720

Pro His Leu Gln Met Pro Pro Ser Leu Gly Gln Met Ser Leu Pro Phe
                725                 730                 735

Asp Gln Pro His Pro Gln Gly Leu Leu Pro Cys Gln Pro Gln Glu His
            740                 745                 750

Ala Val Ser Ser Pro Asp Pro Leu Leu Cys Ser Asp Val Thr Met Val
        755                 760                 765

Glu Asp Ser Cys Leu Ser Gln Pro Val Thr Ala Phe Pro Gln Gly Thr
    770                 775                 780

Trp Ile Gly Glu Asp Ile Phe Pro Pro Leu Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Ala Gln Pro Leu Leu Gln Pro Ser His Tyr Gly Gln Ser
            820                 825                 830

Gly Ile Ser Met Ser His Met Asp Leu Arg Ala Asn Pro Ser Trp
        835                 840                 845
```

<210> SEQ ID NO 4
<211> LENGTH: 3963
<212> TYPE: DNA
<213> ORGANISM: Artificial Sequence
<220> FEATURE:
<223> OTHER INFORMATION: STAT6 NM_003153.5

<400> SEQUENCE: 4

```
ggggcagcca ctgcttacac tgaagaggga ggacgggaga ggagtgtgtg tgtgtgtgtg      60

tgtgtgtgtg tgtatgtatg tgtgtgcttt atcttatttt tctttttggt ggtggtggtg     120

gaagggggga ggtgctagca gggccagcct tgaactcgct ggacagagct acagacctat     180

ggggcctgga agtgcccgct gagaaaggga gaagacagca gaggggttgc cgaggcaacc     240

tccaagtccc agatcatgtc tctgtggggt ctggtctcca agatgccccc agaaaaagtg     300

cagcggctct atgtcgactt tccccaacac ctgcggcatc ttctgggtga ctggctggag     360

agccagccct gggagttcct ggtcggctcc gacgccttct gctgcaactt ggctagtgcc     420

ctactttcag acactgtcca gcaccttcag gcctcggtgg gagagcaggg ggaggggagc     480
```

-continued

```
accatcttgc aacacatcag caccccttgag agcatatatc agagggaccc cctgaagctg    540
gtggccactt tcagacaaat acttcaagga gagaaaaaag ctgttatgga acagttccgc    600
cacttgccaa tgcctttcca ctggaagcag gaagaactca agtttaagac aggcttgcgg    660
aggctgcagc accgagtagg ggagatccac cttctccgag aagccctgca gaagggggct    720
gaggctggcc aagtgtctct gcacagcttg atagaaactc ctgctaatgg gactgggcca    780
agtgaggccc tggccatgct actgcaggag accactggag agctagaggc agccaaagcc    840
ctagtgctga agaggatcca gatttggaaa cggcagcagc agctggcagg gaatggcgca    900
ccgtttgagg agagcctggc cccactccag gagaggtgtg aaagcctggt ggacatttat    960
tcccagctac agcaggaggt aggggcggct ggtggggagc ttgagcccaa gacccgggca   1020
tcgctgactg gccggctgga tgaagtcctg agaaccctcg tcaccagttg cttcctggtg   1080
gagaagcagc ccccccaggt actgaagact cagaccaagt tccaggctgg agttcgattc   1140
ctgttgggct tgaggttcct gggggcccca gccaagcctc cgctggtcag ggccgacatg   1200
gtgacagaga agcaggcgcg ggagctgagt gtgcctcagg gtcctggggc tggagcagaa   1260
agcactggag aaatcatcaa caacactgtg cccttggaga acagcattcc tgggaactgc   1320
tgctctgccc tgttcaagaa cctgcttctc aagaagatca agcggtgtga gcggaagggc   1380
actgagtctg tcacagagga gaagtgcgct gtgctcttct ctgccagctt cacacttggc   1440
cccggcaaac tccccatcca gctccaggcc ctgtctctgc ccctggtggt catcgtccat   1500
ggcaaccaag acaacaatgc caaagccact atcctgtggg acaatgcctt ctctgagatg   1560
gaccgcgtgc cctttgtggt ggctgagcgg gtgccctggg agaagatgtg tgaaactctg   1620
aacctgaagt tcatggctga ggtggggacc aaccgggggc tgctcccaga gcacttcctc   1680
ttcctggccc agaagatctt caatgacaac agcctcagta tggaggcctt ccagcaccgt   1740
tctgtgtcct ggtcgcagtt caacaaggag atcctgctgg gccgtggctt caccttttgg   1800
cagtggtttg atggtgtcct ggacctcacc aaacgctgtc tccggagcta ctggtctgac   1860
cggctgatca ttggcttcat cagcaaacag tacgttacta gccttcttct caatgagccc   1920
gacggaacct ttctcctccg cttcagcgac tcagagattg gggcatcac cattgcccat    1980
gtcatccggg gccaggatgg ctctccacag atagagaaca tccagccatt ctctgccaaa   2040
gacctgtcca ttcgctcact gggggaccga atccgggatc ttgctcagct caaaaatctc   2100
tatcccaaga agcccaagga tgaggctttc cggagccact acaagcctga acagatgggt   2160
aaggatggca ggggttatgt cccagctacc atcaagatga ccgtggaaag ggaccaacca   2220
cttcctaccc cagagctcca gatgcctacc atggtgcctt cttatgacct tggaatggcc   2280
cctgattcct ccatgagcat gcagcttggc ccagatatgg tgccccaggt gtacccacca   2340
cactctcact ccatcccccc gtatcaaggc ctctccccag aagaatcagt caacgtgttg   2400
tcagccttcc aggagcctca cctgcagatg ccccccagcc tgggccagat gagcctgccc   2460
tttgaccagc ctcaccccca gggcctgctg ccgtgccagc ctcaggagca tgctgtgtcc   2520
agccctgacc ccctgctctg ctcagatgtg accatggtgg aagacagctg cctgagccag   2580
ccagtgacag cgtttcctca gggcacttgg attggtgaag acatattccc tcctctgctg   2640
cctcccactg aacaggacct cactaagctt ctcctggagg ggcaagggga gtcgggggga   2700
gggtccttgg gggcacagcc cctcctgcag ccctcccact atgggcaatc tgggatctca   2760
atgtcccaca tggacctaag ggccaacccc agttggtgat cccagctgga gggagaaccc   2820
aaagagacag ctcttctact acccccacag acctgctctg gacacttgct catgccctgc   2880
```

-continued

```
caagcagcag atggggaggg tgccctccta tccccaccta ctcctgggtc aggaggaaaa   2940

gactaacagg agaatgcaca gtgggtggag ccaatccact ccttcctttc tatcattccc   3000

ctgcccacct ccttccagca ctgactggaa gggaagttca ggctctgaga cacaccccaa   3060

catgcctgca cctgcagcgc gcacacgcac gcacacacac atacagagct ctctgagggt   3120

gatggggctg agcaggaggg gggctgggta agagcacagg ttagggcatg gaaggcttct   3180

ccgcccattc tgacccaggg cctaggacgg ataggcagga acatacagac acatttacac   3240

tagaggccag ggatagagga tattgggtct cagccctagg ggaatgggaa gcagctcaag   3300

ggaccctggg tgggagcata ggaggggtct ggacatgtgg ttactagtac aggttttgcc   3360

ctgattaaaa aatctcccaa agccccaaat tcctgttagc caggtggagg cttctgatac   3420

gtgtatgaga ctatgcaaaa gtacaagggc tgagattctt cgtgtatagc tgtgtgaacg   3480

tgtatgtacc taggatatgt taaatgtata gctggcacct tagttgcatg accacataga   3540

acatgtgtct atctgctttt gcctacgtga caacacaaat ttgggagggt gagacactgc   3600

acagaagaca gcagcaagtg tgctggcctc tctgacatat gctaaccccc aaatactctg   3660

aatttggagt ctgactgtgc ccaagtgggt ccaagtggct gtgacatcta cgtatggctc   3720

cacacctcca atgctgcctg ggagccaggg tgagagtctg ggtccaggcc tggccatgtg   3780

gccctccagt gtatgagagg gccctgcctg ctgcatcttt tctgttgccc catccaccgc   3840

cagcttccct tcactcccct atcccattct ccctctcaag gcaggggtca tagatcctaa   3900

gccataaaat aaattttatt ccaaaataac aaaataaata atctactgta cacaatctga   3960

aaa                                                                 3963
```

<210> SEQ ID NO 5
<211> LENGTH: 673
<212> TYPE: PRT
<213> ORGANISM: Artificial Sequence
<220> FEATURE:
<223> OTHER INFORMATION: STAT6 Iso 2

<400> SEQUENCE: 5

```
Met Glu Gln Ala Leu Ala Met Leu Leu Gln Glu Thr Thr Gly Glu Leu
1               5                   10                  15

Glu Ala Ala Lys Ala Leu Val Leu Lys Arg Ile Gln Ile Trp Lys Arg
            20                  25                  30

Gln Gln Gln Leu Ala Gly Asn Gly Ala Pro Phe Glu Glu Ser Leu Ala
        35                  40                  45

Pro Leu Gln Glu Arg Cys Glu Ser Leu Val Asp Ile Tyr Ser Gln Leu
    50                  55                  60

Gln Gln Glu Val Gly Ala Ala Gly Gly Glu Leu Glu Pro Lys Thr Arg
65                  70                  75                  80

Ala Ser Leu Thr Gly Arg Leu Asp Glu Val Leu Arg Thr Leu Val Thr
                85                  90                  95

Ser Cys Phe Leu Val Glu Lys Gln Pro Pro Gln Val Leu Lys Thr Gln
            100                 105                 110

Thr Lys Phe Gln Ala Gly Val Arg Phe Leu Leu Gly Leu Arg Phe Leu
        115                 120                 125

Gly Ala Pro Ala Lys Pro Pro Leu Val Arg Ala Asp Met Val Thr Glu
    130                 135                 140

Lys Gln Ala Arg Glu Leu Ser Val Pro Gln Gly Pro Gly Ala Gly Ala
145                 150                 155                 160
```

-continued

```
Glu Ser Thr Gly Glu Ile Ile Asn Asn Thr Val Pro Leu Glu Asn Ser
                165                 170                 175

Ile Pro Gly Asn Cys Cys Ser Ala Leu Phe Lys Asn Leu Leu Leu Lys
            180                 185                 190

Lys Ile Lys Arg Cys Glu Arg Lys Gly Thr Glu Ser Val Thr Glu Glu
        195                 200                 205

Lys Cys Ala Val Leu Phe Ser Ala Ser Phe Thr Leu Gly Pro Gly Lys
    210                 215                 220

Leu Pro Ile Gln Leu Gln Ala Leu Ser Leu Pro Leu Val Val Ile Val
225                 230                 235                 240

His Gly Asn Gln Asp Asn Asn Ala Lys Ala Thr Ile Leu Trp Asp Asn
                245                 250                 255

Ala Phe Ser Glu Met Asp Arg Val Pro Phe Val Val Ala Glu Arg Val
            260                 265                 270

Pro Trp Glu Lys Met Cys Glu Thr Leu Asn Leu Lys Phe Met Ala Glu
        275                 280                 285

Val Gly Thr Asn Arg Gly Leu Leu Pro Glu His Phe Leu Phe Leu Ala
    290                 295                 300

Gln Lys Ile Phe Asn Asp Asn Ser Leu Ser Met Glu Ala Phe Gln His
305                 310                 315                 320

Arg Ser Val Ser Trp Ser Gln Phe Asn Lys Glu Ile Leu Leu Gly Arg
                325                 330                 335

Gly Phe Thr Phe Trp Gln Trp Phe Asp Gly Val Leu Asp Leu Thr Lys
            340                 345                 350

Arg Cys Leu Arg Ser Tyr Trp Ser Asp Arg Leu Ile Ile Gly Phe Ile
        355                 360                 365

Ser Lys Gln Tyr Val Thr Ser Leu Leu Leu Asn Glu Pro Asp Gly Thr
    370                 375                 380

Phe Leu Leu Arg Phe Ser Asp Ser Glu Ile Gly Gly Ile Thr Ile Ala
385                 390                 395                 400

His Val Ile Arg Gly Gln Asp Gly Ser Pro Gln Ile Glu Asn Ile Gln
                405                 410                 415

Pro Phe Ser Ala Lys Asp Leu Ser Ile Arg Ser Leu Gly Asp Arg Ile
            420                 425                 430

Arg Asp Leu Ala Gln Leu Lys Asn Leu Tyr Pro Lys Lys Pro Lys Asp
        435                 440                 445

Glu Ala Phe Arg Ser His Tyr Lys Pro Glu Gln Met Gly Lys Asp Gly
    450                 455                 460

Arg Gly Tyr Val Pro Ala Thr Ile Lys Met Thr Val Glu Arg Asp Gln
465                 470                 475                 480

Pro Leu Pro Thr Pro Glu Leu Gln Met Pro Thr Met Val Pro Ser Tyr
                485                 490                 495

Asp Leu Gly Met Ala Pro Asp Ser Ser Met Ser Met Gln Leu Gly Pro
            500                 505                 510

Asp Met Val Pro Gln Val Tyr Pro Pro His Ser His Ser Ile Pro Pro
        515                 520                 525

Tyr Gln Gly Leu Ser Pro Glu Glu Ser Val Asn Val Leu Ser Ala Phe
    530                 535                 540

Gln Glu Pro His Leu Gln Met Pro Pro Ser Leu Gly Gln Met Ser Leu
545                 550                 555                 560

Pro Phe Asp Gln Pro His Pro Gln Gly Leu Leu Pro Cys Gln Pro Gln
                565                 570                 575

Glu His Ala Val Ser Ser Pro Asp Pro Leu Leu Cys Ser Asp Val Thr
```

580 585 590

Met Val Glu Asp Ser Cys Leu Ser Gln Pro Val Thr Ala Phe Pro Gln
595 600 605

Gly Thr Trp Ile Gly Glu Asp Ile Phe Pro Pro Leu Leu Pro Pro Thr
610 615 620

Glu Gln Asp Leu Thr Lys Leu Leu Leu Glu Gly Gln Gly Glu Ser Gly
625 630 635 640

Gly Gly Ser Leu Gly Ala Gln Pro Leu Leu Gln Pro Ser His Tyr Gly
645 650 655

Gln Ser Gly Ile Ser Met Ser His Met Asp Leu Arg Ala Asn Pro Ser
660 665 670

Trp

<210> SEQ ID NO 6
<211> LENGTH: 737
<212> TYPE: PRT
<213> ORGANISM: Artificial Sequence
<220> FEATURE:
<223> OTHER INFORMATION: STAT6 Iso 3

<400> SEQUENCE: 6

Met Glu Gln Phe Arg His Leu Pro Met Pro Phe His Trp Lys Gln Glu
1 5 10 15

Glu Leu Lys Phe Lys Thr Gly Leu Arg Arg Leu Gln His Arg Val Gly
20 25 30

Glu Ile His Leu Leu Arg Glu Ala Leu Gln Lys Gly Ala Glu Ala Gly
35 40 45

Gln Val Ser Leu His Ser Leu Ile Glu Thr Pro Ala Asn Gly Thr Gly
50 55 60

Pro Ser Glu Ala Leu Ala Met Leu Leu Gln Glu Thr Thr Gly Glu Leu
65 70 75 80

Glu Ala Ala Lys Ala Leu Val Leu Lys Arg Ile Gln Ile Trp Lys Arg
85 90 95

Gln Gln Gln Leu Ala Gly Asn Gly Ala Pro Phe Glu Glu Ser Leu Ala
100 105 110

Pro Leu Gln Glu Arg Cys Glu Ser Leu Val Asp Ile Tyr Ser Gln Leu
115 120 125

Gln Gln Glu Val Gly Ala Ala Gly Gly Glu Leu Glu Pro Lys Thr Arg
130 135 140

Ala Ser Leu Thr Gly Arg Leu Asp Glu Val Leu Arg Thr Leu Val Thr
145 150 155 160

Ser Cys Phe Leu Val Glu Lys Gln Pro Pro Gln Val Leu Lys Thr Gln
165 170 175

Thr Lys Phe Gln Ala Gly Val Arg Phe Leu Leu Gly Leu Arg Phe Leu
180 185 190

Gly Ala Pro Ala Lys Pro Pro Leu Val Arg Ala Asp Met Val Thr Glu
195 200 205

Lys Gln Ala Arg Glu Leu Ser Val Pro Gln Gly Pro Gly Ala Gly Ala
210 215 220

Glu Ser Thr Gly Glu Ile Ile Asn Asn Thr Val Pro Leu Glu Asn Ser
225 230 235 240

Ile Pro Gly Asn Cys Cys Ser Ala Leu Phe Lys Asn Leu Leu Leu Lys
245 250 255

Lys Ile Lys Arg Cys Glu Arg Lys Gly Thr Glu Ser Val Thr Glu Glu
260 265 270

-continued

```
Lys Cys Ala Val Leu Phe Ser Ala Ser Phe Thr Leu Gly Pro Gly Lys
        275                 280                 285

Leu Pro Ile Gln Leu Gln Ala Leu Ser Leu Pro Leu Val Val Ile Val
    290                 295                 300

His Gly Asn Gln Asp Asn Asn Ala Lys Ala Thr Ile Leu Trp Asp Asn
305                 310                 315                 320

Ala Phe Ser Glu Met Asp Arg Val Pro Phe Val Val Ala Glu Arg Val
                325                 330                 335

Pro Trp Glu Lys Met Cys Glu Thr Leu Asn Leu Lys Phe Met Ala Glu
            340                 345                 350

Val Gly Thr Asn Arg Gly Leu Leu Pro Glu His Phe Leu Phe Leu Ala
        355                 360                 365

Gln Lys Ile Phe Asn Asp Asn Ser Leu Ser Met Glu Ala Phe Gln His
    370                 375                 380

Arg Ser Val Ser Trp Ser Gln Phe Asn Lys Glu Ile Leu Leu Gly Arg
385                 390                 395                 400

Gly Phe Thr Phe Trp Gln Trp Phe Asp Gly Val Leu Asp Leu Thr Lys
                405                 410                 415

Arg Cys Leu Arg Ser Tyr Trp Ser Asp Arg Leu Ile Ile Gly Phe Ile
            420                 425                 430

Ser Lys Gln Tyr Val Thr Ser Leu Leu Leu Asn Glu Pro Asp Gly Thr
        435                 440                 445

Phe Leu Leu Arg Phe Ser Asp Ser Glu Ile Gly Gly Ile Thr Ile Ala
    450                 455                 460

His Val Ile Arg Gly Gln Asp Gly Ser Pro Gln Ile Glu Asn Ile Gln
465                 470                 475                 480

Pro Phe Ser Ala Lys Asp Leu Ser Ile Arg Ser Leu Gly Asp Arg Ile
                485                 490                 495

Arg Asp Leu Ala Gln Leu Lys Asn Leu Tyr Pro Lys Lys Pro Lys Asp
            500                 505                 510

Glu Ala Phe Arg Ser His Tyr Lys Pro Glu Gln Met Gly Lys Asp Gly
        515                 520                 525

Arg Gly Tyr Val Pro Ala Thr Ile Lys Met Thr Val Glu Arg Asp Gln
    530                 535                 540

Pro Leu Pro Thr Pro Glu Leu Gln Met Pro Thr Met Val Pro Ser Tyr
545                 550                 555                 560

Asp Leu Gly Met Ala Pro Asp Ser Ser Met Ser Met Gln Leu Gly Pro
                565                 570                 575

Asp Met Val Pro Gln Val Tyr Pro Pro His Ser His Ser Ile Pro Pro
            580                 585                 590

Tyr Gln Gly Leu Ser Pro Glu Glu Ser Val Asn Val Leu Ser Ala Phe
        595                 600                 605

Gln Glu Pro His Leu Gln Met Pro Pro Ser Leu Gly Gln Met Ser Leu
    610                 615                 620

Pro Phe Asp Gln Pro His Pro Gln Gly Leu Leu Pro Cys Gln Pro Gln
625                 630                 635                 640

Glu His Ala Val Ser Ser Pro Asp Pro Leu Leu Cys Ser Asp Val Thr
                645                 650                 655

Met Val Glu Asp Ser Cys Leu Ser Gln Pro Val Thr Ala Phe Pro Gln
            660                 665                 670

Gly Thr Trp Ile Gly Glu Asp Ile Phe Pro Pro Leu Leu Pro Pro Thr
        675                 680                 685
```

-continued

Glu Gln Asp Leu Thr Lys Leu Leu Leu Glu Gly Gln Gly Glu Ser Gly
690 695 700

Gly Gly Ser Leu Gly Ala Gln Pro Leu Leu Gln Pro Ser His Tyr Gly
705 710 715 720

Gln Ser Gly Ile Ser Met Ser His Met Asp Leu Arg Ala Asn Pro Ser
725 730 735

Trp

<210> SEQ ID NO 7
<211> LENGTH: 32730
<212> TYPE: DNA
<213> ORGANISM: Artificial Sequence
<220> FEATURE:
<223> OTHER INFORMATION: KRAS G12D genomic sequence

<400> SEQUENCE: 7
gattttccta ggcggcggcc gcggcggcgg aggcagcagc ggcggcggca gtggcggcgg 60
cgaaggtggc ggcggctcgg ccagtactcc cggcccccgc catttcggac tgggagcgag 120
cgcggcgcag gcactgaagg cggcggcggg gccagaggct cagcggctcc caggtgcggg 180
agagaggtac ggagcggacc acccctcctg ggcccctgcc cgggtcccga ccctctttgc 240
cggcgccggg cggggccggc ggcgagtgaa tgaattaggg gtccccggag gggcgggtgg 300
ggggcgcggg cgcggggtcg gggcgggctg ggtgagaggg gtctgcaggg gggaggcgcg 360
cggacgcggc ggcgcgggga gtgaggaatg ggcggtgcgg ggctgaggag ggtgaggctg 420
gaggcggtcg ccgctggtgc tgcttcctgg acggggaacc ccttccttcc tcctccccga 480
gagccgcggc tggaggcttc tggggagaaa ctcgggccgg gccggctgcc cctcggagcg 540
gtggggtgcg gtggaggtta ctcccgcggc gccccggcct cccctccccc tctccccgct 600
cccgcacctc ttgcctccct ttccagcact cggctgcctc ggtccagcct tccctgctgc 660
atttggcatc tctaggacga aggtataaac ttctccctcg agcgcaggct ggacggatag 720
tggtcctttt ccgtgtgtag ggatgtgtg agtaagaggg gaggtcacgt tttggaagag 780
cataggaaag tgcttagaga ccactgtttg aggttattgt gtttggaaaa aaatgcatct 840
gcctccgagt tcctgaatgc tcccctcccc catgtatggg ctgtgacatt gctgtggcca 900
caaaggagga ggtggaggta gagatggtgg aagaacaggt ggccaacacc ctacacgtag 960
agcctgtgac ctacagtgaa aaggaaaaag ttaatcccag atggtctgtt ttgcttggtc 1020
aagttaaacc cgaagaaaac ccgcagagca gaagcaaggc tttttccttg ctagttgagt 1080
gtagacagca atagcaaaaa tagtacttga agtttaattt acctgttctt gtcctttccc 1140
ctatttctta tgtattaccc tcatcccctc gtctctttta tactaccctc attttgcaga 1200
tgtgttctac atctcaagag ttattacagt actccaaaac agcacttaca tgatttttta 1260
aacttacaga ggaattgtag caatccacca gctaaccgcc tgaaatagac ttaaacatgt 1320
gcatctcctt tttttttttt tttttgagac acagtctcgc tctgttgccc aggctggagt 1380
gcaatggcgc ggtatcggct cactgaaacc tccgcctcct gggttcaagc aattctcctg 1440
cctcagcctc ccgagtagct gggactagta ggtgcacgcc accatgccca gctaattttt 1500
gtatttttag tagagacaga gtttcatcat gttggtcagg atggtctcca tctgctctgt 1560
tgcccaggct ggagtgcagt ggcgccgtct cggctcactg caacctctgc ctcctgcatt 1620
caagcaattc tcctgcctca gcctcccgaa taactgggat tacaggtgtc tgctgccatg 1680
cccggctaat tttttgtatt tttagtagag acgggggttt caccatgttg gtcaggctgg 1740

-continued

```
tctagaactc ctgacctcgt gatctgcccg cctcggcctc ccacagtggc atgtgcatct   1800
tatagctgaa gtctaagcct tcttaaatct tgagatccat caaaacagac aggttttcta   1860
attgttatac aatgtatatg ttatgtttat aatagaaatc attttacaaa taagttataa   1920
atgggaaagg tctatttgta attatcagct cagaattaac cataaaactg gtgtcactga   1980
agtgactgag gtccaaaatg ctgactctgc atgttataga ctacagatat caaatatggt   2040
tgctaacaat agtttacttt gagactgtag ccatccacag tatatttgct tttaagagat   2100
ggtagatggt aattcagttt tatgaaaaat aaaaatgaat tttcttccat tacaaaattg   2160
ttggattcga gtccagtcca ctccttacta gcttttctaa ctctcggtga gggatcccct   2220
cccagcccat gatcttcatt tggtaagact cctttggaac ccagttctct ctagtggatt   2280
taaatgtgat ttggttttaa aaatctcatt caaggaattt tttttttttc tggaaacaac   2340
caccgcataa acaagtaaac cggaagatac atgtggctct gaattcatat atatacacaa   2400
actctaatcc aatgtctgtc cacagtattt cctaggctag taaacttttt ggccttaacg   2460
acccctctac cctctttgtt tttttgagag agagagtctc actctgtcac ccaggccgga   2520
atgcagtggc gcgatctcgg cccgctacta cctccgactc tcaggctcaa gcgattctcc   2580
cgcctcagct tcccgagtag ccgggattac aggctcccgc caccgggcta attgtatttt   2640
tagatacggg atttcaccat gttggccagg ctggtctcga cctcctgacc tcaggtgatc   2700
cgcccgccta agcctcccaa agtgctggga ttacaggcca ccacacccgg cctacactct   2760
taaaaattat cgaaggggcc gggcacattg gctcttatct gtaatcccag cactttggga   2820
gactgaggcg ggaggatcgc ttgaggccag gagttggaga ccagcgtact caacatagtg   2880
agaccttgtt ataaagaaaa aaaaaatcca ggattaaaaa aaatctttga tttgtttggg   2940
atttattaat atttaccgta ttggaaatta aaacaatttt ttaaaatgta ttcatttaaa   3000
aataataagc ccattacttg gtaacatgaa taaaatattt tatgaaaaat aactattttc   3060
caaaacaaaa ccaaaactta gaaaagtggt attgtttcac acttcagtaa atctctttaa   3120
tgatgtggct taatagaaga tatggattct tatatctgca tctgcattca atctattatg   3180
atcacacatc tggaaaactt gtgaaagaat gggagttaaa agggtaaagg acatcttaat   3240
gttattatga aaacagtttt gacctcttgc acaccagaaa agtcttagta acctgagggg   3300
ttcctagacc acattttgag aactgtttta ggctatgcaa actggttggg gggaggttgg   3360
ggtaggcaga gagctagaag atacatttta gtgtaattct cctcatctat tcctaattgc   3420
tttggcctac atttgaaata aagcgtggag gcaaacggga taagatacat gtttgtagtg   3480
gttgttaact tcaccctaga caagcagcca ataagtctag gtagagcaga gtaaggcggg   3540
gaactatgcc gtgaccgtgt gtgatacaat ttttctagcc tgtggtgctt tttgcggcag   3600
ggcttaggag taaggttagt atgttatcat ttgggaaacc aaattattat tttgggtctt   3660
cagtcaatta tgatgctgtg tatatttagt gtttatctac aatatatgca cattcattaa   3720
tttggagcta ctcatcctat aataaatagt tgtgcattta ctcccatttt tttctgcatt   3780
tctctcctta tttataatta tgtgttacat gagggaaagg aggtgaaatt aaacattcat   3840
attatttcaa aaaatttgaa acaactaact aaaaaaatatg ttttattttc tgtatggtgt   3900
ttgttataca atctgtcaat attcatgcac ctcttgggag acagtgtatg aaaagcaaag   3960
agtaacagtc acatggatta ctgattactg agatatattc acttgcatct tttttttttt   4020
ttgagacgga gtggctctgt cgcccaggct ggagtgcagt ggcgtgatct cggctcactg   4080
caagctccgc ctcctgggtt cacgccattc ttctgcctca gcctcccaag tagctgggac   4140
```

tacaggcgcc cgccaccacg cccggctaat ttttttatat ttttagtaga gacggggttt 4200
caccgggtta gccaggatgg tcttgatctc ctgacctcgt gatccaccct cctcggcctc 4260
ccaaagtgct aggattatag gcgtgagcca ccgtgcccgg ctcacttgca tctcttaaca 4320
gctgttttct tactaaaaac agtgtttatc tctaatcttt ttgtttgttt gtttgttttg 4380
agatggagtc ttactccgtc acccaatctg gagtgcagtg gcgtgatctg ggctcactgc 4440
aacctctgcc tcccgggttc aagtgattct ccttcctcag cctccccagt agctaggact 4500
acaggagagc gccaccacgc ctgattaatt tttgtatttt tagtagagag agggtttcac 4560
catattggcc aggctggtct tgaactcctg gcctcaggtg atccacccgc cttggcctct 4620
gaaagtgctg ggattacagg catgagccgc cgcacccggc tttctaatct ttatcttttt 4680
ttgtgcagcg gtgatacagg attatgtatt gtactgaaca gttaattcgg agttctcttg 4740
gtttttagct ttattttccc cagagatttt tttttttttt tttttttttg agacggagtc 4800
ttgctctatc gccaggctgg agtgcagtgg cgccatctcg gctcattgca acctcggact 4860
cctattttcc ccagagatat ttcacacatt aaaatgtcgt caaatattgt tcttctttgc 4920
ctcagtgttt aaatttttat ttccccatga cacaatccag ctttatttga cactcattct 4980
ctcaactctc atctgattct tactgttaat atttatccaa gagaactact gccatgatgc 5040
tttaaaagtt tttctgtagc tgttgcatat tgacttctaa cacttagagg tgggggtcca 5100
ctaggaaaac tgtaacaata agagtggaga tagctgtcag caacttttgt gagggtgtgc 5160
tacagggtgt agagcactgt gaagtctcta catgagtgaa gtcatgatat gatcctttga 5220
gagcctttag ccgccgcaga acagcagtct ggctatttag atagaacaac ttgattttaa 5280
gataaaagaa ctgtctatgt agcatttatg catttttctt aagcgtcgat ggaggagttt 5340
gtaaatgaag tacagttcat tacgatacac gtctgcagtc aactggaatt ttcatgattg 5400
aattttgtaa ggtattttga aataattttt catataaagg tgagtttgta ttaaaaggta 5460
ctggtggagt atttgatagt gtattaacct tatgtgtgac atgttctaat atagtcacat 5520
tttcattatt tttattataa ggcctgctga aaatgactga atataaactt gtggtagttg 5580
gagctgatgg cgtaggcaag agtgccttga cgatacagct aattcagaat cattttgtgg 5640
acgaatatga tccaacaata gaggtaaatc ttgttttaat atgcatatta ctggtgcagg 5700
accattcttt gatacagata aaggtttctc tgaccatttt catgagtact tattacaaga 5760
taattatgct gaaagttaag ttatctgaaa tgtaccttgg gtttcaagtt atatgtaacc 5820
attaatatgg gaactttact ttccttggga gtatgtcagg gtccatgatg ttcactctct 5880
gtgcattttg attggaagtg tatttcagag tttcgtgaga gggtagaaat ttgtatccta 5940
tctggaccta aaagacaatc tttttattgt aacttttatt tttatgggtt tcttggtatt 6000
gtgacatcat atgtaaaggt tagatttaat tgtactagtg aaatataatt gtttgatggt 6060
tgattttttt aaacttcatc agcagtattt tcctatcttc ttctcaacat tagagaacct 6120
acaactaccg gataaatttt acaaaatgaa ttatttgcct aaggtgtggt ttatataaag 6180
gtactattac caactttacc tttgctttgt tgtcattttt aaatttactc aaggaaatac 6240
taggatttaa aaaaaaattc cttgagtaaa tttaaattgt tatcatgttt ttgaggatta 6300
ttttcagatt tttttagttt aatgaaaatt taccaaagta aagaccagca gcagaatgat 6360
aagtaaagac ctgtaagaca ccttgaaggt catggagtag aacttccatc ccaagcagat 6420
gaggatttat ttaatctcaa agacctccag gaggggacat tccccaactg tccttgttaa 6480

-continued ctcattttca gaacatattt attagcatat tttacatgta atttggatct tcatgttaaa 6540
tttaacatca gtggagatgg aaaataagca tatcgccttg tctttgaaat agccctatat 6600
tgttagattg tttcttaggc ttctttaccc tgggttaagc agtcctaata ctttagcatt 6660
tattctacat ctagtgtact aatttaaaaa aatcagttct gaaaaatttc taagaacttt 6720
cttcaagttc caagctgtga aatctagaac aggtcaaagt gccttattaa cgtactgtac 6780
tgtgtagtgt cttgaagaga cactttgcgc tgaggcaagt tctgagggca ttgggtggcc 6840
ttgggaagat atttatgcag tttagaacct ggagaattga ttagataact aatcataagg 6900
aaacgtcaca tatttttggt actataaaaa agtggagaaa taatgcctat ttgcaaagat 6960
ttgatttaaa catagaaaca actttatttg gcttccaatt ttaagaattt acagcagtaa 7020
aggggaacag tctaattgaa gtagactgcc tatgcaatag tctctgtata tttacttttg 7080
acaagttaat tcaatgtgta ctatagtttt gtttctttga agaggtttga atagtgcacc 7140
cattttaatc tgtattgcaa attcagggtt acttggcaga ctctactatt taaatcagat 7200
gtaaaaggaa gttttaatat aattcacttt atgcctgaaa gtttcctgg gatttggaa 7260 ggtgatttta ctggaaatgc tgtctgtctt ccctgaaaat ctgagaaatt ccattacact 7320
ttgtttccaa tcagaggtca tgagtgctat atgagtatat acagcatgac gtcatgaatg 7380
tgataaagtg ggttaggaaa ccttttgcta atgattgtta aaatgcaata taaatgttga 7440
agaaataaag ctaacagtta agcctttatt tgggcggaag gctgaaaaag tttataaact 7500
taaacctata actctgctta tgatttctgc caaaccagaa gacttgactc tgggaagcat 7560
tggttacctg tgaactttga aactgacggt ccctgacgta gtttagtcac ctgggaaaag 7620
gtatctgaga ttatctctta tctcccaagt tacagtgagt ctctgaggga actgacacat 7680
tacattaagt tcttggtgta gttaaactgt aagaaaggca ggagaactta gtagttaaat 7740
agttggttaa atggaaatgc tgactccatg ttattgtaaa aagttaaaaa tttaggagga 7800
tatggggatt tcactgccat tgcaggtttt gattggtatt taccaatccg tgtgggtcag 7860
agagaaaatt agaaaggata tgactgcaca ttttggaatt attagcagtt tttctacatt 7920
taaaatggaa ataaattttt taaaaattta aatcaagtaa tactgtattt tttggtgatt 7980
tagatttttc aaaatttaca ctaagagata gtaaggaggg tggctattgt ttctttcaat 8040
aatgtctctg agaggttgta actcatctaa ggatacgtag ctaataagtg gtaggatttc 8100
aatttaaatt ctctgagacc aagttaagta gaatttgcac tgtactcttg tataactttt 8160
taaaactgaa aattagctat ctttcaaatt aagaaaatat ttactaatgg agactaattc 8220
agatttgtaa gtataccaaa atttgaactt agcctgctat ctaatggcaa cttagtggca 8280
gaggtatgat gtaaaatcat tcaggtatga cacatagatg gagtatgttt gtattcgagg 8340
ctgtgcacat aatcaccttt acttgtattg tgaagtatat attgttatct tttatgaagc 8400
ccactaaaga gataatgaaa tacctcgtta ttagggcaag attattgaaa actcaaaata 8460
gcccccaaac acaatacttg gctagaaata tataccttta tagttcagag atcatttatt 8520
atcaaaaccc tgaagttttt tttctaaggt aaaatttggt ggaagaggaa aagtctcgtt 8580
ttaaaaaaat gtaggtagtt acagagatca gaatgattag ttgatcactt accaaatata 8640
tattaagtat ctactgtata taatatgcta gtaagaataa atatagcagg aagtattttt 8700
tcccaggctc taattgtttg acatcagcat gcttttattg tggcacttat aattcagttc 8760
aagtattatg cccctctttg atggaacagt ttcctattca gtaaggaaga ccagattaat 8820
cattggattg gtttgtttca tctttagtgt tctgagctgt agagtattta tttaccaagg 8880

```
tttattttaa tttttatttt atttttattt ttccatgttc attgtagaat tcattttacc   8940
tacgaatgaa gtatgtagat tatagagaga aaatttgtaa aattaaactg atactgaaga   9000
ctggtataag aaaagcctta tgtaatttgt aagctgctat tcttctgagt ttatacatat   9060
atctttagta atcaatgagg gatggttggg tgactgccct ccaggggaca tttggcaaca   9120
tctggagatg tttttggttg ccacaacttg ggagagagt actgctactg gcatctattg    9180
agtagatgct attactttaa atggcaaagc tgcagttacc tttgcaccaa cctaatatta   9240
aacttcctgc agtgcacggg aaagccccca caacagggtt atctgacccc aaacctcaat   9300
ggtgttaaga tccaaacctt gatatgttaa cctgtagctt taaacatcct ttaaattgtc   9360
aaattcatgt ccctgacata aggtttatgt tagattttca agtataacaa agatttaaac   9420
tttaactttt gtacgttaat gatatgttag cttactccag tcttctatta aaacattctg   9480
tttttaaaat cagagacaca cagcaatttt ataaatcatt tctcttcaag gctgtgaagc   9540
tctccccact tttgtgagtg ccctctactg gtcaaattat ttgctttata acaagtaaca   9600
gtgaaatcct aagtttgtgt agtttcgctg tttaaattat gggtggcatc aatttataaa   9660
tatattcgtt ttatttaaaa gtcttatatg attgatttcg tatcattttt gctctctgct   9720
aatattaata taaagattac tgtctgtatt agttaggcct aactaagtag gtgagtatag   9780
tgaactaaga aaggaaacga ggcagtatat aagaaaatag ggtggttcag ttgttaacac   9840
ttactgagct tactttgttg aagggactaa aaggcagcag tgtggctctc tgagcttctt   9900
tgcatgcact caggagctgc ttaatggagt ccaaggcttg gtggtgtgtt acaggggatg   9960
ataggagggt cctattcaga agtggcaaat tgtgaaagtg cacattttgt agagttttat  10020
aggactgtag aatagttgtg agcacctgat ttttagaata aacagaaaac tcaggtactg  10080
tatttaggtc aaattaagaa taagtattta ttaagacctg aatataaaac tttactggtc  10140
atggtttttt tctaccttgg gtttttataa atccaaagat ttaaaaacat acaaatggaa  10200
gttggtaatg gaattaagtg aaaggaaaaa atgattttat ggtttggaat ctcctaagat  10260
tctggtttta acaatacaac taattcctta atcctagaaa tgttcttcac tgcccacttt  10320
gtaccatgca gtcttcctgt gggctagaga tacactgagg cgcaaaacag accagattcc  10380
tgccttcatg gagcttatta gttttaggta tctctagatt tcttgtaata cctattacaa  10440
tgcctgcaca tcagttcatt catgtgggtt caacgtagta ctcagtacat ggcaaattca  10500
agttttactt ttcggaactt catggatttt tttcctcaga atatctttta tccataattg  10560
gttgaatctg tagatgcagt acccatggat atggatggcc cactttattt tgaagagcag  10620
tgtttctagg caatcatgct aattatatat gacttaattt agaggcttta tacttaagag  10680
cattacattt ctggcgtctc ttaaccatta ttatttcata atgtgtaggt tatggaacag  10740
ttaaattatt gggatcttaa tatagaaatt agtagaaata agccagatat ggtggctcat  10800
gcctgtaatc ttagcacttt gggaggctga ggctattcgc tgtactattt tttactactt  10860
ttctataggt ttgaaatttt ttcaaaataa aacattgaaa aaagtaaggt aggtagtgtg  10920
tccctcctta atcctttcaa atattttatt ttcactattt ctattaattt tttttttgt   10980
ttttgagatg gagtctcgct ctgttgccca ggctggagtg cagtggcgcg atcttggctc  11040
actgcagcct ccacctcctg ggttccagcc attctcctgc ctcagcctcc tgggtagctg  11100
gtattacagg catgcaccac cacacccaat tactttttgt atttttagta gagacggggt  11160
ttcaccatgt tggccaggct agtctcgaac tcctgacctc gtgatctgcc cgcctcagca  11220
```

-continued

```
gtgtcactgc ttctagaccg ttttcaaggc acagagctta gaaatgcatg ttactaagaa  11280
atcaagagtt aactattttt caccttcttt ctcccgcagt gagaaccctg gttctaccct  11340
gtttctcctt gtgtaaattt taatgctaaa ctatacactt gtgaaataaa aatgataatg  11400
tcattcttaa attatggatc ttgcagtgtt atctaagtaa catagattga gtgatttaac  11460
tttaggtttc cttatttgtg gaatttggat aaatattttt caccccttgag aaaagtgaga  11520
ctcctttctc atcatcagag tatccttaaa ccattaaggc aaacatttgg gaaaaaactg  11580
agctatctgg ctgcataaaa attaagtttt ctttaacaaa gatagaagac aaatgaaaac  11640
ctagaaaaac catttggttc aagtaacagg aagctatctt atatatgaat tagagaaaag  11700
caaacacaca aatagaaaaa aagggatggg gggtactaaa gatataaata gcttgtctac  11760
caaaaaagaa ataaaataaa taacatgaac atataaaaag acacttactt catgaatgtg  11820
atgcaagttc aaacaataaa taacatttct gtactttcat attggctaag gttaaaatga  11880
taactgctag gaagggtatg gagaagtgtg cgccttgcac tgtagtggga gtatagaccc  11940
tcagacttta tggaggtcag tctggaaata tgtttcaaaa tgtaaactac atgtcctttg  12000
accaggtaat tcaacttctt gaaatttatc caaggattta attggataaa tgtttaagat  12060
gtatatataa gaatgtttac tgcagtgttg tttatgattt taaaaaaatg gaaatcatct  12120
tcatgtctac caatagagaa tgggtgaata aattatggta tgtccatata tacaaattac  12180
atagttgttg gaaatattag gtagatttag atatactgat gttcaaaaat gtccattatg  12240
taagtgaagc tgggtcacag caccttgtgt tgagtatgat ttcatctaga aacaaaatta  12300
ctccctcatc ctttgttgtg ttttagtttt ttaaaataag cttataccat tgggctgggg  12360
gaaaagtaaa tactcgtttt ggagagagaa aagggcacta aagtttcaga taccgttaga  12420
ttatttcatg cttatttttc aagcctcaat aaattacata attcacatgt agtcttggat  12480
taaggaaatt gctattaagg ctaaataaat aatatgagag gtatataata taaaatatga  12540
acattatatt ggcattaaga ttggatccac ggtcattcca gcctctcatt cttacctgga  12600
cttcaagtga tcacttgtgg gcaaatgcca tctgacttga acaggttaca catgtatgct  12660
cattatatcg ttattttcaa aatttgtcat ataaatttc cttgagttca ttcagatttt  12720
tgaactagtt ttttctcttg ggagtagtac acacttaatt ctctctagta ctaagctaat  12780
gttcaccatt cttataattt taagtatcca gcatttagta aagaagtctt tgttttcttt  12840
atccttactt ttagtgaatg tcttagtttt taattgaaaa ttctgccatg aaaataagct  12900
ctttaacatc ttcactccct aatcaaaaca gaaatccttc atagccttca gttgtagcta  12960
tccttccctg tgatttgtcc agctccatta tatttatttt gaaatatggt gaccagtttt  13020
gcaaaattat ttcaactgta ggtgcccagt gatttgtaa ggagaagata ctgtttctga  13080
acagttctca gtagccagtg gcctgcccct actttttggc ctgcgtgtag tatataaaat  13140
aatgcagtta actttttata gcacttttca ttttataaag agattttcat ggtctttaat  13200
attaatctat gtataaagtc ctgtatgcag ttttacctac tttcacagct gaaggaacaa  13260
tagcttagag aagatgtgag ataaagtagt ttgcccaagc ccatagcaca aataagtgaa  13320
gttcttcggc tgtccatgga tcgaagactc ccaagtctat ctctagcctg gacttctgtc  13380
ctgagcacca gacatgtatg tatatcaaga tgcctgcagg tcatatccac caggacaacc  13440
catgagtaca gggaattcaa catgcccaat atcactcatc ttttccttcg ccctcccctt  13500
tgtactcatc ccctgtcggt aagctctgtt attttaaaaa attgaaatgt attcacatag  13560
catacaattt acacttttca agtgtacatg gtttttagta tattcacaag ggttgtgcag  13620
```

-continued

```
tcattactac taattccaga atgttattat caccccaaaa gtcccacatc cattagcagc  13680
cactccccaa tcccttctcc caccagcctc taaaaactgc taatttttcc atctctgtgg  13740
atttgtccac tctgattatt tcatataaag agaatcgtac agacgtggcc ttttgtgtct  13800
ggcatcctcc acacaggatg atattttcag agttcgtcta tgtttttgct tgttgatcat  13860
tccttcattc ctttttctgg ctgaataata ctctgttata tggatatacc ttattttgtt  13920
tatctgttca tttgatgggc atttgagtga tttcctcttt ttggcaattt tgaataatgc  13980
cactataaac atttatgtac acgtttttgt gtgaccatat gttttcactt ctctcgggtg  14040
tatatctaag gtacagttgc tgggttatat ggtagctctg tctttgactt tttgaggaac  14100
tgccaagtgg ttttggtagt gattgtactg tttacattcc taccaacaat tttacctaag  14160
tatttctcaa atctatttaa tcttttcggt ccatactgct gttgctgcct tagttcagat  14220
tttgtcattt cttgtaataa ttcgtagctc atctcccagt ctctgctccc ctctctccct  14280
ccctccccct tcttctctct cttatttcca cccattttta acatttatag aagtcaaaag  14340
tctagttcag aaagcagaaa ccatactaga tatttcagca cagagaacta attaggtgtt  14400
ggaagactga aaggcaaaaa aacactgaag taacacagta acatcaagaa tgggcactac  14460
tcctaagatt cagggaatgc tgggaagatt tggggtttat cagaactgga agctcagagg  14520
aggggcccct tgtcgctgag gcttaatccc tgcagaggtg cctttggctg ctactggtga  14580
atctgagtgg gtatgatgag tcagtgtctg ggaagggcca aaacattttg tccctttcta  14640
taatttgtca tgataatgct agtaatgaat ctgatctccc ttcctatttt aaaaaccttt  14700
tagtgatttt gtataggatg aagtttaaaa ctccttactt aatatacaca tgaccctccg  14760
taagctggcc cctgcttgat tgtccagttt cacttcttgg tgcttattct aaggcctcta  14820
agccttagag atcctctaag cctttgagat ccccaaaccc tggactgcgg actggtaccc  14880
acctgtgtgg cctgtgagga actgggctgc acagccggaa ggaggtgagc attacttgcc  14940
ttagctcctg tcagatcggc agcattagat tctaatagga gcgtgaaccg tgttgtgaac  15000
tgcccatgca aggatctagg ttgcatactc cttaggagaa tctaactaat gcttgatggt  15060
ctgaggtgaa acagtttcat cctgaaatca cccccaactc ggtccttgga aaaattgtct  15120
tccacgaaac tggtccctga tgccggaaaa gttggggacc gctgttctaa gctaaagtta  15180
tatggagctc cttggttctg tgtcctcaac atgctgttct atgtttttta cattctgttt  15240
gctccttcct gcttggaatg tccttcccct ccccgtcttt cttaatgcat acaaagttga  15300
tctctcctgt gtgccaccat tgtacttcgt cttgcatatg gtgttacatt cattttattt  15360
taattattta tttacgttca tgtctcttcc actcacctta gttgcttgag gtcagaaact  15420
atataatgtg tgacacggaa tgtgacacct agattttcaa taagtgtttc tatgatacaa  15480
gggagactga tgtgggtaga tgggaatgaa ctcatcaacc tctgtttaca taccctaaat  15540
tccctgtttc ttccctatta taattctgac agtctacaac cgtctttgat ggcttataaa  15600
cggaaagtgc ggaacacatc attctacagt gaatttaaat aacctttcgg aagagtaacg  15660
taaagtactt gagcattaat tgagtaaaag tttctcatct tttcctacag gtgttattaa  15720
gcagtatgta aaaagtcctt acaatactta atacattaag aaaacataca atttcaagag  15780
gaaatccccg agtaatacat tattgacatt ttcagcagtt ctagttatat tgagaagagc  15840
atctcatgga attggcagaa tgaagatgga gattaaatga gatgatgttt gtaatatgct  15900
tatgacagta tctggcatat aagtaagggc tcagtaaatg ttgactgctg taattactat  15960
```

-continued

```
taatagtaat atgattacct ttagtaaaag ttattagttt ctttaggttt tttgtttact  16020
acaatatagt aaacaaaatc tatacttgga atgtatatat tgttttgttt tgatacatgg  16080
aatatgtctc tgtgtcagag tcactgcctg agttggaaaa cccatactcg agtatgttaa  16140
aaggtgaaca cactgaataa tttagttatt aattataatg gaaaaatgac aaacttgatg  16200
ttctggttaa tgaggttatc ttatcttgaa tgagttagct tttaaattcc tcaaaataaa  16260
ggcatttaat aaaccaggaa acacttcatt aaaaaaatta tgcaagtcag tgtaaaagaa  16320
gattaaaatt ccacatgggc aaaggacaca cgttggcgat aaatatgcag ataagaaaaa  16380
aaacctatat aacattatta ctcctcaaag aaattggtat gaaaacaata aaaatgtgta  16440
gcttatcaaa ccaacaaaaa tttaaaaata tgaaatccat tttaagtaat gataaaatgg  16500
gtgcactctt agtgctttat agaatagtag tataatgaac ctcatgtgtg taccaaccag  16560
ctctttcata tcttaacatt tagcaacatt tgatttagct ctttcttttt tccaagatag  16620
aaaagttaat attgttgaag actcctgcat tcttttccct agtcttattt tcttccctcc  16680
cataaatgtg ttaaaatctc tgtgtgtatt gttttggttg tatttttaca taaaacttta  16740
catattatat aaaatttaat tgaaggtaaa atttattaaa ttattcttaa tatatattgt  16800
aatttaaaaa ttaacagctt cattgtcttg ataaaattta tggtatctta aacatgtgct  16860
tgtttttcta agagaacatt gaaacataga ttttaaaaca aattgttgaa agattaaaaa  16920
atctgccttt gcacactgtt acattgaaag tggggcattt gtcgtgaaca ttcatttcaa  16980
atatgtagta tcttcagaat atttgagaag gatttgtatt atataattga aaaatctgtt  17040
aaattgtatt tatgttaact gcttaattct aataaaattt ccattcattt tttagtatct  17100
gcatatattt acatcaaatg gattcattca cttatttaag aggcagtact aattacctat  17160
agcgttcaag actgttaggt agagggtgtg tagtggtgag tacaacaggc gtgagcccta  17220
ccaacacgga gtttaaagcc tagtagagga tatagactta aacaatttca caagtaaata  17280
cataattaca aattataata catgctatga aggaaacata ggaggtacca gagaaggaag  17340
agtgctttgc atttttattt ttaagaccga agagtgctat tggaggactt tgagcaagtg  17400
aatgacatga tctaacctac cttcgttcat tcattcattc attcattttc ttccttcctg  17460
gctcaagcag tcctcccacc tgagctcccc aaatagctgg gactacaggt acacactacc  17520
acacctaatt tttttttgta ttttttgtat ttttgatggg attttaccat gttggccagg  17580
ctggtcttga actcttgacc tcaggtgatc cacctgtctc ggcctcccaa ggtgttggga  17640
ttataggtgc ctagcccatg gtgcctagcc ctaacctaca tttataaact atcacttgct  17700
gctgtgtgga gactatattg tgagattaac agcagggata cctgctagga agcaattgct  17760
gcagattgcc tgagacaaaa tagttatcat ggactagggg gatggtggtg gtggtggtgg  17820
taggtggttg gatgtaggat atattttgaa gataggtaaa tggtgcaaga ttatgggtca  17880
gttttaaatg cttaagtaaa ttttctttgt aagacatttt aggatgccat gttaagaatc  17940
tctttataac tgtcatttaa aaaaaaacca catattttct tagcataatt tcccatagta  18000
acattactat gtcaaaggct atgaacattt gaatgacttt agataaatac tgtaattgct  18060
ttccaaaaat attgtgctta ttatgtcacc agaaatgttt gaattctgtc tacaattcag  18120
tcttgccagt atagtacatt tcatttagaa aaatttttta ctatgtagat ggaaaaaata  18180
atattttagc tgggagtggg gggactatgg ggaataactt tccttcattt aatattttat  18240
tgtgagttag tttaagttac tttattttat cgtagtttcc taaggctaca aattagtaac  18300
cttggtaact tatgtaccta atttaaaagt ttactttttt gaaaggctgg aaatactaat  18360
```

taaaaacgta acaccttcat ccttgtcttt gctccattat taactagttt cattacagaa 18420
tctctgtgtt ttaaaatcag atgggttttc ataaccagta ctttctcaga gtggtaaatt 18480
taaaaaaata tataaagaga ataaataata tttgttgaga atacttcaaa taatgtgaag 18540
agttattaac ttacagcagg agttggcaaa cttttctata aagggccata tgggtctttg 18600
tcacaaagtc ttgggttttt gtttttgttt ttttaaacag ctatttaact attcctagct 18660
aatgggcaat acaaaaacag tgggcaagat ttggcctgtg ggcagtagct tgctgaaacc 18720
ttatttagac tctaaatttt ttgaaagagt ctacattgat gcatattttt ttttcttcct 18780
ccaaatacag ttgacccttg aacaacatgc gtttgagtga ccatgggtcc acttgtgata 18840
cacgtttttt tcccaaccaa atgcagatat ggagggctga cttttcatat acctggatgt 18900
tcctgggcca actgtaggac tagaggctgg gggggtcttg gaaccaatgc cgtgtgtata 18960
ccagggatga ctgtttctta tggcctgacc tgaagttgga acagaatctt tattaatata 19020
taatttttgt tgcgtttgtt ttctctttat atttatccat tctttttaga tcgtatttca 19080
tttaacactt tttcttcttt agtttttacc aagttgcact gaaaatagct cagtgactaa 19140
ttgcacttct aagagtgagg accctagtta aaattaactc taaaaatact gaatttttaa 19200
cctaaacctt ttatttctaa tcaacagtat tatttatgag taggttatag attactttga 19260
aacggaatgt gtctcagaac tttgctatcg atatttttaa ggtctggtag ggaaaagata 19320
ataggaatga gatttatcag tgaatagggg actgctttcc cagtttctcg gtcgcactgg 19380
tgtattcacc atggaagcat cttatgaaat atgtacataa actactaata tcccacatta 19440
caggttgact attctttatc tgaaatgctt aggacctaga agtatttttg gattttggtt 19500
tttcagagta gggatactca gcctacattg gtaagtaaag aatgtgaggt gacaggctgg 19560
gcgcgatggt tgacgcctgt aatcccagca ctttgggagg ccgaggcgga tcacctgagg 19620
tcaggagttg aagaccagcc tggccaatct gtactaaaaa tacaaaaatt agctggacac 19680
agtggcacgt gccagtagtc ccagctactc aggaggctga ggtaggagaa tcgcttgaac 19740
ctgggaggcg gaggttgcag tgactcgaga tcgtgtcact gccctccagc ctaggcaaca 19800
gagcaagact ccatctcaaa aaaaaaaaaa aaaaaaaaaa aaaagaatgt gaggtggcag 19860
caataggtag gaagagtctt tggtcagctt tacatgctct gtagccatgc ctgggtaatg 19920
ggttgactct aagactctgt gctttgctcc cacctcctgc tttttcatta ctctttagaa 19980
tggtttttaa tttgtgatct ataggagttc tttcaagtat ttaataagag aataggctaa 20040
attaagtaaa tgtcaactga atgctcaaat ctctactaaa gagcctctta tttagaaaat 20100
aaatatccat cttttttttc tgactggtga gataattaat ttttattaca gatggtttgg 20160
aaaataccat atgctttaaa agataagcac aaaattatag tctaatatgt aggttttcat 20220
actttaaaaa attgaaaacc aaagaaaaac atttaacata gcatctagta caaagaaaag 20280
agataagcaa gagataaatg tctttttttgg gacagagttt tgctgttgtt gcccaggctg 20340
gagtgcaatg gcacaatctc agctcaccgt aacctccacc tcccgggttc aagtgattct 20400
cctgcctcag cctcccgagt agctgggatt acagtcatgc accaccaggc ccaggtaatt 20460
ttgtatgttt agtagagatg gggtttctcc gtgttggtca ggctgatctc aaactcccga 20520
cctcaggtga tctgcccacc ttggcctccc aaagtgctgg gattacagac atgagccatc 20580
gcacccggcc aagataaatg tcttttaaat tatctccatt aaagacataa cctttataac 20640
attttgatgt atatattacc agtttttaaa cacatagtag atttgtataa atacataaac 20700

-continued

```
acatattatt gtgatcatgc tgcacttaga catctttata ttctccttat actgtaaaca  20760
ttttgaaata ctttactaac aacatttgta atgaccattc tttctctctt tctccctctg  20820
atagaatggt ctacagagta attcataaac taaacatact ttagaggctg ggcgcagtgg  20880
ctcatgcctg taatcccagc actttgagag gctgaggcgt gcagatcacg aggtcaggag  20940
ttagagacca gcctgactaa catggtgaaa ccccatctct actaaaaaaa cagtacaaaa  21000
attagccggg cgtggtggcg tgcacctaga atcccagcta ctcaagaggc tgaggcagga  21060
gaatcactcg agcccaggag gcagaggttg tagtgagccg agattgcacc acagcactcc  21120
agcctgggcg acagagcgag actccatctc aaaaaaaaaa aaaaaagata cattaatact  21180
atagcctaca tgtggaacat taagaaaata attgctttta tgtttatgct ttatacctgt  21240
tgttagccct gcttcttatt tcatgatttc atggcttcac attgtaacat ccctttacca  21300
tatttttgga ggactgtttt ggcagaatgt gtgaaatctt gagcagaagt attacccaaa  21360
agtcagaaga aaatcagatt tttatttcaa gattctgtta aagttaccca ctcccttctt  21420
ttacttaatc ttatagttgc agttctctct ctttttagaa aagaaaaaag aggcccctca  21480
ggatttgcag atgaaacaat attgctcttt agagatatcc atctggctgt tagattattt  21540
ttccacagtt ttcagaagtg gatgaggcca ttagaatctt gagtattgcc catttcctta  21600
tgtgtgcctt tgactataga taaaatagat gcatgacaat tatttataag ttgattgatt  21660
tttcttgtca tttaaatcat cttgaataat agagttggta gagctatccc atttttgaaa  21720
ttattttgtt ttgtcaataa ctttttgtta ccagcatgta cacttgcatt gttgactctc  21780
catataatac ctttaaaaaa tttttttttg tggtaaaata tgcataacat aaagtttacc  21840
atggtagttt tctttcattt gttttgtttt tgtttttttg agacggagcc ttgctctgtt  21900
gccaggctgg agtgcagtgg agcgatcttg gctcactgca acctccgcct cccgggttca  21960
agcaattccc ctgcctcagc ctcctgagta gctgggacta caggcgcccg ccaccacgcc  22020
cggctaatat tttgtatttt aatagagatg gggtttcacc atgttggcca ggatgttctt  22080
gatctcctga cctcatgatc cgcccacctc ggcctcccaa agtgttggga ttgcaagtgt  22140
gagccaccgc gcctagacca tggtagttaa ttttaagtgt tcaattcagt gaccttaagt  22200
gtgttcataa tgttgtgcaa ccatcaccat gttgtctaac cattagcact atctgttttg  22260
agaacttttt tttatcatcc caaattagaa ttctgtacct gtcaaatagt ccccagtaat  22320
cctccctccc ccagcccctg gtaatctgta gtctactttt cgtctttttg aatttgccta  22380
ttttaggttc ctcatataag tggaattatg tggtatttgt ccttttgtgt tggcttactt  22440
catttagcat aatgttttca aggttcatct gtgttgtagc atgtatatac aggttgaagc  22500
atccgttatc caaaatggtt gtgaccagaa gtggtttgga tttcagattt tttttttgga  22560
ttttggaata ttcatagata cttaactggt tcagcatccc tcgtccaaaa atccaaaatc  22620
agatggagct cagtggctca tgcttgtaat cccaacacgt tgggtggcca aggcaggagg  22680
atcgcttgag cccaggagtt caaccagcct gagcaacaca agaccctatc tctccaaaaa  22740
aaaaaaaaaa aaaaaaaaga tgaaagaaaa aaaaatccaa aatcaaatgc tccagtgagc  22800
atttcctttt agcatcatgt caggctctaa aagttacagg ttttggagca ttttggattt  22860
cagatttttg gattaacctg cattaatgct caacctatat gaaattttat tcctttttat  22920
ggctgaataa tgttccactg tatgtatata ctacattttg tttatccatt catctgttaa  22980
cagacactta agttatttcc acattttggg tattataaat agtgctgctg cgaacattgg  23040
tgtacatgta tctgtttgag tccctgtttt tagttatttt ggttatatac ctaggaatgg  23100
```

aattgctgat catatggtaa ttctgtgttt aactttttga ggaactacca ctgttttcca 23160
caatggcatc accattttac attcccacca gcaatgcaca aagatttcag tgtctgtatc 23220
cttgctaaca cttattttcc attttttgag ttttttgtt ttgttttttt aataatagcc 23280
aatcctaatg ggtatgtggt agcatctcat ggttttgatt ttattttcct gactattgat 23340
gatgttgagc atcttttcag gtgcttagtg gccatttgtc cgtcatcttt ggagcaggaa 23400
caatgtcttt tcaagtcctt tgcccatttt taaattgaat tttttgttgt tgagttgtat 23460
ataacacctt ttttgaagta aaaggtgcac tgtaataatc cagactgtgt ttctcccttc 23520
tcaggattcc tacaggaagc aagtagtaat tgatggagaa acctgtctct tggatattct 23580
cgacacagca ggtcaagagg agtacagtgc aatgagggac cagtacatga ggactgggga 23640
gggctttctt tgtgtatttg ccataaataa tactaaatca tttgaagata ttcaccatta 23700
taggtgggtt taaattgaat ataataagct gacattaagg agtaattata gtttttattt 23760
tttgagtctt tgctaatgcc atgcatataa tatttaataa aaatttttaa ataatgttta 23820
tgaggtaggt aatatccctg ttttataaat gaagttcttg ggggattaga gcagtggagt 23880
aacttgctcc agactgcatc ggtagtggtg gtgctgggat tgaaacctag gcctgtttga 23940
ctccacagcc ttctgtactc ttgactattc tacaaaagca agactttaaa ctttttagat 24000
acatcattaa aaaagaaaac cataaaaaag aatatgaaaa gatgatttga gatggtgtca 24060
ctttaacagt cttaaaagca atcgtgtgta tagcatagaa ttgcttggat tggataaaca 24120
gtggcattat atattttaaa aaataaaagt tttgaaagat tgaagaattt gggcattaca 24180
gttctcttaa atctgacaaa gctgcataaa actattaaaa taatcattat tatactattt 24240
tatattctat ttctttgagg gtttagtttt ccaaaaacta catattaagc aaatgaatca 24300
ctcagtggct atgtcatata ataacgagtt agcctagtta taagaagttt aacattttat 24360
ttaagaacat tgttacagca tgtttactgt atagtctagt aatagaggaa aagacatttg 24420
ggtgggtggt agtggtagta tttttataga ggagttacca aatttcagct ctattatcca 24480
agtttaccca gctaatggtg ttcggaaccg ggaatttgag ccaattctga ctctgttgtc 24540
tgctctgctc cttcttttgt gctgtgtctt tgaaagtcac ctaaaattgt gagggaatgt 24600
aatttcaccc caaatttaga gtttatgcac ttgttatatt gaaaatgatt aacatgtaga 24660
agggctttta atggaataag tggtgtagta acttcagtgt tgcctaccta gaaatcaaaa 24720
tctttctagt tgtccacttt gttttttgaa aaagtaatat gaaaattatg ttaatgcttt 24780
aattcaggtt tttgtaaaat attttttatc tttacacatt taacatacgt ttctaaaatt 24840
atagtctgtt atatagcact ttgggtctag aatttttcag tagtttctgt tttactatta 24900
tgatctacct gcatattaac ctattaggtt atagttttac tatacttcta ggtatttgat 24960
cttttgagag agatacaagg tttctgttta aaaaggtaaa gaaacaaaat aactagtaga 25020
agaaggaagg aaaatttggt gtagtggaaa ctaggaatta cattgttttc tttcagccaa 25080
attttatgac aaaagttgtg gacaggtttt gaaagatatt tgtgttacta atgactgtgc 25140
tataactttt ttttctttcc cagagaacaa attaaaagag ttaaggactc tgaagatgta 25200
cctatggtcc tagtaggaaa taaatgtgat ttgccttcta gaacagtaga cacaaaacag 25260
gctcaggact tagcaagaag ttatggaatt ccttttattg aaacatcagc aaagacaaga 25320
caggtaagta acactgaaat aaatacagat ctgttttctg caaaatcata actgttatgt 25380
catttaatat atcagttttt ctctcaatta tgctatacta ggaaataaaa caatatttag 25440

```
taaatgtttt tgtctcttga gagggcattg cttcttaatc cagtgtccat ggtactgctt  25500
ttggctttgg tttctttcta cattgaaaat ttctcttcaa ttctgagcac atgttaacat  25560
ttagaattca agaggtgggg attttttttt cccatggtta catatatata tatatatata  25620
tatatatata tatatatata tatatatata aagaacaggg caacaaattt ttgcgttttc  25680
tatttcggta gtacttttaa accattatgt catgtttcta ggttaaacgt tgttgtattt  25740
gaagaatttt actttggcag aatttttttg aggatgtgtt tatttctgga gaaaggtctc  25800
attaaagaaa gacaataccc agaaagccaa cagaaattct gttactcatt taatgcattt  25860
ttctgacaaa aattattgcc agagagaacc tgaattttgt ttcaaaaatc atctttgttt  25920
taaaaatgac tttttcttca ggtaaaataa aataatttca gttgctatta tttaacctgt  25980
ttgtatgaag agtttaacat ataggaaatg aatacataaa gataggaagg aattaattgt  26040
tatatgtagt catatgtctc ttaatgacag ggatactttc taagaaatac attgttaggt  26100
gattttgtca ttgtgcaaac atcatagaat atacttacac aaaccttggt agtataacct  26160
actatacacc tgggatatgt agtatagtct cttgccccag ggatacaaac ctgtacagta  26220
tgtaactgta ctaatgacta taaggcaatt gttaacacaa tggtaagttt tgtgtgtcta  26280
aacctacact tgggctaccc taagtttata tattttttta aatttctgtt caataataaa  26340
ttaaccttac tttactgtaa ctttttaaac tttttaattt ttcctaacat tttgactttt  26400
gtaatacagc ttaaaacaca cattatacag ctatacaaat ttttctttcc ttatatcttt  26460
attctgtaag ctttttttcca tatttaaaat tttttgtttg tttttactta ttaaactttt  26520
ttgttaaaaa ctaagacatg catgcacatt aacctaggcc tacacagggt caggaccatc  26580
aatatcattg tcttccactt ccacatcttg tcccactgga agatcttcag gggcagtaac  26640
acacgtggag ctgtcatctc ctataataac attgccttct tttggaatac ctcctgaagg  26700
acctatccaa ggctgtttat agttaacttt tttttttttt tttttttttt tttagtaaat  26760
aggaggagta cactataaaa taacaatata ggtgctatac cattatacaa ctgacagtgc  26820
agtaggtttg tttacaccag catcaccaca aacacgtgag caatgtgtcg tactacagtg  26880
ttaggatggc tataacatca ctaagcaata ggaactttta aactccatta taatcttatg  26940
ggaccactat cacatatgca atctcctgtg gaccaaaatg tcattatgtg gtacatgact  27000
gtactaagaa attgatccat ctatattcca tcaatttgtt tagggctttt tctggttaca  27060
tttacctgtg agcccagaaa accagttttg tagaaattaa cttctgtaat gctaggagtt  27120
aaaaaaaatt gctgaacaac ttttacattg ttaaacattt aaaaacaagc gttctagaag  27180
tttatcaaat ttcataaagg tgcaaaaatg taaatgtaaa tcattatcca gctaatatat  27240
atgttgtatt tccctagtag gagagcatat gtacctcttc ctagttatac aaatttgata  27300
tatagtaaag aaacagtaaa ttctacttca agtcattttg ggaggattaa aaactgaatt  27360
tctctagttt gaccattgta cagatttatc tggcaatttt actaaaacct gatttatagg  27420
ttaaacttgg tgtatatcat atatcacttt actttagagg aattaagatt tcacataaat  27480
ccatttccag gttccaaaga ccaggaagag gcttggtttt tgtttttctt tttactgtct  27540
ttacagtctc cttgactttt cttaggagag aaggtactga gaaaacatga ttctaatatt  27600
tattattttt tcttccaaca ttttcttatg aaacattttc aaatacaaaa ttgagtttta  27660
tttaaaacat ttgcaaatat actacctaga ttctaccatt gttgttttat atttgcttta  27720
cttacaactt ttaaaagatg ctttttatac cactgaacat tttagcttac atttcacaaa  27780
gaaaagaaaa aatttaagag actttgcata atgttttaag ggttgcagt aaagaagtgc  27840
```

ttcttatatt ttcttatgca tacaaatcag ctgggcttat taaaatccag attctaattc 27900
agaaggttta ggtggggacc gagtctgcat ttctaacaaa ctcctaggtg gtatttttct 27960
tggtacttgg accatacttt gagtagaaaa gcagtagagg acataaaaag agtcttgtta 28020
gtcccacttt gttgctgtcc acttctcatt tgataatatc ctaaaatagc tgtgtctcct 28080
ttttggtggt tgtatgatta ctacctcaga agtactaatt gattcttgct atttgacctt 28140
aatactttaa tataacacag cattcatatt tgatcagaaa actatctggc ttccttttat 28200
aagagatttt taggttttat acagttttgt ggccttgggt ttttttgttt gatttgtttt 28260
tttgaaggta tataatatgt aagtagataa acaaatttga tttgtagaca tttttatgtg 28320
gatcatctaa ttaaaaatgg agggatacag tatgaaagaa tacttgtact tcttaacaga 28380
gcactcaacc tttcttttac atcctgtttc actgatgtta ttatgtaatt tatgttgcta 28440
aactataaat tagatattta atttctgttc tttgatttcc ttttattatt aaatggactt 28500
gttgatttgc ctagaaatta atttgccttt caaaagtctt attaatcttc ctccgttgaa 28560
attaatttga tatttgcatg cttctggaag actttaaaga gctattccga gtaactgtag 28620
agattataaa atgaaatatg ggaattttaa taaattttac atctccagtt actggtgaaa 28680
atgtcaagtc ctcctttctg cagagtattt tgttactcat ctgttattca gcttatttat 28740
ttatttattt atttatttat ttttctttct ttcttgtttt tttttttga gacggagtct 28800
tgctttgtcg cccaggctgg agtacagtgg tgggatcttg gctcactgca ggctccgcct 28860
cccgggttca caccattctt ctgcctcagc ctcccaagta gctgggacta caggcacccg 28920
ccaccatgcc ttgctaaatt tttgtatttt tagtagagac gggtttcact gtgttagcca 28980
ggatggtctc gatctcttga cctcgtgatc cacctgcctc ggcctcccaa agtgctggga 29040
ttacaggcat gagccaccgc gcctggccct tatttgtttt ttaaacaaaa ttagtgtgca 29100
tatccttgtt gtattttatc ggcaagttgt tttatgccct aactttggg gtcttgatca 29160
tgagcctaaa acacgtaaac acccaaaaag aattatattc cggttaaagg aacaaaacat 29220
tcatttagaa gttctcatcc atgtaaatca gaggctggca aatattttct gtaaagggcc 29280
aagatagtaa atgttttagg ctttgagggc cacaagtggt atctgttgca ttttttttta 29340
attatgaccc tttaaaatgc aaaaatcgtt gttagcttgt gcatagtata aaaataggct 29400
ggccgcatgc tgtggctcat gcctgtaatc ccagaaatga ggtgggaagc cgaggtgggc 29460
acaccacctg aggtcaggag ttcgaggcca gcctggccaa cgtggttgaa accccgtctc 29520
tactaaaaat acaaaactta gccaggcgtg gtggcgggtg cctgttatcc tggctactca 29580
aggggctgag gcagtagaat tgcttgaacc tgagaggcag aggctgtagt gagcccagat 29640
caagccagtg cacaccagcc tggacgaccg agcgagactc tgtctcaaaa aaaaaaaaaa 29700
aaggctgtgg ctgcatttgg tccattggct gtaatatgct gattcctaat tctctgggta 29760
actttagtgt ttgattagct actagaagtt aggttaaact tttgtatttt acaggctaac 29820
tttaataatc ttaaagtaaa acttaacata gttcatggaa aggaaataga aattttaccc 29880
tagtactctt tttttttttt tttttttttt ttgaggcaga gtctccctct gtcacccagg 29940
ctggagtgca gtggtgggat cttggctgat tgcaacctcc tcctcctggg ttcaagcaat 30000
tcttgtgcct cagcctcccg agcagctggg actacaggca cgcaccacca cacctgactg 30060
atttttgtat ttttagtaga gacagggttt cgccatgttg gccaggctgg tcttgaactc 30120
ctggcatcaa gtgatcctcc catctgagcc tcccagtgtg ctgggattac agacgtgagt 30180
cactgtgcct ggtctctagt attttttttt tttttgagac ggtctcactg ttgccaggct 30240
ggagtgcagt ggcgcgatcc tggctcactg caacctccgc ttcccggatt caagcgattt 30300
tcctgcctca gcctcctgag tagctgggac tatgggtgca caccaccacg cccagctaat 30360
ttttgtattt ttagtagaga cggggtttca ccatgttggc caatatggtc tcaatctctt 30420
gacctcgtga tctgcccgtc tcggcctccc aaagtgctgg gattacaggc gtgagccact 30480
gtgcccagct gtacttttta agataagaat tgcagggtat atatttttac caacttaata 30540
acttataatt ttaaaaagct aattacttgg ctagaatata atgcgttaca tattctttac 30600
actcagttca gtccatatct gaaaggcaaa tagaattatt ttctgctagt acattgtgta 30660
gtccctatgt tcctagtgta taaggactgt tacctagttc acatttatct gggttgttga 30720
cagattttcc tggtcccttt ggacagtgca tggccatgtt ggcaaaagct gtcaaaattg 30780
aaacattgac accatgagaa ttgtgtgttt tccagtctgc taaaatcaaa agtgggaggg 30840
ttcagtaagg tgaataacag aagcagagtt ttcggggtat ctgttactcc tcattcggct 30900
tttctgctct ctgggggtct caatttaaat ataatgtgaa aattagtttt acgaacctaa 30960
aaatgttgag tgattcattt cctggttttg ttgttaattt ctagatattt aaattaattg 31020
ttagaagaac cccgttaaag aatgctttgc aaaacaacct ccttatgtgc tatgtctctg 31080
tttaatagta gttgagtttg tgtacatgag atcaatattt tgaactatag ctttttatga 31140
gttaaaaatt gacggaacag ttactgtgca cttgctgtgc accatggtag tctcccaagt 31200
agtggttttt ctgcatttca atagtacatg agataggctg tgggtggcaa ggtttcttga 31260
gaaagtgagg gatgcacagt tgggttttag aatacatctt gttcctccat gcccttcccc 31320
accaaaaggc tggtagtctt gcatttgtat atagttaggg tatttgatgt gttgcttcct 31380
tgacagagtt ttgcaagaat ttgcagattt aacaggaaca aaaacttact taaaacaaaa 31440
tctcttagta aaagcatagt ctagcaagat ttagaatgat actttggcta acagtacttt 31500
ctctatatgg agtgctttgt ttccatagcc tcacaagtat gttttcagat aatagttgag 31560
ttgaaaatgt tgtcaatctc ttgattttaa aaaatttaca tatttaaagt tgtatacttt 31620
tgttcctacg tattttcagt tgttcttaaa gtttaataag tgacatttga aaatgagtat 31680
atgtgtataa aaacaaaagt aggctaggca cggtggctca tgcctataat cctagcactt 31740
tgggaggctg aggcaggcgg atcacaaggt caggagtttg agaccagcct gggcaatatg 31800
gtgaaacccc cctctactaa aaatacaaaa attagctggg tgtggtggtg catgcctgta 31860
gtcccagcta ctcaggaggc tgaggcagga gaatcgcttg aacccggagg tggcggttgc 31920
agtgagccga gattgcacca ctgcagtcca gcctgggcgg cagagcgaga ctccatctca 31980
aaaaaaaaaa acaaaaaaag aaaaagttaa aaaaaaacaa aaaaccccca caaaatgagt 32040
atatgtggca acaagtccta ttctcaaaaa aattattgtg tgctagttaa gagcttaatg 32100
agtagccagt cggtattaaa tatctgtttc agctatattt tatctttaaa aattatctac 32160
agattttgga atgtgaaaaa ctagtgtttt gtttcatagg tatatactgt aggcatttta 32220
aaaataagag ccagtgccag tggtttacag tgtacacaag gataatgttc tcatgttctc 32280
ttgatgtcag tatgacttta aagcatatta tcaagaaata actaagtctg aaaaactgtg 32340
gtaaataact ggtactctaa aacctaagtt tcttattact aaaaataaga aatggtaaaa 32400
gtcaccctgt gctgttaatt atatgagcca ctgaggtcct gacactgaat tcttggtggt 32460
ggataataat ctcttctttt taattattgg cttccaattc tctctgcatt gctggaaaca 32520
aaaatcatat atttcactat tggtggtggg gatgctgtca ctgaaaaagt agacacattc 32580
atattgattt tagaaataag ttaaaatcaa aatttgcttc tgctaaatta gtagaggacc 32640
aatactgttt ttctccttca tagtatgttt tggtacttct acattgacat tataactttt 32700 tttttttaa acagaaatag aagtttacat 32730

<210> SEQ ID NO 8
<211> LENGTH: 188
<212> TYPE: PRT
<213> ORGANISM: Artificial Sequence
<220> FEATURE:
<223> OTHER INFORMATION: KRAS G12D protein Isoform B

<400> SEQUENCE: 8

Met Thr Glu Tyr Lys Leu Val Val Val Gly Ala Asp Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

Gln Ala Gln Asp Leu Ala Arg Ser Tyr Gly Ile Pro Phe Ile Glu Thr
130 135 140

Ser Ala Lys Thr Arg Gln Gly Val Asp Asp Ala Phe Tyr Thr Leu Val
145 150 155 160

Arg Glu Ile Arg Lys His Lys Glu Lys Met Ser Lys Asp Gly Lys Lys
165 170 175

Lys Lys Lys Lys Ser Lys Thr Lys Cys Val Ile Met
180 185

<210> SEQ ID NO 9
<211> LENGTH: 5306
<212> TYPE: DNA
<213> ORGANISM: Artificial Sequence
<220> FEATURE:
<223> OTHER INFORMATION: KRAS G12D mRNA

<400> SEQUENCE: 9
ctaggcggcg gccgcggcgg cggaggcagc agcggcggcg gcagtggcgg cggcgaaggt 60
ggcggcggct cggccagtac tcccggcccc cgccatttcg gactgggagc gagcgcggcg 120
caggcactga aggcggcggc ggggccagag gctcagcggc tcccaggtgc gggagagagg 180
cctgctgaaa atgactgaat ataaacttgt ggtagttgga gctgatggcg taggcaagag 240
tgccttgacg atacagctaa ttcagaatca ttttgtggac gaatatgatc caacaataga 300
ggattcctac aggaagcaag tagtaattga tggagaaacc tgtctcttgg atattctcga 360
cacagcaggt caagaggagt acagtgcaat gagggaccag tacatgagga ctggggaggg 420
ctttctttgt gtatttgcca taaataatac taaatcattt gaagatattc accattatag 480

-continued

```
agaacaaatt aaaagagtta aggactctga agatgtacct atggtcctag taggaaataa    540
atgtgatttg ccttctagaa cagtagacac aaaacaggct caggacttag caagaagtta    600
tggaattcct tttattgaaa catcagcaaa gacaagacag ggtgttgatg atgccttcta    660
tacattagtt cgagaaattc gaaaacataa agaaaagatg agcaaagatg gtaaaaagaa    720
gaaaaagaag tcaaagacaa agtgtgtaat tatgtaaata caatttgtac tttttttctta    780
aggcatacta gtacaagtgg taatttttgt acattacact aaattattag catttgtttt    840
agcattacct aatttttttc ctgctccatg cagactgtta gcttttacct taaatgctta    900
ttttaaaatg acagtggaag tttttttttc ctctaagtgc cagtattccc agagttttgg    960
tttttgaact agcaatgcct gtgaaaaaga aactgaatac ctaagatttc tgtcttgggg   1020
cttttggtgc atgcagttga ttacttctta tttttcttac caattgtgaa tgttggtgtg   1080
aaacaaatta atgaagcttt tgaatcatcc ctattctgtg ttttatctag tcacataaat   1140
ggattaatta ctaatttcag ttgagacctt ctaattggtt tttactgaaa cattgaggga   1200
acacaaattt atgggcttcc tgatgatgat tcttctaggc atcatgtcct atagtttgtc   1260
atccctgatg aatgtaaagt tacactgttc acaaaggttt tgtctccttt ccactgctat   1320
tagtcatggt cactctcccc aaaatattat atttttttcta taaaaagaaa aaaatggaaa   1380
aaaattacaa ggcaatggaa actattataa ggccatttcc ttttcacatt agataaatta   1440
ctataaagac tcctaatagc ttttcctgtt aaggcagacc cagtatgaaa tggggattat   1500
tatagcaacc attttggggc tatatttaca tgctactaaa tttttataat aattgaaaag   1560
attttaacaa gtataaaaaa ttctcatagg aattaaatgt agtctccctg tgtcagactg   1620
ctctttcata gtataacttt aaatcttttc ttcaacttga gtctttgaag atagttttaa   1680
ttctgcttgt gacattaaaa gattatttgg gccagttata gcttattagg tgttgaagag   1740
accaaggttg caaggccagg ccctgtgtga acctttgagc tttcatagag agtttcacag   1800
catggactgt gtccccacgg tcatccagtg ttgtcatgca ttggttagtc aaaatgggga   1860
gggactaggg cagtttggat agctcaacaa gatacaatct cactctgtgg tggtcctgct   1920
gacaaatcaa gagcattgct tttgtttctt aagaaaacaa actctttttt aaaaattact   1980
tttaaatatt aactcaaaag ttgagatttt ggggtggtgg tgtgccaaga cattaatttt   2040
ttttttaaac aatgaagtga aaaagtttta caatctctag gtttggctag ttctcttaac   2100
actggttaaa ttaacattgc ataaacactt ttcaagtctg atccatattt aataatgctt   2160
taaaataaaa ataaaaacaa tccttttgat aaatttaaaa tgttacttat tttaaaataa   2220
atgaagtgag atggcatggt gaggtgaaag tatcactgga ctaggaagaa ggtgacttag   2280
gttctagata ggtgtctttt aggactctga ttttgaggac atcacttact atccatttct   2340
tcatgttaaa agaagtcatc tcaaactctt agtttttttt ttttacaact atgtaattta   2400
tattccattt acataaggat acacttattt gtcaagctca gcacaatctg taaattttta   2460
acctatgtta caccatcttc agtgccagtc ttgggcaaaa ttgtgcaaga ggtgaagttt   2520
atatttgaat atccattctc gttttaggac tcttcttcca tattagtgtc atcttgcctc   2580
cctaccttcc acatgcccca tgacttgatg cagttttaat acttgtaatt cccctaacca   2640
taagatttac tgctgctgtg gatatctcca tgaagttttc ccactgagtc acatcagaaa   2700
tgccctacat cttatttcct cagggctcaa gagaatctga cagataccat aaagggattt   2760
gacctaatca ctaattttca ggtggtggct gatgctttga acatctcttt gctgcccaat   2820
ccattagcga cagtaggatt tttcaaacct ggtatgaata gacagaaccc tatccagtgg   2880
```

-continued

```
aaggagaatt taataaagat agtgctgaaa gaattcctta ggtaatctat aactaggact   2940
actcctggta acagtaatac attccattgt tttagtaacc agaaatcttc atgcaatgaa   3000
aaatacttta attcatgaag cttacttttt ttttttggtg tcagagtctc gctcttgtca   3060
cccaggctgg aatgcagtgg cgccatctca gctcactgca acctccatct cccaggttca   3120
agcgattctc gtgcctcggc ctcctgagta gctgggatta caggcgtgtg ccactacact   3180
caactaattt ttgtattttt aggagagacg gggtttcacc ctgttggcca ggctggtctc   3240
gaactcctga cctcaagtga ttcacccacc ttggcctcat aaacctgttt tgcagaactc   3300
atttattcag caaatattta ttgagtgcct accagatgcc agtcaccaca caaggcactg   3360
ggtatatggt atccccaaac aagagacata atcccggtcc ttaggtagtg ctagtgtggt   3420
ctgtaatatc ttactaaggc ctttggtata cgacccagag ataacacgat gcgtatttta   3480
gttttgcaaa gaaggggttt ggtctctgtg ccagctctat aattgttttg ctacgattcc   3540
actgaaactc ttcgatcaag ctactttatg taaatcactt cattgtttta aaggaataaa   3600
cttgattata ttgttttttt atttggcata actgtgattc ttttaggaca attactgtac   3660
acattaaggt gtatgtcaga tattcatatt gacccaaatg tgtaatattc cagttttctc   3720
tgcataagta attaaaatat acttaaaaat taatagtttt atctgggtac aaataaacag   3780
gtgcctgaac tagttcacag acaaggaaac ttctatgtaa aaatcactat gatttctgaa   3840
ttgctatgtg aaactacaga tctttggaac actgtttagg tagggtgtta agacttacac   3900
agtacctcgt ttctacacag agaaagaaat ggccatactt caggaactgc agtgcttatg   3960
aggggatatt taggcctctt gaatttttga tgtagatggg cattttttta aggtagtggt   4020
taattacctt tatgtgaact ttgaatggtt taacaaaaga tttgtttttg tagagatttt   4080
aaagggggag aattctagaa ataaatgtta cctaattatt acagccttaa agacaaaaat   4140
ccttgttgaa gttttttttaa aaaaagctaa attacataga cttaggcatt aacatgtttg   4200
tggaagaata tagcagacgt atattgtatc atttgagtga atgttcccaa gtaggcattc   4260
taggctctat ttaactgagt cacactgcat aggaatttag aacctaactt ttataggtta   4320
tcaaaactgt tgtcaccatt gcacaatttt gtcctaatat atacatagaa actttgtggg   4380
gcatgttaag ttacagtttg cacaagttca tctcatttgt attccattga tttttttttt   4440
cttctaaaca ttttttcttc aaacagtata taactttttt taggggattt ttttttagac   4500
agcaaaaact atctgaagat ttccatttgt caaaaagtaa tgatttcttg ataattgtgt   4560
agtaatgttt tttagaaccc agcagttacc ttaaagctga atttatattt agtaacttct   4620
gtgttaatac tggatagcat gaattctgca ttgagaaact gaatagctgt cataaaatga   4680
aactttcttt ctaaagaaag atactcacat gagttcttga agaatagtca taactagatt   4740
aagatctgtg ttttagttta atagtttgaa gtgcctgttt gggataatga taggtaattt   4800
agatgaattt aggggaaaaa aaagttatct gcagatatgt tgagggccca tctctccccc   4860
cacaccccca cagagctaac tgggttacag tgttttatcc gaaagtttcc aattccactg   4920
tcttgtgttt tcatgttgaa aatacttttg catttttcct ttgagtgcca atttcttact   4980
agtactattt cttaatgtaa catgtttacc tggaatgtat tttaactatt tttgtatagt   5040
gtaaactgaa acatgcacat tttgtacatt gtgctttctt ttgtgggaca tatgcagtgt   5100
gatccagttg ttttccatca tttggttgcg ctgacctagg aatgttggtc atatcaaaca   5160
ttaaaaatga ccactctttt aattgaaatt aactttttaaa tgtttatagg agtatgtgct   5220
```

```
gtgaagtgat ctaaaatttg taatattttt gtcatgaact gtactactcc taattattgt   5280

aatgtaataa aaatagttac agtgac                                        5306


<210> SEQ ID NO 10
<211> LENGTH: 189
<212> TYPE: PRT
<213> ORGANISM: Artificial Sequence
<220> FEATURE:
<223> OTHER INFORMATION: KRAS G12D protein Isoform A

<400> SEQUENCE: 10

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 11
<211> LENGTH: 32729
<212> TYPE: DNA
<213> ORGANISM: Artificial Sequence
<220> FEATURE:
<223> OTHER INFORMATION: Genomic Sequence for KRAS Wild-Type

<400> SEQUENCE: 11

gattttccta ggcggcggcc gcggcggcgg aggcagcagc ggcggcggca gtggcggcgg     60

cgaaggtggc ggcggctcgg ccagtactcc cggcccccgc catttcggac tgggagcgag    120

cgcggcgcag gcactgaagg cggcggcggg gccagaggct cagcggctcc caggtgcggg    180

agagaggtac ggagcggacc accccctcctg ggcccctgcc cgggtcccga ccctctttgc    240

cggcgccggg cggggccggc ggcgagtgaa tgaattaggg gtccccggag ggcgggtgg    300

ggggcgcggg cgcggggtcg gggcgggctg ggtgagaggg gtctgcaggg gggaggcgcg    360

cggacgcggc ggcgcgggga gtgaggaatg ggcggtgcgg ggctgaggag ggtgaggctg    420

gaggcggtcg ccgctggtgc tgcttcctgg acggggaacc ccttccttcc tcctccccga    480

gagccgcggc tggaggcttc tggggagaaa ctcgggccgg gccggctgcc cctcggagcg    540

gtggggtgcg gtggaggtta ctcccgcggc gccccggcct cccctccccc tctccccgct    600
```

```
cccgcacctc ttgcctccct ttccagcact cggctgcctc ggtccagcct tccctgctgc    660
atttggcatc tctaggacga aggtataaac ttctccctcg agcgcaggct ggacggatag    720
tggtcctttt ccgtgtgtag gggatgtgtg agtaagaggg gaggtcacgt tttggaagag    780
cataggaaag tgcttagaga ccactgtttg aggttattgt gtttggaaaa aaatgcatct    840
gcctccgagt tcctgaatgc tcccctcccc catgtatggg ctgtgacatt gctgtggcca    900
caaaggagga ggtggaggta gagatggtgg aagaacaggt ggccaacacc ctacacgtag    960
agcctgtgac ctacagtgaa aaggaaaaag ttaatcccag atggtctgtt ttgcttggtc   1020
aagttaaacc cgaagaaaac ccgcagagca gaagcaaggc tttttccttg ctagttgagt   1080
gtagacagca atagcaaaaa tagtacttga agtttaattt acctgttctt gtcctttccc   1140
ctatttctta tgtattaccc tcatcccctc gtctctttta tactaccctc attttgcaga   1200
tgtgttctac atctcaagag ttattacagt actccaaaac agcacttaca tgattttttta  1260
aacttacaga ggaattgtag caatccacca gctaaccgcc tgaaatagac ttaaacatgt   1320
gcatctcctt tttttttttt tttttgagac acagtctcgc tctgttgccc aggctggagt   1380
gcaatggcgc ggtatcggct cactgaaacc tccgcctcct gggttcaagc aattctcctg   1440
cctcagcctc ccgagtagct gggactagta ggtgcacgcc accatgccca gctaattttt   1500
gtatttttag tagagacaga gtttcatcat gttggtcagg atggtctcca tctgctctgt   1560
tgcccaggct ggagtgcagt ggcgccgtct cggctcactg caacctctgc ctcctgcatt   1620
caagcaattc tcctgcctca gcctcccgaa taactgggat tacaggtgtc tgctgccatg   1680
cccggctaat tttttgtatt tttagtagag acggggggttt caccatgttg gtcaggctgg  1740
tctagaactc ctgacctcgt gatctgcccg cctcggcctc ccacagtggc atgtgcatct   1800
tatagctgaa gtctaagcct tcttaaatct tgagatccat caaaacagac aggttttcta   1860
attgttatac aatgtatatg ttatgtttat aatagaaatc attttacaaa taagttataa   1920
atgggaaagg tctatttgta attatcagct cagaattaac cataaaactg gtgtcactga   1980
agtgactgag gtccaaaatg ctgactctgc atgttataga ctacagatat caaatatggt   2040
tgctaacaat agtttacttt gagactgtag ccatccacag tatatttgct tttaagagat   2100
ggtagatggt aattcagttt tatgaaaaat aaaaatgaat tttcttccat tacaaaattg   2160
ttggattcga gtccagtcca ctccttacta gcttttctaa ctctcggtga gggatcccct   2220
cccagcccat gatcttcatt tggtaagact cctttggaac ccagttctct ctagtggatt   2280
taaatgtgat ttggttttaa aaatctcatt caaggaattt ttttttttttc tggaaacaac  2340
caccgcataa acaagtaaac cggaagatac atgtggctct gaattcatat atatacacaa   2400
actctaatcc aatgtctgtc cacagtattt cctaggctag taaacttttt ggccttaacg   2460
acccctctac cctctttgtt tttttgagag agagagtctc actctgtcac ccaggccgga   2520
atgcagtggc gcgatctcgg cccgctacta cctccgactc tcaggctcaa gcgattctcc   2580
cgcctcagct tcccgagtag ccgggattac aggctcccgc caccgggcta attgtatttt   2640
tagatacggg atttcaccat gttggccagg ctggtctcga cctcctgacc tcaggtgatc   2700
cgcccgccta agcctcccaa agtgctggga ttacaggcca ccacacccgg cctacactct   2760
taaaaattat cgaaggggcc gggcacattg gctcttatct gtaatcccag cactttggga   2820
gactgaggcg ggaggatcgc ttgaggccag gagttggaga ccagcgtact caacatagtg   2880
agaccttgtt ataaagaaaa aaaaaatcca ggattaaaaa aaatctttga tttgtttggg   2940
```

atttattaat atttaccgta ttggaaatta aaacaatttt ttaaaatgta ttcatttaaa 3000
aataataagc ccattacttg gtaacatgaa taaaatattt tatgaaaaat aactattttc 3060
caaaacaaaa ccaaaactta gaaaagtggt attgtttcac acttcagtaa atctctttaa 3120
tgatgtggct taatagaaga tatggattct tatatctgca tctgcattca atctattatg 3180
atcacacatc tggaaaactt gtgaaagaat gggagttaaa agggtaaagg acatcttaat 3240
gttattatga aaacagtttt gacctcttgc acaccagaaa agtcttagta acctgagggg 3300
ttcctagacc acattttgag aactgtttta ggctatgcaa actggttggg gggaggttgg 3360
ggtaggcaga gagctagaag atacatttta gtgtaattct cctcatctat tcctaattgc 3420
tttggcctac atttgaaata aagcgtggag gcaaacggga taagatacat gtttgtagtg 3480
gttgttaact tcaccctaga caagcagcca ataagtctag gtagagcaga gtaaggcggg 3540
gaactatgcc gtgaccgtgt gtgatacaat ttttctagcc tgtggtgctt tttgcggcag 3600
ggcttaggag taaggttagt atgttatcat ttgggaaacc aaattattat tttgggtctt 3660
cagtcaatta tgatgctgtg tatatttagt gtttatctac aatatatgca cattcattaa 3720
tttggagcta ctcatcctat aataaatagt tgtgcattta ctcccatttt tttctgcatt 3780
tctctcctta tttataatta tgtgttacat gagggaaagg aggtgaaatt aaacattcat 3840
attatttcaa aaaatttgaa acaactaact aaaaaatatg ttttattttc tgtatggtgt 3900
ttgttataca atctgtcaat attcatgcac ctcttgggag acagtgtatg aaaagcaaag 3960
agtaacagtc acatggatta ctgattactg agatatattc acttgcatct tttttttttt 4020
ttgagacgga gtggctctgt cgcccaggct ggagtgcagt ggcgtgatct cggctcactg 4080
caagctccgc ctcctgggtt cacgccattc ttctgcctca gcctcccaag tagctgggac 4140
tacaggcgcc cgccaccacg cccggctaat ttttttatat ttttagtaga gacggggttt 4200
caccgggtta gccaggatgg tcttgatctc ctgacctcgt gatccaccct cctcggcctc 4260
ccaaagtgct aggattatag gcgtgagcca ccgtgcccgg ctcacttgca tctcttaaca 4320
gctgttttct tactaaaaac agtgtttatc tctaatcttt ttgtttgttt gtttgttttg 4380
agatggagtc ttactccgtc acccaatctg gagtgcagtg gcgtgatctg ggctcactgc 4440
aacctctgcc tcccgggttc aagtgattct ccttcctcag cctccccagt agctaggact 4500
acaggagagc gccaccacgc ctgattaatt tttgtatttt tagtagagag agggtttcac 4560
catattggcc aggctggtct tgaactcctg gcctcaggtg atccacccgc cttggcctct 4620
gaaagtgctg ggattacagg catgagccgc cgcacccggc tttctaatct ttatcttttt 4680
ttgtgcagcg gtgatacagg attatgtatt gtactgaaca gttaattcgg agttctcttg 4740
gtttttagct ttattttccc cagagatttt tttttttttt tttttttttg agacggagtc 4800
ttgctctatc gccaggctgg agtgcagtgg cgccatctcg gctcattgca acctcggact 4860
cctattttcc ccagagatat ttcacacatt aaaatgtcgt caaatattgt tcttctttgc 4920
ctcagtgttt aaatttttat ttccccatga cacaatccag ctttatttga cactcattct 4980
ctcaactctc atctgattct tactgttaat atttatccaa gagaactact gccatgatgc 5040
tttaaaagtt tttctgtagc tgttgcatat tgacttctaa cacttagagg tgggggtcca 5100
ctaggaaaac tgtaacaata agagtggaga tagctgtcag caacttttgt gagggtgtgc 5160
tacagggtgt agagcactgt gaagtctcta catgagtgaa gtcatgatat gatcctttga 5220
gagcctttag ccgccgcaga acagcagtct ggctatttag atagaacaac ttgattttaa 5280
gataaaagaa ctgtctatgt agcatttatg catttttctt aagcgtcgat ggaggagttt 5340
gtaaatgaag tacagttcat tacgatacac gtctgcagtc aactggaatt ttcatgattg 5400
aattttgtaa ggtattttga aataattttt catataaagg tgagtttgta ttaaaaggta 5460
ctggtggagt atttgatagt gtattaacct tatgtgtgac atgttctaat atagtcacat 5520
tttcattatt tttattataa ggcctgctga aaatgactga atataaactt gtggtagttg 5580
gagctggtgg cgtaggcaag agtgccttga cgatacagct aattcagaat cattttgtgg 5640
acgaatatga tccaacaata gaggtaaatc ttgttttaat atgcatatta ctggtgcagg 5700
accattcttt gatacagata aaggtttctc tgaccatttt catgagtact tattacaaga 5760
taattatgct gaaagttaag ttatctgaaa tgtaccttgg gtttcaagtt atatgtaacc 5820
attaatatgg gaactttact ttccttggga gtatgtcagg gtccatgatg ttcactctct 5880
gtgcattttg attggaagtg tatttcagag tttcgtgaga gggtagaaat ttgtatccta 5940
tctggaccta aaagacaatc tttttattgt aacttttatt tttatgggtt tcttggtatt 6000
gtgacatcat atgtaaaggt tagatttaat tgtactagtg aaatataatt gtttgatggt 6060
tgattttttt aaacttcatc agcagtattt tcctatcttc ttctcaacat tagagaacct 6120
acaactaccg gataaatttt acaaaatgaa ttatttgcct aaggtgtggt ttatataaag 6180
gtactattac caactttacc tttgctttgt tgtcattttt aaatttactc aaggaaatac 6240
taggatttaa aaaaaaattc cttgagtaaa tttaaattgt tatcatgttt ttgaggatta 6300
ttttcagatt tttttagttt aatgaaaatt taccaaagta aagaccagca gcagaatgat 6360
aagtaaagac ctgtaagaca ccttgaaggt catggagtag aacttccatc ccaagcagat 6420
gaggatttat ttaatctcaa agacctccag gaggggacat tccccaactg tccttgttaa 6480
ctcattttca gaacatattt attagcatat tttacatgta atttggatct tcatgttaaa 6540
tttaacatca gtggagatgg aaaataagca tatcgccttg tctttgaaat agccctatat 6600
tgttagattg tttcttaggc ttctttaccc tgggttaagc agtcctaata ctttagcatt 6660
tattctacat ctagtgtact aatttaaaaa aatcagttct gaaaaatttc taagaacttt 6720
cttcaagttc caagctgtga aatctagaac aggtcaaagt gccttattaa cgtactgtac 6780
tgtgtagtgt cttgaagaga cactttgcgc tgaggcaagt tctgagggca ttgggtggcc 6840
ttgggaagat atttatgcag tttagaacct ggagaattga ttagataact aatcataagg 6900
aaacgtcaca tatttttggt actataaaaa agtggagaaa taatgcctat ttgcaaagat 6960
ttgatttaaa catagaaaca actttatttg gcttccaatt ttaagaattt acagcagtaa 7020
aggggaacag tctaattgaa gtagactgcc tatgcaatag tctctgtata tttacttttg 7080
acaagttaat tcaatgtgta ctatagtttt gtttctttga agaggtttga atagtgcacc 7140
cattttaatc tgtattgcaa attcagggtt acttggcaga ctctactatt taaatcagat 7200
gtaaaaggaa gttttaatat aattcacttt atgcctgaaa gttttcctgg gattttggaa 7260
ggtgatttta ctggaaatgc tgtctgtctt ccctgaaaat ctgagaaatt ccattacact 7320
ttgtttccaa tcagaggtca tgagtgctat atgagtatat acagcatgac gtcatgaatg 7380
tgataaagtg ggttaggaaa ccttttgcta atgattgtta aaatgcaata taaatgttga 7440
agaaataaag ctaacagtta agcctttatt tgggcggaag gctgaaaaag tttataaact 7500
taaacctata actctgctta tgatttctgc caaaccagaa gacttgactc tgggaagcat 7560
tggttacctg tgaactttga aactgacggt ccctgacgta gtttagtcac ctgggaaaag 7620
gtatctgaga ttatctctta tctcccaagt tacagtgagt ctctgaggga actgacacat 7680

-continued

```
tacattaagt tcttggtgta gttaaactgt aagaaaggca ggagaactta gtagttaaat   7740
agttggttaa atggaaatgc tgactccatg ttattgtaaa aagttaaaaa tttaggagga   7800
tatggggatt tcactgccat tgcaggtttt gattggtatt taccaatccg tgtgggtcag   7860
agagaaaatt agaaaggata tgactgcaca ttttggaatt attagcagtt tttctacatt   7920
taaaatggaa ataaattttt taaaaattta aatcaagtaa tactgtattt tttggtgatt   7980
tagatttttc aaaatttaca ctaagagata gtaaggaggg tggctattgt ttctttcaat   8040
aatgtctctg agaggttgta actcatctaa ggatacgtag ctaataagtg gtaggatttc   8100
aatttaaatt ctctgagacc aagttaagta gaatttgcac tgtactcttg tataactttt   8160
taaaactgaa aattagctat ctttcaaatt aagaaaatat ttactaatgg agactaattc   8220
agatttgtaa gtataccaaa atttgaactt agcctgctat ctaatggcaa cttagtggca   8280
gaggtatgat gtaaaatcat tcaggtatga cacatagatg gagtatgttt gtattcgagg   8340
ctgtgcacat aatcaccttt acttgtattg tgaagtatat attgttatct tttatgaagc   8400
ccactaaaga gataatgaaa tacctcgtta ttagggcaag attattgaaa actcaaaata   8460
gcccccaaac acaatacttg gctagaaata tataccttta tagttcagag atcatttatt   8520
atcaaaaccc tgaagttttt tttctaaggt aaaatttggt ggaagaggaa aagtctcgtt   8580
ttaaaaaaat gtaggtagtt acagagatca gaatgattag ttgatcactt accaaatata   8640
tattaagtat ctactgtata taatatgcta gtaagaataa atatagcagg aagtattttt   8700
tcccaggctc taattgtttg acatcagcat gcttttattg tggcacttat aattcagttc   8760
aagtattatg cccctctttg atggaacagt ttcctattca gtaaggaaga ccagattaat   8820
cattggattg gtttgtttca tctttagtgt tctgagctgt agagtattta tttaccaagg   8880
tttattttaa tttttatttt atttttattt ttccatgttc attgtagaat tcattttacc   8940
tacgaatgaa gtatgtagat tatagagaga aaatttgtaa aattaaactg atactgaaga   9000
ctggtataag aaaagcctta tgtaatttgt aagctgctat tcttctgagt ttatacatat   9060
atctttagta atcaatgagg gatggttggg tgactgccct ccaggggaca tttggcaaca   9120
tctggagatg tttttggttg ccacaacttg gggagagagt actgctactg gcatctattg   9180
agtagatgct attactttaa atggcaaagc tgcagttacc tttgcaccaa cctaatatta   9240
aacttcctgc agtgcacggg aaagccccca caacagggtt atctgacccc aaacctcaat   9300
ggtgttaaga tccaaacctt gatatgttaa cctgtagctt taaacatcct ttaaattgtc   9360
aaattcatgt ccctgacata aggtttatgt tagattttca agtataacaa agatttaaac   9420
tttaactttt gtacgttaat gatatgttag cttactccag tcttctatta aaacattctg   9480
tttttaaaat cagagacaca cagcaatttt ataaatcatt tctcttcaag gctgtgaagc   9540
tctccccact tttgtgagtg ccctctactg gtcaaattat ttgctttata acaagtaaca   9600
gtgaaatcct aagtttgtgt agtttcgctg tttaaattat gggtggcatc aatttataaa   9660
tatattcgtt ttatttaaaa gtcttatatg attgatttcg tatcattttt gctctctgct   9720
aatattaata taaagattac tgtctgtatt agttaggcct aactaagtag gtgagtatag   9780
tgaactaaga aaggaaacga ggcagtatat aagaaaatag ggtggttcag ttgttaacac   9840
ttactgagct tactttgttg aagggactaa aaggcagcag tgtggctctc tgagcttctt   9900
tgcatgcact caggagctgc ttaatggagt ccaaggcttg gtggtgtgtt acaggggatg   9960
ataggagggt cctattcaga agtggcaaat tgtgaaagtg cacattttgt agagttttat  10020
aggactgtag aatagttgtg agcacctgat ttttagaata aacagaaaac tcaggtactg  10080
```

tatttaggtc aaattaagaa taagtattta ttaagacctg aatataaaac tttactggtc 10140
atggtttttt tctaccttgg gtttttataa atccaaagat ttaaaaacat acaaatggaa 10200
gttggtaatg gaattaagtg aaaggaaaaa atgattttat ggtttggaat ctcctaagat 10260
tctggtttta acaatacaac taattcctta atcctagaaa tgttcttcac tgcccacttt 10320
gtaccatgca gtcttcctgt gggctagaga tacactgagg cgcaaaacag accagattcc 10380
tgccttcatg gagcttatta gttttaggta tctctagatt tcttgtaata cctattacaa 10440
tgcctgcaca tcagttcatt catgtgggtt caacgtagta ctcagtacat ggcaaattca 10500
agttttactt ttcggaactt catggatttt tttcctcaga atatctttta tccataattg 10560
gttgaatctg tagatgcagt acccatggat atggatggcc cactttattt tgaagagcag 10620
tgtttctagg caatcatgct aattatatat gacttaattt agaggcttta tacttaagag 10680
cattacattt ctggcgtctc ttaaccatta ttatttcata atgtgtaggt tatggaacag 10740
ttaaattatt gggatcttaa tatagaaatt agtagaaata agccagatat ggtggctcat 10800
gcctgtaatc ttagcacttt gggaggctga ggctattcgc tgtactattt tttactactt 10860
ttctataggt ttgaaatttt ttcaaaataa aacattgaaa aaagtaaggt aggtagtgtg 10920
tccctcctta atcctttcaa atattttatt ttcactattt ctattaattt tttttttgt 10980
ttttgagatg gagtctcgct ctgttgccca ggctggagtg cagtggcgcg atcttggctc 11040
actgcagcct ccacctcctg ggttccagcc attctcctgc ctcagcctcc tgggtagctg 11100
gtattacagg catgcaccac cacacccaat tactttttgt atttttagta gagacggggt 11160
ttcaccatgt tggccaggct agtctcgaac tcctgacctc gtgatctgcc cgcctcagca 11220
gtgtcactgc ttctagaccg ttttcaaggc acagagctta gaaatgcatg ttactaagaa 11280
atcaagagtt aactattttt caccttcttt ctcccgcagt gagaaccctg gttctaccct 11340
gtttctcctt gtgtaaattt taatgctaaa ctatacactt gtgaaataaa aatgataatg 11400
tcattcttaa attatggatc ttgcagtgtt atctaagtaa catagattga gtgatttaac 11460
tttaggtttc cttatttgtg gaatttggat aaatattttt caccccttgag aaaagtgaga 11520
ctcctttctc atcatcagag tatccttaaa ccattaaggc aaacatttgg gaaaaaactg 11580
agctatctgg ctgcataaaa attaagtttt ctttaacaaa gatagaagac aaatgaaaac 11640
ctagaaaaac catttggttc aagtaacagg aagctatctt atatatgaat tagagaaaag 11700
caaacacaca aatagaaaaa aagggatggg gggtactaaa gatataaata gcttgtctac 11760
caaaaaagaa ataaaataaa taacatgaac atataaaaag acacttactt catgaatgtg 11820
atgcaagttc aaacaataaa taacatttct gtactttcat attggctaag gttaaaatga 11880
taactgctag gaagggtatg gagaagtgtg cgccttgcac tgtagtggga gtatagaccc 11940
tcagacttta tggaggtcag tctggaaata tgtttcaaaa tgtaaactac atgtcctttg 12000
accaggtaat tcaacttctt gaaatttatc caaggattta attggataaa tgtttaagat 12060
gtatatataa gaatgtttac tgcagtgttg tttatgattt taaaaaaatg gaaatcatct 12120
tcatgtctac caatagagaa tgggtgaata aattatggta tgtccatata tacaaattac 12180
atagttgttg gaaatattag gtagatttag atatactgat gttcaaaaat gtccattatg 12240
taagtgaagc tgggtcacag caccttgtgt tgagtatgat ttcatctaga aacaaaatta 12300
ctccctcatc ctttgttgtg ttttagtttt ttaaaataag cttataccat tgggctgggg 12360
gaaaagtaaa tactcgtttt ggagagagaa aagggcacta aagtttcaga taccgttaga 12420

-continued ttatttcatg cttatttttc aagcctcaat aaattacata attcacatgt agtcttggat 12480
taaggaaatt gctattaagg ctaaataaat aatatgagag gtatataata taaaatatga 12540
acattatatt ggcattaaga ttggatccac ggtcattcca gcctctcatt cttacctgga 12600
cttcaagtga tcacttgtgg gcaaatgcca tctgacttga acaggttaca catgtatgct 12660
cattatatcg ttattttcaa aatttgtcat ataaattttc cttgagttca ttcagatttt 12720
tgaactagtt ttttctcttg ggagtagtac acacttaatt ctctctagta ctaagctaat 12780
gttcaccatt cttataattt taagtatcca gcatttagta aagaagtctt tgttttcttt 12840
atccttactt ttagtgaatg tcttagtttt taattgaaaa ttctgccatg aaaataagct 12900
ctttaacatc ttcactccct aatcaaaaca gaaatccttc atagccttca gttgtagcta 12960
tccttccctg tgatttgtcc agctccatta tatttatttt gaaatatggt gaccagtttt 13020
gcaaaattat ttcaactgta ggtgcccagt gattttgtaa ggagaagata ctgtttctga 13080
acagttctca gtagccagtg gcctgcccct actttttggc ctgcgtgtag tatataaaat 13140
aatgcagtta actttttata gcacttttca ttttataaag agattttcat ggtctttaat 13200
attaatctat gtataaagtc ctgtatgcag ttttacctac tttcacagct gaaggaacaa 13260
tagcttagag aagatgtgag ataaagtagt ttgcccaagc ccatagcaca aataagtgaa 13320
gttcttcggc tgtccatgga tcgaagactc ccaagtctat ctctagcctg gacttctgtc 13380
ctgagcacca gacatgtatg tatatcaaga tgcctgcagg tcatatccac caggacaacc 13440
catgagtaca gggaattcaa catgcccaat atcactcatc ttttccttcg ccctcccctt 13500
tgtactcatc ccctgtcggt aagctctgtt attttaaaaa attgaaatgt attcacatag 13560
catacaattt acacttttca agtgtacatg gtttttagta tattcacaag ggttgtgcag 13620
tcattactac taattccaga atgttattat caccccaaaa gtcccacatc cattagcagc 13680
cactccccaa tcccttctcc caccagcctc taaaaactgc taatttttcc atctctgtgg 13740
atttgtccac tctgattatt tcatataaag agaatcgtac agacgtggcc ttttgtgtct 13800
ggcatcctcc acacaggatg atattttcag agttcgtcta tgtttttgct tgttgatcat 13860
tccttcattc ctttttctgg ctgaataata ctctgttata tggatatacc ttattttgtt 13920
tatctgttca tttgatgggc atttgagtga tttcctcttt ttggcaattt tgaataatgc 13980
cactataaac atttatgtac acgtttttgt gtgaccatat gttttcactt ctctcgggtg 14040
tatatctaag gtacagttgc tgggttatat ggtagctctg tctttgactt tttgaggaac 14100
tgccaagtgg ttttggtagt gattgtactg tttacattcc taccaacaat tttacctaag 14160
tatttctcaa atctatttaa tcttttcggt ccatactgct gttgctgcct tagttcagat 14220
tttgtcattt cttgtaataa ttcgtagctc atctcccagt ctctgctccc ctctctccct 14280
ccctccccct tcttctctct cttatttcca cccattttta acatttatag aagtcaaaag 14340
tctagttcag aaagcagaaa ccatactaga tatttcagca cagagaacta attaggtgtt 14400
ggaagactga aaggcaaaaa aacactgaag taacacagta acatcaagaa tgggcactac 14460
tcctaagatt cagggaatgc tgggaagatt tggggtttat cagaactgga agctcagagg 14520
aggggcccct tgtcgctgag gcttaatccc tgcagaggtg cctttggctg ctactggtga 14580
atctgagtgg gtatgatgag tcagtgtctg ggaagggcca aaacattttg tccctttcta 14640
taatttgtca tgataatgct agtaatgaat ctgatctccc ttcctatttt aaaaaccttt 14700
tagtgatttt gtataggatg aagtttaaaa ctccttactt aatatacaca tgaccctccg 14760
taagctggcc cctgcttgat tgtccagttt cacttcttgg tgcttattct aaggcctcta 14820
agccttagag atcctctaag cctttgagat ccccaaaccc tggactgcgg actggtaccc 14880
acctgtgtgg cctgtgagga actgggctgc acagccggaa ggaggtgagc attacttgcc 14940
ttagctcctg tcagatcggc agcattagat tctaatagga gcgtgaaccg tgttgtgaac 15000
tgcccatgca aggatctagg ttgcatactc cttaggagaa tctaactaat gcttgatggt 15060
ctgaggtgaa acagtttcat cctgaaatca cccccaactc ggtccttgga aaaattgtct 15120
tccacgaaac tggtccctga tgccggaaaa gttggggacc gctgttctaa gctaaagtta 15180
tatggagctc cttggttctg tgtcctcaac atgctgttct atgtttttta cattctgttt 15240
gctccttcct gcttggaatg tccttcccct ccccgtcttt cttaatgcat acaaagttga 15300
tctctcctgt gtgccaccat tgtacttcgt cttgcatatg gtgttacatt cattttattt 15360
taattattta tttacgttca tgtctcttcc actcacctta gttgcttgag gtcagaaact 15420
atataatgtg tgacacggaa tgtgacacct agattttcaa taagtgtttc tatgatacaa 15480
gggagactga tgtgggtaga tgggaatgaa ctcatcaacc tctgtttaca taccctaaat 15540
tccctgtttc ttccctatta taattctgac agtctacaac cgtctttgat ggcttataaa 15600
cggaaagtgc ggaacacatc attctacagt gaatttaaat aacctttcgg aagagtaacg 15660
taaagtactt gagcattaat tgagtaaaag tttctcatct tttcctacag gtgttattaa 15720
gcagtatgta aaaagtcctt acaatactta atacattaag aaaacataca atttcaagag 15780
gaaatccccg agtaatacat tattgacatt ttcagcagtt ctagttatat tgagaagagc 15840
atctcatgga attggcagaa tgaagatgga gattaaatga gatgatgttt gtaatatgct 15900
tatgacagta tctggcatat aagtaagggc tcagtaaatg ttgactgctg taattactat 15960
taatagtaat atgattacct ttagtaaaag ttattagttt ctttaggttt tttgtttact 16020
acaatatagt aaacaaaatc tatacttgga atgtatatat tgttttgttt tgatacatgg 16080
aatatgtctc tgtgtcagag tcactgcctg agttggaaaa cccatactcg agtatgttaa 16140
aaggtgaaca cactgaataa tttagttatt aattataatg gaaaaatgac aaacttgatg 16200
ttctggttaa tgaggttatc ttatcttgaa tgagttagct tttaaattcc tcaaaataaa 16260
ggcatttaat aaaccaggaa acacttcatt aaaaaaatta tgcaagtcag tgtaaaagaa 16320
gattaaaatt ccacatgggc aaaggacaca cgttggcgat aaatatgcag ataagaaaaa 16380
aaacctatat aacattatta ctcctcaaag aaattggtat gaaaacaata aaaatgtgta 16440
gcttatcaaa ccaacaaaaa tttaaaaata tgaaatccat tttaagtaat gataaaatgg 16500
gtgcactctt agtgctttat agaatagtag tataatgaac ctcatgtgtg taccaaccag 16560
ctctttcata tcttaacatt tagcaacatt tgatttagct ctttcttttt tccaagatag 16620
aaaagttaat attgttgaag actcctgcat tcttttccct agtcttattt tcttccctcc 16680
cataaatgtg ttaaaatctc tgtgtgtatt gttttggttg tatttttaca taaaacttta 16740
catattatat aaaatttaat tgaaggtaaa atttattaaa ttattcttaa tatatattgt 16800
aatttaaaaa ttaacagctt cattgtcttg ataaaattta tggtatctta aacatgtgct 16860
tgtttttcta agagaacatt gaaacataga ttttaaaaca aattgttgaa agattaaaaa 16920
atctgccttt gcacactgtt acattgaaag tggggcattt gtcgtgaaca ttcatttcaa 16980
atatgtagta tcttcagaat atttgagaag gatttgtatt atataattga aaaatctgtt 17040
aaattgtatt tatgttaact gcttaattct aataaaattt ccattcattt tttagtatct 17100
gcatatattt acatcaaatg gattcattca cttatttaag aggcagtact aattacctat 17160
agcgttcaag actgttaggt agagggtgtg tagtggtgag tacaacaggc gtgagcccta 17220
ccaacacgga gtttaaagcc tagtagagga tatagactta aacaatttca caagtaaata 17280
cataattaca aattataata catgctatga aggaaacata ggaggtacca gagaaggaag 17340
agtgctttgc atttttattt ttaagaccga agagtgctat tggaggactt tgagcaagtg 17400
aatgacatga tctaacctac cttcgttcat tcattcattc attcattttc ttccttcctg 17460
gctcaagcag tcctcccacc tgagctcccc aaatagctgg gactacaggt acacactacc 17520
acacctaatt ttttttgta ttttttgtat ttttgatggg attttaccat gttggccagg 17580
ctggtcttga actcttgacc tcaggtgatc cacctgtctc ggcctcccaa ggtgttggga 17640
ttataggtgc ctagcccatg gtgcctagcc ctaacctaca tttataaact atcacttgct 17700
gctgtgtgga gactatattg tgagattaac agcagggata cctgctagga agcaattgct 17760
gcagattgcc tgagacaaaa tagttatcat ggactagggg gatggtggtg gtggtggtgg 17820
taggtggttg gatgtaggat atattttgaa gataggtaaa tggtgcaaga ttatgggtca 17880
gttttaaatg cttaagtaaa ttttctttgt aagacatttt aggatgccat gttaagaatc 17940
tctttataac tgtcatttaa aaaaaaacca catattttct tagcataatt tcccatagta 18000
acattactat gtcaaaggct atgaacattt gaatgacttt agataaatac tgtaattgct 18060
ttccaaaaat attgtgctta ttatgtcacc agaaatgttt gaattctgtc tacaattcag 18120
tcttgccagt atagtacatt tcatttagaa aaatttttta ctatgtagat ggaaaaaata 18180
atattttagc tgggagtggg gggactatgg ggaataactt tccttcattt aatattttat 18240
tgtgagttag tttaagttac tttattttat cgtagtttcc taaggctaca aattagtaac 18300
cttggtaact tatgtaccta atttaaaagt ttactttttt gaaaggctgg aaatactaat 18360
taaaaacgta acaccttcat ccttgtcttt gctccattat taactagttt cattacagaa 18420
tctctgtgtt ttaaaatcag atgggttttc ataaccagta ctttctcaga gtggtaaatt 18480
taaaaaaata tataaagaga ataaataata tttgttgaga atacttcaaa taatgtgaag 18540
agttattaac ttacagcagg agttggcaaa cttttctata aagggccata tgggtctttg 18600
tcacaaagtc ttgggttttt gtttttgttt ttttaaacag ctatttaact attcctagct 18660
aatgggcaat acaaaaacag tgggcaagat ttggcctgtg ggcagtagct tgctgaaacc 18720
ttatttagac tctaaatttt ttgaaagagt ctacattgat gcatattttt ttttcttcct 18780
ccaaatacag ttgacccttg aacaacatgc gtttgagtga ccatgggtcc acttgtgata 18840
cacgtttttt tcccaaccaa atgcagatat ggagggctga cttttcatat acctggatgt 18900
tcctgggcca actgtaggac tagaggctgg gggggtcttg gaaccaatgc cgtgtgtata 18960
ccagggatga ctgtttctta tggcctgacc tgaagttgga acagaatctt tattaatata 19020
taatttttgt tgcgtttgtt ttctctttat atttatccat tctttttaga tcgtatttca 19080
tttaacactt tttcttcttt agtttttacc aagttgcact gaaaatagct cagtgactaa 19140
ttgcacttct aagagtgagg accctagtta aaattaactc taaaaatact gaatttttaa 19200
cctaaacctt ttatttctaa tcaacagtat tatttatgag taggttatag attactttga 19260
aacggaatgt gtctcagaac tttgctatcg atattttttaa ggtctggtag ggaaaagata 19320
ataggaatga gatttatcag tgaatagggg actgctttcc cagtttctcg gtcgcactgg 19380
tgtattcacc atggaagcat cttatgaaat atgtacataa actactaata tcccacatta 19440
caggttgact attctttatc tgaaatgctt aggacctaga agtatttttg gattttggtt 19500
tttcagagta gggatactca gcctacattg gtaagtaaag aatgtgaggt gacaggctgg 19560
gcgcgatggt tgacgcctgt aatcccagca ctttgggagg ccgaggcgga tcacctgagg 19620
tcaggagttg aagaccagcc tggccaatct gtactaaaaa tacaaaaatt agctggacac 19680
agtggcacgt gccagtagtc ccagctactc aggaggctga ggtaggagaa tcgcttgaac 19740
ctgggaggcg gaggttgcag tgactcgaga tcgtgtcact gccctccagc ctaggcaaca 19800
gagcaagact ccatctcaaa aaaaaaaaaa aaaaaaaaaa aaaagaatgt gaggtggcag 19860
caataggtag gaagagtctt tggtcagctt tacatgctct gtagccatgc ctgggtaatg 19920
ggttgactct aagactctgt gctttgctcc cacctcctgc tttttcatta ctctttagaa 19980
tggtttttaa tttgtgatct ataggagttc tttcaagtat ttaataagag aataggctaa 20040
attaagtaaa tgtcaactga atgctcaaat ctctactaaa gagcctctta tttagaaaat 20100
aaatatccat cttttttttc tgactggtga gataattaat ttttattaca gatggtttgg 20160
aaaataccat atgctttaaa agataagcac aaaattatag tctaatatgt aggttttcat 20220
actttaaaaa attgaaaacc aaagaaaaac atttaacata gcatctagta caaagaaaag 20280
agataagcaa gagataaatg tctttttttgg gacagagttt tgctgttgtt gcccaggctg 20340
gagtgcaatg gcacaatctc agctcaccgt aacctccacc tcccgggttc aagtgattct 20400
cctgcctcag cctcccgagt agctgggatt acagtcatgc accaccaggc ccaggtaatt 20460
ttgtatgttt agtagagatg gggtttctcc gtgttggtca ggctgatctc aaactcccga 20520
cctcaggtga tctgcccacc ttggcctccc aaagtgctgg gattacagac atgagccatc 20580
gcacccggcc aagataaatg tcttttaaat tatctccatt aaagacataa cctttataac 20640
attttgatgt atatattacc agtttttaaa cacatagtag atttgtataa atacataaac 20700
acatattatt gtgatcatgc tgcacttaga catctttata ttctccttat actgtaaaca 20760
ttttgaaata ctttactaac aacatttgta atgaccattc tttctctctt tctccctctg 20820
atagaatggt ctacagagta attcataaac taaacatact ttagaggctg ggcgcagtgg 20880
ctcatgcctg taatcccagc actttgagag gctgaggcgt gcagatcacg aggtcaggag 20940
ttagagacca gcctgactaa catggtgaaa ccccatctct actaaaaaaa cagtacaaaa 21000
attagccggg cgtggtggcg tgcacctaga atcccagcta ctcaagaggc tgaggcagga 21060
gaatcactcg agcccaggag gcagaggttg tagtgagccg agattgcacc acagcactcc 21120
agcctgggcg acagagcgag actccatctc aaaaaaaaaa aaaaaagata cattaatact 21180
atagcctaca tgtggaacat taagaaaata attgctttta tgtttatgct ttatacctgt 21240
tgttagccct gcttcttatt tcatgatttc atggcttcac attgtaacat ccctttacca 21300
tattttttga ggactgtttt ggcagaatgt gtgaaatctt gagcagaagt attacccaaa 21360
agtcagaaga aaatcagatt tttatttcaa gattctgtta aagttaccca ctcccttctt 21420
ttacttaatc ttatagttgc agttctctct ctttttagaa aagaaaaaag aggcccctca 21480
ggatttgcag atgaaacaat attgctcttt agagatatcc atctggctgt tagattattt 21540
ttccacagtt ttcagaagtg gatgaggcca ttagaatctt gagtattgcc catttcctta 21600
tgtgtgcctt tgactataga taaaatagat gcatgacaat tatttataag ttgattgatt 21660
tttcttgtca tttaaatcat cttgaataat agagttggta gagctatccc atttttgaaa 21720
ttattttgtt ttgtcaataa ctttttgtta ccagcatgta cacttgcatt gttgactctc 21780
catataatac ctttaaaaaa tttttttttg tggtaaaata tgcataacat aaagtttacc 21840
atggtagttt tctttcattt gttttgtttt tgtttttttg agacggagcc ttgctctgtt 21900

-continued

```
gccaggctgg agtgcagtgg agcgatcttg gctcactgca acctccgcct cccgggttca  21960
agcaattccc ctgcctcagc ctcctgagta gctgggacta caggcgcccg ccaccacgcc  22020
cggctaatat tttgtatttt aatagagatg gggtttcacc atgttggcca ggatgttctt  22080
gatctcctga cctcatgatc cgcccacctc ggcctcccaa agtgttggga ttgcaagtgt  22140
gagccaccgc gcctagacca tggtagttaa ttttaagtgt tcaattcagt gaccttaagt  22200
gtgttcataa tgttgtgcaa ccatcaccat gttgtctaac cattagcact atctgttttg  22260
agaacttttt tttatcatcc caaattagaa ttctgtacct gtcaaatagt ccccagtaat  22320
cctccctccc ccagcccctg gtaatctgta gtctactttt cgtctttttg aatttgccta  22380
ttttaggttc ctcatataag tggaattatg tggtatttgt ccttttgtgt tggcttactt  22440
catttagcat aatgttttca aggttcatct gtgttgtagc atgtatatac aggttgaagc  22500
atccgttatc caaaatggtt gtgaccagaa gtggtttgga tttcagattt tttttttgga  22560
ttttggaata ttcatagata cttaactggt tcagcatccc tcgtccaaaa atccaaaatc  22620
agatggagct cagtggctca tgcttgtaat cccaacacgt tgggtggcca aggcaggagg  22680
atcgcttgag cccaggagtt caaccagcct gagcaacaca agaccctatc tctccaaaaa  22740
aaaaaaaaaa aaaaaaaaga tgaaagaaaa aaaaatccaa aatcaaatgc tccagtgagc  22800
atttcctttt agcatcatgt caggctctaa aagttacagg ttttggagca ttttggattt  22860
cagattttttg gattaacctg cattaatgct caacctatat gaaattttat tccttttttat  22920
ggctgaataa tgttccactg tatgtatata ctacattttg tttatccatt catctgttaa  22980
cagacactta agttatttcc acattttggg tattataaat agtgctgctg cgaacattgg  23040
tgtacatgta tctgtttgag tccctgtttt tagttatttt ggttatatac ctaggaatgg  23100
aattgctgat catatggtaa ttctgtgttt aactttttga ggaactacca ctgttttcca  23160
caatggcatc accattttac attcccacca gcaatgcaca aagatttcag tgtctgtatc  23220
cttgctaaca cttattttcc attttttgag ttttttttgtt ttgttttttt aataatagcc  23280
aatcctaatg ggtatgtggt agcatctcat ggttttgatt ttattttcct gactattgat  23340
gatgttgagc atcttttcag gtgcttagtg gccatttgtc cgtcatcttt ggagcaggaa  23400
caatgtcttt tcaagtcctt tgcccatttt taaattgaat tttttgttgt tgagttgtat  23460
ataacacctt ttttgaagta aaaggtgcac tgtaataatc cagactgtgt ttctcccttc  23520
tcaggattcc tacaggaagc aagtagtaat tgatggagaa acctgtctct tggatattct  23580
cgacacagca ggtcaagagg agtacagtgc aatgagggac cagtacatga ggactgggga  23640
gggctttctt tgtgtatttg ccataaataa tactaaatca tttgaagata ttcaccatta  23700
taggtgggtt taaattgaat ataataagct gacattaagg agtaattata gtttttattt  23760
tttgagtctt tgctaatgcc atgcatataa tatttaataa aaatttttaa ataatgttta  23820
tgaggtaggt aatatccctg ttttataaat gaagttcttg ggggattaga gcagtggagt  23880
aacttgctcc agactgcatc ggtagtggtg gtgctgggat tgaaacctag gcctgtttga  23940
ctccacagcc ttctgtactc ttgactattc tacaaaagca agactttaaa ctttttagat  24000
acatcattaa aaaagaaaac cataaaaaag aatatgaaaa gatgatttga gatggtgtca  24060
ctttaacagt cttaaaagca atcgtgtgta tagcatagaa ttgcttggat tggataaaca  24120
gtggcattat atattttaaa aaataaaagt tttgaaagat tgaagaattt gggcattaca  24180
gttctcttaa atctgacaaa gctgcataaa actattaaaa taatcattat tatactattt  24240
tatattctat ttctttgagg gtttagtttt ccaaaaacta catattaagc aaatgaatca  24300
```

ctcagtggct atgtcatata ataacgagtt agcctagtta taagaagttt aacattttat 24360
ttaagaacat tgttacagca tgtttactgt atagtctagt aatagaggaa aagacatttg 24420
ggtgggtggt agtggtagta tttttataga ggagttacca aatttcagct ctattatcca 24480
agtttaccca gctaatggtg ttcggaaccg ggaatttgag ccaattctga ctctgttgtc 24540
tgctctgctc cttcttttgt gctgtgtctt tgaaagtcac ctaaaattgt gagggaatgt 24600
aatttcaccc caaatttaga gtttatgcac ttgttatatt gaaaatgatt aacatgtaga 24660
agggctttta atggaataag tggtgtagta acttcagtgt tgcctaccta gaaatcaaaa 24720
tctttctagt tgtccacttt gtttttgaa aaagtaatat gaaaattatg ttaatgcttt 24780
aattcaggtt tttgtaaaat atttttatc tttacacatt taacatacgt ttctaaaatt 24840
atagtctgtt atatagcact ttgggtctag aatttttcag tagtttctgt tttactatta 24900
tgatctacct gcatattaac ctattaggtt atagttttac tatacttcta ggtatttgat 24960
cttttgagag agatacaagg tttctgttta aaaaggtaaa gaaacaaaat aactagtaga 25020
agaaggaagg aaaatttggt gtagtggaaa ctaggaatta cattgttttc tttcagccaa 25080
attttatgac aaaagttgtg gacaggtttt gaaagatatt tgtgttacta atgactgtgc 25140
tataactttt ttttctttcc cagagaacaa attaaaagag ttaaggactc tgaagatgta 25200
cctatggtcc tagtaggaaa taaatgtgat ttgccttcta gaacagtaga cacaaaacag 25260
gctcaggact tagcaagaag ttatggaatt ccttttattg aaacatcagc aaagacaaga 25320
caggtaagta acactgaaat aaatacagat ctgttttctg caaaatcata actgttatgt 25380
catttaatat atcagttttt ctctcaatta tgctatacta ggaaataaaa caatatttag 25440
taaatgtttt tgtctcttga gagggcattg cttcttaatc cagtgtccat ggtactgctt 25500
ttggctttgg tttctttcta cattgaaaat ttctcttcaa ttctgagcac atgttaacat 25560
ttagaattca agaggtgggg attttttttt cccatggtta catatatata tatatatata 25620
tatatatata tatatatata tatatatata aagaacaggg caacaaattt ttgcgttttc 25680
tatttcggta gtacttttaa accattatgt catgtttcta ggttaaacgt tgttgtattt 25740
gaagaatttt actttggcag aattttttg aggatgtgtt tatttctgga gaaaggtctc 25800
attaaagaaa gacaataccc agaaagccaa cagaaattct gttactcatt taatgcattt 25860
ttctgacaaa aattattgcc agagagaacc tgaattttgt ttcaaaaatc atctttgttt 25920
taaaaatgac tttttcttca ggtaaaataa aataatttca gttgctatta tttaacctgt 25980
ttgtatgaag agtttaacat ataggaaatg aatacataaa gataggaagg aattaattgt 26040
tatatgtagt catatgtctc ttaatgacag ggatactttc taagaaatac attgttaggt 26100
gattttgtca ttgtgcaaac atcatagaat atacttacac aaaccttggt agtataacct 26160
actatacacc tgggatatgt agtatagtct cttgccccag ggatacaaac ctgtacagta 26220
tgtaactgta ctaatgacta taaggcaatt gttaacacaa tggtaagttt tgtgtgtcta 26280
aacctacact tgggctaccc taagtttata tatttttta aatttctgtt caataataaa 26340
ttaaccttac tttactgtaa ctttttaaac tttttaattt ttcctaacat tttgactttt 26400
gtaatacagc ttaaaacaca cattatacag ctatacaaat ttttctttcc ttatatcttt 26460
attctgtaag ctttttcca tatttaaaat tttttgtttg tttttactta ttaaactttt 26520
ttgttaaaaa ctaagacatg catgcacatt aacctaggcc tacacagggt caggaccatc 26580
aatatcattg tcttccactt ccacatcttg tcccactgga agatcttcag gggcagtaac 26640
acacgtggag ctgtcatctc ctataataac attgccttct tttggaatac ctcctgaagg 26700
acctatccaa ggctgtttat agttaacttt ttttttttt ttttttttt tttagtaaat 26760
aggaggagta cactataaaa taacaatata ggtgctatac cattatacaa ctgacagtgc 26820
agtaggtttg tttacaccag catcaccaca aacacgtgag caatgtgtcg tactacagtg 26880
ttaggatggc tataacatca ctaagcaata ggaactttta aactccatta taatcttatg 26940
ggaccactat cacatatgca atctcctgtg gaccaaaatg tcattatgtg gtacatgact 27000
gtactaagaa attgatccat ctatattcca tcaatttgtt tagggctttt tctggttaca 27060
tttacctgtg agcccagaaa accagttttg tagaaattaa cttctgtaat gctaggagtt 27120
aaaaaaaatt gctgaacaac ttttacattg ttaaacattt aaaaacaagc gttctagaag 27180
tttatcaaat ttcataaagg tgcaaaaatg taaatgtaaa tcattatcca gctaatatat 27240
atgttgtatt tccctagtag gagagcatat gtacctcttc ctagttatac aaatttgata 27300
tatagtaaag aaacagtaaa ttctacttca agtcattttg ggaggattaa aaactgaatt 27360
tctctagttt gaccattgta cagatttatc tggcaatttt actaaaacct gatttatagg 27420
ttaaacttgg tgtatatcat atatcacttt actttagagg aattaagatt tcacataaat 27480
ccatttccag gttccaaaga ccaggaagag gcttggtttt tgtttttctt tttactgtct 27540
ttacagtctc cttgactttt cttaggagag aaggtactga gaaaacatga ttctaatatt 27600
tattattttt tcttccaaca ttttcttatg aaacattttc aaatacaaaa ttgagtttta 27660
tttaaaacat ttgcaaatat actacctaga ttctaccatt gttgttttat atttgcttta 27720
cttacaactt ttaaaagatg ctttttatac cactgaacat tttagcttac atttcacaaa 27780
gaaaagaaaa aatttaagag actttgcata atgttttaag gggttgcagt aaagaagtgc 27840
ttcttatatt ttcttatgca tacaaatcag ctgggcttat taaaatccag attctaattc 27900
agaaggttta ggtggggacc gagtctgcat ttctaacaaa ctcctaggtg gtatttttct 27960
tggtacttgg accatacttt gagtagaaaa gcagtagagg acataaaaag agtcttgtta 28020
gtcccacttt gttgctgtcc acttctcatt tgataatatc ctaaaatagc tgtgtctcct 28080
ttttggtggt tgtatgatta ctacctcaga agtactaatt gattcttgct atttgacctt 28140
aatactttaa tataacacag cattcatatt tgatcagaaa actatctggc ttccttttat 28200
aagagatttt taggttttat acagttttgt ggccttgggt tttttgtttt gatttgtttt 28260
tttgaaggta tataatatgt aagtagataa acaaatttga tttgtagaca tttttatgtg 28320
gatcatctaa ttaaaaatgg agggatacag tatgaaagaa tacttgtact tcttaacaga 28380
gcactcaacc tttcttttac atcctgtttc actgatgtta ttatgtaatt tatgttgcta 28440
aactataaat tagatattta atttctgttc tttgatttcc ttttattatt aaatggactt 28500
gttgatttgc ctagaaatta atttgccttt caaaagtctt attaatcttc ctccgttgaa 28560
attaatttga tatttgcatg cttctggaag actttaaaga gctattccga gtaactgtag 28620
agattataaa atgaaatatg ggaattttaa taaattttac atctccagtt actggtgaaa 28680
atgtcaagtc ctcctttctg cagagtattt tgttactcat ctgttattca gcttatttat 28740
ttatttattt atttatttat ttttctttct ttcttgtttt ttttttttga gacggagtct 28800
tgctttgtcg cccaggctgg agtacagtgg tgggatcttg gctcactgca ggctccgcct 28860
cccgggttca caccattctt ctgcctcagc ctcccaagta gctgggacta caggcacccg 28920
ccaccatgcc ttgctaaatt tttgtatttt tagtagagac gggtttcact gtgttagcca 28980
ggatggtctc gatctcttga cctcgtgatc cacctgcctc ggcctcccaa agtgctggga 29040
ttacaggcat gagccaccgc gcctggccct tatttgtttt ttaaacaaaa ttagtgtgca 29100
tatccttgtt gtattttatc ggcaagttgt tttatgccct aacttttggg gtcttgatca 29160
tgagcctaaa acacgtaaac acccaaaaag aattatattc cggttaaagg aacaaaacat 29220
tcatttagaa gttctcatcc atgtaaatca gaggctggca aatattttct gtaaagggcc 29280
aagatagtaa atgttttagg ctttgagggc cacaagtggt atctgttgca ttttttttta 29340
attatgaccc tttaaaatgc aaaaatcgtt gttagcttgt gcatagtata aaaataggct 29400
ggccgcatgc tgtggctcat gcctgtaatc ccagaaatga ggtgggaagc cgaggtgggc 29460
acaccacctg aggtcaggag ttcgaggcca gcctggccaa cgtggttgaa accccgtctc 29520
tactaaaaat acaaaactta gccaggcgtg gtggcgggtg cctgttatcc tggctactca 29580
aggggctgag gcagtagaat tgcttgaacc tgagaggcag aggctgtagt gagcccagat 29640
caagccagtg cacaccagcc tggacgaccg agcgagactc tgtctcaaaa aaaaaaaaaa 29700
aaggctgtgg ctgcatttgg tccattggct gtaatatgct gattcctaat tctctgggta 29760
actttagtgt ttgattagct actagaagtt aggttaaact tttgtatttt acaggctaac 29820
tttaataatc ttaaagtaaa acttaacata gttcatggaa aggaaataga aattttaccc 29880
tagtactctt ttttttttt ttttttttt ttgaggcaga gtctccctct gtcacccagg 29940
ctggagtgca gtggtgggat cttggctgat tgcaacctcc tcctcctggg ttcaagcaat 30000
tcttgtgcct cagcctcccg agcagctggg actacaggca cgcaccacca cacctgactg 30060
atttttgtat ttttagtaga gacagggttt cgccatgttg gccaggctgg tcttgaactc 30120
ctggcatcaa gtgatcctcc catctgagcc tcccagtgtg ctgggattac agacgtgagt 30180
cactgtgcct ggtctctagt attttttttt tttttgagac ggtctcactg ttgccaggct 30240
ggagtgcagt ggcgcgatcc tggctcactg caacctccgc ttcccggatt caagcgattt 30300
tcctgcctca gcctcctgag tagctgggac tatgggtgca caccaccacg cccagctaat 30360
ttttgtattt ttagtagaga cggggtttca ccatgttggc caatatggtc tcaatctctt 30420
gacctcgtga tctgcccgtc tcggcctccc aaagtgctgg gattacaggc gtgagccact 30480
gtgcccagct gtacttttta agataagaat tgcagggtat atatttttac caacttaata 30540
acttataatt ttaaaaagct aattacttgg ctagaatata atgcgttaca tattctttac 30600
actcagttca gtccatatct gaaaggcaaa tagaattatt ttctgctagt acattgtgta 30660
gtccctatgt tcctagtgta taaggactgt tacctagttc acatttatct gggttgttga 30720
cagattttcc tggtcccttt ggacagtgca tggccatgtt ggcaaaagct gtcaaaattg 30780
aaacattgac accatgagaa ttgtgtgttt tccagtctgc taaaatcaaa agtgggaggg 30840
ttcagtaagg tgaataacag aagcagagtt ttcggggtat ctgttactcc tcattcggct 30900
tttctgctct ctgggggtct caatttaaat ataatgtgaa aattagtttt acgaacctaa 30960
aaatgttgag tgattcattt cctggttttg ttgttaattt ctagatattt aaattaattg 31020
ttagaagaac cccgttaaag aatgctttgc aaaacaacct ccttatgtgc tatgtctctg 31080
tttaatagta gttgagtttg tgtacatgag atcaatattt tgaactatag ctttttatga 31140
gttaaaaatt gacggaacag ttactgtgca cttgctgtgc accatggtag tctcccaagt 31200
agtggttttt ctgcatttca atagtacatg agataggctg tgggtggcaa ggtttcttga 31260
gaaagtgagg gatgcacagt tgggttttag aatacatctt gttcctccat gcccttcccc 31320
accaaaaggc tggtagtctt gcatttgtat atagttaggg tatttgatgt gttgcttcct 31380

-continued

```
tgacagagtt ttgcaagaat ttgcagattt aacaggaaca aaaacttact taaaacaaaa  31440

tctcttagta aaagcatagt ctagcaagat ttagaatgat actttggcta acagtacttt  31500

ctctatatgg agtgctttgt ttccatagcc tcacaagtat gttttcagat aatagttgag  31560

ttgaaaatgt tgtcaatctc ttgattttaa aaaatttaca tatttaaagt tgtatacttt  31620

tgttcctacg tattttcagt tgttcttaaa gtttaataag tgacatttga aaatgagtat  31680

atgtgtataa aaacaaaagt aggctaggca cggtggctca tgcctataat cctagcactt  31740

tgggaggctg aggcaggcgg atcacaaggt caggagtttg agaccagcct gggcaatatg  31800

gtgaaacccc cctctactaa aaatacaaaa attagctggg tgtggtggtg catgcctgta  31860

gtcccagcta ctcaggaggc tgaggcagga gaatcgcttg aacccggagg tggcggttgc  31920

agtgagccga gattgcacca ctgcagtcca gcctgggcgg cagagcgaga ctccatctca  31980

aaaaaaaaaa acaaaaaaag aaaaagttaa aaaaaaacaa aaaacccccca caaaatgagt  32040

atatgtggca acaagtccta ttctcaaaaa aattattgtg tgctagttaa gagcttaatg  32100

agtagccagt cggtattaaa tatctgtttc agctatattt tatctttaaa aattatctac  32160

agattttgga atgtgaaaaa ctagtgtttt gtttcatagg tatatactgt aggcatttta  32220

aaaataagag ccagtgccag tggtttacag tgtacacaag gataatgttc tcatgttctc  32280

ttgatgtcag tatgacttta aagcatatta tcaagaaata actaagtctg aaaaactgtg  32340

gtaaataact ggtactctaa aacctaagtt tcttattact aaaaataaga aatggtaaaa  32400

gtcaccctgt gctgttaatt atatgagcca ctgaggtcct gacactgaat tcttggtggt  32460

ggataataat ctcttctttt taattattgg cttccaattc tctctgcatt gctggaaaca  32520

aaaatcatat atttcactat tggtggtggg gatgctgtca ctgaaaaagt agacacattc  32580

atattgattt tagaaataag ttaaaatcaa aatttgcttc tgctaaatta gtagaggacc  32640

aatactgttt ttctccttca tagtatgttt tggtacttct acattgacat tataactttt  32700

tttttttaa acagaaatag aagtttaca                                    32729
```

```
<210> SEQ ID NO 12
<211> LENGTH: 188
<212> TYPE: PRT
<213> ORGANISM: Artificial Sequence
<220> FEATURE:
<223> OTHER INFORMATION: KRAS Wild-type protein Isoform 2B

<400> SEQUENCE: 12

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125
```

```
Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185


<210> SEQ ID NO 13
<211> LENGTH: 5306
<212> TYPE: DNA
<213> ORGANISM: Artificial Sequence
<220> FEATURE:
<223> OTHER INFORMATION: KRAS Wild-type  mRNA

<400> SEQUENCE: 13

ctaggcggcg gccgcggcgg cggaggcagc agcggcggcg gcagtggcgg cggcgaaggt     60

ggcggcggct cggccagtac tcccggcccc cgccatttcg gactgggagc gagcgcggcg    120

caggcactga aggcggcggc ggggccagag gctcagcggc tcccaggtgc gggagagagg    180

cctgctgaaa atgactgaat ataaacttgt ggtagttgga gctggtggcg taggcaagag    240

tgccttgacg atacagctaa ttcagaatca ttttgtggac gaatatgatc caacaataga    300

ggattcctac aggaagcaag tagtaattga tggagaaacc tgtctcttgg atattctcga    360

cacagcaggt caagaggagt acagtgcaat gagggaccag tacatgagga ctggggaggg    420

ctttctttgt gtatttgcca taaataatac taaatcattt gaagatattc accattatag    480

agaacaaatt aaaagagtta aggactctga agatgtacct atggtcctag taggaaataa    540

atgtgatttg ccttctagaa cagtagacac aaaacaggct caggacttag caagaagtta    600

tggaattcct tttattgaaa catcagcaaa gacaagacag ggtgttgatg atgccttcta    660

tacattagtt cgagaaattc gaaaacataa agaaaagatg agcaaagatg gtaaaaagaa    720

gaaaaagaag tcaaagacaa agtgtgtaat tatgtaaata caatttgtac tttttcttta    780

aggcatacta gtacaagtgg taatttttgt acattacact aaattattag catttgtttt    840

agcattacct aatttttttc ctgctccatg cagactgtta gcttttacct taaatgctta    900

ttttaaaatg acagtggaag tttttttttc ctctaagtgc cagtattccc agagttttgg    960

tttttgaact agcaatgcct gtgaaaaaga aactgaatac ctaagatttc tgtcttgggg   1020

cttttggtgc atgcagttga ttacttctta tttttcttac caattgtgaa tgttggtgtg   1080

aaacaaatta atgaagcttt tgaatcatcc ctattctgtg ttttatctag tcacataaat   1140

ggattaatta ctaatttcag ttgagacctt ctaattggtt tttactgaaa cattgaggga   1200

acacaaattt atgggcttcc tgatgatgat tcttctaggc atcatgtcct atagtttgtc   1260

atccctgatg aatgtaaagt tacactgttc acaaaggttt tgtctccttt ccactgctat   1320

tagtcatggt cactctcccc aaaatattat atttttttcta taaaaagaaa aaaatggaaa   1380

aaaattacaa ggcaatggaa actattataa ggccatttcc ttttcacatt agataaatta   1440

ctataaagac tcctaatagc ttttcctgtt aaggcagacc cagtatgaaa tggggattat   1500

tatagcaacc attttggggc tatatttaca tgctactaaa tttttataat aattgaaaag   1560

attttaacaa gtataaaaaa ttctcatagg aattaaatgt agtctccctg tgtcagactg   1620

ctctttcata gtataacttt aaatcttttc ttcaacttga gtctttgaag atagttttaa   1680
```

-continued

```
ttctgcttgt gacattaaaa gattatttgg gccagttata gcttattagg tgttgaagag   1740
accaaggttg caaggccagg ccctgtgtga acctttgagc tttcatagag agtttcacag   1800
catggactgt gtccccacgg tcatccagtg ttgtcatgca ttggttagtc aaaatgggga   1860
gggactaggg cagtttggat agctcaacaa gatacaatct cactctgtgg tggtcctgct   1920
gacaaatcaa gagcattgct tttgtttctt aagaaaacaa actctttttt aaaaattact   1980
tttaaatatt aactcaaaag ttgagatttt ggggtggtgg tgtgccaaga cattaatttt   2040
ttttttaaac aatgaagtga aaaagtttta caatctctag gtttggctag ttctcttaac   2100
actggttaaa ttaacattgc ataaacactt ttcaagtctg atccatattt aataatgctt   2160
taaaataaaa ataaaaacaa tccttttgat aaatttaaaa tgttacttat tttaaaataa   2220
atgaagtgag atggcatggt gaggtgaaag tatcactgga ctaggaagaa ggtgacttag   2280
gttctagata ggtgtctttt aggactctga ttttgaggac atcacttact atccatttct   2340
tcatgttaaa agaagtcatc tcaaactctt agtttttttt ttttacaact atgtaattta   2400
tattccattt acataaggat acacttattt gtcaagctca gcacaatctg taaattttta   2460
acctatgtta caccatcttc agtgccagtc ttgggcaaaa ttgtgcaaga ggtgaagttt   2520
atatttgaat atccattctc gttttaggac tcttcttcca tattagtgtc atcttgcctc   2580
cctaccttcc acatgcccca tgacttgatg cagttttaat acttgtaatt cccctaacca   2640
taagatttac tgctgctgtg gatatctcca tgaagttttc ccactgagtc acatcagaaa   2700
tgccctacat cttatttcct cagggctcaa gagaatctga cagataccat aaagggattt   2760
gacctaatca ctaattttca ggtggtggct gatgctttga acatctcttt gctgcccaat   2820
ccattagcga cagtaggatt tttcaaacct ggtatgaata gacagaaccc tatccagtgg   2880
aaggagaatt taataaagat agtgctgaaa gaattcctta ggtaatctat aactaggact   2940
actcctggta acagtaatac attccattgt tttagtaacc agaaatcttc atgcaatgaa   3000
aaatacttta attcatgaag cttacttttt tttttggtg tcagagtctc gctcttgtca    3060
cccaggctgg aatgcagtgg cgccatctca gctcactgca acctccatct cccaggttca   3120
agcgattctc gtgcctcggc ctcctgagta gctgggatta caggcgtgtg ccactacact   3180
caactaattt ttgtattttt aggagagacg gggtttcacc ctgttggcca ggctggtctc   3240
gaactcctga cctcaagtga ttcacccacc ttggcctcat aaacctgttt tgcagaactc   3300
atttattcag caaatattta ttgagtgcct accagatgcc agtcaccaca caaggcactg   3360
ggtatatggt atccccaaac aagagacata atcccggtcc ttaggtagtg ctagtgtggt   3420
ctgtaatatc ttactaaggc ctttggtata cgacccagag ataacacgat gcgtatttta   3480
gttttgcaaa gaaggggttt ggtctctgtg ccagctctat aattgttttg ctacgattcc   3540
actgaaactc ttcgatcaag ctactttatg taaatcactt cattgtttta aaggaataaa   3600
cttgattata ttgttttttt atttggcata actgtgattc ttttaggaca attactgtac   3660
acattaaggt gtatgtcaga tattcatatt gacccaaatg tgtaatattc cagttttctc   3720
tgcataagta attaaaatat acttaaaaat taatagtttt atctgggtac aaataaacag   3780
gtgcctgaac tagttcacag acaaggaaac ttctatgtaa aaatcactat gatttctgaa   3840
ttgctatgtg aaactacaga tctttggaac actgtttagg tagggtgtta agacttacac   3900
agtacctcgt ttctacacag agaaagaaat ggccatactt caggaactgc agtgcttatg   3960
aggggatatt taggcctctt gaatttttga tgtagatggg cattttttta aggtagtggt   4020
taattacctt tatgtgaact ttgaatggtt taacaaaaga tttgtttttg tagagatttt   4080
```

```
aaagggggag aattctagaa ataaatgtta cctaattatt acagccttaa agacaaaaat   4140

ccttgttgaa gtttttttaa aaaaagctaa attacataga cttaggcatt aacatgtttg   4200

tggaagaata tagcagacgt atattgtatc atttgagtga atgttcccaa gtaggcattc   4260

taggctctat ttaactgagt cacactgcat aggaatttag aacctaactt ttataggtta   4320

tcaaaactgt tgtcaccatt gcacaatttt gtcctaatat atacatagaa actttgtggg   4380

gcatgttaag ttacagtttg cacaagttca tctcatttgt attccattga ttttttttt   4440

cttctaaaca tttttcttc aaacagtata taacttttt tagggattt tttttagac   4500

agcaaaaact atctgaagat ttccatttgt caaaaagtaa tgatttcttg ataattgtgt   4560

agtaatgttt tttagaaccc agcagttacc ttaaagctga atttatattt agtaacttct   4620

gtgttaatac tggatagcat gaattctgca ttgagaaact gaatagctgt cataaaatga   4680

aactttcttt ctaaagaaag atactcacat gagttcttga agaatagtca taactagatt   4740

aagatctgtg ttttagttta atagtttgaa gtgcctgttt gggataatga taggtaattt   4800

agatgaattt aggggaaaaa aaagttatct gcagatatgt tgagggccca tctctccccc   4860

cacaccccca cagagctaac tggggttacag tgttttatcc gaaagtttcc aattccactg   4920

tcttgtgttt tcatgttgaa aatacttttg catttttcct ttgagtgcca atttcttact   4980

agtactattt cttaatgtaa catgtttacc tggaatgtat tttaactatt tttgtatagt   5040

gtaaactgaa acatgcacat tttgtacatt gtgctttctt ttgtgggaca tatgcagtgt   5100

gatccagttg ttttccatca tttggttgcg ctgacctagg aatgttggtc atatcaaaca   5160

ttaaaaatga ccactctttt aattgaaatt aacttttaaa tgtttatagg agtatgtgct   5220

gtgaagtgat ctaaaatttg taatattttt gtcatgaact gtactactcc taattattgt   5280

aatgtaataa aaatagttac agtgac                                        5306
```

```
<210> SEQ ID NO 14
<211> LENGTH: 189
<212> TYPE: PRT
<213> ORGANISM: Artificial Sequence
<220> FEATURE:
<223> OTHER INFORMATION: KRAS Wild-type protein Isoform 2A

<400> SEQUENCE: 14

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140
```

Ser Ala Lys Thr Arg Gln Arg Val Glu Asp Ala Phe Tyr Thr Leu Val
145 150 155 160

Arg Glu Ile Arg Gln Tyr Arg Leu Lys Lys Ile Ser Lys Glu Glu Lys
165 170 175

Thr Pro Gly Cys Val Lys Ile Lys Lys Cys Ile Ile Met
180 185

<210> SEQ ID NO 15
<211> LENGTH: 25
<212> TYPE: PRT
<213> ORGANISM: Artificial Sequence
<220> FEATURE:
<223> OTHER INFORMATION: KRAS fragment

<400> SEQUENCE: 15

Gln Tyr Arg Leu Lys Lys Ile Ser Lys Glu Glu Lys Thr Pro Gly Cys
1 5 10 15

Val Lys Ile Lys Lys Cys Ile Ile Met
20 25

<210> SEQ ID NO 16
<211> LENGTH: 24
<212> TYPE: PRT
<213> ORGANISM: Artificial Sequence
<220> FEATURE:
<223> OTHER INFORMATION: KRAS fragment

<400> SEQUENCE: 16

Lys His Lys Glu Lys Met Ser Lys Asp Gly Lys Lys Lys Lys Lys Lys
1 5 10 15

Ser Lys Thr Lys Cys Val Ile Met
20

<210> SEQ ID NO 17
<211> LENGTH: 12303
<212> TYPE: DNA
<213> ORGANISM: Artificial Sequence
<220> FEATURE:
<223> OTHER INFORMATION: NRas Genomic Sequence

<400> SEQUENCE: 17
ggggccggaa gtgccgctcc ttggtggggg ctgttcatgg cggttccggg gtctccaaca 60
tttttcccgg ctgtggtcct aaatctgtcc aaagcagagg cagtggagct tgaggtaagt 120
ttatctcatg catagtgttc ggctttgggc tgtggaatgt tcaggcgttt cactgatgcc 180
agaaatggag cagaatctat cagctggaga caaaggcctt gggcgggggt ccttccattt 240
ggtgcctacg tggggagatc tttggagaca gaagggagaa tgggaaggag ttgcggcctg 300
gaggcttcct gctagagctg agaagccttc ggggagtaat aggaaggggg atttccattg 360
cttaggctga gggcggggcc caaggactgt tgaaaaatag ctaaggatgg gggttgctag 420
aaaactactc cagaagtgtg aggccgatat taatccggtg tttttgcgtt ctctagtcac 480
tttaagaacc aaatggaagg tcacactagg gttttcattt ccattgatta tagaaagctt 540
taaagtactg tagatgtggc tcgccaatta accctgatta ctggtttcca acaggttctt 600
gctggtgtga aatgactgag tacaaactgg tggtggttgg agcaggtggt gttgggaaaa 660
gcgcactgac aatccagcta atccagaacc actttgtaga tgaatatgat cccaccatag 720
aggtgaggcc cagtggtagc ccgctgacct gatcctgtct ctcacttgtc ggatcatctt 780
tacccatatt ctgtattaaa ggaataagag gagagaaagt aaaaagttat tttgggtata 840

```
cattcagtta tgcaataagc ttaacgtgtt tatagagaac agttcatttt tattagctgc    900
tgaagtttct aaaacctgtc cagtttttaa cagttctgta aactattgca aactcagtgt    960
tgagttcatt catgagtttc ttcatatata acagctctat tacatgagaa acacaggcca   1020
tagtagcgag actgtctgat tgtatgggag ataataggat ggagataaag gattcagaga   1080
tgagtgttct tcaatattta tttattagct agttgaagca gctgagacca gatgattgga   1140
gtagcaagaa cttgagattt ttagtcttta tgcctaggat tttggtccct gtttgcagtt   1200
tatttagttg tgtgatattg agcaactgaa tctctcccaa cctcattttc ctcatgtttt   1260
aaattaccat aaacttgtcc tgcctaccac acagggatgt tatggaaagt taaataatat   1320
atttaagtta tttatgaatg gtaaagcact atgtaatagt acttagggat tctattgtta   1380
ttatgagagt tcatggtaca gattgtcttc agtaagtggc acctaaggct ctttaaataa   1440
agggttttgc cggacacggt ggctcacgcc tgtaatccca gcactttggg aggctgaggc   1500
aggcggatca caaggtcagg agttcaagac cagcctgatc aacatggtga aaccccgtct   1560
ctactaaaaa tacaaaaatt agctgggtgt ggtggcaggc acctgtaatc ccagctactc   1620
aggaggctga ggcaggagaa tcgcttgaac cagaggcaga gggtgcagtg agccgagatc   1680
acaccacaga cctccagcct gggcaacaga gcgagacttc gtctcaaaaa ataaataaat   1740
agataaataa ataaagggtt ttgtaatttt gttcagttta gaaatgccta actttagaga   1800
ttattttaat caacacctgg cctccctacc atctggctac tcgtgtttaa ttgatgaaaa   1860
ctaactctaa tgtagccact ataaaaaatt ggttgctaac ccttggcaaa atctttattt   1920
tgagcttaac agctttaata ttttacatga aatgtttaat attttaatta aatattttta   1980
aatgtttgat ttattgagca atttacataa gtaaaataca taaattttat gtctacagcc   2040
cagtgctttt tgcgtttcta tatagtcatg tagctaccac ccagataaca gtatagagca   2100
cttccagtac tccagagagt tctccaagtg tgatgacatt aaaatacaag taaaagtcct   2160
gttgccataa aaccaaaatg aaagtatttt ttatatgatc tatgcatgtt tgtcttcctg   2220
agaaattaaa cataactata ccttgtttgg aacctttaag aatttgattc aggaatattt   2280
cccaaaggta catctgtcat gataaaaaaa aaaccttctc tgaaacaaag gtatttgtat   2340
atttagtcat aaacacaaat gatgtatata gggccaggtt ataattggtg gaggtatgtt   2400
tagatttctt taagtaaaat aaacagcaca aataaaacag tccagttcat agcttagtga   2460
aatacactgg gtacttaatc tgtagcctcc tggctgcagt agagttgtca tttgagttac   2520
tgtgttttct taatcttttc caggaacaca gtgaccatat ttcttttctg caggcatata   2580
gaatttggtg ggttttcttt tatgtagggt gatattggat actttttgtt tgtgattata   2640
tattagcaat ttgagggaca aaccagatag gcagaaatgg gcttgaatag ttagatgctt   2700
atttaacctt ggcaatagca ttgcattccc tgtggttttt aataaaaatt gaacttccct   2760
ccctccctgc ccccttaccc tccacacccc caggattctt acagaaaaca agtggttata   2820
gatggtgaaa cctgtttgtt ggacatactg gatacagctg gacaagaaga gtacagtgcc   2880
atgagagacc aatacatgag gacaggcgaa ggcttcctct gtgtatttgc catcaataat   2940
agcaagtcat ttgcggatat taacctctac aggtactagg agcattattt tctctgaaag   3000
gatgatcttt gtgttctgaa tctttatggg gaaatgaggt taccacacta gggaagatag   3060
agctttttaa ttatgggaag agttggtttt aggttgtttg acattgagaa tctagggtaa   3120
ttactgaaag ttaatactgg aatttatttt acataatata ctgttactat aaagtttgat   3180
```

aatacataag tgaagcttgc tactgggaat gacttggaac cagagttgtt gtaattagag 3240
atcacgaagg aatttcagag aggaaaacat ctccaagaaa catctttcag tatgtaatgg 3300
aaaagatagg ccaggcacag tggctcacac ctggaatgtc agtgctttgg gaggccaagg 3360
cgggaggatc actttcagcc caggagttgg agaccagcct gggcaacaga gcaagaccct 3420
gtctctacaa aaataaaaat aaaaaaatta gtcacacatg gtggcagcta ctcgggaggc 3480
agaggtggga ggatcacgtg agctcaggag gtcgaggcat gctcactcca ctgcactgct 3540
gcactccagc ctaatcaaca gagcaagatt ctgtctccaa aaaaaataaa aaataaaatg 3600
ataggagtaa gcaaatagga agtccataaa gatgaaaaca aagcaaggga acataaagat 3660
agactttgtc catagaacca taaagtttca aagctagatt ggaccataaa aattctagta 3720
caatattctt attttgcaga atcagaaaca gagttcagaa tgtcgtttgt taggttttgg 3780
agtcaggatt gttattagta gcagagccag gaccaaaaac ccaaagctcc tttttcttag 3840
cacagtgttc ttaaacagaa taatataatg gttaagaatg agaactctgc ctggattgaa 3900
acctagctct gtttattagc gacgtgactc aggggctatg tggctttcct aacctataat 3960
atggaaataa taatacctac ctcatagagt tgtgaagatt acagttttaa taaatacgca 4020
aatcactcag aatagtgcct ggcacacagt aaatgctact taagtgttct gcctaaaggc 4080
ttgagtcttg gcttattttc tatccatgtg aagatgtctg ctctcaaaag cagattggtc 4140
caacactgaa ttcaagtgtt cttttcctaa cctgttgtac ttcccatttt tttttgtct 4200
aaaagtaata gcagtactta ataaaatgcc cacacttggc atgcatctaa taaatgtttt 4260
ttgaatttct agaagtcatt tttcttcttt cttacaagaa atttattcat ttttctatat 4320
gccttagctc aaaccaaaga gtatttaaaa catcttatga aaatgcatat agtagagcaa 4380
gataagatta atgaaaaata ggcttaagtg agaccaaaaa aataagggta aaataaacaa 4440
atttaggagt gagcatattc tgtgattgtg catgaagttc cagtggcttt ctaaaggtgg 4500
actacaaatt tggtcactgt tgtgaaaagg aaagtagcca gctgaaagat tcagtatctg 4560
tatgctgaaa gccgttaagt tgctcggact agaaggaaat tttcccatgg atcctcaaag 4620
aggcttgttt aatgtaaaaa tcagtagtaa cctgacagtg acatggtcca ggtactttag 4680
gctgtcttat cccttaatgt aggctattac catcaagcac agttttgcaa atagccagtg 4740
gaatgtagtt cagatacatg actttgtggg taatccaggg gtagagacta aaacagtact 4800
gtgcagtatg tggttattta cagttaatta agattaaata aaatttaaaa attagttcct 4860
tgactaccaa atgctcaata gccactagta ggtaccatgt tgaacagtac agatatagac 4920
catttccatc atcacataaa gtactgttgg attgtgttgg tcaagacaat ctaaagcaat 4980
tgtttcccag gtgtgctgtg tggtgtgcct tacatgtcat tgaaaggggt gctgtcagga 5040
gttctagatg cttcagcctc cctttactaa gagcagttct tatgttttct attttatcgc 5100
ttgggcttcc agatacaatg ttttgtttta ggtttgtttt ttttgtttgt ttgttttttt 5160
ttttttgaga cggagttttg ctctggttgc ccaagctgga tggagtacgg tggtgcgatc 5220
gcggctcact gcaacctccg cctcccgggt tcgagagatt ctcctgcctc agcttcccga 5280
gtagctggaa ttacaggcgt ccaccaccat gcctgactaa ttttttttgt atttttagta 5340
gacttggggt ttcaccatgt tggccgggct ggtttcaaac tcctgacctc aggtgatcca 5400
cccgcctcgg cctcccagag ggctgggatt acaggtgtga accaccgtgc ccggcctgtt 5460
ttagtttttt agagatggag tctccctctg ttgcccaagc cagagtgcgg tggcatgaca 5520
ctctcagggt tcaacctctc agggatcaag ggatcctccc acctcagctt cctgagtagc 5580
tggaaccaca ggcacatgtg ccaccatgcc cagctaattt ttgtattttt tgtagaagca 5640
aggtttcacc atgttgccca ggctggtctc ggactcctag gtcaagtgat cctcccacct 5700
caatctccta gagtgctaag actataggcg ggagtcacca tgcccagctt catctacaat 5760
ttatttgaag aaaatgtttg agcaccaccc atcttgaaaa gtgatagact gccttccatt 5820
aaatactgtc acacctagtt atttagcagc agtgagcttc actttttata ctttagacct 5880
taatctaaag ggtgatttct agttgccagt taaatccaga gccaagctct ttggagaatc 5940
caggagcctc actaggtcat gtatcaggat aaaataccca tccactccca ttagaaggtg 6000
agcttgtact tatggcttcc tgatggctgc tgcaacaagt ctaaagcagt ctccttagta 6060
tacaatgtct tctctaagtg gtagaaaaaa gcaaaaatac tacaagttaa tagggctaca 6120
taaaatttgc tagtttcttt tttgccctag ccatttattc cttcctgaaa tcttgtctct 6180
ctctcgctct ctctttctct cgctctcact ttctttctct ttttcttttc tcttttcttt 6240
tctttcttcc ctttctttc tttctttttt cctgttgccc aggctggagt gcagtggaac 6300
aattatggct cactgcagcc ttgacctttc tggacccagg tgatcctccc acctcagtct 6360
cccaattagc tgggactaca ggcatgcgcc accacaccca gctataatat atattgtata 6420
tatatttttt atttataaat atatataaat atatatttat atgtgtaaat tatatatatt 6480
tatatattat aaattatata taaatatata tttatatata atatatataa tatatattta 6540
tttttatata ttttatatat attttttggg gggggttggg ggggatggag tctcactctg 6600
tcgcccaggc tagagtgtag tggcgtgatc ttggctcact gcaatcttcg cctcccaggt 6660
tcaagcgatt ctcctgcctc agcttcccga gtagctggga ctataggcgc ctgccaccac 6720
acctggctaa tttttgtatt tttagtagag atggggtttc accatattgg ccaggctggt 6780
cttcaactcc tgaccttgtg atctgcccac ctcaacctcc caaagtgctg ggaatacagg 6840
catgagccac tgcacccagc ctaatctttg tattttttg tagagaccgg gttttgccat 6900
gttgcccagg ctaatctcaa actcctgggt tcaagcagtc tgccctcctc agcctcccaa 6960
agtgctgaga ttgcaggcat gagccactgt acccagccta atcttgtttt tcttatgttc 7020
tgataatata ttcccgtttt tagggagcag attaagcgag taaaagactc ggatgatgta 7080
cctatggtgc tagtgggaaa caagtgtgat ttgccaacaa ggacagttga tacaaaacaa 7140
gcccacgaac tggccaagag ttacgggatt ccattcattg aaacctcagc caagaccaga 7200
caggtatggt acagctttca gcatttgtgc aagagtttgc atcagttgat taactctggt 7260
agagatgtga tccatattca tattctttgt tgttatgcat ttttttcatt tttatttttt 7320
tattttttat tttttttag gcagagtctc actctatctt ctaagctgga gtgcagtggt 7380
gtgatctcag ctcactgcag cctctgtctc ttgggttcaa gtgattctcc tgcctcagcc 7440
tcccaagtag ctgggactac gggcacatca tcatgcccgg ctaatttttg tacttttagt 7500
agagacaggg ttttaccatg ttgcccaggc tggtctcgaa ctcctggcct caagcaatcc 7560
tcccacctgg gcctcccaga gtgctgggat tacaggtgtg agccaccacg cccagcctgt 7620
tgttaggcat ttttagtagt gttctttttc ttaacgcttg tttaaaccca aaatgaactt 7680
actaatattc tgttatggca tgtttactcc tgcattaaca tccacaaata tttcttggga 7740
agatccttga ctaaaaatat ttataaacat tagttatttc tctgtcaaca ccagcccgtt 7800
tatggcttaa gcctcctgaa tggagtcttt agtttaatgt agttttgttc cgtgtttctc 7860
acattaccct tttcctttgc atgaatgttt atttggcaaa atgtgccatt tttatatcag 7920
cctgttcttg tgattcaata ggaatgtgaa atttagtgtt ctcttcctta aatcaccata 7980
ttttatttta tcagctattc gtttagtaat tggaatctta tgtccacata aagagataca 8040
aatgcaagag agcttataat ttggattgtg tccgttgagc tagctctctc attttttttc 8100
attttttcct tttatagggt gttgaagatg ctttttacac actggtaaga gaaatacgcc 8160
agtaccgaat gaaaaaactc aacagcagtg atgatgggac tcagggttgt atgggattgc 8220
catgtgtggt gatgtaacaa ggtgagcata tggtttcttg gcataattac aaatcttagt 8280
atatagtatt gggcaatttg gaggagtgct ggtgttattg tctatatgtt ttttgagttt 8340
ctgcctatcc tcttctgcac attttccata tgacaccctt tctgaaagta ctgaggtcta 8400
aagtgtttaa aacatttgat tattccacag gtatctttat atttttggta acattagaaa 8460
ttataagaca ttatttatga aatgtaggca taccctattc ctggcaatga ccaggaattt 8520
gaaggatcac tactttgaaa ctagttaata aggacatggt ttctgttctt tttttacaga 8580
tacttttaaa gttttgtcag aaaagagcca ctttcaaggt aggacaagtt tggaaatgta 8640
ttctcattcc tgttaatttt gtatatttgt ttttcttata ctctgaatgt gtcacttata 8700
caaattctgt ttctatttca gctgcactga caccctggtc ctgacttccc tggaggagaa 8760
gtattcctgt tgctgtcttc agtctcacag agaagctcct gctacttccc cagctctcag 8820
tagtttagta caataatctc tatttgagaa gttctcagaa taactacctc ctcacttggc 8880
tgtctgacca gagaatgcac ctcttgttac tccctgttat ttttctgccc tgggttcttc 8940
cacagcacaa acacacctct gccaccccag gtttttcatc tgaaaagcag ttcatgtctg 9000
aaacagagaa ccaaaccgca aacgtgaaat tctattgaaa acagtgtctt gagctctaaa 9060
gtagcaactg ctggtgattt ttttttctt tttactgttg aacttagaac tatgctaatt 9120
tttggagaaa tgtcataaat tactgttttg ccaagaatat agttattatt gctgtttggt 9180
ttgtttataa tgttatcggc tctattctct aaactggcat ctgctctaga ttcataaata 9240
caaaaatgaa tactgaattt tgagtctatc ctagtcttca caactttgac gtaattaaat 9300
ccaactttca cagtgaagtg ccttttttcct agaagtggtt tgtagacttc ctttataata 9360
tttcagtgga atagatgtct caaaaatcct tatgcatgaa atgaatgtct gagatacgtc 9420
tgtgacttat ctaccattga aggaaagcta tatctatttg agagcagatg ccattttgta 9480
catgtatgaa attggttttc cagaggcctg ttttggggct ttcccaggag aaagatgaaa 9540
ctgaaagcac atgaataatt tcacttaata atttttacct aatctccact tttttcatag 9600
gttactacct atacaatgta tgtaatttgt ttcccctagc ttactgataa acctaatatt 9660
caatgaactt ccatttgtat tcaaatttgt gtcataccag aaagctctac atttgcagat 9720
gttcaaatat tgtaaaactt tggtgcattg ttatttaata gctgtgatca gtgattttca 9780
aacctcaaat atagtatatt aacaaattac attttcactg tatatcatgg tatcttaatg 9840
atgtatataa ttgccttcaa tccccttctc accccaccct ctacagcttc ccccacagca 9900
ataggggctt gattatttca gttgagtaaa gcatggtgct aatggaccag ggtcacagtt 9960
tcaaaacttg aacaatccag ttagcatcac agagaaagaa attcttctgc atttgctcat 10020
tgcaccagta actccagcta gtaattttgc taggtagctg cagttagccc tgcaaggaaa 10080
gaagaggtca gttagcacaa accctttacc atgactggaa aactcagtat cacgtattta 10140
aacatttttt tttcttttag ccatgtagaa actctaaatt aagccaatat tctcatttga 10200
gaatgaggat gtctcagctg agaaacgttt taaattctct ttattcataa tgttctttga 10260
agggtttaaa acaagatgtt gataaatcta agctgatgag tttgctcaaa acaggaagtt 10320

```
gaaattgttg agacaggaat ggaaaatata attaattgat acctatgagg atttggaggc  10380
ttggcatttt aatttgcaga taataccctg gtaattctca tgaaaaatag acttggataa  10440
cttttgataa aagactaatt ccaaaatggc cactttgttc ctgtctttaa tatctaaata  10500
cttactgagg tcctccatct tctatattat gaattttcat ttattaagca aatgtcatat  10560
taccttgaaa ttcagaagag aagaaacata tactgtgtcc agagtataat gaacctgcag  10620
agttgtgctt cttactgcta attctgggag ctttcacagt actgtcatca tttgtaaatg  10680
gaaattctgc ttttctgttt ctgctccttc tggagcagtg ctactctgta attttcctga  10740
ggcttatcac ctcagtcatt tctttttaa atgtctgtga ctggcagtga ttctttttct  10800
taaaaatcta ttaaatttga tgtcaaatta gggagaaaga tagttactca tcttgggctc  10860
ttgtgccaat agcccttgta tgtatgtact tagagttttc caagtatgtt ctaagcacag  10920
aagtttctaa atggggccaa aattcagact tgagtatgtt ctttgaatac cttaagaagt  10980
tacaattagc cgggcatggt ggcccgtgcc tgtagtccca gctacttgag aggctgaggc  11040
aggagaatca cttcaaccca ggaggtggag gttacagtga gcagagatcg tgccactgca  11100
ctccagcctg ggtgacaaga gagacttgtc tccaaaaaaa aagttacacc taggtgtgaa  11160
ttttggcaca aaggagtgac aaacttatag ttaaaagctg aataacttca gtgtggtata  11220
aaacgtggtt tttaggctat gtttgtgatt gctgaaaaga attctagttt acctcaaaat  11280
ccttctcttt ccccaaatta agtgcctggc cagctgtcat aaattacata ttccttttgg  11340
ttttttaaa ggttacatgt tcaagagtga aaataagatg ttctgtctga aggctaccat  11400
gccggatctg taaatgaacc tgttaaatgc tgtatttgct ccaacggctt actatagaat  11460
gttacttaat acaatatcat acttattaca atttttacta taggagtgta ataggtaaaa  11520
ttaatctcta ttttagtggg cccatgttta gtctttcacc atcctttaaa ctgctgtgaa  11580
tttttttgtc atgacttgaa agcaaggata gagaaacact ttagagatat gtggggtttt  11640
tttaccattc cagagcttgt gagcataatc atatttgctt tatatttata gtcatgaact  11700
cctaagttgg cagctacaac caagaaccaa aaaatggtgc gttctgcttc ttgtaattca  11760
tctctgctaa taaattataa gaagcaagga aaattaggga aaatatttta tttggatggt  11820
ttctataaac aagggactat aattcttgta cattattttt catctttgct gtttctttga  11880
gcagtctaat gtgccacaca attatctaag gtatttgttt tctataagaa ttgttttaaa  11940
agtattcttg ttaccagagt agttgtatta tatttcaaaa cgtaagatga tttttaaaag  12000
cctgagtact gacctaagat ggaattgtat gaactctgct ctggagggag gggaggatgt  12060
ccgtggaagt tgtaagactt ttattttttt gtgccatcaa atataggtaa aaataattgt  12120
gcaattctgc tgtttaaaca ggaactattg gcctccttgg ccctaaatgg aagggccgat  12180
attttaagtt gattatttta ttgtaaatta atccaaccta gttcttttta atttggttga  12240
atgtttttc ttgttaaatg atgtttaaaa aataaaaact ggaagttctt ggcttagtca  12300
taa                                                                12303
```

<210> SEQ ID NO 18
<211> LENGTH: 189
<212> TYPE: PRT
<213> ORGANISM: Artificial Sequence
<220> FEATURE:
<223> OTHER INFORMATION: NRas Amino Acid Sequence

<400> SEQUENCE: 18

-continued

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 19
<211> LENGTH: 4326
<212> TYPE: DNA
<213> ORGANISM: Artificial Sequence
<220> FEATURE:
<223> OTHER INFORMATION: NRas mRNA

<400> SEQUENCE: 19

```
ggggccggaa gtgccgctcc ttggtggggg ctgttcatgg cggttccggg gtctccaaca     60

tttttcccgg ctgtggtcct aaatctgtcc aaagcagagg cagtggagct tgaggttctt    120

gctggtgtga aatgactgag tacaaactgg tggtggttgg agcaggtggt gttgggaaaa    180

gcgcactgac aatccagcta atccagaacc actttgtaga tgaatatgat cccaccatag    240

aggattctta cagaaaacaa gtggttatag atggtgaaac ctgtttgttg gacatactgg    300

atacagctgg acaagaagag tacagtgcca tgagagacca atacatgagg acaggcgaag    360

gcttcctctg tgtatttgcc atcaataata gcaagtcatt tgcggatatt aacctctaca    420

gggagcagat taagcgagta aaagactcgg atgatgtacc tatggtgcta gtgggaaaca    480

agtgtgattt gccaacaagg acagttgata caaaacaagc ccacgaactg gccaagagtt    540

acgggattcc attcattgaa acctcagcca agaccagaca gggtgttgaa gatgcttttt    600

acacactggt aagagaaata cgccagtacc gaatgaaaaa actcaacagc agtgatgatg    660

ggactcaggg ttgtatggga ttgccatgtg tggtgatgta acaagatact tttaaagttt    720

tgtcagaaaa gagccacttt caagctgcac tgacaccctg gtcctgactt ccctggagga    780

gaagtattcc tgttgctgtc ttcagtctca cagagaagct cctgctactt ccccagctct    840

cagtagttta gtacaataat ctctatttga gaagttctca gaataactac ctcctcactt    900

ggctgtctga ccagagaatg cacctcttgt tactccctgt tatttttctg ccctgggttc    960

ttccacagca caaacacacc tctgccaccc caggtttttc atctgaaaag cagttcatgt   1020
```

ctgaaacaga gaaccaaacc gcaaacgtga aattctattg aaaacagtgt cttgagctct 1080
aaagtagcaa ctgctggtga tttttttttt ctttttactg ttgaacttag aactatgcta 1140
atttttggag aaatgtcata aattactgtt ttgccaagaa tatagttatt attgctgttt 1200
ggtttgttta taatgttatc ggctctattc tctaaactgg catctgctct agattcataa 1260
atacaaaaat gaatactgaa ttttgagtct atcctagtct tcacaacttt gacgtaatta 1320
aatccaactt tcacagtgaa gtgccttttt cctagaagtg gtttgtagac ttcctttata 1380
atatttcagt ggaatagatg tctcaaaaat ccttatgcat gaaatgaatg tctgagatac 1440
gtctgtgact tatctaccat tgaaggaaag ctatatctat ttgagagcag atgccatttt 1500
gtacatgtat gaaattggtt ttccagaggc ctgttttggg gctttcccag gagaaagatg 1560
aaactgaaag cacatgaata atttcactta ataattttta cctaatctcc actttttca 1620
taggttacta cctatacaat gtatgtaatt tgtttcccct agcttactga taaacctaat 1680
attcaatgaa cttccatttg tattcaaatt tgtgtcatac cagaaagctc tacatttgca 1740
gatgttcaaa tattgtaaaa ctttggtgca ttgttattta atagctgtga tcagtgattt 1800
tcaaacctca aatatagtat attaacaaat tacattttca ctgtatatca tggtatctta 1860
atgatgtata taattgcctt caatcccctt ctcaccccac cctctacagc ttcccccaca 1920
gcaatagggg cttgattatt tcagttgagt aaagcatggt gctaatggac cagggtcaca 1980
gtttcaaaac ttgaacaatc cagttagcat cacagagaaa gaaattcttc tgcatttgct 2040
cattgcacca gtaactccag ctagtaattt tgctaggtag ctgcagttag ccctgcaagg 2100
aaagaagagg tcagttagca caaacccttt accatgactg gaaaactcag tatcacgtat 2160
ttaaacattt ttttttcttt tagccatgta gaaactctaa attaagccaa tattctcatt 2220
tgagaatgag gatgtctcag ctgagaaacg ttttaaattc tctttattca taatgttctt 2280
tgaagggttt aaaacaagat gttgataaat ctaagctgat gagtttgctc aaaacaggaa 2340
gttgaaattg ttgagacagg aatggaaaat ataattaatt gatacctatg aggatttgga 2400
ggcttggcat tttaatttgc agataatacc ctggtaattc tcatgaaaaa tagacttgga 2460
taacttttga taaaagacta attccaaaat ggccactttg ttcctgtctt taatatctaa 2520
atacttactg aggtcctcca tcttctatat tatgaatttt catttattaa gcaaatgtca 2580
tattaccttg aaattcagaa gagaagaaac atatactgtg tccagagtat aatgaacctg 2640
cagagttgtg cttcttactg ctaattctgg gagctttcac agtactgtca tcatttgtaa 2700
atggaaattc tgcttttctg tttctgctcc ttctggagca gtgctactct gtaattttcc 2760
tgaggcttat cacctcagtc atttcttttt taaatgtctg tgactggcag tgattctttt 2820
tcttaaaaat ctattaaatt tgatgtcaaa ttagggagaa agatagttac tcatcttggg 2880
ctcttgtgcc aatagccctt gtatgtatgt acttagagtt ttccaagtat gttctaagca 2940
cagaagtttc taaatggggc caaaattcag acttgagtat gttctttgaa taccttaaga 3000
agttacaatt agccgggcat ggtggcccgt gcctgtagtc ccagctactt gagaggctga 3060
ggcaggagaa tcacttcaac ccaggaggtg gaggttacag tgagcagaga tcgtgccact 3120
gcactccagc ctgggtgaca agagagactt gtctccaaaa aaaaagttac acctaggtgt 3180
gaattttggc acaaaggagt gacaaactta tagttaaaag ctgaataact tcagtgtggt 3240
ataaaacgtg gtttttaggc tatgtttgtg attgctgaaa agaattctag tttacctcaa 3300
aatccttctc tttccccaaa ttaagtgcct ggccagctgt cataaattac atattccttt 3360
tggttttttt aaaggttaca tgttcaagag tgaaaataag atgttctgtc tgaaggctac 3420
catgccggat ctgtaaatga acctgttaaa tgctgtattt gctccaacgg cttactatag 3480
aatgttactt aatacaatat catacttatt acaattttta ctataggagt gtaataggta 3540
aaattaatct ctattttagt gggcccatgt ttagtctttc accatccttt aaactgctgt 3600
gaattttttt gtcatgactt gaaagcaagg atagagaaac actttagaga tatgtggggt 3660
tttttaccca ttccagagct tgtgagcata atcatatttg ctttatattt atagtcatga 3720
actcctaagt tggcagctac aaccaagaac caaaaaatgg tgcgttctgc ttcttgtaat 3780
tcatctctgc taataaatta taagaagcaa ggaaaattag ggaaaatatt ttatttggat 3840
ggtttctata aacaagggac tataattctt gtacattatt tttcatcttt gctgtttctt 3900
tgagcagtct aatgtgccac acaattatct aaggtatttg ttttctataa gaattgtttt 3960
aaaagtattc ttgttaccag agtagttgta ttatatttca aaacgtaaga tgatttttaa 4020
aagcctgagt actgacctaa gatggaattg tatgaactct gctctggagg gaggggagga 4080
tgtccgtgga agttgtaaga cttttatttt tttgtgccat caaatatagg taaaaataat 4140
tgtgcaattc tgctgtttaa acaggaacta ttggcctcct tggccctaaa tggaagggcc 4200
gatattttaa gttgattatt ttattgtaaa ttaatccaac ctagttcttt ttaatttggt 4260
tgaatgtttt ttcttgttaa atgatgttta aaaaataaaa actggaagtt cttggcttag 4320
tcataa 4326

<210> SEQ ID NO 20
<211> LENGTH: 35550
<212> TYPE: DNA
<213> ORGANISM: Artificial Sequence
<220> FEATURE:
<223> OTHER INFORMATION: Pmp22 genomic sequence

<400> SEQUENCE: 20
agttacaggg agcaccacca gggaacatct cggggagcct ggttggaagc tgcaggctta 60
gtctgtcggc tgcgggtctc tgactgccct gtggggaggg tcttgcctta acatcccttg 120
catttggctg caaagaaatc tgcttggaag aaggggttac gctgtttggc cgggtgagtt 180
ttattggcaa actgtgcctc tgggtgatgt gtgcctatgc tttacaagaa ttgcctaatt 240
tcccaccccc tgcaagccgc aaatgaaaag gattgcagga gagatggtgc atttgtgttg 300
gaattgactg gagattcaga gggcttttta tatccttggt taaaaggtgg atatatactc 360
tggctgggga ggtggggggc catctgagag catctagaaa ccctaatgca tccagattga 420
aaggaagaaa ggaatctaga tgctttttcc cccatggaaa atagctgtgc acacacagct 480
ggcaggtggc cttggtaagc aggttaggga gaagctgcca cctgtggcag agccttggcc 540
agccgggctc tgggtgtggc aagcctggtc agcaggcact gagtagcact tcctctgcca 600
ccattgagaa ccaggcagga ggccagaggc agtgagggac agatgggttg ggtttacctg 660
tctggcagta tatggtgtgg ctgtgacctg ggtggttatt gattaaacta ttgggttcaa 720
aagaaaggaa gaagcgagct gtagcaccca atatatgcac ttttctgtat gtgtattaga 780
ctttattaaa aagtttattt gaaaatcaca aaggaaggga aagaaaaccc tgagttagat 840
atgctcatat ttctaaagtg cttacttaga acagtcctga gtatgttgtg atcacataag 900
tgttggttaa ataaataaat gtccaaatgg cataaaacaa agtaataatt tctagagcaa 960
atctaactta taaaatgacc tgtggaggaa agaaaacact gccatgtctt tagacttttt 1020
tttctacttg catatgcact ttcatttata aatctttatc tatctatcta tatctatcta 1080

-continued

```
tctatctatc tatctaccta cctacctacc tacctatcag agttacaagc tactttagtg   1140
cagaggtggt caggtcttcc ctgaaaggtt gatgtgagag ttaaatgtga tataataata   1200
gtggtggcaa tttgggcact gggcccttat tatgttgcag acacgatgtt aactgctttg   1260
tacatattgt ctccttcaat caccaccata aacctttaaa gcaggcatta ctatttcctt   1320
ttgcacctga gaaaactgaa gctcagtgaa cttgagaaat tgcccaaatt cacaacaaaa   1380
gtaagcaggg tgattaggtt tgttggagcc cagagccaga gtgcctaacc actgcaccat   1440
actgcctctc acagaccatg catataaagt ccaggcaaag tgcttggcat ataacgggca   1500
ctgtaaatgc agtgtttaca agtacacttc attttaatct gataacacga tagttttaaa   1560
aagatcattg tttgaagatc tttttcaaat ttatttttac ttaccgtaag aatatacaat   1620
tagctaaaat agcagctcct ttcaaatcgt aaaataaatat agaattattt gaatcattga   1680
gagtgatgag cttctatgac acagtacact agaggtaggg aagtgtgtgt gtgtgtgtgt   1740
gtgcgcgcgc gtgcgtgaac tgctgcattt tcaggcagaa acctttaaca tccacattcc   1800
tgctccctgt cccgtgcctc aaggctggcc tgcgcacggg agtctcagtt gggcgcgcct   1860
ctgccaagcc gagactgaag gggctagcc tctctccctg taacgctggg cgggccacgt   1920
taggaggcta tgaatcagct gatttccttg gctgctccaa ccccacctca aatggccacc   1980
tcgcacccgc ccgccaaacc ccatggccag gactccagcc aaggctgaca gccaagcccg   2040
actgctgcag gaacactttg cctagagctt attcggtggt agtctggttt tgcctaggct   2100
aggaggagcc caatcccaga ccatgctatc cagtagtcgg ccggactttt cttcccctaa   2160
ttcgcaccca agaggagccc gctagatcaa tccccgccaa tcctaggaag ctggcatgct   2220
tcgtaggtgc agacagtaat agcggggacc ggcgcggggc aggtgtgtcc ggctaagacg   2280
ccaggacagg gcaggggctc caggacccga gaggagaggg acttcttcca gcgctcaagc   2340
gcccgctgcc ctctattagt gggaaaggaa tccagcctca gccccgcgcg ggcgcggtcg   2400
gcgtcggcgg gcccagaagc ccagccctgg gcatccgctg agctacattt ggctgggtct   2460
tcccagagtg ggctgaggag ccagtttctc ggtcaacact aggtctccac ggggccaggg   2520
gagaagggag gtgggaggtg agaaagctca gccgcctctg gtttcgagta aaagtcgccg   2580
cggttttgca gggaccgact ttttcttgag gcgcatttaa ggccaagtga ctgtctcctg   2640
ccctccctct ctcctgcccc ctctcctccc tgagtcccgc cctcccgcac acgctgaccc   2700
agggacacac cctactgcag cgacgcaaac agggcgttgt tcccgttaaa ggggaacgcc   2760
aggagcctcc cactgccccc ttgcttcgcg cgcgcgcagc cccgcagcgc agctttggcg   2820
gcgccagcag cggagccaac gcacccgagt ttgtgtttga ggccaccctg aggatcggga   2880
cagctgttcc tttgggctgt aagtgatttg gtggggagag tgaaggagat ggaggagaaa   2940
tgtgggcatc ttccagtgag ggtgccagaa agcgcagcgc aggcgcgggg ctttggccag   3000
ctccctgggg cttctgttta ggggcacagg gtcccctgtg tgtcctgttt ccctccaatg   3060
ggtcttggag taatacaacg aggagagcct ttatggtcta taagacctta cagggcaagg   3120
gtgatggtgc tggtgtctgg atagcggata agggcggccc agttctcgcc ttgctgaaga   3180
ggcgttgact ctgggacaca ctggcaaaac agtccctgtg gcggacatcc cgagagtgtt   3240
ggactcctgt ggttccccag ttcccagcct cctgccatcg gcttaattca aaccctctgg   3300
gagtcatcag aaatccttgt ttatttcttc cagtgcattc cagagtttct ttgaatgtga   3360
tgcttgtgga gaggaacaga ggggcctggg attgggtact ttccaaactg ggttattgaa   3420
```

-continued acgttgtctc cctggcccaa gactctgcct aaaatggtcc ccagagtctc agccagatct 3480
ttcacagcca tgcatgtcct ctaacaggtc atcccagcct tcagttcccc caaagtttaa 3540
aatgaggggc gaggaccgca ttacttggga taaatgtcct gccggctctg accggctgaa 3600
attctcggac tcagcctttt accctctgtc tctctctccc gtccgctgga catctactcc 3660
cttcggtcca ggctcctggg ctcctgtccc accgcaccca gaccggagct caggcttgtt 3720
ggggttcgtg tcctggcttt gagtgcctgg ggtgcagact ggacccctag gcgagcacgt 3780
gggtctagcg caagagcaga atgccccctg accccagggg ctgcctgggg aagcgcgcgg 3840
tggacgggaa gcgcagggtc cgggcaaccc tctcgagcca ttcttttctt tccacactac 3900
tctggctctg caccacctct ccggagccgc cagagtctgc gcgaggctga gctggggcca 3960
ggaccgttcc tctacgctgg cagagttggg tggaaacttg gagacaaacg gaatgcggag 4020
agcactgggg tctgggaaac cagcctcctc gccgctgtct cccccaccgc atgccacggc 4080
tgtctccagg tctcagacgg aaatctgggc acctactccc ctcaccccta cctccacccc 4140
atagggggaat tcaccatctg aaccggggtc tcggagaacg tgacctctca ccttccaggg 4200
aggtcgccgg gaggtgcttg gggtgggtgg aagcgtgcag tggcctctgc tcatattttc 4260
tggaaacccc tccgttccct gggtggtttt agacgtgcga accgcttgtt ttgtttccaa 4320
aagcaaaaga tgttccgttg caggcgggcc cggctgggcg ctgggcactg ggcgctggtc 4380
ctgcaggcgg ctgctgcccc ctctcggcgg caggcggcgc gaaggctcct gacccgcgcg 4440
ggcggtcggg ctgcgggcgc tgggccaggc cgggccttcc gctagtgcgc gggaccctcc 4500
ctctgcgcgc gcctccgtcg ctcggcccag tgcgttcggc ctcacgccca gcgctctcct 4560
cgcaggcaga aactccgctg agcagaactt gccgccagaa tgctcctcct gttgctgagt 4620
atcatcgtcc tccacgtcgc ggtgctggtg ctgctgttcg tctccacgat cgtcagcgtg 4680
agtgcctggc ggggaggctc cctgcgcggc ccgcccttcc ccatctgggt tcccagcccg 4740
tgctcctgct ggttcaggac tgtgttattt gcagacagtt ggaagtctca gacgtcccag 4800
ggaagtttct ggcaatctgc cccccttccag ttgctttgag aaaacgagag cagattcagt 4860
gataggaacc aagcgagcgc tgggctgggt tagctgcgca ggtctctatt taagccaagt 4920
aacttcagag ccgatctagg gtccccgacc ttcatttgac aagattgttt aacttttttt 4980
tttcttgatg cagcctcgtt gaagaagagg agtatttatg attttttttt ctccaaacca 5040
tagtcagatg ggtgaattaa tttataaaac accctttttag gacttgaaat tggaaagtta 5100
aaatgggctt ttctggaaaa gagttcacag gtcccatgtc ggctttatgg catgaacaca 5160
acacattgtt agtaaagctt ccactggtag gaacaggcca tcagagtaac ttctgttaca 5220
aaactgtcca gcccattaga tcttaaagtt attttcttgg cgatgaagat gagcagacat 5280
tcaggcagtt ttccagtggt ggctttcact tcttaattta aggcacattg taagcatgat 5340
tttctttttc gttttctttt cttttctttt cttttttttt tttttttga gatggagtct 5400
ccagcctgtc acccgggctg gagtgcagtg ccatgatctt ggcttactgc aacctctgcc 5460
ttccgggttc aagccattct cctgcctcag cctgggatta caggtgcccg ccaccacgcc 5520
tggctaattt tttttttttt tgtattttta gtagagacgg ggtttcacta tgttggccag 5580
gcttgtctca aactcctgac ctcatgatcc gcccacctct gcctcccaaa gtgctgggat 5640
tacaggtgtg agccaccgtg cccggcctgt aagcatgatt ttctagtctc tgtgagaaat 5700
aattatgttg ggatttgtg acttagttta acatttacaa gcatcttcac agtatctcca 5760
ttgtgcctgg tgatgatgat atcagactga taggagctat aaacaaggaa atagactgag 5820

-continued agaggcgggc ttggggaatg atcccgagat gctgggagga gagaaggctt gaatgcaggt 5880
gtctaaggtt gagttcatgg ctccttctac tatagtaaac atctctgcac ataatcgttt 5940
ctgtgtgcat gtggaacttc tccatttaca aggtgctttt aagtcataaa acgttggctc 6000
ttaccatgca ggggtgggcg gtgtggctag gtggatgcgg gtgcttttcg ccatccctgg 6060
gcctttctcc ttcccctttt ccttcactcc tccctccctc cctgactcag gatatctatc 6120
tgattctctc tagcaatgga tcgtgggcaa tggacacgca actgatctct ggcagaactg 6180
tagcacctct tcctcaggaa atgtccacca ctgtttctca tcatcaccaa acggtgaggc 6240
tggttttgtg ctccatgagc ttgtcctcag acgcctgtaa cacgtttctc agcccagagc 6300
tggaaacgct tattggaaga cacaagccag aatgtcgttg ctggggtggg gtgggatgtg 6360
acagggagcc atgagtccag ggaaaatggg aggggtggtg atctcgctgg ggaagctgag 6420
atcctgggca tcattgtgat tcactctacc tagagacatg cccttagtgc cctcctgatc 6480
acttaggata atgcttttttg tgattgaaaa aaatatcgac ctgggagctg tgaaggtggt 6540
atgatagcta agcctttggc agaccccctt gggacattgg atcaaacgtg tatctttggt 6600
ttggtggctg tctctattca gaaatgtcct gccccttctt gctgcagtga cagtggggct 6660
agctcactgc accgtcagtt acatggacac aagactggct gcctttccag gtcttgggcc 6720
tcagtgatgc cacctagcat caaaaccttt gaatgtttcc ttgttgcaag atggggactt 6780
gaagctattt gcaaaaccct aagctaagcc ttggggtcct taatccagaa gatcgtattt 6840
ctcctctgtc ctcagcatct ttgcttgtga gatatggaag ccaggcttca tgagggtcaa 6900
attaagggat aattggcagc agaagcacca actaggtacc caaggcaccc agagggaaag 6960
gaacacccag ccaggagccc tgtgtgtttg gatgcagaca ggtggaggta aacaggatga 7020
gctgttttgg tggctgggta ggccatagcg attgatgtta agagcccgtg gacctggatc 7080
cacatgatct tttgttccag aagatgtgtc ctcaggctgg aaggacctag agatacagca 7140
gagctttcct aacatcctgg gtttaaaagg ccacggaaat acagctttaa atgttgctgg 7200
agctactcat agatccagta tatatgttca agatgctaca ccagacgaga gaaaccagtt 7260
tagatccagt tcagtaaaac aggcagtgaa gtggcctttg gtcctggctt tgcataatcc 7320
agttgctttg ctggactttc cctcttacag ctcagtaccc agtaataccc aagcatgtcc 7380
ccagctgaag cattataaac caaattcctt gaaccacagt acaaatagaa actgctaaaa 7440
taataatttg gtaatttaca tggagaagat acgcaaggag tagaaaaccc tgctttatgt 7500
ttttaccttc tgggttgggg agggagcaga gaaaaggtcc cagtcctatt ggagtgagaa 7560
cagtgcttaa tcttgtctct gagtgtgtga aaggcattga attaaagcca tcccagaaat 7620
tacgtggtgg gtttgcatgg tgagttggca actgagtaaa tgaaatactc atgagtgcct 7680
gagaatgtga ccgtagcact gcttgtcccc aaagccacag catccggttt ctcccccttt 7740
agggtctggc tgaagttccc ggagcactcc ggatgggagt ctccgtactc gctactgaca 7800
cctggtggtt acaagtagtg actcagcccg aaaagggcag gctttggtgc tcacaggcgc 7860
catccccaag tggcatctgg ccacgcggct tggcacagaa tcctggactc ttgggcccgg 7920
aagggggcag ttttggcagg cgtgttaaaa cccggcgaag tttcagcaga aacgaggcgg 7980
cagaggagtt gctaagttgt gcttaaacca tctgcaggaa agaaagcaat attgacctgt 8040
agcatgttac agattgacat ttggtgtctt ctgccgttgg aaatagctgt cagttggtgc 8100
tagaagcaga tctcaaagag gcactagggt tattttaatc aggaaacttc ttatctctca 8160

-continued

```
acttgttcct tctgtgccaa gctcatgttc ttgagttcat ttacaatgcc tccttagtgt   8220
gggtttcaaa tctgcctcgt tgctttccgt gaggacccca gagtgtctgt tttccacatc   8280
tcccttctca gctctcacaa tcagggcatt ttgaaaacat ctggacactg cacctgaaca   8340
tgctgggttt gttttcacgc cactcaggct taatctaaat ttgaaatttc catttacact   8400
tccccagtag tggttatctc tgccgctatc ttccccaacg tggcagcact tgctacgact   8460
tcagccttaa gtggcgaatc ctccagggcc tctttgattg agtttaacaa ttgtggctgc   8520
agacaataag ctgaaaaaaa tgtgtacttt ttaaaacatt atactgtctt tacaaatgaa   8580
ctatgctcat tgcgaaccat ttaacttgtc tgtatttgct cttagaaagt atatttgaaa   8640
aaaaatactt gttaagtaat caaaagtaat ttgttattga catcgatttg tgaagaatat   8700
gttgcaagtg tgaaaaaata aatagtggtg caatctcggc tgactacaac ctccacctcc   8760
tgggttcaag cgattttcct gcctcagcct cccgagtagc tgggattata ggcgcccaac   8820
accacgcctg gctaattttt gtatttttag tagagagggg tttcatcatg ttgggcaggc   8880
tggtctcgaa ctcctgacct caggagatcc acccacctca cctcccaaag tgctgggatt   8940
agaggtgtga gccactgcgc catgtgactt ggtatttttt tctgaaagga ctcatttttc   9000
tggtgcatga ccatgacact tcacctctct ctggggggttg ccactcatgt tgttttctac   9060
atgaatgggg cctcctggca tcgtgccatg aggcagtcta acatctaggt tgtgtagttt   9120
gaaagagaca caccagatct tgcccccagg ctacatctta atattagaaa tagttttaga   9180
tttttaacta actgactttg actccgcctg ccttctcgtt tttctaaatg tgtttgtata   9240
ctttctggca ccccctcctt atctgcctcg tgtgggcaga ggtaagagag gcttagtgtg   9300
gggatattcg ttatgatatt gtatccagtg cctctccggc ccagggaata caaggatctg   9360
gaatgcatgg gccttgcctt gatggtcccg agcctggtcg aagagtcagg agatagatat   9420
ggaagggtga atcactccct tggaaggcag agcaggccag gtgcccaaag ggaggcaggc   9480
agacagcgtc tgagttcagg gaggaagcgg atgggaaatc tctggtggga ggtagaatct   9540
gatccatcct ccaaaggatg ggcaggattt aagtcaatac aggcaacggg gaggagaata   9600
ttccctgtga cctaaggtaa gggtagaaca aggcagggga tggggtagac tggttggcta   9660
gtgttctggt taggattagg attgattgtg tataagagaa catcttcaaa tgataggggc   9720
ttaagtaaga tcatttattt ttctctcttt tcaaagaagt ctggaagtag gtagcctgag   9780
agaggtatgg aggttccatg aaattgtcag agatgcagac actttctagc tcatttcttt   9840
gccatctctt gggtttggct gtcatcttca ggaaacaaaa ggctgctaga gctccagcca   9900
tctcatccat gattcaagca gtagggtgga gaaaggaggt ggggaagaat gaatctcctt   9960
ttcttttaat gaaatgtgac atggtcacac ctacacctat ttacaagaga ggctgagaaa  10020
tatagtcatt cggccttggg ggaagcatgg cttttcaaat catagaaacc tggcagcaaa  10080
tacctctctg taagcctggt gtggaatact ttccttgagg gtttgaccat cccctcccat  10140
acccaatcat actcttttgc aatagctcag ttgggcccta tgcagttcca taagtcccag  10200
ttatttcagc attcttcaaa gagtccatct ctgctgcatc ctgggctctg tcagccaccc  10260
caccattctc acatgggctc ttctcagaaa ctttaggacc tgttgaggct tctctctctc  10320
tatttctacc acctctccag gtataagtaa gtcttattat tattattgag acagagtttc  10380
actcttgttg cccaggctgg agttcagtgg cgccatcttg gctcactgca acctccgctt  10440
cccgggttca agcaattctc ctgcctcagc ctcccgggta gctgggatta caggcatgcg  10500
ccaccacgct tggctaattt tttgtatttt tagtagagac gggctttctc catgttggtc  10560
```

aggctggtct cgaactcccg acctcaggtg atccacctgc ctcagcctcc caaagtgctg 10620
agattacaag cgtgagccac catgcctggc catcttatta ttatttaatg agtccagacc 10680
tctcttctga atcccagacc tgtttatcca gctgtctcct ggccacttcc cttgggatat 10740
ctaagagagg cccccaagtc actaggccag agacagtcct tatcttcctc tgccaattca 10800
acccctctgt cactttctag tattttagtg aatgctgctt caccagccag caagccaaac 10860
atctagagtc tgccttgact tgacgcgttt ccttctttct cttctcagca ttgtcacggg 10920
tccctcaggc caccccattg ttccaatgcc tgttgcccac ctgtggtcac gctgcttcct 10980
cgtttgtcag aggcgccagg gcagcctcct aactagtttg cctgaaccct ttcttgctcc 11040
tctgtgactc atttttcata tggaatccag gctgatattt aaaaaagcac aaacctaatt 11100
atatcactcc tcattttgaa acctttcaga ggccgttcat tggtcttaat cttcagatga 11160
aaatctttaa caaggcccat cggaatctac ctgaatgatc cactcctgct tctgttaagt 11220
ctcacctccc atctctcttc ccctcatctt ggaatttcag cgttttctca cgtcctgaaa 11280
tgtgaacttc ccacttcggg agtctctcca tttctcttct gatctttcat gcaggactat 11340
ttcttgaaca actctcgtgt accagagact attgcaggtg ctaaggttac aagagtgaac 11400
aagagcttat gttttactgg acaaaccagt cagtaaacat ggagaatttg gggcaatgg 11460
taagaactat ataagacagg gtaatgggat aaagagggat tgcagtggtg aaggaaggtc 11520
tccttgagga gtggccagga gccagccata tgaacatctc ggggaggttc catacagaag 11580
gaccgtcaag tgcaagatcg ctggggaggg aaggagcttg gcgtagttga gggacagagg 11640
gcagggcaga ctagtgggaa cagagagtga ggggtaagta gaatcacaga ccatctcaaa 11700
ggtacccccc acccccacta ggaaggagtt gggtgcacat ggatgcattt ctaatctttg 11760
tgatttcctt agacctgctg tcttccacgg gtttctcagt ggtccatttg attccaagtt 11820
ggagtgacag tccagaagcc tctataaggc agaatatatc agaaattgta caaggtagaa 11880
atgcatcggt atattttcag tgattatttt gggtgacggg attcttatca ctttggctgt 11940
tttctttctt ttgctgcctt acctgttttc ctcattgaga tcttttattt tcacaatcag 12000
aaaataactg tgaacatttt atgttagaaa attggttttg agtagtaagt aggttccctc 12060
tgccttgatt aagagagtgg agccctgggg catggcacgc agggtccatg gcgtcgcttt 12120
gaatgaggcc agttcctgga gctttagttt gcaaactcat acaatctgga aggctctggt 12180
gagggggagg ggtgtgccaa gcctcctccc caagacccta tgggtgagtt taaaatctac 12240
tgacccaaag gattcaggca aaacatttgc cctgctattg aatgaaccag tgctttttgt 12300
tttgaagtct ccaagatcca aatatcaagt ccaagttctc acaagcattc ccctgctttt 12360
tgtttaattt gtgtggacct gacgtgtagc agaatgggtc agaatactgg aattaagcca 12420
caggcggctt gggagcccaa gagctagaag ggcacagtcc tggcttgccc tggcccctgg 12480
ctggtcttca tcagcttcag tgatgaggca ggacccaggc agtttgtctt cagtaaaatc 12540
tgtctctcag ggcctgtccc tgctcacaaa gtcctctctt gtctcagaag aaaaggtagt 12600
tgataaactt tttcatgctg aggtgttagg cacaaaaaat gtgccccttt ttgaatcact 12660
tttgttttta aaaaggaggc cagtgctcaa caccaaagca tgaagggaat tgttgagctt 12720
tcctgtaatc tgtccccaaa cgtccttggc cacctccatt gtctaagggc agtacctgca 12780
gcccctcatt tcccagtgac aacaggtggg tctgctctgc cacagtgtgt gggcgggacc 12840
agcaccagac gctgagaaga tgaccactta ctactcttct tttccattta aacagcagca 12900
gcagcagcag cagcagcagc agcagcagca acagcaaact catgactatc aataggttgt 12960
gtgaggaatt agatcaatgc tttgggttga aaattagaga aactaaatct tgccagtctc 13020
agcagccccc aacctgagcc cttggtggtc tcctatcatc gctgtcttca aaacgatccc 13080
agacttgttt atcaatttgg tgacactgtc attttggcaa ggacaccaga caatttcctt 13140
gtctgtggct cagcttttgg ccagatttta gaaaacacgg gagaccttct gcatttatgg 13200
gttcatgttt tacattttaa aatcttcgtg gctccctcag ccaacccata atctctaccc 13260
aaggaatggc tctggatttt acaggctctt atgagatgct gagaccctgg tggtacaagg 13320
gaggtacaga ggacggaatg tgttgtcaac atgccaggat ttcaaccctt agggtttctc 13380
tgatgccaat acccaggaat tagtatgaaa tgtttgtttg aacctgtgtc tgaactgtat 13440
gacctggaat ctatagtctt tgctttaaaa aaacttcaat tgtatcccca agatttcacc 13500
agcaccaaga aaacatccct tgcatttcag gagcagggac tggccatggt gcagcctgag 13560
gttgtggatg ttgatctttg gtgcccgaga gaaggctgtc tgggatgaag ccttctgact 13620
gtggtcaggt ccctgccagt gctgggggcc acatgagtgt gcagtcatcc acacacaagt 13680
ggcccccaac actggcaggg acccggagtc atctggccca tccctccttc ctatcccatc 13740
gagccacaga cccctctgca atatgcctac cacatgttca tcctaccact gatggggaac 13800
ttattacctt caagagagcc tcttttgttt ttgaagagct aatagtgaga tccattcatg 13860
tgttcttcaa ctctattgag cctgtcctat gtactgggca ctgttctaga aatggggtgc 13920
acagagatga acaagaaaga gcaggtccct gccattgtgc agctcacaag gagttggagg 13980
aaacaggcaa tacacaatac atgcatcact atgggtagtg gaacatgctc tgcaggaaac 14040
aaatagggtg atccaatgga aagtcatcac tggaggaatg agctgctcag ggaaggcctc 14100
ttccttccat agtgatgtgg tctgagattt agaagacagg gaaggaccag ttataggaag 14160
aaccatggga agaaaattct aggaggtaaa gggaagaacc aaggccctga gttagctgaa 14220
gaaaggaggg tggggaatgc gggagagagg gatgggagca ggatcgctgg tgcctcacag 14280
gctgtggtac tgagaaggac agttgggaca tcattgaagg gttttaagca gaagagtgtc 14340
atgatttgat tcatgttttg taagctcatt ctggctgttg agaatgaatt ctggggagag 14400
gcaagagtgg aaactgggga ccagtgagga gtttgtggtc atagtccaga ctggacatga 14460
tgatgacact gagatgacaa tgatgacaat gacaatgatg ttaagaatac aaacagctca 14520
cgtaagtgcc aggcattctt tgaaaagcaa tgcatttaat cctcacaaga actctaggag 14580
gtagctggtg gcttagctag ggaggggaag tagagaagaa aacaggtctc atgacagggt 14640
ttgctgatgg gttagatgta gggagttagg gaagaatgat tctagatgac tctacgtttt 14700
gggcttgagc aactggtgtg taactgaatc ttggactgag atggggagac tggaggagga 14760
acagaagatt tgcgggaagg tgtagaaatc aggatttata ttttgaccat cagagaggtc 14820
agcaaatcac ttcaatttag aagtctttgg cttaggggag aggtctgggc tggaaattca 14880
aagtcaagag tcattcctct ataccgaagg gtattcaatg ttgtggtgct gaatacagtt 14940
acttggggag gagttgagag cagaaggcag aaaaggggaa cagggttcag agctaagtct 15000
tgggcatgcc aggggttaac gagggtacag gaaggagagg agactgggga tgaacagcca 15060
gtgatgaggg aggaatgcca ggagatattg tcacttaaga aattacctcg gctgggcgcg 15120
gtggctcacg cctataatcc cagcactttg ggaggctgag gcgggcggat tacaaggtca 15180
ggagattgag accatcctgg ctaacacggt gaaaccctgt ctctactaaa aatacaaaac 15240
aaaattagcc gggcgtggtg gccggtgcct gtagtcccag ctactcggga ggctgaggca 15300
ggagaatggc gtgaacccgg gaggcggagc ttgcagtgag ccgagatcgc accactgcac 15360
gccagcctga gcgacagagt gagactccgt ctcaaaaaaa gaaattacct tgttaaaccc 15420
aacactgccc ctcttttgtc cattcacttc tagttgcctt cattcatgcc tgatgtgctg 15480
gacttgggtt ttatcaagtt gcttggcacg tccttaaaga atttaaatct ccacagtgcc 15540
tcctggacaa tgactgcagg gtgacccccg tctctcctct acacgatgac tcttcaaaca 15600
gttgacgatt gcagtttttc tttccttcct tctttcagtg gcttctctgg tgctggtccc 15660
agctgcataa gcagggcctc ttcttgccct tctgaagttt ggtcagtggt ttggcttggc 15720
aggctgatga gcagagaata agggaagccg ctctctcttt gccacaccat tctccttcca 15780
ccctctctag tttttgtgga ttctaagtct gaagaatggt ggtagaataa tttaattcat 15840
tagattgcaa gcatatcatt gacttctctg cacccccagt gtgttgtagt ggaaaaacta 15900
gtagtctggg catcagggaa tccttgtttt tctgcaccgg gtctgcctgt aacaaattag 15960
gtaacctggg gcaggtaccc tggtttccta aaagcagagc aggcattgag gtaggacctg 16020
aagttgaggt aggacctgca cattgcatgg gtcccggagc ctctgttcat gttcaggatg 16080
taattgtggc atcgagggat cctaaaagga ggtggcctct gagctgggcc ttggcaatgg 16140
ggtagaattg cagtaggcag agggagcaga gatgggtttt gtgcttgtaa acgggcattg 16200
gtttactgtc actggtgggg gtagcagctc ttttgttcta gctcttcatt tccataatgc 16260
gtgttctttt ttcatacttt aggggaaaga aggaggagaa ctctattatt tctatgggga 16320
gaattcctcc taaacctgaa gatcttaaaa ctaagcgaat tattccctgt tcattctcca 16380
ctgatgcagt tcatgactgc aattgcaact gcctttcccg tcattttcta tggccaaact 16440
cagtgttttt aagtgagctc ttcttttaaa aaacaaaaac aaaaacaagt ctcctgataa 16500
atccgtttga aagacactaa gttttgaaag ttaagcaggc tttgatcatt catggtacat 16560
tgtgaattac caaggaggga gattgatatc cttcatcgta caatgcactc ccctcctttt 16620
tcttttgtat ctggtggagt aagtcttcca agagcaattc ttagagaaac aaagcctact 16680
ctgtttccct gtttctagag ttttccaaca agggtataaa aaagcctcag acagcttact 16740
attatccagt aacctcaggt acctcagtgg ctgcgtgtta ttccctttag aagtccaaaa 16800
actcactagc agagcaagaa tatggatgtc aaagtgcaga actagaccct gacaaactag 16860
ctctgtgcct gccacaaagc ctcttaatta ggaatgcagt tcattgaata actgtatcaa 16920
agttagctgg aataccttga catgaagatt ccttccactt actgagcagt ttgtgcccac 16980
tagtggccag acacaggctt tgctctagct aaaatacccc caggattacc tgttgagaga 17040
gccgcccacg tcaccttcat cgcctttgtg agctccatgc tggcacatag ttgtctccat 17100
ctgttttgct ttccgcatga atcataggca aagttagcct gaccagcaag cccatttcaa 17160
agccaccagc tgggggagaa gttgaagccc agggggcaag acccacgctg ggctttgggc 17220
atgtttgagc tggtgggcga agcatatggg caaaggccac attgtttagg atggaggcct 17280
ttcagagact cagctatttc tggaatgaca ttcatactga gaaataagga aaatggcgat 17340
ctgtgtgatg gttgtgggtt gggaggtttg ggcgtgggag tcctggtctt ggggtcatgt 17400
gttttgaaaa cagtctagca ctatgcaaat gggaggtgtt aataactctt tgcctctgtg 17460
atttaccctc tcatggcttt ttctctcttg gcctctccaa ggtctcttct gactcttgca 17520
actgtccttc ctttcacttt caacaaaacc tgttctcttg agtcagaaca gttttatgaa 17580
ttgcccagag tgggacttga tatggggcag ggttggttcc atgctggtaa tgaaagatgc 17640

```
acataaactg ttacattgaa aagtgcttca tactttctga gcccttaact cactaggttg  17700
taggccctgg gctaagaata tagctgaggg ggctgatgta tttccttcat tgctcagctg  17760
ctcctacagc aggaatctga ccttgaaatg agctttgatc tttgtgcaac tcgagcttcc  17820
cactatctgc tgggggagct aggtctgggt gctgccacgg cccatgtcag aaagctgtca  17880
gcagctctta taccggacac tctcagaaca ggaggcctgc aaagagcttt agctttagtt  17940
ttgttgttgt tgttgttttt gagacagtct cgctctgtcg cccaggctgg agtgcagtgg  18000
cgccatctcg gctcactgca agctccacct cccgggttca caccattctc ctgcctcagc  18060
ctcccaagta gttgggacta caggtgcccg ccaccacgcc cagctaattt tttgtatttt  18120
tagtagagac gaggtttcac cgtgttagcc aggatggtct caatctcctg acctcgtgat  18180
ccacccgcct tggcctccca aagtgctggg attacaggtg tgagccacgg cgcccggcct  18240
ttttttttt ttttttttg agacgagtct tgctctgttt ccaggctgga gtgcagtggt  18300
gtgatctcgg ctcactgcag tctccgcctt ccgggttcaa gtgattctcc tgctccagcc  18360
tcccaaatag ctgggattac aggcacatgc caccacaccc agctaatttt tgtattttta  18420
gtagagacgg ggtttcacca tgttggccag tatgatctcg atctcctgac cttgtgatcc  18480
acccgctttg gcctcccaaa gtgctgggat tacaggcatg agccaccacg cccggccaga  18540
gctttagttt ttaattccag tgctcagcac caaggttgga tattggctta aaacttccac  18600
tggaaactcc acaaatgttt agcaggcctc cactttgcac caggaactga gtgtggcctg  18660
gaggacagca ggtactcaac ataagttcta ctatttattg catacttgca aattgggtgg  18720
ggcgtgggga agagtatcgc cacactgggg cttgtgttaa tctatagttt agccacttgg  18780
gatgttggtg tcacactagg tttgatctaa atagaacagg tttgtaattg acagcatttt  18840
cacttgcatt atatttctct gaactcgaat cattattttc tgtacagctg acttgttttg  18900
ctgtagcaga gtttggcaga taatagcttg catgtcgaat ccaacctgct tttgtaaata  18960
agattttatt ggataaatgg ctattgaagg aatgggtcac acccactcat ttacatcttg  19020
tccatggcta tggctgattt tgtgatacaa aggcagaatt gagtagttgt taagaagacc  19080
gtatgacctg caaagcctaa agtatttgct ctctgattct ttatagatag tttgctatct  19140
gtgcagatat ttgcactctg actctgtagc acccttatgc tggagaggag atatgaattg  19200
ataccaaagt tgtatcaaaa cacttttgga gttctggcca atgtgctaat aacctggctt  19260
gtgtgaacat tgtggctctc attttctttt ttcttttttt tttttttgag acgagtcttg  19320
ctctgtcgcc caggctggag tgcagtggcg cagtggcgcg atctcggctc actgcaagct  19380
ccgcctccag ggttcacgcc attctcctgc ctcagcctcc agagtagctg ggactacagg  19440
cgcccgccac cacgcccggc taattttttt ttttttgtat ttttagtaga gacgggtttt  19500
cactgtgtta gccagcatgg tctcgatctc ctgacctcgt gatctgccct cctgggcctc  19560
ccaagtgctg ggattacagg cgtgacccac tgcgcccggc ctgtggctcc cattttcata  19620
ctgcttggtg tgacccagat ggaaatgctc cagaacctgg cccctcaata acagcctgta  19680
aatgcttgtt taccctgttt tctcacatca gccttttagg tggggttatt tgcactatcc  19740
tttaacagcg cttcaataac aactcttttg tttgatcatt atgacaaccc aataaaatat  19800
attagtgcct caagtacgta aagcagaatt caaggccaaa aaaatgtatg tggcaagtta  19860
ggtgggcggt cagaagaact tggcaacaga gcccagccct gcctgggctg tcctaaccag  19920
agcacataaa tgctggagag agtcaggctt tgcacgtgct cacacgggac ccttaccttg  19980
gacaggatca aagccctgtc atttctggag tgtgtgatat ctgctgtctc ttactgcgct  20040
```

ggttgttacc tgtctattcc agttctgatg aatggctctg attggggagc agcatcatct 20100
gagcttagaa atgtcctcag ggccctgtgg ggttcccttt gagcaacaac gagagctctt 20160
gaatcttgca ccagcctttt ggagctggaa tggagtttgc tttctcctgg gctgggctct 20220
gtttttttc ctctcgctgt ccttgtgtag cttttgatca atggcactgg aggaaaggaa 20280
aatcccttgt tgttttcctg ggcatgtgga agcccagtcc tgcccagaat tccactagcc 20340
ctttgagttt tggaatcctg actcttagta agtcaataga gtgctgcatc tgtttttacc 20400
tttgtaatct tttaaattgg ttttaattat ttaagtaata caagtattat aatacatgaa 20460
aatatcctca actgaaaggc ttcttgacca aactcttctt cgttgcaaca gtagttcctg 20520
ggggaaccca ctgacatcaa tttgacacaa ctttggctct ttctctacga atatttgcat 20580
gcctgtggat gtctatacgc aattacatag ttttttggtg tttgttttca taatgatgac 20640
atgttgtgtg tgcaccttac tcttttcatt gtcttggaga cctttcaaag actcttcatt 20700
ttctaactca tgattttttt aactgctgca aaatatttca ttgtgaggat ataccataat 20760
ttattttccc tcatagaaat gctacaatca atgtccttat ttattttcct ctgagtatat 20820
gttcactgtt tttccaggat atagtagata agcacttgaa cacatatagt gtcattacgc 20880
tagaggtgtt acaattttta aactactttt aatggcaaaa attacaatta cttttgtatc 20940
aacctaatat attctgccac aaaatggctg gtcacaaaag gattataata ataatattat 21000
tattattcct gtgaatggtg tctgcaggta gctatcactt atttgttctg ctgatattat 21060
ccattttttt tgaattttgc ctattggctg gatgaaaatt ggtgtcaccc tcctcatggg 21120
tttctcttgc atttccttgg ttgctagtga ggttgggcac cttttacgat gtttattggc 21180
tgttcatatt tctcctttgc taatcacatg gcttttcaat tttatactta gctgttttct 21240
ctttgttctg tctgtaattt aattttgtta atgatgcgaa ctagagattt aattttatgt 21300
tttaccaaat gaatagccaa cactatgtat tgtctgttgt atttttcccc actggtttat 21360
atgatgttgt gtattatcta ccaaatttac atgtatgctt ccaaagtctt attccatccc 21420
attcttttat ttttctttca tgattaacac catatttttg aattgctaaa actttataat 21480
ataaatataa gctttgtatg tctataaata aaatacattt tattaattat aattatatgt 21540
tatataatta taatataagc acttgaacat atatacttct ataattatat attatataat 21600
tatatatcat acttctatga tatgttctat aattatatat tgtatatatc atagttctat 21660
gatatgttct ataattatat attataaagt tacaattaat tgtatattta atttatacca 21720
tatactgtaa taagcaaaat atagaaatat gttttaaatc tggtaggtgg tatcttgact 21780
cattggtttt atatgttttt ctgattttct ttttgttcat ttgttcgttt tggtttttag 21840
ttgctgttgt gtttacttca aattttttct tatctgtcat tgctcattgt tttttagatg 21900
aatttttaat tgattttttt ccagttccag ttgcaatatg gattaggaca gcattgaatt 21960
tgtagattat tttggatgaa attggcatct ttataacttt gagtgtttct atccaggaac 22020
ttagtatgtt tctttagtac ttcttttatg tacttgaata aaatttgtct aacttgttga 22080
tgtatcccca aagaaccaga catttttatt aaatgtattt taatattttt ttctgtctca 22140
ttagtctgtg cttttatcca tattaagtca attaattttt ggacttattt cattgttttt 22200
tttctggctt cttgagttga aagtgtagtt cactcttttt aaggattttt ctagcaaatg 22260
cttagaagtg tatacattgt cctctgagaa ctgctttggt tacaacccac aggtgtgcca 22320
tgtggctctc tatataattc cttgctgaag aagtttttac ttttcatctt gttttttta 22380

```
atccgaggaa ttatctggaa cactgttttt aaatttccaa atttattttg gctagtttgt  22440
ttttaatgtc taatttctgt ttgcctttag gtatatgttg agcctacatc atttctgctt  22500
ctatatttat tgagatattc tttgttgccc ttatagtcag tttgaaaagc tgtcccatgt  22560
gtgtttgaaa ataactttgc tatatagaca caagttttct atacatctat taggacagat  22620
ttgttaatcc tcttatgtaa tctatattct ttcttctttt tggtctacct gacatctatt  22680
ttgaggaagg aagctaaagt cttctactgt tattgtgatt ttaacaattt cttctcatat  22740
tttgattact ttttgatttt aactttttca ggccatgtta ttatatgcat aatgatttat  22800
tttcttcagt catagatcat gtaaaccaga agtaaagatc aaataaacca aatctttcct  22860
ctatgaaaca accaaacaac tctctggcca cttttatcct ttcaacataa gttctatttt  22920
ttattattaa tttatcttct ttcttttttg ttaacatttg cctgaagctt cttttcagaa  22980
tctttttgt ttttgactgt tgcttgtttt aggtgtatct attatattag aatatagcta  23040
caatgtctct cttttttttt tttttttttt tttttgagac agagtctctc tctgtgccca  23100
ggctggagtg cagtggtgtg atcttggctc actacaacct ccacctcctg agttcaagcg  23160
attctctgcc tcaacctccc aagtagctgg gactataggt gtccaccagc acacctggcc  23220
aattttttttg tatttttcgt agagatgggg ttttggcatg ttggccaggc tggtcttgaa  23280
ctcctggcct caagtgatct acctgcctca gcctcccaaa atgtcttaat caaagataaa  23340
attccatatc ttatgagtgc cttgaaccca ttcacatata atgtggttga tgatagactt  23400
actatcttaa tgcatgtgtt ttatttattg tgcttatggt tgaaaaccat cttcttcatc  23460
tctggatcat cagagtcaac cagagggctt ggctcaaagc agtaggtatt caacaaatgc  23520
tcattgaata aaaatgtcct tgatcctcta attctgattt gattcgagaa ataacttatg  23580
gcaaagagct caattgtaat ggggttggga ctaaaattca agttaatgtt gaaagatgtt  23640
tcaagaagta tttaggttat attattaaat attagacact ttctgtttat atagatttaa  23700
catataaaga ttttaagttt tctgtgtatg tgaggtctcg tagtagtttc tgctgaaaat  23760
gacaggggcg cggggttaag ggtgaagaca gtatctcagg attggagaag gaaatctaag  23820
atattgtctc caccagccat actcctcatg aacatgcaca tggaaggaca tttcccagcc  23880
aaagtgaatc cctttatttg ttttagtttc agatttgagt ctcagatttc tttgtaattc  23940
cagctgcatc taccaaagtg ctagataatt tttttatttt aagcaaacaa tattatgaga  24000
acattatctt tattgcaaag tgctcctcca gaagaacctc tatgctggat aaagacaaac  24060
atttgattaa ggttatgtaa gagtgaaatc aggatggctc acaacccatt agccgtcatt  24120
ttcttacttt aattgacaaa gaaattgaaa aaatgaaaga agcatatgtt gtgcttgaat  24180
gtgaagagtg ctagactaga atcaaaggcc tcttagattt ggctgtgtca tttgggctca  24240
tgaaaacacc tctggaaatc tctttcagtg caaaggagct ggactagttg atctctcagg  24300
tttcttccaa ctctaaaata tctccagtct gtgccttgga aacatcttag gtgaaaatct  24360
aggaacagtt aacctaattt gcacccttaa aattctgcca tgagctgctt acaactcaaa  24420
acaagtttat cttactcagt tactaattat aaaccatcca gatttcagag ctgtgagtac  24480
tgggtgaagc attgaaggta tgcttttgaa gccattacat atggcagtta ctgagctgaa  24540
aggattaaat gctgcagctt ccccagttgc ccttcctcca tgagagcagt gcctgccccc  24600
agcattctgt ggcacttgga agacaagaca gaggccaaat gcagattttt accctgggct  24660
tccctctaca gtgtggaact caggttgttt cttctttcct ccctgaaatg acatgagttt  24720
gcagcggatg gtgaactgaa gaaaccatag gaggctctgt cttcttgcct gaatttcagt  24780
```

tggaagcttg gagatttggg gttcaacaga gataaggaag tgtaagcctt catcccgtct 24840
ggtggttggc gatcacacac cgctctgtgc tgaggctaat ggccatgatc agagttgacc 24900
aaaaaaaaaa aaaaaaaaaa atacgggttg tccaagcaaa ttgatttcca tacctataga 24960
gagcatacct ttcttcatca gtattttctt ccattcttcc aaaaaattac tttgggctct 25020
aacagccatt cccgtgatct ttacctctcc ttggggaatg cagataattt gaatagtggt 25080
tttaagctat ttttcttgga atacagaagt tctgataagc ccttcaaaga cccctgaggg 25140
caagaagagg gaaggtagta ggcagggctc aggccctctt taacacagac acatgtacat 25200
aagtaacaca tttgcaccaa cactggaagg aaattcaata tattttaaaa tgactttaac 25260
tcctagtgat ggaactatag atattttttt acagcccttc cctgaatgtt cacatgtgtt 25320
ttttatatat atgtgtgtgt cacgtatttg tatatgtgta tatacacata tatatagaaa 25380
cacgtacata tttgtatgca tatttgtaca tataggtata tatgtatgta atgtgtacat 25440
attggcacat gtgtgtgttt gtatatgtat atatcagtac atatagatgt atgtatatat 25500
gtatatattt tttcctccaa aataaacaat aaagaatgtc ttcttagatt gcaaaagtga 25560
attgtctgag ttctgctaag gaaaaaggac ttctgcttct gctgcctgtg aggactgtgc 25620
tgtcagcagt catggccctt caggccctgc acctcgaggc agagccctcc cccggccatg 25680
gccagctctc ctaaccaagt gtctctttcc cccagaatgg ctgcagtctg tccaggccac 25740
catgatcctg tcgatcatct tcagcattct gtctctgttc ctgttcttct gccaactctt 25800
caccctcacc aagggggca ggttttacat cactggaatc ttccaaattc ttgctggtaa 25860
gttgtggatg gtaaagtcca tgtggaagcg gggtgcatcc aagtctgcgg aatgattagt 25920
ttagtagaag gatgtggcct cagaatgact gatgttcatg agtctcccca ctggatgctt 25980
tccataaagt gagggtgggt gcttgtatgt gtgggtgtgt acctgtatgt gtcttagaac 26040
ttgggactta gaactctccc cttctccctg gaatgagatg catatgaaag agaacttaga 26100
ggatctggaa ggaaggtccc cacccaagcc aggcgtatca acaggaatga aactgcaatc 26160
tggacacata atcagaggtg aatactgagg ctatctgtag agcaaaggtc aggcttgaga 26220
gctgtttctg tagattacat tatgcctcca gaaaatggcc ctgatgtgct aagaactagc 26280
aaagtagtta tcaggtatgt gtcttccacc aataggtagt gatgaagcca cactgacaaa 26340
ttctcacctt ccttgcttcc agttcctaga ttctactggg ctttgattga ctgttgtcat 26400
cctctggtgt cttcattttg acactcttgt gtcacatatt gtcatttcca aacatggggc 26460
tatgacaaca catgaaaaca catgagaggt ctccttaatc tcctgcctaa actgtcttca 26520
agttccctct ttaaatacgt tattaatatg catagtgtgc agagtcctag aaacttctgt 26580
tacacagggt gacatcttcc aactttgtct ctggattctg cctagcatct tacatgctta 26640
catcttacat cttacatctt acatcttgca ttctgcctag catcttacat tagctcttac 26700
atgtctgtct gttgacttac tgttgactga accagcaggg cattggagag aagtaagagc 26760
tagatgtagt ggtggattct gtggtccaaa ttcatagatc acaaacttca tatgtaccag 26820
agtatgtcta ggtactggga gatgttctca attctgaccc tctgagaggg caaaggatgt 26880
agcatctctt ctctgagttg gttgtcagaa tgcccatggt accatttcac cactctgtcc 26940
ccaggagcag tcattggaag gttgacgtaa atagggttgt atgggaagac acagcccaag 27000
gttagatgtt ggtgaccttg tctagaagac agagagttcc cctttcctga aaaaaggaag 27060
taaatgatta accacttctc attaaacact caaatacaac atttcaatac tcatggtttt 27120

-continued gagatttcaa aaccagacag tgctttgcta cttacacatg tcttatgaca ccaagccaag 27180
ctcctggatg gttgctggct ctgttaaatg actaattatg caaggagata tcatttctag 27240
gtacgttaaa gtgaagagtt acccttactc aattttcagt tggaataaaa acaactgtaa 27300
catattctgg ggtttctttt ttttttctc actcgtttta gtttgatatc aaatcaaata 27360
atgatcatat ccattgcatc agtggatatg ccctcaagat aatatggatt tagaaccaga 27420
actttcataa tgtatttcta ttgaaatgtt agtttcataa gcgatgattg ggttttcatg 27480
cccatgtgtg agatgtgcct cgctcaaacc ttgttatgat ttggcacgtt acccatctga 27540
tgtgaaaaaa attacatttt atttgtacag gctcgttatt ttactgatga ataatttgag 27600
cccaccagag gataaatgaa tgaccaaggt cacccagctc atgacaggga cggttgagtg 27660
ttacactgaa tatagtgagg tacttcttat attttaaaga cagaatgcac caaaaaattt 27720
aaagaacaca aaatccaagg cagaagctct gccttttata ttatctttta ttggaactga 27780
tttacaatgg aaggtaaatg caaatttgca ccatgtatta ttctgaagtt ccaaacatct 27840
gtgatgaata caagcctgta ctataagacc cagtcacatt gaaaatatgg agctgagaag 27900
aggtaagctg ctgttgaatg ggctccttgg gatagccagt accttcatct tcattcatcc 27960
tgctgagctg tttcggcttt aagttcttta acaatgtctt tttagcaaca tcattacatc 28020
attttaggcc aaaactcaaa gtccagagat aagaaccctt aagtcactca tgtaactgca 28080
ctgtgtgtta aaagtatttc agttcagcca aacactcttc tcctaggtat tgcgatttaa 28140
gtatatttac taatccactc ttgcttcact attttcattc tcctccaaag tcaatacaag 28200
atgtttagaa ctgtgctgga agtgcagaat tccgaatgta aaagcgcatg actttgtcct 28260
ctttatcccc tttacatcta gctgcttacg tctcatgaaa ctgaattttc agttatctgt 28320
tggtccacat ttgaataaga aattatcttg aatttgaaat gctgagctgt aatagcagtt 28380
gtaatttgta agtcctgaga gtgtcctgtc ctccgttgtt aatcccagtc aagatcatct 28440
gagagttggt ctccagggaa cctcagatct ctaggatgtt gcactggaaa tggctgcagg 28500
atctttccac taattctgag aactgaaaga gttaggaact ctatttggag agttcctggt 28560
tcccttatcg tgtgacagtt ctaagtcaat tttgtcatgt ggttttctga ctcacagact 28620
agtaagaagt tagtaattag agagctaagt agattagggt tgttggagat gagaaaccca 28680
cgttttggga aaacctggca agtgacaact taacatcaag gaagtagtca gaaaagctaa 28740
aactgacaaa cagaaggtag aagaaagtag ctccacactc atgggatgtg aaatctacaa 28800
gcgtgcatgc ccggcaaatg cctctccaat gcactggagc gttttaagtg gaaaccacta 28860
gaatctctgt gtagtctccg gaagtggctg tgagggctgc attatctctg cacagcttcc 28920
tcttggtggg cccagctgtg atctttatgg atggcacaca tcagctttca ggaaaagcac 28980
atgaaaggtg ctagggctct tggagctgac tgtaggtttg ggagttgtct gtctccttgc 29040
tctagattac agctctgtgt gttgtgtggg gtctccatgg tttgccaaat tatctcttcc 29100
tcacttagcc acaaggctga cagttaggaa ctatctcttc ttgattgcat taggttggct 29160
gcttcctgaa tgcatatcaa aaggctcctt cctttagttc agtgctttca acctgagctg 29220
tgcatcagaa tcacctgagg tcctttaaaa aaaaaaaaaa gacagtgggc ggggcgcagt 29280
ggctcacgcc tgtaatccca gcactttggg aggctgaggt gggcagatca cttgaggtca 29340
ggagttcaag accagcccgg ccaacatggt gaaaccctgt ctctactaaa aataaaaata 29400
aaaaaatagc caggcgtggt ggtgcgtgcc tgtagtccca gctacttggg aaactgaggc 29460
agagaagaat cacttgaacc taggaggtgg aggttgcagt gagccaagat catgccactg 29520
cactccagcc tgggggtgac agagtaagac tgtctcaaaa aaaaagaaaa aagaaaagaa 29580
aaaagacagt attcaggtct catccctgga gactctcatt taatagttgt gggatggatc 29640
cactgcctag gtgactctga tgtgcattta gggttgggaa ccactgacat agccattaaa 29700
ctgtccctaa tcccactgta aggttttcta ggatattttc ccagaaataa ctaaaccacc 29760
ttcttagaga aggaacatcc tgatcctgcg tctggacttt ggagtcattc ttattttcag 29820
aacctatagc catctattcc ttgacaagat ctgttgggtt gggttgcact agactggaaa 29880
acatcaagaa attaatctag acacagacct aaaaggaaga tttgcacgtt ttgatttatt 29940
ttactgctta cacccagcat caagctccat gtggggcaca tagaggagcc tgaataaaac 30000
tattattggt tggatgatta gataattgtg tttcctcggc agaatcaaac tcaagtcaaa 30060
tgtgtggtta ccgggattaa gaacagaaag aatagagggg actcctgagt gagtttcact 30120
ttctctctct ttttgttatt gttgttcatt tgttttgtta atagaaagat caatatagct 30180
atagagcatt taaaataaaa ggatttgggc caggtgtggt ggcgaatgcc tgtaatccca 30240
acactttgaa agactgaggt gagaggattg cttaaagcca ggagttcaag accagcctgg 30300
gcaacaaagc gagatgccat ctctacaaaa aatgatttaa aaattagtgg ggtgccttgg 30360
agcacgcctg tggtcccagc tattcaggag gctgaggcag gaggattgct tgaggctgag 30420
aggtcaagac tacagtgaac tatgatcagg cccctgcact tgctccagcc tggtgacaga 30480
gtgagaccct gcctctctag gaaaaaaaaa aaaagaattt ggtggggggg gattaataaa 30540
agttcagtgc catcctgttc agagtgattc aaaggtggct taagtcaaat accacattta 30600
gaaatttttg ttagggacgg atgattatgg atgtctcact ggccatgccc aaatcagagt 30660
caatgctatg ggtggctttc taggcagcaa tggtcatttg gatactgaaa atgtaaaagg 30720
agtgggcttc aatcacagaa acacagagaa gtctcttgct ttcagaggaa caggcctcac 30780
agccccttcc tgccctccct tgttgccctg aggatgaagt gggagggaga aaaaggcacc 30840
cactcatcaa cccaacatca tagctgcacc ttccagtgac caccctggtg gtctcactga 30900
catccctttc cagccaactt ctctctgact tctgccccag gctctcaaat gaaagtgctt 30960
ttgcgaggtt accaaagtac actttgaagt ctttaatttg ttggatcact ctgctccttt 31020
caatactgtt agctacttac tctttgaagc tctattcccc tggcttctga gacatcgctg 31080
tgttcccact tgcctgagtg aacacaccag gcggtcatgc tggcctctcc tctctccctc 31140
accccacagc cagccttcta ctgaatcctg catttgggta gcatcctccg taggcattac 31200
gcccatttct ttgtcttgac tcactaaccc cagtgcagct atgcaaaggc ctcctcatgc 31260
accttccagc tacctgcctt gtccctgccc ctgaatccat tttctgcacc atggccagag 31320
tgatcattct aaaacgtgcg tctgatcatg tttctcctct gctgaagttt cctcagaggc 31380
ttctcatcac agcttcctta acatgtcatg taaggccctc tctttcctga cccttagtga 31440
gctaatcagc ctattatatg agagtccgtg tggcttctcc agttctccag tttggactca 31500
gcgcccgtct atgctcttgg ggcatctggt gcatttcctt ccctctctcg aaattccatc 31560
gaactatatt gaaattatat gcaaatgtct gtcttctaga cacacagtcc ttaaggtagg 31620
agccatgtct cacttatctt ggtacatcta gagcagcagc tagaacaggg cccgcatgca 31680
ataggcactc attaaatgtt cactgaacca aagggaatgg agatgataag gatgtactgg 31740
gaattccctc agctacttcc tttgaccttg gccccttggg tgcttccttc cagaggctct 31800
gggctctaat cactctcatg gggttgcagt cactgttaaa ggagcttaag actttctctt 31860
caaaagggct ttaggcagaa cttgcaggaa gttgttgcag acctacccat cctgagacag 31920
ggagaaactc ttgtaagttg aatgctcagc acatttgtat tgtctggaca gggtcagtgt 31980
ccttctgctt aaagatgacc tatgctccca gactcaggcc cctaccaggg agtcccggtc 32040
attgccaaag agcagaacat ctgcctgtgc ctcagggcct cacttaccct tgccacaggg 32100
acctggtgat acatctccac ctactggttg ctgagaaagt gagtcacagt ccacttacta 32160
ggggtatttg gcttttggag atgactactg gatgacatta actgtcttgg gttgcagaca 32220
gagggaaccc agccaaagaa tcatcctttt ctctatttca gggtacatct attgctttac 32280
atgcagacaa tcttgtaata atatattccc taaaacatca gtctcatgac aacaatcata 32340
taaagtgtgt atcctctctt tggctttgta gatatctaag tttactgctt atcacggtta 32400
agcttagagt cattcacttc tgagattcta ctaagatgaa agtcatacac attaagctgt 32460
gtagttagtc gctgcacttc tctatactgc ctctttctat ccctcttgtt caaggatgga 32520
atctggtatc tcctcttagt cagtgaaatc ggggagtagc tggtccactc agctcctgag 32580
gcatttctca tgccagatct ggttagacag cccatttggg agccctgcct gcatgatgat 32640
aagtgttgtc ctgccctgct agcactctgt taacaccttt ctctctgcca aggtcatgtt 32700
tccttttttta tagccctgcc ttcattagat aagtcagaca gagcccaaga gacaacttca 32760
gtatttctta aagacaagag ttagcacttt ggagatgcaa gccgtggaag agtggggcaa 32820
gataattaag gatcctggac ctcaaggcaa ataaagtgtg tccccagcag atcaaaactg 32880
ctgttttctg caatcaacaa ttaacccgca atgatttcgc tcctgacatg gccatctttg 32940
ctgtcttctg aacttcctgt aggtggcagg tcctggatgc tgtcccattt tggttccaag 33000
actattgtgt ggctctcttg acaggggcca gtcaagtggc agttttctcc tctgagttgc 33060
aggaggacag gcttaacagg gtggttcatg tggcgtattc ccacttctgc actgtcttca 33120
aacaaagttg cagtgtccag taaaacagca gcccaaatag cagtgaggtt agatgtaggt 33180
ggccgggcgg tgggggggcg cgggtgcatt gggaactctg gaactgcatg aatcccacac 33240
ggcatactgg atttataata gagtcactca gagcttctca aagaccctgt tttcagggag 33300
gaaacagacc aggctttgtg cagctccagg ctggggtgct gacatcactg gacccctcct 33360
tgtgggggga cgctgtctgt cacgtgagct ggggccatca gtttgagcgt ggctgctcca 33420
cagggcccaa gatggaggct tttcttctct ttccaacacc gaagggctgc attggtgggc 33480
cagggagggt ggcctgaccc acctgcatat ccagtgccct ttagccttct ttgggcttca 33540
aatgcaacct tggggcaccc agggaaatgg agcttgcctt tgatcatctt ccccctctgc 33600
agcgtggctt cccagtcata ctgtcggctg catccttatt cctcactttc tttttccctc 33660
tccacacatt tctttgtctg tttggcagtg cccataggca ttgcttgctt cacctggtat 33720
gtggcaactc tgttaggggg accataggcc cctgtggtct gcatggagct taatcctttt 33780
accatggcgt gactccaata atggtaaaat gtcacttcac ttccattggc tttaggtaat 33840
gccaccactc acttgtagag tggcatatag atttccaggg gtttccatac ccaaccaccc 33900
ttggaaagag acaggtaggt ttttcttgca gcctgaatgc ctgctggcca tgtagtgtgg 33960
cctgggaatt ggtgacagtg aaagaaagag aaatagggca gaaaatgtaa agaaaaccct 34020
caggtattaa ggcctaggtg gccaagattg gaaatagaga gcaagttgtt ttccttgttc 34080
ccatattttt gtgctacctc ctttcaattc tggacctgga agcagatttc cttccagagg 34140
tagaaatgtt cttcctaccc agcaattgtc agcatccggg gtggcggaga gggggccgct 34200
ctgccatgga ctctccgtca cccagcttgt ccctctcctt ccccaggtct gtgcgtgatg 34260
agtgctgcgg ccatctacac ggtgaggcac ccggagtggc atctcaactc ggattactcc 34320
tacggtttcg cctacatcct ggcctgggtg gccttccccc tggcccttct cagcggtgtc 34380
atctatgtga tcttgcggaa acgcgaatga ggcgcccaga cggtctgtct gaggctctga 34440
gcgtacatag ggaagggagg aagggaaaac agaaagcaga caaagaaaaa agagctagcc 34500
caaaatccca aactcaaacc aaaccaaaca gaaagcagtg gaggtggggg ttgctgttga 34560
ttgaagatgt atataatatc tccggtttat aaaacctatt tataacactt tttacatata 34620
tgtacatagt attgtttgct ttttatgttg accatcagcc tcgtgttgag ccttaaagaa 34680
gtagctaagg aactttacat cctaacagta taatccagct cagtattttt gttttgtttt 34740
ttgtttgttt gttttgtttt acccagaaat aagataactc catctcgccc cttccctttc 34800
atctgaaaga agatacctcc ctcccagtcc acctcattta gaaaaccaaa gtgtgggtag 34860
aaaccccaaa tgtccaaaag cccttttctg gtgggtgacc cagtgcatcc aacagaaaca 34920
gccgctgccc gaacctctgt gtgaagcttt acgcgcacac ggacaaaatg cccaaactgg 34980
agcccttgca aaaacacggc ttgtggcatt ggcatacttg cccttacagg tggagtatct 35040
tcgtcacaca tctaaatgag aaatcagtga caacaagtct ttgaaatggt gctatggatt 35100
taccattcct tattatcact aatcatctaa acaactcact ggaaatccaa ttaacaattt 35160
tacaacataa gatagaatgg agacctgaat aattctgtgt aatataaatg gtttataact 35220
gcttttgtac ctagctaggc tgctattatt actataatga gtaaatcata aagccttcat 35280
cactcccaca tttttcttac ggtcggagca tcagaacaag cgtctagact ccttgggacc 35340
gtgagttcct agagcttggc tggtctaggc ctgttctgtg cctccaagga ctgtctggca 35400
atgacttgta ttggccacca actgtagatg tatatatggt gcccttctga tgctaagact 35460
ccagaccttt tgtttttgct ttgcatttc tgattttata ccaactgtgt ggactaagat 35520
gcattaaaat aaacatcaga gtaactcact 35550

<210> SEQ ID NO 21
<211> LENGTH: 1828
<212> TYPE: DNA
<213> ORGANISM: Artificial Sequence
<220> FEATURE:
<223> OTHER INFORMATION: Pmp22 mRNA

<400> SEQUENCE: 21
agttacaggg agcaccacca gggaacatct cggggagcct ggttggaagc tgcaggctta 60
gtctgtcggc tgcgggtctc tgactgccct gtggggaggg tcttgcctta acatcccttg 120
catttggctg caaagaaatc tgcttggaag aaggggttac gctgtttggc cgggcagaaa 180
ctccgctgag cagaacttgc cgccagaatg ctcctcctgt tgctgagtat catcgtcctc 240
cacgtcgcgg tgctggtgct gctgttcgtc tccacgatcg tcagccaatg gatcgtgggc 300
aatggacacg caactgatct ctggcagaac tgtagcacct cttcctcagg aaatgtccac 360
cactgtttct catcatcacc aaacgaatgg ctgcagtctg tccaggccac catgatcctg 420
tcgatcatct tcagcattct gtctctgttc ctgttcttct gccaactctt caccctcacc 480
aaggggggca ggttttacat cactggaatc ttccaaattc ttgctggtct gtgcgtgatg 540
agtgctgcgg ccatctacac ggtgaggcac ccggagtggc atctcaactc ggattactcc 600
tacggtttcg cctacatcct ggcctgggtg gccttccccc tggcccttct cagcggtgtc 660
atctatgtga tcttgcggaa acgcgaatga ggcgcccaga cggtctgtct gaggctctga 720
gcgtacatag ggaagggagg aagggaaaac agaaagcaga caaagaaaaa agagctagcc 780
caaaatccca aactcaaacc aaaccaaaca gaaagcagtg gaggtggggg ttgctgttga 840
ttgaagatgt atataatatc tccggtttat aaaacctatt tataacactt tttacatata 900
tgtacatagt attgtttgct ttttatgttg accatcagcc tcgtgttgag ccttaaagaa 960
gtagctaagg aactttacat cctaacagta taatccagct cagtattttt gttttgtttt 1020
ttgtttgttt gttttgtttt acccagaaat aagataactc catctcgccc cttccctttc 1080
atctgaaaga agatacctcc ctcccagtcc acctcattta gaaaaccaaa gtgtgggtag 1140
aaaccccaaa tgtccaaaag cccttttctg gtgggtgacc cagtgcatcc aacagaaaca 1200
gccgctgccc gaacctctgt gtgaagcttt acgcgcacac ggacaaaatg cccaaactgg 1260
agcccttgca aaaacacggc ttgtggcatt ggcatacttg cccttacagg tggagtatct 1320
tcgtcacaca tctaaatgag aaatcagtga caacaagtct ttgaaatggt gctatggatt 1380
taccattcct tattatcact aatcatctaa acaactcact ggaaatccaa ttaacaattt 1440
tacaacataa gatagaatgg agacctgaat aattctgtgt aatataaatg gtttataact 1500
gcttttgtac ctagctaggc tgctattatt actataatga gtaaatcata aagccttcat 1560
cactcccaca tttttcttac ggtcggagca tcagaacaag cgtctagact ccttgggacc 1620
gtgagttcct agagcttggc tgggtctagg ctgttctgtg cctccaagga ctgtctggca 1680
atgacttgta ttggccacca actgtagatg tatatatggt gcccttctga tgctaagact 1740
ccagaccttt tgtttttgct ttgcattttc tgattttata ccaactgtgt ggactaagat 1800
gcattaaaat aaacatcaga gtaactca 1828

<210> SEQ ID NO 22
<211> LENGTH: 483
<212> TYPE: DNA
<213> ORGANISM: Artificial Sequence
<220> FEATURE:
<223> OTHER INFORMATION: Pmp22 Coding sequence

<400> SEQUENCE: 22
atgctcctcc tgttgctgag tatcatcgtc ctccacgtcg cggtgctggt gctgctgttc 60
gtctccacga tcgtcagcca atggatcgtg ggcaatggac acgcaactga tctctggcag 120
aactgtagca cctcttcctc aggaaatgtc caccactgtt tctcatcatc accaaacgaa 180
tggctgcagt ctgtccaggc caccatgatc ctgtcgatca tcttcagcat tctgtctctg 240
ttcctgttct tctgccaact cttcaccctc accaaggggg gcaggtttta catcactgga 300
atcttccaaa ttcttgctgg tctgtgcgtg atgagtgctg cggccatcta cacggtgagg 360
cacccggagt ggcatctcaa ctcggattac tcctacggtt tcgcctacat cctggcctgg 420
gtggccttcc ccctggccct tctcagcggt gtcatctatg tgatcttgcg gaaacgcgaa 480
tga 483

<210> SEQ ID NO 23
<211> LENGTH: 160
<212> TYPE: PRT
<213> ORGANISM: Artificial Sequence
<220> FEATURE:
<223> OTHER INFORMATION: Pmp protein sequence

<400> SEQUENCE: 23

Met Leu Leu Leu Leu Leu Ser Ile Ile Val Leu His Val Ala Val Leu
1 5 10 15

```
Val Leu Leu Phe Val Ser Thr Ile Val Ser Gln Trp Ile Val Gly Asn
            20                  25                  30

Gly His Ala Thr Asp Leu Trp Gln Asn Cys Ser Thr Ser Ser Ser Gly
        35                  40                  45

Asn Val His His Cys Phe Ser Ser Ser Pro Asn Glu Trp Leu Gln Ser
    50                  55                  60

Val Gln Ala Thr Met Ile Leu Ser Ile Ile Phe Ser Ile Leu Ser Leu
65                  70                  75                  80

Phe Leu Phe Phe Cys Gln Leu Phe Thr Leu Thr Lys Gly Gly Arg Phe
                85                  90                  95

Tyr Ile Thr Gly Ile Phe Gln Ile Leu Ala Gly Leu Cys Val Met Ser
            100                 105                 110

Ala Ala Ala Ile Tyr Thr Val Arg His Pro Glu Trp His Leu Asn Ser
        115                 120                 125

Asp Tyr Ser Tyr Gly Phe Ala Tyr Ile Leu Ala Trp Val Ala Phe Pro
    130                 135                 140

Leu Ala Leu Leu Ser Gly Val Ile Tyr Val Ile Leu Arg Lys Arg Glu
145                 150                 155                 160


<210> SEQ ID NO 24
<211> LENGTH: 16
<212> TYPE: DNA
<213> ORGANISM: Artificial Sequence
<220> FEATURE:
<223> OTHER INFORMATION: proviso seq

<400> SEQUENCE: 24

atcttcaatc aacagc                                                    16


<210> SEQ ID NO 25
<211> LENGTH: 2108
<212> TYPE: DNA
<213> ORGANISM: Artificial Sequence
<220> FEATURE:
<223> OTHER INFORMATION: CEBPb  NC_000020.11:c50192690-50190583

<400> SEQUENCE: 25

ttactgcccc caaaaggctt tgtaaccatt ctcaaaaaaa agtttattaa aagtgttctt     60

aatgcttgaa acggaaaaga ttcccaaaat atacagacgc ctcttttctc atagaaatag    120

attatttttt ataatacaaa aaaagaccaa aaaacaaaac aaaacaaaac atcaacagca    180

acaagcccgt aggaacatct ttaagcgatt actcagggcc cggctgacag ttacacgtgg    240

gttgcgtcag tcccgtgtac acacgcgttc agccatgttt aaaccgattg catcaacttc    300

gaaaccggcc cgcccgccgg cgcctggaga ggggcagagg gagaagcaga gagtttatca    360

ttcatctgta cacatagacg tttcttcttt aaataacacc acgggcggga gccccatctg    420

catgtgcggt tggtttggac aaaaatatag atatatatat ataataaaat attaaaatta    480

ccgacgggct ccccgcgctg ccaagtgccc cagtgccaaa gttttgccgg cgccgccggg    540

ggcgggggcg agggcgcggg cgcgggcgct ccccggagtc tcagccccgg ccggcagggg    600

gacgcgcgcg ggggccgcgc tagcagtggc cggaggaggc gagcaggggc tcgggcagct    660

gcttgaacaa gttccgcagg gtgctgagct cgcgcgacag ctgctccacc ttcttctgca    720

gccgctcgtt ctcggccgtg agctccagga ccttgtgctg cgtctccagg ttgcgcatct    780

tggccttgtc gcggctcttg cgcacggcga tgttgttgcg ctcgcgccgg atcttgtact    840

cgtcgctgtg cttgtccacg gtcttcttgg ccttgctctt gacctgcgag ggcgccggcg    900
```

-continued

```
cggcccccgc gtagcaggcg gtcgggggcg ccttggcgtc agcggggctc ggcgtgccgg    960

gcgggctgga cgaggaggac gtggagaggc tcccgctgct gccgctcggc accgcctggt   1020

agccgaggta agcgcgcagc gcgtacggga agcccgccgc catgcctgcg ccgccgcccg   1080

gcgccccggc ctcctccttc cgcttgcagt ccgcgggctc gaagcccggc tccgccttga   1140

gctcggcggg cggcggcggc ggcgggggcg gtgggtgcag gggcgcgaag cagccggggt   1200

gcagcgcgcc cttggcggcc cccaggcgcc ccaggctcac gtagccgtac tcggccggct   1260

tcttgcagtt cttgcccccg tagtcgtcgg agaagaggtc ggagaggaag tcgtggtgct   1320

gcccggagga ggcgggcgcg ggggcgggcg cgggcggagc cgcctcgaag gtgtccgtgg   1380

ccgtggcggg cgccggggcc tgcggcgcgc ccagcggctc caggtacggg ctgaagtcga   1440

tggcgcgctc gtggtcgccg atgctgccca gctcgccggc ggggggggcgc ggcccgggtc   1500

tggccgcggg gggcgccgcg ggggccgcct tgccgccgta cgcagcagcc aagcagtccg   1560

cctcgtagta gaagttggcc acttccatgg atttaaaggc aggcggcggc ggcggcaggg   1620

ggagacatgc tgggtcccag gccaccaggc gttgcatgaa cgcgggtgcc cggggagggg   1680

gcctggggct gcccgctccg gccggcccgc aggtggcgcg gcctccctgc tctgagctgt   1740

cgccgctgcg tcgctgctgc tgctgccgcc gctgccgggg tggccgctat tagtgagggg   1800

gctggtggct ggaccctcgg gtgggtcccc ttcccagtcc cgtgcgcggc tctgactcgc   1860

taaagtttct cctgagcccg gttatttata agggcggccc gtagcaaccg ctgcgtcacg   1920

ccggcccctc ccgccgcgcc gccgggacgc gaaggacacg gccgcggccg cccgagaccc   1980

ccgggaggac ggcggcaggg cgcagcggag ggaccgggca cccggagcgc gttttcgggg   2040

ggcccccggg acgcaggggc ggcctcacgc cccctgccca cccccgcccg gccgccccgg   2100

gattggga                                                            2108
```

<210> SEQ ID NO 26
<211> LENGTH: 345
<212> TYPE: PRT
<213> ORGANISM: Artificial Sequence
<220> FEATURE:
<223> OTHER INFORMATION: CEBPn Amino Acid

<400> SEQUENCE: 26

```
Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
                85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140
```

```
Leu Gly Ala Ala Lys Gly Ala Leu His Pro Gly Cys Phe Ala Pro Leu
145                 150                 155                 160

His Pro Pro Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Ala Pro Ala Pro
                245                 250                 255

Ser Gln Val Lys Ser Lys Ala Lys Lys Thr Val Asp Lys His Ser Asp
            260                 265                 270

Glu Tyr Lys Ile Arg Arg Glu Arg Asn Asn Ile Ala Val Arg Lys Ser
        275                 280                 285

Arg Asp Lys Ala Lys Met Arg Asn Leu Glu Thr Gln His Lys Val Leu
    290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
            340                 345
```

<210> SEQ ID NO 27
<211> LENGTH: 2113
<212> TYPE: DNA
<213> ORGANISM: Artificial Sequence
<220> FEATURE:
<223> OTHER INFORMATION: CEBP NM_005194.3

<400> SEQUENCE: 27

```
tcccaatccc ggggcggccg ggcgggggtg ggcagggggc gtgaggccgc ccctgcgtcc     60

cgggggcccc ccgaaaacgc gctccgggtg cccggtccct ccgctgcgcc ctgccgccgt    120

cctcccgggg gtctcgggcg gccgcggccg tgtccttcgc gtcccggcgg cgcggcggga    180

ggggccggcg tgacgcagcg gttgctacgg gccgccctta taaataaccg ggctcaggag    240

aaactttagc gagtcagagc cgcgcacggg actgggaagg ggacccaccc gagggtccag    300

ccaccagccc cctcactaat agcggccacc ccggcagcgg cggcagcagc agcagcgacg    360

cagcggcgac agctcagagc agggaggccg cgccacctgc gggccggccg gagcgggcag    420

ccccaggccc cctccccggg cacccgcgtt catgcaacgc ctggtggcct gggacccagc    480

atgtctcccc ctgccgccgc cgccgcctgc ctttaaatcc atggaagtgg ccaacttcta    540

ctacgaggcg gactgcttgg ctgctgcgta cggcggcaag gcggcccccg cggcgccccc    600

cgcggccaga cccgggccgc gcccccccgc cggcgagctg ggcagcatcg gcgaccacga    660

gcgcgccatc gacttcagcc cgtacctgga gccgctgggc gcgccgcagg ccccggcgcc    720

cgccacggcc acggacacct tcgaggcggc tccgcccgcg cccgcccccg cgcccgcctc    780

ctccgggcag caccacgact tcctctccga cctcttctcc gacgactacg gggcaagaa    840

ctgcaagaag ccggccgagt acggctacgt gagcctgggg cgcctggggg ccgccaaggg    900
```

```
cgcgctgcac cccggctgct tcgcgcccct gcacccaccg cccccgccgc cgccgccgcc    960

cgccgagctc aaggcggagc cgggcttcga gcccgcggac tgcaagcgga aggaggaggc   1020

cggggcgccg ggcggcggcg caggcatggc ggcgggcttc ccgtacgcgc tgcgcgctta   1080

cctcggctac caggcggtgc cgagcggcag cagcgggagc ctctccacgt cctcctcgtc   1140

cagcccgccc ggcacgccga gccccgctga cgccaaggcg cccccgaccg cctgctacgc   1200

gggggccgcg ccggcgccct cgcaggtcaa gagcaaggcc aagaagaccg tggacaagca   1260

cagcgacgag tacaagatcc ggcgcgagcg caacaacatc gccgtgcgca agagccgcga   1320

caaggccaag atgcgcaacc tggagacgca gcacaaggtc ctggagctca cggccgagaa   1380

cgagcggctg cagaagaagg tggagcagct gtcgcgcgag ctcagcaccc tgcggaactt   1440

gttcaagcag ctgcccgagc ccctgctcgc ctcctccggc cactgctagc gcggcccccg   1500

cgcgcgtccc cctgccggcc ggggctgaga ctccggggag cgcccgcgcc cgcgccctcg   1560

cccccgcccc cggcggcgcc ggcaaaactt tggcactggg gcacttggca gcgcggggag   1620

cccgtcggta attttaatat tttattatat atatatatct atatttttgt ccaaaccaac   1680

cgcacatgca gatggggctc ccgcccgtgg tgttatttaa agaagaaacg tctatgtgta   1740

cagatgaatg ataaactctc tgcttctccc tctgcccctc tccaggcgcc ggcgggcggg   1800

ccggtttcga agttgatgca atcggtttaa acatggctga acgcgtgtgt acacgggact   1860

gacgcaaccc acgtgtaact gtcagccggg ccctgagtaa tcgcttaaag atgttcctac   1920

gggcttgttg ctgttgatgt tttgttttgt tttgtttttt ggtctttttt tgtattataa   1980

aaaataatct atttctatga gaaaagaggc gtctgtatat tttgggaatc ttttccgttt   2040

caagcattaa gaacactttt aataaacttt tttttgagaa tggttacaaa gccttttggg   2100

ggcagtaaaa aaa                                                      2113
```

```
<210> SEQ ID NO 28
<211> LENGTH: 322
<212> TYPE: PRT
<213> ORGANISM: Artificial Sequence
<220> FEATURE:
<223> OTHER INFORMATION: CEBPb Iso 2

<400> SEQUENCE: 28

Met Glu Val Ala Asn Phe Tyr Tyr Glu Ala Asp Cys Leu Ala Ala Ala
1               5                   10                  15

Tyr Gly Gly Lys Ala Ala Pro Ala Ala Pro Pro Ala Ala Arg Pro Gly
            20                  25                  30

Pro Arg Pro Pro Ala Gly Glu Leu Gly Ser Ile Gly Asp His Glu Arg
        35                  40                  45

Ala Ile Asp Phe Ser Pro Tyr Leu Glu Pro Leu Gly Ala Pro Gln Ala
    50                  55                  60

Pro Ala Pro Ala Thr Ala Thr Asp Thr Phe Glu Ala Ala Pro Pro Ala
65                  70                  75                  80

Pro Ala Pro Ala Pro Ala Ser Ser Gly Gln His His Asp Phe Leu Ser
                85                  90                  95

Asp Leu Phe Ser Asp Asp Tyr Gly Gly Lys Asn Cys Lys Lys Pro Ala
            100                 105                 110

Glu Tyr Gly Tyr Val Ser Leu Gly Arg Leu Gly Ala Ala Lys Gly Ala
        115                 120                 125

Leu His Pro Gly Cys Phe Ala Pro Leu His Pro Pro Pro Pro Pro Pro
    130                 135                 140
```

Pro Pro Pro Ala Glu Leu Lys Ala Glu Pro Gly Phe Glu Pro Ala Asp
145 150 155 160

Cys Lys Arg Lys Glu Glu Ala Gly Ala Pro Gly Gly Gly Ala Gly Met
165 170 175

Ala Ala Gly Phe Pro Tyr Ala Leu Arg Ala Tyr Leu Gly Tyr Gln Ala
180 185 190

Val Pro Ser Gly Ser Ser Gly Ser Leu Ser Thr Ser Ser Ser Ser Ser
195 200 205

Pro Pro Gly Thr Pro Ser Pro Ala Asp Ala Lys Ala Pro Pro Thr Ala
210 215 220

Cys Tyr Ala Gly Ala Ala Pro Ala Pro Ser Gln Val Lys Ser Lys Ala
225 230 235 240

Lys Lys Thr Val Asp Lys His Ser Asp Glu Tyr Lys Ile Arg Arg Glu
245 250 255

Arg Asn Asn Ile Ala Val Arg Lys Ser Arg Asp Lys Ala Lys Met Arg
260 265 270

Asn Leu Glu Thr Gln His Lys Val Leu Glu Leu Thr Ala Glu Asn Glu
275 280 285

Arg Leu Gln Lys Lys Val Glu Gln Leu Ser Arg Glu Leu Ser Thr Leu
290 295 300

Arg Asn Leu Phe Lys Gln Leu Pro Glu Pro Leu Leu Ala Ser Ser Gly
305 310 315 320

His Cys

<210> SEQ ID NO 29
<211> LENGTH: 147
<212> TYPE: PRT
<213> ORGANISM: Artificial Sequence
<220> FEATURE:
<223> OTHER INFORMATION: CEBPb Iso 3

<400> SEQUENCE: 29

Met Ala Ala Gly Phe Pro Tyr Ala Leu Arg Ala Tyr Leu Gly Tyr Gln
1 5 10 15

Ala Val Pro Ser Gly Ser Ser Gly Ser Leu Ser Thr Ser Ser Ser Ser
20 25 30

Ser Pro Pro Gly Thr Pro Ser Pro Ala Asp Ala Lys Ala Pro Pro Thr
35 40 45

Ala Cys Tyr Ala Gly Ala Ala Pro Ala Pro Ser Gln Val Lys Ser Lys
50 55 60

Ala Lys Lys Thr Val Asp Lys His Ser Asp Glu Tyr Lys Ile Arg Arg
65 70 75 80

Glu Arg Asn Asn Ile Ala Val Arg Lys Ser Arg Asp Lys Ala Lys Met
85 90 95

Arg Asn Leu Glu Thr Gln His Lys Val Leu Glu Leu Thr Ala Glu Asn
100 105 110

Glu Arg Leu Gln Lys Lys Val Glu Gln Leu Ser Arg Glu Leu Ser Thr
115 120 125

Leu Arg Asn Leu Phe Lys Gln Leu Pro Glu Pro Leu Leu Ala Ser Ser
130 135 140

Gly His Cys
145

<210> SEQ ID NO 30
<211> LENGTH: 75245
<212> TYPE: DNA

<213> ORGANISM: Artificial Sequence
<220> FEATURE:
<223> OTHER INFORMATION: STAT3 Genomic Sequence

<400> SEQUENCE: 30
gaattatgca tgacggcgtg cctcggccag gctggggctg ggcgaggatt ggctgaaggg 60
gctgtaattc agcggtttcc ggagctgcgg cggcgcagac tgggaggggg agccgggggt 120
tccgacgtcg cagccgaggg aacaagcccc aaccggatcc tggacaggca ccccggcttg 180
gcgctgtctc tccccctcgg ctcggagagg cccttcggcc tgagggagcc tcgccgcccg 240
tccccggcac acgcgcagcc ccggcctctc ggcctctgcc ggagaaacag gtgaaggggg 300
tgcagggtgg ggccgttggg gaggcctggg gacccggggg ctccgcagcg gcagggggcc 360
tctgggacct tggggatgtt gtgatggacg ctgcagtggg gccgggagag atgaagagac 420
gcggagggtc gccctgaggg aagactcttc gggatgacag gagcgggcct cggaagggac 480
tcggggcgct ggagggaagt ttcgttcttc ggagaaacag aacgcgctcg agggggcacc 540
gtggggcgag ggcgcactcg gttgcggcgg caggagtgag ggacagtccc ccgatttcct 600
gctccctggg gccctgggga cgttccggcc accggagcga ctgtcacgcc gacggggatc 660
accggcgcga gtgggggtc ggaaagcgcc tcctccccgc ccggtcggcg gctcccgctg 720
agccacttcc tccgcttgcc ctgttcccgc tccttcagga gacagctgtg ccctttttgga 780 ggcaggaata ggtgtgtctg tcgcctgcag ccttacgggc tggctggtcg tgggtaggct 840
ttattgcata agaatcaagt ttcctgtagg gaaattgaca gaccggtact ctttctaaat 900
tccctcgcat ctttttctag gttaaattat gctcccccca cgtccccgcc ttgtaaaaaa 960
gagaaaaaaa gacaaaataa aatccccatc aacccgtcaa gccagctcta gagagagaaa 1020
taaacctctt gacattgtcc ttttccaaat acctggtaaa gtcggccaga agataaataa 1080
ttgagccatt gcatttactg gattgtggtg ttgcttaatt gcataggacg gaatgaacca 1140
attgagagtg ggagttttct gtctcagagc caagatcttg ggtaaatgca gaggagaggg 1200
aaacaaagac aggctggcct tgaaaaaacc atgtgtgcaa actttacatg catttggggg 1260
gtgtggttgc actgaagtta acaagattca aaccgtcgcc caagttggta tttccatgtt 1320
tggtacacat cactctgtgc catatcaggt cgttgttaag tgtggtgaca aaatcagtgg 1380
ttagtcattt ttttaattaa aaatgtgtat agtgtgtacc tgctggtctt actgtatgtg 1440
caactaaagg tttacatagt ctgtgtatgg gttgtaaatt tttggctggc tgtgctgata 1500
aagcattggg cttgaataaa gcaaagcaga aaatcatctc aatcttttat atgtggattt 1560
agactgtgtt atgacttggt tcagccagtt ttctatctta ttttatatta aatatgtctg 1620
tgttctctga gtcagcacat ttatttcctt attacatgtt ccagacagga gtgctagccc 1680
agtttttgtt cagtttgcac agtgggatgg ggaaacaagt ctggaattta aaaaaaaatg 1740
ttttagaggt tggagccttg attttagtct ctatattagc acatccatca caaagaacca 1800
ttagtaaatt catgaatctt ttgtttttta tgtagttcat ttgagaagaa taatcactta 1860
gaaatatcca cagtgccagg catggtggtg cacacctctg atcccagcta attgaaggct 1920
gaggtgggag gattccttga gtccaggagt tgagtctggt ctgggcaaca tggtgagagg 1980
ccaggaattg ggtctagagt ctagtctaag caccataatg agaacccatc tttaagaaag 2040
aaagaaagga aaggaggaag aaaggaaaga aaaagaaata cccacagcac agttatgaat 2100
taacccacaa aggacttgtg aggtgggtag ttcacataac aattacccta atatcgtaga 2160
taagaaaatt gaggccaaag gatcaagaca cttggccaac gcagcagagt gccatagtgg 2220
tggaatttgt gcctccttct gtatattttg tgaaaagtat cagtgaaatt cttttttttt 2280
ttttttttga gtcagagtct tgctctgttg cccaggctag agtgcagtgg cgcaatcttg 2340
gctcactgca acctctgcct cctgggttca agcgattctc ctgcctcagc ctcccaagta 2400
gctgggacta caggcgtgcg ccaccacgcc cagctaattt ttgtattttt agtagagacc 2460
ggggttttac catattggcc aggctggtct tgaactcctg accttgtgat ttgcccacct 2520
ctatctccca aagtgctggg attacaggtg tgagccaccg cgcccagtaa gtatcagtga 2580
aattctaaca tatatctgaa cagtaaaata ccaccaatag gctgaaagac ttcatgggag 2640
gtaaatattc aataaacagg tgaaaaaaga aatacaaatg gagcttgctt agattatttt 2700
tctaattgct atgtctaact tgggaagtga ggaactgttt ttggtcagca taatttacca 2760
tcagaattta gctatttact aatgaaaaga aatactaatc taggtttgtt ttagattaag 2820
gacagtcatg acctaaatgt catttaaacc agagtgcatt gtggcttgat cagtggtcat 2880
ttctgtctct agaaagttgc tttaacttct ctgcctctac gtgtctcttg acattcagat 2940
atgaggtggg gtagaggtgg tgaccaactt tccagacgcc tgagtccaaa ccttcttagc 3000
ttatggtttt cttaggtgat gtgcaaatca acaaatatat actttttttt tttttttttt 3060
gagttggagt tgcactctat cacccaggct ggagtgcagt ggcatgatcg tggctcactg 3120
caacctcctc ctcccgggtt caagtgattc tcgcacctca gcctcctgag tagctgggat 3180
tacaggtgcc cgccactacg cccggctaat ttttgtattt ttagtagaga taaggtttca 3240
ctatattgac caggctggtc tcaaactcct gacctcaaga gatctgccca cctcagcctc 3300
ccaaagtgct gggattacag gcgtgaacca ccttgcctgg ccaacatata tatacctttt 3360
gcaactttgt cagagttgct atgaagaata agttgtatct tgttcacaga aattgcagtc 3420
tactggggga gctgataaat gttttaacca tccaatgtaa catgttgtca tcaaagagat 3480
ggtgagactt tacacttgtg ctaacaaggt agctgttcta cataaaagaa catacagtac 3540
agatgtagaa cttttctgtt atcatagaac gttctattgg acagtgctag gctgaatgct 3600
acagatcttc agagaaagga gaggttatga ggcctggagt tgtctagaaa gtctttttgc 3660
caaagaggga tttcaactgg gtcccaaata atgggtggaa tttgataggt gtaaagaatt 3720
tgcggtggtt tatgcctgta atcccagcac tttgggaggc tgaggcagga ggattgcttg 3780
agcccaggag tttgagacca gcttgggcaa cgtggtaaaa ctccctctcc cctaaaaata 3840
aaaaaaatta gccaggcctg gtggcgtgga cctgtagtcc cagctactgg tgagactaag 3900
gtgggaggat cacccaagcc ccgggggtta aggctgcagt gagccgtgat cccgccaccg 3960
cactccagcc tgggtgacag agtgagaccc tgtctccaaa aaaaaaaaaa attcctggta 4020
gcccggtaga ctaggagggt aagtagggga gaagtgatta cttacaaaag acattgaata 4080
caggaccaag gaatttcagt tctgttcttt tgtaggggaa gcttttaaaa ctttcggggc 4140
gccgggcgcg gtggctcacg cctgtaatcc cagcactttg ggaggcccag acgcgcggat 4200
cacgaggcca ggagatcgag accatcctgg ctaacacggt gaaaccccat ctctactaaa 4260
aatacaaaaa aaagtagccg ggcgttgtgg cgggcgtctg tagtcccagc tactcgggag 4320
gctgaggcag gagaagagcg tgaactcggg aggcggagct tgcagtgagc cgatatcgca 4380
ccactgcact ccagcctggg cgacagagcg agactccgtc tcaaaaaaaa aaaaaaataaa 4440 taaataaata aataaataaa actttggagc cgaagcactg atgtttaatc atagagtgct 4500
tactatgtgt taggcacagg cctgattgcc tgatgctggt taatttgtac aaagtaaatc 4560

```
agtgcatatg ccctctgccc taggggagtt attaactgga gtctgacatt gtacaaaggt   4620
aggtatcctg actagtttga tttggtactt tgggtgaaaa aagtatagtg tgcttaagtg   4680
cagaagtgtt ttttgaggat ttttgattgg atacaaacca ccactcatat tttatgtctt   4740
tggcacttaa aaatttcacc ataacttttg agtcatttat aaaaaaccact gaaagagtac   4800
ttgagggaca tccccgaatc ctgaagaact tctggtgttc tggagcagcc tcagtgagat   4860
ccaggaggat ggcattgctg ggctggccca gcccttattg attatggtgt aaagaattaa   4920
tatggtggtt atatactctt tgttagacac cttggcttac aagacgtaag cgtaaagtgt   4980
agtgcgcttt agtcagtatg gccacatggt cctttggtgg taaattgttt gagatgcctc   5040
cagtttttaa aaggagtagc atatcgggcc aggagcagtg gctcatgcct ataatcccag   5100
cactttggaa ggccgaggca agaggattgc ttgagcccag gagttcaaga ccagcctggg   5160
caacatagtg agaccacttt gtttctttaa aaaaaaaaaa aaggcaaaaa caggctgggc   5220
atggtggctg atgcctgtaa tcccagcgct ttgtgaggca gaggtgagcg gatcacttga   5280
ggtcaggagt ttgagaccag cctggccaac atggtaaaac cccgtctcta ctaaaaatac   5340
aaaaattagc caggtgtggt ggcacacgcc tgtagttcca gctactctgg aggctgagcc   5400
aggagaattg cttgaacctg ggaggtggag gctgcagtga gccaagatcc tgccactgca   5460
ctccagactg ggggacagag tgagacattc tgacagtgct acactgaatg ctacatgtct   5520
tcagaggaag gagaggttat gaggcctggg aataacatat ggaagaatga atttctgtta   5580
tggtcagttc tcatttgtca tgttaggatt actgcaactc ttacccagcc gggtgtggtg   5640
gctcatgcct gtaattccag cactttggga ggctgtgggc ggatcacgag gtcaggagat   5700
cgagaccatc ctggctaaca cggtgaaact ccgcctctac taaaaataca aaaaattagc   5760
ccagcgtggt ggcagacgcc tgtagtccca gctactcagg aggctgaggc aggagaatgg   5820
catgagtcct ggaggcggag cttgcagtga gctgagatcg tgccactgca ctccagcctg   5880
ggcaacagag tgggactcca tctcaaaaaa aaaagaaaaa aaaaaggatt accgcaactc   5940
tttaattcag atcagcaaac atgttgagag ccaggtattg cgtcaggcag gatccaagga   6000
taatgaaata ttgtccgttt tcatgaaact ggagatgttg cagggaccga ggtgtgtgct   6060
atgccagtat ggaagtagga caggggagac gacagggcag tgagtggttc aagactctgg   6120
ctctgaagtc aaacagatct gggactgaat cctggatctg ccacttccta gtcagaatct   6180
gagcctctat tttcttatct gtaaaagaag attataacag tgcttatctt gtaggtactg   6240
ttgacgattc aataagataa tgtggataaa atgcttagca tagtgcctgg cacatagtaa   6300
gagctcggta aatctaagtt cttactaaat atccaagaaa agagattaat tcttttcagg   6360
agtgagagaa agtcatcatt attgaggggc tttatcagat gggaacacct gaatagggtt   6420
ttataggatg aataggaatt ctttccacga agttgcgtta caaaaagttg cattcaaggc   6480
tgaaggaaca tgagggtgca gaggcttaaa acagccttgt gtgttcaggg agctataagt   6540
agaagttctt aatttaggag aactaaacca aggggaaagg aggccaagga accacagttc   6600
ttatcccttt tctgttaata attgggttta aatgtcatta aaataagtta ttttgtcctt   6660
tttagaaaag taataacatg ctattataaa aaaaaagact tgtaggaata taaaatgtgt   6720
gttttacatg tatcctgtta attgacttgc ttttattcag attttttgca gccctttctg   6780
tttaccaggt tatcttggag acatatttat tccaaattcc tttttttttt tttttttgag   6840
atggagtctc gctctgtcgc ccaggctgga gtgcagtggc gctatcttgg ctcattgcaa   6900
gctccgcctc ccgggttcac gccactctcc tgcctcagcc tcccgagtag ctgggactac   6960
```

aggcgcccgc caccacgccc agctaatgtt ttttttttta tatttttagt agcgacaggg 7020
tttcaccgtg ttagccagga tggtctcaat ctcctcacat tgtgatccgc ctgcctcggc 7080
ctcccaaagt gctgggatta caggcgtgag ccagcacgcc tggccttcca aattcctttt 7140
aacagcctag caaaagaata ataaggaagg taaatctgcc cctacaagaa aataatgctt 7200
cgacgatccg gctttccttc ctgctacccc cagccataag aataaatgac cttgctcatc 7260
actgaaattt tacctgacct ttgaattttt aactgcgtca gccaaagaac ttatattttg 7320
agtattccta aggtgattgc tattgtagtt ttgaaacact tggttggtat gtttgagggt 7380
ttcatggtcc aaagttacta tagcagttaa aagagtggac tatcaggtca gacctattgg 7440
gctttaatcc cagttctgcc ttctcttaga ccttgggcct gttgttttca cttctctggt 7500
tttcagtttc tctgtccaca attgtggaaa cgaggtccac ttgtagagta attgagagga 7560
tgaagcaaga tgatgcatat caagtacttt gcatagtgcc gggcagacag gtaacattca 7620
agtgctaata attactatta ttactattta ttttttgaga caggttctca ctctgtcacc 7680
taggctggag tgcagcggtg agatcacagc tcatgacagc cttgacctcc taggctcaag 7740
tgatcctcct gcctcagcct tcggggtagc tggggctaca ggtgtgtgct accaccctca 7800
gctaattttc taattttttt gagtcaggat ctcgtcacgt tgcctaggct gaattactct 7860
tattaaaaac tataatatca ggccgagtgc ggtggctcac gcctgtaatc ccagcacttt 7920
gggaggccaa ggcgggtgga tcacctgagg tcaggagttc aagaccagcc tgcccaacag 7980
agtgagaccc cccccgtctc tactaaaaat ataaaaatta gccagttgtg gtggtgggca 8040
cctgtaatcc cagctactcg ggaggctgag gcaggataat cgcttgaacc cgggaggcgg 8100
aggttgcggt gaaccgagat cgtgccactg cactacagcc tgggtgacag agtgagactc 8160
tgtctcaaaa aaaccgaaaa acaaaaagca taattagggt ggtaacgctt atacataggg 8220
gcaggtggaa taaaacataa ttaggaggtc gggcatggtg gctcacgcct gtaattccag 8280
cactttggga ggccgaggcg ggtcaggagt tcaagaccag cctgcccaac atagtgagac 8340
cccgtctcta ctaaaaatat aaaatttagc ctgttgtggt ggcgggtgcc tgtagtccca 8400
gctacccggg aggctgaggc aggagaattg cttttgaacc caggaggtgg gggttgcagt 8460
gagctgagat cgcgccgctg cactccagcc tgggagacag agcaagactc cgtcacaaaa 8520
acaaaaaaca aaaaactgtc atatcaaaaa ctaaactaaa atggtaatat ctgttagata 8580
ttacaaagtc aggcaaatta tgattcatgg cagccactaa tgacccaaag gagagaaaga 8640
ataattagca gattctaacc taatgggaaa aaaactaaat gaatagggat gggggactta 8700
cattctgtta gaggaaattg aggctgtcat ataaaaggaa taggtaaggc aaactgtaaa 8760
ttcctgttta cacaaatgcc cttctgataa atctctgcat tgcccacagt ccatgattac 8820
ctctccctta ttttaagtaa tatttaacac attaaaaatg gattaccacc caaggaattg 8880
ctcccgaccc agaaagtgca ggtagtgttg aaggtttgag ggaagaggga atgattagag 8940
ttggttgtgt ctcaggaaga agccaacagg aggaacctta ttttgagtca ggtaaagaag 9000
gtgggagtga ggaggcatcc cggtggccag gtatgaagct gggagctgat tgctgcacat 9060
tactcagctg aattaaatgt gccctcacat ctgtgtgtgt gcgtacatgc aaatgtacat 9120
gtgtatgagt tagttggagg ggtagacctt tattttcctg tcctgtaact ttcctttgca 9180
aactaatctg tattcagaac agtgttgcag ttaagaacca cccagcttgt ccatgaaaca 9240
ggttctctca ccccatctcc ccagttttag agaaggcagg aaagaaaagg cagtgctttt 9300

-continued

```
cttttttcct ggccgtatgc ggggcaggaa gaagccagca gagcttgaaa gagaaagtaa   9360
accttctggg aaataaacgg cttggcttcc ctattgtgga ggaggagtgc aaattattag   9420
ggggatgttt gggtagtttt tgtagaagcc atttctgaaa actgatttgg attagtgaag   9480
gtaagcccaa tttaggaaaa ccctgcccag tctggtgtca gccacctgtt tcccgctttg   9540
tttgattgat ttgattagtt tgtggtattc tgacctctca tttttattac aagagttgga   9600
agatttgagt ctgaacttga gcacctgctt cggtgaaagc ttcctaaaat gcatgttttt   9660
tcacattttt tctcatgttc attttgtttt gctttttagc aaacactttt tctgacagaa   9720
tctaaaagca ttagactttt cttgttttcc ccttctctcc ccacaatgta atcttgaaaa   9780
cccaaatgtt agctgtgtaa attacctctc ccgtaaacca aacaaagtgc aatattgcat   9840
tgagttagca ttgaaatagt cggcctttga attttttttct acttgtggtt tagacataat   9900
aaatatttca tctcagactg actttctcga caaatcagtt ttgcatttgg gcctcttttc   9960
atcagtatgt ttagggaaag cacatttatt gaaacattaa ccaaaatgaa acataattag  10020
gaggccggga gcgatggctc acgcctgtaa tcccagcact ttgggagacc aaggcatgtg  10080
gattgcttga ggtcaggagt tcaagaccat ccttgccgac ttggtgaaat cctgtttcta  10140
ctgaaaatac aaaaaactag ctgggtgtgg tgacgcgtgc ctgtaatccc agctactctg  10200
gaggctaaag caagagaatc gcttgaacct gggaggcaga ggttgcagtg agtcgagatc  10260
gtgccactgc actccagcct gggcaacaga gactccgtct caaacaacca aaaaaacaaa  10320
aacaagcata attagggtgg taacgcttat acataggggc aggtggaata attgaagcat  10380
tctggagcca gaaataatca actgattaag aataatctgg ctgggtgcgg tggctcacgc  10440
ctgtaatccc agctactcag gaggctgagg caggagaatc gcttgaacct gggaggtgga  10500
ggttgcagtg agccgagatc gcgccattgc actccagcct gggctatgga gcaagactcc  10560
atctcaaaaa aaaaaaaaaa aaaaatcctg tttctgcaga aatatcccag gtgtcctggg  10620
tcagcagtgc cccatagatt ccacggacgt ttaccctaag ttttccaatg ggagttcata  10680
cctctatacc cagtgagaat attttctgag taatgggaat gagattggag atgtagggta  10740
gagaagatcc atacagtctt tgggttaaac tttttcctct ttgcctagga aagattaatg  10800
ctaatcttaa ccacagattt gtagtaagaa tgtatcagtt ttgtcattca gttctagact  10860
ccagttttct ttattgtaat accaatattt tagagtaaat tttgaaatga atcagtacaa  10920
aagatatgta gtaagtggaa agttagtccg caccttatcc ttgggactct ttcccaggga  10980
cagctagtta cctactattt atctctcctg agttacttca tatgtatgca tgcaaacatg  11040
ttattctctg ggtgttgttc cttccatata tagcagcaaa tacaccaaac tctgtatttt  11100
gctttttgtc actttatctt agagaatact caatgcaaat acatgtgtat atacctcatg  11160
tttaaaaaat ctacatagta aaattagcca ggcatggtag tgtgtgcctg taatcccagc  11220
tactcgggag gctgtggtgg gagaatcact tgaaccctga gatcacacca ctggactcca  11280
gcctgggcca cagagcaaga ttctgtctca aaaaacaaaa acaaaaaacaa aaaaactaca  11340
gagtagtatt ctaggctatg catatcataa atttgatttc ctaatgatag gcatagatga  11400
tttgcctggg cggcaaatta gcgttggctg tgtctcagga agaagccaac aggaggaacc  11460
ttattttgag tcaggttcca aagacagaaa cattgtctga catttgtttt tgggcttata  11520
tgaataaatc tgtacacata tatttttaat gttttaatcg taatatgtat actatttgga  11580
aatgtggctt tttagttaac agagtgcatg ttttacccca ttgcacttaa acattaactt  11640
ggggataatt aaatgagtct gtcacttgga caggcaggaa ttgtaccccc cacaaaccca  11700
```

taaaccgcca attttttttt tttgagacag agcctcattc tgttgcccag gctggagtgc 11760
agtggtgcga tctgggccca ctgtaagctc agcctcccgg gttcatgcca ttctcctgcc 11820
tcagcctccc aagtagctgg gactacaggc gcccgtcaca atgcccggct aatttttttgt 11880
atttttagta gagtcggggt ttcaccatgt tagccaggat ggtctctatc tcctgacctt 11940
gtgatccgcc cgctttggcc tcccaaagtg ctggaattac aggtgtgagc caccgcacct 12000
ggccggtttt tttttttttt tttgagatgg agtcttgctc tgttgccagg ctggagtgca 12060
atggcatgat ctccgctcac tgcaacctcc acctcccggg ttcaagtgat tctcctgcct 12120
cagcctcctg agtagctggg actacaggcg tgtgccacca cgcacagcta atttttgtaa 12180
ttttagtaga gatggggttt cattaataat cattaatatt agacaactgt cagactcaca 12240
gtggtggata caaactttct caaattctga tttttactct aaagctcaaa ttttatcatt 12300
ggcaacaaat attgtcagtt gctttccctg aacagacagc ttcccttctt tcatttttga 12360
gaaaatatct gccagtatcc cagttggttt atcaatcatt ctttctcttt ttttttttga 12420
gacggagtct cactctgtca cccaggctgg agtgcagtgg catgatctcg gctcactgca 12480
acctccacct cccaggttcc agcaattctc ctgcctcagc ctcccgagta gctgggatta 12540
caggggctag cagccacacc tggctaattt ttgcattttt agtagagaca gggttttacc 12600
atgttggcca ggctgatctt gaactcctga cctcatgata tgcccacctt ggcctcccaa 12660
agtgctggga ttacaggtgt gagccattgc gcccggctct attatttctt ttctttcttt 12720
ctttttcttt ttttttttg agatggagtt tcgctcttgt tgcccaggct ggagtgcaat 12780
ggcgcgatct cggctcacca caacctccgc ctcccgaatt caagtgattc tcttgcctaa 12840
gcctcccgag tagctgggat tacaggcatg tgccaccaca cccgtctagt tttgtatttt 12900
tattagagat gggggtttct ccatgttggt caggctggtc tcgaactccc aacctcagga 12960
gatctgcctg cctcagcctc ccaaagtact gggattacag ttttgagcca cctgacccgg 13020
tttgcttatt atttctttta aatttaaaaa ataataaata aaggggccat gagagcgaag 13080
agtttgagaa aggttggtct aaaggtttta acataagaat ccctgggtta tttgcttaaa 13140
aagaagaaag aatctatgga tctgcctgag agggtctgat gtagtttatc tggggtcatc 13200
ctcacaggca tagcagatat tctgattcag atggtccttg gtccttagtt tgagaaatgt 13260
ggctttacaa ggcccataga atataaagtc ttctttggat tagtgaagtc atgtccacag 13320
ggtttagaaa atgtttttgt tttagagata aaggtaagtg gaagagtaga catgtagtga 13380
atgagggaaa atgttttaga gatttctttt tattctgttt actcttcttg gtatgcacgt 13440
acctgaatat taaggatatt ttatgaagtc atgacattac cagattaatg ttggttttgt 13500
tttaaggtac tttctgactg ctggggttaa ttcctacaga cgattctggt aaagaatagc 13560
ctttaagttt taaaagtgtt gacttatttc agatgtctta ataaagttaa cttccagtta 13620
ttacatgtaa cgtatataaa gctctcattt tcctttattc tcgttaattg tttgcataac 13680
aaattcaaag ggaaatttgc ttggcagaga tcagatagca gagatgagat ttaaaaacag 13740
gtaatttggc tactagcctg ggagtttgaa gattccaagt ttgcatccat gtgtagtcac 13800
ttaacatttc tgtccttatc tgtaaatggg aataacacct acttgatagg gttgttacat 13860
tatcttggcc acctcaggtt ctctttggct gagtgattga ctggaaaacg caatgtgaat 13920
tcatgcttca gactgggttc tttttttttt tttttttga gatggagttt cactcttatt 13980
gcccaggctg gagtgcaatg gcacgatctc agctcactgc aacctctgcc tcccaggttc 14040
aagcgattct cctgcctcag gctcccgagt agctgggatt acaggcatgc accaccatgc 14100
ctggctaatt tttttgtatt tttagtagag acggggtttc actgtgttgg tcagactggt 14160
ttcaaactcc tgacctcagg tgatccacct gcttcagtct cccaaagtgc tgggattaca 14220
ggcatgagcc accgcaccca gcccaggcta ggttctatat gggtgtgctt tttagaattt 14280
agatcatggg ctatccccaa cacaaactgg ataatgtttc tttctagatt ctctctaagc 14340
gtgtattctc tttctttcct aggcacagcc accacttcac ttacattgtg ggattataat 14400
ttcatgagta gtggaatttc cttaaccttc tcttgtgtgg gagctgaagg acaaaatgag 14460
atattctctg aagagtggtt acatcatgca aaactatgat gtgtaatgag gtcacttagt 14520
tttctaagta cattatacat tttgataaga ttttcataga aaagcttgtc tccttgggga 14580
gatcactcat cttccatctt gactattatt taaactttat gggtcagatt tatcttttta 14640
aaaacttaac cataaagctc aattaatttt tttttttttt ttttgagacg gagtctcgct 14700
ctgttgccca ggctggagtg tagtggcgcg atctcggctc actgcaagct ctgcctccca 14760
ggttcatgcc attctcctgc ctcagcctcc tgactagatg ggactacagg cgcccgccac 14820
gatgcccggc taattttttg tatttttagt agagacgggg tttcaccgtg ttaggatggt 14880
ctcgatctcc tgacctcgtg atccacccgc ctcggcctcc caaagtgctg ggattacaag 14940
cgtgagccac cgcgcccggc tcaattaata tattttaaaa attaatagac tttattattt 15000
ttattttatt ttatttttga ggcagagtct cgctctgtca cccaggctga gtgcagtggt 15060
gtgatcttgg ctcactgcaa actccacctc ccgggctcaa gtgattctcc tgcctcagcc 15120
tcctaagtag ctaggattac aggtgcctgc caccataccc ggctagtttt tgtaatttta 15180
gtagatacgt gtttctttc ttttcttttc ttttttttga gatggagttt cactcttttt 15240
gcccaggctg gagtgcaatg gcatgatctc ggctcactgc aacctccgcc tcccaggttc 15300
aagtgattct cctgcctcag cctcccaagt agctgagatt atagttgtct gccaccacgc 15360
ctggctaatt ttttgtatgt ttgatagaga cagggtttca ctatgttagc caggatgtct 15420
cgatctcttg acctcgtgat ccgcctgcct tggcctccca aagtgctggg attacaggcg 15480
tgagccactg cggccagtct agactttatt ttttaaagca gtgttagttt tacagaaaaa 15540
ttatgtggaa agtacagaga gtttccatat accccttact ttctcccaca acttctatta 15600
ttaacatctt gcattagtat agtacgtccc ttacaactaa tgaaccaact cgatacatta 15660
ttattaacca aattcctgag tttattttat ttctattttt attttattat tattattttt 15720
tagaggtagg gtctcactgt gttgtccagg ccaggttgca gtggcatcat catagcttgc 15780
tatagcctga aactcctggg ctcaagcaat cctcctgcct cagtctccca aagtgttgga 15840
attacaggtg tgagccactc tgtccagcct gaagtccata gtttacatta catttcactc 15900
tgttgagcat tctatggatt ttgacaaatg tgtgatgatg tatatttgcc agtacacaat 15960
tatataaaat agttttactg ccctagaaac cccctgtgct ccacctattc attcctctgc 16020
tgaaccactg gcaaccactg atcttttata atatctccat agttttgtct tttccagaat 16080
gtcatatagt tggacataca gtgtgtagcc ttttcagatt ggcttctttc agtaaatgat 16140
atgcatttca ggtttcttca tgtttttttg tggcttgata ggttgtttct tttcattggt 16200
gagtaatact ctattgtatg gatataccac atgttgttta tcaaacattc acctgaagga 16260
tagacatctt ggttgcttcc aagtttgagc agttatgaat aaagctgcta taaacattcc 16320
agtgcaggac ttttcacctc ctctggataa atatcaagga gtgcaattgc tagatcatat 16380
ggtaagagta tgtttagttt tgtaagaagc tatcaaacta tattcaaagt gactgtacca 16440

-continued

```
ttatacattc ccatcagcag tgagtgagag ttcctgttac tccacatctt caccagcatt  16500
tagtggtgtc agtgttttgg attttagcca ttttaatggg tgtataatgg tatacctatt  16560
aaaattggtt ttttttggag acagagtttc acagtttcac tcttgttgcc ctggctggag  16620
tgcaatggcg caatctcggc tcactgcagc ctccgcctcc cagtttcaag tgattctcct  16680
gcctcagcct cccaagtagc tgggattaca ggtgcacgcc accatgttct gctaattttt  16740
ttgtatttta gtagagatgg ggtttcactg tgttacccag gctggtcttg aactcctgag  16800
ctcaggtaat ccacctgcct cagcttccca aagtgttagg attacaggca tgagccaccg  16860
cacctggcct caattttttt ttttttttt ttgagacaga gttttgctcc tgttgaccag  16920
gctggagtgc agtggcacaa tctcggctca ctgcaacctc cgcctcctga gttcaagcga  16980
ttctcctgcc acagcctcct gagtagctgg gattataggc gcccgccact acgcctggct  17040
aattttttt ttttttttaa ttagagacga ggtttctcca tgttggtcag gctggtcttg  17100
aactccccgt tctcaggtga tccgcctgcc tcagcctccc aaagtgctga gattacaggt  17160
gtgagccacc gtgccccgcc tgttttggct tttactgtga agacgtgtta gccgctgtga  17220
tgactagcaa gtgtggccct ccacccagtc gctctgggct cccagctcct gcatcctgct  17280
gcaaacttga catcttccct caagtaactt gtagttgtct cctgtctact tgcccaaaat  17340
ataactctta aacttttctc tctgcaagtt tgtgcctctc tccctgtctg acttccccat  17400
ctaaataaat ggtagaccac catctactcc tttgtgcaag ccagaaatct aggaatcatc  17460
cttaaattcc ctgttctgtc ttatctctgc tttcattcaa agcatcagca aatcctgttg  17520
gttctacctc tgaagtttc tcaaatactg ttacttgact catcctgact tttgtttctg  17580
ctttatgtta ggctaaatgc cctgaaaact cttttgtaca aaacacctag aaatactgga  17640
taaactgggc ttaacaggga ggcccggtgt ggtggctcac gcctgtaatc ccagaacttt  17700
gggaggccaa ggtgggtgga tcacctgagg tcaggagttc cagaccagcc tggccaatac  17760
gtagtgaaac cccacctcta ctaaaaaaaa aaaaaaaaat tagctgggtg ttgtggtgca  17820
cacctgtagg tggtgcatgc ttgaacttgg gaggcggagg ttgcagcgag ctgagatcgc  17880
gccactgcac ttcagcctgg gtgacagagc aggattctgt ctcttaaaaa aaaaaacaaa  17940
aaaagaaaaa caggaaaatc ttcagaagca aaaaccaaac aatctcacca aagaaatgag  18000
aagatggctg ggcgcggtgg ctcacgcctg taatcccagc actttgggag gccgaggcgg  18060
gcagatcacc cgagatgggc agatcacccg aggtcaggaa ttcgagacca gcctggccaa  18120
tatggtgaaa ccccgtctct gctaaaaata caaaaaattag ccaggtgtgg tggcaggcgc  18180
ctgtaatccc agctactcag gaggctgagg caggagaatc gcttgaacct gggaggcgga  18240
ggttgcagtg agccgagatc atgccactgt actctagcct ggacgacaga gcaagactct  18300
gtctcaaaaa aaaaaaaggc tgggtgtggt ggctcatgcc tataatccta gcactttggg  18360
aggccaaggt gggcggatca cttgaggcca ggtgaacatg gcgaaacccc atctctacta  18420
aaaatactaa agttagctgg gcatggtggt gggtgcctgt aatcccagct actcgggagg  18480
cgaggcagga gaatcgcttg aaccaggagg tggaggttac agtgaaccga gatctcgcca  18540
ccgcactcta gtctgggcga cagagcaaga ctccgtctca aaaaacaaca acaaaaaacc  18600
aacacatggc caaagtgcag tgacttacat ctgtataatc ccaatgtttt gggaggctga  18660
ggcaggagga tcgcttgagt ccaggaattt gagaccagcc tgggcaacat agacctcatc  18720
accaaaaaaa aaatattttt taattagctg ggtttggcag catgtacctg tagtcctagc  18780
```

```
tactcaggag gctgaggtgg gaggatcact taggcccagg agtttgatag ttcgaggtta  18840
tagtgagcta tgatcctgcc actgcactcc agcctgggcc acagagtgag accctgtctc  18900
ttagaaacaa aacaaaacaa aaaaaagaaa ctgaattaaa aacaacaaga acaaaaatgc  18960
tgctttttgt tattgagttg tagcccaagt ttcttgaggg taaagcattg aaaagcaggc  19020
agtaatagat ttgctgttta aagagattta cttgcagcac tattcacaat agcaaagaca  19080
tggaatcaac ctaaatgccc atcagtgaca aattggataa agaaaatgtg gtacatacac  19140
tgtggaatac tatgcagcca taaaaaacaa cgagatcatg tttttgtttg tttgtttgtt  19200
tgtttgtttt tgagatggag tcttgctcta ttgcccaggc tggaatgcag gtggcacgat  19260
ttcagctcac tgcaacctcc gcctcccagg ttcaagcaat tctctgcctc agcctcccga  19320
gtagctggga ttacaggtgc cctccaccat gcctggctaa tttttgtatt tctagtagag  19380
atggggtttc accgtgttgg gcaggctgtt cttgaactcc tgacctcatg atcctcccac  19440
ctcggcctcc caaagtgccg ggattacgtg tgagccaccg tgctcggctg agatcatgtt  19500
tttgcaggaa catggatgga gctggaggct attatcctta gcaaagtaat gcaggaacag  19560
aaaaccgaag accacgtgtt ctcacttata agtgggagct aaatgataag gacttgtgaa  19620
cacaaagaag gaaaccacag atactggggt ttacttgagg gtggagagtg ggaggaggga  19680
gaggaacaga aaagataact attgggtatt gggcttaata cttaatattt tatcaaaata  19740
agctgtacaa caaacccctc tgacatgagt ttacctatat aacaaacttg cacgtgtaac  19800
cccaaaccta aaataaaagt taaaaaaaaa aaaaaaggct ggttgcattg ggaggctgag  19860
gcaggcagag cacttgaggc caggaattcg agaccagctt ggctaacgtg gagaaaccct  19920
gtctctacta aaaattcaaa aattagccag gtgtggtggt gcatgcctgc agtcccagct  19980
accagggagg ctgaggcagg agaattgctt gaactcagga ggcagaggtt gcagtgagct  20040
gagattgcac cactgcattc cagcctgggc gacagggcga gaccttgtct caaaaaaacaa  20100
aacaaaacaa aacaaaaacc tgtcactttg ggaatatctc aaacctagtc atccaagtgg  20160
ttgtacgatt ttagtgtctg catatcaata tttagtgtga tctactttct tagattctca  20220
aatactgcca atgggcacat gtcatgaaat aatgtctttt agaggacaag agagtgctaa  20280
agtctcatta ttgcagttta agaaaaacaa ttctgtaaca gtttaacttt ataggaaatg  20340
ccttttgttt atttattttt tttcttttga ggcttagatt tttattttta tgtttttaga  20400
gatggggtct tcctatgtta cccaggctgg ccttgaattc ctgggctcaa gtgatcttcc  20460
tgcttcagcc tcctgagtag ctgggactag acgtccacta ctgctcctgg ctggaagttt  20520
agattttaat ttaaactctt ctattgggaa actttgtatg tttgctttac cacttaacat  20580
ttgcatgcat tattgtacct attgtctcct acttaaggaa gggcagttta tgctgttata  20640
tgaagtgaat taacctccta tggtacttca gttttctcta tgctaaaagt gtgttctaga  20700
tttttgaaaa acttacttaa ttttcattca tttattcaaa tatttgagca ttctgtagtt  20760
gctggggaaa tagcagtgaa ctgaagaatg tctttgttct tatggggctt aagttcctag  20820
ttgatcatat tggaaggaga tacatgaaaa aagaaatata tgaacaatgg agggcgatga  20880
gtactgtaaa ggagaattca gcaggggaga tgttgctgtt ttagatagag gggtgtcaag  20940
agacattgtg cagagacctg aacgaagtga gggagcaagc catggagata tctagggaaa  21000
gagcctatca ggtggagaga agagtcctag ggcagaaacg ggcaaggtgt gttccaggag  21060
cagagagggg acagctgtga gcaaggggag agttgtaggg aaggaggcaa agagagacat  21120
ctggggcaaa atggattgac tggtgggccg tggtaggact ttggattttt tcctgagtgg  21180
```

gttttgagca ggggaatgaa atgatctgac tctggttttt tttttttttg gagacaaaat 21240
cttgctctgt tgccgaggct gaagtgcagt ggcgcaatct cggctcattg caacatctac 21300
ttcctgggtt caagctatgc tcctgcctca gcctcccgag tagctaggat tacaggcttg 21360
ggccaccatg ccggcgaatt tctgttttta tttttatttt ttatttattt ttatgtttat 21420
gtttttttgag acggagtctc gctgtgtcac ccaggctgga gtgcagtggc gcgatctcag 21480
ctcactgcaa cctctgcctc cccggttcaa gcaacttctc ctgcctcagc ctcccgagta 21540
gctgagatta caggcgcctg ccactacacc tggctaattt ttgtattttt agtagaaacg 21600
ggatttcacc ttgttggcca ggctggtctc gaactcctga ccttaattta tctgctcgcc 21660
ttggcctccc aaagtgctgg gatgacaggt ttgagccacc gtgccagcca ggactcttat 21720
tttgaaagga tctgtaatgt ggagaataga aggtagaggg acaaggatga aagcatccag 21780
gccagttagc ctagtccagc tatctaggta agagatgctg gtggcctgga ttaaggctgc 21840
gtcagtggga ggttgtgaga aaggctcacc ttcctttttt tttttttttt tttttttga 21900
gacaggatct tactctgtct cccaggctgg agtgcagtgg tgcaatctca gcttactaca 21960
acctccgcct cctgggctca agtgataccc ccacctcagc ctcccaagta gctgggatca 22020
caggcttgcg ccactatatc cggctaattt ttgtatattt cgtagagaca gggttttgcc 22080
atgttgccta ggctggtctc aaactcctga gctcaagtga tccacccgcc tcagcctcct 22140
aaagtgctgg gattataggc ctgagccatt gtgcccggtc acttccagat tttgaagaca 22200
gagccaacag gatttgttaa tggattaggt gtggcaggag gagggggagg aagagagaga 22260
gagactggag ttgaagttaa ggctcatttc aaggttttta gcctcaacat gtgcaggaat 22320
ggagttgtca cttgctagaa tgggggagac tggaggagaa gccggctggg agaggttttt 22380
aatgaagggg ttggctttgg atacattaag tttgacatgc attttagaca tccaggtgga 22440
gatattgaag aggcagttgg ctataagtgt ctgatgttca tattagcgga tggggctaga 22500
gacataaatt tgagaattgt cagtgtataa acgttgtttt gaaagaaagt ggggctgaat 22560
aatttagaaa ggagtgcata gagaaaataa gtttactatt aaaatagctt taacaggccg 22620
ggcacggtgg ctcatgcctg taatcccagc actttgggag gctggggtgg gcagatcaaa 22680
aggtcaggag tttgagacca gcctggccaa tatggtgaaa ccctgtctct actgaaaata 22740
caaaaattag ccaggcgttg taccgggcac ctgtagtccc agctacttgg gaggttgagg 22800
caggagaatc acttcaaccc gggaggtgga ggttgcagtg agccaagatc acgccactgc 22860
actccatcct gggcaacaga gcaagactcc gtctcaaaaa aaaaaacaaa aaaaaacaaa 22920
aaaaaaaaac tttaacagca aagcctcttc ctttaaaatt atgaattttt ttcttatgga 22980
agttggactc tttcattatt aagtctacat tcaatcacta tgttagtaaa aatgttgttc 23040
tagttgccga atgcaataaa ccagctcaga cttagtggcc taaagcagca atcatttgac 23100
tatgttcgaa gatgccgtgg gcaggaattt agataacagc agggatggct tgtctttgct 23160
ctgcgatgtc tgaggtctca ctgagaaaac tcaagcggct gggggtaata atcatctgga 23220
attttcttta ctcctgtatc tgatgtctgg gctgcgatga ctcaaaggct gatttcagct 23280
gagactgtag accacgtgcc tacttgtggc ctccccttt gccttgggtt tctcacagaa 23340
tgtggctggt tctggagaat gagacttcca atgaaatcag gtggaaatga catctcgccg 23400
ctttcagcat gctctattgg ttggaacagt tatggactta gctagattca aaggaaggga 23460
acaaagaccc cctcctctca gagagtgggg cataatgaga gaatttaggg ccatgttatc 23520

-continued

```
caaccaccac aaatgccttc tgaatttgag gttctgcctc aaaagttcat agttcctttg  23580
actgaaggac ttctatatat ccaagcatcg tcagccccag gtatattgtt ccatgtaagt  23640
gaccaggact accttagtat ttcgtatagg gaaagtgacc tgaataaatt tgagaaaaga  23700
atcttccttc tctccagtaa gcactgaggt aagcattgag ccatattata ggtttatgac  23760
tttgagactc agaaatttaa attcttggcc aggcgcagtg gctcacgcct gtaaccccaa  23820
cactttggga ggccaaggca ggcagatcac ttgaggtcag gagtttgaga ccaacctggc  23880
caaaatggtg aaactccatc tctacgaaaa atacaaaaat tagccaggtg tggtggcggg  23940
cacctgtaat cccagctact tgggaggctg aggtaagaga atggcttaag ttctctttat  24000
ctgctttatt tcagttgcct ctcttagatg aatattaatg acttacatag cattttagat  24060
cagtggatgt ttttgtgatt cttttatttg agctttggcc aaagataaca gtacccacag  24120
gtttttttcca gctactcgct cttctccctt cagtggccct cgagcctgga aaatctgaca  24180
tgacaatgtg cttgctcaac ctaccactgt tttctttttg aaaagtttgg cagcctgttt  24240
ctgactccta tgaaggtgaa ttcctcagca ttcacagttt attagaaaaa tactttgctt  24300
ctctccaaac tcgaaattca agataaccaa acctatatat aggctgatct ttcaggatgc  24360
agttgtcatg ttgatgccat gcttttcagt atcgtggcca tcatctgttc agtaggggag  24420
gtgtacttct gtaatgggag gtggtggtta tgtgtgtgtg caagtgttta tttggtgtct  24480
taagttagcc tgtgggaagt tctaaatcag gatggtacgt ggttgccagc agagagctgc  24540
tcctcaagtg aaggaggtag aatcaaagcc aataggaaag agcctcagat gcttatatat  24600
gtaccgtggg gattcagagt gaaagcagtc attggactag gggtggggtt agggagagcc  24660
tgtctgacag acacaagaaa gggatggata acgccaccca gagaaaaaag catttaggc  24720
aagaacaaat atgaaaaagg aacaaagtct gtgggtgggg ggcaaggagg agataagttg  24780
acttgaagga agacaacact tatgaaagtc acctggaggc tgggtgccat ggctcatgcc  24840
tataatcgca gcactttggg aggccgaggt aggaggacaa cttgagccca ggagttcgag  24900
accatcctgg gcaacatggt gagactgagt ctctaccaaa aaaaaaaaaa aaagaaaatt  24960
atccagacat ggtggcatgt gcctgtaatc ccagttactc aggaggctga ggtgggaggg  25020
ttgcttgagc ccaggaggtt gaggctgcag tgagctgtga tcgtattatt gcactccagc  25080
ctgggtaaca gagcaagacc ctgtctcaaa aaatgaaagt catctgtagg ctggagagag  25140
gaactggaag gggctaaagt tggctgagta gttacagagc ctgagataag ggtaaagatt  25200
ttgcattgga caatgagatg ttagtgtgtg tttttgagct ggggagtgct gtgattttac  25260
tcttattgaa gaatcactga aggattattc ttgaatcagt gattcttgat cattcttgaa  25320
tttttcaaac agcaaaactg gaagagttgg cctattcctc agaatatttt ctaattgggc  25380
gcagtgtcct cacttgggag aacctggcta cacactttag ttgtaattca ctccagtcgt  25440
tcattcattc aatacctatt ttttcagcac ctattatgag ccagacacta tgctggatgc  25500
cagggttcag ggtaggacac gctagtgagc aaaagccaag actcttcttg tcttcatggg  25560
gctttcagtc cagcatagtg gttatgagtc caagttaatg gagtcacagt acttgggtgc  25620
aagtcatggt gatggtgata gaaggaaggc atgtgtgagg gccagtggca ggcaggagcc  25680
tggtgttttt gaggacctga agaaggagca gagtgagtgc caggaactta gccaccagct  25740
ggtaccagcc atacgagagg ggcagagcca gccaggatgt cggtcatgct agtaatgagt  25800
acaaacactt acatgctgca cgctattggg ctcctgagtg ctacgtgttc attagctcga  25860
tgaatttgta cagcaaccct gtgaggtaag cactgttctc tcccctttct atagatgagg  25920
```

aaattaaggc acaaagagga taaataactg gcaccagcta cacgctaagt gatcgaagtg 25980
gtggaaccag gattcaaatc catgctattc tgccttaaga taacaaatct tgttttttag 26040
cctaagaaca gagcagtcat caggagggtt ttaagtaggg gtgtggcaag atcaagtttg 26100
tgtcttgaaa aggtctctct acccacagtg tggaaaatgg cctggaggca agcacacaga 26160
tgttgggaga cagttaacag ctcttgccat ggccccctat gcattttggc tctgatgttt 26220
ctgcctgatt tttctcttgc ctctgcctct tttcctgagg ggatggcagg ttttaccatt 26280
cagctggagt acaaaccctg aaccctttt ggttaaatat ctacttgctt ttcctacagt 26340
attattttga gttgctgtgg ctgtaatgtc ttgagggaat cgagcttgac agtaatttat 26400
agaacaaaca gtttttagag actgtgtggc ccaattgccc tctcaatgtt ggcactcctg 26460
ccatgacatt taccatgctg agcatgtgac cgccatctga ataccaaatg ccacaggaac 26520
ctgggaggtt gtcacttact cctccctttc tctgagtcac ctttgccctt cagtcagtca 26580
ccaagtccca tcacatgtag ctctgtaatg tcacagaaga tggatgtctg cctcaaaaca 26640
cttacaatgc tgctacctaa attgggcagc cacgacctcc caccaggatt attgcagcct 26700
gagggatctt tttgaaatgt aaatcaaact atcacttgtc tgtttaaagc ttttcaaaga 26760
cttaccccat tgcccttgga agaaagtgca gatatcttga caggagagcc ttctccagcc 26820
tcctcttctg ccgtggtctc cttgtacagt ctctacagtg tactgcttca ttagaaccct 26880
ggagattatt atttgctagt tctgggctaa gaactggcac ctggctttgt agagctcctc 26940
aggagattct gaggcgtatt cagagttgag ccctgatctc tgctctgatt tcgaggttct 27000
cgttatattt attaatgatc acgaaaaaat ttattattat tctttggcct cactttagca 27060
tcatctgagg aatttttttt ttttttgac agagttttgc tcttgttgcc caggctggag 27120
tgcaatggcg tgatctcagc tcactgcaac ctccgcctcc cgggttcaag agattctcct 27180
gcctcagcct cccaagtagc tgaaattaca ggcatccacc accatgcctg ctaatgtttt 27240
tgtatttttt agtagaggtg ggctttcaca gtgttggtca ggctggtttt gaactcctga 27300
cgtcagctga tccacccacc taggcccccc agagtgctgg gattacaggt gtgagccacc 27360
gtgcccagcc gtagctttcg aaatttgaaa cctggtccca ctgtcagagg ttccaatttg 27420
gcactggttt ggttcccagg catctttctt gctgtatata ttttttagtg tcagccaggg 27480
tggagacctc tgtattactt catggggaag aatttgggag aagatgttgt gaggagacag 27540
gttctagtcc tagagtgatt tatcctttct cgtacagatt tccaggtatt tgaggggcca 27600
ctcttctgta attcatgttt ttctctccta acctcactcc tgttgcctgc atcttcttgc 27660
tgagcaaaat attcaaggtc ttcaactcct cacaccctgg ttgtccctcc ctggatgtgt 27720
ttggttgttt tagtgttcca tttcaatttt gatacacaga attagaatag catccagatg 27780
tgggtctgtt acagctagac tactagatcc ttcaaaatcc aagtactagt atgtctatta 27840
aaataccata agatcacatt ggctagttac aatggttggt ttgtgggtta cttaaaaatc 27900
aactaaaatt cttttttttt ttttgagatg gagttttgct cttgttgcct aggctggaat 27960
gcaatgacac aatcttggct cactgccacc tctgcctccc aggttcaagc aattccccctg 28020
ccttagcctc ctgagtagct gggattacag gcatgtgcca ccatggccag ctaattctgt 28080
atttttagta gagatgaggt tttccatgt tggtcaggct ggtctcgaac tcccgacctc 28140
aggtgatcca cctgcctcag cctcccaaag tgctgggatt acaggcgtga gccactgagc 28200
ctggccaaaa ttcccacttt ctaatactcc tgtagtagct gggtacggtg ggtcacatct 28260

-continued gtaatcccag cacttttgga ggctgaggct ggaggatcgc ttgagcctag gagttcgaga 28320
ccagcctggg caagatggcc agacgccatc tctaatttaa aaaaaagaaa aaacaagact 28380
cctatagtgg tgaagaacag acattccgaa aacagactgt gcgttatgat tccagctcca 28440
tgcctttact acctgtgttg tgactttgga taaatcactt aaaaatcttt ttttttttt 28500
tttttttttg agacggagtc ttgctctgcc gcccaggctg gagtgcagtg gcgcgatctc 28560
ggctcactgc aagctctgcc tcccaggttc acaccattct cctgcctcag cctcccaagt 28620
agctgggact gcaggtgccc gccactacac ctggctaatt ttttgtattt ttagtagaga 28680
cggggtttca ccgtgttagc caggatggtc tcgatctcct gtcctcgtga tccacccgcc 28740
tcagcctctc aaagtgttgg gattacaggc gtgagccacc gcacccggcc aaatcactta 28800
aaattctgtg cctcagtttc tcctctgtaa agtgggataa aaatagtacc tatctgatag 28860
ggttgttaca attatgaaat gagcaaataa gtatgtcaag tgtttaaaac agcgcctggc 28920
ttcttgtaaa aagtgctata taaatcatag ctataatcat tacttatttc gactgctctt 28980
taaccaaggt tcttattttt catctttttc ttttgttttg aatatcactt agtgttttca 29040
ccttttactc tttttaggac ctagagccat cctaggtgaa atacgtatgg agatatttga 29100
tcaggtcacc acccagctct cctgacctcc cttctctcct taaattaaca tgccaaatca 29160
cagcatcact gactccttcc ctcccgatat gataagagtg tgcattgaaa tgcatgtatt 29220
ttacttagca gggaaagctg attagtgatt atcacactta acccctagtg aatctgatgg 29280
attaacctgc tttccaggac actaaggaaa tgggtttaag ataagaaata tctggctggg 29340
tgcggtggct ttacgcctgt aatcccagca ctttgggagg ccgaggtggg cagatcacga 29400
ggtcaggtga ttgagatcat cctggctaac acgatgaaac cccctcttta ctaaaaatac 29460
aaaaaattag ccgggtgtgg tggcgggcgc ctggagtccc agctactcgg gaggctgagg 29520
caagagaatg gtgtgaaccc aggaggcaga gcttgcagtg agctgagatt gtgcccaccg 29580
cattccagcc tgggcaacag agtgagacta catctcaaaa aaaaaaaaaa aaaaagtaag 29640
aaatgtccat gaaagggaga ccctggggga aaggaacaat aactgcagct ctgaggatct 29700
ggcaccagca gcaccagcac agagggatgc tgtacaacca ttattgattt taactttaca 29760
acagttcttc aaaggagaga gagttccctg ttttactgaa gagaaagccc atttggtagt 29820
gaaataccat tcccaaagac aaatagctaa taaatgtcag gcagggtttt gcacccaggc 29880
ccatccagct cccgtctcta ctgtcctttc ccccacacca cactgataca gaggaatgtg 29940
tctggttggg gaagtggaag tgttcccaag tggggaggtc atctgatgca caaatttggt 30000
ctgttttgtg ggttttcttg ttttagtttt agtttttgta gagctcagac ctgttcttag 30060
gcagctttaa caatcaactg tgcactcagt aattgacaaa tcatgtttgt tacttttaat 30120
ttagagggaa ttaggtttgt taagctcttg ctccttcttt agagatgggg tctagctctg 30180
tcacccaggc tggagcgcag tggtatgatc acagctcact gcagtctcaa tctgctcaag 30240
tgatcctcct gcctcagcct ccatgggact acaagcatgg gccaccatgc taggctaatt 30300
ttaaaaaaat ttttttgtag aggcaaggtc tcacggtgtt gcccaggctg gtcttgaact 30360
cctgagctca agcaatccct cttccacctt ggcctctcaa agtgctagaa ttataggcat 30420
gagccaccat gcctggcctt tacttctttc atatattcaa attttgtcat attagtaggg 30480
aactataact caagttttct tatagattga tgttcatttt tacaagcttg atcgtcattg 30540
gtttttaatt ttaaagcaaa tcctgttata tgtaattgaa cattacagta attatagtaa 30600
tttgtttcag attgggcact caagtgttaa tattttgtct ctttaggaaa tcaaaactag 30660

```
atttatatat agacttctta ttgcaagtat ctagtcttaa atcttacaaa ggtactattt  30720
ggacttaaaa ctatgaaatt gtgtgcttac tatataagtg tacttatttt gagttatgtt  30780
ttaaacttga aattccattc ttaatgtcta gagtaattat gaatggttaa attatgaatg  30840
actctaatag tttaaagcta cagtatttat ttatttattt atttaattta ttttttgaga  30900
tggagtttcg ctcttgtcgc ccaggctgga gtgtagtggc accatcttgg ttcactgcaa  30960
cctctgcctc gcgggttcaa gtgattctcc tgcctcagcc tcccaagtgg ctgggattac  31020
aggtgtattt caccatgcct ggctaatttt tgtattttta gtagagacag gcttttgcca  31080
tgttagcctg gctggtctcg aactcctgac ctcaggtgac ctaccctcct cagcctccca  31140
aggattacaa gcatgagcca ccacacctgg cctacagtat tttaatgtgg actctctgtc  31200
atccattatg ctgtttatcc tgtggtgaaa attttatgaa gattgaatgt ttttctctag  31260
cgtgaattgc tttctcttac ttttctcatt tttttccttc ctaatctact tgcagatact  31320
tcagattatt tttagaacgt ggtatggtga gaacaaataa attggggttt ccaaatctta  31380
ataaattatg tggccctcag tgggattagc agggttgtat tgaaaacacc aatagaaaca  31440
aaatagttct tttatgcgct ttaaataaaa atttcttttc aggccaggcg cagtggctca  31500
cacctgtaat cccagcaccc tgggaggctg aggcaggcag atcacctcag gtcaggagtt  31560
taagacaagc ctggccaaca tggtgaagcg ccgtctctac taaaaataca aaaattagcc  31620
gggtatgatg gcgcatgcct gtaatcccag ctactccaga ggctgaggca tgagaatcac  31680
ttgaactcag gagatggagg ttgcagtgag ctgagatggt gccactgcac tctagcctgg  31740
gcaacagagt gagattctgt ctcaaacaac aacaacaaca ataacaaaac atctcttttc  31800
aggccaggta ctgtggctca cgcctgtaat cccagcactt tgggaggcca aaacaggagg  31860
gtcgcttgag accaggagtt tgagaccagc ttgggcagct ggtctctatt tgaacaaaca  31920
aacaaacaaa cacaatactc ttttcataga aaaatgttta ctacacaata aactttaaaa  31980
gaatatgcag ctgtattaat gctatgactc caatgtaaaa aaaaaaaaat atatatatat  32040
atatacacac acacaaacac attctgaaat agatttaaag gaattacatc aacatgtcaa  32100
tttttatttt ttcggagaca gggtctcgct gtgtcaccca agctggagta cagtggtgca  32160
atcacagctc actgcagcct tgacttcctg gcctcaagtg atcctccccc ctcagcctcc  32220
caaagtgctg ggtcacaga ccaccacacc tggcaacatg tcagtttttg ttctgcatag  32280
tgggatggtg ggatatggat gtttttatct tttattttct tttttatatt tttctaaatt  32340
ttccacattg aacattattt tataatcttt caaacatatc tcttaaaagg actggttcct  32400
atagaattca gtgcaagaaa tcttctgtgt ttctttatac tttggttgcc ttgatcactg  32460
ggcctttcct gacagcaaag aagaggttag tgtaggcagc agataaaaca caggtatgct  32520
ctatttaaaa tgcatgtatt tataataaaa gtataggtgg tacccaaagg aaaatgtcat  32580
gacacattgc aaagtggaac agaagttatc tttagatcac tttctgttct ggattattgt  32640
atgagcctga ttttcgtctc tctttccgcc ttccctcacc ctcgttgtaa atccactagt  32700
gcatggatgt gaagtacaag tcttaacttt aaaaagtttt atgaagctgt gtagtaaatc  32760
ccttttgtaa gtggtcttga ctgcgtttct caatatatct tttggtttca ttagattcaa  32820
gtatataaat gagaactgta actttggaca gactttttca gtcatcttta cggtaataag  32880
ttcccaatta gacaatagtt atttgtttta tgacttgctg ttggtaggtt atccccaagg  32940
gactgagaaa ttcctgtttt gaaaagtcca aaaagtcttt gatgacttgc tgtttcattt  33000
```

ttttcttttc tcttcagtta tagaaaacag gattacaccc accttgcctt tgtacagtgc 33060
atctactatc tgctgactta acctgagtaa atgctttgaa ttgagcccca tataatgtcc 33120
taaggcagcc tatatggagt aatgaattgt cttctctctt atgcacccag agtggtagtt 33180
ggcactcaag ttgttcctca gataactttg tgtgttctgg ggctcaatga agtagttatt 33240
aagtcacagg cttggggaga acattcatcc tatggcattg aatgaagtgt tgcccaattc 33300
tagaatgtct aataaaattt ttttaaaaac ccacaggctt agaattattc cgtagatatg 33360
aagtaatgta gttagaactt agtggagttc tttagattaa cttgtaattt gaaaaaccaa 33420
aattgaaatt gtgaaataac atgggctctt tgaggtcttt tccagtaaaa cagttacagt 33480
aaagctgctt ggcagtgatt ttcctagaca ctttggctag tcatctcctg tgactgctgt 33540
taattaaata tggtttgtag ctaagcagcc tgtaaggaga agactatgga agtatttgca 33600
tattctctcc ttgaaaatac tacctggtct ttggctttaa gttatacttt tattttcccc 33660
tgtagaataa ctattaaagt attacctatg gtgattagac taagaagtaa aacatgaaat 33720
cagtcattgt tggtgccctg gtgccttctt tttttttttt ttgagacaga gtctcactct 33780
gttgcccagg ctggagtgca atggcacgat cttggctcac tgcaacctct gcctcccagg 33840
ttcaagcgat tctcctgcct cagcctccca agtagctgag actacaggcg cccaccacca 33900
cgcctggcta atttttgaat ttttagtaga gacagggttt cactatattg gctaggctgg 33960
tctcaaactc ctgaccttgt gatccgccca cctcagcctc ccaaagtgct gggattatag 34020
gtgttagcca ctgtgcccag cctggtgctt taattttatg gaaaaaacta ctagctggtt 34080
tctgttttaa gaaataacac aggccgggtg ccatgacttg cgcttgtact cccagcagtt 34140
tgggaggccg aggcgggcgg atcacgaggt caggagtttg agaccagcct ggccaacata 34200
gtgaaacccc gtctctacta aaaatacaaa aattagccgg gcgtggtggg gcatgcctgt 34260
agtcccagct actcgggagg ctgaggcagg agaatcgctt gaacctggga ggtggaggct 34320
gcagtgagcc aagatcgccc cactgcacac cagcccgggt gacagtattt catctcaaaa 34380
aaaaaaaaaa aaaaaagaac acaattattg tactacttac tagccctcct ctgtccccag 34440
ctaaaaataa gaacagcaac aaccaaaaaa tccttagtta tgtactggaa atgaattaga 34500
taattttcaa taacttacac gtttttagga tatgttagtt tgaaaatgca aatattcatg 34560
catgacccca gtgttaatct atgatggagc aggtatagtg ggatgctgtt tcatgattta 34620
atttggacct tcagggagta gactgtgatg cctctgcatt tgtatccaag acaaataatt 34680
aaatagtcta tttttggctg ggcatgatgc ctcatgcctg cagtcccagc actttgggag 34740
gctgaggtgg gaggatcgct tgaggccagg agttcaagat cagtctgggc aacaaaatga 34800
gaccttgtct ctacaaaaac tacaaaaaat tagctgaaca ttgtggcttg tgcccctagt 34860
cccagctact caggtccctg agttaggagg attgcttgag cccaggagtt ggaggttaca 34920
gtgatctata tttgccactg cactccagcc tgggtgacag agagagaccc tgtctcaaaa 34980
aataaagtct gtttttaaaa ttaattttaa acactggagt ttattacaaa aagcagttgg 35040
ttcttttttt aaatcatttt tttttaggag aaccaccgct ttttggctac attgtctaga 35100
gtagcagtgt tcaataaaaa taagatccaa gtcacatatg taatgttaag ttttctttta 35160
gtttcttttt cttttctttt cttttctctt ctttctttct ttctttcttt tttttttttt 35220
tgatatgcag tctcactctg ttgcccaggc tggagtgcag tggcacgatc tcggcccact 35280
gcaacctccg cctcccgggt tcaagcaatt ctcctgcctc agcctcccga gtagctggga 35340
ctacaggcat gtgccaccat acccagctaa tttttgtatt tttagtagag atggagcttt 35400
gccatgttgg ccagtctggt ctcaaactcc tgacctcggg tgatccacat gctttggcct 35460
ccctaagtgc tgggattaca ggcatgagcc accatgccct accaatgtta agttttctag 35520
tagccatatt aaaagaagta aaaagaaatg ggtgaagtta attttaataa tatattttat 35580
ttaacccaat atatctaaaa tattatcatt tcaacatgaa caagatactt tacattcttt 35640
tgtttttcac taagtcctca aaatccagtg tgtattttat attgacagca tagttcagtt 35700
tgaagcagcc acatttcaag tgctcagtag ccacatgtgg ctagtgactc catactggac 35760
tgtgtaggtt tagagtttca gtaaatttgt atgcaataga atctacataa attggcatat 35820
tatgcagatt tctttgtatg cacatcagtt cttgcatagc ataagtcagg tcatgatgct 35880
tttagtctat gaggcagatt tttttttttt tttttttgag acagagtctc acttggtcac 35940
ccaggctgga gtgtagatgc acaatcttgg ctcactgcaa cctccatgtg aggcagattt 36000
taacttggcc ctaatgcaaa tattgtaaga gagatctaat ggcctttgat ttcttacaga 36060
gggcaatcaa tacatgccat ggttacaatg cttcagcata tagtatgcac gtcagccact 36120
gcttttactc tggctagtgc ttagtgtacc tgtaccactg cccaggcagc atttgtcctg 36180
tggcaggtga atcttagggt ggaaggtggc aagtaacatt gctttttttt gagagggagt 36240
cttgctgtat tgcccaggct ggagtgcagt ggtgcgatct cggctcacta caacctccac 36300
ctcccgggtt caagtgattc tcctgcctca gcctcctgag tagctgggat tacagacggc 36360
caccaccatg ctcggctaat ttttgtattt ttagtagaga cggggtttca ctatgttggc 36420
caggctggtc tcgaactcct gacctcgtga tccacccgcc tcggcctccc aaagttctgg 36480
gattacaggt gtgagccacc gtgcccagcc tacattttta aattaattaa ttataagcag 36540
gatctcactg tgttggccag actggtcttg aactgataag agttcaagac cagcctaggc 36600
aacatggtaa aaccctgtct actaaaaaat acaaaaaaaa aaattagctg ggcatggtgg 36660
tgcgtgccta taatcccagc tacttgggag gctgaggcag gaaaatcgct tgaacccggg 36720
agactgaagt tgcagtgagg tgagattgca ccactgcact ccagcctagg cgattccatc 36780
tcaaaaacaa taacaacaaa ataacattgt tggaatattt agttaattta tagaagcgta 36840
ttggcctaat tggggcaaat accttattct gacattctct ctatttgctt tactgagctt 36900
tttcaccagt ggaatttaag cccttgatac atgaggaggg aaaatacctt ggagctgtgc 36960
tgcacatgta aagtacacag gagatttaga aaacttcgta gcaaaaaaaa gagtgtaaag 37020
tatctcatta atagtttttg tgggctggac acggtggctc aagcctatac tcttggcaca 37080
ttgggaggct gagatgcatg agtctaggag tttgagacca gcctgggcaa cacagtagga 37140
ccccgtctct acaaaaataa tcagccagat gtggtgcgca tctgtagtcc cagttacttg 37200
agaggctgag gtgggaggat cgtttgagct gggaagttga ggctacagtg agctgtgatt 37260
gaaccactgc actccagcct gggtgacaga gtgcctgtct ccaaaaaaata aataaataaa 37320
taataaatatg ttttgtatgt tcatatgttg caataacatt ttggatatat taaatgaaat 37380
aaaatacatt aaaattaatt tcacctgttt cttttctttt cttttttttt tttttttttg 37440
agatggagtc tcgctatgtc atcaggctgg agtgcagtgg cacgatctcg gctcactgca 37500
acctcctcct cctgggttca agcgattctt ctgcctcagc ctccctagta gctgggatta 37560
aaggcatgtg ccaccacacc cagctaattt ttgtattttt agtagagacg ggtttcacc 37620
atattggcca ggatggtctc gatctcctga cctcatgatc cgcctgcctt ggcctcccaa 37680
agttctggga ttacaggcgt gagccactgc acccagcctc ttttaacttt ttaagtatgg 37740
ctaccagaaa atttaaaatg catgtgtggc ctgtattcta tttctgttgg atgctgctgc 37800
cttagattat taattattca atgtaaagac tgctgggagg tactacctgc acttccctga 37860
atatatgctt gagagctcca ccagccgtct tcacagtagc aagaggggta ttctgagtct 37920
gtcccccaaa gagggaggga gaagtgcagc cctctcaggt tctgtcagaa aacctgatcc 37980
caggccaggc gtggtagctt acgcctgtaa tcccagcact ttgggaggtt gaggcaggag 38040
gattgcttaa gcccaggagt tcgagaccag cctgggcaac acagtgaaga ccctatctct 38100
acaaaaattt ttttaaaaaa attagccagg tgcagcaatg ctgcctgtac tcccagctgc 38160
ttgggaggct gaggtaggag gattgcctga gcccaggagt tagaggttgc aggagttaga 38220
ggttccacga tcgcaccttt cattccgtta catttgctgc cttgagaaca gaagacctgc 38280
tggttttgtt gccagtttgc tcagtcattt ttatgaaaaa gccagtgcta actaggtgct 38340
tcttcgtgcc ttctctgaga atcaagaact ctagtatgtt tgcgtgtgtt cagtctctca 38400
ttaaatgttc tcactatccc agagaaccat ctcattggac cttggtctgt acataccttc 38460
atctttggct ctgacttgta attattttta gaacttctct tttttttttt ttggagacag 38520
agttttgctc tagttgccag actggaatgc agtggcacga tctcagctca cctcaacctc 38580
tgccttccag gttcaagcaa ttctcctgcc tcaacctctt gagtagctgt aattacaggc 38640
atgtgccacc acgcctggct aattttgtgt ttttagtaga gacagggttt ctccaagttg 38700
gtcaggctgg tctcaaactc ccgacctcag gtgatctgcc cgccttggcc tcccaaagtg 38760
ctgggattac aggcgtaagc cactgcgcct ggcctaattt tagaacttgt taaaacaact 38820
tggcctctat tgatatttcc atgacccatg ctattcagaa agaggattac aggtaattag 38880
ctggctgggt ttctcatacc agagcatttc actgggatgt tcctgaacct gggacaactt 38940
ttatgcctgg catttttctt tccttctctg ttgtcccaga ctaagcaatt tttaaaatag 39000
ttattatttg ttgagtagga gaatctcagg cagatcttcc tggatcctca tttatacttt 39060
taaacctgta gtcttggaat tagtgctctg tcccccaacc ccaaacatcc aatttctaca 39120
ttttggctac agtacaggtt tactgtgtat aactaaaagg gctgtggagg agaaagaaag 39180
gaaccgacat ttgttgggca tctgttatgt gccatgcact gagctggatg ctgtaggaat 39240
atctcaatac ctctgaggag tgggaattat tatctctatt ttatagacaa gggaatagaa 39300
atctgggagt taagtaattt tttaatttca cacacttctg gtagataatg gattctagaa 39360
cctggcataa tagccacttg tcatcccagt gtaaaagaga tgtgtggcca gatggggtgg 39420
ctcacatatg taatcccagc actttgggaa gccgaggcag gaggatgact tgagcccagg 39480
agttcaagac cagcctgggc atgttttgtt tgtctcacga aacatttttt aaaaaatgag 39540
tgtggcatgg tgttgtgtgc ctatagtccc agctcctcgg gaggctgagg tgggaggatc 39600
tcttgagccc atgatcatgc cattgcactc tagcctgggc cacagagcaa gactctgtct 39660
tcaaaaaata ataaaaagga gctgtgatta tcccaaggtg gggattgtga atgtgtttgt 39720
attgttctaa actgggagaa acaggctggg tgtgttggct tatgcctgta atctcagcac 39780
tttgggaggc caaggtggga ggatcacttg agtccaggag ttcaaggcca ccctgggcaa 39840
caggcaaaaa atagagaccc catctctatt ttttaaaaat aaaataaact gggagaaaga 39900
agcagggtcc tccccagagc atctttatcc ctagtcacag acctgacacc tgtgttgggc 39960
aatggctact tctagattgt ttacccctac tgggacttgt ggtgaacata tgcacacttt 40020
ggtttacagt tgggacccct gattttagca ggatggccca atggaatcag ctacagcagc 40080
ttgacacacg gtacctggag cagctccatc agctctacag tgacagcttc ccaatggagc 40140
tgcggcagtt tctggcccct tggattgaga gtcaagattg gtaagtcctt cttaagtgac 40200
tctccaaatt gttaggtttc agtttgagtc aagagacatg aactcttaat gtcatgcctt 40260
gctgttccat taaaaaatgt atgggtacag gtgatgggga aaatgagatc aggagataaa 40320
ggggcaccct ttggtcttgt aaagcctttt ttatcttaga agggcatgtg ggcaactgtc 40380
tttgacacat tgaaaccgcc tgtatggtgg tggatgtctt gaaggttgat ttggacctca 40440
tttacttggg cagatcctct atatattctg ataatccagt gatgtggtag acatattttt 40500
tctctgaatg tgaattctgt catagctaga actttgggtt gatacttgta attccccttt 40560
agttaaagga aggagccaca ggggtgtatt agtctgttct caatttgcta taaagaaata 40620
cctgagactg ggtaatttat aagaaaagag gtttaatcgg ctcatagttc tgcaggctat 40680
ataggaagca tagcagcatc tgctgctggg gaggcctcag caagcttcca atcatggcgg 40740
aaggcagaga gggagcaggc aggtcacatg gccacagcaa gagcaagaga gcaaggggga 40800
ggtgccacac acttttaaac tatcagatct cacaagaact cactgtctcg aggacagtat 40860
caacagggat ggtattaaac cattcatgag aaacccaccc ccatgatcca gtcaccttcc 40920
accaggcccc acctcaaaca gtgggggtta catttcagta tgagatttgg gcagggatgt 40980
agatccaaac tagatcacag gataagggaa gtagattcca ttcatagagc agataatggc 41040
acagatgtcc agcaactatt ttcttcactt taatatgctc aggctcacta ctgattttgg 41100
tttaattcag gccagtgtta atatgacctg gtttttccag aatgcatact ctgatttggt 41160
gaagggccag gaggtgattc acagatgttg gagataggcc atcccagcct gggattactt 41220
atttgtacta ataaatctga ccagagttaa ttgagggttt aaagcaaaac agcatatctg 41280
tctactttgc tcaaatattt tacaaataca acagattatg agagtgggta ataatatctg 41340
gaataattgt ttttttgttt tgtggttttt tttttttttt ttttgagatg gagtctggct 41400
gtagcccagg ctggagtgca gtggtacagt ctcggctcac tgcacctctg cctcttggat 41460
tcaagcgatt ctcccgcctc agcctcccga gtagctggga ttacaggtgc ccaccaccac 41520
acctggctaa ttttttattt ttagtagaga cagcgtttca ccatgttggc caggttggtc 41580
tggaactcct gacctcaggt gatccgcctg cctcagcctc ccaaagtgct gggattacag 41640
gcatgagcca ccatgcctgg cctggaataa ttgttaataa ttattacatt gatggcattt 41700
tattgctgag caagaagaat ctaacatgat gaatgggtta tagcatcagg tttgctttgt 41760
tttttgtttt ttttcctctt tcttgatggt gatttctgtg tttgtgtgta tgcgtcggct 41820
tcagagccat tctttatcat tcttcctttt cctagggcat atgcggccag caaagaatca 41880
catgccactt tggtgtttca taatctcctg ggagagattg accagcagta tagccgcttc 41940
ctgcaagagt cgaatgttct ctatcagcac aatctacgaa gaatcaagca gtttcttcag 42000
gtatgatgag aaactgagga caaggagaaa caggacccgc agagtcgggt gttagtgttc 42060
tttcctggaa gcatctcttt tctcatttgg ctaagtaacg agaatctatc ttgtattttc 42120
aatcacagga gaagtaatta gccctttctc aaagctctgt atacttaccc gtgagcatca 42180
ttacctgaga atcacttctc ttgtcacagt tgaagtaata aagtgattgt tatgttaatc 42240
atacatgtta gcatgttaac gcggtccact gataggaaga tgactctcac tgttacatgt 42300
taaatgtttg accataatgg gatacttctt gactaagtca gtagcttccc tgcaagacca 42360
ggatagtata ctgtgtaaag actcagacaa ggccaggcat ggtggctcac gcctgtaatc 42420
ccaacacctt aggaggttga ggtgggagga ttgcttgagc ctgggagttt tgagaccagc 42480
ttgggcaaca taacaagaca ccatctctac agaaattttt tttaaaaact agctgattgt 42540
ggtggcatgc acctgtagtc ccagctactc agaaggctga ggtgagaaaa ttgtttgagc 42600
ctgggaggtc gaagctgcaa taagccgtga ttgcgccact gcactccagc ctggcggaca 42660
gagtgagagc cagtctcaaa aaaaaaaaaa aaagactcag gctaatgtgc cttctgttac 42720
agaaatagta acgacctccc cttcgccccc cgccgacaga gagccttcac ccaggctctg 42780
aagcctttgt tccgttgttt cctagaataa atgctttcct tgatgaatac attagtttta 42840
aggtgccaca gttcagtcca catctccatg gtctgctgct gatttttatt ctctttctct 42900
cctacttata gagcaggtat cttgagaagc caatggagat tgcccggatt gtggcccggt 42960
gcctgtggga agaatcacgc cttctacaga ctgcagccac tgcggcccag gtgagacctg 43020
agacaaaaca aatccctggt ctgggaggaa tggaaaatca aacaacttta taatgagata 43080
aattattaga tctactaaaa aagaaggaaa agaaattaaa tagatcaata atcataaaaa 43140
tacattgaaa aactctaaaa aaaaagaaag ttccaccccc caaaatacat tgaaaaactc 43200
taaaaaaaag aaagttccac caaaagaatc caacagaccc aatggtttaa aagttttgtt 43260
ttgttctgac aaattttctt tgtttttctt tttttttttt tctgagacag agttttgctc 43320
ttgttaccca ggctagagtg caatggcgcg atcttggctc actgcaacct ccacctccag 43380
ggttcaagtg attctcctgc ctcagcctca agagtagctg ggattatagg cgtgtgccac 43440
cacacccagc taattttgta tttttagtag agacggggtt tcttcatgtt ggtcaggctg 43500
gtctcgaact cctgacctca ggtgatccgc ccgcctcagc ctcccacagt gctgggatta 43560
caggcgtgag ccactgtgcc cggcctgttc tgacaaactt tcatagtaca gattattcca 43620
atatcattca aacttttcca aagtatagga aaacaaggga tgttttcagc ttattttatg 43680
aggctggaaa aatcctcata tcaaaaccta aaaaacagcc aggtgtagta gctcacgcct 43740
gtaatcccag cactttggga ggctgagacg ggcagattgc ctgagcctca ggagttcgag 43800
accagctggg gcaatgtagc gagacctcat ctctcttttt tttttttttt gagacagagt 43860
ctctctctgt cgtccaggct ggagtgcagt ggtgccatct tagctcactg caacctccgc 43920
ctcccaggtt caagcgattc tcttgcctca gcctcccgac tagctgggac tacaggtgtg 43980
tgccaccaag cctggctaat tttttgtatt ttttttagta gagatggggt ttcaccttgt 44040
taggcaggat ggtcttgatc tcctgacttc atgatccacc ggccacagcc tcccaaagtg 44100
ctgggattat aggcatgagc caccacgccc agcctttttt tttttttgga gacagagtct 44160
tgctctgttg ccaggctgga gtgcagtggc gtgatctcag ctcactgcaa cttctgcctc 44220
ccaggttcaa gctattcccc tgcctcagcc tcccaagtag ctgggactac aggcgcgcgc 44280
caccacaccc agctaatttt ttgtgttttt agtagagatg gggtttcact gtgttagcca 44340
ggatggtctc gatctcttga cctcgtgatc cgcccgcctc ggcctcccaa agtgctggga 44400
ttacaggcgt gagcaaccgc acctggctta attaaggatc tttctaaaca caagaaagaa 44460
tatttatcag aaaccaaagg gagcatgatg cacagtggtg aaacactatt ctcagtaaaa 44520
acagcaaaag ataaggatgt cttttaccat tgatactttt ctgagggatc cagcctatgc 44580
aaaaagaaaa agaaatgagg gtacaaatat tggaaagcaa gggacagaac tcttattatt 44640
tacagataga taggtcttcc tcgaagatcc aagagaaaca aaactaacaa taacaattgg 44700
aactagcaag gtttagaaag gccattgtat acaagataaa tatttttaga atctgcagtt 44760
cccctaatca gtagcagcag taacctgtta gaagatgtaa tgaaagtaaa gatctgggcc 44820
aggcacgatg tctcacgcct gtaatccaag cactttggga ggccaaggtg ggcagatcat 44880
gaggtcaaga gattgagacc atcctggcca acatgatgaa accccatctc tactaaaaat 44940
acaaaaatta gctgggtgtg gtggtacgcg cctgtagtcc cagctactcg ggaagctggg 45000
gcaggagaat cgcttgaacc tgggaggcgg aggttgtagt gaaccaagat tgcgccactg 45060
cactcctggg cgacagagcg agactccgac tgaaaaaaaa aaaaaaaaaa aaagaaagat 45120
ctgattcata gtagtaaaac taaatgtatg caatttgcat atactattgg tatgtatggg 45180
aaaatatctg gaaacacata tactaaatca ttaaagtagt cggtcatagg agactttttt 45240
actttctgtg aggggtttta ccgtctttaa tatcctataa tcagggacat tttttctttt 45300
tctccgtgac cccctgcttt ttaaaaaatt gtggtgaaat acacataaca ttacatttca 45360
aatttacctt tgtaaccttt gttttttttt tttttttttg agacagtctc actctgtcac 45420
ccaggctgga gtgcagtggt gtgatcacag ctcactgcag cctcaaccac ctgggcccta 45480
gcgatcctcc tgcctcagcc ttatgagtag ctgggactac aggcacatgc caccatgccc 45540
agctaatttt tttttttttt ttttttggta gagatgggct cttgccatgt ttcccaggct 45600
ggtgttgaac tcctgggctc atcaactgat gagaaagagc tctccaggca gaaagaagat 45660
catgttcaaa gacagaaaca gaaatgtgta ttcttgggag aagtgtagaa agttcagcat 45720
ctgattgggt cggggaagac aagctagtca aggccacatg atgttttaat tagtcatgcc 45780
taacagtggg gccctggaag agcagtttac cacaaggggc caactgcttc ggtttgaacc 45840
cgcagccctg ccacttgctc tgtaacctta agtaaacaat ttttactctc tctgttcctc 45900
caatgggagt gataacaata ccttcttcat agaattaatt catacatgta aaatgcttag 45960
aacagtatct gacacataaa tgcaaaataa tttaactgct ttctgctgct gctgacatca 46020
ctatcatcac cctcaccatt actgtaggaa atggggaccc agtgaagaat tttttttttt 46080
tcttttgaga cagagtctca ctctgtcacc caggccggag tgcagtgacg cgatttcggc 46140
ccactgcaac ctctgcctct caggttcaag cgattctcat gtctcagctt cccaagtagc 46200
tgggattaca ggcatgagcc accacactgg gctaattttt tgtattttta gtgagatagg 46260
gtttcaccat attggccagg ctggtctcaa actcctgacc tcaggtgatc catccacctc 46320
ggcctcccaa agtgctggga ttacaggcat aagccactgt gtccggccct agtgaggaat 46380
tttaagcaga aaactgatat gctcaggtgt gagcgaggtg gtaggtaaca cttactgtgc 46440
agtgccctgt agcccaagag gttagcacac aggcatttgc tcaggcagca ctaggatttt 46500
ctgctgtgga aaacctttgt attttatcct gctccacaag ataaaaataa gtggtttaag 46560
tcaatttgga tagaggctcc aacttaccat gggaggtagg aaagccaaag ttatcccaag 46620
gatgttttca atcgtacgga ttaggggtct gcaaactgtg agcgtggccc aaatccagcc 46680
tgctgcttgt ttttgtaaat gaggtttttt cggaacccag ccacactcat ttatttatgc 46740
attatctgtg gctgctttgg tgctgcagtg gcagggctat ttgtggcagg gactgtatga 46800
cccaggaaac caaaaatatt taccctctgt cccttagaga aaaagtttgc aacccctgat 46860
ataaagctat aagttggtta tttgtggcct caacccaggc ctcactgcta ttttttctgt 46920
ttacaatacc tggcatgctc ttaagtgtct agaattggtt aaagatagaa gagtggatgt 46980
aatccctgct accaagggct gtcaggctag ttgggattat aagtacacaa acactcaaag 47040
tgagaaaaac acagaaaagg atgtgtgtca ttttgtctaa ggaagttgaa taagatttct 47100
caggaaaaga aacatttgaa ctgaatttga aggtgagtga gttcaggtgt gtttgggctg 47160
aagcccaggc catgctgagt ggatagcggg tgggaagaga gtgtggaaac acactgcatg 47220

-continued

```
cagggaagag ttgggagtct ggggtgacca aggcacaggg agggaaagtt gaagttatca  47280
attgtgtgaa acagctttct gtgttggcct gagatgttta tagctggaag cagtggggag  47340
ccaatacagt tttttacgaa ggtattagag gtgggtttct gtgggtgatc gttaatcatg  47400
ttttctccct ttaagtgtag tcctgcttga gaaatagaca tgagaaagga atgaaggtta  47460
aaacatcagc tgtattgttg gtaaaactag aatggaaagt gtggcttgag ctggtaacca  47520
taggggcttt ccaatgcctg tgccctgagt tagatcttgg ggtagagaga ctggatgtgc  47580
agagcagcac ccccacccca ccccagccat ccatatggag cttcagctgc catagaccaa  47640
caaggcagag ggataggcct ctagacctgc ttctagaaac caggctgctg ctcttgctta  47700
tggtgggccc taggaaggca agagtgagag gagggaggca ccagcttagg tgctgggttc  47760
tttgaagatc tgtgtgtaca cagagtcttt ctctccatct taccaatcag atgagtcact  47820
gtcactgtgg gaagaagtag gggcatgggt caccttccca aaacttctaa gaagtttgta  47880
ttctgtgggc ttggataggg accatgggaa aggaagagaa tggttgccca taaaactggc  47940
tgtagtgtgg cctcaaactt ctggacttaa atgatcctcc cacctcagcc tcccaagtag  48000
ctagaactac aggtatatgc caccatgccc agctagttaa aaaaaaattt ttttttttt  48060
ttggttgaga tgaggtctct ttctatgttc cctgggccgg tctcaaactc ccagcctcaa  48120
gtgatcctcc tgccttggtt tcccaaagtg ctaggattat aggtgggagc taccatgcct  48180
agcccaagcc tgtaattttt tttttttttt tttgagatgg agtttcactt ttgttgctca  48240
ggctggagtg catggcgcag tcttggctca ccacaacctc cacctcccgg gttcaggcga  48300
ttctccttcc tcagcctccc gagtagctgg gattacaggc atgcaccacc aagctcagct  48360
aactttgtat ttttagtaga gatgggtttc tccgtgtcgg tcaggctggt ctcaaactcc  48420
tgacctcagg taatctgccc accttggcct cccaaagtgc tgggattaca ggcatcagcc  48480
accgcacctg gcacgaacct gtaattttta agtttcatat gctatttatt ttttgttatt  48540
tctttaattc attcattcat ttattcattc gagatggggc ctcactatgt tgactaggct  48600
agttttgaac tcctggcctc aagcagtcct cccacttcag ccttcccaag tgctgatatt  48660
ataggtgtga gctgctacat ccagccttct ttcttctttt tctttttcca tgtgctattt  48720
gacattttcc aaggtaccag cctccccttc tccccaagat aatatctttt aatatggaat  48780
ttcatcccta gggcaggact ttttttttat tatccctcag aaatatactg gacaccacgt  48840
ttaagtagac atccaacatc tgctgtcata aattgttttg aattttttga catacttgcc  48900
catgaggttt ttgaaggcat agaccatgtc ttagctgaac atgtggtctc ttagtgccat  48960
aaagggggtt tatggtatga cctgtgtagt gtcacctgtg tagtgacagc accactgcct  49020
ctgtttccct tcctcttgtg atggcagcag cgtctcaagc caaacaagaa gggtagttag  49080
ggtgggatgg aagctgggta gaggtattcc tctccccata gttctgtgtt cacatgtgca  49140
ttgacctcct ttttggcagc aagggggcca ggccaaccac cccacagcag ccgtggtgac  49200
ggagaagcag cagatgctgg agcagcacct tcaggatgtc cggaagagag tgcaggtgat  49260
gcaagttaca agcctcgggc agggagcttt cattaatttt tttttttttt tttgagacag  49320
ggtcttgctc tgccactcag gctgggctgc agtggcatga tcacagctca ctgcagcctc  49380
gacctctcag gcccaagcga tcctcctacc tcatcctccc aagtagccgg gaccacaggc  49440
atgcaccacc acgcccagct aattaaaaaa aaaaaatttg tagagatggg ggtctccctg  49500
tgttgtccag gctgatcatg aactcctggg ctcaagtgat cctcccaact cagcctctca  49560
aagtgctggc attacaggcg tgagccactg cacctggcca acagggagcc ttctcttggg  49620
```

```
gatactgcct gcaggtcctg catgtatctt ttttgaggtt ttggcttcat ttgaattctc  49680
ctcagaaact ttatattttc tgttcccaag gaaatctttc tttacttctg tttttttgtt  49740
tgcttatttt aaacaggatc tagaacagaa aatgaaagtg gtagagaatc tccaggatga  49800
ctttgatttc aactataaaa ccctcaagag tcaaggaggc aagtgaatat tagagatgtt  49860
aaaatctcta gaaagtgagt ttgtgttgtt gagttgaaag actcatttgt cttaactctg  49920
tttagatctt aaggcgggcg gggcgcaagg gaggtacggg tcctcaaagg agcctggtca  49980
ttaaggacag gagtattccc tcaggtccag gagtattccc tcaggtccag gagtattccc  50040
tcaggtcaag gagtattccc tcaggtcaag gagtattccc tcaggtccag gagtattccc  50100
tcaggtccag gagtattccc tcaggtccag gagtattccc tcaggtccag gagtattccc  50160
tcaggtccag gagtattccc tcaggtcaag gagtattccc tcaggtccag gagtattccc  50220
tcaggtccag gagtattccc tcaggtccag gagtattccc tcaggtccag gagtattccc  50280
tcaggtccag gagtattccc tcaggtcaag gagtattccc tcaggtccag gagtattccc  50340
tcaggtccag gagtattccc tcaggtccag gagtattccc tcaggtcaag gagtattccc  50400
tcaggtccag gagtattccc tcaggtccag gagtattccc tcaggtccag gagtattccc  50460
tcaggtccag gagtattccc tcaggtccag gagtattccc tcaggtccag gagtattccc  50520
tcaggtccag gagtattccc tcaggtccag gagtattccc tcaggtcaag gagtattccc  50580
tcaggtccag gagtattccc tcaggtccag gagtattccc tcaggtccag gagtattccc  50640
tcaggtcaag gagtattccc tcaggtcaag gagtattccc tcaggtcaag gagtttttc  50700
ttccttcgca gacatgcaag atctgaatgg aaacaaccag tcagtgacca ggcagaagat  50760
gcagcagctg gaacagatgc tcactgcgct ggaccagatg cggagagtaa gggcataggt  50820
cggaccactt cccccatgtg tctcgctcac ttgcgggatt tcagcgtctt gtggcagaac  50880
ttgcttggtt tctaagaagt tcctgctctg gagttgacta aagaatgtgg ttagagacag  50940
tctgaggaaa tgttttctga ctttgttttg gtttccaacc agagcatcgt gagtgagctg  51000
gcggggcttt tgtcagcgat ggagtacgtg cagaaaactc tcacggacga ggagctggct  51060
gactggaaga ggcggcaaca gattgcctgc attggaggcc cgcccaacat ctgcctagat  51120
cggctagaaa actggtaaag gatgaaagaa gcttttcctt tctttctcga aagctagatt  51180
gaattctgat cttaactgca ggcccacaga attggtacta tatctccaac gtggggactt  51240
ttccatattc aaatttagcc caagaattaa agtttttact ttatttcggc caggcgctgt  51300
ggctcacacc tgtaatccca gcactttggg agaccaagat gggcggatca cttgaggtca  51360
ggagtttgag accagcctgg ccaacatggt gaaaacacat ctctactaaa aacataaaaa  51420
aattagccgg gcgtggtggt gcgcacctgt agtcccagct actctgggcg gctgaggcag  51480
gagaatcact tgaacctggg atatggaagt tgcagtgagc ggagatctta ctaccgcaca  51540
ccaaccagcc tgggagacag agtgagactc catctcaaaa aaataaaaat aaaataaagt  51600
ttttacttta tttggagaaa ctttgtttta aaaaatgtat ttatattatt atattttaag  51660
tatattttac ttaataattc aattaaggct tttggtttaa ctgtatttaa cagatagaca  51720
aaccttttaa ttttagttat tttagtaatc taaaatgaca catgcccttt ttaagggaaa  51780
aaattcaaat acagaaaatt aatcaagaga agaaaaaatt tttaaatgaa atcatcagca  51840
gtactagtag ttaaaattta gttgatgctc aatctagaca tctgtcatta tgtatataca  51900
cattatgtat atacacataa agatagaaat ttatacagtt tatattagga tcattttttt  51960
```

ttcttttttt ggagtcaggg tctcactgtg ttacccagtc tagagtacag ttatgcagtc 52020
atggctcact ggagccttga cctcctgggc tcaggcagtc ttcccacctt agccttctca 52080
gtagctggga ctacaggcat gcaccaccac acctggctaa tttttaaatt ttttatagag 52140
acagggtctt actttgttgc ctgggctggt ctcaaattcc tgggctcaag ggatcatccc 52200
acttcggcct ctcaaaagct ctggaattat agatgtgagc tgccgtgccc agcccaggat 52260
cttcctttat atgcttttct gtaatttgca cttttacctt catccagcat atcttactgc 52320
aacccttcct gtgcaaggcc ctatagtgag catgttgcac cagcttgcct taggagaaac 52380
ttgagataca gagcctgcac tggaaattta gcgcaactct acatgagaat gcctgtctat 52440
tcatatcctc actaaccctg agtgttgtta atttactgaa agcagtttta aatgcttcct 52500
gaccagggaa cgaagaagct taagttctgg gaatgggagg atagaagtgc cagaaaagag 52560
ctcaggagtt cagaaatccc tgcagcggtc cccctccctc tcctttcact ttctgtcttt 52620
ctggtctttt ggtctttgtt acactagtga taaaccatca aagaatgatg gaatgatgct 52680
aacttctctc ttttttaat ttttttgaga cagagtctca ctctgtcacc caggttagag 52740
tgcagtggca tgatcttggc ttactgcaac ctcctcctcc caggttcaag cgattcttag 52800
tcacaacctt ccaagtagct gggattacag gcccatgcca ccatgcctgg ctattttttt 52860
gtattttagt agatcgacct gcctcggcct ctcaaatttt tgggattaca ggtgtcagcc 52920
actgcacctg gcctaatatc tctattcttg gagatagatt taatgagctt tttctccctc 52980
tctattcact tattccttgt gcatgttatc aatattttga aacataatgt catgtccttt 53040
gatcagttga aggctgacat tgaaaaggct tatggggatt gggtgttgtg gctcacgcct 53100
gtaaatccca atgctttggg aggcagagtc gggaggatca cttgaaccca ggagtttgag 53160
accagcctgg gcaacaaagt gagatcccat ccctacaaaa atttaaaaaa ctagacatgt 53220
gccattacac ttcagcctgg gtgacagagt gagactccat ctcaaaaaac taaactaaac 53280
taaacaggca tggtggcaca cacctatagt tctagctact caggaagctg aggtaggagg 53340
atcactcatg tccaggagtt ggaggaggca gtgagctatg atcatgccat tgcactgcac 53400
taggccacag agtgggaccc tgtctcaaaa aaaaaaaaag aaagaaagaa aagaaagggc 53460
tcatgtagtt caagcccttc tcttcatgca aggggatgct aaggcccatg atggtgaagg 53520
gcctggcaaa gcttgcacag atagtgtgtg acagagctgg ctcaaaccca tctttgggag 53580
ctgtctaatc tctttttctg agtctttatg ttcatagaca agttaggatg agtaaagtaa 53640
gtgctaaatt ccatatttcg tgttctgcat atctgggctc agatgcttgt cattttccag 53700
tgataactcc atcaatgcct cctagtggta taaattttaa tacttcttgt gtgcccagcc 53760
ccctcttaga aatttgagat tttaggaagg gactagtaat aaaaggtaaa ataaattatt 53820
ttctggccag gcatggtggc tcacacctgt aatgccagta cttcgggagg tcgaggcaga 53880
tggatcacct gaggtcagga gttcaagacc agcctggcca acaaggcaaa atcccatctc 53940
tactaaaaat gcaaaaatta tccgggagtg gtggtgggtg cctgtaatcc cagctacttg 54000
ggaggctgag gcaggagaat cacttgaact tgggaggcgg aggttgcagt gagctgagac 54060
tgtgccactg cactccagcc tgggcaacag agtaagactc tatctcaaaa aaaaaaaaaa 54120
aaaaaaaaag gccaggcgca gtggcttaca cctgtaatct ctcaggaggc tcaggcagga 54180
gaatcacttg aacccgggaa atggaggttg cagtgagccg agattgcacc actgcactcc 54240
agctcaaaaa ataaataaat aaataaatta ttttcttttt ttatttattt tttcagcatc 54300
cacccaacat ggtgaaaaat tcctcttttc ttaatgtcac tgaactgtaa acttaagatg 54360
aaaaattgta aatttcatgc tatatatatt tcaccacaat aaaaaaattc cttgttctta 54420
ttgtagtggt ctccatgtct tcagtatttc cttccccttc tccatctcac ctgtatacat 54480
tcactttggt aattagcatc tttcttaatt tattggcagg ataacgtcat tagcagaatc 54540
tcaacttcag acccgtcaac aaattaagaa actggaggag ttgcagcaaa aagtttccta 54600
caaaggggac cccattgtac agcaccggcc gatgctggag gagagaatcg tggagctgtt 54660
tagaaactta atgaaaaggt aatttagcat ccttgtccct ttccctcatc taaaaaatac 54720
ctaaagactc acgtggtaga gtgagaggcg ggctgacttc tggtcatggc cgtggcgcgt 54780
gagcccatct tctctttcct cagtgccttt gtggtggagc ggcagccctg catgcccatg 54840
catcctgacc ggcccctcgt catcaagacc ggcgtccagt tcactactaa agtcaggtag 54900
gccatgccac ttccatttcc agtagagatt ttactgaggg acactgttag ggtgagggta 54960
gagttggtgg ccagggtcat tctttccagg tgtggtgtca caggcagtac actgttgcgg 55020
ggttgaaatt tgttgccata ctatctgctt gctctctgat tctgatgtca aaagcaaaag 55080
agcagtcatc tttttgaagg tacctgggca tattcctatg attgtagacc tggagtctca 55140
ggccacagct tctccttctg cccaagggac aaaataatgt catctatttt ctgttctttg 55200
aggctactct tccctgtgga ttttaaggga aagagtaagg cttagtgatg gggaagctga 55260
gaggccccag ggcaggtggg tggtgggcct gtagggtgag gtgttacttt cacactcaag 55320
tcagaacagg tgtgctgggg ttttgacctt ctgcagcaaa atttccctcc tcagaaactt 55380
agtatggtgt tcggtttcag gattaataga acaaaatgcc agctgcacag catgtgttcc 55440
tgtaatattt ttcattatat ggctttgatt atccttttgt gaatctctca caactttaag 55500
ttgttagttc ttagatgttt tctcagtacc tttggcttga aggagtgata ctcatctttt 55560
gtttttgttt gagacagggt ctcactctca cccaggctgg tgtgcagtgg catgatctca 55620
gctcactgca acctccatct cccaggttca agtgattctt gtgcctcagc ctcctgagta 55680
actgggaata gaggtgcgtg ccaccacacc cggctaattt tttttttttt gagacagagt 55740
ctcgctcttt cggccaggcc agagtgcgtg ttgcaatctc aactcactgc aacctccacc 55800
tcccaggttc aagcgattct cctgccttag cctccctgag tagctggacc ggcacactcc 55860
accatgcccg gctaattttt gtatttttag tagagacagg gtttctccat gttggccagg 55920
ctggtctcaa aactcctgac ctcagtaatc cacccacccc ggcctccaaa agtgctggga 55980
ttacagatgt gagccaccac gctcggcctt tttttttttt tttttttttt tgagatggag 56040
tctttctcta tcacccaggc tagagtgctg aggtgtgatc tcggatcact gcagcctctg 56100
cctcctgggt tcaagtgatt ctcctgcctc agcctcccaa gtagctggga ttacaggtac 56160
ctgccaccat gcccggctga tttttgtatt tttagtagag acggggtttc accatcttgg 56220
ccaggctggt ctcgaactcc tgaccttgtg atccacctgc cttggcctcc caaagtgctg 56280
ggattacagg tgtgagtcac cgcacccagc cctattttaa ttttttttaaa gagagagata 56340
ggggccaggc acggtggctc tcgcctgtaa tcccagcact ttgggaggcc aaggtgggtg 56400
gatcacctga ggtcgggagt tcgagaccat cctgaccaac atggagaaac tctgtctcta 56460
ctaaaaatac aaaattagct gagcgtggtg gcgcgcgcct gtaatcccag ctacttgaga 56520
ggctgaggca ggagaatcac ttgaacccag gaggcggagg ttgcggtgaa cggagattgc 56580
gccattgcac tccagcctgg gtaacgagag aaactgtctc aaaaaaaaaa aaagagaaag 56640
agagatagga tctcgctctg tcatctaggc tagagtgcag tggcatgatc atagatcact 56700

-continued

```
gtagccttga actcctgggc acaagtgatc ctcttgcctc agcctcccga gtaactgcga  56760
ctacaggtac atgctaccac accccgctaa tttttaaatt ttttatagat gtgggctctc  56820
actttgttgc ccagactgtt atggaactcc tgggctcaag ggatcctccc agcttggcct  56880
cccacagtgc tgagattata gatgtgagcc tgtaattata gacagcttgg cctatttacc  56940
tgttggaaat gaagaattat gaattttaca tttcttcaag aaaaggttat gggagagtta  57000
ctgacttttt ttccttggat tttttctttt taaataggtt gctggtcaaa ttccctgagt  57060
tgaattatca gcttaaaatt aaagtgtgca ttgacaagta agtactccta tcttagctct  57120
gtttttcaaa tgaggaatag aaaaatgaga actttgacag acatcatttg aactagagac  57180
tctgtcttta ttcagagatc ttcattttgt ggacaaaagt tttcaaaagc cttggggtgc  57240
attgtcattt acgtgtctga acaaagccac aaagctgggg gtacagattt gatttgtggt  57300
tgctattgtg acaaccagtc cctcttttcc ttgtttagtt ttttacttgt acatgtcatt  57360
catgcatatt atatataaga ctgagatcat gtgttaatta acgactggga tacgttctgc  57420
aaaatgtatc attaggcaat tttgttgtgc aaatgttgta gagtatatag tccttacaca  57480
aacctgggtg gcagaaccta ctgcacacct acgctatgtg gcagagccta ctggtcgtag  57540
gctgtaaacc tgtacagtat gttactgtgc tgaataccgt aggcaattgt aacacatctc  57600
aatgaagtag gaatttttca gctccatgat aatcttatgg gaccaccatc atatatgcat  57660
tttgttgttg accgaaacgt cgttatatat tctttccata catagcatgt ggaaagaata  57720
gatctctttt ttttaattgt tccacacttt accatataat ggaatacgca aaatttcaca  57780
ataccttca ggatgtaaaa tacatatacc ctttgacgac attagaaaag agaaaatgtg  57840
ggccgggcgc ggtggctcat gcctgtaatc ccagcacttt gggaggccga ggcgggcgga  57900
tcacgaggtc aggagatcga gaccatcctg ggtaacacgg tgaaaccccg tctctactaa  57960
aaatacaaaa aaactagctg ggcgtggtgg cgggcacctg tagtcccagc tactcaggag  58020
gctgaggcag gagaatggca tgaacctggg aggtggagtt tgcagtgagc caagatcaca  58080
ccactgcact ccagcctggg cgacagagac tccatctcaa aaaaaaaaaa aaagaaaaga  58140
aaagagaaaa tgtggctggg cgcggtggct cacgcctgta atctcagcac tttgggaggc  58200
tgaggtgggc agatcacctg aggtcgagag ttcgaaacca gcccgaccaa catggagaaa  58260
ccttgtctct actaaaaata caaaattagc caggtgtgtt ggcgcatgcc cgtaatccca  58320
gctacacggg aggctgaggc aggagaatca cttgaactca ggaggtggag gttgtggtga  58380
gccgagatca caccattgca ctccagcctg ggcaacaaga gcgaaactat ctcaaaaaaa  58440
aaaaaagaaa aaagaaaaga taaaatgcat tcttattttt agttgatgta attatgtgga  58500
aatttcatga ggatgcactg gaaaataatg aaataaggga gttgacgaag gtggtaggtt  58560
taataagtac atatgcaata tgaaacatag gttccccttc ctatggggag gcaaccaact  58620
gtgcctgcta cgcagaggtg ttatgttgcg ctgatcaact gtaactgaat agtttaaaga  58680
aatgcccagg agcacagagg ttttttcatg acagtaaata acaggtggtc aaagtaggct  58740
ttttgaagaa acacagagcc tattttatta acaacagtct gtgttcttac agagactctg  58800
gggacgttgc agctctcaga gggtaagttc agcctagagg cttccttttg ttccgtttaa  58860
cctaacttca tcctccggct acttggtcac ctacatagtt gattgttccc ctgtgattca  58920
gatcccggaa atttaacatt ctgggcacaa acacaaaagt gatgaacatg gaagaatcca  58980
acaacggcag cctctctgca gaattcaaac acttggtatg tgggaggagc tccccttcac  59040
aaagggcctc tggctgccgg agagggctag ggagagcctc acaggacacc tgcctttttc  59100
```

ttttcttaca gaccctgagg gagcagagat gtgggaatgg gggccgagcc aattgtgatg 59160
taagttttgt tggggatgaa agacaactgg ggtgttttcc ttgagggaga gaggggtaaa 59220
gatccttctt aatccccaga attagaaaca tcaacctgtt ctttcagctg tagttattcc 59280
aaaaagtcac ttcaggccaa agtgacatga acagaagttc catgtgccat ggagctctct 59340
ggcttggaac atttccgtga atatctggga gttggctcct ccttaaggag aagtggaaag 59400
tcccttgctg agttgttctc cacacccatg tggtataaag cagctttcca ccttgcctgg 59460
ggctttccaa attccccatc cagctcctgc ggctgaccct gcttggctcc atttttagtg 59520
ccctgttttt ctctcccact gaggtgggat agagggtgta aaagcaacag atttgagtta 59580
aactttaaaa taaatgacca ccttgcatta gcttgcttag gaaaagagta cataaaataa 59640
aatgaacaaa caaaaaccca tcttgttctt tatccccctt attttctgct tttcattgat 59700
tcagattatt ggattcttat tgtcaagaat aaactttaaa caaacaaaca aaaaaaggta 59760
aatgtgacgg aaggctagtt ttcagtcatt tttaaaaatt gtgatgcccc gttctttttc 59820
ttacatttgt cccctgaaca attcttcctc tttaaaatgt agcagtccta gctgggcgtg 59880
ctggctcaca ccccgtactt tgggatgcca aggcaggctg gtcacttgag gtcaggagtt 59940
caagaccagc ctggccaaca tggtgaaagc ccgtctctac taaagataca aaaattagct 60000
gggtgtggtg gtgcacgcct gtagtcccag ttactgggga ggctgaggca tgagaatcgc 60060
ttgaacctga gaggtggagc ttgcagtgag ccaagatttt gccactgcac tctagcctgg 60120
gcaacagagt gaaactctgt ctcaaaaaaa taaataaaat aaaatgtagc agtccttttt 60180
aaaaatgtgg aattttactt gacagtagag tgaagtagcc tgtatgcaat gatatgggaa 60240
aatgtacatg acatattaag aaaaagcaaa atgtaaaata atttgaatag tattattagt 60300
atatgtgttt taaaaataca ctatactctt atgtgtattc atatgtatat taagaaattc 60360
tggaggaata taccagcagt gctatgtgta ttagtgctgc tgttggtatc catggctatt 60420
ctagactgtc tctgtgatat ttgcatttta aactgaatat attactttta taatcagaaa 60480
aatagtatta aaaatgaatt ataatttaat ttcttttttc tttttttttt ttgagtcgga 60540
gtctcgttct atcggattgc agtggtgcga tctcagctca ctgcaacctc tgcctcctag 60600
gttcaagcga ttctcctgtc tcagcctccc aagtagctgg gacgataggt gcatgccacc 60660
acgcctggct aatttttgca tttttagtag agacagggtt tcaccatatt ggtcaggctg 60720
gtcttgaact cctgacctcg tgatccaccc atctcggcct ccgaaagtgc tgggattaca 60780
ggcatgagcc gctgtgccca gactagaatt caatttttga gaattcattg acaactctta 60840
cttaaaataa ggttgctgta ctgatgtgag acattgttgt agtcagtttg gaaaacaatt 60900
tggcagtata aaaatgaaca tacctgtaaa ccaacggtgc cattcccagg atttaatagc 60960
agagaaatct ttgcatatat gtcccaggag acatatataa agtggacatc agcctgatta 61020
taagctctaa atgcaaccca aataaatacc catcaacatt agaatgaata cattatttgt 61080
ggtatagaca caatggaata ctccgcagct gtgaaaagga atacactgca gatacacata 61140
accatgtgga ttcatttcac atcaagtgaa aagtgaatcc caaaagaatt cattggagtc 61200
cataagtgta aggttcacaa atgtcccaaa ctaaacaata cctgcattgc ttagataaac 61260
aaatatggta aaactgtaaa aaaacaaaac aaaacaagac aaaaagggct aggaaatgat 61320
aaacccaaaa gacaaaatag cagttatttc tgagggagga gggaagggga tggggttggg 61380
gaagggcacc cagagaattt taggagtgat ggacttttcc ttaaattgaa tggtgggttc 61440

```
atattgtttt gttattcttt gtgccttacg tattttacaa ataaccaatt ggatctatgt  61500
aatattataa tacaaactga gtaaaggatt aggttgagga tcacagcatt ggaagttctt  61560
ggtgttgaag agagtaagtg ccgagcaagt tgtgtccctg gcagtttgtt tgtgaccacc  61620
tggtggctta cccttcttgg tgtggtgagg cttggcatgt cactttcctt ggctgtggct  61680
gttagtactg aatgccattc tctctgagga aaagtgtcct tctctttttt attgattgac  61740
tgattgattg agacagagtc tcactctgtc acccaggctg gagtgcagtg gcgtgatctc  61800
ggctcactgc atcctctgcc tcctgggttc aagcgattct cctgcctcag cctcctgagt  61860
agctgggact acaggcgccc actaccacac ccagctaatt tttgtattct tagtagaaac  61920
ggggtttcac caaattattg gccaggctgg tctcgaactc ctgaccatgt gatccacctg  61980
cctcggcctc ccaaaatgct gggattgtag gtgtgagcca tcacgctcag cctttttttt  62040
tatttaattt aatttttttt taagacaggg tctcactctg tcaccccagc tagagtgcag  62100
tggcacaatc atagctcgct gcagcctcca tctcctaggc tcaagccatc ctcccacctc  62160
agcctctcga gtagctgggg ctataggtgt gcaccaccac acccagctaa tttttgtatt  62220
ttttgcagag atggagtttt gctgtgctgc ttagactggt ctcgaactcc tgggctcagg  62280
caatcctcct gccttggcct cccaaagtgc tgggattaca ggcatgagcc accacacctg  62340
gcctaagagt gtccttctcg ttactgtagg cttccctgat tgtgactgag gagctgcacc  62400
tgatcacctt tgagaccgag gtgtatcacc aaggcctcaa gattgaccta gaggtaagtt  62460
ctgcagcaga atcggtgaga ggctacgtac aggggtgact caggacaaaa acttccactg  62520
ggatttttac aagagaaggt ggaatgatta ctgtttgctt aacactgtgt ttatttttgc  62580
ttacttttct ccaaaaaaat ccttggcatc ccatctggca ataaagtctt gcttgaatgc  62640
ttagaagatg tgtgtatatt cagctttcag caaacttgat atgaaaatct ctatttagaa  62700
attgattggc cgggcgcggt ggctcacgcc tgtaatccca gcactttggg aggctgaggc  62760
gggtggatca cgaggtcagg agttcgagac cagcctggcc aacatgacga aaccccgtct  62820
ctactaaaat acaaaaatta gctgggtatg gtggcggacg cctataatcc cagctactcg  62880
ggaggctgag gcaggagaat cacttgaacc tgggaggcag aggttgcagt gagctgagat  62940
tgtgccattg cactccagcc tgggtgacag agtgagactc cgtctcaaaa aaaaaaaaaa  63000
gaaattagaa ctgactttat aaagtttggg cataagagtc ttagcagcca gtgtgtttag  63060
tatacagaaa attgtggcaa tgacattctc ctttcccaac tttcttgatt tttaaattaa  63120
gatataccta gaaaagcagg aatcctggtc tttgattcct gagacctccc tgtttcatgt  63180
gaagatacag cttcaagtct tggagaatgc ctccaaggtc ttaaaaatgg ggaatctgtg  63240
gattgtgagt caagctttga gcaagtcagg ttttacaagg gaccggtata ttccgactgc  63300
agcctgagtt gtgtggccac gctgggcatt ctttccacta tgagtgctca ctgagctgac  63360
tcactcacac tcctcgccta gagttggcag caggtgtggt ttatggcatg tcctttcatt  63420
ctgagccccg tgagatgcgg gtgaagagat ttccaaggct gtgagagccc ctctgcctcc  63480
ccagctcagt ccccactccc tccgcagacc cactccttgc cagttgtggt gatctccaac  63540
atctgtcaga tgccaaatgc ctgggcgtcc atcctgtggt acaacatgct gaccaacaat  63600
cccaaggtta gtgccccctc cttttagttg gtgccccggg atctcttgcg acttaggggt  63660
acctagtata gacaatgagc accatccctc atctaaacaa gcaaatgtgt tctttccaat  63720
agaatgtaaa cttttttacc aagcccccaa ttggaacctg ggatcaagtg gccgaggtcc  63780
tgagctggca gttctcctcc accaccaagc gaggactgag catcgagcag ctgactacac  63840
```

```
tggcagagaa actcttgggt ccgcatttca ccccttctcc ctcccgccca cccgcccaga  63900
aaagggatcc ggcccatagg gctgttcatt tgggccatgt ctactgagca ttaggccatg  63960
tttctttcct gagcaaggcg ctgtgctggt gccaggaaac aggggagttg ggagttgggg  64020
gtgcagagac agtttgcagt tttcagtcga ggtgatcatt tttgaggtgg gaggtagatt  64080
tcttttctcc tggttgctgt ctcattcacc cactctatct aactttagaa gatcttttaa  64140
gtgtgtgttg gaaggtggca ctaaaggctt gacattccct gtccattttt ttaataaact  64200
ataggctagt tggttttttt tgtcttattt tatttattta tttatttttt tgagacgagt  64260
cttgctctgt tgcccaggct ggagtgcagt agtgtgatct cggctcactg caacctccgc  64320
cttctgggtt caagcgattc ttctgcctcg gcctcccgag tagctgagac tacaggtgct  64380
caccaccacg cccagctaat ttttgtattt ttagtagaga cggggtttta ccatgttggc  64440
caggatagtc tccgtctctt cacctcgtga tccgcccacc tcggcctcct aaagtgctgg  64500
gattacaggc ttgagccact gtgcccagcg taggctagtt tttaaaaaag aattagtgga  64560
atattttatg tgccacctgg gctagaagta gctttgttct aataaagctg ttgccaccaa  64620
atacacctgt ctgacacccg atgtcagctt gttagtgagt gctgctgttg gttcccagcc  64680
taccacccga ggttgggaag agcaggggga cttgttatat caccctccat ccctgctggg  64740
ctacccagca acacaagtga gtcaaatgat gggatagtgt ttgtcctcat gtgcacacac  64800
acaacagtgc ctaccttcaa agatgtgaaa gctgattatt ttgtggccca ttgtgggatg  64860
aatgtgtgtg tgttctgttt taagaaataa cctcttgacc ccaagctgaa aatgtactac  64920
ttgactcttt ttctttcctt caggacctgg tgtgaattat tcagggtgtc agatcacatg  64980
ggctaaattt tgcaaagtaa gcaatcttgt taaattctcg tgggaatggg aatgctcacc  65040
tgcacggctg tcgttgaggg ctctggcttg aaggccctga actcttggtc cagcggccag  65100
taggacctgc ctgaaggtag acgggcctga ggatttgggt gatgcactgc acccctagga  65160
agggaagggc tgggatggca gtagacttgg ctttcccatt actcttttct ccaggaaaac  65220
atggctggca agggcttctc cttctgggtc tggctggaca atatcattga ccttgtgaaa  65280
aagtacatcc tggccctttg gaacgaaggg taggttggac agagtgtgca cagatgtaac  65340
caagtcccct gctctcagca agccagtggc aggggatgga tgccctgtta gcaataacaa  65400
cattgttcct cctccttggc tccaggtaca tcatgggctt tatcagtaag gagcgggagc  65460
gggccatctt gagcactaag cctccaggca ccttcctgct aagattcagt gaaagcagca  65520
aagaaggagg cgtcactttc acttgggtgg agaaggacat cagcggtaag ggaggctccc  65580
acccacccca cctgctggtg gctgctgagg cctcatcact gcttctagtt gcaagcacct  65640
actgcccct ggtgggtgga gatggccttg actccctgtt tcactcagac tcgcaaaaca  65700
catttgcgtg acttctaaat ccttccagct gaaggattgg tttgctttgt tttgcttgct  65760
ccagtgacta tttgttgaga attttgcaat ttaaattgta ttcttcatct ctttttctac  65820
ttaaccctgt taatatatct tacgcaagta gttatattca agtttatttt ctatgaccca  65880
actagtagcc tcttcttaat tagaagccag cctgaatatt tccacagtgc caggccactg  65940
aacagggtgt tcagggtctc aacactaggg tggcttaagt cttttcccct tcgaggaaag  66000
aaaaaatggg cagttttctc tgagatgacc tagctgtagg ttccatgatc tttccttccc  66060
atgtcctgtg acaggtaaga cccagatcca gtccgtggaa ccatacacaa agcagcagct  66120
gaacaacatg tcatttgctg aaatcatcat gggctataag atcatggatg ctaccaatat  66180
```

cctggtgtct ccactggtct atctctatcc tgacattccc aaggaggagg cattcggaaa 66240
gtattgtcgg ccagagagcc aggagcatcc tgaagctgac ccaggtagtt gttgattttc 66300
catgttcctg gcatttaatt tttgggaaaa gttggaaatt ttgggatcct tggaggatag 66360
ataggcaaat gcctgaataa cctgggggat aattatttct ccttatggga aagaattgta 66420
gtgagtgctt ttgttggggt gaccgatggg atttgagagg agaatcagaa tcacttagag 66480
tagtgtagtt cctgctccac agagagtgca tgagtctaaa gaggggatac agcctgggca 66540
atatggtgaa acctcgtctc tacaaaaaat ccaaaaaaat tacccggtgt ggtggcacgc 66600
atttgtagtc gtagctactt gggaggctga ggtgggagga tcacctgagc caaggagttc 66660
aaggctgtag tgagcggtga tcatgccacc gcactccagc ctggctgata gagtgagata 66720
ctgtgtcaaa aaataaaaat aaagagggga tcaatacaca tacgtccccc aaaacatgcc 66780
tgaaacacga gaagggaaag tgagggcagt taacaggatg ccctgctggc acagtgcttc 66840
ttagtagatg ctagaaggtt tgaggcccag atttcagccc agcatatggc tttttgcctg 66900
taactgaacc atgtcagtgt gccagatggt ctgaagaaag ggtttctgga ggaaattatt 66960
attagctgca tgggagtatg gtttacacta gagtagaaga gctgggagca tcacgtttga 67020
aggggaagac agtgactggg tggaggggca agggattagt atttagagtg tgcaactatt 67080
gaaaataagg tatattttaa tgtgtaagag gacatgtact tatatgttat atataaatta 67140
ttttagctgg gtgaagtggc tcatgcctat agtcctagca ctttgggagg cccaggcggg 67200
aggatcactt gagcctggga gtttgagaac agcctagaca acatagtgag accctatcta 67260
tacaaaaata atttttttta aattagccac gtgtggtggt ttgtgcctgt agtcctagct 67320
actcgggagg ctgaggtggg aggattgctt aagcccagga ggttgaggct gcagtgagcc 67380
atgatcgcac cactgcactc cagcctgggt gacagagcaa gaccttgact caccaaaaaa 67440
aaaaaaaaaa aaaagagaga gaaattaaaa atactgtaat ctcagctggg catgggggtt 67500
cacacctgca gtcctagcac tttgggaggc tgaagcagga ggatcacttg aggccaggaa 67560
ctcaagacca gcctggcaac atagcaagac cccactacac acacacacac acacacacac 67620
aaagaagaga aagaaaaaaa cgaaacaaaa ctgtaatctc tgcagctgtc ctcagtgtgg 67680
agggggtagc cctgtctgtt ccccttcagc acttgctgtt ttgactctct gggttctttg 67740
tgcaggtctt gatggggagt ctctggtttg ccattctttg tttgatttaa ctttctgtaa 67800
tcataaagcc aatgatgggc tttttttttt tttttttttt tagactaagt cttgctctat 67860
cacccaagct ggagtgcagt ggcaccatct cggctcactg caacctccac ctcccggttc 67920
aagcaattct cctgcctcag cctcccgagt agctgggatt atgggcttgt gccaccatgc 67980
ccagctgatt tttgtatttt ttgtagagaa agggtttcgc catgttggcc aggctggcct 68040
cgaactcctg acctcaggtg atctgcccac ttcagcctcc caaagtgctg ggattacagg 68100
cgtgagccac tgtgcctggc ctaatgatgg gctctttaat gtgatccttt agggttggcg 68160
ccttgcccta gttgctgttg aaaaaactat ttttgtccaa atagcacaca cacagaaacc 68220
taccaacttc cctcccactt tttcctagga attccttctg agggatttct tgagatgggg 68280
cagaatgggg cttggaagag ggagttggag ctaattgacc gttgcctttc tcctttgttg 68340
gggtcctgag tcttgttcct gctgtaagag ttactcactt cctgtctgcc acctatctcc 68400
ctttgcatgt gtgcttcagt tgggagatct gtttatcagc ccctgccaca cggctctttg 68460
ttccttctgc agaggacgtt ggggtcccac ggctggtcct tttgactcat tttgctttca 68520
aggtcccacc tcccagtctg aggctgcatc ctccattacc atcgcccttc ctgtgggctg 68580
ggaggccagg tcctttcctg cccagcgatg tcagcgtttc ctcaggggcc aggcactcat 68640
caggagaaag gaactaatta cttgagtaat ttgccttgcc ttgctgagag gagtgtgccc 68700
tgagggactc catgtgagtg tggtgacggg tgtgggggtg tccctgtgtt attttaaaat 68760
gggtgccttc aggacgatga gcatgtgacc atttcctctc tatttccatc acaagagtat 68820
tatggtatga gggtctcagg ttagattatc ctcccaagac tcttctctct tccttctcta 68880
ctggaagccc acatagcatt tccttatggc ttgagggaga ggttcggagc cacttacaaa 68940
ttagataaag tacatttaca atcttgtaca aagccacaca atgaagtcat ttttctcagc 69000
ttttttttt ttttttttt tttttttgag cctgagtctc gctctatcgt ccagactgga 69060
gtgcagtggc gcgatcttgc ttcactgaaa cctctgcctc ccaggttcaa gagattctca 69120
tacctcagcc tcctgagtag ctgggattac agacatgcac cactatgcct ggctaatttt 69180
tggattttta gtagagaccg ggtttcaccc tgttggccag gctggtctcg aacccctgac 69240
ctcaagtgat cttcccgcct gggcctccca aagtgctggg attataggtg tgagccacag 69300
tgcccagcct tgtttttgtt tttgttttgt tttgacagtc tgtcactctg tcacccaggc 69360
tggagtgcag tggtgcgatc tcacctcact tcagcctctg cctcccaggt tcaagtgatt 69420
ctcctgtctc agcctcctga gtagctggga ttacaggcgt gccaccacgc ccagctattt 69480
ttgtaatttc attaaagaca gggtttcccc atgttggtga ggctggtctt gaactcctgg 69540
cctcaagtga tccacctgct tcagcctccc aaagtgcagg gattacaggc atgagccact 69600
gtgcctggcc tcagctatct tgaatgctgg agaattaaat ccttttctgt ctagggtgtc 69660
agctccctaa gggctgggcc aaaacagttg gatttataag acactagagt cttgcctcag 69720
tagctccttt gaattctgca ctgaattgat cagtttcttg gcccaaagta aactcagatg 69780
gcagcccaag agccactctg cagtgccttc tttcacatgg tcatcatgct ctctgatccc 69840
tcaggttctg tctaagcctc atgttttatg accgtgctgt tctcagccca cctcaccctg 69900
ccccatgcct tctcaatggt ttgttcacct gaattcccca gatttcatgc cagtatcccc 69960
aaggttcctt gacctcttgg tgtaagcatt cagcatctaa aattcatttt attcccgtca 70020
acgcatttct aactgtagaa caagaattat aaatgacaaa gctcatagaa aattggcacc 70080
ttgtcttccc cctccctctt attttataca taaaagagaa tatgggctgg gcattgtggc 70140
caaggctggg catgatagct catacttgta atccagcact ttgggagggt gaggcagatg 70200
gatcacctga ggtcaggagt tcaagaccag cctggccaac atggtgaaac ctcatctcta 70260
ctaaaattac aaaaaaaaaa ttagctaggc atggtggcag atgcctgtaa tccagctact 70320
caggaggctg atgaaggaga atcacttgaa ccctggaggc agaggttgta gagagccaag 70380
atggcgctac tgcactccaa cctgggcgaa agagagcaag actccgtctc aaaaaaaaaa 70440
aagacaaaaa ttagccaggc atggtggtgc cacctgtagt cccagctgct tgggagccta 70500
aggcaggaga atcgttttga cctgggagta ggaggttgcg gtaaccgaga ttgtgccact 70560
gcacttgagc ctgggcaaca gagtgagact ctgtctcaaa acaataagaa caacagcaac 70620
aaaagagaga gaccatgcct tgctccaggt ctcttagcta ttgaagatgt acctggaccc 70680
aggtctccgg tcttctagtt gaagcaattg tactgcctta caaagtcaca ttctctttgg 70740
tgctttttga ttgacgtatt tatccaacta gaaagttact catgccctca tccaaaaatg 70800
tggtagaggc cagattagtg ctggtaggaa taagagatat aacctttggc tttggaacca 70860
caagcattag cagtctccat gttctttaaa gacttggtga tattggtatt taggctggac 70920

-continued accatgcaaa gactacacag gctcggttcc tgcatgcaga gaagttatct aagagatatg 70980
accaggccgg aatagaatgc tcagaccacg tggaggctgt taaactttta cataatctag 71040
ggaaagaagg gacacaaggt ggcattagtc tagggtcagg tgggaaaagg ttatgctgaa 71100
aagtctctgc agctcaggac agctttgtgc aaagaactga agttcacagc tgctagtgcc 71160
tgggagatca aatagtataa atgagggcag acaaccctga ggggcagatg gagctttcca 71220
gacaatcttg gcatgaggat gagtgagttt caaatcagtc ctgccgaggc agatggcttc 71280
ctccagctct gcttactgaa tgcgaagtca cagtcagtaa gaaaactggt tttcttcttc 71340
ccaggcgctg ccccatacct gaagaccaag tttatctgtg tgacaccgta agtggcttcc 71400
tttccccgtt ttgccttcat ttctaatatc ctcagttatc cctgggaatg ggacactggg 71460
tgagagttaa tctgccaaag gttggaagcc cctgggctat gtttagtact caaagtgacc 71520
ttgtgtgttt aaaaagcttg agcttttatt tttctgttgg agaccagagt ttgatggctt 71580
gtgtgtgtgt gttttgttct tttttttttt tccattgtgt cttgtcaacc ccccgtttcc 71640
cctcctgctg ccccccattt cctacagaac gacctgcagc aataccattg acctgccgat 71700
gtccccccgc actttagatt cattgatgca gtttggaaat aatggtgaag gtgctgaacc 71760
ctcagcagga gggcagtttg gtgagtattt ggttgacaga ctttgtccct ataagggaag 71820
ttggtcccct ttgtgtgatg ctctcacatg tacacaccga gagctggtca ctcggaatgg 71880
taggagattc tagagctttg ctttccaaaa gagatggtat gaatgccaca tgtgtgagta 71940
taaatcttct agcagccaca ctggaaatag acgaacttaa tttttacaat atattttatt 72000
taacccacta aatccaacat actctcaatt taacatttca gaaaaagttg aggctgggtg 72060
agtggctcat gcctgtaatc ccagcacttt gggaggccga ggtgggtgga tcacttgagg 72120
tcaggagttc gagaccagtc tgaccaaaat ctctaaaata taaaaattag ctgggcatgg 72180
tggcgcatac ctgtaatccc agctactcaa gaagctgagg tgggaggatc gcttgagcct 72240
gggaggtgga ggttgcagtg agcagagatc gtgccactgc actccagcct gggcgacaga 72300
gtgagactcc atctcaaata aacaaaacta aactaaaaag aaaaagttga gaccttttttt 72360
tattcttttt tttcatacta agcctttaaa atccagtggg cttttgacag ccacagcaca 72420
gctcagtttg gacaaaccaa atctcaaatg cttggtggcc acgtgtgtct cggggctcct 72480
gaattaaaca gtagatcaag ggcagaagat ctcaggacag ccttagagct tctgtaaaca 72540
tggagctctg ggaatcagtt aaggtgggaa tgagaaagga cccttcccga ggcagggtcc 72600
tccagggagg agggtaaatc tggcttttct gaccatccct gggccttaag gggcaggaga 72660
ttggatagca gtggtagcct gggccctgtc ctctgaaggg ctgggggcgt ggcctgccag 72720
ttgcagaggg tggacaactg aactagtttt ccctgtctgt ccctccagag tccctcacct 72780
ttgacatgga gttgacctcg gagtgcgcta cctcccccat gtgaggagct gagaacggaa 72840
gctgcagaaa gatacgactg aggcgcctac ctgcattctg ccacccctca cacagccaaa 72900
ccccagatca tctgaaacta ctaactttgt ggttccagat ttttttaat ctcctacttc 72960
tgctatcttt gagcaatctg ggcactttta aaaatagaga aatgagtgaa tgtgggtgat 73020
ctgcttttat ctaaatgcaa ataaggatgt gttctctgag acccatgatc aggggatgtg 73080
gcggggggtg gctagaggga gaaaaaggaa atgtcttgtg ttgttttgtt cccctgccct 73140
cctttctcag cagctttttg ttattgttgt tgttgttctt agacaagtgc ctcctggtgc 73200
ctgcggcatc cttctgcctg tttctgtaag caaatgccac aggccaccta tagctacata 73260
ctcctggcat tgcacttttt aaccttgctg acatccaaat agaagatagg actatctaag 73320
ccctaggttt ctttttaaat taagaaataa taacaattaa agggcaaaaa acactgtatc 73380
agcatagcct ttctgtattt aagaaactta agcagccggg catggtggct cacgcctgta 73440
atcccagcac tttgggaggc cgaggcggat cataaggtca ggagatcaag accatcctgg 73500
ctaacacggt gaaaccccgt ctctactaaa agtacaaaaa attagctggg tgtggtggtg 73560
ggcgcctgta gtcccagcta ctcgggaggc tgaggcagga gaatcgcttg aacctgagag 73620
gcggaggttg cagtgagcca aaattgcacc actgcacact gcactccatc ctgggcgaca 73680
gtctgagact ctgtctcaaa aaaaaaaaaa aaaaaaagaa acttcagtta acagcctcct 73740
tggtgcttta agcattcagc ttccttcagg ctggtaattt atataatccc tgaaacgggc 73800
ttcaggtcaa acccttaaga catctgaagc tgcaacctgg cctttggtgt tgaaatagga 73860
aggtttaagg agaatctaag cattttagac ttttttttat aaatagactt attttccttt 73920
gtaatgtatt ggccttttag tgagtaaggc tgggcagagg gtgcttacaa ccttgactcc 73980
ctttctccct ggacttgatc tgctgtttca gaggctaggt tgtttctgtg ggtgccttat 74040
cagggctggg atacttctga ttctggcttc cttcctgccc caccctcccg accccagtcc 74100
ccctgatcct gctagaggca tgtctccttg cgtgtctaaa ggtccctcat cctgtttgtt 74160
ttaggaatcc tggtctcagg acctcatgga agaagagggg gagagagtta caggttggac 74220
atgatgcaca ctatggggcc ccagcgacgt gtctggttga gctcagggaa tatggttctt 74280
agccagtttc ttggtgatat ccagtggcac ttgtaatggc gtcttcattc agttcatgca 74340
gggcaaaggc ttactgataa acttgagtct gccctcgtat gagggtgtat acctggcctc 74400
cctctgaggc tggtgactcc tccctgctgg ggccccacag gtgaggcaga acagctagag 74460
ggcctccccg cctgcccgcc ttggctggct agctcgcctc tcctgtgcgt atgggaacac 74520
ctagcacgtg ctggatgggc tgcctctgac tcagaggcat ggccggattt ggcaactcaa 74580
aaccaccttg cctcagctga tcagagtttc tgtggaattc tgtttgttaa atcaaattag 74640
ctggtctctg aattaagggg gagacgacct tctctaagat gaacagggtt cgccccagtc 74700
ctcctgcctg gagacagttg atgtgtcatg cagagctctt acttctccag caacactctt 74760
cagtacataa taagcttaac tgataaacag aatatttaga aaggtgagac ttgggcttac 74820
cattgggttt aaatcatagg gacctagggc gagggttcag ggcttctctg gagcagatat 74880
tgtcaagttc atggccttag gtagcatgta tctggtctta actctgattg tagcaaaagt 74940
tctgagagga gctgagccct gttgtggccc attaaagaac agggtcctca ggccctgccc 75000
gcttcctgtc cactgccccc tccccatccc cagcccagcc gagggaatcc cgtgggttgc 75060
ttacctacct ataaggtggt ttataagctg ctgtcctggc cactgcattc aaattccaat 75120
gtgtacttca tagtgtaaaa atttatatta ttgtgaggtt ttttgtcttt tttttttttt 75180
tttttttttg gtatattgct gtatctactt taacttccag aaataaacgt tatataggaa 75240
ccgtc 75245

<210> SEQ ID NO 31
<211> LENGTH: 770
<212> TYPE: PRT
<213> ORGANISM: Artificial Sequence
<220> FEATURE:
<223> OTHER INFORMATION: STAT3 Amino Acid Sequence

<400> SEQUENCE: 31

Met Ala Gln Trp Asn Gln Leu Gln Gln Leu Asp Thr Arg Tyr Leu Glu
1 5 10 15

```
Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430
```

```
Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770
```

<210> SEQ ID NO 32
<211> LENGTH: 4953
<212> TYPE: DNA
<213> ORGANISM: Artificial Sequence
<220> FEATURE:
<223> OTHER INFORMATION: STAT3 mRNA NM_003150.3

<400> SEQUENCE: 32

```
ggtttccgga gctgcggcgg cgcagactgg gagggggagc cgggggttcc gacgtcgcag      60

ccgagggaac aagccccaac cggatcctgg acaggcaccc cggcttggcg ctgtctctcc     120
```

```
ccctcggctc ggagaggccc ttcggcctga gggagcctcg ccgcccgtcc ccggcacacg    180
cgcagccccg gcctctcggc ctctgccgga gaaacaggat ggcccaatgg aatcagctac    240
agcagcttga cacacggtac ctggagcagc tccatcagct ctacagtgac agcttcccaa    300
tggagctgcg gcagtttctg gccccttgga ttgagagtca agattgggca tatgcggcca    360
gcaaagaatc acatgccact ttggtgtttc ataatctcct gggagagatt gaccagcagt    420
atagccgctt cctgcaagag tcgaatgttc tctatcagca caatctacga agaatcaagc    480
agtttcttca gagcaggtat cttgagaagc caatggagat tgcccggatt gtggcccggt    540
gcctgtggga agaatcacgc cttctacaga ctgcagccac tgcggcccag caagggggcc    600
aggccaacca ccccacagca gccgtggtga cggagaagca gcagatgctg gagcagcacc    660
ttcaggatgt ccggaagaga gtgcaggatc tagaacagaa aatgaaagtg gtagagaatc    720
tccaggatga ctttgatttc aactataaaa ccctcaagag tcaaggagac atgcaagatc    780
tgaatggaaa caaccagtca gtgaccaggc agaagatgca gcagctggaa cagatgctca    840
ctgcgctgga ccagatgcgg agaagcatcg tgagtgagct ggcggggctt ttgtcagcga    900
tggagtacgt gcagaaaact ctcacggacg aggagctggc tgactggaag aggcggcaac    960
agattgcctg cattggaggc ccgcccaaca tctgcctaga tcggctagaa aactggataa   1020
cgtcattagc agaatctcaa cttcagaccc gtcaacaaat taagaaactg gaggagttgc   1080
agcaaaaagt ttcctacaaa ggggacccca ttgtacagca ccggccgatg ctggaggaga   1140
gaatcgtgga gctgtttaga aacttaatga aaagtgcctt tgtggtggag cggcagccct   1200
gcatgcccat gcatcctgac cggcccctcg tcatcaagac cggcgtccag ttcactacta   1260
aagtcaggtt gctggtcaaa ttccctgagt tgaattatca gcttaaaatt aaagtgtgca   1320
ttgacaaaga ctctggggac gttgcagctc tcagaggatc ccggaaattt aacattctgg   1380
gcacaaacac aaaagtgatg aacatggaag aatccaacaa cggcagcctc tctgcagaat   1440
tcaaacactt gaccctgagg gagcagagat gtgggaatgg gggccgagcc aattgtgatg   1500
cttccctgat tgtgactgag gagctgcacc tgatcacctt tgagaccgag gtgtatcacc   1560
aaggcctcaa gattgaccta gagacccact ccttgccagt tgtggtgatc tccaacatct   1620
gtcagatgcc aaatgcctgg gcgtccatcc tgtggtacaa catgctgacc aacaatccca   1680
agaatgtaaa ctttttttacc aagcccccaa ttggaacctg ggatcaagtg gccgaggtcc   1740
tgagctggca gttctcctcc accaccaagc gaggactgag catcgagcag ctgactacac   1800
tggcagagaa actcttggga cctggtgtga attattcagg gtgtcagatc acatgggcta   1860
aattttgcaa agaaaacatg gctggcaagg gcttctcctt ctgggtctgg ctggacaata   1920
tcattgacct tgtgaaaaag tacatcctgg ccctttggaa cgaagggtac atcatgggct   1980
ttatcagtaa ggagcgggag cgggccatct tgagcactaa gcctccaggc accttcctgc   2040
taagattcag tgaaagcagc aaagaaggag gcgtcacttt cacttgggtg gagaaggaca   2100
tcagcggtaa gacccagatc cagtccgtgg aaccatacac aaagcagcag ctgaacaaca   2160
tgtcatttgc tgaaatcatc atgggctata agatcatgga tgctaccaat atcctggtgt   2220
ctccactggt ctatctctat cctgacattc ccaaggagga ggcattcgga aagtattgtc   2280
ggccagagag ccaggagcat cctgaagctg acccaggcgc tgccccatac ctgaagacca   2340
agtttatctg tgtgacacca acgacctgca gcaataccat tgacctgccg atgtcccccc   2400
gcactttaga ttcattgatg cagtttggaa ataatggtga aggtgctgaa ccctcagcag   2460
```

-continued gagggcagtt tgagtccctc acctttgaca tggagttgac ctcggagtgc gctacctccc 2520
ccatgtgagg agctgagaac ggaagctgca gaaagatacg actgaggcgc ctacctgcat 2580
tctgccaccc ctcacacagc caaaccccag atcatctgaa actactaact ttgtggttcc 2640
agattttttt taatctccta cttctgctat ctttgagcaa tctgggcact tttaaaaata 2700
gagaaatgag tgaatgtggg tgatctgctt ttatctaaat gcaaataagg atgtgttctc 2760
tgagacccat gatcagggga tgtggcgggg ggtggctaga gggagaaaaa ggaaatgtct 2820
tgtgttgttt tgttcccctg ccctcctttc tcagcagctt tttgttattg ttgttgttgt 2880
tcttagacaa gtgcctcctg gtgcctgcgg catccttctg cctgtttctg taagcaaatg 2940
ccacaggcca cctatagcta catactcctg gcattgcact ttttaacctt gctgacatcc 3000
aaatagaaga taggactatc taagccctag gtttcttttt aaattaagaa ataataacaa 3060
ttaaagggca aaaaacactg tatcagcata gcctttctgt atttaagaaa cttaagcagc 3120
cgggcatggt ggctcacgcc tgtaatccca gcactttggg aggccgaggc ggatcataag 3180
gtcaggagat caagaccatc ctggctaaca cggtgaaacc ccgtctctac taaaagtaca 3240
aaaaattagc tgggtgtggt ggtgggcgcc tgtagtccca gctactcggg aggctgaggc 3300
aggagaatcg cttgaacctg agaggcggag gttgcagtga gccaaaattg caccactgca 3360
cactgcactc catcctgggc gacagtctga gactctgtct caaaaaaaaa aaaaaaaaaa 3420
agaaacttca gttaacagcc tccttggtgc tttaagcatt cagcttcctt caggctggta 3480
atttatataa tccctgaaac gggcttcagg tcaaaccctt aagacatctg aagctgcaac 3540
ctggcctttg gtgttgaaat aggaaggttt aaggagaatc taagcatttt agactttttt 3600
ttataaatag acttattttc ctttgtaatg tattggcctt ttagtgagta aggctgggca 3660
gagggtgctt acaaccttga ctccctttct ccctggactt gatctgctgt ttcagaggct 3720
aggttgtttc tgtgggtgcc ttatcagggc tgggatactt ctgattctgg cttccttcct 3780
gccccaccct cccgacccca gtccccctga tcctgctaga ggcatgtctc cttgcgtgtc 3840
taaaggtccc tcatcctgtt tgttttagga atcctggtct caggacctca tggaagaaga 3900
gggggagaga gttacaggtt ggacatgatg cacactatgg ggccccagcg acgtgtctgg 3960
ttgagctcag ggaatatggt tcttagccag tttcttggtg atatccagtg gcacttgtaa 4020
tggcgtcttc attcagttca tgcagggcaa aggcttactg ataaacttga gtctgccctc 4080
gtatgagggt gtatacctgg cctccctctg aggctggtga ctcctccctg ctggggcccc 4140
acaggtgagg cagaacagct agagggcctc cccgcctgcc cgccttggct ggctagctcg 4200
cctctcctgt gcgtatggga acacctagca cgtgctggat gggctgcctc tgactcagag 4260
gcatggccgg atttggcaac tcaaaaccac cttgcctcag ctgatcagag tttctgtgga 4320
attctgtttg ttaaatcaaa ttagctggtc tctgaattaa gggggagacg accttctcta 4380
agatgaacag ggttcgcccc agtcctcctg cctggagaca gttgatgtgt catgcagagc 4440
tcttacttct ccagcaacac tcttcagtac ataataagct taactgataa acagaatatt 4500
tagaaaggtg agacttgggc ttaccattgg gtttaaatca tagggaccta gggcgagggt 4560
tcagggcttc tctggagcag atattgtcaa gttcatggcc ttaggtagca tgtatctggt 4620
cttaactctg attgtagcaa aagttctgag aggagctgag ccctgttgtg gcccattaaa 4680
gaacagggtc ctcaggccct gcccgcttcc tgtccactgc cccctcccca tccccagccc 4740
agccgaggga atcccgtggg ttgcttacct acctataagg tggtttataa gctgctgtcc 4800
tggccactgc attcaaattc caatgtgtac ttcatagtgt aaaaatttat attattgtga 4860
ggttttttgt cttttttttt tttttttttt tttggtatat tgctgtatct actttaactt 4920
ccagaaataa acgttatata ggaaccgtaa aaa 4953

<210> SEQ ID NO 33
<211> LENGTH: 32729
<212> TYPE: DNA
<213> ORGANISM: Artificial Sequence
<220> FEATURE:
<223> OTHER INFORMATION: Genomic Sequence

<400> SEQUENCE: 33
ttttttaaaa ttaagaaaag gaatcaattt aattaaatac caaaaagttt tacatattcc 60
tgaattttca accagctaca aaaagcatgg atttttctta ttagaaaaca aaactgttac 120
aaaaaattta aataaataaa tagctgccat aaaatttcaa cataatatat agtcaactag 180
ttctgtgtta tggtcagtta atagaaagat agcgggaatg atgatatgag caaaagtaaa 240
cagaacaaag aagaaaaaag ataggaaaaa gaaagttaga cagagaagag aaaaataaag 300
aaagtgcttt attgaatgag ctaattacat gaggtcacca agaggaacat cctctaactg 360
aggcgctgtg atgacaacaa cacccgatgc tgtcattgtc ctggtgtctt cctcaccctg 420
gcgtaaagga gatgcccaag ctctgcacag gaaggcatcg tcggcaagct ctcttctccg 480
acactccacc ggaaggatca cagagctgtg gtcttggcct ggatggatcg cagctctctc 540
cacctgaggg cccccagctg gagggaccgg agaacactgg cgtctggcag ccccgtttcc 600
actcctacca agaaggctca aagacgacgg tcagctcagg cttttcttct tgaagtgttt 660
ctaacgcact tttgtctcca taattgaaat acatttcaga caacctgtaa aagcaaatag 720
aaagcctggg ttgcactctt cagataactc tgtcagagtc gttaacctta aaagtctcat 780
ctcttcattt ccctaaactc cacacacttc taaaatgtaa aaaaaaaaaa aaaaaaaaaa 840
gagggaccac aactcccaga gtgctccgcg tcctcgccgc cgtcgccgcc gccgagacca 900
agatggccgc gagactccgc accttcttca agaatgcctg ggccaaggag ccggtgctcg 960
tcgtgtcctt cgtcactggg agcctcagac cccaggacc ccagcctgga gtggctgaag 1020
aaactgtgag cacctccaat gacagaggag gcccctccca cggctcccaa taaaaatgtg 1080
gggaaaaaaa aaaaaaagct ctaagtgccc aatgtggttc ctgttatatt tttaactatc 1140
tagttgggaa aatgttaagc atacataaaa gtatagaaaa tagtataatg aacccccctgt 1200 gtccattacc caagttcgac aattaaacag gtcatgtcaa cttgtttctt ctattgccca 1260
cccactcctc ccacccatgg attattttaa atactgcatt taatgcatct atcaataatt 1320
cactttgtga cactaaaata taattacaat gtcactatca caccaaaatc gtttaacaat 1380
aatttcttag tatcactgta tgtccagtca gcatttacgc ttcctcaact gtcttgtaaa 1440 ttttttttacc ttatgttcat ttagtcacta acctgatcaa ttctacacat tgcatttgcc 1500
caggatgcct ctcacatctt cgatgtaagt tcttcctcct ctttaataaa gtttcccttg 1560
caacttaact aataaatcca cccatttgtc ctgcaccatt tataaccatc tcaatttggt 1620
ggtgttatat actgaatgtt tgtcttcctt aacaattccc atgatgaagc ccgaacccct 1680
aatgtacggt acttaaaggt gaggcccttg ggaagtagtt agagttagat gaagttgtga 1740
gggtggggcc ctcagtatgg ggtgagtgcc cttacaggag agatatcaga gagtttgttc 1800
tttctcccct gtcttctctc ccttgcctcc cctccctcca tgcaatcaca taacaagaag 1860
gtagccatct gcaaatcagg aagaggactc tcgccagcaa ccaaattcat cagagacttg 1920

-continued

```
atttggact ttctagcctc cagtattgtg agataataaa tctgtgtttg agtcacacag   1980
tctaaagcag cttgttatcg cagcctgaga aaacgggttg attgcattca tggattcttc   2040
aatctatttt gagcctgtcc ctcagcctgg gtccagaatg tccctcaggg ctaggtcagt   2100
gatgctacat gtagcagtgt ccccagcttt gacctgacca atcctttgtt tgttccccca   2160
tctctcttag ctctgggaat attggcttgt cctgcagcaa atgtgctcca ttatgttggc   2220
acaaggatgc aaggctgatt caaacttgta tttattcaaa cctgcattcc aacaagttct   2280
cagccttgag atcattaata tggacagaag tccctggact aatggaattt atattttggg   2340
agcagagata gataataaat aaacaagaaa atgacatagc acataagatg tgctacactg   2400
cagaggagaa tgagaagaga agaaaaagtg cttctatttt cagtagaata gtcaaagaca   2460
gcctcgcaga gaagaccttt aagcagagaa tttaggaagg tacagggaat aatgcaggtg   2520
gatactgaag ggagagagt tctaggccag aagaaaagca agtgcaaaaa tccagagatg   2580
acagtgttct tgcaaaacag caaggagatc actgtactgg ggcagaataa gcaagggttg   2640
ggagaagcgg aatcttcgga agcaggagag gctggattat gtggggcatg gaagccacca   2700
tgagtttgtt gctctgatta tgaaagtgat aagaagacga tgttgacaag agtgatatga   2760
tgcgagttac gttttagctg aatcccttgt ctgctaaaat cagaataaca gatgcagggt   2820
gacctgtcag aatgccacca tgacaatcca gacaccaggt gatggtggct tgagccaagg   2880
aagaagccgt gaagctggcc tgaagtggtc agggagtggc caagctggga aggcagagct   2940
cacaggatgt gctgacacat tggacatgat tataaggaaa aagagacagt gacgacagaa   3000
ccagaaatgt tttggcccga gcaacttgga ggaagtgacc atcgactgaa atggggaaga   3060
atcaggtttc gggtagaaga gagtagcaag ggtgtggatc tagatgtgac gtttgagagg   3120
tttattaaac cttcaagaag aaagatcagc caagcacgga gacacagaat ttatggacat   3180
ataatctgga ggccacagca cacatatcat gaagccagaa gaccagataa tttaaatgag   3240
ggagaaagtg tagggaagaa aaattagccc agcgactaag ctctgaggat tcaacacata   3300
agggtcagga tgatgaagaa gaggccagaa aggagactga gtagaaggat ctgatgaaat   3360
aggagaaaac ccaggagagc atgttggcct taaagccaag cagtgaaaac gtcttcaggg   3420
aaaagtgcaa tcatcacggc tgacagaacc gtgggactcg ccaggaagct cttgctagag   3480
aggagacgac tacctcagta gtatcacaga ggtgggctgg caatatcctg acacactgtc   3540
gaatttcgtg taatttccca tcttgctatt cctggagcac tcttttccca tttagaaatc   3600
ctcagaaacc gccaggcacg gaggctcaca cctgtaatcc cagcacttgg ggaggccgag   3660
gcaggcagat cacgaggtca ggagatggag accatcctgg ctaacacagt gaaaccccaa   3720
ctctactaaa aatacaaaaa attagccggg tgtggtggca ggcgcctgtg gtcccagcta   3780
cttgggaggc cgaggcagga gaatggcgtg aacccgggag gcggagcttg cagtgagccg   3840
agatcatgcc actgcactcc agcctgggcg acagagcaag actctgtctc aaggaaaaaa   3900
aaaataaatc ctcagaaaca aaacaacaag atccccacta tgtaaagacc cttccaattt   3960
ggatgaccca tagacgagtt ctacgaagtt cggttccttg tgtagaacag aatcctcctt   4020
ggccatgatc gcatgagggc ttgtgtttct ttggggaatg tgggtgaaat ccagcttagc   4080
cttggtgatt ctaaccatct cagtgaagtg gaatgtgtag tttaacccca tattctctat   4140
tttaaaatat ccaccacaac tgacccaggc ccaacctaat cttgagtggc tgcaaatgaa   4200
gcgagagcca tcctggattt tgataacagt caacgtttcc tgagaactca gagtcccacc   4260
acgggcatct ctgcagagca cactcacccc aggttctgca ggaggcagct ctgctgtttc   4320
```

-continued agcacttcac agaacatcat gacccccagg tcgcccaggt cattgttgcc caggctcagc 4380
tttcgcaggc tctggctgga ggtcagaagt gtggaaagat cccagcagca gtgtgacgtg 4440
aggttgcagt tgtctaatct gcaaaaaggg ggtgatttaa agaaaatgtc cccttaacca 4500
tccccctagc tccccaagat tttagcatct tagcctgtct tgtttcaggt ggaaaaaaaa 4560
aaagcacagg agcacaggac taactagctt caagcagcct tgtatgctgg taattattct 4620
tctctctctt tttcaaatcc actgcattgc acagatcaaa ttagtaacag tggtttgttc 4680
attgatttac caaattctgt gcctttccct acatttccat aaaatgtaag tgtcatactg 4740
ccctccttgt tttgtggtac agaaaactgt gatggtaagg actcaagttc ctacatctat 4800
atcatctgga aggactcctc ccagtcccat gatcctgtaa caaggcaaac actaagaaga 4860
cacctcactt ctaagataca gattatcttg tggccactct gcctaaacgt ccctccaccc 4920
ttggccacca tgtgttctca ttgctgtaat aaaccaaagg acttactcca acacctgaag 4980
cttgcagtcg gggtgcaaga gtccctcaca gagtagtttg atccccttgt ctccgagagt 5040
gttgcctcgc aggtaaaggt gcgtgagatt ctgattagtg ctgagtaccg aggacaaagc 5100
tgaacaacag actgacgtaa ggccagaatt caccaacctg tagaaggaca gggagaagag 5160
tcctcagtac ccagctgttc cccaacattg tgcagctgct ttgactcagt gcctcgtcct 5220
ctctcagcag ctgcagcctt cagctcagag agcaggagcc agcatctcag atatgatctg 5280
gggagagcaa gacctgctgt ctctggctgt cacaggagac acaaatgatg tctcagcaga 5340
tgctttgctg tatgagtccg acagaaagag ccaaggcaaa ctgagccagt taccccatac 5400
tcctcctcct cctcacacag ctttcctccg gccaggagtg ctcctcagca ccacttcttc 5460
cagaaacaca tcccagtggt tatcctcaac taataatccc cgtaacactg cagacaccca 5520
cactgcaggg gccttttttt ttttttttaa gagagacagg aaaaaaaaat cctcctcatg 5580
ggaagtcggt gctgatttaa acatcaaaga caacaggtga acgtccattg tgaccttcta 5640
agctgtagct agggctgtga caggaacacg gcggggccct tagcaattgc cacctcccgc 5700
cttcctgcgc ccccaaatgc ccctttcaca tctttctcgc tgcagccctc aaccacgttg 5760
gagaggtggg aggatcgctt gagtccagga agtcgaggct gcagtgagcc atgattgcgc 5820
tgccacactc tagcctgggt gacagagtga gaccctgcct aaataaataa ataaataagg 5880
ccaggtgcag tggcttatgc ctgtaatccc agcactttgg gaggtccagc actttgggag 5940
ggtggatcac gaggtcagga gttcaaaacc agcctggcca acatggtgaa agcccatctc 6000
tactaaaaat ataaaaatta gttagggtgg tggtgggcac ctgtaatccc agctacttgg 6060
gaggctgagg caggagaatt gcttgaacct gggaggcaga ggttgcagtg agccgagatt 6120
gccactgcac ttcaacctgg gcaacaaagt gagactctgt ctcaaaaata aataaataaa 6180
tagaaaaagc caggctcttg ctcagtcacc caggccaagt gcacagctca ctgcagtctt 6240
aaactcctgg gctcagacaa tccacccacc ttggcctccc aaagtgctgg gattacaggc 6300
atgagccact gtgcctgacc cagagaccag tcttatttga ttattatatc aacctggcaa 6360
ggaaggagtg cagctaaaac tattacatac attttacata ttagaaatct aaggcttata 6420
aaaattacat gtttctctca aggccacaga gcaggtgtgt ggtggggagg gatccagacc 6480
tggactttcc accttttagt ctcatcttct ccccactgcc ctttctgtcc acctctctct 6540
tccttctgca cagcaaaagg ccttttagag cataaaaccc caaaaatgca tcaatctcga 6600
tggaattaag agttttgatg tactattctt gagtcaaatt aagcccattc tatcacccag 6660

-continued gaagagcata agagctctaa aatcactggt ggcgtaattc ctaggagcac agatgcttct 6720
attccatgaa gccaggaata gcgcaggtga ttgcctcctt cctgccagag tccttggcaa 6780
tggcatgttt tttaagctct ttggtgtcta cgaggcagga aaaatagaaa tacagaaaaa 6840
gtgtattcag acagtaaagc atgaacagat gaccagcagg aaaaagtgat tatccatcca 6900
ctggtttcta tcttcccaat taaggaagag tcaaactgaa aagacacagt aagtaagact 6960
aataggcaaa tgaagcccaa gagagacaga caaaaacaaa gcaagttttg agtggcttct 7020
actaagctct catccccggt aagaattcta tcagagggtt gttgttaatt aacatgcaga 7080
agggattagt agcattcctg gcaaaggcca gggacattct agtagaatgg ggatggtctt 7140
caaagaggaa aagagaaaat attttttaaa ttatgtaatt aaagttatgc aggctttacc 7200
actatttcca aaaaggagta gaatggatta ttcaacagat gtttggggag cactacacag 7260
tagtagtaga aattgcaaca gacggtgcag ttttgttaag aaaacgtcat atccaaattg 7320
tgaaaatgct ggtaactatt aagcaacggt tacactgaac acataataaa atgtttaaag 7380
aatcaaacaa ccatgtccca ccaaccaatc cttggattag aggaatgtga ttgacatctc 7440
gatttcaacc aatccaccta actgagctct acatttacca agcacggata tcttgccatg 7500
tactgtatta agttaattgg ttggggattt ttatttatta actacctgcc tatgtcacaa 7560
aactgtctca taatgaaaac tgaatcccag tgctttggga ggccaaggtg ggaggaccac 7620
ttgaggccag gagtttgaga ccagcctggg caacatagca agaccctgtc tctacataaa 7680
aaattttaaa cattttaaac attacccagg catggtagta cacacctgta gtcctagcta 7740
gtcagaaggc tgaggcagga agattgcttg agcccaggag agttcaaggc tacagtgagc 7800
tatgatccta ccactgcact ccagtctgag ccacagagca aaaccctgtc ttaaaaaaag 7860
aaaagaaaag aaaggaaaat aaggaaagga aaggggaaag ggaaaggggg gggggagggg 7920
aagggaaggg agaaagagaa agaaagaaag agagagagag agaaagaaag aaagaaagag 7980
aaaaagaaaa agagagaaag aaaggaggag gaggaagaag gaaggaagga aggaaggaat 8040
ctgaagaaga agatcaaaca ttttttgagt atttattgtg tgcttgacat ggatgacgac 8100
tttaaacagg gttatctcat tgaatgatca caacctcaag atgggaatgt tagttttatc 8160
cctgctttta aatggacaaa atgaggatca cagtaattaa aaaataagta ggagcttctt 8220
agatggatag tagaaagtgg gaaagtgggg gtaaccttcc aggcaaaagg aaaagagtag 8280
caagaataag gaagattaaa agaaccacca agatgtttca aaactaattc atagctgggc 8340
acagtgatgt ccacctatag tcccagctac ttgggcggct gagacgggag gattgcttga 8400
gcccaggagt gcagatgaga tcaggcactc tgggtggtat ggctgtagat gaacccagga 8460
attcaaattc agcctgagca tcatagcaag tccccatctc taaaacagca aaacaaaact 8520
catccaatat gactcaaaat ggagtgcaag gtatggcagg agagagggca gtatcaggga 8580
cagccttgtg tgccaagcta agatgtcact ctgactgcag agaagaactt ttgaagattt 8640
ttgaacaaag ggtcaatatt ttcaaatttg catcttaaaa agttccctct ggtgtagtga 8700
tgagtggtag agggaaccga aagcagagca tttaggaccg tcccccgttt actcactcag 8760
cagcctcctg gaaagcccca ctattcaatg aggcaggagg aagagggcag gagcaggtca 8820
gagaacgggg gtggaaggtg gggtatgata attaaaccaa tgttgcaaat gctcagcatg 8880
tgtgaccctt gagcagtatt gagacaggca gtacacaata tgcagccaga gatgaggacc 8940
caaagttcga gagaaaaaaa tgtagctata cctaacacat aggctatacc taacacatag 9000
gctataccta acacgtaggc tatacctaac ccataggcta tacctaacac acaggctatg 9060

```
cctaacccat aggctatacc taacacacag ccacatgtat ggctgtacct aacacataaa   9120
atgcataaaa gtctcgactg attaatgcca cttatagata cctatctcaa agcaaataca   9180
catgcataaa actatatata caaatgtgct ttttgcagag ttgtttgtaa tagtggaaaa   9240
gaacagttat cccaaaatgc atgatttgat taaataaatt atggtaaagc acactatggg   9300
atattatgcc ccaatcgata gatctacaca aatcagcatg gaaatttatc catgataaat   9360
gaaaaaagga tatcacagaa aaatatttat attatggttc tagtttcaat agatagggtg   9420
ttatggattg aattgtttcc tctaagactt tatatgtgga agtcctaggc cccagtactt   9480
cagattgtga ccttatttgg tgatacggtt actgaaaatg taattagtta agatcaggtc   9540
gttacaaatc taacatgact tgtgttcttt cacagggaaa cttgggacat ggagaaagac   9600
acacacagac acagggaaga caccacgtag agataaaggc aatggtgtgg cagaggcatc   9660
tacaggtcaa ggaatggcaa aatgtgtcag caagatgaca ttccaccaga agccaaagag   9720
aagcatgaac agattcccca cagccctcag aaggacccag cctgctagca tcttaatctc   9780
acacttctgg cctccagaac tgagggacaa taaatttctg ttgtttaagc tgctctgttt   9840
gtgatacttt attacagtag ctctaacaga ctaggcattt aaaatactac ataacaatgt   9900
attacaaatg caacatgaaa atcacatagg tcttcattca cattactgat ataaatacca   9960
cccagatcag catatacagg aaatccattt gtccataatt agcaaccaat atatgttcac  10020
aaagctctga tactcccttg gatggattga tggatggatg gatggatgga tggatggatg  10080
gatggatgga ttgacggatg gaaaatagag ggatggatga tggatggatg gatggatgga  10140
cagatgaatg gattatataa caatctattg tattaaaaaa agtctggatg gttgttcatc  10200
agactattgt aaatggctct ctcagaagag ggctgagaag gagctttcac tttccacttt  10260
gtctgtacta tgatatgttt acaccaagca tgtgttactt ttctaataaa aagtttgtga  10320
atgatatctg ggtttgagac ctactgttgt tgaaattgag aggtatatga gaattctcag  10380
ggagtttaga aatatttagt aacaacaaca acaaaaaagg taaaccaggc gggtgtgtgg  10440
ctcacgcctg taatcccaac actttgggag gccaaggcag gcagatcacc tgaggtcaga  10500
aattcgagac cagcctggca aacatggtga aaccccgtat ctactaaaaa tacaaaaatt  10560
agccaggcat ggcagtgcac acctgtagtc cctgctactc agaaggctga ggcagaagaa  10620
ttgttggaac ccgggaggca gaggttgcag tgagccaaga ttgcgccact gcattttagc  10680
ctgggtgaca gagtaagact ccaactcaaa aaaaaaaaaa aaaaaaaaaa cacaactaaa  10740
ccagtcgtga aatccccaga ccacaggaag agaagccaat gcaggatcca gggaggggga  10800
agctataaca ttagcaggaa agactaagta gtgacctaaa aataagagcg aagaaggctt  10860
ccaaagagga agagtgaaat gaattaaagg cagcagatgt caactaaagt aaggactggg  10920
aaggacctgt acgacctata aggacccagc ctgctgatgc ctcagtctca gactttggcc  10980
tcctgaactg agaggcaata aactcttgtt gtttaggccg ctctgtttgt gatactttat  11040
tacagcagct ctaccaggtt aggtattgac aatagtaact acatagagca tattacagat  11100
gcatcaggca catttgtaat tggcttgttt gtcatgtgga atttggaacc aggatcactg  11160
agagtcacct gagtgcctac gcctgggcct cttcggttcc atctgctttg cctggagggc  11220
tcttccggct ccttcacagc ccatcccacg cttcactgag cacctgctcc aatgtcaccc  11280
gctcggagag gcactcgcca aacgtgagca gagaagcacc cctcgccgtc actccagttt  11340
ttcttatagc tcttatacac agggtatatt gtttagcatg tctattatct gttatcactt  11400
```

ccctaaaaga acggttgtga aaacaggatt ttggtctgtt ttactcactg ctgctgtcag 11460
tgcccaccac agagccccca gagggcctgc aaaatgaagg gacaaaatca tgtctgttga 11520
acaaacttag agaagcagaa gtcaaattgc caaggaagag taatattcta aggcgatttg 11580
ctaaggaagg gtaataccct aaggcgagga aatgaaggca ctgcaggaag acttcataga 11640
aagagatatg gtcacatctg aggattggct gatgggagag gtccaaggaa gtatcagagc 11700
tttgtgaaca gaggttggtt gttaattatg gattagtgga ttactcctct gggaagacct 11760
ttcctgccaa attttgtctt gaatgctgat ctggctggta tatatattaa taatgtgaat 11820
gaatgaagac ctatccaatt tgcttattgt atttgtagat attattgtca gaatgaagat 11880
tcaaaactgc ctagtcaatg ggtcaaaaga caggtaagat gaggtttagc aaagctaaat 11940
tggaggtccc acccttaagc tgagagccag atgaagaagc cctgtagaga gcccattagc 12000
aacatctcct aaggcaatgc actgggaatt aaggcagtgg cttgggaggt cacagacgtt 12060
tgtctacact gagttccact accttctctc tgagtgtcct tggacaaagt tatgaggctc 12120
cctgaatttt attttctcct ctttaaattg gagacacaga taccctaccc tatagcatct 12180
ttctgaagcc aactgagaaa atccatgtaa gaacatgaaa gagcaggtga tacagggaaa 12240
gtgatacagg aaagtggtac agggaaagtg catgattatt agtgggtatt ccctactact 12300
gtttactgca gaattccaac atgaatcaaa aggcttatgt aactgccaaa aaaaacaagg 12360
aaatcagaga ttccaccagt gaaaccatag ttctctgcaa caggaggtaa aacatccacc 12420
atgcatcatc aggtctgggc accacatttc aaagacagac actaacaaac cagcctgtgt 12480
acctgggaga gcatggctac ataggtgaag gtgctgagcc atgacactgt tgaggatata 12540
gaggctgcag tgtaagagtc ctctcctagt gtagaggctg cagggtgaga gctctttcct 12600
agtgtagagg ctgcatgcac tatgcgataa cttgcatgct tgcaagcatg cacacataaa 12660
atgggtgact attcatgtga gtgtcttgga agcaagtttt tccctcaaca ggcaattggg 12720
ctgcaccatc tctaaggttt cttccaacac taagaaactc tagttctata atcataaatt 12780
agcataaatt atcttattag cagcagtata cattatatgc ctccagtcct tcaaagcatt 12840
tctgatgttt ttacctcctt actctacctt cagctctgcc tgaccaaagt aaccccccatc 12900
cacattttcc aaataattca cctctgaaaa gaagttactt ttctggtaag acacccatga 12960
agacttaccc cagtttctgc aggttacact gtggattctt ggctttttca cataaaattg 13020
cgactcctga gtctcccaag gcattctccc ccacatagag tctggtcagg gaatggctgg 13080
tgctcaatac tgatgcaaga tcctgacaac atgctgatgt gaggcagcag ctgaccaacc 13140
ttccatagag atggcagaat gtcagtcatg tctctcaccc acgctccacc atggacaagg 13200
aagcacccgt acctgccact gcctctactc cagtttacac atggaaaggg agtggacaca 13260
agctctatgt acacttctga tttccttttc catttggtgg aataacaagt aagcattctc 13320
caagctccca ccaatactac atcttcccag ctccctacat tcagctttat tgtggtaaaa 13380
tacgtgtaaa ataaaattta ccattttaac catttttaag tgcacaatta atggccttaa 13440
gcacttcaca ttgttgtgca accatcacca ccaccatctc cagaactcct ttcatcttgc 13500
agaactgaaa ctccataacc attaaacaat gtcttcccac tctccgccct cccattgcct 13560
gcaaccacgt ttcttcctgt ctctatgaat ctgtctgttc tagacacctc ctataaggac 13620
aatcagagta tttgcccttt cgagtctagc ttatcttact tagcataatg tccccgaggc 13680
tcatccatgt tgtagtgtgt actagaattc tttttaaagc tgaatgtaca tatatagcac 13740
ttttcaacac ccttcatccg ttgaaggacg tttggttatt tccacctttt ggctatttct 13800
aatagtgttg ctatggacat agatgtacaa ataacatgtt tgagttcctg ccttctgttt 13860
tttttaatgc ttcctctgtc acccaggcgg gagtacagtg acgggatctt gactcactgc 13920
aacccccgcc tcccaggttc aaaagattct cttgcctcca ccccgagtaa ctgggattac 13980
aggcatgcac caccatgcct ggctaatttt tgtattttta gtagagacaa ggttttacta 14040
tgatggccag gctagtctcg aactcccgac ctccagtgat ccacctgcct cagcctccca 14100
aaatgctggg attacaggtg tgagccaccg ctcctggctg agttcctgct ttgaactctt 14160
ttgcagatat acccagcagt ggaaatgctg gctccagtag taattctgta tttatttttt 14220
aggaattgct gtgctgtttt ccatagtggc tgcatcattt acattcccac cagcaacaca 14280
caatggcttc catttctccg cacccacacc aatacttgtt gttttctagt tttcttgctt 14340
ttgtttgata atagccatcc taatgggtga gaaatggccc ttccattttt aagtggtttt 14400
ttctctcctt caaaatgcaa gtctcccaga agcactcagg gaagggctgc atacaacatc 14460
gagggtctgc attgctttag caccattttt cttatacaat atgaggaccc agggcttgtc 14520
atgaagttct aaaactcctc taaagcaatg cattacactg atttttttctt tttgtcagct 14580
aggcagtagg caccctaaag gcagacatct tctttttgtt attatttatg ctccttgtca 14640
gggttgagtg tgtggctttc cccacgacaa acactcactg accgcaatgc tagacacccc 14700
aagacaagca cacgcagtca cccgagccgc caaggccatt ctcactcaaa ccccagccca 14760
ccgggcctca ctgaagccag agtgcgcagc acgcctcgct ggcagaactt ccttagggga 14820
acgggctcga ctcaccagag cttcttcaga ttgcacaaca ggtgcttcag tcccacacac 14880
agaagtctga ttccgaagtc accgagggcg ttgtcactca ggtccagctc caccagcttc 14940
tggttgctgc tgaggaccaa ggagatgtcg aagcagcact catgcgagag gccacagcgc 15000
cccaaccttc atgccaagaa cagaggcaga aagcatcaga acacacctga ccagagagct 15060
ccagaacaga ggaagcatca ggacacacct gatcaggaag ctccggaata gagaaagcat 15120
cagaacacat ctgatcagag agctccggaa tacagaaagc atcagaacac acctgaccag 15180
agagctccgg aatagagaaa gcatcagaac acatctgacc agagagctcc agaatagaga 15240
aagcatcagg acacacctga caagagagct ctggaataga gaaagcatca ggacacacct 15300
gaccagagag ctctggaata gagaatgcat caggacacac ctgaccagag agctccggaa 15360
tagagaaagc atcaggacac acctgaccag agagctccgg aatagagaaa gcatcaggac 15420
acacctgacc agagagctct ggaatagaga aagcatcagg acacacctga ccagagagct 15480
ctggaataga gaaagcatca gaatacacct gaccagagag ctccggaata cagcacaagg 15540
cacattggga ggtcagcccc cagtctcccc agtcacagca gagggatcac ctgtcagtga 15600
actcccggcc gtaaacagtg ccgggtgcat tgagatcacc ccccagacat gtgaatggtg 15660
cgctcctggt ttgtaagtga agcgggcggt gtgggcctgt gcacccacct ccttccctcg 15720
tgttcctaac cattgacgtg cccgcagtcg gcactgccct cgccagtgct gcactcagct 15780
atttcttgtc ttcaccaaca ttgtcacccc attgtgtttg acgatttcat cccagccctc 15840
catctatatt gaaaggaaaa gcagctctga ttctttttct tttcttttct tttctttttt 15900
taaagacagg gtctcacttt gttgcacagg ctggagtgca ctggcgagat catagctcac 15960
tgccacctcg aactcctggg ctcaagggat ccacctgcct cagcctccca agtggctgca 16020
aatacaggca tgtgctacca tgcttagcca ttttatttta tttatatttt atttttatta 16080
ttattattat cttctaaaga caaggtctca ccagcttgct caggctggtt ttgaactcct 16140
gggctcaggt gatctgccca cctcagcctc tcaaagtgct gggattccac atcccgctgc 16200
agctctgatt cttgattagt ttccccgtca cacacatgca cacaaacaca cacgcacatc 16260
actaccaccg tcaccaccac caccagcaac aaaaactata ctttatccct gtcatggggg 16320
caagaacaac attctagctt ctttccaggg caatagttca taggtcctgg agcctgttag 16380
accaccttcc tttctgtccc tatccttaca ccaacttcaa gcaaatggac aaatggatct 16440
ctacttctct gcgaagcatc tcactgtccc ctacccttcc ctgtttgtgt ctgcctctcc 16500
agaatcatac aggggcaatg gcagtgggga gagaatttgg gcatgaagtt ggagaaataa 16560
ggttaaatgt cccaaacaac cagtctccat ggcactacga tttgaaattt accaaaagag 16620
caaagatgaa gagtgtgatc tatatacata atggaatact gctcagccat agaaaagaat 16680
gaagtcacat ctttgaagcc acacagatgg aactggaggc cattacctta agtgaaacaa 16740
ctcagaaaca gagtcaaata ccacacgttc tcacttacaa gtgggagcta aacaaagggt 16800
aacatccata gagcatggaa tgatagacac tagagcctca gaagggtggg agggtgggag 16860
ccaggtgagg gctggaaaat tatttattgg gtacaatgtt cactatttgg gtaagagtta 16920
cactaaggcc gggcacggtg gctcacgcct gtaatcccag cactttggga ggccgaggcg 16980
ggtggatcac gaggtcagga gtttgagacc agcctagcca atacggtgaa accttgtccc 17040
tactaaaaat acaaaaatca gctgggcgtg gtggcccatg cctgtaatcc caactactcg 17100
aagaattgct tgaacccagg aggtggatgt tgcagtgagc cgagatcact ccactgtact 17160
ccagcctggg caacacggcg agagtccatc tcaaaaaaaa aggggtagtt acagtaaaag 17220
cccagacact accactgtgc agtaacatat ccatgaaaca aagctgctct tgcgccccct 17280
acatctacaa aaataaatac ataaagtaaa aaataaagag cagagcagac agaaagcatt 17340
taagccaccg aacagcacaa tcgaatcaga attttctaaa ggaccatctt acttttgtgc 17400
agagaatggt cgggtgaggg aaaaaggcag acacagggag accaaagagc caacattcat 17460
tcagtgcgtg cttttgacca ctgatgggta ctaagatgtc tgtccaggcg tggcaaagat 17520
gacagcaaga caaacaaacg caaaccccat ccccggggag ctgatggtct aggaggtcac 17580
tgcgtgtcca ggcaagtggt gacagttgct ggacctgggc tggtggggtg aggacgagga 17640
aaagtggaaa acagctcggg taggaggaaa aattgataag actggtgaca aggtgagtgt 17700
gttgagccgg agagggaggt agcaaaatgt cctagagtgg cggactttaa cacttgctgt 17760
gcagctcctc aaaaatgcag acgcctgcat gcgtccacag agcagggaat gaaacagagc 17820
tagtgaggcg gcccaggcac cagcgcggtg gggcgtgtga atctgattca tggtgtggga 17880
gaaagcaagc acattttttta ttattattat tattattatt attttgaaat ggaatctcgc 17940
tctgtcaccc aggctggagt gcaatggcac gatctcggct cactgccatc tccgcctccc 18000
gggtacacac agttctcctg cctcagcctc ccgagtagct gggactacag gtgtgagcaa 18060
gcacattatt aataaagtca caggagattc cctgtgacat ttcaacccat acaaagcatt 18120
ctgaccaggc tgggcaacgt gatgagacca catctctaca aaaaaaatac aaaaattagc 18180
cagcatggtg gtgcatgcct gtagtcccag ctactcgggg gagctgaggt gggaggattg 18240
cttgagcctg ggaggtcgag gctgcagtaa gctgtgatca cacactccag cctgggtgac 18300
agagagaggt cctgtctcaa agaaaaaaaa aaaaagtatt ttcatagttt ttaggtgagg 18360
ttgccattgt tgtaaatggc aaattctcca actctcatct atgaacatgg cccatgagga 18420
aatggaatat atcgagcatc atggttgttt caagaaatga cttttttttt agttcctcat 18480
tcattcttcc ccacacaaaa cttccccagc tggcctccaa cccattctac cttctcactt 18540
gttctgggct gaactgtgcc cccccaaaaa tttacatgtt gaagccctaa tcctcaagac 18600
ctcataatgt ggctgttttg ggaaatgggg tctttaaagg agtgactaga ttaacattag 18660
gtcttgtgta gtcatgcctg actgtgccta atccatcagg actgctgtcc ctgtaagaag 18720
aggagactag gccactcttc cccccaaggc aagatggcat cagtacacag ggagaagggg 18780
gcatctacaa accaaggagg gcggcctcag aagaaaccaa ccctgctgac accttgatct 18840
tagactttcg gcctcagaac tgcaagaaaa tgaatttttg ttgttgaagc cattcagtct 18900
gtggcacttt gttacagcag aaaccacacc accggccggg tgcggtggct catgcctgta 18960
atcccagcat tttgggaggc cgaggcgggc ggatcacctg aggtcaggac ttcgagacta 19020
gcctggacaa catgatgaaa ccccatctct actaaaaata caaaaaatta gctgggtatg 19080
gtggtgggtg cctgtaatcc cagctactca ggaggctgag gcaggagaat cacttgaacc 19140
caggaggcag agattgcagt gagccgaggt cacggcattg cactccagcc tgggcaataa 19200
gagcaaaact ctgcctcaaa aaaagaaaaa aagaaaaaga aaagaaagaa accacaccag 19260
caacctggtc ctgaagatct ttctccagtc tgtttctctc tctctctctc atatgaactt 19320
gcactcacac agatcacatg cacggggact caccacaatc tccgaatgtt acagccagga 19380
tgctggagcg tttcacacaa cactctcatc cctgggtccc ccagagaatt gtcactgagg 19440
tccaattcag ttagactctg gctggtgctc agaactgaaa agaggccccg gcaaaaactg 19500
gaagtgaggt ggctgttcac caatctagga attagaagga agacagacag aaaagaaatc 19560
agcctcgaat aataactaac tggagctggg ggccggggtg cctggcacca gttcagagaa 19620
atgccttccg gggattaaga aatgggtcac gaaaccaaaa attgttccca gagaaatgaa 19680
gagggctgga tgagccttgg taaaagcagt tctgcctcct ctcggacgga gagcatgagc 19740
ctgtgactgt ggcggactgt ggcaccctac agcctgctcc ccagtgtcct cctctcgccc 19800
ttaccagtcc actgtcccaa catggccctg aacgttctgt gctgggtgat cagagggcag 19860
tcctcactcc tggctacaca acagcatcag gagtgctcac aaaaatcctc aggccaggct 19920
gggcatggtg gctcacacct gtaatcccag cactttggga ggccgaggcg ggcagatcac 19980
ctgaggtcag gagttcaaga tcagcctggc caacatggtg aaaccctctc tctactaaaa 20040
atacaaaaat taattgggtg tggtggcacg agcctgtcat cccagctatt agggaggctg 20100
aggcaggaga atcacttgaa cctgggaggt ggaagttgca gtgagccaag atcatgccac 20160
agcactccag cctgggcaac agagcaagac ttcatctcaa aaaaaaaaaa aagaaaaaga 20220
aaatcgcaag cccaggccac atccatggaa ataaaatcag aagctctgag gtggaactag 20280
atgaattttt taaatttttt ttcagatgaa acccaagctg gaatgcagtg ccatgatcat 20340
agctcactgc agcctcaaac tcctgggctc aagcaatcct cttgcctcag cctcccgagt 20400
agctgaggtt acaggcacga gtcactgtgt ccagctatat ggatcttttt tatttaaaaa 20460
aagccaggtg gctccaacat gcagtcacat ttttgctttt gtttttctgt agagaggtgc 20520
tctcactttg ctgctcaggt aggacttgaa ttcctggctt caagcaatcc ccccatcttg 20580
gcctcccaaa acctaggatt acaggcaaga gccactgcac ccacacatgc agtcaccttt 20640
gaatcacctg tagctctcat tcaaatgcaa agtctagctc tctaggtcta agattgggtc 20700
cacaatcctg catttctaat agatgctcag gcttctggtt ctcagaaggg actggaacat 20760
acaaagcaag ctcctgccct cagagtaagg cagctgccat ctagaaagat gggtgctgag 20820
ccccctacca gggctccagt cagagtctgt cctcagagta aggcaggtgc catctagagg 20880

```
gatgggtgct gagcccccta ccagggctcc cgtcagagtc tgtcctcaga gtaaggcagg  20940
tgccatctag agggatgggt gctgagcccc ctaccagggt tccagtcaga gtctgtcctg  21000
aggaaggaag gtgctatcta gagaaatggg tgctgagcct cctaccgggg cttcagtgag  21060
agtctgtcct cagaggaagg aaggtgctat ctagagaaat gggtgctgag ccccctgcca  21120
gggctccaat cagagtctgt cctcagagga aggaaggtgc tatctagaga aatggttgct  21180
gagcctccta ccggggcttc agtgagagtc tgtcctcaga gtaaggcagg tgccatctag  21240
agggatgggt gctgagcccc ctgccagggc tccaatcaga gtctgtcctc agaggaagga  21300
aggtgctatc tagagaaatg ggtgctgagc ctcctaccgg ggcttcagtg agagtctgtc  21360
ctcagaggaa ggaaggtgct atctagagaa atgggtgctg agccccctgc cagggctcca  21420
atcagagtct gtcctcagag gaaggaaggt gctatctaga gaaatgggtg ctgagcctcc  21480
taccggggct tcagtgagag tctgtcctca gagtaaggca ggtgccatct agagggatgg  21540
gtgctgagcc ccctaccagg gctccagtca gaatctgtcc tcagaggaag gaaggtgcta  21600
tctagagaaa tgggtgctga gcctcctacc ggggcttcag tgagagtgtg caaaccttcc  21660
tcacagatgt gtgatcttca taaggtctcc ctgccctctc caccttccac ctcactctta  21720
atgagtagtt ctgcctactt ttctctctgt cttactcttc ttctcccatt tctatggtct  21780
gaatgtttgt gtgccccaaa atccatacgc tgaaatccta accctcaaca tgacgtatca  21840
ggcgatgggg cctttgaggt gtggttaagt tatgagggtg gagccctcag gagtgggatt  21900
gctgtcctta ggaaagggac cccagagagc tgccttgcct cttcaccatg taaggacaca  21960
gtgagaaggc accatcgacc agggaacagg ccctcaccaa acaccagatc tgccagagcc  22020
tggatcatgg acttcccagc ctccagaacc gtaaggtgaa ccttcctttt gcttataagc  22080
caaccagcct gcagtgtttt gttatggcaa cctgatgaat gaagacaact gtcttttttc  22140
cagtcactcg gaactgtttg ctgccgtaga aaccgtaccc tgctttccca cacctgccct  22200
ctctctcaac accgtaagcc cccagcctgg ctgccccttt ccttctctca ctctctcact  22260
gcccatcctc cggaagctgg ctgagcgggg acacccaccc gtgccccgct ggtgaacagg  22320
ttcgtcccct tgtgctttgg atactctgca agtttccttg tcagagccca tgaccccctc  22380
cccgacatct gcacttgttt ccggactgtc ccacagccag acctcaagtc cctgtgacca  22440
ggacctgggt cttcaccacc actgcggccc tgtgggcagt cagtccttca tggccaaacc  22500
atgactagga aggtggtcct ggtcatggta atgtcaacgg atcaagaaag ctgaaactca  22560
ttgttgcctg tggaagggcc aagcctcctg tttcccttaa ttttgcccca cgtcaagtgt  22620
cttctatcca ggctaaactc acacatcaca gggtggccac cttcctacaa ccactgtggg  22680
tggtccttct gcaggaggca ctgaacgata aacccaaaag ggactcagaa gtcaggtgac  22740
tcaaccactt cattgcacag acttggccac tagcttccaa ccacccagca agtgtgtgaa  22800
cagacccgaa aacggggttt tggcaatgcc cagtgcagag caacatgggg gcctagaaag  22860
agggtctcca catttctgct ctatttccct tgatttacct tcatcatgtt tttttccaag  22920
gaaactgtgt ctctctccac tgtcacctgc acacactttt tctcagactg cattcatgat  22980
ttggctcata ccagtcttca gtgcagaatt cctttaattt cttctctatg cgcccaggtc  23040
ccaccattcc ttaaaggagg cttagattgc acatttctaa gaaacatccc cccagcctcc  23100
agctctgagg ccctctgtcc cctcgctcct gggacacaga ctctctggca ttgttctgcc  23160
ccacagacat tgactgactc ttaggcacta gtgctccaag tagcttacaa gaaatttcag  23220
ttgacaaata tttgtaggca atcctacatc ctacttaata ccttgtgcta aactggcatt  23280
```

```
ccccaaacat ttgttccttg ttttattttt tttttcctca tcccatttat ccacctacca  23340
tacatcaatc tttgctcatg aaggagtctc aaacagacag tggtggcatt atgatgtagc  23400
tgtggcaaca gtatttggaa gatagttgaa aagagatgag aggaggcaag cgccaagaag  23460
aagctggcga ggaagcagga ggaagcacct ggaagccgag tttccttacc catgagaaca  23520
ggcagcatga gaggagcttg ggaggacaca ctgcaccata tcaaggtgtc ggccttcctt  23580
ttcctcctcc tcttcctcct tgggcatgtt atggagaaac cccagggaca gtgactccac  23640
ccgatgacag ttctcaatgc aaaaggaaga aaccatgtgg tccattctgg tggagagatt  23700
gatctcaatc ttggggaaat agtccatggc cctttgcacg aagtcctcct cctgcatctc  23760
gtacaaacag tagaacaatt ccagctggct gggctggatc tgcagctttt tagctttggc  23820
tttcacttca atccatttca gcagctccag cctgatttgc tgagagatct tgcaacttaa  23880
tttcttctcc aagtaggagg tcctctcctg gtttaccagg ccaaagagga aacgtacaac  23940
aaaaatcaaa tacccctttt cgaatttgcc atagttttcc agaaggactg tcacgtctcg  24000
gctgggaagc ttcaaacgac tccctggaac gttcgtcctt ccttcctttt cctcttccag  24060
caggtagtac atggcggcaa agaactcctg gaaagtcatg tggatgaagc tgtagaactt  24120
ctcgcagtcc acttcctttt ggaacaggtt catcctcagg aaagcagaca catccgcctt  24180
ctgcagtcca tgattcctga ggtcggactc ctcaaacagg attttctggt tccagattcc  24240
atctgcagcc aaagagcaga gcccccagag gtgggcgcag aggccgtgct cctggctccc  24300
tccccggggc tgcagcaaac tggaaaggaa gaagacgtac accgcggtgg tggtcttgga  24360
tgtctgggca aggctcttgc cactctccat ctgctgtttc agtccagtgc acacgatcca  24420
gcagaccagg gggatgaagc acatggtgaa gaggacctcg ttctcctgaa tcagactgaa  24480
ggctgccctg gcttgggcct catcagagaa gtacttgaag aagtactctt tccttttggc  24540
ctcggagaaa cccaggatct ccacatgccg aggatggtcc agcaagtgct gcagtttctc  24600
cagggccaca ggtctcgtgg tgatgagcag agaggcctcg ggaagcagct tctttctgat  24660
gaggctgctc aggagaatgt ctccccgctc ggccttctgc cagtcagtgc agagcggtcc  24720
tatgtgctcg tcaaaggcac cttgcagctc atcgaagccg tccatgagga agaggattct  24780
ggagggtttt ctcacgatct tgtggatggg tgggtttggg tcggggcagc agctcatgat  24840
caggtccccc aggctcctct gtgtcacaag gctcacctct cgacagtgga tatagaacag  24900
atagtcaaac ctgtcttggt agagtgtccc cgacgcccag tccaacatca tcttcctggc  24960
caggattgtt ttcccaatcc ctgccgcccc ctggaacacc acggtgtgca caggctcaga  25020
atgctcatca tcggggtcaa acagcaactc catcttaatg ggactcacgg ggctctcaca  25080
cgtcttggtc ttgccgatgg ccagaagctc ctgctccctc tcctgctggc tccggtgctc  25140
cttgatgaga cgcagtcgtg tgtagcgttt gttgaggctc acactctcac ccagacgggc  25200
attcctgtct tcaatgcact ggaatctgct tctcacgtac tttctgtact tcttacggta  25260
atctacggca aagacaggaa gttaggggga aagtatacac acatccacct gagatgcgct  25320
ctcagctggg gcctgtcatc ggaagcgagt ggtaaccgga atggagaaat ggaaggtgca  25380
gctcctcccc actgggtagg aaaggtgccg agaatctctg gtgtcaagtt tttaagatac  25440
acagctgagc agaaggccca tctctatgtg tagctaccag cccaaagatc atttgaatca  25500
atcttattcc tttaagtaat ctgcatccta tgccttatca aacttgaaac gcttaatcac  25560
cgccgctggc tctgggactg caagagccac acaaacatga atttgtttct tcaactgaca  25620
```

atggatttcc tgagacaggc ctttgcattc caaagagcag gaacctatag tatggccaag 25680
ttacccagct gctcagcttc ccagagcctc ctgaaccagg tcttaaaact caactagaag 25740
caccacccca gtcgcttacc tttcttcatt ttacaaatag agattctcga aaggtactcc 25800
agtaaaccca tccactcctc ttcaatgctg tcttcctggc atatcacagt gggattcgaa 25860
acacgtgcat tatctgaacc taaaagggaa aaaaaaggtg tcaaaaccca gaactattat 25920
cacagaggat gcaattgaaa cctggcctaa tatttggcat gagagaggag accccaaaca 25980
tcccccaaat caaaacatgg ctctgagttg cagaggacag gtatccagtc aaaagtctgg 26040
ttgggagcat ttctgcactc ctagtttcaa aacaacttct gctgtccacc tgccaagcat 26100
gtgttcccac tgtccccagt ctcagaatct cttcctcagg cctggaaatc aatcagcaaa 26160
catgcgaagc aggctaagtt tcttttaccc tcgtttgctt ttgcctgccc ctggcagcct 26220
gattgtgagg gcatctccaa gctctcctat atccccaaca cggctgtggg ctaagaaagg 26280
tcacccttcc ctgaccgcag ttccctgcaa tccattttac acacgtcttc tattgtcaag 26340
tctagatgtc tggttcttca agagtgagaa cgaccagtct atttcgtgcc taatctagtg 26400
gttgggaatc ctggctgact ttagaatcac ccaggaagct ttaaaaatat ggacttcagg 26460
actgcacgcc cagaggttct ttttcagtcc ctctgaggtg aggcccagga accatcacat 26520
actaaaagct cccaggtgat tccaacatgc atctgtgttg agaatcacaa atccaaacag 26580
tcactagata gcatatctta agaaggcatt ctataggaga aattcaggtt aggtaaaaca 26640
agagttagtc actaggggaa atatataaga cagataactt caggtgggca ggaatctaca 26700
agtaacataa atgatttttt tttttttttt gagacagggc ctcactctat tgcccaggct 26760
ggagtgcaat gacacaatca tggctccctg cagcctcaac ctcctgggct caagtgatcc 26820
tcccacctca gcctccagaa cagctgggac tattgacacg tgccaccaca cctaactaat 26880
gtttgcattt tttgtagaga caggttctca ctatgttgcc caggctggtc tcaaactcct 26940
gggctcaagc aatcctccca tcttggcctc ctgaagtgct gggattacag gcataagcca 27000
ctgcgcccag cccataaaag acctctgaca gctgtctact tggtaaccat atcacaaaat 27060
aaaatccaaa aaatctaagc caaaaccaaa atcttattct tttttttttaa gagacagagt 27120
cttgctttgt ttccaaagct ggagggcagt ggcatggtca tagctcactc cagcctggaa 27180
ctcctgagct caagtgatgc acccacttca gccacctgag taactgggac tcaggtagga 27240
gccatgacag taaattagcc aaagtctatt acctaaaacc taaccccacc ccaggaaaca 27300
aacaaacaaa cttctaaccc tagttataac ttttctgcct caaaatccag atatggaagc 27360
aaagacggtg tagtggttaa gagccaggct ttgatcagag acatgccctg ctttttaccc 27420
cagctctggt tatggctaga aataaaccat gggccagtta ggatctcttc caggctcacc 27480
tcattcactt gcaggaggga taataccaga agctgtttca tgggtttctt gaatgtgcca 27540
taaaatccat aaaaactgct tagcaaagta cttctacagt tgtgattatg acactttcat 27600
ttgggtatgt gagtatataa gtactgacac aatgataatt gctttattta cttagagatg 27660
aggtctccct atgttgctca ggctggtttt gagctcctgg gctcaagcga tcctcctgcc 27720
ttagcctcct gagtagctgg gactacaggt gagagccatt gcagcaactg gtttctgacc 27780
tcccccggct gcacactgct gtctgtttcc ccagtgtcat tacacccaca ctgctgccct 27840
gccttaacat gtgtctccct atccactgac tcatttgtac tcctccttcc catcaccacc 27900
agctctacat catcatcctg caataccctg cccttctctg agccctacct ttgcctagaa 27960
cacaagacaa aagaaagaac cttatcccca atgtgtacat ggggattaag agaatttctt 28020
ttacattcca attcccaaag tggtggtgaa aggaaaggct tctgccccaa actccacggt 28080
tcttcaagga gagaggctgc cctctgggcc ataggaagca gaggcccaag cctgctgacc 28140
acacagcaga tactggacaa aacatgtggt ctgagaagct ggatggagaa ttggaggcag 28200
gtctaggcac tgctgagatt cagataaaga gggactaatc atggcaggtg cccagggggt 28260
aggtacagtc tgcatcagct ttttaaagga gttagagaaa gcaaacagtt tgcctccacc 28320
ttctcatagc actaccgtga gaggggaaaa gagaaaaaac caagacaata caagaaaaaa 28380
aaattttttt ttgaaacagg gtcttgctct ttagcccagg ctggagtgcc gtggtgcaat 28440
ctcagctcac tgcaacctcc actccccatg ttcaagcaat tctcctacct cagcctcctg 28500
agtagctggg attacaggtg cccaccacca cacccggcta attttttttg tatttttagt 28560
agagatgggg ttttgccatg ttggccaggc tggtgttgaa ctcctgacct caggtgatcc 28620
acccacctca gcctcacaaa gtgctggaat tacaggcatg agccaccatg cccggccatg 28680
atttaaaaaa aaaaaaatca tactaacttc tgtgcatcaa aggacacagt taaccaaatg 28740
aaaagacaac ccacagaata ggagaaaata tttgtaaatc atatatctga tatggggtta 28800
atatctagaa tacataaaga actcctacaa ggcaacaaca aaagccaaac ctggtctgaa 28860
aatgagaaaa gaacttgaac agaactttct ctgaagaagc tctataaatg gccaacaagc 28920
agtgaaaatg tgctcagcat cacttatcat tagggaaacg gaaatcaaaa ctacagtgag 28980
ataccacctc acactcatta gaatggctac tataaaaaag aaaaaataaa taaaaataac 29040
gtgttcttag gatatggaga aattggaacc cttgtgtgct gttggtggga aatggtgcag 29100
atggtatcta aaacagtaga gcagttcttc aaaatattta acagaattac cgtatgattc 29160
agaaatttca cttctgagta tataccccag agaattcaaa gcagggtctt gaagagatat 29220
ttgtgcacca acactcataa cagcattaac aataacaaaa aggtagaagt aatccaggtg 29280
ttcatcaaca gataactaaa caaaatttgg tatatggtac catggagtat ttatacagtc 29340
ttttttaaag gaagggaatt ccgacacatg ctacaacata gttgaacccg gaggacatta 29400
tgctgagtga aataaactac tcataaagga aaaaatgctg tatgtttcca cttatatgag 29460
gtacccagag tagtaagatt cacagagatg gcaaatagaa tggtggttac cagggctggg 29520
agaatgaggc aatgaggagt tatcattcaa tgggtgagga gtttcagttt tgcaagatga 29580
aaacagttct ggagactggt tgcacaatgt gagtgtacct aacactactg aactgtacat 29640
ttaaaaatta ttacggccgg gcgcggtggc tcacacctgt aattccagca ctttgcgagg 29700
ccgaggcggg tggatcacct gaggtcggga gtttgagacc aacctgacca acatggagaa 29760
accccatctc tactaaaaat acaaaattag ccgggcgtgg aggtgcaatg cctgtaatcc 29820
cagctacttg ggaggctgag gcaggaaaat cgcttgaacc cgggaggtgg aggttgcagt 29880
gagccaagat ctcaccattg cactccagcc tgggcaacaa gagcaactcc gtctcaaaaa 29940
aaaatatata tatatatata tataaagatg gaaaattgta cactatgtgc acttggccac 30000 aattttttttt aaaagtcttc cttccactca ccccacttcg gctcatctct ttttgctttc 30060
tcataaaggt ctctcctgtt gatcgcagcg aagatccaca cggccatggc ccacgccttc 30120
tcctccccat tgaagtcgat cattagcgtg gctagatcca catggtctgc cttctctgtc 30180
tgacccctcg ggagggggat gcagcccttc tggggaggat agtcctctaa gtgcatctta 30240
aatttcttca agtccacatc ctccaggtcc tccaggtacc tggccagctt gcagcgggtg 30300
cttgccatct tcatctgcag ctgttttcag ggtccttagg cttcggtcca cactaagata 30360
ccaggcagtg aacacggcac acggatgagt ctttttttaaa gtctccactt tgagagatat 30420
aaattatcaa aaactcagca aacagaaaga aaaaaatgtc acatgactgt aacaagtcaa 30480
aatctttaat tttgaaaagt tagccaaggc cgggcacagt ggctcacgcc tgtaatccca 30540
gcactttgag aggccaaggc aggcagatca cctgagctga ggaattcaag accagcctgg 30600
ccaacatggc aaaactgtgt ctctactaaa agtacaaaaa tgagccgggt gtggtggcgg 30660
gcgcctgtaa tcccagctac tcaggaagtt gaggtaggag aattgattga acccgggaag 30720
tggaggctgc agtgagccaa gatcacgcca ctgcactcca gcctaggcga cacagcaaga 30780
ctccatctca aaaaaaaaaa agttagccaa atgcttacca gaaagttctc ctgttggctc 30840
gatccaggag tgtgtcctga gccatggaag aaaggtttcc ctatggaggg aaaaatatgc 30900
aaacaaatcc ataaacagga ttgtattaca gtttacggtg aacaaccact tcacgatgcc 30960
atcttgaccc atcagcaaga aaatttttgt cccgttgatt acggggctat gacattggac 31020
aaactcttca ctattcctca acttcagttt cctcatctac aaaatgagaa agcagaagag 31080
aatgttttca gttcctccaa actgaaggct ctggctcttt gcttctgttt ttgtgaggga 31140
agagggatga gagacaatag aaggagaagg ccaggaggtg agtaagtgtg ttgataacag 31200
aacaggacgt ggctagggag agaggagaga gaacataaaa gcttgcagag gaggggacag 31260
tctttgactg cacttctatc aaccagtgga ttgaagtgag atgaagctgg gagtgcataa 31320
tggagaataa taaaaacata catccctgta atcccagcac tttgggaggc cgaggtgggc 31380
ggatcacctg aggtcaggag ttggagacca ggctcaccaa acaacaggga gaaatcccgt 31440
ctctactaaa aatacaaaaa ttaaccgggc atggtaccag gcacctgtaa tcccagctac 31500
tcgggaggct gaggcaggag aatcgcttga acccaggagg cggaggttgc gatgagccaa 31560
gatcacacca ctgcactcca gcctgggcaa taagagcaaa actccatctc aaaaaaataaa 31620
atagaataaa ataaaataaa taaaaacata catcctttaa tgtctccttg caaaattcgc 31680
aattgttatc attataattc acattaattt agagctttcc acaggctagg cactcactga 31740
tgtttttccc catctaacct gcacagagct ctatgaggtg cacctattcc tagccccatt 31800
ttatagatgc ataaactgag tcttaggggg actaggaagc ctgccgaggg gtttagaacc 31860
aggaaggaac agagccagga ttttgaccag agatatgaga ccatgtcttc catcacttgt 31920
ttcagtcaga caaagacaaa gacaacaaaa tagatgacta aaagacacac ttccccagca 31980
tttatcacag gtgtatcact gcagcattca ccaacatagt cttcccaact agactgtgag 32040
ttccacaaaa actagcaatc acctgctgta tctttagatc ttccatatct cctagagtcc 32100
ggatggatga acaagttggc tttgtttgga attgttccct ccttgatccc ttgattatac 32160
tctatttggc aaagcacctc aacctaaagc cataaataac actcaaggga ggcagagagc 32220
ctggaaaacg gtggagctct ccaaattgga atttctgtga ctgcagttca atgtcaagat 32280
gcctcagact cactcatctc tcccgtccca tctccattcc tgcctatcta ctcctcgcct 32340
cctgagccct gcaaacccag ccctgtgcat cctgaggtga ctgctctcca gacagcccta 32400
ttagctccgc ataccctccc agctcctgcc catcctgagg tgactgctct ccagacagcc 32460
ctattagctc cgcataccct cccagctcct gccccatcag tccttccatc tgcatcagga 32520
ttctgccttt cttctgtgct ccttccaccc taacaccagc acaaaaatct gctgcccttt 32580
ggtctttaag gaggtttgtt tccttctgta tatcccatcc atcttctccc ctgggaggga 32640
tactgggcaa atctgctgaa gtcgtgggtg taaactatgg ttgctgccgc tgtcctcccc 32700
gcttcccccc gccacataca cacacacga 32729

-continued

<210> SEQ ID NO 34
<211> LENGTH: 1036
<212> TYPE: PRT
<213> ORGANISM: Artificial Sequence
<220> FEATURE:
<223> OTHER INFORMATION: NLRP3 Canonical

<400> SEQUENCE: 34

```
Met Lys Met Ala Ser Thr Arg Cys Lys Leu Ala Arg Tyr Leu Glu Asp
1               5                   10                  15

Leu Glu Asp Val Asp Leu Lys Lys Phe Lys Met His Leu Glu Asp Tyr
            20                  25                  30

Pro Pro Gln Lys Gly Cys Ile Pro Leu Pro Arg Gly Gln Thr Glu Lys
        35                  40                  45

Ala Asp His Val Asp Leu Ala Thr Leu Met Ile Asp Phe Asn Gly Glu
    50                  55                  60

Glu Lys Ala Trp Ala Met Ala Val Trp Ile Phe Ala Ala Ile Asn Arg
65                  70                  75                  80

Arg Asp Leu Tyr Glu Lys Ala Lys Arg Asp Glu Pro Lys Trp Gly Ser
                85                  90                  95

Asp Asn Ala Arg Val Ser Asn Pro Thr Val Ile Cys Gln Glu Asp Ser
            100                 105                 110

Ile Glu Glu Glu Trp Met Gly Leu Leu Glu Tyr Leu Ser Arg Ile Ser
        115                 120                 125

Ile Cys Lys Met Lys Lys Asp Tyr Arg Lys Lys Tyr Arg Lys Tyr Val
    130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
            180                 185                 190

Thr Lys Thr Cys Glu Ser Pro Val Ser Pro Ile Lys Met Glu Leu Leu
        195                 200                 205

Phe Asp Pro Asp Asp Glu His Ser Glu Pro Val His Thr Val Val Phe
    210                 215                 220

Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
                245                 250                 255

Phe Tyr Ile His Cys Arg Glu Val Ser Leu Val Thr Gln Arg Ser Leu
            260                 265                 270

Gly Asp Leu Ile Met Ser Cys Cys Pro Asp Pro Asn Pro Pro Ile His
        275                 280                 285

Lys Ile Val Arg Lys Pro Ser Arg Ile Leu Phe Leu Met Asp Gly Phe
    290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
        355                 360                 365
```

```
Glu Ile Leu Gly Phe Ser Glu Ala Lys Arg Lys Glu Tyr Phe Phe Lys
    370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415

Ile Val Cys Thr Gly Leu Lys Gln Gln Met Glu Ser Gly Lys Ser Leu
            420                 425                 430

Ala Gln Thr Ser Lys Thr Thr Thr Ala Val Tyr Val Phe Phe Leu Ser
        435                 440                 445

Ser Leu Leu Gln Pro Arg Gly Gly Ser Gln Glu His Gly Leu Cys Ala
    450                 455                 460

His Leu Trp Gly Leu Cys Ser Leu Ala Ala Asp Gly Ile Trp Asn Gln
465                 470                 475                 480

Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
        515                 520                 525

Phe Ala Ala Met Tyr Tyr Leu Leu Glu Glu Glu Lys Glu Gly Arg Thr
    530                 535                 540

Asn Val Pro Gly Ser Arg Leu Lys Leu Pro Ser Arg Asp Val Thr Val
545                 550                 555                 560

Leu Leu Glu Asn Tyr Gly Lys Phe Glu Lys Gly Tyr Leu Ile Phe Val
                565                 570                 575

Val Arg Phe Leu Phe Gly Leu Val Asn Gln Glu Arg Thr Ser Tyr Leu
            580                 585                 590

Glu Lys Lys Leu Ser Cys Lys Ile Ser Gln Gln Ile Arg Leu Glu Leu
        595                 600                 605

Leu Lys Trp Ile Glu Val Lys Ala Lys Ala Lys Lys Leu Gln Ile Gln
    610                 615                 620

Pro Ser Gln Leu Glu Leu Phe Tyr Cys Leu Tyr Glu Met Gln Glu Glu
625                 630                 635                 640

Asp Phe Val Gln Arg Ala Met Asp Tyr Phe Pro Lys Ile Glu Ile Asn
                645                 650                 655

Leu Ser Thr Arg Met Asp His Met Val Ser Ser Phe Cys Ile Glu Asn
            660                 665                 670

Cys His Arg Val Glu Ser Leu Ser Leu Gly Phe Leu His Asn Met Pro
        675                 680                 685

Lys Glu Glu Glu Glu Glu Glu Lys Glu Gly Arg His Leu Asp Met Val
    690                 695                 700

Gln Cys Val Leu Pro Ser Ser Ser His Ala Ala Cys Ser His Gly Leu
705                 710                 715                 720

Val Asn Ser His Leu Thr Ser Ser Phe Cys Arg Gly Leu Phe Ser Val
                725                 730                 735

Leu Ser Thr Ser Gln Ser Leu Thr Glu Leu Asp Leu Ser Asp Asn Ser
            740                 745                 750

Leu Gly Asp Pro Gly Met Arg Val Leu Cys Glu Thr Leu Gln His Pro
        755                 760                 765

Gly Cys Asn Ile Arg Arg Leu Trp Leu Gly Arg Cys Gly Leu Ser His
    770                 775                 780
```

-continued

```
Glu Cys Cys Phe Asp Ile Ser Leu Val Leu Ser Ser Asn Gln Lys Leu
785                 790                 795                 800

Val Glu Leu Asp Leu Ser Asp Asn Ala Leu Gly Asp Phe Gly Ile Arg
                805                 810                 815

Leu Leu Cys Val Gly Leu Lys His Leu Leu Cys Asn Leu Lys Lys Leu
            820                 825                 830

Trp Leu Val Ser Cys Cys Leu Thr Ser Ala Cys Cys Gln Asp Leu Ala
        835                 840                 845

Ser Val Leu Ser Thr Ser His Ser Leu Thr Arg Leu Tyr Val Gly Glu
    850                 855                 860

Asn Ala Leu Gly Asp Ser Gly Val Ala Ile Leu Cys Glu Lys Ala Lys
865                 870                 875                 880

Asn Pro Gln Cys Asn Leu Gln Lys Leu Gly Leu Val Asn Ser Gly Leu
                885                 890                 895

Thr Ser Val Cys Cys Ser Ala Leu Ser Ser Val Leu Ser Thr Asn Gln
            900                 905                 910

Asn Leu Thr His Leu Tyr Leu Arg Gly Asn Thr Leu Gly Asp Lys Gly
        915                 920                 925

Ile Lys Leu Leu Cys Glu Gly Leu Leu His Pro Asp Cys Lys Leu Gln
    930                 935                 940

Val Leu Glu Leu Asp Asn Cys Asn Leu Thr Ser His Cys Cys Trp Asp
945                 950                 955                 960

Leu Ser Thr Leu Leu Thr Ser Ser Gln Ser Leu Arg Lys Leu Ser Leu
                965                 970                 975

Gly Asn Asn Asp Leu Gly Asp Leu Gly Val Met Met Phe Cys Glu Val
            980                 985                 990

Leu Lys Gln Gln Ser Cys Leu Leu  Gln Asn Leu Gly Leu  Ser Glu Met
        995                 1000                1005

Tyr Phe  Asn Tyr Glu Thr Lys  Ser Ala Leu Glu Thr  Leu Gln Glu
    1010                1015                1020

Glu Lys  Pro Glu Leu Thr Val  Val Phe Glu Pro Ser  Trp
    1025                1030                1035
```

<210> SEQ ID NO 35
<211> LENGTH: 4470
<212> TYPE: DNA
<213> ORGANISM: Artificial Sequence
<220> FEATURE:
<223> OTHER INFORMATION: pyrin

<400> SEQUENCE: 35

```
gtagatgagg aaactgaagt tgaggaatag tgaagagttt gtccaatgtc atagccccgt     60

aatcaacggg acaaaaattt tcttgctgat gggtcaagat ggcatcgtga agtggttgtt    120

caccgtaaac tgtaatacaa tcctgtttat ggatttgttt gcatattttt ccctccatag    180

ggaaaccttt cttccatggc tcaggacaca ctcctggatc gagccaacag gagaactttc    240

tggtaagcat ttggctaact tttttttttt tgagatggag tcttgctgtg tcgcctaggc    300

tggagtgcag tggcgtgatc ttggctcact gcagcctcca cttcccgggt tcaatcaatt    360

ctcctacctc aacttcctga gtagctggga ttacaggcgc ccgccaccac acccggctca    420

tttttgtact tttagtagag acacagtttt gccatgttgg ccaggctggt cttgaattcc    480

tcagctcagg tgatctgcct gccttggcct ctcaaagtgc tgggattaca ggcgtgagcc    540

actgtgcccg gccttggcta acttttcaaa attaaagatt ttgacttgtt acagtcatgt    600

gacatttttt tctttctgtt tgctgagttt ttgataattt atatctctca aagtggagac    660
```

-continued

```
tttaaaaaag actcatccgt gtgccgtgtt cactgcctgg tatcttagtg tggaccgaag    720
cctaaggacc ctgaaaacag ctgcagatga agatggcaag cacccgctgc aagctggcca    780
ggtacctgga ggacctggag gatgtggact tgaagaaatt taagatgcac ttagaggact    840
atcctcccca gaagggctgc atccccctcc cgaggggtca gacagagaag gcagaccatg    900
tggatctagc cacgctaatg atcgacttca atggggagga gaaggcgtgg gccatggccg    960
tgtggatctt cgctgcgatc aacaggagag acctttatga gaaagcaaaa agagatgagc   1020
cgaagtgggg ttcagataat gcacgtgttt cgaatcccac tgtgatatgc caggaagaca   1080
gcattgaaga ggagtggatg ggtttactgg agtacctttc gagaatctct atttgtaaaa   1140
tgaagaaaga ttaccgtaag aagtacagaa agtacgtgag aagcagattc cagtgcattg   1200
aagacaggaa tgcccgtctg ggtgagagtg tgagcctcaa caaacgctac acacgactgc   1260
gtctcatcaa ggagcaccgg agccagcagg agagggagca ggagcttctg gccatcggca   1320
agaccaagac gtgtgagagc cccgtgagtc ccattaagat ggagttgctg tttgaccccg   1380
atgatgagca ttctgagcct gtgcacaccg tggtgttcca gggggcggca gggattggga   1440
aaacaatcct ggccaggaag atgatgttgg actgggcgtc ggggacactc taccaagaca   1500
ggtttgacta tctgttctat atccactgtc gggaggtgag ccttgtgaca cagaggagcc   1560
tgggggacct gatcatgagc tgctgccccg acccaaaccc acccatccac aagatcgtga   1620
gaaaaccctc cagaatcctc ttcctcatgg acggcttcga tgagctgcaa ggtgcctttg   1680
acgagcacat aggaccgctc tgcactgact ggcagaaggc cgagcgggga gacattctcc   1740
tgagcagcct catcagaaag aagctgcttc ccgaggcctc tctgctcatc accacgagac   1800
ctgtggccct ggagaaactg cagcacttgc tggaccatcc tcggcatgtg gagatcctgg   1860
gtttctccga ggccaaaagg aaagagtact tcttcaagta cttctctgat gaggcccaag   1920
ccagggcagc cttcagtctg attcaggaga acgaggtcct cttcaccatg tgcttcatcc   1980
ccctggtctg ctggatcgtg tgcactggac tgaaacagca gatggagagt ggcaagagcc   2040
ttgcccagac atccaagacc accaccgcgg tgtacgtctt cttcctttcc agtttgctgc   2100
agccccgggg agggagccag gagcacggcc tctgcgccca cctctggggg ctctgctctt   2160
tggctgcaga tggaatctgg aaccagaaaa tcctgtttga ggagtccgac ctcaggaatc   2220
atggactgca gaaggcggat gtgtctgctt tcctgaggat gaacctgttc caaaaggaag   2280
tggactgcga gaagttctac agcttcatcc acatgacttt ccaggagttc tttgccgcca   2340
tgtactacct gctggaagag gaaaaggaag gaaggacgaa cgttccaggg agtcgtttga   2400
agcttcccag ccgagacgtg acagtccttc tggaaaacta tggcaaattc gaaaaggggt   2460
atttgatttt tgttgtacgt ttcctctttg gcctggtaaa ccaggagagg acctcctact   2520
tggagaagaa attaagttgc aagatctctc agcaaatcag gctggagctg ctgaaatgga   2580
ttgaagtgaa agccaaagct aaaaagctgc agatccagcc cagccagctg gaattgttct   2640
actgtttgta cgagatgcag gaggaggact tcgtgcaaag ggccatggac tatttcccca   2700
agattgagat caatctctcc accagaatgg accacatggt ttcttccttt tgcattgaga   2760
actgtcatcg ggtggagtca ctgtccctgg ggtttctcca taacatgccc aaggaggaag   2820
aggaggagga aaaggaaggc cgacaccttg atatggtgca gtgtgtcctc ccaagctcct   2880
ctcatgctgc ctgttctcat ggattggtga acagccacct cacttccagt tttgccgggg   2940
gcctcttttc agttctgagc accagccaga gtctaactga attggacctc agtgacaatt   3000
```

-continued

```
ctctggggga cccagggatg agagtgttgt gtgaaacgct ccagcatcct ggctgtaaca   3060

ttcggagatt gtggttgggg cgctgtggcc tctcgcatga gtgctgcttc gacatctcct   3120

tggtcctcag cagcaaccag aagctggtgg agctggacct gagtgacaac gccctcggtg   3180

acttcggaat cagacttctg tgtgtgggac tgaagcacct gttgtgcaat ctgaagaagc   3240

tctggttggt cagctgctgc ctcacatcag catgttgtca ggatcttgca tcagtattga   3300

gcaccagcca ttccctgacc agactctatg tgggggagaa tgccttggga gactcaggag   3360

tcgcaatttt atgtgaaaaa gccaagaatc cacagtgtaa cctgcagaaa ctggggttgg   3420

tgaattctgg ccttacgtca gtctgttgtt cagctttgtc ctcggtactc agcactaatc   3480

agaatctcac gcacctttac ctgcgaggca acactctcgg agacaagggg atcaaactac   3540

tctgtgaggg actcttgcac cccgactgca agcttcaggt gttggaatta gacaactgca   3600

acctcacgtc acactgctgc tgggatcttt ccacacttct gacctccagc cagagcctgc   3660

gaaagctgag cctgggcaac aatgacctgg gcgacctggg ggtcatgatg ttctgtgaag   3720

tgctgaaaca gcagagctgc ctcctgcaga acctggggtt gtctgaaatg tatttcaatt   3780

atgagacaaa aagtgcgtta gaaacacttc aagaagaaaa gcctgagctg accgtcgtct   3840

ttgagccttc ttggtaggag tggaaacggg gctgccagac gccagtgttc tccggtccct   3900

ccagctgggg gccctcaggt ggagagagct gcgatccatc caggccaaga ccacagctct   3960

gtgatccttc cggtggagtg tcggagaaga gagcttgccg acgatgcctt cctgtgcaga   4020

gcttgggcat ctcctttacg ccagggtgag gaagacacca ggacaatgac agcatcgggt   4080

gttgttgtca tcacagcgcc tcagttagag gatgttcctc ttggtgacct catgtaatta   4140

gctcattcaa taaagcactt tctttatttt tctcttctct gtctaacttt ctttttccta   4200

tctttttctt tctttgttct gtttactttt gctcatatca tcattcccgc tatctttcta   4260

ttaactgacc ataacacaga actagttgac tatatattat gttgaaattt tatggcagct   4320

atttatttat ttaaattttt tgtaacagtt ttgttttcta ataagaaaaa tccatgcttt   4380

ttgtagctgg ttgaaaattc aggaatatgt aaaacttttt ggtatttaat taaattgatt   4440

cctttttctta attttaaaaa aaaaaaaaaa                                   4470
```

```
<210> SEQ ID NO 36
<211> LENGTH: 922
<212> TYPE: PRT
<213> ORGANISM: Artificial Sequence
<220> FEATURE:
<223> OTHER INFORMATION: NLR family pyrin domain 2

<400> SEQUENCE: 36

Met Lys Met Ala Ser Thr Arg Cys Lys Leu Ala Arg Tyr Leu Glu Asp
1               5                   10                  15

Leu Glu Asp Val Asp Leu Lys Lys Phe Lys Met His Leu Glu Asp Tyr
            20                  25                  30

Pro Pro Gln Lys Gly Cys Ile Pro Leu Pro Arg Gly Gln Thr Glu Lys
        35                  40                  45

Ala Asp His Val Asp Leu Ala Thr Leu Met Ile Asp Phe Asn Gly Glu
    50                  55                  60

Glu Lys Ala Trp Ala Met Ala Val Trp Ile Phe Ala Ala Ile Asn Arg
65                  70                  75                  80

Arg Asp Leu Tyr Glu Lys Ala Lys Arg Asp Glu Pro Lys Trp Gly Ser
                85                  90                  95

Asp Asn Ala Arg Val Ser Asn Pro Thr Val Ile Cys Gln Glu Asp Ser
```

-continued

```
            100                 105                 110

Ile Glu Glu Glu Trp Met Gly Leu Leu Glu Tyr Leu Ser Arg Ile Ser
        115                 120                 125

Ile Cys Lys Met Lys Lys Asp Tyr Arg Lys Lys Tyr Arg Lys Tyr Val
    130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
            180                 185                 190

Thr Lys Thr Cys Glu Ser Pro Val Ser Pro Ile Lys Met Glu Leu Leu
        195                 200                 205

Phe Asp Pro Asp Asp Glu His Ser Glu Pro Val His Thr Val Val Phe
    210                 215                 220

Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
                245                 250                 255

Phe Tyr Ile His Cys Arg Glu Val Ser Leu Val Thr Gln Arg Ser Leu
            260                 265                 270

Gly Asp Leu Ile Met Ser Cys Cys Pro Asp Pro Asn Pro Pro Ile His
        275                 280                 285

Lys Ile Val Arg Lys Pro Ser Arg Ile Leu Phe Leu Met Asp Gly Phe
    290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
        355                 360                 365

Glu Ile Leu Gly Phe Ser Glu Ala Lys Arg Lys Glu Tyr Phe Phe Lys
    370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415

Ile Val Cys Thr Gly Leu Lys Gln Gln Met Glu Ser Gly Lys Ser Leu
            420                 425                 430

Ala Gln Thr Ser Lys Thr Thr Thr Ala Val Tyr Val Phe Phe Leu Ser
        435                 440                 445

Ser Leu Leu Gln Pro Arg Gly Gly Ser Gln Glu His Gly Leu Cys Ala
    450                 455                 460

His Leu Trp Gly Leu Cys Ser Leu Ala Ala Asp Gly Ile Trp Asn Gln
465                 470                 475                 480

Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
        515                 520                 525
```

```
Phe Ala Ala Met Tyr Tyr Leu Leu Glu Glu Glu Lys Glu Gly Arg Thr
    530                 535                 540

Asn Val Pro Gly Ser Arg Leu Lys Leu Pro Ser Arg Asp Val Thr Val
545                 550                 555                 560

Leu Leu Glu Asn Tyr Gly Lys Phe Glu Lys Gly Tyr Leu Ile Phe Val
                565                 570                 575

Val Arg Phe Leu Phe Gly Leu Val Asn Gln Glu Arg Thr Ser Tyr Leu
            580                 585                 590

Glu Lys Lys Leu Ser Cys Lys Ile Ser Gln Gln Ile Arg Leu Glu Leu
        595                 600                 605

Leu Lys Trp Ile Glu Val Lys Ala Lys Ala Lys Lys Leu Gln Ile Gln
    610                 615                 620

Pro Ser Gln Leu Glu Leu Phe Tyr Cys Leu Tyr Glu Met Gln Glu Glu
625                 630                 635                 640

Asp Phe Val Gln Arg Ala Met Asp Tyr Phe Pro Lys Ile Glu Ile Asn
                645                 650                 655

Leu Ser Thr Arg Met Asp His Met Val Ser Ser Phe Cys Ile Glu Asn
            660                 665                 670

Cys His Arg Val Glu Ser Leu Ser Leu Gly Phe Leu His Asn Met Pro
        675                 680                 685

Lys Glu Glu Glu Glu Glu Glu Lys Glu Gly Arg His Leu Asp Met Val
    690                 695                 700

Gln Cys Val Leu Pro Ser Ser Ser His Ala Ala Cys Ser His Gly Leu
705                 710                 715                 720

Gly Arg Cys Gly Leu Ser His Glu Cys Cys Phe Asp Ile Ser Leu Val
                725                 730                 735

Leu Ser Ser Asn Gln Lys Leu Val Glu Leu Asp Leu Ser Asp Asn Ala
            740                 745                 750

Leu Gly Asp Phe Gly Ile Arg Leu Leu Cys Val Gly Leu Lys His Leu
        755                 760                 765

Leu Cys Asn Leu Lys Lys Leu Trp Leu Val Asn Ser Gly Leu Thr Ser
    770                 775                 780

Val Cys Cys Ser Ala Leu Ser Ser Val Leu Ser Thr Asn Gln Asn Leu
785                 790                 795                 800

Thr His Leu Tyr Leu Arg Gly Asn Thr Leu Gly Asp Lys Gly Ile Lys
                805                 810                 815

Leu Leu Cys Glu Gly Leu Leu His Pro Asp Cys Lys Leu Gln Val Leu
            820                 825                 830

Glu Leu Asp Asn Cys Asn Leu Thr Ser His Cys Cys Trp Asp Leu Ser
        835                 840                 845

Thr Leu Leu Thr Ser Ser Gln Ser Leu Arg Lys Leu Ser Leu Gly Asn
    850                 855                 860

Asn Asp Leu Gly Asp Leu Gly Val Met Met Phe Cys Glu Val Leu Lys
865                 870                 875                 880

Gln Gln Ser Cys Leu Leu Gln Asn Leu Gly Leu Ser Glu Met Tyr Phe
                885                 890                 895

Asn Tyr Glu Thr Lys Ser Ala Leu Glu Thr Leu Gln Glu Glu Lys Pro
            900                 905                 910

Glu Leu Thr Val Val Phe Glu Pro Ser Trp
        915                 920
```

<210> SEQ ID NO 37
<211> LENGTH: 719

<212> TYPE: PRT
<213> ORGANISM: Artificial Sequence
<220> FEATURE:
<223> OTHER INFORMATION: NLR family pyrin domain 3

<400> SEQUENCE: 37

```
Met Lys Met Ala Ser Thr Arg Cys Lys Leu Ala Arg Tyr Leu Glu Asp
1               5                   10                  15

Leu Glu Asp Val Asp Leu Lys Lys Phe Lys Met His Leu Glu Asp Tyr
            20                  25                  30

Pro Pro Gln Lys Gly Cys Ile Pro Leu Pro Arg Gly Gln Thr Glu Lys
        35                  40                  45

Ala Asp His Val Asp Leu Ala Thr Leu Met Ile Asp Phe Asn Gly Glu
    50                  55                  60

Glu Lys Ala Trp Ala Met Ala Val Trp Ile Phe Ala Ala Ile Asn Arg
65                  70                  75                  80

Arg Asp Leu Tyr Glu Lys Ala Lys Arg Asp Glu Pro Lys Trp Gly Ser
                85                  90                  95

Asp Asn Ala Arg Val Ser Asn Pro Thr Val Ile Cys Gln Glu Asp Ser
            100                 105                 110

Ile Glu Glu Glu Trp Met Gly Leu Leu Glu Tyr Leu Ser Arg Ile Ser
        115                 120                 125

Ile Cys Lys Met Lys Lys Asp Tyr Arg Lys Lys Tyr Arg Lys Tyr Val
    130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
            180                 185                 190

Thr Lys Thr Cys Glu Ser Pro Val Ser Pro Ile Lys Met Glu Leu Leu
        195                 200                 205

Phe Asp Pro Asp Asp Glu His Ser Glu Pro Val His Thr Val Val Phe
    210                 215                 220

Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
                245                 250                 255

Phe Tyr Ile His Cys Arg Glu Val Ser Leu Val Thr Gln Arg Ser Leu
            260                 265                 270

Gly Asp Leu Ile Met Ser Cys Cys Pro Asp Pro Asn Pro Pro Ile His
        275                 280                 285

Lys Ile Val Arg Lys Pro Ser Arg Ile Leu Phe Leu Met Asp Gly Phe
    290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
        355                 360                 365

Glu Ile Leu Gly Phe Ser Glu Ala Lys Arg Lys Glu Tyr Phe Phe Lys
    370                 375                 380
```

Tyr Phe Ser Asp Glu Ala Gln Ala Arg Ala Ala Phe Ser Leu Ile Gln
385 390 395 400

Glu Asn Glu Val Leu Phe Thr Met Cys Phe Ile Pro Leu Val Cys Trp
405 410 415

Ile Val Cys Thr Gly Leu Lys Gln Gln Met Glu Ser Gly Lys Ser Leu
420 425 430

Ala Gln Thr Ser Lys Thr Thr Thr Ala Val Tyr Val Phe Phe Leu Ser
435 440 445

Ser Leu Leu Gln Pro Arg Gly Gly Ser Gln Glu His Gly Leu Cys Ala
450 455 460

His Leu Trp Gly Leu Cys Ser Leu Ala Ala Asp Gly Ile Trp Asn Gln
465 470 475 480

Lys Ile Leu Phe Glu Glu Ser Asp Leu Arg Asn His Gly Leu Gln Lys
485 490 495

Ala Asp Val Ser Ala Phe Leu Arg Met Asn Leu Phe Gln Lys Glu Val
500 505 510

Asp Cys Glu Lys Phe Tyr Ser Phe Ile His Met Thr Phe Gln Glu Phe
515 520 525

Phe Ala Ala Met Tyr Tyr Leu Leu Glu Glu Glu Lys Glu Gly Arg Thr
530 535 540

Asn Val Pro Gly Ser Arg Leu Lys Leu Pro Ser Arg Asp Val Thr Val
545 550 555 560

Leu Leu Glu Asn Tyr Gly Lys Phe Glu Lys Gly Tyr Leu Ile Phe Val
565 570 575

Val Arg Phe Leu Phe Gly Leu Val Asn Gln Glu Arg Thr Ser Tyr Leu
580 585 590

Glu Lys Lys Leu Ser Cys Lys Ile Ser Gln Gln Ile Arg Leu Glu Leu
595 600 605

Leu Lys Trp Ile Glu Val Lys Ala Lys Ala Lys Lys Leu Gln Ile Gln
610 615 620

Pro Ser Gln Leu Glu Leu Phe Tyr Cys Leu Tyr Glu Met Gln Glu Glu
625 630 635 640

Asp Phe Val Gln Arg Ala Met Asp Tyr Phe Pro Lys Ile Glu Ile Asn
645 650 655

Leu Ser Thr Arg Met Asp His Met Val Ser Ser Phe Cys Ile Glu Asn
660 665 670

Cys His Arg Val Glu Ser Leu Ser Leu Gly Phe Leu His Asn Met Pro
675 680 685

Lys Glu Glu Glu Glu Glu Glu Lys Glu Gly Arg His Leu Asp Met Val
690 695 700

Gln Cys Val Leu Pro Ser Ser Ser His Ala Ala Cys Ser His Gly
705 710 715

<210> SEQ ID NO 38
<211> LENGTH: 979
<212> TYPE: PRT
<213> ORGANISM: Artificial Sequence
<220> FEATURE:
<223> OTHER INFORMATION: NLR family pyrin domain 4

<400> SEQUENCE: 38

Met Lys Met Ala Ser Thr Arg Cys Lys Leu Ala Arg Tyr Leu Glu Asp
1 5 10 15

Leu Glu Asp Val Asp Leu Lys Lys Phe Lys Met His Leu Glu Asp Tyr
20 25 30

```
Pro Pro Gln Lys Gly Cys Ile Pro Leu Pro Arg Gly Gln Thr Glu Lys
        35                  40                  45

Ala Asp His Val Asp Leu Ala Thr Leu Met Ile Asp Phe Asn Gly Glu
    50                  55                  60

Glu Lys Ala Trp Ala Met Ala Val Trp Ile Phe Ala Ala Ile Asn Arg
65                  70                  75                  80

Arg Asp Leu Tyr Glu Lys Ala Lys Arg Asp Glu Pro Lys Trp Gly Ser
                85                  90                  95

Asp Asn Ala Arg Val Ser Asn Pro Thr Val Ile Cys Gln Glu Asp Ser
            100                 105                 110

Ile Glu Glu Glu Trp Met Gly Leu Leu Glu Tyr Leu Ser Arg Ile Ser
        115                 120                 125

Ile Cys Lys Met Lys Lys Asp Tyr Arg Lys Lys Tyr Arg Lys Tyr Val
    130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
            180                 185                 190

Thr Lys Thr Cys Glu Ser Pro Val Ser Pro Ile Lys Met Glu Leu Leu
        195                 200                 205

Phe Asp Pro Asp Asp Glu His Ser Glu Pro Val His Thr Val Val Phe
    210                 215                 220

Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
                245                 250                 255

Phe Tyr Ile His Cys Arg Glu Val Ser Leu Val Thr Gln Arg Ser Leu
            260                 265                 270

Gly Asp Leu Ile Met Ser Cys Cys Pro Asp Pro Asn Pro Pro Ile His
        275                 280                 285

Lys Ile Val Arg Lys Pro Ser Arg Ile Leu Phe Leu Met Asp Gly Phe
    290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
        355                 360                 365

Glu Ile Leu Gly Phe Ser Glu Ala Lys Arg Lys Glu Tyr Phe Phe Lys
    370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415

Ile Val Cys Thr Gly Leu Lys Gln Gln Met Glu Ser Gly Lys Ser Leu
            420                 425                 430

Ala Gln Thr Ser Lys Thr Thr Thr Ala Val Tyr Val Phe Phe Leu Ser
        435                 440                 445

Ser Leu Leu Gln Pro Arg Gly Gly Ser Gln Glu His Gly Leu Cys Ala
```

```
    450                 455                 460

His Leu Trp Gly Leu Cys Ser Leu Ala Ala Asp Gly Ile Trp Asn Gln
465                 470                 475                 480

Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
        515                 520                 525

Phe Ala Ala Met Tyr Tyr Leu Leu Glu Glu Glu Lys Glu Gly Arg Thr
    530                 535                 540

Asn Val Pro Gly Ser Arg Leu Lys Leu Pro Ser Arg Asp Val Thr Val
545                 550                 555                 560

Leu Leu Glu Asn Tyr Gly Lys Phe Glu Lys Gly Tyr Leu Ile Phe Val
                565                 570                 575

Val Arg Phe Leu Phe Gly Leu Val Asn Gln Glu Arg Thr Ser Tyr Leu
            580                 585                 590

Glu Lys Lys Leu Ser Cys Lys Ile Ser Gln Gln Ile Arg Leu Glu Leu
        595                 600                 605

Leu Lys Trp Ile Glu Val Lys Ala Lys Ala Lys Lys Leu Gln Ile Gln
    610                 615                 620

Pro Ser Gln Leu Glu Leu Phe Tyr Cys Leu Tyr Glu Met Gln Glu Glu
625                 630                 635                 640

Asp Phe Val Gln Arg Ala Met Asp Tyr Phe Pro Lys Ile Glu Ile Asn
                645                 650                 655

Leu Ser Thr Arg Met Asp His Met Val Ser Ser Phe Cys Ile Glu Asn
            660                 665                 670

Cys His Arg Val Glu Ser Leu Ser Leu Gly Phe Leu His Asn Met Pro
        675                 680                 685

Lys Glu Glu Glu Glu Glu Glu Lys Glu Gly Arg His Leu Asp Met Val
    690                 695                 700

Gln Cys Val Leu Pro Ser Ser Ser His Ala Ala Cys Ser His Gly Leu
705                 710                 715                 720

Gly Arg Cys Gly Leu Ser His Glu Cys Cys Phe Asp Ile Ser Leu Val
                725                 730                 735

Leu Ser Ser Asn Gln Lys Leu Val Glu Leu Asp Leu Ser Asp Asn Ala
            740                 745                 750

Leu Gly Asp Phe Gly Ile Arg Leu Leu Cys Val Gly Leu Lys His Leu
        755                 760                 765

Leu Cys Asn Leu Lys Lys Leu Trp Leu Val Ser Cys Cys Leu Thr Ser
    770                 775                 780

Ala Cys Cys Gln Asp Leu Ala Ser Val Leu Ser Thr Ser His Ser Leu
785                 790                 795                 800

Thr Arg Leu Tyr Val Gly Glu Asn Ala Leu Gly Asp Ser Gly Val Ala
                805                 810                 815

Ile Leu Cys Glu Lys Ala Lys Asn Pro Gln Cys Asn Leu Gln Lys Leu
            820                 825                 830

Gly Leu Val Asn Ser Gly Leu Thr Ser Val Cys Cys Ser Ala Leu Ser
        835                 840                 845

Ser Val Leu Ser Thr Asn Gln Asn Leu Thr His Leu Tyr Leu Arg Gly
    850                 855                 860

Asn Thr Leu Gly Asp Lys Gly Ile Lys Leu Leu Cys Glu Gly Leu Leu
865                 870                 875                 880
```

His Pro Asp Cys Lys Leu Gln Val Leu Glu Leu Asp Asn Cys Asn Leu
885 890 895

Thr Ser His Cys Cys Trp Asp Leu Ser Thr Leu Leu Thr Ser Ser Gln
900 905 910

Ser Leu Arg Lys Leu Ser Leu Gly Asn Asn Asp Leu Gly Asp Leu Gly
915 920 925

Val Met Met Phe Cys Glu Val Leu Lys Gln Gln Ser Cys Leu Leu Gln
930 935 940

Asn Leu Gly Leu Ser Glu Met Tyr Phe Asn Tyr Glu Thr Lys Ser Ala
945 950 955 960

Leu Glu Thr Leu Gln Glu Glu Lys Pro Glu Leu Thr Val Val Phe Glu
965 970 975

Pro Ser Trp

<210> SEQ ID NO 39
<211> LENGTH: 979
<212> TYPE: PRT
<213> ORGANISM: Artificial Sequence
<220> FEATURE:
<223> OTHER INFORMATION: NLR family pyrin domain 5

<400> SEQUENCE: 39

Met Lys Met Ala Ser Thr Arg Cys Lys Leu Ala Arg Tyr Leu Glu Asp
1 5 10 15

Leu Glu Asp Val Asp Leu Lys Lys Phe Lys Met His Leu Glu Asp Tyr
20 25 30

Pro Pro Gln Lys Gly Cys Ile Pro Leu Pro Arg Gly Gln Thr Glu Lys
35 40 45

Ala Asp His Val Asp Leu Ala Thr Leu Met Ile Asp Phe Asn Gly Glu
50 55 60

Glu Lys Ala Trp Ala Met Ala Val Trp Ile Phe Ala Ala Ile Asn Arg
65 70 75 80

Arg Asp Leu Tyr Glu Lys Ala Lys Arg Asp Glu Pro Lys Trp Gly Ser
85 90 95

Asp Asn Ala Arg Val Ser Asn Pro Thr Val Ile Cys Gln Glu Asp Ser
100 105 110

Ile Glu Glu Glu Trp Met Gly Leu Leu Glu Tyr Leu Ser Arg Ile Ser
115 120 125

Ile Cys Lys Met Lys Lys Asp Tyr Arg Lys Lys Tyr Arg Lys Tyr Val
130 135 140

Arg Ser Arg Phe Gln Cys Ile Glu Asp Arg Asn Ala Arg Leu Gly Glu
145 150 155 160

Ser Val Ser Leu Asn Lys Arg Tyr Thr Arg Leu Arg Leu Ile Lys Glu
165 170 175

His Arg Ser Gln Gln Glu Arg Glu Gln Glu Leu Leu Ala Ile Gly Lys
180 185 190

Thr Lys Thr Cys Glu Ser Pro Val Ser Pro Ile Lys Met Glu Leu Leu
195 200 205

Phe Asp Pro Asp Asp Glu His Ser Glu Pro Val His Thr Val Val Phe
210 215 220

Gln Gly Ala Ala Gly Ile Gly Lys Thr Ile Leu Ala Arg Lys Met Met
225 230 235 240

Leu Asp Trp Ala Ser Gly Thr Leu Tyr Gln Asp Arg Phe Asp Tyr Leu
245 250 255

-continued

```
Phe Tyr Ile His Cys Arg Glu Val Ser Leu Val Thr Gln Arg Ser Leu
            260                 265                 270

Gly Asp Leu Ile Met Ser Cys Cys Pro Asp Pro Asn Pro Pro Ile His
        275                 280                 285

Lys Ile Val Arg Lys Pro Ser Arg Ile Leu Phe Leu Met Asp Gly Phe
    290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
        355                 360                 365

Glu Ile Leu Gly Phe Ser Glu Ala Lys Arg Lys Glu Tyr Phe Phe Lys
    370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415

Ile Val Cys Thr Gly Leu Lys Gln Gln Met Glu Ser Gly Lys Ser Leu
            420                 425                 430

Ala Gln Thr Ser Lys Thr Thr Thr Ala Val Tyr Val Phe Phe Leu Ser
        435                 440                 445

Ser Leu Leu Gln Pro Arg Gly Gly Ser Gln Glu His Gly Leu Cys Ala
    450                 455                 460

His Leu Trp Gly Leu Cys Ser Leu Ala Ala Asp Gly Ile Trp Asn Gln
465                 470                 475                 480

Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
        515                 520                 525

Phe Ala Ala Met Tyr Tyr Leu Leu Glu Glu Glu Lys Glu Gly Arg Thr
    530                 535                 540

Asn Val Pro Gly Ser Arg Leu Lys Leu Pro Ser Arg Asp Val Thr Val
545                 550                 555                 560

Leu Leu Glu Asn Tyr Gly Lys Phe Glu Lys Gly Tyr Leu Ile Phe Val
                565                 570                 575

Val Arg Phe Leu Phe Gly Leu Val Asn Gln Glu Arg Thr Ser Tyr Leu
            580                 585                 590

Glu Lys Lys Leu Ser Cys Lys Ile Ser Gln Gln Ile Arg Leu Glu Leu
        595                 600                 605

Leu Lys Trp Ile Glu Val Lys Ala Lys Ala Lys Lys Leu Gln Ile Gln
    610                 615                 620

Pro Ser Gln Leu Glu Leu Phe Tyr Cys Leu Tyr Glu Met Gln Glu Glu
625                 630                 635                 640

Asp Phe Val Gln Arg Ala Met Asp Tyr Phe Pro Lys Ile Glu Ile Asn
                645                 650                 655

Leu Ser Thr Arg Met Asp His Met Val Ser Ser Phe Cys Ile Glu Asn
            660                 665                 670

Cys His Arg Val Glu Ser Leu Ser Leu Gly Phe Leu His Asn Met Pro
```

```
        675                 680                 685

Lys Glu Glu Glu Glu Glu Lys Glu Gly Arg His Leu Asp Met Val
    690                 695                 700

Gln Cys Val Leu Pro Ser Ser Ser His Ala Ala Cys Ser His Gly Leu
705                 710                 715                 720

Val Asn Ser His Leu Thr Ser Ser Phe Cys Arg Gly Leu Phe Ser Val
                725                 730                 735

Leu Ser Thr Ser Gln Ser Leu Thr Glu Leu Asp Leu Ser Asp Asn Ser
            740                 745                 750

Leu Gly Asp Pro Gly Met Arg Val Leu Cys Glu Thr Leu Gln His Pro
        755                 760                 765

Gly Cys Asn Ile Arg Arg Leu Trp Leu Gly Arg Cys Gly Leu Ser His
    770                 775                 780

Glu Cys Cys Phe Asp Ile Ser Leu Val Leu Ser Ser Asn Gln Lys Leu
785                 790                 795                 800

Val Glu Leu Asp Leu Ser Asp Asn Ala Leu Gly Asp Phe Gly Ile Arg
                805                 810                 815

Leu Leu Cys Val Gly Leu Lys His Leu Leu Cys Asn Leu Lys Lys Leu
            820                 825                 830

Trp Leu Val Asn Ser Gly Leu Thr Ser Val Cys Cys Ser Ala Leu Ser
        835                 840                 845

Ser Val Leu Ser Thr Asn Gln Asn Leu Thr His Leu Tyr Leu Arg Gly
    850                 855                 860

Asn Thr Leu Gly Asp Lys Gly Ile Lys Leu Leu Cys Glu Gly Leu Leu
865                 870                 875                 880

His Pro Asp Cys Lys Leu Gln Val Leu Glu Leu Asp Asn Cys Asn Leu
                885                 890                 895

Thr Ser His Cys Cys Trp Asp Leu Ser Thr Leu Leu Thr Ser Ser Gln
            900                 905                 910

Ser Leu Arg Lys Leu Ser Leu Gly Asn Asn Asp Leu Gly Asp Leu Gly
        915                 920                 925

Val Met Met Phe Cys Glu Val Leu Lys Gln Gln Ser Cys Leu Leu Gln
    930                 935                 940

Asn Leu Gly Leu Ser Glu Met Tyr Phe Asn Tyr Glu Thr Lys Ser Ala
945                 950                 955                 960

Leu Glu Thr Leu Gln Glu Glu Lys Pro Glu Leu Thr Val Val Phe Glu
                965                 970                 975

Pro Ser Trp


<210> SEQ ID NO 40
<211> LENGTH: 1016
<212> TYPE: PRT
<213> ORGANISM: Artificial Sequence
<220> FEATURE:
<223> OTHER INFORMATION: NLR family pyrin domain 6

<400> SEQUENCE: 40

Met Lys Met Ala Ser Thr Arg Cys Lys Leu Ala Arg Tyr Leu Glu Asp
1               5                   10                  15

Leu Glu Asp Val Asp Leu Lys Lys Phe Lys Met His Leu Glu Asp Tyr
            20                  25                  30

Pro Pro Gln Lys Gly Cys Ile Pro Leu Pro Arg Gly Gln Thr Glu Lys
        35                  40                  45

Ala Asp His Val Asp Leu Ala Thr Leu Met Ile Asp Phe Asn Gly Glu
    50                  55                  60
```

```
Glu Lys Ala Trp Ala Met Ala Val Trp Ile Phe Ala Ala Ile Asn Arg
65                  70                  75                  80

Arg Asp Leu Tyr Glu Lys Ala Lys Arg Asp Glu Pro Lys Trp Gly Ser
                85                  90                  95

Asp Asn Ala Arg Val Ser Asn Pro Thr Val Ile Cys Gln Glu Asp Ser
            100                 105                 110

Ile Glu Glu Glu Trp Met Gly Leu Leu Glu Tyr Leu Ser Arg Ile Ser
        115                 120                 125

Ile Cys Lys Met Lys Lys Asp Tyr Arg Lys Lys Tyr Arg Lys Tyr Val
    130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
            180                 185                 190

Thr Lys Thr Cys Glu Ser Pro Val Ser Pro Ile Lys Met Glu Leu Leu
        195                 200                 205

Phe Asp Pro Asp Asp Glu His Ser Glu Pro Val His Thr Val Val Phe
    210                 215                 220

Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
                245                 250                 255

Phe Tyr Ile His Cys Arg Glu Val Ser Leu Val Thr Gln Arg Ser Leu
            260                 265                 270

Gly Asp Leu Ile Met Ser Cys Cys Pro Asp Pro Asn Pro Pro Ile His
        275                 280                 285

Lys Ile Val Arg Lys Pro Ser Arg Ile Leu Phe Leu Met Asp Gly Phe
    290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
        355                 360                 365

Glu Ile Leu Gly Phe Ser Glu Ala Lys Arg Lys Glu Tyr Phe Phe Lys
    370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415

Ile Val Cys Thr Gly Leu Lys Gln Gln Met Glu Ser Gly Lys Ser Leu
            420                 425                 430

Ala Gln Thr Ser Lys Thr Thr Thr Ala Val Tyr Val Phe Phe Leu Ser
        435                 440                 445

Ser Leu Leu Gln Pro Arg Gly Gly Ser Gln Glu His Gly Leu Cys Ala
    450                 455                 460

His Leu Trp Gly Leu Cys Ser Leu Ala Ala Asp Gly Ile Trp Asn Gln
465                 470                 475                 480
```

```
Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
        515                 520                 525

Phe Ala Ala Met Tyr Tyr Leu Leu Glu Glu Glu Lys Glu Gly Arg Thr
    530                 535                 540

Asn Val Pro Gly Ser Arg Leu Lys Leu Pro Ser Arg Asp Val Thr Val
545                 550                 555                 560

Leu Leu Glu Asn Tyr Gly Lys Phe Glu Lys Gly Tyr Leu Ile Phe Val
                565                 570                 575

Val Arg Phe Leu Phe Gly Leu Val Asn Gln Glu Arg Thr Ser Tyr Leu
            580                 585                 590

Glu Lys Lys Leu Ser Cys Lys Ile Ser Gln Gln Ile Arg Leu Glu Leu
        595                 600                 605

Leu Lys Trp Ile Glu Val Lys Ala Lys Ala Lys Lys Leu Gln Ile Gln
    610                 615                 620

Pro Ser Gln Leu Glu Leu Phe Tyr Cys Leu Tyr Glu Met Gln Glu Glu
625                 630                 635                 640

Asp Phe Val Gln Arg Ala Met Asp Tyr Phe Pro Lys Ile Glu Ile Asn
                645                 650                 655

Leu Ser Thr Arg Met Asp His Met Val Ser Ser Phe Cys Ile Glu Asn
            660                 665                 670

Cys His Arg Val Glu Ser Leu Ser Leu Gly Phe Leu His Asn Met Pro
        675                 680                 685

Lys Glu Glu Glu Glu Glu Glu Lys Glu Gly Arg His Leu Asp Met Val
    690                 695                 700

Gln Cys Val Leu Pro Ser Ser Ser His Ala Ala Cys Ser His Gly Leu
705                 710                 715                 720

Val Asn Ser His Leu Thr Ser Ser Phe Cys Arg Gly Leu Phe Ser Val
                725                 730                 735

Leu Ser Thr Ser Gln Ser Leu Thr Glu Leu Asp Leu Ser Asp Asn Ser
            740                 745                 750

Leu Gly Asp Pro Gly Met Arg Val Leu Cys Glu Thr Leu Gln His Pro
        755                 760                 765

Gly Cys Asn Ile Arg Arg Leu Cys Asn Gln Lys Leu Val Glu Leu Asp
    770                 775                 780

Leu Ser Asp Asn Ala Leu Gly Asp Phe Gly Ile Arg Leu Leu Cys Val
785                 790                 795                 800

Gly Leu Lys His Leu Leu Cys Asn Leu Lys Lys Leu Trp Leu Val Ser
                805                 810                 815

Cys Cys Leu Thr Ser Ala Cys Cys Gln Asp Leu Ala Ser Val Leu Ser
            820                 825                 830

Thr Ser His Ser Leu Thr Arg Leu Tyr Val Gly Glu Asn Ala Leu Gly
        835                 840                 845

Asp Ser Gly Val Ala Ile Leu Cys Glu Lys Ala Lys Asn Pro Gln Cys
    850                 855                 860

Asn Leu Gln Lys Leu Gly Leu Val Asn Ser Gly Leu Thr Ser Val Cys
865                 870                 875                 880

Cys Ser Ala Leu Ser Ser Val Leu Ser Thr Asn Gln Asn Leu Thr His
                885                 890                 895

Leu Tyr Leu Arg Gly Asn Thr Leu Gly Asp Lys Gly Ile Lys Leu Leu
```

```
            900                 905                 910

Cys Glu Gly Leu Leu His Pro Asp Cys Lys Leu Gln Val Leu Glu Leu
        915                 920                 925

Asp Asn Cys Asn Leu Thr Ser His Cys Cys Trp Asp Leu Ser Thr Leu
    930                 935                 940

Leu Thr Ser Ser Gln Ser Leu Arg Lys Leu Ser Leu Gly Asn Asn Asp
945                 950                 955                 960

Leu Gly Asp Leu Gly Val Met Met Phe Cys Glu Val Leu Lys Gln Gln
                965                 970                 975

Ser Cys Leu Leu Gln Asn Leu Gly Leu Ser Glu Met Tyr Phe Asn Tyr
            980                 985                 990

Glu Thr Lys Ser Ala Leu Glu Thr  Leu Gln Glu Glu Lys  Pro Glu Leu
        995                 1000                1005

Thr Val  Val Phe Glu Pro Ser  Trp
    1010                1015
```

<210> SEQ ID NO 41
<211> LENGTH: 15
<212> TYPE: DNA
<213> ORGANISM: Artificial Sequence
<220> FEATURE:
<223> OTHER INFORMATION: STAT6 Antisense Oligonucleotide

<400> SEQUENCE: 41
gaaaggttcc gtcgg 15

<210> SEQ ID NO 42
<211> LENGTH: 16
<212> TYPE: DNA
<213> ORGANISM: Artificial Sequence
<220> FEATURE:
<223> OTHER INFORMATION: STAT6 Antisense Oligonucleotide

<400> SEQUENCE: 42
ggctagtaac gtactg 16

<210> SEQ ID NO 43
<211> LENGTH: 17
<212> TYPE: DNA
<213> ORGANISM: Artificial Sequence
<220> FEATURE:
<223> OTHER INFORMATION: STAT6 Antisense Oligonucleotide

<400> SEQUENCE: 43
gaaaggttcc gtcgggc 17

<210> SEQ ID NO 44
<211> LENGTH: 17
<212> TYPE: DNA
<213> ORGANISM: Artificial Sequence
<220> FEATURE:
<223> OTHER INFORMATION: STAT6 Antisense Oligonucleotide

<400> SEQUENCE: 44
ctgagtcgct gaagcgg 17

<210> SEQ ID NO 45
<211> LENGTH: 20
<212> TYPE: DNA
<213> ORGANISM: Artificial Sequence
<220> FEATURE:
<223> OTHER INFORMATION: STAT6 Antisense Oligonucleotide

<400> SEQUENCE: 45
cgctcacacc gcttgatctt 20

<210> SEQ ID NO 46
<211> LENGTH: 20
<212> TYPE: DNA
<213> ORGANISM: Artificial Sequence
<220> FEATURE:
<223> OTHER INFORMATION: STAT6 Antisense Oligonucleotide

<400> SEQUENCE: 46
agaagaaggc tagtaacgta 20

<210> SEQ ID NO 47
<211> LENGTH: 20
<212> TYPE: DNA
<213> ORGANISM: Artificial Sequence
<220> FEATURE:
<223> OTHER INFORMATION: STAT6 Antisense Oligonucleotide

<400> SEQUENCE: 47
gagaaaggtt ccgtcgggct 20

<210> SEQ ID NO 48
<211> LENGTH: 20
<212> TYPE: DNA
<213> ORGANISM: Artificial Sequence
<220> FEATURE:
<223> OTHER INFORMATION: STAT6 Antisense Oligonucleotide

<400> SEQUENCE: 48
gcaagatccc ggattcggtc 20

<210> SEQ ID NO 49
<211> LENGTH: 20
<212> TYPE: DNA
<213> ORGANISM: Artificial Sequence
<220> FEATURE:
<223> OTHER INFORMATION: STAT6 Antisense Oligonucleotide

<400> SEQUENCE: 49
gtgcgtgtgc gcgctgcagg 20

<210> SEQ ID NO 50
<211> LENGTH: 20
<212> TYPE: DNA
<213> ORGANISM: Artificial Sequence
<220> FEATURE:
<223> OTHER INFORMATION: KRAS Antisense Oligonucleotide

<400> SEQUENCE: 50
gcccttgtac ttttgcatag 20

<210> SEQ ID NO 51
<211> LENGTH: 14
<212> TYPE: DNA
<213> ORGANISM: Artificial Sequence
<220> FEATURE:
<223> OTHER INFORMATION: KRAS Antisense Oligonucleotide

<400> SEQUENCE: 51
ccatcagctc caac 14

<210> SEQ ID NO 52
<211> LENGTH: 14

<212> TYPE: DNA
<213> ORGANISM: Artificial Sequence
<220> FEATURE:
<223> OTHER INFORMATION: KRAS Antisense Oligonucleotide

<400> SEQUENCE: 52
gccatcagct ccaa 14

<210> SEQ ID NO 53
<211> LENGTH: 14
<212> TYPE: DNA
<213> ORGANISM: Artificial Sequence
<220> FEATURE:
<223> OTHER INFORMATION: KRAS Antisense Oligonucleotide

<400> SEQUENCE: 53
cgccatcagc tcca 14

<210> SEQ ID NO 54
<211> LENGTH: 15
<212> TYPE: DNA
<213> ORGANISM: Artificial Sequence
<220> FEATURE:
<223> OTHER INFORMATION: KRAS Antisense Oligonucleotide

<400> SEQUENCE: 54
ccatcagctc caact 15

<210> SEQ ID NO 55
<211> LENGTH: 15
<212> TYPE: DNA
<213> ORGANISM: Artificial Sequence
<220> FEATURE:
<223> OTHER INFORMATION: KRAS Antisense Oligonucleotide

<400> SEQUENCE: 55
gccatcagct ccaac 15

<210> SEQ ID NO 56
<211> LENGTH: 15
<212> TYPE: DNA
<213> ORGANISM: Artificial Sequence
<220> FEATURE:
<223> OTHER INFORMATION: KRAS Antisense Oligonucleotide

<400> SEQUENCE: 56
cgccatcagc tccaa 15

<210> SEQ ID NO 57
<211> LENGTH: 16
<212> TYPE: DNA
<213> ORGANISM: Artificial Sequence
<220> FEATURE:
<223> OTHER INFORMATION: KRAS Antisense Oligonucleotide

<400> SEQUENCE: 57
ccatcagctc caacta 16

<210> SEQ ID NO 58
<211> LENGTH: 16
<212> TYPE: DNA
<213> ORGANISM: Artificial Sequence
<220> FEATURE:
<223> OTHER INFORMATION: KRAS Antisense Oligonucleotide

<400> SEQUENCE: 58
gccatcagct ccaact 16

<210> SEQ ID NO 59
<211> LENGTH: 16
<212> TYPE: DNA
<213> ORGANISM: Artificial Sequence
<220> FEATURE:
<223> OTHER INFORMATION: KRAS Antisense Oligonucleotide

<400> SEQUENCE: 59
cgccatcagc tccaac 16

<210> SEQ ID NO 60
<211> LENGTH: 16
<212> TYPE: DNA
<213> ORGANISM: Artificial Sequence
<220> FEATURE:
<223> OTHER INFORMATION: KRAS Antisense Oligonucleotide

<400> SEQUENCE: 60
acgccatcag ctccaa 16

<210> SEQ ID NO 61
<211> LENGTH: 17
<212> TYPE: DNA
<213> ORGANISM: Artificial Sequence
<220> FEATURE:
<223> OTHER INFORMATION: NRAS Antisense Oligonucleotide

<400> SEQUENCE: 61
gcctacgcca tcagctc 17

<210> SEQ ID NO 62
<211> LENGTH: 15
<212> TYPE: DNA
<213> ORGANISM: Artificial Sequence
<220> FEATURE:
<223> OTHER INFORMATION: NRAS Antisense Oligonucleotide

<400> SEQUENCE: 62
ggattgtcag tgcgc 15

<210> SEQ ID NO 63
<211> LENGTH: 15
<212> TYPE: DNA
<213> ORGANISM: Artificial Sequence
<220> FEATURE:
<223> OTHER INFORMATION: NRAS Antisense Oligonucleotide

<400> SEQUENCE: 63
attcggtact ggcgt 15

<210> SEQ ID NO 64
<211> LENGTH: 20
<212> TYPE: DNA
<213> ORGANISM: Artificial Sequence
<220> FEATURE:
<223> OTHER INFORMATION: NRAS Antisense Oligonucleotide

<400> SEQUENCE: 64
ggattgtcag tgcgcttttc 20

<210> SEQ ID NO 65
<211> LENGTH: 20
<212> TYPE: DNA
<213> ORGANISM: Artificial Sequence
<220> FEATURE:
<223> OTHER INFORMATION: NRAS Antisense Oligonucleotide

<400> SEQUENCE: 65
gacttgctat tattgatggc 20

<210> SEQ ID NO 66
<211> LENGTH: 20
<212> TYPE: DNA
<213> ORGANISM: Artificial Sequence
<220> FEATURE:
<223> OTHER INFORMATION: NRAS Antisense Oligonucleotide

<400> SEQUENCE: 66
tactcgctta atctgctccc 20

<210> SEQ ID NO 67
<211> LENGTH: 20
<212> TYPE: DNA
<213> ORGANISM: Artificial Sequence
<220> FEATURE:
<223> OTHER INFORMATION: NRAS Antisense Oligonucleotide

<400> SEQUENCE: 67
atcaactgtc cttgttggca 20

<210> SEQ ID NO 68
<211> LENGTH: 20
<212> TYPE: DNA
<213> ORGANISM: Artificial Sequence
<220> FEATURE:
<223> OTHER INFORMATION: NRAS Antisense Oligonucleotide

<400> SEQUENCE: 68
gcgtatttct cttaccagtg 20

<210> SEQ ID NO 69
<211> LENGTH: 20
<212> TYPE: DNA
<213> ORGANISM: Artificial Sequence
<220> FEATURE:
<223> OTHER INFORMATION: NRAS Antisense Oligonucleotide

<400> SEQUENCE: 69 gtttttcat tcggtactgg 20

<210> SEQ ID NO 70
<211> LENGTH: 20
<212> TYPE: DNA
<213> ORGANISM: Artificial Sequence
<220> FEATURE:
<223> OTHER INFORMATION: NRAS Antisense Oligonucleotide

<400> SEQUENCE: 70
aacagggagt aacaagaggt 20

<210> SEQ ID NO 71
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 71
cagttgctac tttagagctc 20

<210> SEQ ID NO 72
<211> LENGTH: 17
<212> TYPE: DNA
<213> ORGANISM: Artificial Sequence
<220> FEATURE:
<223> OTHER INFORMATION: PMP22 Antisense Oligonucleotide

<400> SEQUENCE: 72
caaacagcgt aacccct 17

<210> SEQ ID NO 73
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 73
agcaccgcga cgtggaggac 20

<210> SEQ ID NO 74
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 74
tggacagact gcagccattc 20

<210> SEQ ID NO 75
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 75
gtaaaacctg cccccttgg 20

<210> SEQ ID NO 76
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 76
ctcattcgcg tttccgcaag 20

<210> SEQ ID NO 77
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 77
ctttaaggct caacacgagg 20

<210> SEQ ID NO 78
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 78
ttggggtttc tacccacact 20

<210> SEQ ID NO 79
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 79
cacctgtaag ggcaagtatg 20

<210> SEQ ID NO 80
<211> LENGTH: 20
<212> TYPE: DNA
<213> ORGANISM: Artificial Sequence
<220> FEATURE:
<223> OTHER INFORMATION: PMP22 Antisense Oligonucleotide

<400> SEQUENCE: 80
tccagtgagt tgtttagatg 20

<210> SEQ ID NO 81
<211> LENGTH: 20
<212> TYPE: DNA
<213> ORGANISM: Artificial Sequence
<220> FEATURE:
<223> OTHER INFORMATION: C/EBPBeta Antisense Oligonucleotide

<400> SEQUENCE: 81
tcacggtccc aaggagtcta 20

<210> SEQ ID NO 82
<211> LENGTH: 15
<212> TYPE: DNA
<213> ORGANISM: Artificial Sequence
<220> FEATURE:
<223> OTHER INFORMATION: C/EBPBeta Antisense Oligonucleotide

<400> SEQUENCE: 82
gctcgtggtc gccga 15

<210> SEQ ID NO 83
<211> LENGTH: 15
<212> TYPE: DNA
<213> ORGANISM: Artificial Sequence
<220> FEATURE:
<223> OTHER INFORMATION: C/EBPBeta Antisense Oligonucleotide

<400> SEQUENCE: 83
cgtagtcgtc ggaga 15

<210> SEQ ID NO 84
<211> LENGTH: 16
<212> TYPE: DNA
<213> ORGANISM: Artificial Sequence
<220> FEATURE:
<223> OTHER INFORMATION: C/EBPBeta Antisense Oligonucleotide

<400> SEQUENCE: 84
tcgtggtcgc cgatgc 16

<210> SEQ ID NO 85

<211> LENGTH: 16
<212> TYPE: DNA
<213> ORGANISM: Artificial Sequence
<220> FEATURE:
<223> OTHER INFORMATION: C/EBPBeta Antisense Oligonucleotide

<400> SEQUENCE: 85
tcgcgccgga tcttgt 16

<210> SEQ ID NO 86
<211> LENGTH: 17
<212> TYPE: DNA
<213> ORGANISM: Artificial Sequence
<220> FEATURE:
<223> OTHER INFORMATION: C/EBPBeta Antisense Oligonucleotide

<400> SEQUENCE: 86
cgctcgtggt cgccgat 17

<210> SEQ ID NO 87
<211> LENGTH: 17
<212> TYPE: DNA
<213> ORGANISM: Artificial Sequence
<220> FEATURE:
<223> OTHER INFORMATION: C/EBPBeta Antisense Oligonucleotide

<400> SEQUENCE: 87
ccgtagtcgt cggagaa 17

<210> SEQ ID NO 88
<211> LENGTH: 17
<212> TYPE: DNA
<213> ORGANISM: Artificial Sequence
<220> FEATURE:
<223> OTHER INFORMATION: C/EBPBeta Antisense Oligonucleotide

<400> SEQUENCE: 88
tgcccccgta gtcgtcg 17

<210> SEQ ID NO 89
<211> LENGTH: 17
<212> TYPE: DNA
<213> ORGANISM: Artificial Sequence
<220> FEATURE:
<223> OTHER INFORMATION: C/EBPBeta Antisense Oligonucleotide

<400> SEQUENCE: 89
cggatcttgt actcgtc 17

<210> SEQ ID NO 90
<211> LENGTH: 20
<212> TYPE: DNA
<213> ORGANISM: Artificial Sequence
<220> FEATURE:
<223> OTHER INFORMATION: C/EBPBeta Antisense Oligonucleotide

<400> SEQUENCE: 90
taagcgcgca gcgcgtacgg 20

<210> SEQ ID NO 91
<211> LENGTH: 20
<212> TYPE: DNA
<213> ORGANISM: Artificial Sequence
<220> FEATURE:
<223> OTHER INFORMATION: STAT3 Antisense Oligonucleotide

<400> SEQUENCE: 91
cgcgccggat cttgtactcg 20

<210> SEQ ID NO 92
<211> LENGTH: 15
<212> TYPE: DNA
<213> ORGANISM: Artificial Sequence
<220> FEATURE:
<223> OTHER INFORMATION: STAT3 Antisense Oligonucleotide

<400> SEQUENCE: 92
atttgttgac gggtc 15

<210> SEQ ID NO 93
<211> LENGTH: 15
<212> TYPE: DNA
<213> ORGANISM: Artificial Sequence
<220> FEATURE:
<223> OTHER INFORMATION: STAT3 Antisense Oligonucleotide

<400> SEQUENCE: 93
cgacaatact ttccg 15

<210> SEQ ID NO 94
<211> LENGTH: 16
<212> TYPE: DNA
<213> ORGANISM: Artificial Sequence
<220> FEATURE:
<223> OTHER INFORMATION: STAT3 Antisense Oligonucleotide

<400> SEQUENCE: 94
gaactggacg ccggtc 16

<210> SEQ ID NO 95
<211> LENGTH: 16
<212> TYPE: DNA
<213> ORGANISM: Artificial Sequence
<220> FEATURE:
<223> OTHER INFORMATION: STAT3 Antisense Oligonucleotide

<400> SEQUENCE: 95
cacaattggc tcggcc 16

<210> SEQ ID NO 96
<211> LENGTH: 20
<212> TYPE: DNA
<213> ORGANISM: Artificial Sequence
<220> FEATURE:
<223> OTHER INFORMATION: STAT3 Antisense Oligonucleotide

<400> SEQUENCE: 96
cgtagattgt gctgatagag 20

<210> SEQ ID NO 97
<211> LENGTH: 20
<212> TYPE: DNA
<213> ORGANISM: Artificial Sequence
<220> FEATURE:
<223> OTHER INFORMATION: STAT3 Antisense Oligonucleotide

<400> SEQUENCE: 97
gccacaatcc gggcaatctc 20

<210> SEQ ID NO 98
<211> LENGTH: 20
<212> TYPE: DNA

<213> ORGANISM: Artificial Sequence
<220> FEATURE:
<223> OTHER INFORMATION: STAT3 Antisense Oligonucleotide

<400> SEQUENCE: 98
agttttctag ccgatctagg 20

<210> SEQ ID NO 99
<211> LENGTH: 20
<212> TYPE: DNA
<213> ORGANISM: Artificial Sequence
<220> FEATURE:
<223> OTHER INFORMATION: STAT3 Antisense Oligonucleotide

<400> SEQUENCE: 99
cgacaatact ttccgaatgc 20

<210> SEQ ID NO 100
<211> LENGTH: 20
<212> TYPE: DNA
<213> ORGANISM: Artificial Sequence
<220> FEATURE:
<223> OTHER INFORMATION: STAT3 Antisense Oligonucleotide

<400> SEQUENCE: 100
aggtaggcgc ctcagtcgta 20

<210> SEQ ID NO 101
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 101
caggtaggcg cctcagtcgt 20

<210> SEQ ID NO 102
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 102
ctccgagagt gttgcctcgc 20

<210> SEQ ID NO 103
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 103
gtaaaggtgc gtgagattct 20

<210> SEQ ID NO 104
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 104
gtcgaagcag cactcatgcg 20

<210> SEQ ID NO 105
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 105
agtccatggc cctttgcacg 20

<210> SEQ ID NO 106
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 106
gcagtgtgac gtgaggttgc 20

<210> SEQ ID NO 107
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 107
cgagagtgtt gcctcgcagg 20

<210> SEQ ID NO 108
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 108
atcgcagcga agatccacac 20

<210> SEQ ID NO 109
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 109
atcttaatgg gactcacggg 20

<210> SEQ ID NO 110
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 110
gatctccaca tgccgaggat 20

<210> SEQ ID NO 111
<211> LENGTH: 20
<212> TYPE: DNA
<213> ORGANISM: Artificial Sequence
<220> FEATURE:

-continued

```
<223> OTHER INFORMATION: NLRP3 Antisense Oligonucleotide

<400> SEQUENCE: 111

tccgagagtg ttgcctcgca                                              20


<210> SEQ ID NO 112
<211> LENGTH: 20
<212> TYPE: DNA
<213> ORGANISM: Artificial Sequence
<220> FEATURE:
<223> OTHER INFORMATION: NLRP3 Antisense Oligonucleotide

<400> SEQUENCE: 112

tggttgctgc tgaggaccaa                                              20
```

METHODS OF LOADING EXTRACELLULAR VESICLES

CROSS-REFERENCE TO RELATED APPLICATION

This PCT application claims the priority benefit of U.S. Provisional Application No. 63/150,497, filed on Feb. 17, 2021, which is herein incorporated by reference in its entirety.

REFERENCE TO SEQUENCE LISTING SUBMITTED ELECTRONICALLY VIA EFS-WEB

The content of the electronically submitted sequence listing (Name: 4000_126PC02_Seqlisting_ST25.txt, Size: 464,866 bytes; and Date of Creation: Feb. 17, 2022) submitted in this application is incorporated herein by reference in its entirety.

FIELD OF DISCLOSURE

The present disclosure relates to methods of loading an extracellular vesicle (EV) with a payload (e.g., antisense oligonucleotides). In some aspects, the methods comprise modulating one or more of the following during the loading process: salt concentration, temperature, loading time, and feed concentrations. The present disclosure also relates to EVs (e.g., exosomes) comprising a payload, wherein the payload is loaded using the methods described herein.

BACKGROUND OF DISCLOSURE

Many bioactive compounds have potent biological activity that is of therapeutic interest. However, these compounds often exhibit toxicity in non-target organs. One way to limit exposure of non-target tissues is to chemically conjugate small molecules to affinity-based reagents such as antibodies, which can direct the therapeutic compound to specific cell types (Dosio, F. et al., *Toxins* (*Basel*) 3 (7): 848-883 (2011)), but this approach is limited by the number of molecules of the compound of interest that can be attached to an antibody (typically 2-6 molecules per antibody), and by the availability/existence of antibodies that specifically bind to targeted, relevant diseased/effector cells without binding to non-target cells. These two issues limit the use of antibody-drug conjugates (ADC) by decreasing potency and increasing systemic toxicity, respectively. Accordingly, there is a need for delivery systems with a higher payload than ADCs that can selectively target specific tissues or organs while at the same time limiting overall systemic exposure to the therapeutic compound.

EVs are important mediators of intercellular communication. As drug delivery vehicles, EVs offer many advantages over traditional drug delivery methods (e.g., peptide immunization, DNA vaccines) as a new treatment modality in many therapeutic areas. However, despite its advantages, many EVs have had limited clinical efficacy. For example, dendritic-cell derived exosomes (DEX) were investigated in a Phase II clinical trial as maintenance immunotherapy after first line chemotherapy in patients with inoperable non-small cell lung cancer (NSCLC). However, the trial was terminated because the primary endpoint (at least 50% of patients with progression-free survival (PFS) at 4 months after chemotherapy cessation) was not reached. Besse, B., et al., *Oncoimmunology* 5 (4): c1071008 (2015).

Accordingly, new and more effective engineered EVs (e.g., comprising greater payload concentration) are necessary to better enable therapeutic use and other applications of EV-based technologies.

BRIEF SUMMARY OF THE DISCLOSURE

Provided herein is a method of loading a payload to an extracellular vesicle comprising mixing the payload with the extracellular vesicle in a loading buffer comprising a salt at a concentration lower than about 200 mM, about 190 mM, about 180 mM, about 170 mM, about 160 mM, about 150 mM, about 140 mM, about 130 mM, about 120 mM, or about 110 mM.

In some aspects, the salt concentration is between about 1 mM and about 150 mM, between about 5 mM and about 150 mM, between about 10 mM and about 150 mM, between about 20 mM and about 150 mM, between about 30 mM and about 150 mM, between about 40 mM and about 150 mM, between about 50 mM and about 150 mM, between about 60 mM and about 150 mM, between about 70 mM and about 150 mM, between about 80 mM and about 150 mM, between about 10 mM and about 130 mM, between about 20 mM and about 130 mM, between about 30 mM and about 130 mM, between about 40 mM and about 130 mM, between about 50 mM and about 130 mM, between about 10 mM and about 120 mM, between about 20 mM and about 120 mM, between about 30 mM and about 120 mM, between about 40 mM and about 120 mM, between about 50 mM and about 120 mM, between about 60 mM and about 120 mM, between about 70 mM and about 120 mM, between about 80 mM and about 120 mM, between about 50 mM and about 100 mM, between about 100 mM and about 150 mM, or between about 90 mM and about 110 mM. In certain aspects, the salt concentration is about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 m, about 180 mM, or about 190 mM. In some aspects, the salt concentration is about 50 mM, about 60 mM, about 70 mM, about 80 mM, about 90 mM, about 100 mM, about 110 mM, about 120 mM, about 130 mM, about 140 mM, or about 150 mM.

Also provided herein is a method of loading a payload to an extracellular vesicle comprising mixing the payload with the extracellular vesicle in a loading buffer comprising a salt at a concentration between about 200 mM and about 450 mM. In some aspects, the salt concentration is about 200 mM, about 250 mM, about 300 mM, about 350 mM, about 400 mM, or about 450 mM.

For any of the methods provided above, in some aspects, the salt comprises NaCl (sodium chloride), KCl (potassium chloride), $PO_4$ (phosphate salt), $CaCl_2$) (calcium chloride), $MgCl_2$ (magnesium chloride), $Mg_2SO_4$ (magnesium sulfate), $ZnCl_2$ (zinc chloride), $MnCl_2$ (manganese chloride), $MnSO_4$ (manganese sulfate), NaSCN (sodium thiocyanate), KSCN (potassium thiocyanate), LiCl (lithium chloride), $K_2HPO_4$ (dipotassium phosphate), $Na_2SO_4$ (sodium sulfate), $NaPO_4$ (sodium phosphate), $K_2SO_4$ (potassium phosphate), sodium acetate, sodium bromide, sodium iodide, potassium bromide, lithium bromide, sodium fluoride, potassium fluoride, lithium fluoride, lithium iodide, potassium acetate, lithium acetate, potassium iodide, calcium sulfate, sodium sulfate, chromium trichloride, chromium sulfate, sodium citrate, iron (III) chloride, yttrium (III) chloride, potassium sulfate, ferrous chloride, calcium citrate, magnesium phosphate, ferric chloride, arginine-HCl, or any combination thereof. In some aspects, the buffer comprising the salt increases the loading of the payload to the EV by at least about 2 fold, at least about 3 fold, at least about 4 fold, at least about 5 fold, at least about 6 fold, at least about 7 fold, at least about 8 fold, at least about 9 fold, at least about 10 fold, at least about 12 fold, at least about 14 fold, at least about 16 fold, at least about 18 fold, at least about 20 fold, at least about 25-fold, at least about 30-fold, at least about 35-fold, at least about 40-fold, at least about 45-fold, or at least about 50-fold or more compared to a corresponding loading buffer without the salt or with a lower concentration of the salt.

Provided herein is a method of loading a payload to an extracellular vesicle comprising mixing the payload with the extracellular vesicle at a loading temperature higher than 4° C.

In some aspects, the loading temperature is between about 5° C. and about 40° C., between about 10° C. and about 40° C., between about 15° C. and about 40° C., between about 20° C. and about 40° C., between about 25° C. and about 40° C., between about 30° C. and about 40° C., between about 35° C. and about 40° C., between about 5° C. and about 38° C., between about 10° C. and about 38° C., between about 15° C. and about 38° C., between about 20° C. and about 38° C., between about 25° C. and about 38° C., between about 30° C. and about 38° C., between about 35° C. and about 38° C., between about 5° C. and about 37° C., between about 10° C. and about 37° C., between about 15° C. and about 37° C., between about 20° C. and about 37° C., between about 25° C. and about 37° C., between about 30° C. and about 37° C., or between about 35° C. and about 37° C. In certain aspects, the loading temperature is about 5° C., about 10° C., about 15° C., about 20° C., about 25° C., about 30° C., about 35° C., about 37° C., about 40° C., about 50° C., about 55° C., about 60° C., about 65° C., or about 70° C.

In some aspects, the loading temperature increases the loading of the payload to the EV by at least about 2 fold, at least about 3 fold, at least about 4 fold, at least about 5 fold, at least about 6 fold, at least about 7 fold, at least about 8 fold, at least about 9 fold, at least about 10 fold, at least about 12 fold, at least about 14 fold, at least about 16 fold, at least about 18 fold, at least about 20 fold, at least about 15-fold, at least about 20-fold, at least about 25-fold, at least about 30-fold, at least about 35-fold, at least about 40-fold, at least about 45-fold, or at least about 50-fold or more compared to the loading at a reference temperature, which is lower than the loading temperature.

Provided herein is a method of loading a payload to an extracellular vesicle comprising mixing the payload with the extracellular vesicle for a loading duration longer than about one hour.

In some aspects, the loading duration is between about one hour and about 48 hours, between about one hour and about 42 hours, between about one hour and about 36 hours, between about one hour and about 30 hours, between about one hour and about 24 hours, between about six hours and about 48 hours, between about six hours and about 42 hours, between about six hours and about 36 hours, between about six hours and about 30 hours, between about six hours and about 24 hours, between about 12 hours and about 48 hours, between about 12 hours and about 42 hours, between about 12 hours and about 36 hours, between about 12 hours and about 30 hours, or between about 12 hours and about 24 hours. In certain aspects, the loading duration is about 6 hours, about 12 hours, about 24 hours, about 30 hours, about 36 hours, about 42 hours, about 48 hours, about three days, about four days, about five days, about six days, or about seven days.

In some aspects, the loading duration increases the loading of the payload to the EV by at least about 2 fold, at least about 3 fold, at least about 4 fold, at least about 5 fold, at least about 6 fold, at least about 7 fold, at least about 8 fold, at least about 9 fold, or at least about 10 fold, at least about 12 fold, at least about 14 fold, at least about 16 fold, at least about 18 fold, at least about 20 fold, at least about 25-fold, at least about 30-fold, at least about 35-fold, at least about 40-fold, at least about 45-fold, or at least about 50-fold or more compared to the loading for a reference duration, which is shorter than the loading duration.

Also provided herein is a method of loading a payload to an extracellular vesicle comprising mixing the payload with the extracellular vesicle in a loading buffer comprising a salt at a concentration lower than 200 mM, at a loading temperature between about 5° C. and about 50° C., and for a loading duration between one hour to about 48 hours.

In some aspects, the salt concentration is between about 1 mM and about 150 mM, between about 5 mM and about 150 mM, between about 10 mM and about 150 mM, between about 20 mM and about 150 mM, between about 30 mM and about 150 mM, between about 40 mM and about 150 mM, between about 50 mM and about 150 mM, between about 60 mM and about 150 mM, between about 70 mM and about 150 mM, between about 80 mM and about 150 mM, between about 10 mM and about 130 mM, between about 20 mM and about 130 mM, between about 30 mM and about 130 mM, between about 40 mM and about 130 mM, between about 50 mM and about 130 mM, between about 10 mM and about 120 mM, between about 20 mM and about 120 mM, between about 30 mM and about 120 mM, between about 40 mM and about 120 mM, between about 50 mM and about 120 mM, between about 60 mM and about 120 mM, between about 70 mM and about 120 mM, between about 80 mM and about 120 mM, between about 50 mM and about 100 mM, between about 100 mM and about 150 mM, or between about 90 mM and about 110 mM. In certain aspects, the salt concentration is about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 m, about 180 mM, or about 190 mM. In some aspects, the salt concentration is about 50 mM, about 60 mM, about 70 mM, about 80 mM, about 90 mM, about 100 mM, about 110 mM, about 120 mM, about 130 mM, about 140 mM, or about 150 mM.

In some aspects, salt comprises NaCl (sodium chloride), KCl (potassium chloride), $PO_4$ (phosphate salt), $CaCl_2$) (calcium chloride), $MgCl_2$ (magnesium chloride), $Mg_2SO_4$ (magnesium sulfate), $ZnCl_2$ (zinc chloride), $MnCl_2$ (manganese chloride), $MnSO_4$ (manganese sulfate), NaSCN (sodium thiocyanate), KSCN (potassium thiocyanate), LiCl (lithium chloride), $K_2HPO_4$ (dipotassium phosphate), $Na_2SO_4$ (sodium sulfate), $NaPO_4$ (sodium phosphate), $K_2SO_4$ (potassium phosphate), sodium acetate, sodium bromide, sodium iodide, potassium bromide, lithium bromide, sodium fluoride, potassium fluoride, lithium fluoride, lithium iodide, potassium acetate, lithium acetate, potassium iodide, calcium sulfate, sodium sulfate, chromium trichloride, chromium sulfate, sodium citrate, iron (III) chloride, yttrium (III) chloride, potassium sulfate, ferrous chloride, calcium citrate, magnesium phosphate, ferric chloride, arginine-HCl, or any combination thereof.

In some aspects, the loading temperature is between about 5° C. and about 40° C., between about 10° C. and about 40° C., between about 15° C. and about 40° C., between about 20° C. and about 40° C., between about 25° C. and about 40° C., between about 30° C. and about 40° C., between about 35° C. and about 40° C., between about 5° C. and about 38° C., between about 10° C. and about 38° C., between about 15° C. and about 38° C., between about 20° C. and about 38° C., between about 25° C. and about 38° C., between about 30° C. and about 38° C., between about 35° C. and about 38° C., between about 5° C. and about 37° C., between about 10° C. and about 37° C., between about 15° C. and about 37° C., between about 20° C. and about 37° C., between about 25° C. and about 37° C., between about 30° C. and about 37° C., or between about 35° C. and about 37° C. In certain aspects, the loading temperature is about 5° C., about 10° C., about 15° C., about 20° C., about 25° C., about 30° C., about 35° C., about 37° C., about 40° C., or about 50° C.

In some aspects, the loading duration is between about one hour and about 48 hours, between about one hour and about 42 hours, between about one hour and about 36 hours, between about one hour and about 30 hours, between about one hour and about 24 hours, between about six hours and about 48 hours, between about six hours and about 42 hours, between about six hours and about 36 hours, between about six hours and about 30 hours, between about six hours and about 24 hours, between about 12 hours and about 48 hours, between about 12 hours and about 42 hours, between about 12 hours and about 36 hours, between about 12 hours and about 30 hours, or between about 12 hours and about 24 hours. In certain aspects, the loading duration is about 6 hours, about 12 hours, about 24 hours, about 30 hours, about 36 hours, about 42 hours, or about 48 hours.

In some aspects, the salt concentration is between about 50 mM and about 150 mM, the loading temperature is between about 30° C. and about 40° C., and the loading duration is between about 20 hours and about 30 hours. In some aspects, the salt concentration is between about 50 mM and about 150 mM, the loading temperature is between about 30° C. and about 40° C., and the loading duration is between about 12 hours and about 30 hour.

The present disclosure further provides a method of loading a payload to an extracellular vesicle comprising mixing the payload with the extracellular vesicle in a loading buffer comprising a salt at a concentration of about 100 mM, at a loading temperature of about 37° C., and for a loading duration of about 24 hours.

In some aspects, the loading at the salt concentration at the loading temperature for the loading duration increases loading of the payload to the extracellular vesicle by at least about 2 fold, at least about 3 fold, at least about 4 fold, at least about 5 fold, at least about 6 fold, at least about 7 fold, at least about 8 fold, at least about 9 fold, at least about 10 fold, at least about 12 fold, at least about 14 fold, at least about 16 fold, at least about 18 fold, at least about 20 fold, at least about 25-fold, at least about 30-fold, at least about 35-fold, at least about 40-fold, at least about 45-fold, or at least about 50-fold or more compared to the loading without the salt, at a temperature of 4° C., and/or for a duration of one hour.

Also provided herein is a method of loading a payload to an extracellular vesicle comprising mixing the payload with the extracellular vesicle in a loading buffer comprising a salt at a concentration of between about 150 mM and about 450 mM, at a loading temperature of between about 37° C. to about 70° C., and for a loading duration between about 24 hours and about seven days. In some aspects, the salt concentration is about 150 mM, about 200 mM, about 250 mM, about 300 mM, about 350 mM, about 400 mM, or about 450 mM. In some aspects, the salt comprises NaCl (sodium chloride), KCl (potassium chloride), $PO_4$ (phosphate salt), $CaCl_2$) (calcium chloride), $MgCl_2$ (magnesium chloride), $Mg_2SO_4$ (magnesium sulfate), $ZnCl_2$ (zinc chloride), $MnCl_2$ (manganese chloride), $MnSO_4$ (manganese sulfate), NaSCN (sodium thiocyanate), KSCN (potassium thiocyanate), LiCl (lithium chloride), $K_2HPO_4$ (dipotassium phosphate), $Na_2SO_4$ (sodium sulfate), $NaPO_4$ (sodium phosphate), $K_2SO_4$ (potassium phosphate), sodium acetate, sodium bromide, sodium iodide, potassium bromide, lithium bromide, sodium fluoride, potassium fluoride, lithium fluoride, lithium iodide, potassium acetate, lithium acetate, potassium iodide, calcium sulfate, sodium sulfate, chromium trichloride, chromium sulfate, sodium citrate, iron (III) chloride, yttrium (III) chloride, potassium sulfate, ferrous chloride, calcium citrate, magnesium phosphate, ferric chloride, arginine-HCl, or any combination thereof.

For the methods described in the above paragraph, in some aspects, the loading temperature is about 37° C., about 40° C., about 45° C., about 50° C., about 55° C., about 60° C., about 65° C., or about 70° C. In some aspects, the loading duration is about 24 hours, about two days, about three days, about four days, about five days, about six days, or about seven days.

For any of the methods provided above, in some aspects, the method further comprises, after the mixing, measuring the amount of payload loaded to the EVs and determining the load density of the EVs. In some aspects, one or more loading parameters are adjusted to further increase the load density of the EVs, and wherein the one or more loading parameters are selected from: a salt concentration of the loading buffer, loading temperature, loading duration, payload feed concentration, EV feed concentration, or a combination thereof. In some aspects, the amount of payload loaded to the EVs is measured using particle counters, nanoparticle tracking analysis (NTA), ultraviolet adsorption, visible adsorption, fluorescence, near infrared, infrared, static light scattering, dynamic light scattering, obscuration, Raman spectroscopy, turbidity, or a combination thereof.

Also provided herein is a method of decreasing the dissociation of a payload from an extracellular vesicle (EV) after EV loading comprising loading the payload to the EV according to any of the loading methods provided herein (e.g., such as those provided above). In some aspects, the dissociation of the payload from the EV is reduced by at least about 10%, at least about 20%, at least about 30%, at least about 40%, at least about 50%, at least about 60%, at least about 70%, at least about 80%, at least about 90%, or about 100% compared to the corresponding dissociation observed when the payload is not loaded to the EV according to any of the loading methods provided herein.

Provided herein is a method of increasing the stability of an extracellular vesicle (EV) loaded with a payload comprising loading the payload to the EV according to any of the loading methods provided herein. In some aspects, the stability of the EV loaded with the payload is increased by at least about at least about 1 fold, at least about 2 fold, at least about 3 fold, at least about 4 fold, at least about 5 fold, at least about 6 fold, at least about 7 fold, at least about 8 fold, at least about 9 fold, at least about 10 fold, at least about 12 fold, at least about 14 fold, at least about 16 fold, at least about 18 fold, at least about 20 fold, at least about 25-fold, at least about 30-fold, at least about 35-fold, at least about 40-fold, at least about 45-fold, or at least about 50-fold or more compared to the corresponding stability observed when the payload is not loaded to the EV according to any of the loading methods of the present disclosure.

Present disclosure further provides a method of improving one or more properties of an extracellular vesicle after loading with a payload comprising loading the payload to the EV according to any of the loading methods provided herein. In some aspects, the one or more properties comprise: inter-particle interaction, particle rigidity, particle size, or a combination thereof. In some aspects, the improvement in the one or more properties allow for increased filterability of the EV.

For any of the methods provided above, in some aspects, the loading buffer further comprises one or more components. In certain aspects, the one or more components comprise tris, sucrose, glucose, trehalose, mannose, sorbitol, mannitol, glycerol, histidine, arginine, methionine, tryptophan, tyrosine, sodium phosphate, potassium phosphate, polymers, surfactants (e.g., polysorbates 80 and 20), chelating agents (e.g., EDTA, citrate), inorganic acids, or any combination thereof.

In some aspects, the loading buffer further comprises sucrose. In certain aspects, the sucrose is at a concentration lower than about 10% w/v, lower than about 9% w/v, lower than about 8% w/v, lower than about 7% w/v, lower than about 6% w/v, lower than about 5% w/v, lower than about 4% w/v, lower than about 3% w/v, or lower than about 2.5% w/v. In some aspects, the sucrose is at a concentration between about 1% w/v and about 10% w/v, between about 2% w/v and about 10% w/v, between about 3% w/v and about 10% w/v, between about 4% w/v and about 10% w/v, between about 5% w/v and about 10% w/v, between about 1% w/v and about 8% w/v, between about 2% w/v and about 8% w/v, between about 3% w/v and about 8% w/v, between about 4% w/v and about 8% w/v, between about 5% w/v and about 8% w/v, between about 1% w/v and about 5% w/v, between about 2% w/v and about 5% w/v, between about 3% w/v and about 5% w/v, between about 4% w/v and about 5% w/v, or between about 5% w/v and about 6% w/v.

In some aspects, the loading buffer is at an osmolarity between about 100 and about 600 mOsm/kg. In some aspects, the loading buffer is at an osmolarity between about 275 and about 450, between about 280 and about 450, between about 300 and about 450, between about 275 and about 400, between about 280 and about 400, between about 300 and about 400, between about 275 and about 380, between about 280 and about 380, between about 300 and about 380, between about 275 and about 350, between about 280 and about 350, between about 300 and about 350, between about 275 and about 310, between about 280 and about 310, or between about 300 and about 310 mOsm/kg. In certain aspects, the loading buffer is at an osmolarity of about 360, about 370, about 380, about 390, about 395, or about 400 mOsm/kg. In some aspects, the loading buffer is at an osmolarity between about 100 and about 600 mOsm/kg.

In some aspects, the loading buffer is at a pH between about 6 and about 8. In certain aspects, the pH is between about 6 and about 7 or between about 7 and about 8. In some aspects, the pH is about 6, about 7, or about 8. In some aspects, the loading buffer is at a pH of about 9.

In some aspects, a payload which can be loaded in an EV using any of the loading methods provided herein comprises a peptide, a small molecule, an oligonucleotide, an antisense oligonucleotide (ASO), a PMO, a mRNA, a miRNA, a lcRNA, an antagomir, a tRNA, a siRNA, peptide nucleic acid, a cell penetrating peptide, an adjuvant, a protein, a carbohydrate, a sugar, an amino acid, or any combination thereof.

In some aspects, the payload comprises a nucleic acid. In some aspects, the nucleic acid comprises a contiguous sequence in length that is less than about 40, less than about 35, less than about 30, less than about 25, less than about 20, less than about 19, less than about 18, less than about 17, less than about 16, or less than about 15 nucleotides.

In some aspects, the nucleic acid comprises a contiguous sequence in length between about 10 and about 30, between about 14 and about 30, between about 15 and about 30, between about 16 and about 30, between about 17 and about 30, between about 18 and about 30, between about 19 and about 30, between about 20 and about 30, between about 10 and about 25, between about 14 and about 25, between about 15 and about 25, between about 16 and about 25, between about 17 and about 25, between about 18 and about 25, between about 19 and about 25, between about 20 and about 25, between about 10 and about 22, between about 14 and about 22, between about 15 and about 22, between about 16 and about 22, between about 17 and about 22, between about 18 and about 22, between about 19 and about 22, or between about 20 and about 22.

In some aspects, the payload comprises an antisense oligonucleotide. In certain aspects, the antisense oligonucleotide specifically binds to one or more genes and reduces an expression of the protein encoded by the one or more genes. In some aspects, the one or more genes comprise STAT6, Kras, Nras, PMP22, C/EBPβ, STAT3, NLRP3, or any combination thereof.

In some aspects, the payload in the loading buffer is at a concentration between about 100 μM and about 1000 μM). In some aspects, the payload in the loading buffer is at a concentration between about 100 μM and about 200 μM, between about 200 μM and about 300 μM, between about 300 μM and about 400 μM, between about 400 μM and about 500 μM, between about 500 μM and about 600 μM, between about 600 μM and about 700 μM, between about 700 μM and about 800 μM, between about 800 μM and about 900 μM, or between about 900 μM and 1000 μM. In certain aspects, the payload in the loading buffer is at a concentration of about 100 μM, about 200 μM, about 300 μM, about 400 μM, about 500 μM, about 600 μM, about 700 μM, about 800 μM, about 900 μM, or about 1000 μM. In some aspects, the payload in the loading buffer is at a concentration between about 1000 μM and about 2500 μM. In some aspects, the payload comprises the nucleotide sequence set forth in any one of SEQ ID NOs: 41 to 112, and the concentration of the payload is about 600 μM.

In some aspects, the payload is conjugated to an anchoring moiety. In certain aspects, the anchoring moiety a sterol, GM1, a lipid, a phospholipid, a vitamin, a small molecule, a peptide, or a combination thereof.

In some aspects, the anchoring moiety comprises at least 6 carbon atoms, at least 7 carbon atoms, at least 8 carbon atoms, at least 9 carbon atoms, at least 10 carbon atoms, at least 11 carbon atoms, at least 12 carbon atoms, at least 13 carbon atoms, at least 14 carbon atoms, at least 15 carbon atoms, at least 16 carbon atoms, at least 17 carbon atoms, at least 18 carbon atoms, at least 19 carbon atoms, at least 20 carbon atoms, at least 25 carbon atoms, at least 30 carbon atoms, at least 35 carbon atoms, at least 40 carbon atoms, at least 45 carbon atoms, at least 50 carbon atoms, at least 55 carbon atoms, at least 60 carbon atoms, at least 65 carbon atoms, at least 70 carbon atoms, at least 75 carbon atoms, at least 80 carbon atoms, at least 85 carbon atoms, or at least 90 carbon atoms.

In some aspects, the anchoring moiety comprises a sterol, a steroid, a hopanoid, a hydroxysteroid, a secosteroid, an analog thereof, or any combination thereof. In certain aspects, the anchoring moiety comprises ergosterol, 7-dehydrocholesterol, cholesterol, 24S-hydroxycholesterol, lanosterol, cycloartenol, fucosterol, saringosterol, campesterol, β-sitosterol, sitostanol, coprostanol, avenasterol, stigmasterol, or any combination thereof. In some aspects, the anchoring moiety is a cholesterol or derivative having a structure selected from the group consisting of

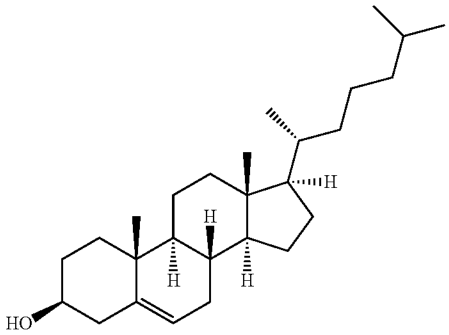

,

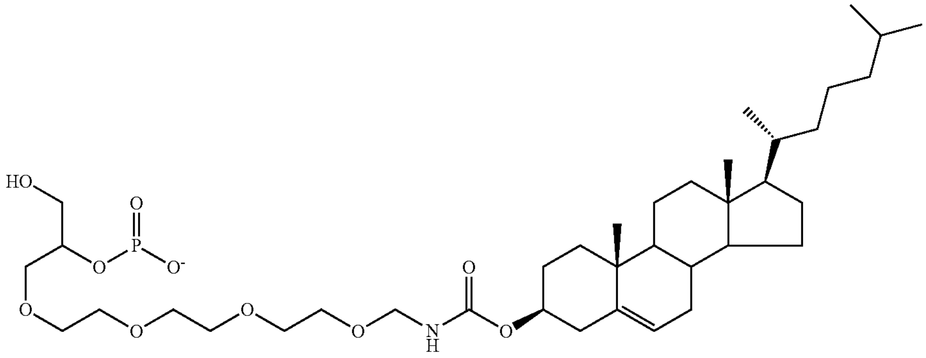

, and (Chol2)

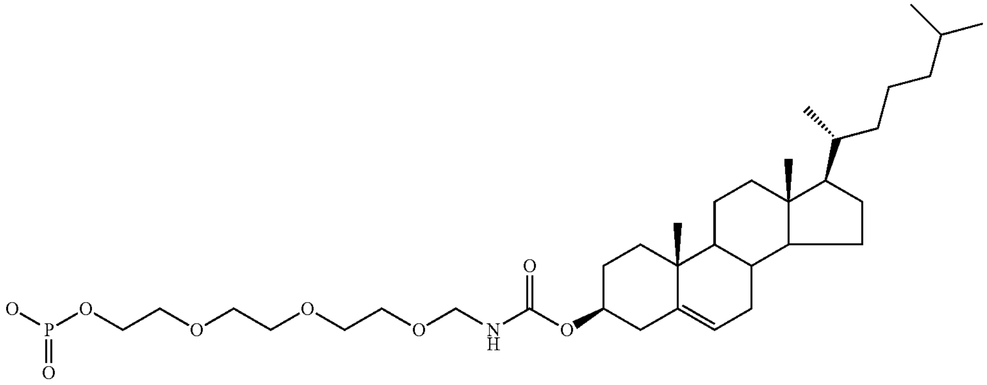

.

In some aspects, the anchoring moiety comprises a steroid, which is dihydrotestosterone, uvaol, hecigenin, diosgenin, progesterone, cortisol, or any combination thereof. In certain aspects, the anchoring moiety comprises a lipid.

In some aspects, the anchoring moiety comprises a $C_2$-$C_{60}$ chain. In certain aspects, the anchoring moiety comprises $C_4$-$C_{40}$, $C_2$-$C_{38}$, $C_2$-$C_{36}$, $C_2$-$C_{34}$, $C_2$-$C_{32}$, $C_2$-$C_{30}$, $C_4$-$C_{30}$, $C_2$-$C_{28}$, $C_4$-$C_{28}$, $C_2$-$C_{26}$, $C_4$-$C_{26}$, $C_2$-$C_{24}$, $C_4$-$C_{24}$, $C_6$-$C_{24}$, $C_8$-$C_{24}$, $C_{10}$-$C_{24}$, $C_2$-$C_{22}$, $C_4$-$C_{22}$, $C_6$-$C_{22}$, $C_8$-$C_{22}$, $C_{10}$-$C_{22}$, $C_2$-$C_{20}$, $C_4$-$C_{20}$, $C_6$-$C_{20}$, $C_8$-$C_{20}$, $C_{10}$-$C_{20}$, $C_2$-$C_{18}$, $C_4$-$C_{18}$, $C_6$-$C_{18}$, $C_8$-$C_{18}$, $C_{10}$-$C_{18}$, $C_{12}$-$C_{18}$, $C_{14}$-$C_{18}$, $C_{16}$-$C_{18}$, $C_2$-$C_{16}$, $C_4$-$C_{16}$, $C_6$-$C_{16}$, $C_8$-$C_{16}$, $C_{10}$-$C_{16}$, $C_{12}$-$C_{16}$, $C_{14}$-$C_{16}$, $C_2$-$C_{15}$, $C_4$-$C_{15}$, $C_6$-$C_{15}$, $C_8$-$C_{15}$, $C_9$-$C_{15}$, $C_{10}$-$C_{15}$, $C_{11}$-$C_{15}$, $C_{12}$-$C_{15}$, $C_{13}$-$C_{15}$, $C_2$-$C_{14}$, $C_4$-$C_{14}$, $C_6$-$C_{14}$, $C_8$-$C_{14}$, $C_9$-$C_{14}$, $C_{10}$-$C_{14}$, $C_{11}$-$C_{14}$, $C_{12}$-$C_{14}$, $C_2$-$C_{13}$, $C_4$-$C_{13}$, $C_6$-$C_{13}$, $C_7$-$C_{13}$, $C_8$-$C_{13}$, $C_9$-$C_{13}$, $C_{10}$-$C_{13}$, $C_{10}$-$C_{13}$, $C_{11}$-$C_{13}$, $C_2$-$C_{12}$, $C_4$-$C_{12}$, $C_6$-$C_{12}$, $C_7$-$C_{12}$, $C_8$-$C_{12}$, $C_9$-$C_{12}$, $C_{10}$-$C_{12}$, $C_2$-$C_{11}$, $C_4$-$C_{11}$, $C_6$-$C_{11}$, $C_7$-$C_{11}$, $C_8$-$C_1$, $C_9$-$C_{11}$, $C_2$-$C_{10}$, $C_4$-$C_{10}$, $C_2$-$C_9$, $C_4$-$C_9$, $C_2$-$C_8$, $C_2$-$C_7$, $C_4$-$C_7$, $C_2$-$C_6$, or $C_4$-$C_6$ chain.

In some aspects, the anchoring moiety comprises a straight chain fatty acid, a branched fatty acid, an unsaturated fatty acid, a monounsaturated fatty acid, a polyunsaturated fatty acid, a hydroxyl fatty acid, a polycarboxylic acid, or any combination thereof.

In some aspects, the anchoring moiety comprises a straight chain fatty acid, which is butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, heptacosanoic acid, or any combination thereof. In some aspects, the anchoring moiety comprises a branched fatty acid, which is isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyldecanoic acid, α-heptylundecanoic acid, 2-decyltetradecanoic c acid, 2-undecyltetradecanoic acid, 2-decylpentadecanoic acid, 2-undecylpentadecanoic acid, Fine oxocol 1800 acid (product of Nissan Chemical Industries, Ltd.), anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid, and 26-methyloctacosanoic acid, or any combination thereof. In some aspects, the anchoring moiety comprises an unsaturated fatty acid, which is 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, a-eleostearic acid, B-eleostearic acid, punicic acid, 6,9,12,15-octadecatetraenoic acid, parinaric acid, 5,8,11,14-eicosatetraenoic acid, 5,8,11,14,17-eicosapentaenoic acid, 7,10,13,16,19-docosapentaenoic acid, 4,7,10,13,16,19-docosahexaenoic acid, or any combination thereof. In some aspects, the anchoring moiety comprises a hydroxy fatty acid, which is a-hydroxylauric acid, α-hydroxymyristic acid, α-hydroxypalmitic acid, α-hydroxystearic acid, α-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid, or any combination thereof. In some aspects, the anchoring moiety comprises a polycarboxylic acid, which is oxalic acid, malonic acid, succinic acid, glutaric acid, adipic acid, pimelic acid, suberic acid, azelaic acid, sebacic acid, D,L-malic acid, or any combination thereof.

In some aspects, the anchoring moiety comprises a phospholipid. In certain aspects, the phospholipid is phosphatidyl choline, phosphatidyl ethanolamine, phosphatidyl glycerol, phosphatidyl serine, phosphatidic acid, 2 lysophosphatidyl choline, sphingomyelin, or any combination thereof.

In some aspects, the anchoring moiety comprises a vitamin. In some aspects, the anchoring moiety comprises vitamin D, vitamin K, niacin, pyridoxine, vitamin E, or any combination thereof.

In some aspects, the anchoring moiety further comprises a linker between the payload and the anchoring moiety.

In some aspects, the linker comprises a non-cleavable linker. In some aspects, the non-cleavable linker comprises polyethylene glycol (PEG), glycerol, alkyl, phosphorothioate, succinimide, maleimide, or any combination thereof. In some aspects, the non-cleavable linker comprises polyethylene glycol (PEG) characterized by a formula R3-(O—$CH_2$—$CH_2$)$_n$— or R3-(O—$CH_2$—$CH_2$)$_n$—O—, wherein R3 being hydrogen, methyl or ethyl and n is an integer between 2 and 200. In some aspects, the non-cleavable linker comprises diethylene glycol, triethylene glycol, tetraethylene glycol (TEG), hexaethylene glycol (HEG), pentaethylene glycol, or any combination thereof. In some aspects, wherein the linker comprises a polyglycerol (PG) having the formula ((R3-O—($CH_2$—CHOH—$CH_2$O)$_n$—), wherein R3 is hydrogen, methyl or ethyl, and n is an integer between 3 and 200. In some aspects, the linker comprises a diglycerol, triglycerol, tetraglycerol (TG), pentaglycerol, a hexaglycerol (HG), or any combination thereof. In some aspects, the linker comprises alkyl.

In some aspects, the linker comprises a cleavable linker. In some aspects, cleavable linker is a redox cleavable linker, a reactive oxygen species cleavable linker, a pH dependent cleavable linker, an enzymatic cleavable linker, a protease cleavable linker, an esterase cleavable linker, an oxidoreductate cleavable linker, a phospholipase cleavable linker, a phosphatase cleavable linker, a photoactivated cleavable linker, a self-immolative linker, or any combination thereof. In some aspects, the cleavable linker is a self-immolative linker. In some aspects, the cleavable linker is a cinnamyl group, a naphthyl group, a biphenyl group, a heterocyclic ring, a homoaromatic group, coumarin, furan, thiophene, thiazole, oxazole, isoxazole, pyrrole, pyrazole, pyridine, imidazonc, triazole, or any combination thereof.

In some aspects, wherein the linker has the formula:

$$-A_a-Y_y-$$

wherein each -A- is independently an amino acid unit, a is independently an integer from 1 to 12; —Y— is a spacer unit, and y is 0, 1, or 2. In some aspects, -$A_a$- is a dipeptide, a tripeptide, a tetrapeptide, a pentapeptide, or a hexapeptide. In some aspects, a is 2 and -$A_a$- is selected from the group consisting of valine-alanine, valine-citrulline, glutamic acid-valine-citrulline, phenylalanine-lysine, N-methylvaline-citrulline, glycine-histidine-leucine-glycine, cyclohexylalanine-lysine, and beta-alanine-lysine. In some aspects, -$A_a$- is valine-alanine or valine-citrulline or glutamic acid-valine-citrulline. In some aspects, -$A_a$- is arginine, lysine, or both. In some aspects, y is 1. In some aspects, —Y— is a self-immolative spacer. In some aspects, —$Y_y$— has the formula (V):

(V)

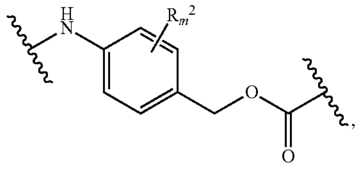

wherein each $R^2$ is independently $C_{1-8}$ alkyl, —O—($C_{1-8}$ alkyl), halogen, nitro, or cyano; and m is an integer from 0 to 4. In some aspects, m is 0, 1, or 2. In some aspects, m is 0. In some aspects, the cleavable linker is valine-alanine-p-aminobenzylcarbamate or valine-citrulline-p-aminobenzylcarbamate.

In some aspects, the anchoring moiety comprises:

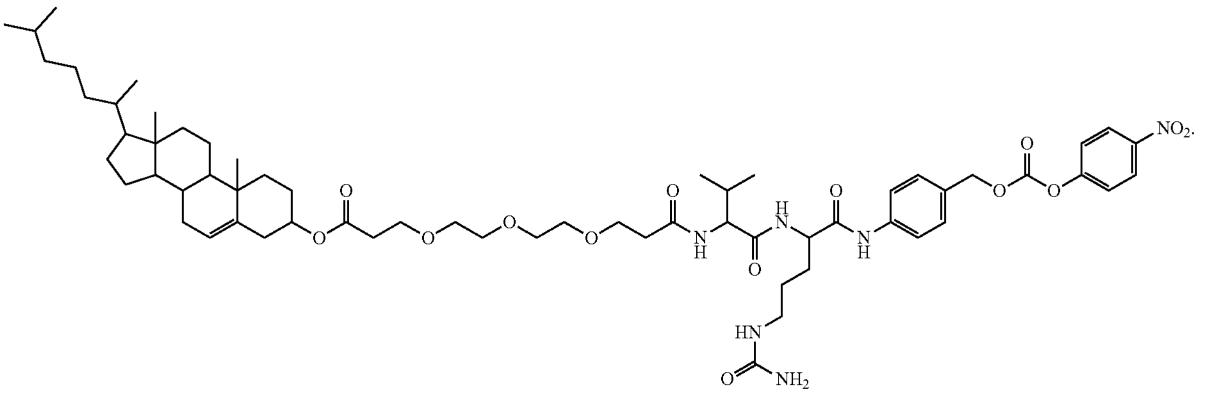 [SMILES: CC(C)CCCC(C)C1CCC2C3CC=C4CC(OC(=O)CCOCCOCCOCCC(=O)NC(C(=O)NC(CCCNC(N)=O)C(=O)Nc5ccc(COC(=O)Oc6ccc([N+](=O)[O-])cc6)cc5)C(C)C)CCC4(C)C3CCC12C]

In some aspects, the method comprises (i) a payload comprises the nucleotide sequence set forth in any one of SEQ ID NOs: 41 to 112, and (ii) a linker selected from the linker combinations of TABLE 1 or TABLE 2.

In some aspects, the payload is conjugated to a cholesterol. In some aspects, the payload comprises 5'GbsCbsAbsdAsdGsdAsdTs(5MdC)s(5MdC)s(5MdC)sdGsdGsdAsdTsdTs(5MdC)sdGsGbsTbs Cb3', wherein Nb is an LNA, dN is a DNA, (5MdC) is 5-Methyl-dC, s is phosphorothioate, TEG is triethylene glycol, and HEG is hexaethylene glycol. In some aspects, the payload is linked to the cholesterol by TEG-HEG.

In some aspects, the extracellular vesicle is at a concentration of at least about $1\times10^{11}$, at least about $2\times10^{11}$, at least about $3\times10^{11}$, at least about $4\times10^{11}$, at least about $5\times10^{11}$, at least about $6\times10^{11}$, at least about $7\times10^{11}$, at least about $8\times10^{11}$, at least about $9\times10^{11}$, at least about $1\times10^{12}$, at least about $2\times10^{12}$, at least about $3\times10^{12}$, at least about $4\times10^{12}$, at least about $5\times10^{12}$, at least about $6\times10^{12}$, at least about $7\times10^{12}$, at least about $8\times10^{12}$, at least about $9\times10^{12}$, at least about $1\times10^{13}$, at least about $2\times10^{13}$, at least about $3\times10^{13}$, at least about $4\times10^{13}$, at least about $5\times10^{13}$, at least about $6\times10^{13}$, at least about $7\times10^{13}$, at least about $8\times10^{13}$, at least about $9\times10^{13}$, or at least about $1\times10^{14}$ particles/mL. In some aspects, the extracellular vesicle is at a concentration between about $1\times10^{12}$ and about $5\times10^{13}$ particles/mL, about $1\times10^{12}$ and about $4\times10^{13}$ particles/mL, about $1\times10^{12}$ and about $3\times10^{13}$ particles/mL, about $1\times10^{12}$ and about $2\times10^{13}$ particles/mL, about $2\times10^{12}$ and about $5\times10^{13}$ particles/mL, about $2\times10^{12}$ and about $4\times10^{13}$ particles/mL, about $2\times10^{12}$ and about $3\times10^{13}$ particles/mL, about $2\times10^{12}$ and about $2\times10^{13}$ particles/mL, about $3\times10^{12}$ and about $5\times10^{13}$ particles/mL, about $3\times10^{12}$ and about $4\times10^{13}$ particles/mL, about $3\times10^{12}$ and about $3\times10^{13}$ particles/mL, about $3\times10^{12}$ and about $2\times10^{13}$ particles/mL, about $4\times10^{12}$ and about $5\times10^{13}$ particles/mL, about $4\times10^{12}$ and about $4\times10^{13}$ particles/mL, about $4\times10^{12}$ and about $3\times10^{13}$ particles/mL, about $4\times10^{12}$ and about $2\times10^{13}$ particles/mL, about $5\times10^{12}$ and about $5\times10^{13}$ particles/mL, about $5\times10^{12}$ and about $4\times10^{13}$ particles/mL, about $5\times10^{12}$ and about $3\times10^{13}$ particles/mL, or about $5\times10^{12}$ and about $2\times10^{13}$ particles/mL. In some aspects, the extracellular vesicle is at a concentration between about $5\times10^{12}$ and about $2\times10^{13}$ particles/mL. In some aspects, the extracellular vesicle is at a concentration of about $1\times10^{13}$ particles/mL.

In some aspects, the extracellular vesicle further comprises a protein in the membrane of the extracellular vesicle. In some aspects, the protein comprises prostaglandin F2 receptor negative regulator (the PTGFRN protein); basigin (the BSG protein); immunoglobulin superfamily member 2 (the IGSF2 protein); immunoglobulin superfamily member 3 (the IGSF3 protein); immunoglobulin superfamily member 8 (the IGSF8 protein); integrin beta-1 (the ITGB1 protein); integrin alpha-4 (the ITGA4 protein); 4F2 cell-surface antigen heavy chain (the SLC3A2 protein); a class of ATP transporter proteins (the ATP1A1, ATP1A2, ATP1A3, ATP1A4, ATP1B3, ATP2B1, ATP2B2, ATP2B3, ATP2B4 proteins); a functional fragment thereof; and any combination thereof. In some aspects, the protein comprises a PTGFRN protein or a functional fragment thereof.

Provided herein is an extracellular vesicle prepared by any one of the methods disclosed herein.

Provided herein is an extracellular vesicle comprising payloads on the external surface of the extracellular vesicle, wherein the number of payloads on the surface of the extracellular vesicle is at least about 1000, at least about 2000, at least about 3000, at least about 4000, at least about 5000, at least about 6000, at least about 7000, at least about 8000, at least about 9000, at least about 10,000, at least about 11,000, at least about 12000, at least about 13,000, at least about 14,000, at least about 15,000, at least about 16,000, at least about 17,000, at least about 18,000, at least about 20,000, at least about 22,000, at least about 24,000, at least about 26,000, at least about 28,000, at least about 30,000, at least about 35,000, or at least about 40,000. In some aspects, the number of payloads on the surface of the extracellular vesicle is between about 5,000 and about 20,000, about 6,000 and about 20,000, about 7,000 and about 20,000, about 8,000 and about 20,000, about 9,000 and about 20,000, about 10,000 and about 20,000, about 5,000 and about 18,000, about 6,000 and about 18,000, about 7,000 and about 18,000, about 8,000 and about 18,000, about 9,000 and about 18,000, about 10,000 and about 18,000, about 5,000 and about 15,000, about 6,000 and about 15,000, about 7,000 and about 15,000, about 8,000 and about 15,000, about 9,000 and about 15,000, or about 10,000 and about 15,000. In some aspects, the number of payloads on the surface of the extracellular vesicle is between about 10,000 and about 15,000. In some aspects, the payload comprises the nucleotide sequence set forth in any one of SEQ ID NOs: 41 to 112.

In some aspects, the payload of an extracellular vesicle disclosed herein is conjugated to a sterol, GM1, a lipid, a phospholipid, a vitamin, a small molecule, a peptide, or a combination thereof. In some aspects, the payload is conjugated to a cholesterol. In some aspects, the payload comprises the structure: 5'GbsCbsAbsdAsdGsdAsdTs(5MdC)s(5MdC)s(5MdC)sdGsdGsdAsdTsdTs(5MdC)sdGsGbsTbs Cb3', wherein Nb is an LNA, dN is a DNA, (5MdC) is 5-Methyl-dC, and s is phosphorothioate.

The present disclosure further provides a population of extracellular vesicles, comprising any of the extracellular vesicles described herein. In some aspects, at least about 30%, at least about 40%, at least about 50%, at least about 60%, at least about 70%, at least about 80%, at least about 90%, at least about 95%, at least about 96%, at least about 97%, at least about 98%, at least about 99% or about 100% of the extracellular vesicles are the extracellular vesicle of any one of the extracellular vesicles described herein.

Also provided herein is a composition comprising any of the extracellular vesicles or population of extracellular vesicles described herein. Provided herein is a pharmaceutical composition comprising the extracellular vesicles or population of extracellular vesicles described herein.

Also provided herein is a method of treating a disease or condition in a subject in need thereof comprising administering the extracellular vesicle or the population of extracellular vesicles described herein.

BRIEF DESCRIPTION OF THE DRAWINGS/FIGURES

Figure 1B:
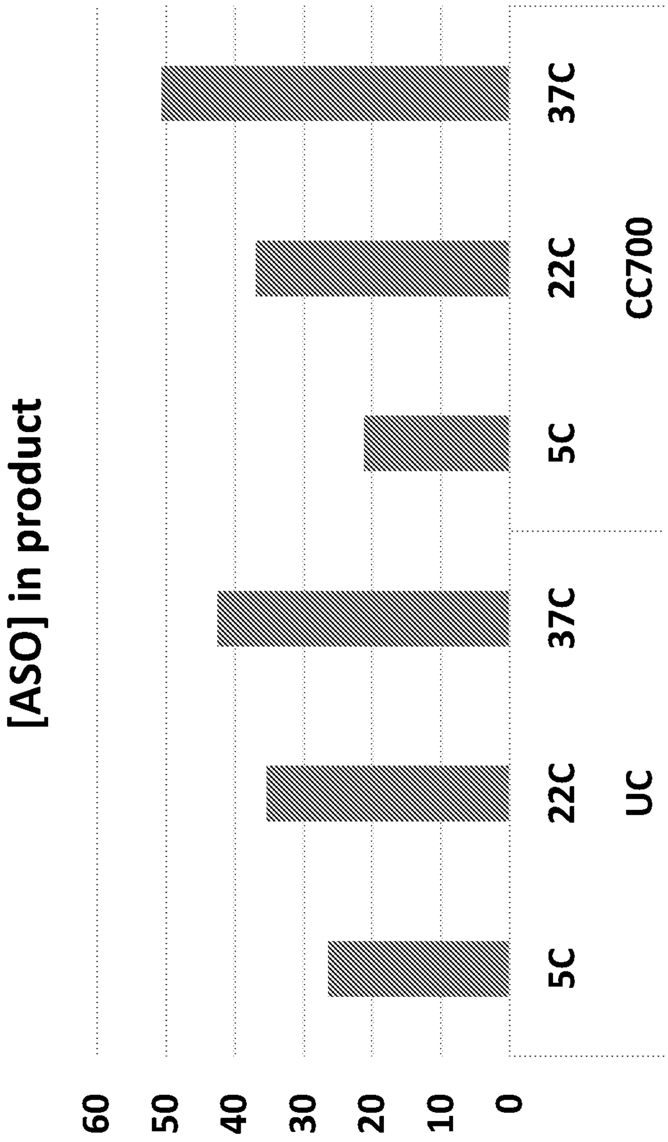

FIG. 1A shows the effects of increasing time and temperature on ASO loading of extracellular vesicles. FIG. 1B shows the concentration of ASOs loaded in EVs after cleanup with ultracentrifugation (UC) and chromatography using Capto Core 700 resin (CC700).

Figure 2B:
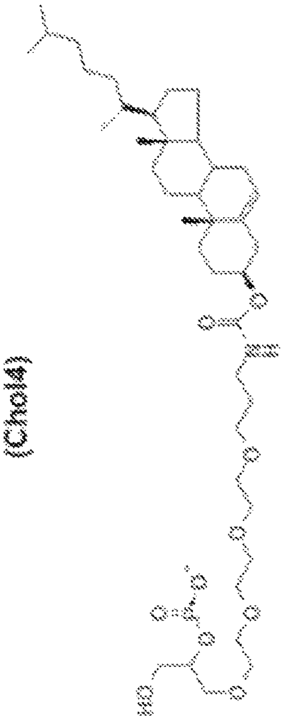
Figure 2A:
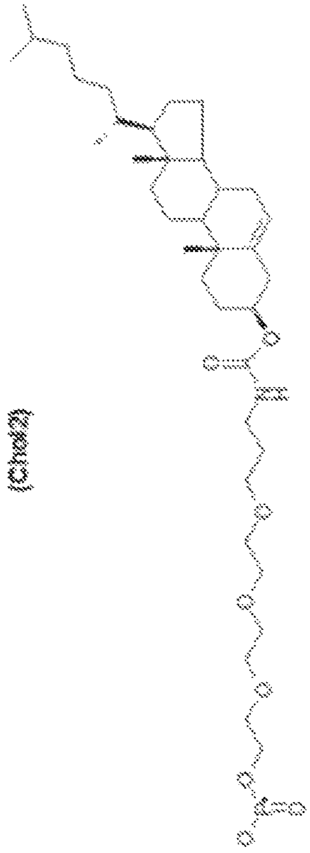

FIGS. 2A and 2B provide illustration of two exemplary cholesterol moieties that can be used to conjugate a payload (e.g., ASO) disclosed herein. FIG. 2A provides the structure for Chol2. FIG. 2B provides the structure for Chol4.

FIGS. 3A, 3B, 3C, 3D, 3E, 3F, and 3G provide tables listing the sequences for exemplary ASOs that can be loaded onto EVs using the loading methods provided herein. In FIG. 3A, the ASOs target the STAT6 transcript. In FIG. 3B, the ASOs target the KRAS transcript. In FIG. 3C, the ASOs target the NRAS transcript. In FIG. 3D, the ASOs target the PMP22 transcript. In FIG. 3E, the ASOs target the C/EBPβ transcript. In FIG. 3F, the ASOs target the STAT3 transcript. In FIG. 3G, the ASOs target the NLRP3 transcript.

Figure 4:
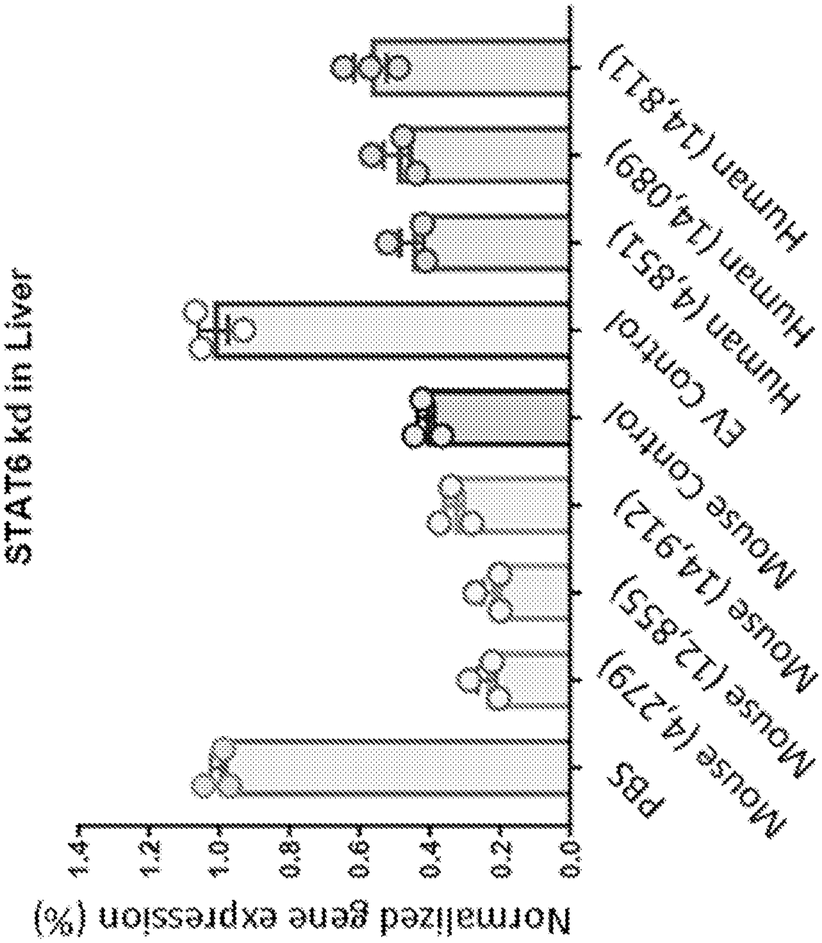

FIG. 4 shows the knockdown of STAT6 expression in the liver after treatment with EVs loaded with different amounts of mouse and human STAT6-targeting ASOs. The specific ASO density of the different EVs are shown in parentheses. STAT6 expression is shown normalized to the control (PBS-treated alone or treated with the vehicle control).

Figure 5:
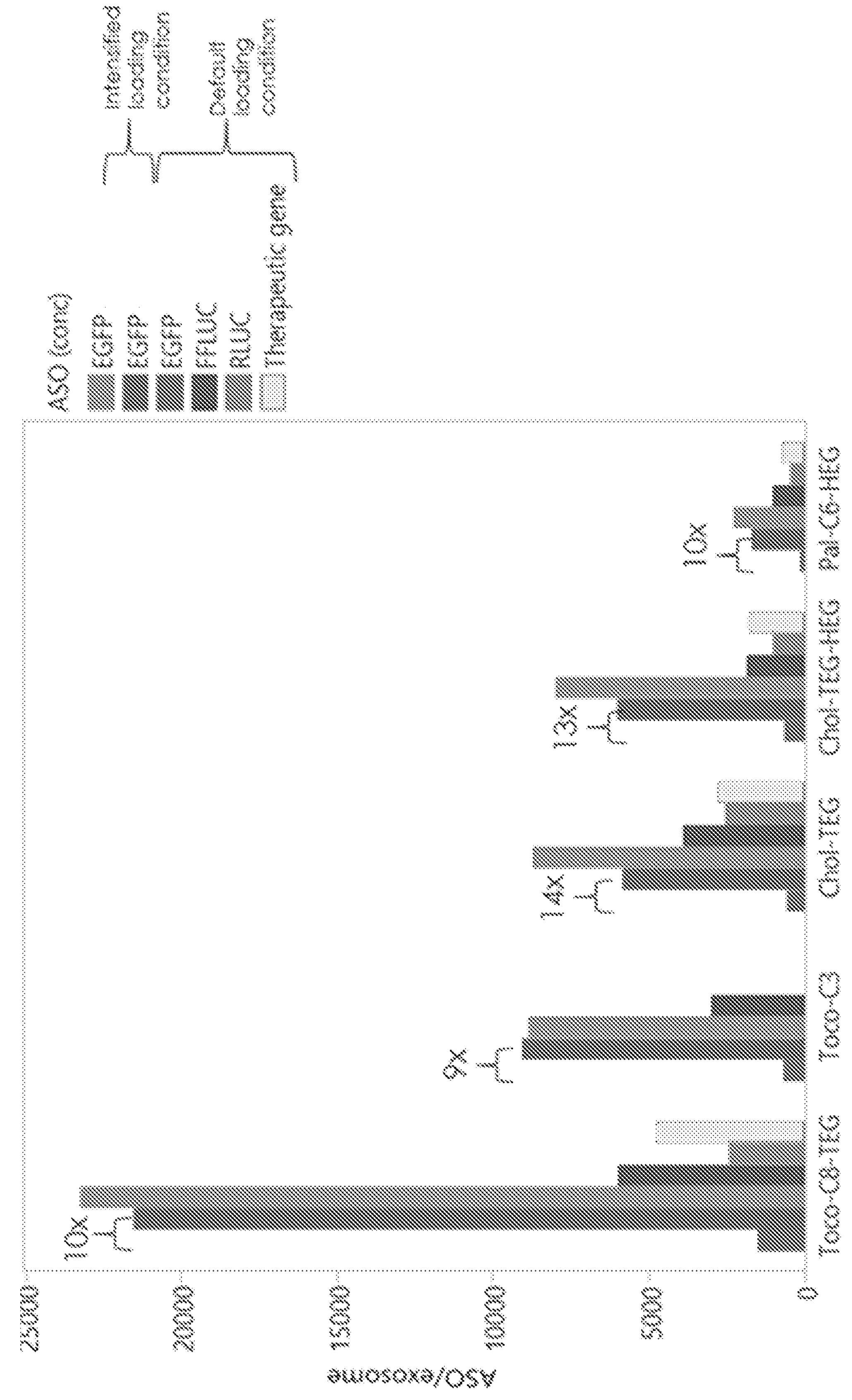

FIG. 5 provides a comparison of the loading density (ASOs per EV) for four different ASO sequences synthesized with different lipid-linkers. The ASOs targeted one of the following: green fluorescent protein ("EGFP"), firefly luciferase ("FFLUC"), *Renilla* luciferase ("RLUC"), and a therapeutic gene ("therapeutic gene"). Toco=tocopherol, Chol=cholesterol, Pal=palmitate, C6=hexamethylene, C8-octamethylene, TEG=tetraethylene glycol, HEG=hexaethylene glycol.

DETAILED DESCRIPTION

The present disclosure is directed to methods of loading a payload (e.g., antisense oligonucleotides) in an EV (e.g., on the exterior surface of the EVs), comprising modulating (e.g., increasing or decreasing) one or more parameters of the loading process (referred to herein as "loading parameters"). In some aspects, the one or more parameters comprise: salt concentration, loading temperature, loading duration, payload feed concentration, EV feed concentration, or combinations thereof. As demonstrated herein, modulating the one or more parameters can increase the amount of the payload that is loaded in the EVs (e.g., on the exterior surface of the EVs). Non-limiting examples of the various aspects are shown in the present disclosure.

Before the present disclosure is described in greater detail, it is to be understood that this invention is not limited to the particular compositions or process steps described, as such can, of course, vary. As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible.

The headings provided herein are not limitations of the various aspects of the disclosure, which can be defined by reference to the specification as a whole. It is also to be understood that the terminology used herein is for the purpose of describing particular aspects only, and is not intended to be limiting, since the scope of the present disclosure will be limited only by the appended claims.

Accordingly, the terms defined immediately below are more fully defined by reference to the specification in its entirety.

I. Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The terms "administration," "administering," and grammatical variants thereof refer to introducing a composition, such as an EV of the present disclosure, into a subject via a pharmaceutically acceptable route. The introduction of a composition, such as an EV of the present disclosure, into a subject is by any suitable route, including intratumorally, orally, pulmonarily, intranasally, parenterally (intravenously, intra-arterially, intramuscularly, intraperitoneally, or subcutaneously), rectally, intralymphatically, intrathecally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

As used herein, the term "agonist" refers to a molecule that binds to a receptor and activates the receptor to produce a biological response. Receptors can be activated by either an endogenous or an exogenous agonist. Non-limiting examples of endogenous agonist include hormones, neurotransmitters, and cyclic dinucleotides. Non-limiting examples of exogenous agonist include drugs, small molecules, and cyclic dinucleotides. The agonist can be a full, partial, or inverse agonist.

The term "amino acid substitution" refers to replacing an amino acid residue present in a parent or reference sequence (e.g., a wild type sequence) with another amino acid residue. An amino acid can be substituted in a parent or reference sequence (e.g., a wild type polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In some aspects, substitution patterns can be described according to the schema An (YZ), wherein A is the single letter code corresponding to the amino acid residue substituting the amino acid naturally or originally present at position n, and Y and Z are alternative substituting amino acid residues that can replace A.

The terms "anion" and "cation" refer to negatively and positively charged ions, respectively. A "divalent" cation refers to a cation with a valence of 2+. Examples of divalent cations include, but are not limited to, $Ca^{2+}$, $Mg^{2+}$, $Co^{2+}$, $Ni^{2+}$, $Zn^{2+}$, $Ba^{2+}$, $Sr^{2+}$, $Al^{2+}$, $Ag^{2+}$, $Cu^{2+}$, and $Mn^{2+}$. A "monovalent" cation refers to a cation with a valence of 1+. Examples of monovalent cations include, but are not limited to, $Li^{+}$, $K^{+}$, $Na^{+}$, $NH_4^{+}$, $Cu^{+}$. Examples of anions include, but are not limited to, $SCN^{-}$, $Cl^{-}$, $SO_4^{-}$, and $PO_4$. In some aspects, the anion and/or the cation (e.g., monovalent cation or divalent cation) can be present in a salt, e.g., a mixture of at least one anion and at least one cation of complementary valences. Any salt comprising an anion or a cation disclosed herein can be used in the methods disclosed herein.

As used herein, the term "antagonist" refers to a molecule that blocks or dampens an agonist mediated response rather than provoking a biological response itself upon bind to a receptor. Many antagonists achieve their potency by competing with endogenous ligands or substrates at structurally defined binding sites on the receptors. Non-limiting examples of antagonists include alpha blockers, beta-blocker, and calcium channel blockers. The antagonist can be a competitive, non-competitive, or uncompetitive antagonist.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, $(scFv)_2$, Fab, Fab', and $F(ab')_2$, F $(ab1)_2$, Fv, dAb, and Fd fragments, diabodies, and antibody-related polypeptides. Antibody includes bispecific antibodies and multispecific antibodies so long as they exhibit the desired biological activity or function. In some aspects of the present disclosure, the biologically active molecule is an antibody or a molecule comprising an antigen binding fragment thereof.

The terms "antibody-drug conjugate" and "ADC" are used interchangeably and refer to an antibody linked, e.g., covalently, to a therapeutic agent (sometimes referred to herein as agent, drug, or active pharmaceutical ingredient) or agents. In some aspects of the present disclosure, the biologically active molecule is an antibody-drug conjugate.

As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "aryl" refers to a carbocyclic aromatic group. Examples of aryl groups include, but are not limited to, phenyl, naphthyl and anthracenyl. A carbocyclic aromatic group can be unsubstituted or substituted with one or more groups including, but not limited to, —$C_{1-8}$ alkyl, —O—($C_{1-8}$ alkyl), -aryl, —C(O)R', —OC(O)R', —C(O)OR', —$C(O)NH_2$, —C(O)NHR', —$C(O)N(R')_2$—, —NHC(O)R', —$S(O)_2R'$, —S(O)R', —OH, -halogen, —$N_3$, —$NH_2$, —NH(R'), —$N(R')_2$ and —CN, wherein each R' is independently H, —$C_{1-8}$ alkyl, or aryl.

The term "arylene" refers to an aryl group which has two covalent bonds and can be in the ortho, meta, or para configurations as shown in the following structures:

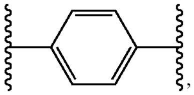,
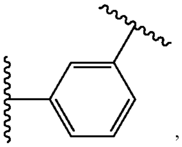,
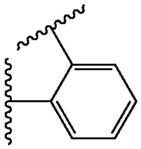, in which the phenyl group can be unsubstituted or substituted with up to four groups including, but not limited to, —$C_{1-8}$ alkyl, —O—($C_{1-8}$ alkyl), -aryl, —C(O)R', —OC(O)R', —C(O)OR', —$C(O)NH_2$, —C(O)NHR', —$C(O)N(R')_2$—, —NHC(O)R', —$S(O)_2R'$, —S(O)R', —OH, -halogen, —$N_3$, —$NH_2$, —NH(R'), —$N(R')_2$ and —CN, wherein each R' is independently H, —C1-s alkyl, or aryl.

As used herein, the term "arylalkyl" or "aralkyl" is meant to include those radicals in which an aryl group or heteroaryl group is attached to an alkyl group to create the radicals -alkyl-aryl and -alkyl-heteroaryl, wherein alkyl, aryl and heteroaryl are defined herein. Exemplary "arylalkyl" or "aralkyl" groups include benzyl, phenethyl, pyridylmethyl and the like.

As, used herein, the term "aryloxy" refers to the group —O-aryl, where aryl is as defined herein. In certain aspects, the aryl portion of the aryloxy group is phenyl or naphthyl.

The term "heteroaryl" or "heteroaromatic" refers to a polyunsaturated, 5-, 6- or 7-membered aromatic moiety containing at least one heteroatom (e.g., 1 to 5 heteroatoms, such as 1-3 heteroatoms) selected from N, O, S, Si and B (for example, N, O and S), wherein the nitrogen and sulfur atoms are optionally oxidized, and the nitrogen atom(s) are optionally quaternized. The "heteroaryl" group can be a single ring or be fused to other aryl, heteroaryl, cycloalkyl or heterocycloalkyl rings (e.g., from 1 to 3 other rings). When the "heteroaryl" group includes a fused aryl, cycloalkyl or heterocycloalkyl ring, then the "heteroaryl" group is attached to the remainder of the molecule via the heteroaryl ring. A heteroaryl group can be attached to the remainder of the molecule through a carbon- or heteroatom.

In some aspects, the heteroaryl group has from 4 to 10 carbon atoms and from 1 to 5 heteroatoms selected from O, S and N. Non-limiting examples of heteroaryl groups include pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Exemplary heteroaryl groups include imidazolyl, pyrazolyl, thiadiazolyl, triazolyl, isoxazolyl, isothiazolyl, imidazolyl, thiazolyl, oxadiazolyl, and pyridyl. Other exemplary heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, pyridin-4-yl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable aryl group substituents described below.

As used herein, the term "alkyl," by itself or as part of another substituent, means, unless otherwise stated, a straight or branched chain hydrocarbon radical having the number of carbon atoms designated (e.g., $C_1$-$C_{10}$ means one to ten carbon atoms). Typically, an alkyl group will have from 1 to 24 carbon atoms, for example having from 1 to 10 carbon atoms, from 1 to 8 carbon atoms or from 1 to 6 carbon atoms. A "lower alkyl" group is an alkyl group having from 1 to 4 carbon atoms. The term "alkyl" includes di- and multivalent radicals. For example, the term "alkyl" includes "alkylene" wherever appropriate, e.g., when the formula indicates that the alkyl group is divalent or when substituents are joined to form a ring. Non-limiting examples of alkyl radicals include, but are not limited to, methyl, ethyl, n-propyl, iso-propyl, n-butyl, tert-butyl, isobutyl, sec-butyl, as well as homologs and isomers of, for example, n-pentyl, n-hexyl, n-heptyl and n-octyl.

The term "alkylene" by itself or as part of another substituent means a divalent (diradical) alkyl group, wherein alkyl is defined herein. "Alkylene" is exemplified, but not limited, by $-CH_2CH_2CH_2CH_2-$. In some aspects, an "alkylene" group comprises 1 to 24 carbon atoms, for example, having 10 or fewer carbon atoms (e.g., 1 to 8 or 1 to 6 carbon atoms). A "lower alkylene" group is an alkylene group having from 1 to 4 carbon atoms.

The term "alkenyl" by itself or as part of another substituent refers to a straight or branched chain hydrocarbon radical having from 2 to 24 carbon atoms and at least one double bond. A typical alkenyl group has from 2 to 10 carbon atoms and at least one double bond. In certain aspects, alkenyl groups have from 2 to 8 carbon atoms or from 2 to 6 carbon atoms and from 1 to 3 double bonds. Exemplary alkenyl groups include vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like.

The term "alkynyl" by itself or as part of another substituent refers to a straight or branched chain, unsaturated or polyunsaturated hydrocarbon radical having from 2 to 24 carbon atoms and at least one triple bond. A typical "alkynyl" group has from 2 to 10 carbon atoms and at least one triple bond. In one aspect of the disclosure, alkynyl groups have from 2 to 6 carbon atoms and at least one triple bond. Exemplary alkynyl groups include prop-1-ynyl, prop-2-ynyl (i.e., propargyl), ethynyl and 3-butynyl.

The terms "alkoxy," "alkylamino" and "alkylthio" (or thioalkoxy) are used in their conventional sense and refer to alkyl groups that are attached to the remainder of the molecule via an oxygen atom, an amino group, or a sulfur atom, respectively.

The term "heteroalkyl," by itself or in combination with another term, refers to a stable, straight or branched chain hydrocarbon radical consisting of the stated number of carbon atoms (e.g., $C_2$-$C_{10}$, or $C_2$-$C_8$) and at least one heteroatom chosen, e.g., from N, O, S, Si, B and P (in certain aspects, N, O and S), wherein the nitrogen, sulfur and phosphorus atoms are optionally oxidized, and the nitrogen atom(s) are optionally quaternized. The heteroatom(s) is/are placed at any interior position of the heteroalkyl group. Examples of heteroalkyl groups include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3$, $-CH=CH-O-CH_3$, $-CH_2-Si(CH_3)_3$, $-CH_2-CH=N-OCH_3$, and $-CH=CH-N(CH_3)-CH_3$. Up to two heteroatoms can be consecutive, such as, for example, $-CH_2-NH-OCH_3$ and $-CH_2-O-Si(CH_3)_3$.

The term "heteroalkylene," by itself or as part of another substituent, refers to a divalent radical derived from heteroalkyl, as exemplified, but not limited by, $-CH_2-CH_2-S-CH_2-CH_2-$ and $-CH_2-S-CH_2-CH_2-NH-CH_2-$. Typically, a heteroalkyl group will have from 3 to 24 atoms (carbon and heteroatoms, excluding hydrogen) (3- to 24-membered heteroalkyl). In another example, the heteroalkyl group has a total of 3 to 10 atoms (3- to 10-membered heteroalkyl) or from 3 to 8 atoms (3- to 8-membered heteroalkyl). The term "heteroalkyl" includes "heteroalkylene" wherever appropriate, e.g., when the formula indicates that the heteroalkyl group is divalent or when substituents are joined to form a ring.

The term "cycloalkyl," by itself or in combination with other terms, represents a saturated or unsaturated, non-aromatic carbocyclic radical having from 3 to 24 carbon atoms, for example, having from 3 to 12 carbon atoms (e.g., $C_3$-$C_8$ cycloalkyl or $C_3$-$C_6$ cycloalkyl). Examples of cycloalkyl include, but are not limited to, cyclopropyl, cyclobutyl, cyclopentyl, cyclohexyl, cycloheptyl, 1-cyclohexenyl, 3-cyclohexenyl, cycloheptyl and the like. The term "cycloalkyl" also includes bridged, polycyclic (e.g., bicyclic) structures, such as norbornyl, adamantyl and bicyclo[2.2.1]heptyl. The "cycloalkyl" group can be fused to at least one (e.g., 1 to 3) other ring selected from aryl (e.g., phenyl), heteroaryl (e.g., pyridyl) and non-aromatic (e.g., carbocyclic or heterocyclic) rings. When the "cycloalkyl" group includes a fused aryl, heteroaryl or heterocyclic ring, then the "cycloalkyl" group is attached to the remainder of the molecule via the carbocyclic ring.

The term "heterocycloalkyl," "heterocyclic," "heterocycle," or "heterocyclyl," by itself or in combination with other terms, represents a carbocyclic, non-aromatic ring (e.g., 3- to 8-membered ring and for example, 4-, 5-, 6- or 7-membered ring) containing at least one and up to 5 heteroatoms selected from, e.g., N, O, S, Si, B and P (for example, N, O and S), wherein the nitrogen, sulfur and phosphorus atoms are optionally oxidized, and the nitrogen atom(s) are optionally quaternized (e.g., from 1 to 4 heteroatoms selected from nitrogen, oxygen and sulfur), or a fused ring system of 4- to 8-membered rings, containing at least one and up to 10 heteroatoms (e.g., from 1 to 5 heteroatoms selected from N, O and S) in stable combinations known to those of skill in the art. Exemplary heterocycloalkyl groups include a fused phenyl ring. When the "heterocyclic" group includes a fused aryl, heteroaryl or cycloalkyl ring, then the "heterocyclic" group is attached to the remainder of the molecule via a heterocycle. A heteroatom can occupy the position at which the heterocycle is attached to the remainder of the molecule.

As used herein, the term "associated with" refers to the interaction between a first moiety (e.g., payload) and a second moiety (e.g., EV). For instance, in some aspects, the first moiety can be encapsulated within the second moiety (e.g., a payload can be in the lumen of the EV). In some aspects, the first moiety can be linked or fused to the second moiety (e.g., a payload can be linked to the exterior surface and/or the luminal surface of an EV).

The term "biologically active molecule," as used herein, refers to any molecule that can be attached to an EV via an anchoring moiety, wherein the molecule can have a therapeutic or prophylactic effect in a subject in need thereof, or be used for diagnostic purposes. In some aspects, such molecules of interest are also referred to herein as "moieties of interest." Accordingly, by way of example, the term biologically active molecule include proteins (e.g., antibodies, proteins, polypeptides, and derivatives, fragments, and variants thereof), lipids and derivatives thereof, carbohydrates (e.g., glycan portions in glycoproteins), or small molecules. In some aspects, the biologically active molecule comprises an antigen, adjuvant, immune modulator, targeting moiety, or combinations thereof. Non-limiting examples of such biologically active molecules are provided in, e.g., WO 2020/0191361 A2, which is incorporated herein by reference in its entirety. In certain aspects, the biologically active molecule is a payload (e.g., antisense oligonucleotide).

The term "C1-s alkyl" as used herein refers to a straight chain or branched, saturated hydrocarbon having from 1 to 8 carbon atoms. Representative "$C_{1-8}$ alkyl" groups include, but are not limited to, methyl, ethyl, n-propyl, n-butyl, n-pentyl, n-hexyl, n-heptyl, n-octyl, isopropyl, see-butyl, isobutyl, tert-butyl, isopentyl, and 2-methylbutyl.

The term "C1-10 alkylene" refers to a saturated, straight chain hydrocarbon group of the formula $-(CH_2)_{1-10}-$. Examples of $C_{1-10}$ alkylene include methylene, ethylene, propylene, butylene, pentylene, hexylene, heptylene, octylene, nonylene, and decalene.

The term "$C_{3-8}$ carbocycle" refers to a 3-, 4-, 5-, 6-, 7- or 8-membered saturated or unsaturated non-aromatic carbocyclic ring. Representative C3-8 carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and -cyclooctadienyl. A C3-8 carbocycle group can be unsubstituted or substituted with one or more groups including, but not limited to, $-C_{1-8}$ alkyl, $-O-(C_{1-8}$ alkyl), aryl, $-C(O)R'$, $-OC(O)R'$, $-C(O)OR'$, $-C(O)NH_2$, $-C(O)NHR'$, $-C(O)N(R')_2-$, NHC(O)R', $-S(O)_2R'$, $-S(O)R'$, $-OH$, -halogen, $-N_3$, $-NH_2$, $-NH(R')$, $-N(R')_2$ and $-CN$, where each R' is independently H, $-C_{1-8}$ alkyl, or aryl.

The term "$C_{3-8}$ carbocyclo" refers to a $C_{3-8}$ carbocycle group defined above wherein one or more of the carbocycle's hydrogen atoms is replaced with a bond.

The term "$C_{3-8}$ heterocycle" refers to an aromatic or non-aromatic $C_{3-8}$ carbocycle in which one to four of the ring carbon atoms are independently replaced with a heteroatom selected from the group consisting of O, S and N. Representative examples of a $C_{3-8}$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_{3-8}$ heterocycle can be unsubstituted or substituted with up to seven groups including, but not limited to, $-C_{1-8}$ alkyl, $-O-(C_{1-8}$ alkyl), -aryl, $-C(O)R'$, $-OC(O)R'$, $-C(O)OR'$, $-C(O)NH_2$, $-C(O)NHR'$, $-C(O)N(R')_2$, $-NHC(O)R'$, $-S(O)_2R'$, $-S(O)R'$, $-OH$, -halogen, $-N_3$, $-NH_2$, $-NH(R')$, $-N(R')_2$, and $-CN$, wherein each R' is independently H, $-C_{1-8}$ alkyl, or aryl.

The term "$C_{3-8}$ heterocyclo" refers to a $C_{3-8}$ heterocycle group defined above wherein one of the heterocycle group's hydrogen atoms is replaced with a bond. A $C_{3-8}$ heterocyclo can be unsubstituted or substituted with up to six groups including, but not limited to, $-C_{1-8}$ alkyl, $-O-(C_{1-8}$ alkyl), -aryl, $-C(O)R'$, $-OC(O)R'$, $-C(O)OR'$, $-C(O)NH_2$, $-C(O)NHR'$, $-C(O)N(R')_2$, $-NHC(O)R'$, $-S(O)_2R'$, $-S(O)R'$, $-OH$, -halogen, $-N_3$, $-NH_2$, $-NH(R')$, $-N(R')_2$ and $-CN$, wherein each R' is independently H, $-C_{1-8}$ alkyl, or aryl.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In certain aspects, a string of amino acids can be conservatively replaced with a structurally similar string that differs in order and/or composition of side chain family members.

As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some aspects, two or more sequences are said to be "completely conserved" or "identical" if they are 100% identical to one another. In some aspects, two or more sequences are said to be "highly conserved" if they are at least 70% identical, at least 80% identical, at least 90% identical, or at least 95% identical to one another. In some aspects, two or more sequences are said to be "highly conserved" if they are about 70% identical, about 80% identical, about 90% identical, about 95%, about 98%, or about 99% identical to one another. In some aspects, two or more sequences are said to be "conserved" if they are at least 30% identical, at least 40% identical, at least 50% identical, at least 60% identical, at least 70% identical, at least 80% identical, at least 90% identical, or at least 95% identical to one another. In some aspects, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of a polynucleotide or polypeptide or can apply to a portion, region or feature thereof.

The terms "excipient" and "carrier" are used interchangeably and refer to an inert substance added to a pharmaceutical composition to further facilitate administration of a compound.

As used herein, the terms "extracellular vesicle," "EV," and grammatical variants thereof, are used interchangeably and refer to a cell-derived vesicle comprising a membrane that encloses an internal space. Extracellular vesicles comprise all membrane-bound vesicles (e.g., exosomes, nanovesicles) that have a smaller diameter than the cell from which they are derived. In some aspects, extracellular vesicles range in diameter from 20 nm to 1000 nm, and can comprise various macromolecular payload either within the internal space (i.e., lumen), displayed on the external surface of the extracellular vesicle, and/or spanning the membrane. In some aspects, the payload can comprise nucleic acids, proteins, carbohydrates, lipids, small molecules, and/or combinations thereof. In certain aspects, an extracellular vehicle comprises an exosomal protein. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. In some aspects, the extracellular vesicles are produced by cells that express one or more transgene products. Unless indicated otherwise, EV comprises an exosome, nanovesicles, microsomes, microvesicles, extracellular bodies, apoptotic bodies, or combinations thereof. In certain aspects, an EV useful for the present disclosure is an exosome.

As used herein, the term "exosome" refers to an extracellular vesicle with a diameter between 20-300 nm (e.g., between 40-200 nm). Exosomes comprise a membrane that encloses an internal space (i.e., lumen), and, in some aspects, can be generated from a cell (e.g., producer cell) by direct plasma membrane budding or by fusion of the late endosome with the plasma membrane.

In certain aspects, an exosome comprises an exosomal protein. As described infra, exosome can be derived from a producer cell, and isolated from the producer cell based on its size, density, biochemical parameters, or a combination thereof. In some aspects, the exosomes of the present disclosure are produced by cells that express one or more transgene products.

As used herein, the term "functional fragment" refers to a protein fragment that retains protein function. For instance, in some aspects, a functional fragment of an exosomal protein, e.g., PTGFRN, retains the ability to anchor a biologically active molecule on the luminal surface or on the external surface of the EV.

Whether a fragment is a functional fragment can be assessed by any art known methods to determine the protein content of EVs including Western Blots, FACS analysis and fusions of the fragments with autofluorescent proteins like, e.g., GFP.

As used herein, "anchoring" a biologically active molecule on the luminal or external surface of an EV of the present disclosure refers to attaching covalently the biologically active molecule to the luminal or external surface of the EV, respectively.

As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present disclosure, the term homology encompasses both to identity and similarity.

In some aspects, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

In the context of the present disclosure, substitutions (even when they are referred to as amino acid substitution) are conducted at the nucleic acid level, i.e., substituting an amino acid residue with an alternative amino acid residue is conducted by substituting the codon encoding the first amino acid with a codon encoding the second amino acid.

As used herein, the term "identity" refers to the overall monomer conservation between polymeric molecules, e.g., between polypeptide molecules or polynucleotide molecules (e.g. DNA molecules and/or RNA molecules). The term "identical" without any additional qualifiers, e.g., protein A is identical to protein B, implies the sequences are 100% identical (100% sequence identity). Describing two sequences as, e.g., "70% identical," is equivalent to describing them as having, e.g., "70% sequence identity."

Calculation of the percent identity of two polypeptide sequences, for example, can be performed by aligning the two sequences for optimal comparison purposes (e.g., gaps can be introduced in one or both of a first and a second polypeptide sequences for optimal alignment and non-identical sequences can be disregarded for comparison purposes). In certain aspects, the length of a sequence aligned for comparison purposes is at least 30%, at least 40%, at least 50%, at least 60%, at least 70%, at least 80%, at least 90%, at least 95%, or 100% of the length of the reference sequence. The amino acids at corresponding amino acid positions are then compared.

When a position in the first sequence is occupied by the same amino acid as the corresponding position in the second sequence, then the molecules are identical at that position.

The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at worldwideweb.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity (% ID) or of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

An "immune response", as used herein, refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, cosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4+ cell, a CD8+ T cell, or a Treg cell, or activation or inhibition of any other cell of the immune system, e.g., NK cell. Accordingly an immune response can comprise a humoral immune response (e.g., mediated by B-cells), cellular immune response (e.g., mediated by T cells), or both humoral and cellular immune responses. In some aspects of the present disclosure, the biologically active molecule is a molecule capable of eliciting an immune response.

In some aspects, an immune response is an "inhibitory" immune response. An inhibitory immune response is an immune response that blocks or diminishes the effects of a stimulus (e.g., antigen). In certain aspects, the inhibitory immune response comprises the production of inhibitory antibodies against the stimulus. In some aspects, an immune response is a "stimulatory" immune response. A stimulatory immune response is an immune response that results in the generation of effectors cells (e.g., cytotoxic T lymphocytes) that can destroy and clear a target antigen (e.g., tumor antigen or viruses).

As used herein, the terms "isolated," "purified," "extracted," and grammatical variants thereof are used interchangeably and refer to the state of a preparation of desired EVs (e.g., a plurality of EVs of known or unknown amount and/or concentration), that has undergone one or more processes of purification, e.g., a selection or an enrichment of the desired EV preparation. In some aspects, isolating or purifying as used herein is the process of removing, partially removing (e.g., a fraction) of the EVs from a sample containing producer cells. In some aspects, an isolated EV composition has no detectable undesired activity or, alternatively, the level or amount of the undesired activity is at or below an acceptable level or amount. In some aspects, an isolated EV composition has an amount and/or concentration of desired EVs at or above an acceptable amount and/or concentration. In some aspects, the isolated EVs composition is enriched as compared to the starting material (e.g., producer cell preparations) from which the composition is obtained. This enrichment can be by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%, at least about 99.9999%, or greater than 99.9999% as compared to the starting material. In some aspects, isolated EV preparations are substantially free of residual biological products. In some aspects, the isolated EV preparations are 100% free, at least about 99% free, at least about 98% free, at least about 97% free, at least about 96% free, at least about 95% free, at least about 94% free, at least about 93% free, at least about 92% free, at least about 91% free, or at least about 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

The terms "linked," "fused," and grammatical variants thereof are used interchangeably and refer to a first moiety, e.g., a first amino acid sequence or nucleotide sequence, covalently or non-covalently joined to a second moiety, e.g., a second amino acid sequence or nucleotide sequence, respectively. The first moiety can be directly joined or juxtaposed to the second moiety or alternatively an intervening moiety can covalently join the first moiety to the second moiety. The term "linked" means not only a fusion of a first moiety to a second moiety at the C-terminus or the N-terminus, but also includes insertion of the whole first moiety (or the second moiety) into any two points, e.g., amino acids, in the second moiety (or the first moiety, respectively). In one aspect, the first moiety is linked to a second moiety by a peptide bond or a linker. The first moiety can be linked to a second moiety by a phosphodiester bond or a linker. The linker can be a peptide or a polypeptide (for polypeptide chains) or a nucleotide or a nucleotide chain (for nucleotide chains) or any chemical moiety (for polypeptide or polynucleotide chains or any chemical molecules). The term "linked" is also indicated by a hyphen (-).

As used herein, the term "loading" or "loaded" refers to the introduction of a moiety of interest (e.g., payload, e.g., ASO) into, onto, or otherwise associate with an EV, such that the moiety of interest is associated with the EV. As described herein, in some aspects, an EV loaded with a payload refers to an EV where the payload is linked or conjugated to the exterior surface of the EV.

The term "loading efficiency" refers to a ratio of payload (e.g., antisense oligonucleotide) loaded onto an EV compared to total payload (e.g., antisense oligonucleotide) in solution (e.g., payload loaded/payload total). As is apparent from the present disclosure, in some aspects, an increase in loading efficiency means that more of the payload (e.g., ASOs) in the solution (comprising the mixture of EVs and payloads) has been loaded onto the EVs compared to a reference value (e.g., loading efficiency observed with a loading method that differs from the present disclosure). Unless indicated, the term "loading efficiency" and "loading density" can be used interchangeably herein.

As used herein the term "lumen-engineered EV" refers to an EV with the luminal surface of the membrane or the lumen of the EV modified in its composition so that the luminal surface or the lumen of the engineered EV is different from that of the EV prior to the modification or of the naturally occurring EV.

The engineering can be directly in the lumen (i.e., the void within the EV) or in the membrane of the EV, in particular the luminal surface of the EV, so that the lumen and/or the luminal surface of the EV is changed. For example, the membrane is modified in its composition of a protein, a lipid, a small molecule, a carbohydrate, etc. so that the luminal surface of the EV is modified. Similarly, the contents in the lumen can be modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some aspects, a lumen-engineered EV comprises an exogenous protein (i.e., a protein that the EV does not naturally express) or a fragment or variant thereof that can be exposed on the luminal surface or lumen of the EV or can be an anchoring point (attachment) for a moiety exposed on the inner layer of the EV.

As used herein, the term "macromolecule" refers to nucleic acids, proteins, lipids, carbohydrates, metabolites, or combinations thereof.

The term "modified," when used in the context of EVs described herein, refers to an alteration or engineering of an EV and/or its producer cell, such that the modified EV is different from a naturally-occurring EV. In some aspects, a modified EV described herein comprises a membrane that differs in composition of a protein, a lipid, a small molecular, a carbohydrate, etc. compared to the membrane of a naturally-occurring EV. For instance, as demonstrated herein, the EVs described herein have been modified to comprise an increased amount of a payload (e.g., antisense oligonucleotide) that is not naturally found in EVs. In certain aspects, such modifications to the membrane change the exterior surface of the EV (e.g., surface-engineered EVs). In certain aspects, such modifications to the membrane change the luminal surface of the EV (e.g., lumen-engineered EV described herein).

As used herein, the terms "modified protein" or "protein modification" refers to a protein having at least 15% identity to the non-mutant amino acid sequence of the protein. A modification of a protein includes a fragment or a variant of the protein. A modification of a protein can further include chemical, or physical modification to a fragment or a variant of the protein.

As used herein, the terms "modulate," "modify," and grammatical variants thereof, generally refer when applied to a specific concentration, level, expression, function or behavior, to the ability to alter, by increasing or decreasing, e.g., directly or indirectly promoting/stimulating/up-regulating or interfering with/inhibiting/down-regulating the specific concentration, level, expression, function or behavior, such as, e.g., to act as an antagonist or agonist. In some instances, a modulator can increase and/or decrease a certain concentration, level, activity or function relative to a control, or relative to the average level of activity that would generally be expected or relative to a control level of activity.

As used herein, the term "nanovesicle" refers to an extracellular vesicle with a diameter between 20-250 nm (e.g., between 30-150 nm) and is generated from a cell (e.g., producer cell) by direct or indirect manipulation such that the nanovesicle would not be produced by the cell without the manipulation. Appropriate manipulations of the cell to produce the nanovesicles include but are not limited to serial extrusion, treatment with alkaline solutions, sonication, or combinations thereof. In some aspects, production of nanovesicles can result in the destruction of the producer cell. In some aspects, population of nanovesicles described herein are substantially free of vesicles that are derived from cells by way of direct budding from the plasma membrane or fusion of the late endosome with the plasma membrane. Nanovesicles, once derived from a producer cell, can be isolated from the producer cell based on its size, density, biochemical parameters, or a combination thereof.

As used herein, the term "payload" refers to a biologically active molecule (e.g., a therapeutic agent) that acts on a target (e.g., a target cell) that is contacted with the EV described herein. Non-limiting examples of payloads that can be introduced into an EV include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA, phosphorodiamidate morpholino oligomer (PMO), peptide-conjugated phosphorodiamidate morpholino oligomer (PPMO), and antisense oligonucleotides), amino acids (e.g., amino acids comprising a detectable moiety or a toxin or that disrupt translation), polypeptides (e.g., enzymes), lipids, carbohydrates, and small molecules (e.g., small molecule drugs and toxins). In some aspects, the payload comprises an antisense oligonucleotide.

The terms "pharmaceutically-acceptable carrier," "pharmaceutically-acceptable excipient," and grammatical variations thereof, encompass any of the agents approved by a regulatory agency of the U.S. Federal government or listed in the U.S. Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term "pharmaceutical composition" refers to one or more of the compounds described herein (e.g., EVs), mixed or intermingled with, or suspended in one or more other chemical components, such as pharmaceutically-acceptable carriers and excipients. One purpose of a pharmaceutical composition is to facilitate administration of preparations of EVs to a subject.

The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. In certain aspects, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In certain aspects, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects of the present disclosure, the biologically active molecule is a polynucleotide (e.g., antisense oligonucleotide).

The terms "polypeptide," "peptide," and "protein" are used interchangeably herein to refer to polymers of amino acids of any length. The polymer can comprise modified amino acids.

The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term "polypeptide," as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some aspects, a "peptide" can be less than or equal to 50 amino acids long, e.g., about 5, 10, 15, 20, 25, 30, 35, 40, 45, or 50 amino acids long.

The terms "prevent," "preventing," and variants thereof as used herein, refer partially or completely delaying onset of an disease, disorder and/or condition; partially or completely delaying onset of one or more symptoms, features, or clinical manifestations of a particular disease, disorder, and/or condition; partially or completely delaying onset of one or more symptoms, features, or manifestations of a particular disease, disorder, and/or condition; partially or completely delaying progression from a particular disease, disorder and/or condition; and/or decreasing the risk of developing pathology associated with the disease, disorder, and/or condition.

In some aspects, preventing an outcome is achieved through prophylactic treatment.

As used herein, the term "producer cell" refers to a cell used for generating an EV.

A producer cell can be a cell cultured in vitro, or a cell in vivo. A producer cell includes, but not limited to, a cell known to be effective in generating EVs, e.g., HEK293 cells, Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, RPTEC/TERT1 cells. In certain aspects, a producer cell is not an antigen-presenting cell. In some aspects, a producer cell is not a dendritic cell, a B cell, a mast cell, a macrophage, a neutrophil, Kupffer-Browicz cell, cell derived from any of these cells, or any combination thereof.

As used herein, "prophylactic" refers to a therapeutic or course of action used to prevent the onset of a disease or condition, or to prevent or delay a symptom associated with a disease or condition.

As used herein, a "prophylaxis" refers to a measure taken to maintain health and prevent or delay the onset of a bleeding episode, or to prevent or delay symptoms associated with a disease or condition.

A "recombinant" polypeptide or protein refers to a polypeptide or protein produced via recombinant DNA technology. Recombinantly produced polypeptides and proteins expressed in engineered host cells are considered isolated for the purpose of the disclosure, as are native or recombinant polypeptides which have been separated, fractionated, or partially or substantially purified by any suitable technique. The polypeptides disclosed herein can be recombinantly produced using methods known in the art. Alternatively, the proteins and peptides disclosed herein can be chemically synthesized. In some aspects of the present disclosure, the exosomal proteins present in EVs, are recombinantly produced by overexpressing the exosomal proteins in the producer cells, so that levels of exosomal proteins in the resulting EVs are significantly increased with respect to the levels of exosomal proteins present in EVs of producer cells not overexpressing such exosomal proteins.

As used herein, the term "exosomal proteins" refers to EV proteins that have been identified on the surface of EVs. See, e.g., U.S. Pat. No. 10,195,290, which is incorporated herein by reference in its entirety. Non-limiting examples of exosomal proteins include: prostaglandin F2 receptor negative regulator ("PTGFRN"); basigin ("BSG"); immunoglobulin superfamily member 2 ("IGSF2"); immunoglobulin superfamily member 3 ("IGSF3"); immunoglobulin superfamily member 8 ("IGSF8"); integrin beta-1 ("ITGB1"); integrin alpha-4 ("ITGA4"); 4F2 cell-surface antigen heavy chain ("SLC3A2"); and a class of ATP transporter proteins ("ATP1A1," "ATP1A2," "ATP1A3," "ATP1A4," "ATP1B3," "ATP2B1," "ATP2B2," "ATP2B3," "ATP2B"). In some aspects, an exosomal protein can be a whole protein or a fragment thereof (e.g., functional fragment, e.g., the smallest fragment that is capable of anchoring another moiety on the external surface or on the luminal surface of the EV. In some aspects, an exosomal protein can anchor a biologically active molecule to the external surface or the lumen of the EV. Non-limiting examples of other exosomal proteins that can be used with the present disclosure include: aminopeptidase N (CD13); Neprilysin, AKA membrane metalloendopeptidase (MME); ectonucleotide pyrophosphatase/phosphodiesterase family member 1 (ENPP1); Neuropilin-1 (NRP1); CD9, CD63, CD81, PDGFR, GPI anchor proteins, lactadherin, LAMP2, and LAMP2B.

Additional exosomal proteins that have been identified within the lumen of E. See, e.g., U.S. Publ. No. 2020/0347112 A1, which is incorporated herein by reference in its entirety.

Non-limiting examples of exosomal proteins include: myristoylated alanine rich Protein Kinase C substrate ("MARCKS"); myristoylated alanine rich Protein Kinase C substrate like 1 ("MARCKSL1"); and brain acid soluble protein 1 ("BASP1"). In some aspects, an exosomal protein can be a whole protein or a fragment thereof (e.g., functional fragment, e.g., the smallest fragment that is capable of anchoring a moiety on the luminal surface of the EV. In some aspects, an exosomal can anchor a moiety to the luminal surface of the EV. In some aspects of the present disclosure, a moiety can be covalently attached to an exosome.

As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art. It is understood that percentage of similarity is contingent on the comparison scale used, i.e., whether the amino acids are compared, e.g., according to their evolutionary proximity, charge, volume, flexibility, polarity, hydrophobicity, aromaticity, isoelectric point, antigenicity, or combinations thereof.

The term "spacer" as used herein refers to a bifunctional chemical moiety which is capable of covalently linking together two spaced moieties (e.g., a cleavable linker and a biologically active molecule) into a normally stable dipartate molecule.

Unless otherwise indicated, reference to a compound that has one or more stereocenters intends each stereoisomer, and all combinations of stereoisomers, thereof.

The terms "subject," "patient," "individual," and "host," and variants thereof are used interchangeably herein and refer to any mammalian subject, including without limitation, humans, domestic animals (e.g., dogs, cats and the like), farm animals (e.g., cows, sheep, pigs, horses and the like), and laboratory animals (e.g., monkey, rats, mice, rabbits, guinea pigs and the like) for whom diagnosis, treatment, or therapy is desired, particularly humans. The methods described herein are applicable to both human therapy and veterinary applications.

As used herein, the term "substantially free" means that the sample comprising EVs, comprises less than 10% of macromolecules, e.g., contaminants, by mass/volume (m/v) percentage concentration. Some fractions can contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein the term "surface-engineered EV" refers to an EV with the membrane or the surface of the EV modified in its composition so that the surface of the engineered EV is different from that of the EV prior to the modification or of the naturally occurring EV.

As used herein the term "surface-engineered exosome" refers to an exosome with the membrane or the surface of the exosome (external surface or luminal surface) modified in its composition so that the surface of the engineered exosome is different from that of the exosome prior to the modification or of the naturally occurring exosome.

The engineering can be on the surface and/or in the membrane of the EV so that the surface of the EV is changed. For example, the membrane can be modified in its composition of, e.g., a protein, a lipid, a small molecule, a carbohydrate, or a combination thereof. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. In some aspects, a surface-engineered EV comprises an exogenous protein (i.e., a protein that the EV does not naturally express) or a fragment or variant thereof that can be exposed to the surface of the EV or can be an anchoring point (attachment) for a moiety exposed on the surface of the EV. In some aspects, a surface-engineered EV comprises a higher expression (e.g., higher number) of a natural EV, e.g., exosomal protein (e.g., PTGFRN) or a fragment or variant thereof that can be exposed to the surface of the EV or can be an anchoring point (attachment) for a moiety exposed on the surface of the EV.

As used herein the term "therapeutically effective amount" is the amount of reagent or pharmaceutical compound comprising an EV described herein that is sufficient to a produce a desired therapeutic effect, pharmacologic and/or physiologic effect on a subject in need thereof. A therapeutically effective amount can be a "prophylactically effective amount" as prophylaxis can be considered therapy.

The terms "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one aspect, the term "treating" or "treatment" means inducing an immune response in a subject against an antigen.

As used herein, the term "variant" of a molecule (e.g., functional molecule, antigen, or exosomal proteins) refers to a molecule that shares certain structural and functional identities with another molecule upon comparison by a method known in the art. For example, a variant of a protein can include a substitution, insertion, deletion, frame shift or rearrangement in another protein.

Naturally occurring variants are called "allelic variants," and refer to one of several alternate forms of a gene occupying a given locus on a chromosome of an organism (Genes 11, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, variants or derivatives include, e.g., modified polypeptides. In some aspects, variants or derivatives of, e.g., polypeptides, polynucleotides, lipids, glycoproteins, are the result of chemical modification and/or endogenous modification. In some aspects, variants or derivatives are the result of in vivo modification. In some aspects, variants or derivatives are the result of in vitro modification. In yet some aspects, variant or derivatives are the result of intracellular modification in producer cells.

II. Method of Loading a Payload

Described herein are methods of loading an EV with a payload, such that the loading efficiency of the EV is increased.

In some aspects, a method of producing an EV comprises modifying the isolated EV by directly introducing one or more moieties of interest (e.g., payload) into or onto the EVs. For instance, as described herein, a payload (e.g., ASO) can be introduced to the EV by mixing the payload with the EV, e.g., under the loading conditions described herein. In some aspects, the payload is conjugated to a cholesterol, such that the mixing of the payload with the EV allows the cholesterol to interact with the lipid membrane of the EV, and thereby, attach the payload to the exterior surface of the EV. As used herein, the term "mixing" refers to the process of bringing a payload and an EV in closer proximity, such that the EV can be loaded with the payload, e.g., the payload associates with (e.g., conjugated to) the exterior surface of the EV, the payload associates with (e.g., conjugated to) the luminal surface of the EV, the payload is within the lumen of the EV, or any combination thereof. Unless indicated otherwise, the mixing can performed using any suitable methods known in the art. For example, in some aspects, the mixing can occur in a batch mode (e.g., payloads and EVs are added at the beginning of the mixing process). In some aspects, the mixing can occur in a continuous process (e.g., payloads and EVs are continuously added to the mixture during the course of the mixing process, e.g., in a continuous stirred-tank reactor (CSTR)). In some aspects, the mixing can occur in a semi-batch mode. In some aspects, the mixing can occur in a semi-continuous mode.

In certain aspects, the one or more moieties (e.g., payload) are introduced to the EV by transfection. In some aspects, the one or more moieties (e.g., payload) can be introduced into the EV using synthetic macromolecules such as cationic lipids and polymers (Papapetrou et al., *Gene Therapy* 12: Si 18-S130 (2005)). In certain aspects, chemicals such as calcium phosphate, cyclodextrin, or polybrene, can be used to introduce the one or more moieties (e.g., payload) to the EV.

In some aspects, one or more moieties (e.g., payload) can be conjugated to the surface of the EV (i.e., conjugated or linked directly to the exterior surface of the EV or to the luminal surface of the EV). Conjugation can be achieved chemically or enzymatically, by methods known in the art.

In some aspects, the EV comprises one or more moieties (e.g., payload) that are chemically conjugated. Chemical conjugation can be accomplished by covalent bonding of the one or more moieties (e.g., payload and/or targeting moiety) to another molecule, with or without use of a linker or affinity ligand disclosed herein. The formation of such conjugates is within the skill of artisans and various techniques are known for accomplishing the conjugation, with the choice of the particular technique being guided by the materials to be conjugated. In certain aspects, polypeptides are conjugated to the EV. In some aspects, non-polypeptides, such as lipids, carbohydrates, nucleic acids, and small molecules, are conjugated to the EV.

As described herein, loading a payload to an EV using the methods provided herein can not only increase the loading efficiency but also improve one or more additional properties of the EVs. As demonstrated herein (see, e.g., Example 6), in some aspects, the loading parameters provided herein (e.g., salt concentration, loading temperature, loading duration, payload feed concentration, EV feed concentration) can improve the stability of the EVs after the loading of the payload. As used herein, the term "stability" refers to the ability of a compound (e.g., EVs loaded with a payload, such as those described herein) to retain its chemical, physical, microbiological, and/or biopharmaceutical properties within specified limits throughout its shelf-life. For example, in some aspects, the payload-loaded EVs remain stable after multiple (e.g., at least two, at least three, at least four, or at least five) freeze-and-thaw treatments. In some aspects, the payload-loaded EVs remain stable and are less likely to aggregate during subsequent purification steps. Not to be bound by any one theory, because of the increased stability, the payload remains associated with the EV once loaded to the EVs. Accordingly, in some aspects, the loading methods provided herein can help decrease the dissociation of a payload from an EV after the EV loading. And, as is apparent from the present disclosure, in some aspects, the increased loading efficiency can improve the potency of the EVs (see, e.g., Example 4).

II.A. Salt Concentration

In some aspects, the present disclosure provides a method of loading an EV with a payload, comprising mixing the payload with the EV in a buffer (also referred to herein as the "loading buffer") comprising a salt, wherein the concentration of the salt ("salt concentration") is increased compared to a reference buffer (e.g., corresponding buffer that does not comprise the salt or has a salt concentration that is less than that of the loading buffer of the present disclosure). In some aspects, the salt concentration of the loading buffer is greater than about 0.1-fold, greater than about 0.2-fold, greater than about 0.3-fold, greater than about 0.4-fold, greater than about 0.5-fold, greater than about 0.6-fold, greater than about 0.7-fold, greater than about 0.8-fold, greater than about 0.9-fold, greater than about 1-fold, greater than about 2-fold, greater than about 3-fold, greater than about 4-fold, greater than about 5-fold, greater than about 6-fold, greater than about 7-fold, greater than about 8-fold, greater than about 9-fold, greater than about 10-fold, greater than about 15-fold, greater than about 20-fold, greater than about 25-fold, greater than about 30-fold, greater than about 35-fold, greater than about 40-fold, greater than about 45-fold, or greater than about 50-fold, compared to the salt concentration of the reference buffer.

In some aspects, the salt concentration of the loading buffer is at least about 1 mM, at least about 5 mM, at least about 10 mM, at least about 20 mM, at least about 30 mM, at least about 40 mM, at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, at least about 150 mM, at least about 160 mM, at least about 170 mM, at least about 180 mM, at least about 190 mM, at least about 200 mM, at least about 225 mM, at least about 250 mM, at least about 275 mM, at least about 300 mM, at least about 325 mM, at least about 350 mM, at least about 375 mM, at least about 400 mM, at least about 425 mM, at least about 450 mM, at least about 475 mM, or at least about 500 mM. In some aspects, the salt concentration of the loading buffer is less than about 500 mM, less than about 475 mM, less than about 450 mM, less than about 425 mM, less than about 400 mM, less than about 375 mM, less than about 350 mM, less than about 325 mM, or less than about 300 mM. In some aspects, the salt concentration of the loading buffer is less than about 200 mM, less than about 190 mM, less than about 180 mM, less than about 170 mM, less than about 160 mM, less than about 150 mM, less than about 140 mM, less than about 130 mM, less than about 120 mM, or less than about 110 mM.

In some aspects, the salt concentration of the loading buffer is between about 1 mM and about 150 mM, between about 5 mM and about 150 mM, between about 10 mM and about 150 mM, between about 20 mM and about 150 mM, between about 30 mM and about 150 mM, between about 40 mM and about 150 mM, between about 50 mM and about 150 mM, between about 60 mM and about 150 mM, between about 70 mM and about 150 mM, between about 80 mM and about 150 mM, between about 10 mM and about 140 mM, between about 20 mM and about 140 mM, between about 30 mM and about 140 mM, between about 40 mM and about 140 mM, between about 50 mM and about 140 mM, between about 10 mM and about 130 mM, between about 20 mM and about 130 mM, between about 30 mM and about 130 mM, between about 40 mM and about 130 mM, between about 50 mM and about 130 mM, between about 10 mM and about 120 mM, between about 20 mM and about 120 mM, between about 30 mM and about 120 mM, between about 40 mM and about 120 mM, between about 50 mM and about 120 mM, between about 60 mM and about 120 mM, between about 70 mM and about 120 mM, between about 80 mM and about 120 mM, between about 50 mM and about 100 mM, between about 100 mM and about 150 mM, or between about 90 mM and about 110 mM.

In some aspects, the salt concentration of the loading buffer is about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 m, about 180 mM, or about 190 mM. In certain aspects, the salt concentration of the loading buffer is about 50 mM, about 60 mM, about 70 mM, about 80 mM, about 90 mM, about 100 mM, about 110 mM, about 120 mM, about 130 mM, about 140 mM, or about 150 mM. In certain aspects, the salt concentration of the loading buffer is about 100 mM. In certain aspects, the salt concentration of the loading buffer is about 110 mM. In certain aspects, the salt concentration of the loading buffer is about 120 mM. In some aspects, the salt concentration of the loading buffer is about 130 mM. In some aspects, the salt concentration of the loading buffer is about 140 mM. In some aspects, the salt concentration of the loading buffer is about 150 mM. In certain aspects, the salt concentration of the loading buffer is about 90 mM. In certain aspects, the salt concentration of the loading buffer is about 80 mM.

In some aspects, the salt concentration of the loading buffer is between about 25 mM and about 500 mM. In some aspects, the salt concentration is between about 150 mM and about 450 mM. In some aspects, the salt concentration of the loading buffer is about 150 mM or more. For example, in some aspects, the salt concentration of the loading buffer is about 175 mM.

In some aspects, the salt concentration of the loading buffer is about 200 mM. In some aspects, the salt concentration of the loading buffer is about 225 mM. In some aspects, the salt concentration of the loading buffer is about 250 mM. In some aspects, the salt concentration of the loading buffer is about 275 mM. In some aspects, the salt concentration of the loading buffer is about 300 mM.

In some aspects, the salt concentration of the loading buffer is about 325 mM. In some aspects, the salt concentration of the loading buffer is about 350 mM. In some aspects, the salt concentration of the loading buffer is about 375 mM. In some aspects, the salt concentration of the loading buffer is about 400 mM. In some aspects, the salt concentration of the loading buffer is about 425 mM.

In some aspects, the salt concentration of the loading buffer is about 450 mM. In some aspects, the salt concentration of the loading buffer is about 475 mM. In some aspects, the salt concentration of the loading buffer is about 500 mM.

As demonstrated herein, the salt concentration of the loading buffer can affect the loading efficiency of a payload (e.g., antisense oligonucleotide) in an EV. For instance, Applicant has identified that an increase in salt concentration (e.g., particularly within the range of salt concentrations disclosed herein) of the loading buffer can increase the loading efficiency of an EV.

Accordingly, in some aspects, mixing a payload (e.g., antisense oligonucleotide) with an EV in a loading buffer comprising one or more of the salt concentrations disclosed herein increases the loading of the payload in the EV (e.g., onto the exterior surface, onto the luminal surface, and/or within the lumen) by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to loading the payload in an EV in the reference buffer (e.g., does not comprise the salt or comprises the salt but at a lower concentration). As is apparent from the present disclosure, the increase in the loading of the payload results in an increase in the payload concentration of the EV.

For instance, in some aspects, mixing the payload and the EVs in a loading buffer with increased salt concentration (e.g., range of salt concentrations described herein) increases the amount of payload (e.g., number of antisense oligonucleotides) that is associated with the exterior surface of the EV. In some aspects, the amount of payload that is associated with the exterior surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is loaded with the reference buffer). In some aspects, mixing the payload and the EVs in a loading buffer with increased salt concentration increases the amount of payload that is associated with the luminal surface of the EV. In some aspects, the amount of payload that is associated with the luminal surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the luminal surface of the EV when the payload is loaded with the reference buffer). In some aspects, mixing the payload and the EVs in a loading buffer with increased salt concentration increases the amount of payload that is associated with the lumen of the EV. In some aspects, the amount of payload that is associated with the lumen of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload within the lumen of the EV when the payload is loaded with the reference buffer). In some aspects, mixing the payload and the EVs in a loading buffer with increased salt concentration increases the amount of payload that is associated with the exterior surface of the EV, the luminal surface of the EV, the lumen of the EV, or any combination thereof.

The loading buffer described herein can comprise any suitable salts known in the art. In some aspects, the salt comprises a monovalent salt, divalent salt, trivalent salt, or combinations thereof. In certain aspects, the salt comprises a monovalent salt. In some aspects, the salt comprises a divalent salt. In some aspects, the salt comprises a trivalent salt. Non-limiting examples of such salts are provided further below. In some aspects, the salt comprises NaCl (sodium chloride), KCl (potassium chloride), $PO_4$ (phosphate salt), $CaCl_2$) (calcium chloride), $MgCl_2$ (magnesium chloride), $Mg_2SO_4$ (magnesium sulfate), $ZnCl_2$ (zinc chloride), $MnCl_2$ (manganese chloride), $MnSO_4$ (manganese sulfate), NaSCN (sodium thiocyanate), KSCN (potassium thiocyanate), LiCl (lithium chloride), $K_2HPO_4$ (dipotassium phosphate), $Na_2SO_4$ (sodium sulfate), NaPO4 (sodium phosphate), $K_2SO_4$ (potassium phosphate), sodium acetate, sodium bromide, sodium iodide, potassium bromide, lithium bromide, sodium fluoride, potassium fluoride, lithium fluoride, lithium iodide, potassium acetate, lithium acetate, potassium iodide, calcium sulfate, sodium sulfate, chromium trichloride, chromium sulfate, sodium citrate, iron (III) chloride, yttrium (III) chloride, potassium sulfate, ferrous chloride, calcium citrate, magnesium phosphate, ferric chloride, arginine-HCl, or any combination thereof. In some aspects, the salt comprises NaCl.

In some aspects, increased loading efficiency can be achieved by any of the following: changing salt or salt concentration, changing pH, or adding organic modifiers, organic solvents, small molecules, detergents, zwitterions, amino acids, polymers, polyols (e.g., sucrose, glucose, trehalose, mannose, sorbitol, mannitol, glycerol, etc.) antioxidants (e.g., methionine), EDTA, EGTA, Polysorbate 20, Polysorbate 80, ethylene glycol, propylene glycol, polyethylene glycol, polypropylene glycol, and/or urea, adding excipients that alter the polarity of the solution, adding excipients that modulate the structure of the EVs, or any combination thereof.

In some aspects, increased loading efficiency can be achieved by increasing the concentration of a monovalent salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or any combination thereof.

II.B. Loading Temperature

As demonstrated herein, Applicant has further identified that increasing the temperature at which the payload and the EVs are mixed (also referred to herein as "loading temperature") can also increase the loading efficiency of the EV. Accordingly, in some aspects, the present disclosure provides a method of loading an EV with a payload, comprising mixing the payload with the EV at a loading temperature that is higher than about 0° C. (e.g., higher than about 2° C. or higher than about 4° C.). In some aspects, the loading temperature is at least about 0° C., at least about 1° C., at least about 2° C., at least about 3° C., at least about 4° C., at least about 5° C., at least about 10° C., at least about 15° C., at least about 20° C., at least about 25° C., at least about 30° C., at least about 35° C., at least about 37° C., at least about 40° C., at least about 45° C., at least about 50° C., at least about 55° C., at least about 60° C., at least about 65° C., at least about 70° C., at least about 75° C., or at least about 80° C. In certain aspects, the loading temperature is between about 0° C. and about 40° C., between about 1° C. and about 40° C., between about 2° C. and about 40° C., between about 3° C. and about 40° C., between about 4° C. and about 40° C., between about 5° C. and about 40° C., between about 10° C. and about 40° C., between about 15° C. and about 40° C., between about 20° C. and about 40° C., between about 25° C. and about 40° C., between about 30° C. and about 40° C., between about 35° C. and about 40° C., between about 5° C. and about 38° C., between about 10° C. and about 38° C., between about 15° C. and about 38° C., between about 20° C. and about 38° C., between about 25° C. and about 38° C., between about 30° C. and about 38° C., between about 35° C. and about 38° C., between about 5° C. and about 37° C., between about 10° C. and about 37° C., between about 15° C. and about 37° C., between about 20° C. and about 37° C., between about 25° C. and about 37° C., between about 30° C. and about 37° C., or between about 35° C. and about 37° C..

In some aspects, the loading temperature is about 0° C., about 1° C., about 2° C., about 3° C., about 4° C., about 5° C., about 10° C., about 15° C., about 20° C., about 25° C., about 30° C., about 35° C., about 37° C., about 40° C., about 45° C., about 50° C., about 55° C., about 60° C., about 65° C., about 70° C., about 75° C., or about 80° C.

In some aspects, the loading temperature is between about 0° C. to about 80° C. In some aspects, the loading temperature is between about 37° C. to about 70° C. In some aspects, the loading temperature is about 37° C. In some aspects, the loading temperature is about 40° C. In some aspects, the loading temperature is about 45° C. In some aspects, the loading temperature is about 50° C. In some aspects, the loading temperature is about 55° C. In some aspects, the loading temperature is about 60° C. In some aspects, the loading temperature is about 65° C. In some aspects, the loading temperature is about 70° C. In some aspects, the loading temperature is about 75° C. In some aspects, the loading temperature is about 80° C.

In some aspects, mixing the payload and the EVs at a loading temperature described herein increases the loading of the payload in the EV (e.g., onto the exterior surface, onto the luminal surface, and/or within the lumen) by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to loading the payload in an EV at a reference temperature (e.g., lower than the loading temperature). As is apparent from the present disclosure, the increase in the loading of the payload results in an increase in the payload concentration of the EV.

In some aspects, increasing the loading temperature at which the payload and the EV are mixed increases the amount of payload (e.g., number of antisense oligonucleotides) that is associated with the exterior surface of the EV. In some aspects, the amount of payload that is associated with the exterior surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is loaded at the reference temperature). In some aspects, increasing the loading temperature at which the payload and the EV are mixed increases the amount of payload that is associated with the luminal surface of the EV. In some aspects, the amount of payload that is associated with the luminal surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the luminal surface of the EV when the payload is loaded at the reference temperature).

In some aspects, increasing the loading temperature at which the payload and the EVs are mixed increases the amount of payload that is associated with the lumen of the EVs. In some aspects, the amount of payload that is associated with the lumen of the EVs is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload within the lumen of the EV when the payload is loaded at the reference temperature). In some aspects, increasing the loading temperature at which the payload and the EVs are mixed increases the amount of payload that is associated with the exterior surface of the EVs, the luminal surface of the EVs, the lumen of the EVs, or any combination thereof.

II.C. Loading Duration

As demonstrated herein, in some aspects, increasing the time in which a payload and the EVs are allowed to mix (also referred to herein as "loading duration") can also increase the loading efficiency of the payload (e.g., antisense oligonucleotide) in the EV. In some aspects, the present disclosure provides a method of loading an EV with a payload, comprising mixing the payload with the EV at a loading duration of at least about 5 minutes (e.g., at least about one hour).

In certain aspects, the loading duration is between about five minutes and about 48 hours, between about five minutes and about 42 hours, between about five minutes and about 36 hours, between about five minutes and about 40 hours, between about five minutes and about 24 hours, between about 10 minutes and about 48 hours, between about 10 minutes and about 42 hours, between about 10 minutes and about 36 hours, between about 10 minutes and about 30 hours, between about 10 minutes and about 24 hours, between about 20 minutes and about 48 hours, between about 20 minutes and about 42 hours, between about 20 minutes and about 36 hours, between about 20 minutes about 30 hours, between about 20 minutes and about 24 hours, between about 30 minutes and about 48 hours, between about 30 minutes and about 42 hours, between about 30 minutes and about 36 hours, between about 30 minutes and about 30 hours, between about 30 minutes and about 24 hours, between about one hour and about 48 hours, between about one hour and about 42 hours, between about one hour and about 36 hours, between about one hour and about 30 hours, between about one hour and about 24 hours, between about six hours and about 48 hours, between about six hours and about 42 hours, between about six hours and about 36 hours, between about six hours and about 30 hours, between about six hours and about 24 hours, between about 12 hours and about 48 hours, between about 12 hours and about 42 hours, between about 12 hours and about 36 hours, between about 12 hours and about 30 hours, or between about 12 hours and about 24 hours. In certain aspects, the loading duration is about six hours, about 12 hours, about 24 hours, about 30 hours, about 36 hours, about 42 hours, or about 48 hours.

In some aspects, the loading duration is between about one hour and about 10 days. In some aspects, the loading duration is between about 24 hours and about seven days. In some aspects, the loading duration is about one hour. In some aspects, the loading duration is about six hours. In some aspects, the loading duration is about 12 hours. In some aspects, the loading duration is about 24 hours. In some aspects, the loading duration is about two days, In some aspects, the loading duration is about three days. In some aspects, the loading duration is about four days, In some aspects, the loading duration is about five days. In some aspects, the loading duration is about six days. In some aspects, the loading duration is about seven days. In some aspects, the loading duration is about eight days. In some aspects, the loading duration is about nine days. In some aspects, the loading duration is about 10 days.

In some aspects, mixing the payload and the EVs at a loading duration described herein (e.g., at least about 24 hours) increases the loading of the payload in the EV (e.g., onto the exterior surface, onto the luminal surface, and/or within the lumen) by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to loading the payload in an EV at a reference duration (e.g., shorter than the loading duration). As is apparent from the present disclosure, the increase in the loading of the payload results in an increase in the payload concentration of the EV.

In some aspects, increasing the loading duration increases the amount of payload (e.g., number of antisense oligonucleotides) that is associated with the exterior surface of the EV. In some aspects, the amount of payload that is associated with the exterior surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is mixed with the EV for the reference duration). In some aspects, increasing the loading duration increases the amount of payload that is associated with the luminal surface of the EV. In some aspects, the amount of payload that is associated with the luminal surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the luminal surface of the EV when the payload is mixed with the EV for the reference duration). In some aspects, increasing the loading duration increases the amount of payload that is associated with the lumen of the EVs. In some aspects, the amount of payload that is associated with the lumen of the EVs is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the luminal surface of the EV when the payload is mixed with the EV for the reference duration). In some aspects, increasing the loading duration increases the amount of payload that is associated with the exterior surface of the EVs, the luminal surface of the EVs, the lumen of the EVs, or any combination thereof.

II.D. Payload Feed Concentration

In some aspects, a method of loading an EV with a payload (e.g., antisense oligonucleotide) provided herein comprises increasing the payload feed concentration at which the EV and the payload are mixed, wherein the increase in the payload feed concentration enhances the loading efficiency of the payload. As used herein, the term "payload feed concentration" refers to the amount of payload that is mixed with EVs in the loading methods described herein.

In some aspects, the payload feed concentration is at least about 10 μM, at least about 20 μM, at least about 30 μM, at least about 40 μM, at least about 50 μM, at least about 60 μM, at least about 70 μM, at least about 80 μM, at least about 90 μM, at least about 100 PM, at least about 150 μM, at least about 200 μM, at least about 250 μM, at least about 300 μM, at least about 350 μM, at least about 400 μM, at least about 450 μM, at least about 500 μM, at least about 550 μM, at least about 600 μM, at least about 650 μM, at least about 700 μM, at least about 750 μM, at least about 800 μM, at least about 850 μM, at least about 900 μM, at least about 950 μM, at least about 1000 μM, at least about 1050 μM, at least about 1100 μM, at least about 1150 PM, at least about 1200 μM, at least about 1250 μM, at least about 1300 μM, at least about 1350 μM, at least about 1400 μM, at least about 1450 μM, at least about 1500 μM, at least about 1600 μM, at least about 1700 μM, at least about 1800 μM, at least about 1900 μM, at least about 2000 μM, at least about 2100 μM, at least about 2200 μM, at least about 2300 μM, at least about 2400 μM, at least about 2500 μM, at least about 2600 μM, at least about 2700 μM, at least about 2800 μM, at least about 2900 μM, or at least about 3000 μM. In some aspects, the payload feed concentration is about 600 μM. In some aspects, the payload feed concentration is about 800 μM.

In some aspects, the payload feed concentration is between about 50 μM and about 1000 μM, between about 100 μM and about 1000 μM, between about 200 PM and about 1000 μM, between about 300 μM and about 1000 μM, between about 400 μM and about 1000 μM, between about 500 μM and about 1000 μM, between about 50 μM and about 900 μM, between about 100 μM and about 900 μM, between about 200 μM and about 900 μM, between about 300 μM and about 900 μM, between about 400 μM and about 900 μM, between about 500 μM and about 900 μM, between about 50 μM and about 800 μM, between about 100 μM and about 800 μM, between about 200 μM and about 800 μM, between about 300 μM and about 800 μM, between about 400 μM and about 800 μM, between about 500 μM and about 800 μM, between about 50 μM and about 700 μM, between about 100 μM and about 700 μM, between about 200 μM and about 700 μM, between about 300 μM and about 700 μM, between about 400 μM and about 700 μM, or between about 500 μM and about 700. In some aspects, the payload feed concentration is between about 1000 μM and about 1100 μM, between about 1200 μM and about 1300 μM, between about 1300 μM and about 1400 μM, between about 1400 μM and about 1500 μM, between about 1500 μM and about 1600 μM, between about 1600 μM and about 1700 μM, between about 1700 μM and about 1800 μM, between about 1800 μM and about 1900 μM, between about 1900 μM and about 2000 μM, between about 2000 μM and about 2100 μM, between about 2100 μM and about 2200 μM, between about 2200 μM and about 2300 μM, between about 2300 μM and about 2400 μM, between about 2400 μM and about 2500 μM, between about 2500 μM and about 2600 μM, between about 2600 μM and about 2700 μM, between about 2700 μM and about 2800 μM, between about 2800 μM and about 2900 μM, or between about 2900 μM and about 3000 μM.

As described herein, in some aspects, increasing the payload feed concentration increases the loading of the payload in the EV (e.g., onto the exterior surface, onto the luminal surface, and/or within the lumen) by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared a reference payload feed concentration (e.g., less than the payload feed concentration described herein). As is apparent from the present disclosure, the increase in the loading of the payload results in an increase in the payload concentration of the EV.

In some aspects, increasing the payload feed concentration increases the amount of payload (e.g., number of antisense oligonucleotides) that is associated with the exterior surface of the EV. In some aspects, the amount of payload that is associated with the exterior surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is mixed with the EV at the reference payload feed concentration). In some aspects, increasing the payload feed concentration increases the amount of payload that is associated with the luminal surface of the EV. In some aspects, the amount of payload that is associated with the luminal surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is mixed with the EV at the reference payload feed concentration). In some aspects, increasing the payload feed concentration increases the amount of payload that is associated with the lumen of the EVs. In some aspects, the amount of payload that is associated with the lumen of the EVs is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is mixed with the EV at the reference payload feed concentration). In some aspects, increasing the payload feed concentration increases the amount of payload that is associated with the exterior surface of the EVs, the luminal surface of the EVs, the lumen of the EVs, or any combination thereof.

II.E. EV Feed Concentration

In some aspects, the present disclosure provides a method of loading an EV with a payload (e.g., antisense oligonucleotide), comprising mixing the payload and the EV at an increased EV feed concentration, wherein the increase in the EV feed concentration enhances the loading efficiency of the payload. As used herein, the term "EV feed concentration" refers to the amount of EVs that is mixed with a payload in the loading methods of the present disclosure.

In some aspects, the EV feed concentration is at least about $1\times10^{11}$ particles/mL (p/mL), at least about $2\times10^{11}$ p/mL, at least about $3\times10^{11}$ p/mL, at least about $4\times10^{11}$ p/mL, at least about $5\times10^{11}$ p/mL, at least about $6\times10^{11}$ p/mL, at least about $7\times10^{11}$ p/mL, at least about $8\times10^{11}$ p/mL, at least about $9\times10^{11}$ p/mL, at least about $0.1\times10^{13}$ p/mL, at least about $0.2\times10^{13}$ p/mL, at least about $0.3\times10^{13}$ p/mL, at least about $0.4\times10^{13}$ p/mL, at least about $0.5\times10^{13}$ p/mL, at least about $0.6\times10^{13}$ p/mL, at least about $0.7\times10^{13}$ p/mL, at least about $0.8\times10^{13}$ p/mL, at least about $0.9\times10^{13}$ p/mL, at least about $1.0\times10^{13}$ p/mL, at least about $1.1\times10^{13}$ p/mL, at least about $1.2\times10^{13}$ p/mL, at least about $1.3\times10^{13}$ p/mL, at least about $1.4\times10^{13}$ p/mL, at least about $1.5\times10^{13}$ p/mL, at least about $1.6\times10^{13}$ p/mL, at least about $1.7\times10^{13}$ p/mL, at least about $1.8\times10^{13}$ p/mL, at least about $1.9\times10^{13}$ p/mL, at least about $2.0\times10^{13}$ p/mL, at least about $2.1\times10^{13}$ p/mL, at least about $2.2\times10^{13}$ p/mL, at least about $2.3\times10^{13}$ p/mL, at least about $2.4\times10^{1'}$ p/mL, at least about $2.5\times10^{13}$ p/mL, at least about $2.6\times10^{'3}$ p/mL, at least about $2.7\times10^{13}$ p/mL, at least about $2.8\times10^{13}$ p/mL, at least about $2.9\times10^{13}$ p/mL, at least about $3.0\times10^{13}$ p/mL, at least about $4\times10^{1}$ p/mL, at least about $5\times10^{1}$ p/mL, at least about $6\times10^{13}$ p/mL, at least about $7\times10^{13}$ p/mL, at least about $8\times10^{13}$ p/mL, at least about $9\times10^{13}$ p/mL, or at least about $1\times10^{14}$ p/mL. In certain aspects, the EV feed concentration is about $1.0\times10^{13}$ p/mL. In some aspects, the EV feed concentration is about $1.4\times10^{13}$ p/mL. In some aspects, the EV feed concentration is about $6.0\times10^{12}$ p/mL.

In some aspects, the EV feed concentration is between about $0.2\times10^{13}$ p/mL and about $2.0\times10^{13}$ p/mL, between about $0.4\times10^{13}$ p/mL and about $2.0\times10^{13}$ p/mL, between about $0.6\times10^{13}$ p/mL and about $2.0\times10^{13}$ p/mL, between about $0.8\times10^{13}$ p/mL and about $2.0\times10^{13}$ p/mL, between about $1.0\times10^{3}$ p/mL and about $2.0\times10^{13}$ p/mL, between about $0.2\times10^{13}$ p/mL and about $1.8\times10^{13}$ p/mL, between about $0.4\times10^{13}$ p/mL and about $1.8\times10^{13}$ p/mL, between about $0.6\times10^{13}$ p/mL and about $1.8\times10^{13}$ p/mL, between about $0.8\times10^{13}$ p/mL and about $1.8\times10^{13}$ p/mL, between about $1.0\times10^{13}$ p/mL and about $1.8\times10^{13}$ p/mL, between about $0.2\times10^{13}$ p/mL and about $1.6\times10^{13}$ p/mL, between about $0.4\times10^{13}$ p/mL and about $1.6\times10^{13}$ p/mL, between about $0.6\times10^{13}$ p/mL and about $1.6\times10^{3}$ p/mL, between about $0.8\times10^{13}$ p/mL and about $1.6\times10^{13}$ p/mL, between about $1.0\times10^{13}$ p/mL and about $1.6\times10^{3}$ p/mL, between about $0.2\times10^{13}$ p/mL and about $1.4\times10^{13}$ p/mL, between about $0.4\times10^{13}$ p/mL and about $1.4\times10^{13}$ p/mL, between about $0.6\times10^{13}$ p/mL and about $1.4\times10^{13}$ p/mL, between about $0.8\times10^{13}$ p/mL and about $1.4\times10^{13}$ p/mL, between about $1.0\times10^{13}$ p/mL and about $1.4\times10^{13}$ p/mL, between about $0.2\times10^{13}$ p/mL and about $1.2\times10^{13}$ p/mL, between about $0.4\times10^{13}$ p/mL and about $1.2\times10^{13}$ p/mL, between about $0.6\times10^{13}$ p/mL and about $1.2\times10^{13}$ p/mL, between about $0.8\times10^{13}$ p/mL and about $1.2\times10^{13}$ p/mL, or between about $1.0\times10^{13}$ p/mL and about $1.2\times10^{13}$ p/mL. In some aspects, the EV feed concentration is between about $2\times10^{13}$ p/mL and about $1\times10^{14}$ p/mL, between about $3\times10^{13}$ p/mL and about $1\times10^{14}$ p/mL, between about $4\times10^{13}$ p/mL and about $1\times10^{'4}$ p/mL, between about $5\times10^{13}$ p/mL and about 1x1014 p/mL, between about $6\times10^{13}$ p/mL and about $1\times10^{14}$ p/mL, between about $7\times10^{13}$ p/mL and about $1\times10^{11}$ p/mL, between about $8\times10^{13}$ p/mL and about $1\times10^{14}$ p/mL, or between about $9\times10^{3}$ p/mL and about $1\times10^{14}$ p/mL.

In some aspects, increasing the EV feed concentration increases the loading of the payload in the EV (e.g., onto the exterior surface, onto the luminal surface, and/or within the lumen) by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared a reference EV feed concentration (e.g., less than the feed concentration described herein). As is apparent from the present disclosure, the increase in the loading of the payload results in an increase in the payload concentration of the EV.

In some aspects, increasing the EV feed concentration increases the amount of payload (e.g., number of antisense oligonucleotides) that is associated with the exterior surface of the EV. In some aspects, the amount of payload that is associated with the exterior surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is mixed with the EV at the reference EV feed concentration). In some aspects, increasing the EV feed concentration increases the amount of payload that is associated with the luminal surface of the EV. In some aspects, the amount of payload that is associated with the luminal surface of the EV is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is mixed with the EV at the reference EV feed concentration). In some aspects, increasing the EV feed concentration increases the amount of payload that is associated with the lumen of the EVs. In some aspects, the amount of payload that is associated with the lumen of the EVs is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is mixed with the EV at the reference EV feed concentration). In some aspects, increasing the EV feed concentration increases the amount of payload that is associated with the exterior surface of the EVs, the luminal surface of the EVs, the lumen of the EVs, or any combination thereof.

As is apparent from the present disclosure, in some aspects, a loading method of the present disclosure can comprise modulating multiple (e.g., two or more) loading parameters, such as those described herein. In some aspects, the salt concentration, loading temperature, loading duration, payload feed concentration, EV feed concentration, or combinations thereof, are increased.

For example, in some aspects, method of loading EVs with a payload provided herein comprises increasing both the salt concentration of the loading buffer (e.g., about 150 mM or higher) and the loading temperature (e.g., about 37° C. or higher). In some aspects, when the payload and EVs are mixed under such a condition, the loading efficiency is increased by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to the loading efficiency observed when the payload and the EV are mixed: (i) in a loading buffer with reduced salt concentration; (ii) at a decreased loading temperature; or (iii) in a loading buffer with reduced salt concentration and at a decreased loading temperature.

In some aspects, loading methods provided herein can comprise modulating multiple loading parameters to increase the loading efficiency of a payload in an EV. For example, in some aspects, a method of loading EVs with a payload provided herein comprises increasing both the salt concentration of the loading buffer (e.g., about 150 mM or higher) and the loading duration (e.g., for at least about 24 hours). In some aspects, the method comprises increasing both the loading temperature (e.g., about 37° C. or higher) and the loading duration (e.g., for at least about 24 hours). In some aspects, the loading method provided herein comprises increasing the salt concentration of the loading buffer (e.g., about 150 mM or higher), increasing the loading temperature (e.g., about 37° C. or higher), and increasing the loading duration (e.g., for at least about 24 hours). In some aspects, when the payload and EVs are mixed under such a condition, the loading efficiency is increased by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to the loading efficiency observed when the payload and the EV are mixed: (i) in a loading buffer with reduced salt concentration; (ii) at a decreased loading temperature; (iii) for shorter loading duration; or (iv) in any combination of (i) to (iii).

In some aspects, loading methods provided herein can comprise increasing both the salt concentration of the loading buffer (e.g., about 150 mM or higher) and the payload feed concentration (e.g., about 800 μM or more). In some aspects, a loading method comprises increasing both the loading temperature (e.g., about 37° C. or higher) and the payload feed concentration (e.g., about 800 μM or more). In some aspects, a method of loading an EV with a payload provided herein comprises increasing both the loading duration (e.g., for at least about 24 hours) and the payload feed concentration (e.g., about 800 μM or more). In some aspects, to increase the loading efficiency, loading method provided herein comprises increasing the salt concentration of the loading buffer (e.g., about 150 mM or higher), the loading temperature (e.g., about 37° C. or higher), the loading duration (e.g., for at least about 24 hours), and the payload feed concentration (e.g., about 800 μM or more). In some aspects, when the payload and EVs are mixed under such a condition, the loading efficiency is increased by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to the loading efficiency observed when the payload and the EV are mixed: (i) in a loading buffer with reduced salt concentration; (ii) at a decreased loading temperature; (iii) for shorter loading duration; (iv) with reduced payload feed concentration; or (v) in any combination of (i) to (iv).

In some aspects, a method of loading an EV with a payload provided herein comprises increasing both the salt concentration of the loading buffer (e.g., about 150 mM or higher) and the EV feed concentration (e.g., about $1.4\times10^{13}$ p/mL or higher). In some aspects, a loading method comprises increasing both the loading temperature (e.g., about 37° C. or higher) and the EV feed concentration (e.g., about $1.4\times10^{13}$ p/mL or higher). In some aspects, a loading method comprises increasing both the loading duration (e.g., for at least about 24 hours) and the EV feed concentration (e.g., about $1.4\times10^{13}$ p/mL or higher). In some aspects, the loading method comprises increasing both the payload feed concentration (e.g., about 800 μM or more) and the EV feed concentration (e.g., about $1.4\times10^{13}$ p/mL or higher). In some aspects, an EV loading method described herein comprises increasing: the salt concentration of the loading buffer (e.g., about 150 mM or higher), the loading temperature (e.g., about 37° C. or higher), the loading duration (e.g., for at least about 24 hours), the payload feed concentration (e.g., about 800 μM or more), and the EV feed concentration (e.g., about $1.4\times10^{13}$ p/mL or higher). In some aspects, when the payload and EVs are mixed under such a condition, the loading efficiency is increased by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to the loading efficiency observed when the payload and the EV are mixed: (i) in a loading buffer with reduced salt concentration; (ii) at a decreased loading temperature; (iii) for shorter loading duration; (iv) with reduced payload feed concentration; (v) with reduced EV feed concentration; or (vi) in any combination of (i) to (v).

As demonstrated herein, it is not necessary to adjust (e.g., increase) all of the loading parameters provided above (salt concentration, loading temperature, loading duration, payload feed concentration, and EV feed concentration) to increase the loading efficiency of an EV. In some aspects, increasing one or more of the loading parameters described herein can allow other loading parameters to remain constant or reduced without negatively affecting loading efficiency. For instance, in some aspects, salt concentration, loading temperature, payload feed concentration, and/or EV feed concentration can be increased (e.g., to the ranges recited herein) while the loading duration is less than the values provided herein (see, e.g., Section IIC).

Accordingly, when one or more of the loading parameters described herein (e.g., salt concentration, loading temperature, payload feed concentration, and/or EV feed concentration) are increased, the loading duration can be less than about 1 hour. In certain aspects, the loading duration can be about 30 seconds, about 1 minute, about 2 minutes, about 3 minutes, about 4 minutes, about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 1 hour. Similarly, it will be apparent to those skilled in the arts based on the disclosures provided herein, that increasing the loading duration can allow other loading parameters (e.g., salt concentration, loading temperature, payload feed concentration, and/or EV feed concentration) to remain constant or be reduced without negatively affecting loading efficiency.

In some aspects, provided herein is a method of loading an EV with a payload (e.g., antisense oligonucleotide), comprising mixing the payload with the EV (i) in a loading buffer having a salt concentration of at least about 1 mM, (ii) at a loading temperature of greater than about 4° C., and (iii) for a loading duration of at least about one hour. In some aspects, (i) the salt concentration of the loading buffer is less than about 200 mM, (ii) the loading temperature is between about 5° C. and about 40° C., and (iii) the loading duration is between about one hour and about 48 hours. In certain aspects, (i) the salt concentration is between about 50 mM and about 150 mM, (ii) the loading temperature is between about 15° C. and about 40° C., and (iii) the loading duration is between about 12 hours and about 36 hours. In certain aspects, (i) the salt concentration is about 100 mM, (ii) the loading temperature is about 37° C., and (iii) the loading duration is about 24 hours. In some aspects, (i) the salt concentration is between about 1 mM and about 500 mM, (ii) the loading temperature is between about 0° C. to about 80° C., and (iii) the loading duration is between about five minutes and about 10 days. In some aspects, (i) the salt concentration is between about 150 mM and about 450 mM, (ii) the loading temperature is between about 37° C. to about 70° C., and (iii) the loading duration is between about 24 hours and about seven days.

In some aspects, the above exemplary method further comprises increasing the payload feed concentration, the EV feed concentration, or both. Accordingly, in certain aspects, (i) the salt concentration of the loading buffer is less than about 200 mM, (ii) the loading temperature is between about 5° C. and about 40° C., (iii) the loading duration is between about one hour and about 48 hours, (iv) the payload feed concentration is between about 50 M and about 1000 μM, and (v) the EV feed concentration is between about $0.2\times10^{13}$ p/mL and about $2.0\times10^{3}$ p/mL. In certain aspects, (i) the salt concentration is between about 50 mM and about 150 mM, (ii) the loading temperature is between about 15° C. and about 40° C., (iii) the loading duration is between about 12 hours and about 36 hours, (iv) the payload feed concentration is between about 100 μM and about 1000 M, and (v) the EV feed concentration is between about $0.5\times10^{13}$ p/mL and about $2.0\times10^{13}$ p/mL. In some aspects, (i) the salt concentration is about 100 mM, (ii) the loading temperature is about 37° C., (iii) the loading duration is about 24 hours, (iv) the payload feed concentration is about 600 μM, and (v) the EV feed concentration is about $1.0\times10^{13}$ p/mL. In some aspects, (i) the salt concentration is between about 1 mM and about 500 mM, (ii) the loading temperature is between about 0° C. to about 80° C., (iii) the loading duration is between about five minutes and about 10 days, (iv) the payload feed concentration is between about 10 μM and about 2500 μM, and (v) the EV feed concentration is between about $1\times10^{11}$ p/mL and about $1\times10^{14}$p/mL.

In some aspects, (i) the salt concentration is between about 150 mM and about 450 mM, (ii) the loading temperature is between about 37° C. to about 70° C., (iii) the loading duration is between about 24 hours and about seven days, (iv) the payload feed concentration is between about $6\times10^{12}$ p/mL and about $1.4\times10^{13}$ p/mL.

In some aspects, loading an EV with a payload (e.g., antisense oligonucleotide) using the above recited salt concentration, loading temperature, loading duration, payload feed concentration, and/or EV feed concentration increases the loading of the payload in the EV (e.g., onto the exterior surface, onto the luminal surface, and/or within the lumen) by at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to loading the payload with a reduced salt concentration (e.g., buffer does not comprise a salt), decreased loading temperature (e.g., about 4° C. or less), shorter loading duration (e.g., about one hour or less), reduced payload feed concentration (e.g., less than about 50 μM), and/or reduced EV feed concentration (e.g., less than about $0.5\times10^{3}$ p/mL).

In some aspects, using the above recited salt concentration, loading temperature, loading duration, payload feed concentration, and/or EV feed concentration increases the amount of payload (e.g., number of antisense oligonucleotides) that is associated with the exterior surface of the EV, e.g., by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the exterior surface of the EV when the payload is loaded using reduced salt concentration (e.g., buffer does not comprise a salt), decreased loading temperature (e.g., about 4° C. or less), shorter loading duration (e.g., about one hour or less), reduced payload feed concentration (e.g., less than about 50 μM), and/or reduced EV feed concentration (e.g., less than about $0.5\times10^{13}$ p/mL)). In some aspects, using the above recited salt concentration, loading temperature, loading duration, payload feed concentration, and/or EV feed concentration increases the amount of payload (e.g., number of antisense oligonucleotides) that is associated with the luminal surface of the EV, e.g., by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload on the luminal surface of the EV when the payload is loaded using reduced salt concentration (e.g., buffer does not comprise a salt), decreased loading temperature (e.g., about 4° C. or less), shorter loading duration (e.g., about one hour or less), reduced payload feed concentration (e.g., less than about 50 μM), and/or reduced EV feed concentration (e.g., less than about $0.5\times10^{13}$ p/mL)). In some aspects, using the above recited salt concentration, loading temperature, loading duration, payload feed concentration, and/or EV feed concentration increases the amount of payload (e.g., number of antisense oligonucleotides) that is associated with the lumen of the EV, e.g., by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference amount (e.g., amount of payload within the lumen of the EV when the payload is loaded using reduced salt concentration (e.g., buffer does not comprise a salt), decreased loading temperature (e.g., about 4° C. or less), shorter loading duration (e.g., about one hour or less), reduced payload feed concentration (e.g., less than about 50 μM), and/or reduced EV feed concentration (e.g., less than about $0.5\times10^{13}$ p/mL)).

II.F. Other Loading Parameters

II.F.1. Sucrose Concentration

In some aspects, the loading methods described herein can further comprise modulating one or more additional parameters during the loading process. For instance, in some aspects, a loading buffer useful for the present disclosure (e.g., comprising a salt within the range of concentrations recited herein) further comprises one or more components. Non-limiting examples of such one or more components include a sucrose, histidine, arginine, methionine, sodium phosphate, potassium phosphate, or any combination thereof.

In some aspects, a loading buffer that can be used with the present disclosure additionally comprises a sucrose. In certain aspects, the concentration of the sucrose in the loading buffer is at least about 1% w/v, at least about 2% w/v, at least about 3% w/v, at least about 4% w/v, at least about 5% w/v, at least about 6% w/v, at least about 7% w/v, at least about 8% w/v, at least about 9% w/v, or at least about 10% w/v. In some aspects, the concentration of the sucrose is about 10% w/v, about 9% w/v, about 8% w/v, about 7% w/v, about 6% w/v, about 5% w/v, about 4% w/v, about 3% w/v, about 2% w/v or about 1% w/v.

In some aspects, the concentration of the sucrose in the loading buffer is between about 1% w/v and about 10% w/v, between about 2% w/v and about 10% w/v, between about 3% w/v and about 10% w/v, between about 4% w/v and about 10% w/v, between about 5% w/v and about 10% w/v, between about 1% w/v and about 9% w/v, between about 2% w/v and about 9% w/v, between about 3% w/v and about 9% w/v, between about 4% w/v and about 9% w/v, between about 5% w/v and about 9% w/v, between about 1% w/v and about 8% w/v, between about 2% w/v and about 8% w/v, between about 3% w/v and about 8% w/v, between about 4% w/v and about 8% w/v, between about 5% w/v and about 8% w/v, between about 1% w/v and about 7% w/v, between about 2% w/v and about 7% w/v, between about 3% w/v and about 7% w/v, between about 4% w/v and about 7% w/v, between about 5% w/v and about 7% w/v, between about 1% w/v and about 6% w/v, between about 2% w/v and about 6% w/v, between about 3% w/v and about 6% w/v, between about 4% w/v and about 6% w/v, or between about 5% w/v and about 6% w/v. In certain aspects, the sucrose concentration of the loading buffer is about 5% w/v.

II.F.2. Osmolarity

In some aspects, a loading method described herein comprises modulating the osmolarity of the loading buffer used to mix a payload and the EV as described herein. In certain aspects, the osmolarity of the loading buffer is between about 100 mOsm/kg to about 600 mOsm/kg (e.g., between about 250 mOsm/kg to about 500 mOsm/kg). In certain aspects, the osmolarity of the loading buffer is between about 275 mOsm/kg and about 450 mOsm/kg, between about 280 mOsm/kg and about 450 mOsm/kg, between about 300 mOsm/kg and about 450 mOsm/kg, between about 275 mOsm/kg and about 400 mOsm/kg, between about 280 mOsm/kg and about 400 mOsm/kg, between about 300 mOsm/kg and about 400 mOsm/kg, between about 275 mOsm/kg and about 380 mOsm/kg, between about 280 mOsm/kg and about 380 mOsm/kg, between about 300 mOsm/kg and about 380 mOsm/kg, between about 275 mOsm/kg and about 350 mOsm/kg, between about 280 mOsm/kg and about 350 mOsm/kg, between about 300 mOsm/kg and about 350 mOsm/kg, between about 275 mOsm/kg and about 310 mOsm/kg, between about 280 mOsm/kg and about 310 mOsm/kg, or between about 300 mOsm/kg and about 310 mOsm/kg.

In some aspects, the osmolarity of the loading buffer is about 360 mOsm/kg, about 370 mOsm/kg, about 380 mOsm/kg, about 390 mOsm/kg, about 395 mOsm/kg, or about 400 mOsm/kg. In some aspects, the osmolarity of the loading buffer is about 395 mOsm/kg.

II.F.3. pH

In some aspects, a loading buffer which can be used (e.g., to mix a payload with EVs) with the present disclosure has a pH between about 6 and about 8. In certain aspects, the pH of the loading buffer is between about 6 and about 7 or between about 7 and about 8. In some aspects, the pH is about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, or about 8. In certain aspects, the pH of the loading buffer is about 7.2. In some aspects, a loading buffer useful for the present disclosure has a pH of about 9.

II.G. Payload

As will be apparent to those skilled in the arts, the loading methods provided herein can be used to load an EV with any suitable payload known in the art. Non-limiting examples of payloads that can be loaded in an EV using the methods described herein include a peptide, a small molecule, an oligonucleotide, an antisense oligonucleotide (ASO), a phosphorodiamidate morpholino oligomer (PMO), an mRNA, an miRNA, an lcRNA, an antagomir, a tRNA, a siRNA, a peptide nuclei acid, a cell penetrating peptide, an adjuvant, a protein, a carbohydrate, a sugar, an amino acid, or any combination thereof. In some aspects, the payload comprises a nucleic acid. In some aspects, the payload comprises a peptide. In some aspects, the payload comprises a small molecule. In certain aspects, the payload comprises an antisense oligonucleotide (ASO) (also referred to herein as "antisense ASO" and "oligomer"). In some aspects, the payload comprises a mRNA. In some aspects, the payload comprises a miRNA. In some aspects, the payload comprises a lcRNA. In some aspects, the payload comprises an antagomir. In some aspects, the payload comprises a tRNA. In some aspects, the payload comprises a siRNA. In some aspects, the payload comprises a peptide nucleic acid. In some aspects, the payload comprises a cell penetrating peptide. In some aspects, the payload comprises an adjuvant. In some aspects, a payload comprises a protein. In some aspects, a payload comprises a carbohydrate. In some aspects, a payload comprises a sugar. In some aspects, a payload comprises an amino acid. In certain aspects, the payload contains a domain (e.g., charged substituents) designed to increase the solubility of the payload. Non-limiting examples of such domains include cell penetrating peptides, polyanions (e.g., polyglutamic acid), polycations (e.g., polylysine, polyarginine, polyethylenimine), and combinations thereof. Accordingly, the loading methods described herein can be used to increase the number of ASOs that are associated with the exterior surface of an EV.

In some aspects, a payload (e.g., ASO) useful for the present disclosure comprises a contiguous nucleotide sequence of from about 10 to about 30, such as 10-20, 14-20, 16-20, or 15-25, nucleotides in length. In certain aspects, the payload is 20 nucleotides in length. In certain aspects, the payload is 18 nucleotides in length. In certain aspects, the payload is 19 nucleotides in length. In certain aspects, the payload is 17 nucleotides in length. In certain aspects, the payload is 16 nucleotides in length. In certain aspects, the payload is 15 nucleotides in length. In some aspects, the payload is 14 nucleotides in length. In some aspects, the payload is 13 nucleotides in length. In certain aspects, the payload is 12 nucleotides in length. In some aspects, the payload is 11 nucleotides in length. In further aspects, the payload is 10 nucleotides in length.

In some aspects, the payload comprises a contiguous nucleotide sequence of from about 10 to about 50 nucleotides in length, e.g., about 10 to about 45, about 10 to about 40, about 10 or about 35, or about 10 to about 30. In certain aspects, the payload is 21 nucleotides in length. In certain aspects, the payload is 22 nucleotides in length. In certain aspects, the payload is 23 nucleotides in length. In certain aspects, the payload is 24 nucleotides in length. In certain aspects, the payload is 25 nucleotides in length. In certain aspects, the payload is 26 nucleotides in length. In certain aspects, the payload is 27 nucleotides in length. In certain aspects, the payload is 28 nucleotides in length. In certain aspects, the payload is 29 nucleotides in length. In certain aspects, the payload is 30 nucleotides in length. In certain aspects, the payload is 31 nucleotides in length. In certain aspects, the payload is 32 nucleotides in length. In certain aspects, the payload is 33 nucleotides in length. In certain aspects, the payload is 34 nucleotides in length. In certain aspects, the payload is 35 nucleotides in length. In certain aspects, the payload is 36 nucleotides in length. In certain aspects, the payload is 37 nucleotides in length. In certain aspects, the payload is 38 nucleotides in length. In certain aspects, the payload is 39 nucleotides in length. In certain aspects, the payload is 40 nucleotides in length. In certain aspects, the payload is 41 nucleotides in length. In certain aspects, the payload is 42 nucleotides in length. In certain aspects, the payload is 43 nucleotides in length. In certain aspects, the payload is 44 nucleotides in length. In certain aspects, the payload is 45 nucleotides in length. In certain aspects, the payload is 46 nucleotides in length. In certain aspects, the payload is 47 nucleotides in length. In certain aspects, the payload is 48 nucleotides in length. In certain aspects, the payload is 49 nucleotides in length. In certain aspects, the payload is 50 nucleotides in length.

In various aspects, the payload (e.g., ASO) of the disclosure does not comprise RNA (units). In some aspects, the payload comprises one or more DNA units. In certain aspects, the payload useful for the present disclosure is a linear molecule or is synthesized as a linear molecule. In some aspects, the payload is a single stranded molecule, and does not comprise short regions of, for example, at least 3, 4 or 5 contiguous nucleotides, which are complementary to equivalent regions within the same payload (i.e. duplexes)—in this regard, the payload is not (essentially) double stranded. In some aspects, the payload is essentially not double stranded. In some aspects, the payload is not a siRNA. In various aspects, the payload that can be used with the loading methods described herein consists entirely of the contiguous nucleotide region. Thus, in some aspects, the payload is not substantially self-complementary.

In some aspects, the present disclosure includes fragments of payloads (e.g., ASOs). For example, the disclosure includes at least one nucleotide, at least two contiguous nucleotides, at least three contiguous nucleotides, at least four contiguous nucleotides, at least five contiguous nucleotides, at least six contiguous nucleotides, at least seven contiguous nucleotides, at least eight contiguous nucleotides, or at least nine contiguous nucleotides of the payload (e.g., ASOs) disclosed herein. Fragments of any of the sequences disclosed herein are contemplated as part of the disclosure.

In some aspects, a payload useful for the present disclosure comprises one or more nucleoside analogs. In certain aspects, one or more of the nucleoside analogs comprise a 2'-O-alkyl-RNA; 2'-O-methyl RNA (2'-OMe); 2'-alkoxy-RNA; 2'-O-methoxyethyl-RNA (2'-MOE); 2'-amino-DNA; 2'-fluro-RNA; 2'-fluoro-DNA; arabino nucleic acid (ANA); 2'-fluoro-ANA; bicyclic nucleoside analog (LNA), or any combination thereof. In certain aspects, one or more of the nucleoside analogs are a sugar modified nucleoside. In further aspects, the sugar modified nucleoside is an affinity enhancing 2' sugar modified nucleoside. In some aspects, one or more of the nucleoside analogs comprises a nucleoside comprising a bicyclic sugar. In certain aspects, one or more of the nucleoside analogs comprises an LNA. In further aspects, one or more of the nucleoside analogs are selected from the group consisting of constrained ethyl nucleoside (cEt), 2',4'-constrained 2'-O-methoxyethyl (cMOE), α-L-LNA, β-D-LNA, 2'-O,4'—C-ethylene-bridged nucleic acids (ENA), amino-LNA, oxy-LNA, thio-LNA, and any combination thereof.

In some aspects, the payload that can be loaded in an EV using the loading methods provided herein comprises a phosphorodiamidate morpholino oligomer (PMO), a peptide-conjugated phosphorodiamidate morpholino oligomer (PPMO), or both.

II.G.1. The Target

As will be apparent to those skilled in the arts, a payload targeting any specific molecule (e.g., gene) of interest can be used with the present disclosure. For instance, in some aspects, the loading methods provided herein can be used for any molecule (e.g., gene) where a payload (e.g., ASO) that specifically binds to the molecule can be generated. Accordingly, in some aspects, payloads (e.g., ASO) useful for the present disclosure are capable of down-regulating (e.g., reducing or inhibiting) the expression of any gene or protein of interest in a cell. Non-limiting examples of such targets are described further below.

II.G.1.a. STAT6

In some aspects, the payloads (e.g., ASOs) provided herein are capable of down-regulating (e.g., reducing or inhibiting) the expression of any gene or protein of interest in a cell. In certain aspects, the payloads described herein (e.g., can be loaded in EVs using the loading methods of the present disclosure) target one or more regions of the STAT6 pre-mRNA (e.g., intron regions, exon regions, and/or exon-intron junction regions). In some aspects, the payload is capable of targeting all isoforms of the STAT6 protein. In certain aspects, the payload targets specific STAT6 isoforms (e.g., Isoform 1 and Isoform 2, Isoform 1 and Isoform 3, or Isoform 2 and Isoform 3). Unless indicated otherwise, the term "STAT6," as used herein, can refer to STAT6 from one or more species (e.g., humans, non-human primates, dogs, cats, guinea pigs, rabbits, rats, mice, horses, cattle, and bears).

STAT6 (STAT6) is also known as signal transducer and activator of transcription 6. Synonyms of STAT6/STAT6 are known and include IL-4 STAT; STAT, Interleukin4-Induced; Transcription Factor IL-4 STAT; STAT6B; STAT6C; and D12S1644. The sequence for the human STAT6 gene can be found under publicly available GenBank Accession Number NC_000012.12:c57111413-57095404. The human STAT6 gene is found at chromosome location 12q13.3 at 57111413-57095404, complement.

The sequence for the human STAT6 pre-mRNA transcript (SEQ ID NO: 2) corresponds to the reverse complement of residues 57111413-57095404, complement, of chromosome 12q13.3. The STAT6 mRNA sequence (GenBank Accession No. NM_001178078.1) is provided in SEQ ID NO: 4, except that the nucleotide "t" in SEQ ID NO: 4 is shown as "u" in the mRNA. The sequence for human STAT6 protein can be found under publicly available Accession Numbers: P42226-1, (canonical sequence, SEQ ID NO: 3), P42226-2 (SEQ ID NO: 5), and P42226-3 (SEQ ID NO: 5), each of which is incorporated by reference herein in its entirety.

Natural variants of the human STAT6 gene product are known. For example, natural variants of human STAT6 protein can contain one or more amino acid substitutions selected from: M118R, D419N, and any combination thereof. Additional variants of human STAT6 protein resulting from alternative splicing are also known in the art. STAT6 Isoform 2 (identifier: P42226-2 at UniProt) differs from the canonical sequence (SEQ ID NO: 4) as follows: deletion of residues 1-174 and substitution of 175PSE177 with 175MEQ177 relative to SEQ ID NO: 4. The sequence of STAT6 Isoform 3 (identifier: P42226-3) differs from the canonical sequence (SEQ ID NO: 4) as follows: deletion of residues 1-110 relative to SEQ ID NO: 4. Therefore, the payloads described herein (e.g., ASOs) can be designed to reduce or inhibit expression of the natural variants of the STAT6 protein.

An example of a target nucleic acid sequence of the payloads (e.g., ASOs) is STAT6 pre-mRNA. SEQ ID NO: 2 represents a human STAT6 genomic sequence (i.e., reverse complement of nucleotides 57111413-57095404, complement, of chromosome 12q13.3). SEQ ID NO: 2 is identical to a STAT6 pre-mRNA sequence except that nucleotide "t" in SEQ ID NO: 2 is shown as "u" in pre-mRNA. In certain aspects, the "target nucleic acid" comprises an intron of a STAT6 protein-encoding nucleic acids or naturally occurring variants thereof, and RNA nucleic acids derived therefrom, e.g., pre-mRNA. In some aspects, the target nucleic acid comprises an exon region of a STAT6 protein-encoding nucleic acids or naturally occurring variants thereof, and RNA nucleic acids derived therefrom, e.g., pre-mRNA. In yet some aspects, the target nucleic acid comprises an exon-intron junction of a STAT6 protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. The human STAT6 protein sequence encoded by the STAT6 pre-mRNA is shown as SEQ ID NO: 3. In some aspects, the target nucleic acid comprises an untranslated region of a STAT6 protein-encoding nucleic acids or naturally occurring variants thereof, e.g., 5' UTR, 3' UTR, or both.

In some aspects, a payload of the disclosure (e.g., ASO) hybridizes to a region within the introns of a STAT6 transcript, e.g., SEQ ID NO: 11. In certain aspects, the payload hybridizes to a region within the exons of a STAT6 transcript, e.g., SEQ ID NO: 11. In some aspects, the payload hybridizes to a region within the exon-intron junction of a STAT6 transcript, e.g., SEQ ID NO: 11. In some aspects, the payload hybridizes to a region within a STAT6 transcript (e.g., an intron, exon, or exon-intron junction), e.g., SEQ ID NO: 11.

In some aspects, binding of an payload targeting a STAT6 transcript disclosed herein to a mRNA transcript encoding STAT6 can reduce expression levels and/or activity levels of STAT6.

In some aspects, the payload comprises an ASO that can specifically target a STAT6 transcript. In some aspects, the nucleotide sequence of an ASO, or the contiguous nucleotide sequence thereof, has at least about 80% sequence identity to a sequence set forth in any one of SEQ ID NOs: 41 to 50 (i.e., the sequences in FIG. 3A), such as at least about 80%, at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity.

In some aspects, the ASO (or contiguous nucleotide portion thereof) is selected from, or comprises, one of the sequences selected from the group consisting of SEQ ID NOs: 41 to 50, or a region of at least 10 contiguous nucleotides thereof, wherein the ASO (or contiguous nucleotide portion thereof) can optionally comprise one, two, three, or four mismatches when compared to the corresponding STAT6 transcript.

In some aspects, the ASO comprises the sequence set forth in SEQ ID NO: 41. In some aspects, the ASO comprises the sequence set forth in SEQ ID NO: 42. In some aspects, the ASO comprises the sequence set forth in SEQ ID NO: 43. In some aspects, the ASO comprises the sequence set forth in SEQ ID NO: 44. In some aspects, the ASO comprises the sequence set forth in SEQ ID NO: 45. In some aspects, the ASO comprises the sequence set forth in SEQ ID NO: 46.

In some aspects, the ASO comprises the sequence set forth in SEQ ID NO: 47. In some aspects, the ASO comprises the sequence set forth in SEQ ID NO: 48. In some aspects, the ASO comprises the sequence set forth in SEQ ID NO: 49. In some aspects, the ASO comprises the sequence set forth in SEQ ID NO: 50.

In some aspects the ASO comprises or consists of a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a sequence set forth in SEQ ID NOs: 41 to 50. In some aspects, the ASO (or contiguous nucleotide portion thereof) is selected from, or comprises, one of the sequences selected from the group consisting of SEQ ID NOs: 41 to 50 or a region of at least 8, 9, 10, 11, 12, 13, 14, 15, 16, 17, 18, 19, or 20 contiguous nucleotides thereof. In some aspects, the ASO (or contiguous nucleotide portion thereof) is selected from, or comprises, one of the sequences selected from the group consisting of SEQ ID NOs: 41 to 50 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four mismatches when compared to the corresponding STAT6 transcript. In some aspects, the ASO (or contiguous nucleotide portion thereof) is selected from, or comprises, one of the sequences selected from the group consisting of SEQ ID NOs: 41 to 50 except for 1, 2, 3, 4, 5, 6, 7, 8, 9 or 10 substitutions, wherein the substituted ASO can bind to the STAT6 transcript. In some aspects, the ASO (or contiguous nucleotide portion thereof) is selected from, or comprises, one of the sequences selected from the group consisting of SEQ ID NOs: 41 to 50 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four additional 5' and/or 3' nucleotides complementary to the corresponding STAT6 transcript.

II.G.1.b KRAS

In some aspects, the payloads (e.g., ASOs) provided herein are capable of down-regulating (e.g., reducing or inhibiting) the expression of a KRAS mRNA or KRAS protein, e.g., in a cell. In certain aspects, the payloads described herein (e.g., can be loaded in EVs using the loading methods of the present disclosure) target one or more regions of the KRAS pre-mRNA (e.g., intron regions, exon regions, and/or exon-intron junction regions). In some aspects, the payload is capable of targeting all isoforms of the KRAS protein. In certain aspects, the payload targets specific KRAS isoforms. Unless indicated otherwise, the term "KRAS," as used herein, can refer to KRAS from one or more species (e.g., humans, non-human primates, dogs, cats, guinea pigs, rabbits, rats, mice, horses, cattle, and bears).

KRAS is known in the art by various names. Such names include: KRAS Proto-Oncogene, GTPase; V-Ki-Ras2 Kirsten Rat Sarcoma 2 Viral Oncogene Homolog; GTPase KRas; C-Ki-Ras; K-Ras 2; KRAS2; RASK2; V-Ki-Ras2 Kirsten Rat Sarcoma Viral Oncogene Homolog; Kirsten Rat Sarcoma Viral Proto-Oncogene; Cellular Transforming Proto-Oncogene; Cellular C-Ki-Ras2 Proto-Oncogene; Transforming Protein P21; PR310 C-K-Ras Oncogene; C-Kirsten-Ras Protein; K-Ras P21 Protein; and Oncogene KRAS2.

The sequence for the human KRAS gene can be found at chromosomal location 12p12.1 and under publicly available GenBank Accession Number NC_000012 (25,204,789-25,250,936). The genomic sequence for human wild-type KRAS transcript corresponds to the reverse complement of residues 25,204,789-25,250,936 of NC_000012 (SEQ ID NO: 11). The KRAS G12D genomic sequence provided in SEQ ID NO: 7 differs from SEQ ID NO: 11 in that it has a guanine to adenine substitution at nucleotide position 5,587. An exemplary KRAS G12D mRNA sequence is provided in SEQ ID NO: 9, except that the nucleotide "t" in SEQ ID NO: 33 is shown as "u" in the mRNA. The KRAS G12D mRNA provided in SEQ ID NO: 9 differs from the wild-type mRNA sequence (e.g., GenBank Accession No. NM_004985.5; SEQ ID NO: 13) in that it has a guanine to adenine substitution at nucleotide position 225. The sequence for human KRAS protein can be found under publicly available Accession Numbers: P01116 (canonical sequence), A8K8Z5, BOLPF9, P01118, and Q96D10, each of which is incorporated by reference herein in its entirety.

There are two isoforms of the human KRAS protein (P01116), resulting from alternative splicing. Isoform 2A (Accession Number: P01116-1; SEQ ID NO: 14) is the canonical sequence. It is also known as K-Ras4A. Isoform 2B (Accession Number: P01116-2; also known as K-Ras4B; SEQ ID NO: 12) differs from the canonical sequence as follows: (i) 151-153: RVE →GVD; and (ii) 165-189: QYRLKKISKEEKTPGCVKIKKCIIM (SEQ ID NO: 15)→KIKEKMSKDGKKKKKKSKTKCVIM (SEQ ID NO: 16). In some aspects, payloads disclosed herein can reduce or inhibit expression of KRAS protein Isoform 2A, Isoform 2B, or both.

Natural variants of the human KRAS gene product are known. For example, natural variants of human KRAS protein can contain one or more amino acid substitutions selected from: K5E, K5N, G10GG, G10V, G12A, G12C, G12F, G12I, G12L, G12R, G12S, G12V, G13C, G13D, G13E, G13R, G13V, V141, L19F, T20M, Q22E, Q221H, Q22K, Q22R, Q2511, N26Y, F28L, E31K, D33E, P34L, P34Q, P34R, 136M, R41K, DS7N, T581, A59T, G60D, G60R, G60S, G60V, Q61A, Q61H, Q61K, Q61L, Q61P, Q61R, E63K, S65N, R68S, Y71H, T74A, L791, R971, Q99E, M111L, K117N, K117R, D119G, S122F, T144P, A146P, A146T, A146V, K147E, K147T, R149K, L159S, I163S, R164Q, I183N, I84M, or combinations thereof. Natural variants that are specific to KRAS protein Isoform 2B contain one or more amino acid substitutions selected from: V152G, D153V, F1561, F156L, or combinations thereof. The payloads of the present disclosure can be designed to reduce or inhibit expression of one or more of the variants of the KRAS protein (e.g., any variants known in the art). In some aspects, a KRAS mutant has an amino acid substitution of G12D. In some aspects, the payloads of the present disclosure target one or more KRAS mutants. In certain aspects, a KRAS mutant that the payloads target is KRAS G12D (SEQ ID NO: 8). Exemplary sequences for KRAS G12D mRNA and KRAS G12D protein are provided in SEQ ID NO: 9 and SEQ ID NO: 8, respectively.

In some aspects, a target nucleic acid sequence of a payload (e.g., ASO) disclosed herein comprises one or more regions of a KRAS pre-mRNA. For example, SEQ ID NO: 7 (described above) is identical to a KRAS pre-mRNA sequence except that nucleotide "t" in SEQ ID NO: 7 is shown as "u" in the pre-mRNA. As used herein, the term "target nucleic acid sequence" refers to a nucleic acid sequence that is complementary to a payload disclosed herein. In certain aspects, the target nucleic acid sequence comprises an exon region of a KRAS protein-encoding nucleic acids or naturally occurring variants thereof, and RNA nucleic acids derived therefrom, e.g., pre-mRNA. In some aspects, the target nucleic acid sequence comprises an intron of a KRAS protein-encoding nucleic acids or naturally occurring variants thereof, and RNA nucleic acids derived therefrom, e.g., pre-mRNA. In further aspects, the target nucleic acid sequence comprises an exon-intron junction of a KRAS protein-encoding nucleic acids or naturally occurring variants thereof, and RNA nucleic acids derived therefrom, e.g., pre-mRNA. In some aspects, for example ,when used in research or diagnostics, the target nucleic acid can be a cDNA or a synthetic oligonucleotide derived from DNA or RNA nucleic acid targets described herein. In some aspects, the target nucleic acid comprises an untranslated region of a KRAS protein-encoding nucleic acids or naturally occurring variants thereof, e.g., 5' UTR, 3' UTR, or both.

Accordingly, in some aspects, a payload (e.g., ASO) disclosed herein hybridizes to an exon region of a KRAS transcript, e.g., SEQ ID NO: 7 or SEQ ID NO: 9. In some aspects, a payload of the present disclosure hybridizes to an intron region of a KRAS transcript, e.g., SEQ ID NO: 7. In some aspects, a payload hybridizes to an exon-intron junction of a KRAS transcript, e.g., SEQ ID NO: 7. In some aspects, a payload of the present disclosure hybridizes to a region within a KRAS transcript (e.g., an intron, exon, or exon-intron junction), e.g., SEQ ID NO: 7, wherein the payload has a design described elsewhere herein.

In some aspects, a target nucleic sequence of the payloads disclosed herein is a KRAS mRNA, e.g., SEQ ID NO: 9. Accordingly, in certain aspects, a payload disclosed herein can hybridize to one or more regions of a KRAS mRNA. In some aspects, payloads of the present disclosure target mRNA encoding a particular isoform of KRAS protein. In certain aspects, payloads disclosed herein can target all isoforms of KRAS protein, including any variants thereof (e.g., those described herein). In some aspects, a KRAS protein that can be targeted by payloads of the present disclosure comprises a G12D amino acid substitution.

In some aspects, the payload comprises an ASO that can specifically target a KRAS transcript. In some aspects, the nucleotide sequence of an ASO, or the contiguous nucleotide sequence thereof, has at least about 80% sequence identity to a sequence set forth in any one of SEQ ID NOs: 51 to 61 (i.e., the sequences in FIG. 3B), such as at least about 80%, at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity.

In some aspects, the ASO (or contiguous nucleotide portion thereof) is selected from, or comprises, one of the sequences selected from the group consisting of SEQ ID NOs: 51 to 61, or a region of at least 10 contiguous nucleotides thereof, wherein the ASO (or contiguous nucleotide portion thereof) can optionally comprise one, two, three, or four mismatches when compared to the corresponding KRAS transcript.

In some aspects, the ASO comprises the sequence set forth in SEQ ID NO: 51. In some aspects, the ASO comprises the sequence set forth in SEQ ID NO: 52. In some aspects, the ASO comprises the sequence set forth in SEQ ID NO: 53. In some aspects, the ASO comprises the sequence set forth in SEQ ID NO: 54. In some aspects, the ASO comprises the sequence set forth in SEQ ID NO: 55. In some aspects, the ASO comprises the sequence set forth in SEQ ID NO: 56. In some aspects, the ASO comprises the sequence set forth in SEQ ID NO: 57. In some aspects, the ASO comprises the sequence set forth in SEQ ID NO: 58. In some aspects, the ASO comprises the sequence set forth in SEQ ID NO: 59. In some aspects, the ASO comprises the sequence set forth in SEQ ID NO: 60. In some aspects, the ASO comprises the sequence set forth in SEQ ID NO: 610.

In some aspects the ASO comprises or consists of a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a sequence set forth in SEQ ID NOs: 51 to 61. In some aspects, the ASO (or contiguous nucleotide portion thereof) is selected from, or comprises, one of the sequences selected from the group consisting of SEQ ID NOs: 51 to 61 or a region of at least 8, 9, 10, 11, 12, 13, 14, 15, 16, 17, 18, 19, or 20 contiguous nucleotides thereof. In some aspects, the ASO (or contiguous nucleotide portion thereof) is selected from, or comprises, one of the sequences selected from the group consisting of SEQ ID NOs: 51 to 61 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four mismatches when compared to the corresponding KRAS transcript. In some aspects, the ASO (or contiguous nucleotide portion thereof) is selected from, or comprises, one of the sequences selected from the group consisting of SEQ ID NOs: 51 to 61 except for 1, 2, 3, 4, 5, 6, 7, 8, 9 or 10 substitutions, wherein the substituted ASO can bind to the KRAS transcript. In some aspects, the ASO (or contiguous nucleotide portion thereof) is selected from, or comprises, one of the sequences selected from the group consisting of SEQ ID NOs: 51 to 61 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four additional 5' and/or 3' nucleotides complementary to the corresponding KRAS transcript.

II.G.1.c NRAS

In some aspects, the payloads (e.g., ASOs) provided herein are capable of down-regulating (e.g., reducing or inhibiting) the expression of a NRas mRNA or NRas protein, e.g., in a cell. In certain aspects, the payloads described herein (e.g., can be loaded in EVs using the loading methods of the present disclosure) target one or more regions of the NRas pre-mRNA (e.g., intron regions, exon regions, and/or exon-intron junction regions). In some aspects, the payload is capable of targeting all isoforms of the NRas protein. In certain aspects, the payload targets specific NRas isoforms. Unless indicated otherwise, the term "NRas," as used herein, can refer to NRas from one or more species (e.g., humans, non-human primates, dogs, cats, guinea pigs, rabbits, rats, mice, horses, cattle, and bears).

NRas is an oncogene encoding a membrane protein that shuttles between the Golgi apparatus and the plasma membrane. NRas-encoding genomic DNA can be found at Chromosomal position 1p13.2 (i.e., nucleotides 5001 to 17438 of GenBank Accession No. NG_007572).

Specifically, a combination of time-lapse microscopy and photobleaching techniques have revealed that in the absence of palmitoylation, GFP-tagged N-Ras undergoes rapid exchange between the cytosol and ER/Golgi membranes, and that wild-type GFP-N-Ras is recycled to the Golgi complex by a nonvesicular mechanism. N-ras mutations have been described in melanoma, thyroid carcinoma, teratocarcinoma, fibrosarcoma, neuroblastoma, rhabdomyosarcoma, Burkitt lymphoma, acute promyelocytic leukemia, T cell leukemia, and chronic myelogenous leukemia. Oncogenic N-Ras can induce acute myeloid leukemia (AML)- or chronic myelomonocytic leukemia (CMML)-like disease in mice.

Neuroblastoma RAS viral oncogene (NRas) is known in the art by various names. Such names include: GTPase NRas, N-ras protein part 4, neuroblastoma RAS viral (v-ras) oncogene homolog neuroblastoma RAS viral oncogene homolog, transforming protein N-Ras, and v-ras neuroblastoma RAS viral oncogene homolog.

The NRAS gene provides instructions for making a protein called N-Ras that is involved primarily in regulating cell division. The mRNA sequence encoding human NRAS can be found at NCBI Reference sequence NM_002524.5 and is represented by the coding sequence (SEQ ID NO: 19).

Natural variants of the human NRas gene product are known. For example, natural variants of human NRas protein can contain one or more amino acid substitutions selected from: G12D, G13D, T50I, G60E, and any combinations thereof. Additional variants of human NRas protein resulting from alternative splicing are also known in the art, such as: G13R, Q61K, Q61R, and P34L. Therefore, the payloads of the present disclosure can be designed to reduce or inhibit expression of the natural variants of the NRas protein.

SEQ ID NO: 17 is identical to a NRas pre-mRNA sequence except that nucleotide "t" in SEQ ID NO: 17 is shown as "u" in pre-mRNA. In certain aspects, the "target nucleic acid" comprises an intron of a NRas protein-encoding nucleic acids or naturally occurring variants thereof, and RNA nucleic acids derived therefrom, e.g., pre-mRNA. In certain aspects, the target nucleic acid comprises an exon region of a NRas protein-encoding nucleic acids or naturally occurring variants thereof, and RNA nucleic acids derived therefrom, e.g., pre-mRNA. In certain aspects, the target nucleic acid comprises an exon-intron junction of a NRas protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. The human NRas protein sequence encoded by the NRas pre-mRNA is shown as SEQ ID NO: 18. In certain aspects, the target nucleic acid comprises an untranslated region of a NRas protein-encoding nucleic acids or naturally occurring variants thereof, e.g., 5' UTR, 3' UTR, or both.

In certain aspects, the payloads of the disclosure also are capable of down-regulating (e.g., reducing or removing) expression of the NRas mRNA or protein. In this regard, the payload of the disclosure can affect indirect inhibition of NRas protein through the reduction in NRas mRNA levels, typically in a mammalian cell, such as a human cell, such as a tumor cell. In particular, the present disclosure is directed to payloads that target one or more regions of the NRas pre-mRNA (e.g., intron regions, exon regions, and/or exon-intron junction regions). Unless indicated otherwise, the term "NRas," as used herein, can refer to NRas from one or more species (e.g., humans, non-human primates, dogs, cats, guinea pigs, rabbits, rats, mice, horses, cattle, and bears).

In some aspects, a payload of the disclosure hybridizes to a region within the introns of a NRAS transcript, e.g., SEQ ID NO: 17 or SEQ ID NO: 19. In certain aspects, a payload of the disclosure hybridizes to a region within the exons of a NRAS transcript, e.g., SEQ ID NO: 17 or SEQ ID NO: 19. In certain aspects, a payload of the disclosure hybridizes to a region within the exon-intron junction of a NRAS transcript, e.g., SEQ ID NO: 17 or SEQ ID NO: 19. In some aspects, a payload of the disclosure hybridizes to a region within a NRAS transcript (e.g., an intron, exon, or exon-intron junction), e.g., SEQ ID NO: 17 or SEQ ID NO: 19.

In some aspects, the payload of the present disclosure hybridizes to multiple target regions within the NRas transcript (e.g., genomic sequence, SEQ ID NO: 17). In some aspects, the payload hybridizes to two different target regions within the NRas transcript. In some aspects, the payload hybridizes to three different target regions within the NRas transcript. In some aspects, the payloads that hybridizes to multiple regions within the NRas transcript (e.g., genomic sequence, SEQ ID NO: 17) are more potent (e.g., having lower EC50) at reducing NRas expression compared to payloads that hybridizes to a single region within the NRas transcript (e.g., genomic sequence, SEQ ID NO: 17).

In some aspects, the payload (e.g., ASO) targets a mRNA encoding a particular isoform of NRAS protein (e.g., Isoform 1, NCBI ID: NP_001229821.1). In some aspects, the payload targets all isoforms of NRas protein. In certain aspects, the payload targets two isoforms (e.g., Isoform 1 and Isoform 2 (NCBI ID:NP_009089.4), Isoform 2 and Isoform 3(NCBI ID: NP_001123995), and Isoform 3 and Isoform 4(NCBI ID: NP_001229820.1)) of NRas protein.

The payloads of the disclosure comprise a contiguous nucleotide sequence which corresponds to the complement of a region of NRas transcript, e.g., a nucleotide sequence corresponding to SEQ ID NO: 17.

In some aspects, binding of a payload (e.g., ASO) targeting a NRas transcript disclosed herein to a mRNA transcript encoding NRas can reduce expression levels and/or activity levels of NRas.

In some aspects, the payload comprises an ASO that can specifically target a NRas transcript. In some aspects, the nucleotide sequence of an ASO, or the contiguous nucleotide sequence thereof, has at least about 80% sequence identity to a sequence set forth in any one of SEQ ID NOs: 62 to 71 (i.e., the sequences in FIG. 3C), such as at least about 80%, at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity.

In some aspects, the ASO (or contiguous nucleotide portion thereof) is selected from, or comprises, one of the sequences selected from the group consisting of SEQ ID NOs: 62 to 71, or a region of at least 10 contiguous nucleotides thereof, wherein the ASO (or contiguous nucleotide portion thereof) can optionally comprise one, two, three, or four mismatches when compared to the corresponding NRas transcript.

In some aspects, the ASO comprises the sequence set forth in SEQ ID NO: 62. In some aspects, the ASO comprises the sequence set forth in SEQ ID NO: 63. In some aspects, the ASO comprises the sequence set forth in SEQ ID NO: 64. In some aspects, the ASO comprises the sequence set forth in SEQ ID NO: 65. In some aspects, the ASO comprises the sequence set forth in SEQ ID NO: 66. In some aspects, the ASO comprises the sequence set forth in SEQ ID NO: 67.

In some aspects, the ASO comprises the sequence set forth in SEQ ID NO: 68. In some aspects, the ASO comprises the sequence set forth in SEQ ID NO: 69. In some aspects, the ASO comprises the sequence set forth in SEQ ID NO: 70. In some aspects, the ASO comprises the sequence set forth in SEQ ID NO: 71.

In some aspects the ASO comprises or consists of a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a sequence set forth in SEQ ID NOs: 62 to 71. In some aspects, the ASO (or contiguous nucleotide portion thereof) is selected from, or comprises, one of the sequences selected from the group consisting of SEQ ID NOs: 62 to 71 or a region of at least 8, 9, 10, 11, 12, 13, 14, 15, 16, 17, 18, 19, or 20 contiguous nucleotides thereof. In some aspects, the ASO (or contiguous nucleotide portion thereof) is selected from, or comprises, one of the sequences selected from the group consisting of SEQ ID NOs: 62 to 71 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four mismatches when compared to the corresponding NRas transcript. In some aspects, the ASO (or contiguous nucleotide portion thereof) is selected from, or comprises, one of the sequences selected from the group consisting of SEQ ID NOs: 62 to 71 except for 1, 2, 3, 4, 5, 6, 7, 8, 9 or 10 substitutions, wherein the substituted ASO can bind to the NRas transcript. In some aspects, the ASO (or contiguous nucleotide portion thereof) is selected from, or comprises, one of the sequences selected from the group consisting of SEQ ID NOs: 62 to 71 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four additional 5' and/or 3' nucleotides complementary to the corresponding NRas transcript.

II.G.1.d PMP22

In some aspects, the payloads (e.g., ASOs) provided herein are capable of down-regulating (e.g., reducing or inhibiting) the expression of a PMP22 mRNA or PMP22 protein, e.g., in a cell. In certain aspects, the payloads described herein (e.g., can be loaded in EVs using the loading methods of the present disclosure) target one or more regions of the PMP22 pre-mRNA (e.g., intron regions, exon regions, and/or exon-intron junction regions). In some aspects, the payload is capable of targeting all isoforms of the PMP22 protein. In certain aspects, the payload targets specific PMP22 isoforms. Unless indicated otherwise, the term “PMP22,” as used herein, can refer to STAT6 from one or more species (e.g., humans, non-human primates, dogs, cats, guinea pigs, rabbits, rats, mice, horses, cattle, and bears).

Peripheral myelin protein 22 (PMP22) is also known as growth arrest-specific protein 3 (GAS-3), is encoded by the PMP22 gene. PMP22 is a 22 kDa transmembrane glycoprotein made up of 160 amino acids, and is mainly expressed in the Schwann cells of the peripheral nervous system. Schwann cells show high expression of PMP22, where it can constitute 2-5% of total protein content in compact myelin. Compact myelin is the bulk of the peripheral neuron's myelin sheath, a protective fatty layer that provides electrical insulation for the neuronal axon. The level of PMP22 expression is relatively low in the central nervous system of adults.

In humans, the PMP22 gene is located on chromosome 17p11.2 and spans approximately 40kb. The gene contains six exons conserved in both humans and rodents, two of which are 5' untranslated exons (1a and 1b) and result in two different RNA transcripts with identical coding sequences. The two transcripts differ in their 5' untranslated regions and have their own promoter regulating expression. The remaining exons (2 to 5) include the coding region of the PMP22 gene, and are joined together after post-transcriptional modification (i.e. alternative splicing). The PMP22 protein is characterized by four transmembrane domains, two extracellular loops (ECL1 and IECL2), and one intracellular loop. ECL1 has been suggested to mediate a homophilic interaction between two PMP22 proteins, whereas ECL2 has been shown to mediate a heterophilic interaction between PMP22 protein and Myelin protein zero (MPZ or MPO).

PMP22 plays an essential role in the formation and maintenance of compact myelin. When Schwann cells come into contact with a neuronal axon, expression of PMP22 is significantly up-regulated, whereas PMP22 is down-regulated during axonal degeneration or transection. PMP22 has shown association with zonula-occludens 1 and occludin, proteins that are involved in adhesion with other cells and the extracellular matrix, and also support functioning of myelin. Along with cell adhesion function, PMP22 is also up-regulated during Schwann cell proliferation, suggesting a role in cell-cycle regulation. PMP22 is detectable in non-neural tissues, where its expression has been shown to serve as growth-arrest-specific (gas-3) function.

Improper gene dosage of the PMP22 gene can cause aberrant protein synthesis and function of myelin sheath. Since the components of myelin are stoichiometrically set, any irregular expression of a component can cause destabilization of myelin and neuropathic disorders. Alterations of PMP22 gene expression are associated with a variety of neuropathies, such as Charcot-Marie-Tooth type 1A (CMT1A), Dejerine-Sottas disease, and Hereditary Neuropathy with Liability to Pressure Palsy (HNPP). Too much PMP22 (e.g. caused by gene duplication) results in CMT1A. Gene duplication of PMP22 is the most common genetic cause of CMT where the overproduction of PMP22 results in defects in multiple signaling pathways and dysfunction of transcriptional factors like KNOX20, SOX10 and EGR2.

The sequence for the human PMP22 gene can be found under publicly available as NCBI RefSeq Acc. No. NM_000304. Alternative RefSeq mRNA transcripts have accession numbers NM_001281455, NM-001281456, NM-153321, and NM_153322, respectively. The human PMP22 gene is found at chromosome location 17p12 at 15,229,777-15,265,326.

The sequence for the human PMP22 pre-mRNA transcript (SEQ ID NO: 20) corresponds to the reverse complement of residues 15,229,777-15,265,326, of chromosome location 17p12. The PMP22 mRNA sequence (GenBank Accession No. NM_000304.4) is provided in SEQ ID NO: 21. The sequence for human PMP22 protein can be found under publicly available Uniprot Accession Number Q01453 (canonical sequence, SEQ ID NO: 23). Potential PMP22 isoforms have Uniprot Accession Numbers A8MU75, J3KQW0, A0A2R8Y5L5, J3KT36, and J3QS08, respectively. The publicly available contents of the database entries corresponding to accession numbers disclosed herein are incorporated by reference in their entireties.

Natural variants of the human PMP22 gene product are known. For example, natural variants of human PMP22 protein can contain one or more amino acid substitutions selected from L16P, S22F, A25-26, D37V, V65F, S72L, S79C, G93R, L105R, G107V, T118N, L147R, H12Q, L16P, L19P, M69K, L71P, S72L, S72P, S72W, S76I, S79P, L80P, L80R, A84, G100E, G100R, L105R, C109R, S149R, G150C, G150D, R157W, S22F, V30M, A67T, S23T, W28R, A67P, Δ115-118, and any combination thereof.

The payloads of the present disclosure can be designed to reduce or inhibit expression of the natural variants of the PMP22 protein.

An example of a target nucleic acid sequence of the payloads is PMP22 pre-mRNA. SEQ ID NO: 20 represents a human PMP22 genomic sequence (i.e., reverse complement of nucleotides 15,229,777-15,265,326, complement, of chromosome 17p12). SEQ ID NO: 20 is identical to a PMP22 pre-mRNA sequence except that nucleotide "t" in SEQ ID NO: 20 is shown as "u" in pre-mRNA.

In some aspects, the contiguous nucleotide sequence is at least about 80%, at least about 85%, at least about 90%, at least about 95%, or about 100% complementary to the nucleic acid sequence within the PMP22 transcript. In some aspects, the payload is capable of reducing PMP22 protein expression in a human cell (e.g., a Schwan cell), wherein the human cell expresses the PMP22 protein.

In some aspects, a payload (e.g., ASO) of the disclosure hybridizes to a region within the introns of a PMP22 transcript, e.g., SEQ ID NO: 20. In certain aspects, a payload of the disclosure hybridizes to a region within the exons of a PMP22 transcript, e.g., SEQ ID NO: 20. In certain aspects, a payload of the disclosure hybridizes to a region within the exon-intron junction of a PMP22 transcript, e.g., SEQ ID NO: 20.

In some aspects, the payload of the present disclosure hybridizes to multiple target regions within the PMP22 transcript (e.g., genomic sequence, SEQ ID NO: 20). In some aspects, the payload hybridizes to two different target regions within the PMP22 transcript. In some aspects, the payload hybridizes to three different target regions within the PMP22 transcript. In some aspects, the payloads that hybridizes to multiple regions within the PMP22 transcript (e.g., genomic sequence, SEQ ID NO: 20) are more potent (e.g., having lower EC50) at reducing PMP22 expression compared to payloads that hybridizes to a single region within the PMP22 transcript (e.g., genomic sequence, SEQ ID NO: 20).

In some aspects, binding of a payload (e.g., ASO) targeting a PMP22 transcript disclosed herein to a mRNA transcript encoding PMP22 can reduce expression levels and/or activity levels of PMP22.

In some aspects, the payload comprises an ASO that can specifically target a PMP22 transcript. In some aspects, the nucleotide sequence of an ASO, or the contiguous nucleotide sequence thereof, has at least about 80% sequence identity to a sequence set forth in any one of SEQ ID NOs: 72 to 81 (i.e., the sequences in FIG. 3D), such as at least about 80%, at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity.

In some aspects, the ASO (or contiguous nucleotide portion thereof) is selected from, or comprises, one of the sequences selected from the group consisting of SEQ ID NOs: 72 to 81, or a region of at least 10 contiguous nucleotides thereof, wherein the ASO (or contiguous nucleotide portion thereof) can optionally comprise one, two, three, or four mismatches when compared to the corresponding PMP22 transcript.

In some aspects, the ASO comprises the sequence set forth in SEQ ID NO: 72. In some aspects, the ASO comprises the sequence set forth in SEQ ID NO: 73. In some aspects, the ASO comprises the sequence set forth in SEQ ID NO: 74. In some aspects, the ASO comprises the sequence set forth in SEQ ID NO: 75. In some aspects, the ASO comprises the sequence set forth in SEQ ID NO: 76. In some aspects, the ASO comprises the sequence set forth in SEQ ID NO: 77.

In some aspects, the ASO comprises the sequence set forth in SEQ ID NO: 78. In some aspects, the ASO comprises the sequence set forth in SEQ ID NO: 79. In some aspects, the ASO comprises the sequence set forth in SEQ ID NO: 80. In some aspects, the ASO comprises the sequence set forth in SEQ ID NO: 81.

In some aspects the ASO comprises or consists of a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a sequence set forth in SEQ ID NOs: 72 to 81. In some aspects, the ASO (or contiguous nucleotide portion thereof) is selected from, or comprises, one of the sequences selected from the group consisting of SEQ ID NOs: 72 to 81 or a region of at least 8, 9, 10, 11, 12, 13, 14, 15, 16, 17, 18, 19, or 20 contiguous nucleotides thereof. In some aspects, the ASO (or contiguous nucleotide portion thereof) is selected from, or comprises, one of the sequences selected from the group consisting of SEQ ID NOs: 72 to 81 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four mismatches when compared to the corresponding PMP22 transcript. In some aspects, the ASO (or contiguous nucleotide portion thereof) is selected from, or comprises, one of the sequences selected from the group consisting of SEQ ID NOs: 72 to 81 except for 1, 2, 3, 4, 5, 6, 7, 8, 9 or 10 substitutions, wherein the substituted ASO can bind to the PMP22 transcript. In some aspects, the ASO (or contiguous nucleotide portion thereof) is selected from, or comprises, one of the sequences selected from the group consisting of SEQ ID NOs: 72 to 81 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four additional 5' and/or 3' nucleotides complementary to the corresponding PMP22 transcript.

II.G.1.e C/EBPβ

In some aspects, the payloads (e.g., ASOs) provided herein are capable of down-regulating (e.g., reducing or inhibiting) the expression of a C/EBPβ mRNA or CEBP/β protein, e.g., in a cell. In certain aspects, the payloads described herein (e.g., can be loaded in EVs using the loading methods of the present disclosure) target one or more regions of the CEBP/β pre-mRNA (e.g., intron regions, exon regions, and/or exon-intron junction regions). In some aspects, the payload is capable of targeting all isoforms of the CEBP/P protein. In certain aspects, the payload targets specific CEBP/P isoforms. Unless indicated otherwise, the term "CEBP/β," as used herein, can refer to CEBP/P from one or more species (e.g., humans, non-human primates, dogs, cats, guinea pigs, rabbits, rats, mice, horses, cattle, and bears).

CE3P/β (CEBP/β) is also known as CCAAT/enhancer-binding protein beta. Synonyms of CEBP/β/CEBP/β are known and include C/EBP beta; Liver activator protein; LAP; Liver-enriched inhibitory protein; LIP; Nuclear factor NF-IL6; transcription factor 5; TCF-5; CEBPB; CEBPb; CEBPβ; CEBP/B; and TCF5. The sequence for the human CEBP/β gene can be found under publicly available GenBank Accession Number NC_000020.11 (50190583..50192690). The human CEBP/β gene is found at chromosome location 20q13.13 at 50190583-50192690.

The sequence for the human CEBP/β pre-mRNA transcript (SEQ ID NO: 251) corresponds to the reverse complement of residues 50190583-50192690 of chromosome 20q13.13. The CEBP/β mRNA sequence (GenBank Accession No. NM_001285878.1) is provided in SEQ ID NO: 27, except that the nucleotide "t" in SEQ ID NO: 27 is shown as "u" in the mRNA. The sequence for human CEBP/β protein can be found under publicly available Accession Numbers: P17676, (canonical sequence, SEQ ID NO: 26), P17676-2 (SEQ ID NO: 28), and P17676-3 (SEQ ID NO: 29), each of which is incorporated by reference herein in its entirety.

Natural variants of the human CEBP/β gene product are known. For example, natural variants of human CEBP/β protein can contain one or more amino acid substitutions selected from: A241 P, A253G, G195S, and any combination thereof. Additional variants of human CEBP/β protein resulting from alternative splicing are also known in the art. CEBP/β Isoform 2 (identifier: P17676-2 at UniProt) differs from the canonical sequence (SEQ ID NO: 27) as follows: deletion of residues 1-23 relative to SEQ ID NO: 27. The sequence of CEBP/P Isoform 3 (identifier: P17676-3) differs from the canonical sequence (SEQ ID NO: 23) as follows: deletion of residues 1-198 relative to SEQ ID NO: 27. Therefore, the payload described herein (e.g., ASO) can be designed to reduce or inhibit expression of the natural variants of the protein.

An example of a target nucleic acid sequence of the payloads is CEBP/β pre-mRNA. SEQ ID NO: 25 represents a human CEBP/β genomic sequence (i.e., reverse complement of nucleotides 50190583-50192690 of chromosome 20q13.13). SEQ ID NO: 25 is identical to a CEBP/β pre-mRNA sequence except that nucleotide "t" in SEQ ID NO: 25 is shown as "u" in pre-mRNA. In certain aspects, the "target nucleic acid" comprises an intron of a CEBP/P protein-encoding nucleic acids or naturally occurring variants thereof, and RNA nucleic acids derived therefrom, e.g., pre-mRNA. In certain aspects, the target nucleic acid comprises an exon region of a CEBP/β protein-encoding nucleic acids or naturally occurring variants thereof, and RNA nucleic acids derived therefrom, e.g., pre-mRNA. In certain aspects, the target nucleic acid comprises an exon-intron junction of a CEBP/β protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. The human CEBP/β protein sequence encoded by the CEBP/β pre-mRNA is shown as SEQ ID NO: 26. In certain aspects, the target nucleic acid comprises an untranslated region of a CEBP/β protein-encoding nucleic acids or naturally occurring variants thereof, e.g., 5' UTR, 3' UTR, or both.

In some aspects, a payload (e.g., ASO) of the disclosure hybridizes to a region within the introns of a CEBP/β transcript, e.g., SEQ ID NO: 25. In certain aspects, a payload of the disclosure hybridizes to a region within the exons of a CEBP/β transcript, e.g., SEQ ID NO: 251.

In certain aspects, an ASO of the disclosure hybridizes to a region within the exon-intron junction of a CEBP/β transcript, e.g., SEQ ID NO: 25. In some aspects, a payload of the disclosure hybridizes to a region within a CEBP/β transcript (e.g., an intron, exon, or exon-intron junction), e.g., SEQ ID NO: 25, wherein the payload has a design according to formula: 5' A-B-C 3' as described elsewhere herein.

In some aspects, the payload targets a mRNA encoding a particular isoform of CEBP/β protein (e.g., Isoform 1). In some aspects, the payload targets all isoforms of CEBP/β protein. In certain aspects, the payload targets two isoforms (e.g., Isoform 1 and Isoform 2, Isoform 1 and Isoform 3, or Isoform 2 and Isoform 3) of CEBP/β protein.

In some aspects, binding of a payload (e.g., ASO) targeting a CEBPb transcript disclosed herein to a mRNA transcript encoding CEBPb can reduce expression levels and/or activity levels of CEBPb.

In some aspects, the payload comprises an ASO that can specifically target a CEBPb transcript. In some aspects, the nucleotide sequence of an ASO, or the contiguous nucleotide sequence thereof, has at least about 80% sequence identity to a sequence set forth in any one of SEQ ID NOs: 82 to 91 (i.e., the sequences in FIG. 3E), such as at least about 80%, at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity.

In some aspects, the ASO (or contiguous nucleotide portion thereof) is selected from, or comprises, one of the sequences selected from the group consisting of SEQ ID NOs: 82 to 91, or a region of at least 10 contiguous nucleotides thereof, wherein the ASO (or contiguous nucleotide portion thereof) can optionally comprise one, two, three, or four mismatches when compared to the corresponding CEBPb transcript.

In some aspects, the ASO comprises the sequence set forth in SEQ ID NO: 82. In some aspects, the ASO comprises the sequence set forth in SEQ ID NO: 83. In some aspects, the ASO comprises the sequence set forth in SEQ ID NO: 84. In some aspects, the ASO comprises the sequence set forth in SEQ ID NO: 85. In some aspects, the ASO comprises the sequence set forth in SEQ ID NO: 86. In some aspects, the ASO comprises the sequence set forth in SEQ ID NO: 87.

In some aspects, the ASO comprises the sequence set forth in SEQ ID NO: 88. In some aspects, the ASO comprises the sequence set forth in SEQ ID NO: 89. In some aspects, the ASO comprises the sequence set forth in SEQ ID NO: 90. In some aspects, the ASO comprises the sequence set forth in SEQ ID NO: 91.

In some aspects the ASO comprises or consists of a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a sequence set forth in SEQ ID NOs: 82 to 91. In some aspects, the ASO (or contiguous nucleotide portion thereof) is selected from, or comprises, one of the sequences selected from the group consisting of SEQ ID NOs: 82 to 91 or a region of at least 8, 9, 10, 11, 12, 13, 14, 15, 16, 17, 18, 19, or 20 contiguous nucleotides thereof. In some aspects, the ASO (or contiguous nucleotide portion thereof) is selected from, or comprises, one of the sequences selected from the group consisting of SEQ ID NOs: 82 to 91 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four mismatches when compared to the corresponding CEBPb transcript. In some aspects, the ASO (or contiguous nucleotide portion thereof) is selected from, or comprises, one of the sequences selected from the group consisting of SEQ ID NOs: 82 to 91 except for 1, 2, 3, 4, 5, 6, 7, 8, 9 or 10 substitutions, wherein the substituted ASO can bind to the CEBPb transcript. In some aspects, the ASO (or contiguous nucleotide portion thereof) is selected from, or comprises, one of the sequences selected from the group consisting of SEQ ID NOs: 82 to 91 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four additional 5' and/or 3' nucleotides complementary to the corresponding CEBPb transcript.

II.G.1.f STAT3

In some aspects, the payloads (e.g., ASOs) provided herein are capable of down-regulating (e.g., reducing or inhibiting) the expression of any gene or protein of interest in a cell.

In certain aspects, the payloads described herein (e.g., can be loaded in EVs using the loading methods of the present disclosure) target one or more regions of the STAT3 pre-mRNA (e.g., intron regions, exon regions, and/or exon-intron junction regions). In some aspects, the payload is capable of targeting all isoforms of the STAT3 protein. In certain aspects, the payload targets specific STAT3 isoforms. Unless indicated otherwise, the term "STAT3," as used herein, can refer to STAT3 from one or more species (e.g., humans, non-human primates, dogs, cats, guinea pigs, rabbits, rats, mice, horses, cattle, and bears).

Signal transducer and activator of transcription 3 (STAT3) is known in the art by various names. Such names include: DNA-binding protein APRF, and acute-phase response factor.

The mRNA encoding human STAT3 can be found at Genbank Accession Number NM_003150.3, and is represented by the sequence (SEQ ID NO: 32).

Natural variants of the human STAT3 gene product are known. For example, natural variants of human STAT3 protein can contain one or more amino acid substitutions selected from: R382L, R382Q, OR R382W, and any combinations thereof. Additional variants of human STAT3 protein resulting from alternative splicing are also known in the art, such as: R382W, F384L, F384S, T3891, N395Y, R423Q, N425Y, 11437Y, Del-463, S611N, F621V, T6221, V637L, V637M, Del-644, Y657C, P330S, K392R, N646K, K658N, Del-701, or T716M. Therefore, the payloads of the present disclosure can be designed to reduce or inhibit expression of the natural variants of the STAT3 protein.

SEQ ID NO: 30 is identical to a STAT3 pre-mRNA sequence except that nucleotide "t" in SEQ ID NO: 30 is shown as "u" in pre-mRNA. In certain aspects, the "target nucleic acid" comprises an intron of a STAT3 protein-encoding nucleic acids or naturally occurring variants thereof, and RNA nucleic acids derived therefrom, e.g., pre-mRNA. In certain aspects, the target nucleic acid comprises an exon region of a STAT3 protein-encoding nucleic acids or naturally occurring variants thereof, and RNA nucleic acids derived therefrom, e.g., pre-mRNA. In certain aspects, the target nucleic acid comprises an exon-intron junction of a STAT3 protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. The human STAT3 protein sequence encoded by the STAT3 pre-mRNA is shown as SEQ ID NO: 31. In certain aspects, the target nucleic acid comprises an untranslated region of a STAT3 protein-encoding nucleic acids or naturally occurring variants thereof, e.g., 5' UTR, 3' UTR, or both.

In some aspects, the target nucleic acid comprises an exon-intron junction of a STAT3 protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. The human STAT3 protein sequence encoded by the STAT3 pre-mRNA is shown as SEQ ID NO: 32. In certain aspects, the target nucleic acid comprises an untranslated region of a STAT3 protein-encoding nucleic acids or naturally occurring variants thereof, e.g., 5' UTR, 3' UTR, or both.

In some aspects, a payload (e.g., ASO) hybridizes to a region within the introns of a STAT3 transcript, e.g., SEQ ID NO: 30 or SEQ ID NO: 32. In certain aspects, a payload of the disclosure hybridizes to a region within the exons of a STAT3 transcript, e.g., SEQ ID NO: 41 or SEQ ID NO: 32. In certain aspects, a payload of the disclosure hybridizes to a region within the exon-intron junction of a STAT3 transcript, e.g., SEQ ID NO: 30 or SEQ ID NO: 32. In some aspects, a payload of the disclosure hybridizes to a region within a STAT3 transcript (e.g., an intron, exon, or exon-intron junction), e.g., SEQ ID NO: 30 or SEQ ID NO: 32.

In some aspects, the payload targets a mRNA encoding a particular isoform of STAT3 protein (e.g., Isoform 1). In some aspects, the payload targets all isoforms of STAT3 protein. In certain aspects, the payload targets two isoforms (e.g., Isoform 1 (UniProt ID: P40763-1) and Isoform 2 (UniProt ID: P40763-2), Isoform 2 and Isoform 3 (UniProt ID: P40763-3) of STAT3 protein.

In some aspects, a payload of the disclosure hybridizes to a region within the introns of a STAT3 transcript, e.g., SEQ ID NO: 30 or SEQ ID NO: 32. In certain aspects, a payload of the disclosure hybridizes to a region within the exons of a STAT3 transcript, e.g., SEQ ID NO: 30 or SEQ ID NO: 32. In certain aspects, a payload of the disclosure hybridizes to a region within the exon-intron junction of a STAT3 transcript, e.g., SEQ ID NO: 30 or SEQ ID NO: 32. In some aspects, a payload of the disclosure hybridizes to a region within a STAT3 transcript (e.g., an intron, exon, or exon-intron junction), e.g., SEQ ID NO: 30 or SEQ ID NO: 32, wherein the payload has a design according to formula: 5' A-B-C 3' as described elsewhere herein.

In some aspects, the payload of the present disclosure hybridizes to multiple target regions within the STAT3 transcript (e.g., genomic sequence, SEQ ID NO: 30). In some aspects, the payload hybridizes to two different target regions within the STAT3 transcript. In some aspects, the payload hybridizes to three different target regions within the STAT3 transcript. In some aspects, the payloads that hybridizes to multiple regions within the STAT3 transcript (e.g., genomic sequence, SEQ ID NO: 30) are more potent (e.g., having lower EC50) at reducing STAT3 expression compared to payloads that hybridizes to a single region within the STAT3 transcript (e.g., genomic sequence, SEQ ID NO: 30).

The payloads of the disclosure comprise a contiguous nucleotide sequence which corresponds to the complement of a region of STAT3 transcript, e.g., a nucleotide sequence corresponding to SEQ ID NO: 30.

In some aspects, binding of an payload targeting a STAT3 transcript disclosed herein to a mRNA transcript encoding STAT3 can reduce expression levels and/or activity levels of STAT3.

In some aspects, the payload comprises an ASO that can specifically target a STAT3 transcript. In some aspects, the nucleotide sequence of an ASO, or the contiguous nucleotide sequence thereof, has at least about 80% sequence identity to a sequence set forth in any one of SEQ ID NOs: 92 to 101 (i.e., the sequences in FIG. 3F), such as at least about 80%, at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity.

In some aspects, the ASO (or contiguous nucleotide portion thereof) is selected from, or comprises, one of the sequences selected from the group consisting of SEQ ID NOs: 92 to 101, or a region of at least 10 contiguous nucleotides thereof, wherein the ASO (or contiguous nucleotide portion thereof) can optionally comprise one, two, three, or four mismatches when compared to the corresponding STAT3 transcript.

In some aspects, the ASO comprises the sequence set forth in SEQ ID NO: 92. In some aspects, the ASO comprises the sequence set forth in SEQ ID NO: 93. In some aspects, the ASO comprises the sequence set forth in SEQ ID NO: 94. In some aspects, the ASO comprises the sequence set forth in SEQ ID NO: 95. In some aspects, the ASO comprises the sequence set forth in SEQ ID NO: 96. In some aspects, the ASO comprises the sequence set forth in SEQ ID NO: 97.

In some aspects, the ASO comprises the sequence set forth in SEQ ID NO: 98. In some aspects, the ASO comprises the sequence set forth in SEQ ID NO: 99. In some aspects, the ASO comprises the sequence set forth in SEQ ID NO: 100. In some aspects, the ASO comprises the sequence set forth in SEQ ID NO: 101.

In some aspects the ASO comprises or consists of a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a sequence set forth in SEQ ID NOs: 92 to 101. In some aspects, the ASO (or contiguous nucleotide portion thereof) is selected from, or comprises, one of the sequences selected from the group consisting of SEQ ID NOs: 92 to 101 or a region of at least 8, 9, 10, 11, 12, 13, 14, 15, 16, 17, 18, 19, or 20 contiguous nucleotides thereof. In some aspects, the ASO (or contiguous nucleotide portion thereof) is selected from, or comprises, one of the sequences selected from the group consisting of SEQ ID NOs: 92 to 101 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four mismatches when compared to the corresponding STAT3 transcript. In some aspects, the ASO (or contiguous nucleotide portion thereof) is selected from, or comprises, one of the sequences selected from the group consisting of SEQ ID NOs: 92 to 101 except for 1, 2, 3, 4, 5, 6, 7, 8, 9 or 10 substitutions, wherein the substituted ASO can bind to the STAT3 transcript. In some aspects, the ASO (or contiguous nucleotide portion thereof) is selected from, or comprises, one of the sequences selected from the group consisting of SEQ ID NOs: 92 to 101 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four additional 5' and/or 3' nucleotides complementary to the corresponding STAT3 transcript.

II.G.1.g NLRP3

In some aspects, the payloads (e.g., ASOs) provided herein are capable of down-regulating (e.g., reducing or inhibiting) the expression of any gene or protein of interest in a cell. In certain aspects, the payloads described herein (e.g., can be loaded in EVs using the loading methods of the present disclosure) target one or more regions of the NLRP3 pre-mRNA (e.g., intron regions, exon regions, and/or exon-intron junction regions). In some aspects, the payload is capable of targeting all isoforms of the NLRP3 protein. In certain aspects, the payload targets specific NLRP3 isoforms. Unless indicated otherwise, the term "NLRP3," as used herein, can refer to STAT6 from one or more species (e.g., humans, non-human primates, dogs, cats, guinea pigs, rabbits, rats, mice, horses, cattle, and bears).

NLRP3 (NLRP3) is also known as NLR family pyrin domain containing 3. Unless indicated otherwise, the term "NLRP3," as used herein, can refer to NLRP3 from one or more species (e.g., humans, non-human primates, dogs, cats, guinea pigs, rabbits, rats, mice, horses, cattle, and bears). Synonyms of NLRP3/NLRP3 are known and include NLRP3; Clorf7; CIAS1; NALP3; PYPAF1; nucleotide-binding oligomerization domain, leucine rich repeat and pyrin domain containing 3; cold-induced autoinflammatory syndrome 1 protein; cryopyin; NACHT, LRR and PYD domains-containing protein 3; angiotensin/vasopressin receptor AII/AVP-like; caterpiller protein 1.1; CLR1.1; cold-induced autoinflammatory syndrome 1 protein; and PYRIN-containing APAF1-like protein 1. The sequence for the human NLRP3 gene can be found under publicly available GenBank Accession Number NC_000001.11: 247416156-247449108. The human NLRP3 gene is found at chromosome location 1q44 at 247,416,156-247,449,108.

The sequence for the human NLRP3 pre-mRNA transcript (SEQ ID NO: 33) corresponds to the reverse complement of residues 247,416,156-247,449,108 of chromosome 1q44. The NLRP3 mRNA sequence (GenBank Accession No. NM_001079821.2) is provided in SEQ ID NO: 35, except that the nucleotide "t" in SEQ ID NO: 35 is shown as "u" in the mRNA. The sequence for human NLRP3 protein can be found under publicly available Accession Numbers: Q96P20, (canonical sequence, SEQ ID NO: 34), Q96P20-2 (SEQ ID NO: 36), Q96P20-3 (SEQ ID NO: 37), Q96P20-4 (SEQ ID NO: 38), Q96P20-5 (SEQ ID NO: 39), and Q96P20-6 (SEQ ID NO: 40), each of which is incorporated by reference herein in its entirety.

Natural variants of the human NLRP3 gene product are known. For example, natural variants of human NLRP3 protein can contain one or more amino acid substitutions selected from: D2111, 1174T, V200M, R262L, 4262P, R262W, L266H, D305G, D305N, L307P, Q308K, F311S, T350M, A354V, L355P, E356D, H360R, T407P, T4381, T438N, A441T, A441V, R490K, F525C, F525L, G571R, Y572C, F575S, E629G, L634F, M664T, Q705K, Y861C, and R920Q, and any combinations thereof. Additional variants of human NLRP3 protein resulting from alternative splicing are also known in the art. NLRP3 Isoform 1 (identifier: Q96P20-2 at UniProt) differs from the canonical sequence (SEQ ID NO: 35) as follows: deletion of residues 721-777 and 836-892 relative to SEQ ID NO: 35. The sequence of NLRP3 Isoform 3 (identifier: Q96P20-3) differs from the canonical sequence (SEQ ID NO: 35) as follows: deletion of residues 720-1036 relative to SEQ ID NO: 35. The sequence of NLRP3 Isoform 4 (identifier: Q96P20-4) differs from the canonical sequence (SEQ ID NO: 35) as follows: deletion of residues 721-777 relative to SEQ ID NO: 35. The sequence of NLRP3 Isoform 5 (identifier: Q96P20-5) differs from the canonical sequence (SEQ ID NO: 35) as follows: deletion of residues 836-892 relative to SEQ ID NO: 35. The sequence of NLRP3 Isoform 6 (identifier: Q96P20-6) differs from the canonical sequence (SEQ ID NO: 35) as follows: deletion of residues 776-796 relative to SEQ ID NO: 35. Therefore, the payloads of the present disclosure can be designed to reduce or inhibit expression of the natural variants of the NLRP3 protein.

An example of a target nucleic acid sequence of the payloads is NLRP3 pre-mRNA. SEQ ID NO: 33 represents a human NLRP3 genomic sequence (i.e., reverse complement of nucleotides 247,416,156-247,449,108 of chromosome 1q44). SEQ ID NO: 33 is identical to a NLRP3 pre-mRNA sequence except that nucleotide "t" in SEQ ID NO: 33 is shown as "u" in pre-mRNA. In certain aspects, the "target nucleic acid" comprises an intron of a NLRP3 protein-encoding nucleic acids or naturally occurring variants thereof, and RNA nucleic acids derived therefrom, e.g., pre-mRNA. In certain aspects, the target nucleic acid comprises an exon region of a NLRP3 protein-encoding nucleic acids or naturally occurring variants thereof, and RNA nucleic acids derived therefrom, e.g., pre-mRNA. In certain aspects, the target nucleic acid comprises an exon-intron junction of a NLRP3 protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. The human NLRP3 protein sequence encoded by the NLRP3 pre-mRNA is shown as SEQ ID NO: 35. In certain aspects, the target nucleic acid comprises an untranslated region of a NLRP3 protein-encoding nucleic acids or naturally occurring variants thereof, e.g., 5' UTR, 3' UTR, or both.

In some aspects, a payload (e.g., ASO) hybridizes to a region within the introns of a NLRP3 transcript, e.g., SEQ ID NO: 33. In certain aspects, a payload of the disclosure hybridizes to a region within the exons of a NLRP3 transcript, e.g., SEQ ID NO: 33. In certain aspects, a payload of the disclosure hybridizes to a region within the exon-intron junction of a NLRP3 transcript, e.g., SEQ ID NO: 33. In some aspects, a payload of the disclosure hybridizes to a region within a NLRP3 transcript (e.g., an intron, exon, or exon-intron junction), e.g., SEQ ID NO: 33.

In some aspects, the payload targets a mRNA encoding a particular isoform of NLRP3 protein (e.g., Isoform 1). In some aspects, the payload targets all isoforms of NLRP3 protein. In certain aspects, the payload targets two isoforms (e.g., Isoform 1 and Isoform 2, Isoform 3 and Isoform 4, and Isoform 5 and Isoform 6) of NLRP3 protein.

In some aspects, binding of an payload targeting a NLRP3 transcript disclosed herein to a mRNA transcript encoding NLRP3 can reduce expression levels and/or activity levels of NLRP3.

In some aspects, the payload comprises an ASO that can specifically target a NLRP3 transcript. In some aspects, the nucleotide sequence of an ASO, or the contiguous nucleotide sequence thereof, has at least about 80% sequence identity to a sequence set forth in any one of SEQ ID NOs: 102 to 112 (i.e., the sequences in FIG. 3G), such as at least about 80%, at least about 85%, at least about 90%, at least about 91%, at least about 92%, at least about 93%, at least about 94%, at least about 95%, at least about 96% sequence identity, at least about 97% sequence identity, at least about 98% sequence identity, at least about 99% sequence identity, such as about 100% sequence identity.

In some aspects, the ASO (or contiguous nucleotide portion thereof) is selected from, or comprises, one of the sequences selected from the group consisting of SEQ ID NOs: 102 to 112, or a region of at least 10 contiguous nucleotides thereof, wherein the ASO (or contiguous nucleotide portion thereof) can optionally comprise one, two, three, or four mismatches when compared to the corresponding NLRP3 transcript.

In some aspects, the ASO comprises the sequence set forth in SEQ ID NO: 102. In some aspects, the ASO comprises the sequence set forth in SEQ ID NO: 103. In some aspects, the ASO comprises the sequence set forth in SEQ ID NO: 104. In some aspects, the ASO comprises the sequence set forth in SEQ ID NO: 105. In some aspects, the ASO comprises the sequence set forth in SEQ ID NO: 106. In some aspects, the ASO comprises the sequence set forth in SEQ ID NO: 107. In some aspects, the ASO comprises the sequence set forth in SEQ ID NO: 108. In some aspects, the ASO comprises the sequence set forth in SEQ ID NO: 109. In some aspects, the ASO comprises the sequence set forth in SEQ ID NO: 110. In some aspects, the ASO comprises the sequence set forth in SEQ ID NO: 111. In some aspects, the ASO comprises the sequence set forth in SEQ ID NO: 112.

In some aspects the ASO comprises or consists of a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a sequence set forth in SEQ ID NOs: 102 to 112. In some aspects, the ASO (or contiguous nucleotide portion thereof) is selected from, or comprises, one of the sequences selected from the group consisting of SEQ ID NOs: 102 to 112 or a region of at least 8, 9, 10, 11, 12, 13, 14, 15, 16, 17, 18, 19, or 20 contiguous nucleotides thereof. In some aspects, the ASO (or contiguous nucleotide portion thereof) is selected from, or comprises, one of the sequences selected from the group consisting of SEQ ID NOs: 102 to 112 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four mismatches when compared to the corresponding NLRP3 transcript. In some aspects, the ASO (or contiguous nucleotide portion thereof) is selected from, or comprises, one of the sequences selected from the group consisting of SEQ ID NOs: 102 to 112 except for 1, 2, 3, 4, 5, 6, 7, 8, 9 or 10 substitutions, wherein the substituted ASO can bind to the NLRP3 transcript. In some aspects, the ASO (or contiguous nucleotide portion thereof) is selected from, or comprises, one of the sequences selected from the group consisting of SEQ ID NOs: 102 to 112 or a region of at least 8, 9, 10, 11, 12, 13, 14, 15, 16, 17, 18, 19, or 20 contiguous nucleotides thereof, wherein the ASO (or contiguous nucleotide portion thereof) can optionally comprise one, two, three, or four additional 5' and/or 3' nucleotides complementary to the corresponding NLRP3 transcript.

II.G.2 Anchoring Moiety

One or more anchoring moieties (AMs) can be used to anchor a payload (or any other moieties of interest) to EVs (e.g., exosomes). In some aspects, the payload is linked directly to the anchoring moiety. In some aspects, the payload is linked to the anchoring moiety via a linker, such as those described herein. In some aspects, the payload can be attached to an anchoring moiety and/or linker via reaction between a "reactive group" (RG; e.g., amine, thiol, hydroxy, carboxylic acid, or azide) with a "reactive moiety" (RM; e.g., maleimide, succinate, NHS). Several potential synthetic routes are envisioned, for example:

[AM]-/Reactive moiety/+/Reactive group/-[payload]

[AM]-[Linker]n-/Reactive moiety/+/Reactive group/-[payload]

[AM]-/Reactive moiety/+/Reactive group/-[Linker]n-[payload]

[AM]-[Linker]n-/Reactive moiety/+/Reactive group/-[Linker]n-[payload]

The anchoring moiety can insert into the lipid bilayer of an EV allowing the loading of the payload. In some aspect, an anchoring moiety can be chemically conjugated to a payload to enhance its hydrophobic character, and thereby, enhance the loading of the EV with the payload. In some aspects, the anchoring moiety comprises a sterol (e.g., cholesterol), GM1, a lipid, a vitamin, a small molecule, a peptide, or a combination thereof.

In some aspects, the anchoring moiety is a lipid. Any suitable lipid known in the art can be used as the anchoring moiety (e.g., palmitic acid or glycosylphosphatidylinositols). In some aspects, the anchoring moiety is a sterol, e.g., cholesterol. Additional hydrophobic moieties include, for example, phospholipids, lysophospholipids, fatty acids, or vitamins (e.g., vitamin D or vitamin E).

In some aspects, anchoring moieties are chemically attached. In certain aspects, an anchoring moiety can be attached to a payload (e.g., ASO) enzymatically. In some aspects, an anchoring moiety can be attached to a payload via modification of cell culture conditions. For example, by using a culture medium where myristic acid is limiting, some other fatty acids including shorter-chain and unsaturated, can be attached to an N-terminal glycine. For example, in BK channels, myristate has been reported to be attached post-translationally to internal serine/threonine or tyrosine residues via a hydroxyester linkage.

The anchoring moiety can be conjugated to a payload directly or indirectly via a linker combination, at any chemically feasible location, e.g., at the 5' and/or 3' end of the payload. In certain aspects, the anchoring moiety is conjugated only to the 3' end of the payload. In certain aspects, the anchoring moiety is conjugated only to the 5' end of the payload. In some aspects, the anchoring moiety is conjugated at a location which is not the 3' end or 5' end of the payload.

Non-limiting examples of anchoring moieties (including their structure) are provided below:

| Modification | Modifying Group |
| --- | --- |
| S-Palmitoylation | 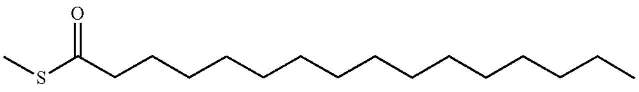 [SMILES: CCCCCCCCCCCCCCCC(=O)SC] |
| N-Palmitoylation | 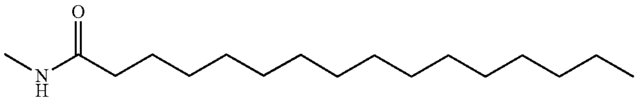 [SMILES: CCCCCCCCCCCCCCCC(=O)NC] |
| N-Myristoylation | 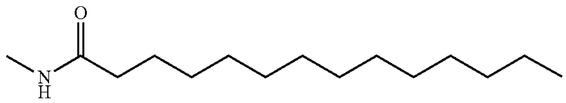 [SMILES: CCCCCCCCCCCCCC(=O)NC] |
| O-Acylation | 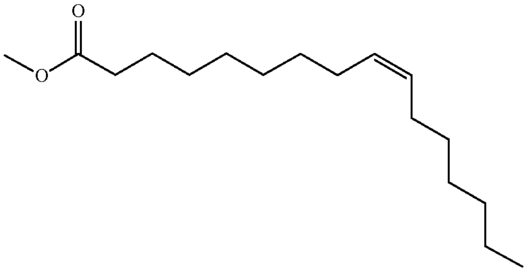 [SMILES: CCCCCC/C=C\CCCCCCCC(=O)OC] |
| Farnesylation | 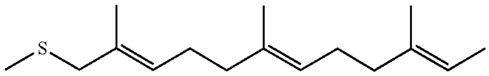 [SMILES: C/C=C(\C)CC/C=C(\C)CC/C=C(\C)CSC] |
| Geranylgeranylation | 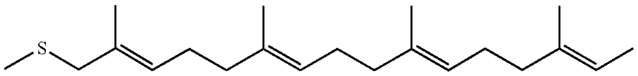 [SMILES: C/C=C(\C)CC/C=C(\C)CC/C=C(\C)CC/C=C(\C)CSC] |
| Cholesterol | 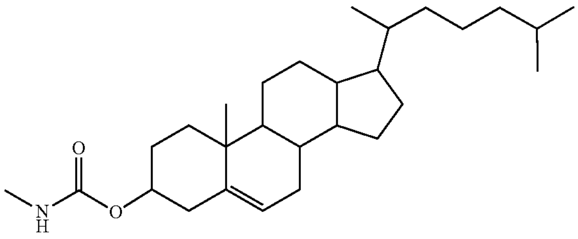 [SMILES: CNC(=O)OC1CCC2(C)C(=CCC3C4CCC(C(C)CCCC(C)C)C4CCC32)C1] |

In some aspects, an anchoring moiety useful for the present disclosure comprises two or more types of anchoring moieties disclosed herein. For example, in some aspects, an anchoring moiety can comprise two lipids, e.g., a phospholipids and a fatty acid, or two phospholipids, or two fatty acids, or a lipid and a vitamin, or cholesterol and a vitamin, etc. which taken together have 6-80 carbon atoms (i.e., an equivalent carbon number (ECN) of 6-80).

In some aspects, the combination of anchoring moieties, e.g., a combination of the lipids (e.g., fatty acids) has an ECN of 6-80, 8-80, 10-80, 12-80, 14-80, 16-80, 18-80, 20-80, 22-80, 24-80, 26-80, 28-80, 30-80, 4-76, 6-76, 8-76, 10-76, 12-76, 14-76, 16-76, 18-76, 20-76, 22-76, 24-76, 26-76, 28-76, 30-76, 6-72, 8-72, 10-72, 12-72, 14-72, 16-72, 18-72, 20-72, 22-72, 24-72, 26-72, 28-72, 30-72, 6-68, 8-68, 10-68, 12-68, 14-68, 16-68, 18-68, 20-68, 22-68, 24-68, 26-68, 28-68, 30-68, 6-64, 8-64, 10-64, 12-64, 14-64, 16-64, 18-64, 20-64, 22-64, 24-64, 26-64, 28-64, 30-64, 6-60, 8-60, 10-60, 12-56, 14-56, 16-56, 18-56, 20-56, 22-56, 24-56, 26-56, 28-56, 30-56, 6-52, 8-52, 10-52, 12-52, 14-52, 16-52, 18-52, 20-52, 22-52, 24-52, 26-52, 28-52, 30-52, 6-48, 8-48, 10-48, 12-48, 14-48, 16-48, 18-48, 20-48, 22-48, 24-48, 26-48, 28-48, 30-48, 6-44, 8-44, 10-44, 12-44, 14-44, 16-44, 18-44, 20-44, 22-44, 24-44, 26-44, 28-44, 30-44, 6-40, 8-40, 10-40, 12-40, 14-40, 16-40, 18-40, 20-40, 22-40, 24-40, 26-40, 28-40, 30-40, 6-36, 8-36, 10-36, 12-36, 14-36, 16-36, 18-36, 20-36, 22-36, 24-36, 26-36, 28-36, 30-36, 6-32, 8-32, 10-32, 12-32, 14-32, 16-32, 18-32, 20-32, 22-32, 24-32, 26-32, 28-32, or 30-32.

II.G.1.a. Cholesterol and Other Sterols

In some aspects, the anchoring moiety comprises a sterol, steroid, hopanoid, hydroxysteroid, secosteroid, or analog thereof with lipophilic properties. In some aspects, the anchoring moiety comprises a sterol, such as a phytosterol, mycosterol, or zoosterol. Exemplary zoosterols include cholesterol and 24S-hydroxycholesterol; exemplary phytosterols include ergosterol (mycosterol), campesterol, sitosterol, and stigmasterol. In some aspects, the sterol is selected from ergosterol, 7-dehydrocholesterol, cholesterol, 24S-hydroxy-cholesterol, lanosterol, cycloartenol, fucosterol, saringosterol, campesterol, P-sitosterol, sitostanol, coprostanol, avenasterol, or stigmasterol. Sterols can be found either as free sterols, acylated (sterol esters), alkylated (steryl alkyl ethers), sulfated (sterol sulfate), or linked to a glycoside moiety (steryl glycosides), which can be itself acylated (acylated sterol glycosides).

In some aspects, the anchoring moiety comprises a steroid. In some aspects, the steroid is selected from dihydrotestosterone, uvaol, hecigenin, diosgenin, progesterone, or cortisol.

For example, sterols can be conjugated to the payload (e.g., ASO) directly or via a linker combination at the available —OH group of the sterol. Exemplary sterols have the general skeleton shown below:

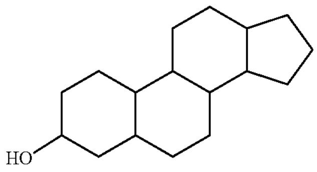 [SMILES: OC1CCC2C(CCC3C4CCCC4CCC23)C1]

As a further example, ergosterol has the structure below:

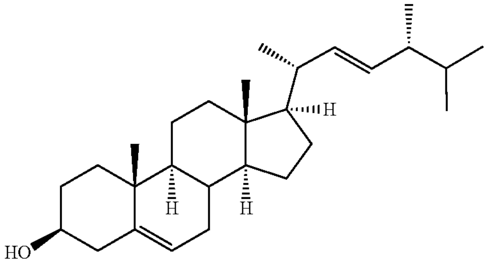

Cholesterol has the structure below:

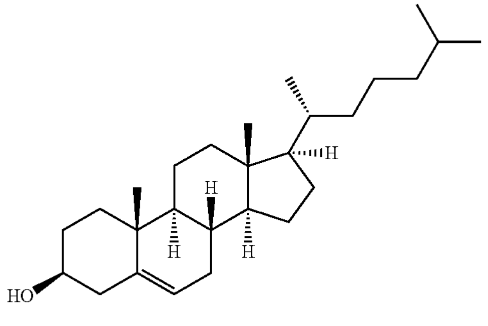

Accordingly, in some aspects, the free —OH group of a sterol or steroid is used to conjugate the payload directly or via a linker combination, to the sterol (e.g., cholesterol) or steroid. In some aspects, the cholesterol that can be used to conjugate a payload described herein (e.g., ASO) has the structure shown in FIG. 2A. In some aspects, the cholesterol that can be used to conjugate a payload described herein (e.g., ASO) has the structure shown in FIG. 2B. As described herein, the cholesterol shown in FIG. 2A can be attached to a linker, e.g., triethylene glycol (referred to herein as "chol2"). In some aspects, the cholesterol shown in FIG. 2B can be attached to a linker, e.g., tetraethylene glycol (referred to herein as "chol4").

II.G.2.b. Fatty Acids

In some aspects, the anchoring moiety is a fatty acid. In some aspects, the fatty acid is a short-chain, medium-chain, or long-chain fatty acid. In some aspects, the fatty acid is a saturated fatty acid. In some aspects, the fatty acid is an unsaturated fatty acid. In some aspects, the fatty acid is a monounsaturated fatty acid. In some aspects, the fatty acid is a polyunsaturated fatty acid, such as an omega-3 or omega-6 fatty acid.

In some aspects, the lipid, e.g., fatty acid, has a $C_2$-$C_{60}$ chain. In some aspects, the lipid, e.g., fatty acid, has a $C_2$-$C_{28}$ chain. In some aspects, the fatty acid, has a $C_2$-$C_{40}$ chain. In some aspects, the fatty acid, has a $C_2$-$C_{12}$ or $C_4$-$C_{12}$ chain. In some aspects, the fatty acid, has a $C_4$-$C_{40}$ chain. In some aspects, the fatty acid, has a $C_4$-$C_{40}$, $C_2$-$C_{38}$, $C_2$-$C_{36}$, $C_2$-$C_{34}$, $C_2$-$C_{32}$, $C_2$-$C_{30}$, $C_4$-$C_{30}$, $C_2$-$C_{28}$, $C_4$-$C_{28}$, $C_2$-$C_{26}$, $C_4$-$C_{26}$, $C_2$-$C_{24}$, $C_4$-$C_{24}$, $C_6$-$C_{24}$, $C_8$-$C_{24}$, $C_{10}$-$C_{24}$, $C_2$-$C_{22}$, $C_4$-$C_{22}$, $C_6$-$C_{22}$, $C_8$-$C_{22}$, $C_{10}$-$C_{22}$, $C_2$-$C_{20}$, $C_4$-$C_{20}$, $C_6$-$C_{20}$, $C_5$-$C_{20}$, $C_{10}$-$C_{20}$, $C_2$-$C_{18}$, $C_4$-$C_{18}$, $C_6$-$C_{18}$, $C_8$-$C_{18}$, $C_{10}$-$C_{18}$, $C_{12}$-$C_{18}$, $C_{14}$-$C_{18}$, $C_{16}$-$C_{18}$, $C_2$-$C_{16}$, $C_4$-$C_{16}$, $C_6$-$C_{16}$, $C_5$-$C_{16}$, $C_{10}$-$C_{16}$, $C_{12}$-$C_{16}$, $C_{14}$-$C_{16}$, $C_2$-$C_{18}$, $C_4$-$C_{15}$, $C_6$-$C_{15}$, $C_8$-$C_{15}$, $C_9$-$C_{15}$, $C_{10}$-$C_{15}$, $C_{11}$-$C_{15}$, $C_{12}$-$C_{15}$, $C_{13}$-$C_{15}$, $C_2$-$C_{14}$, $C_4$-$C_{14}$, $C_6$-$C_{14}$, $C_5$-$C_{14}$, $C_9$-$C_{14}$, $C_{10}$-$C_{14}$, $C_{11}$-$C_{14}$, $C_{12}$-$C_{14}$, $C_2$-$C_{13}$, $C_4$-$C_{13}$, $C_6$-$C_{13}$, $C_7$-$C_{13}$, $C_5$-$C_{13}$, $C_9$-$C_{13}$, $C_{10}$-$C_{13}$, $C_{10}$-$C_{13}$, $C_{11}$-$C_{13}$, $C_2$-$C_{12}$, $C_4$-$C_{12}$, $C_6$-$C_{12}$, $C_7$-$C_{12}$, $C_8$-$C_{12}$, $C_9$-$C_{12}$, $C_{10}$-$C_{12}$, $C_2$-$C_{11}$, $C_4$-$C_{11}$, $C_6$-$C_{11}$, $C_7$-$C_{11}$, $C_8$-$C_{11}$, $C_9$-$C_{11}$, $C_2$-$C_{10}$, $C_4$-$C_{10}$, $C_2$-$C_9$, $C_4$-$C_9$, $C_2$-$C_8$, $C_2$-$C_7$, $C_4$-$C_7$, $C_2$-$C_6$, or $C_4$- $C_6$, chain. In some aspects, the fatty acid has a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, $C_{50}$, $C_{51}$, $C_{52}$, $C_{53}$, $C_{54}$, $C_{55}$, $C_{56}$, $C_{57}$, $C_{58}$, $C_{59}$, or $C_{60}$ chain.

In some aspects, the anchoring moiety comprises two fatty acids, each of which is independently selected from a fatty acid having a chain with any one of the foregoing ranges or numbers of carbon atoms. In some aspects, one of the fatty acids is independently a fatty acid with a C6-C21 chain and one is independently a fatty acid with a C12-C36 chain. In some aspects, each fatty acid independently has a chain of 11, 12, 13, 14, 15, 16, or 17 carbon atoms.

Suitable fatty acids include saturated straight-chain fatty acids, saturated branched fatty acids, unsaturated fatty acids, hydroxy fatty acids, and polycarboxylic acids. In some aspects, such fatty acids have up to 32 carbon atoms.

Examples of useful saturated straight-chain fatty acids include those having an even number of carbon atoms, such as butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, and heptacosanoic acid.

Examples of suitable saturated branched fatty acids include isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, a-ethyl-hexanoic acid, α-hexyldecanoic acid, a-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.). Suitable saturated odd-carbon branched fatty acids include anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid, and 26-methyloctacosanoic acid.

Examples of suitable unsaturated fatty acids include 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, a-eleostearic acid, 0-eleostearic acid, punicic acid, 6,9,12,15-octadecatetraenoic acid, parinaric acid, 5,8,11,14-eicosatetraenoic acid, 5,8,11,14,17-eicosapentaenoic acid, 7,10,13,16,19-docosapentaenoic acid, 4,7,10,13,16,19-docosahexaenoic acid, and the like.

Examples of suitable hydroxy fatty acids include a-hydroxylauric acid, a-hydroxymyristic acid, a-hydroxypalmitic acid, a-hydroxystearic acid, co-hydroxylauric acid, a-hydroxyarachic acid, 9-hydroxy-12-octadecenoic acid, ricinoleic acid, a-hydroxybehenic acid, 9-hydroxy-trans-10,12-octadecadienic acid, kamolenic acid, ipurolic acid, 9,10-dihydroxystearic acid, 12-hydroxystearic acid and the like.

Examples of suitable polycarboxylic acids include oxalic acid, malonic acid, succinic acid, glutaric acid, adipic acid, pimelic acid, suberic acid, azelaic acid, sebacic acid, D,L-malic acid, and the like.

In some aspects, each fatty acid is independently selected from propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, or octatriacontanoic acid.

In some aspects, each fatty acid is independently selected from a-linolenic acid, stearidonic acid, eicosapentaenoic acid, docosahexaenoic acid, linoleic acid, gamma-linoleic acid, dihomo-gamma-linoleic acid, arachidonic acid, docosatetraenoic acid, palmitoleic acid, vaccenic acid, paullinic acid, oleic acid, claidic acid, gondoic acid, eurcic acid, nervonic acid, mead acid, adrenic acid, bosseopentaenoic acid, ozubondo acid, sardine acid, herring acid, docosahexaenoic acid, or tetracosanolpentaenoic acid, or another monounsaturated or polyunsaturated fatty acid.

In some aspects, one or both of the fatty acids is an essential fatty acid. In view of the beneficial health effects of certain essential fatty acids, the therapeutic benefits of disclosed therapeutic-loaded exosomes can be increased by including such fatty acids in the therapeutic agent. In some aspects, the essential fatty acid is an n-6 or n-3 essential fatty acid selected from the group consisting of linolenic acid, gamma-linolenic acid, dihomo-gamma-linolenic acid, arachidonic acid, adrenic acid, docosapentaenoic n-6 acid, alpha-linolenic acid, stearidonic acid, the 20:4n-3 acid, eicosapentaenoic acid, docosapentaenoic n-3 acid, or docosahexaenoic acid.

In some aspects, each fatty acid is independently selected from all-cis-7,10,13-hexadecatrienoic acid, a-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid, or lipoic acid. In some aspects, the fatty acid is selected from eicosapentaenoic acid, docosahexaenoic acid, or lipoic acid. Other examples of fatty acids include all-cis-7,10,13-hexadecatrienoic acid, a-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid). In some aspects, the fatty acid is a medium-chain fatty acid such as lipoic acid.

Fatty acid chains differ greatly in the length of their chains and can be categorized according to chain length, e.g. as short to very long. Short-chain fatty acids (SCFA) are fatty acids with chains of about five or less carbons (e.g. butyric acid). In some aspects, the fatty acid is a SCFA. Medium-chain fatty acids (MCFA) include fatty acids with chains of about 6-12 carbons, which can form medium-chain triglycerides. In some aspects, the fatty acid is a MCFA. Long-chain fatty acids (LCFA) include fatty acids with chains of 13-21 carbons. In some aspects, the fatty acid is a LCFA. In some aspects, the fatty acid is a LCFA. Very long chain fatty acids (VLCFA) include fatty acids with chains of 22 or more carbons, such as 22-60, 22-50, or 22-40 carbons. In some aspects, the fatty acid is a VLCFA.

II.G.2.c. Phospholipids

In some aspects, the anchoring moiety comprises a phospholipid. Phospholipids are a class of lipids that are a major component of all cell membranes. They can form lipid bilayers because of their amphiphilic characteristic. The structure of the phospholipid molecule generally consists of two hydrophobic fatty acid "tails" and a hydrophilic "head" consisting of a phosphate group. For example, a phospholipid can be a lipid according to the following formula:

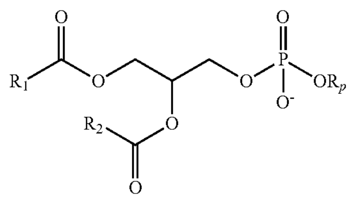

in which $R_p$ represents a phospholipid moiety and $R_1$ and $R_2$ represent fatty acid moieties with or without unsaturation that can be the same or different.

A phospholipid moiety can be selected, for example, from the non-limiting group consisting of phosphatidyl choline, phosphatidyl ethanolamine, phosphatidyl glycerol, phosphatidyl serine, phosphatidic acid, 2 lysophosphatidyl choline, and a sphingomyelin.

Particular phospholipids can facilitate fusion to a lipid bilayer, e.g., the lipid bilayer of an exosomal membrane. For example, a cationic phospholipid can interact with one or more negatively charged phospholipids of a membrane. Fusion of a phospholipid to a membrane can allow one or more elements of a lipid-containing composition to bind to the membrane or to pass through the membrane.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

The phospholipids using as anchoring moieties in the present disclosure can be natural or non-natural phospholipids. Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide.

Phospholipids include, but are not limited to, glycerophospholipids such as phosphatidylcholines, phosphatidylethanolamines, phosphatidylserines, phosphatidylinositols, phosphatidy glycerols, and phosphatidic acids.

II.G.2.d. Lysolipids (e.g., lysophospholipids)

In some aspects, the anchoring moiety comprises a lysolipid, e.g., a lysophospholipid. Lysolipids are derivatives of a lipid in which one or both fatty acyl chains have been removed, generally by hydrolysis. Lysophospholipids are derivatives of a phospholipid in which one or both fatty acyl chains have been removed by hydrolysis.

In some aspects, the anchoring moiety comprises any of the phospholipids disclosed above, in which one or both acyl chains have been removed via hydrolysis, and therefore the resulting lysophospholipid comprises one or no fatty acid acyl chain.

In some aspects, the anchoring moiety comprises a lysoglycerophospholipid, a lysoglycosphingoliopid, a lysophosphatidylcholine, a lysophosphatidylethanolamine, a lysophosphatidylinositol, or a lysophosphatidylserine.

II.G.2.e. Vitamins

In some aspects, the anchoring moiety comprises a lipophilic vitamin, e.g., folic acid, vitamin A, vitamin E, pyridoxone, niacin, or vitamin K.

In some aspects, the anchoring moiety comprises vitamin A. Vitamin A is a group of unsaturated nutritional organic compounds that includes retinol, retinal, retinoic acid, and several provitamin A carotenoids (most notably beta-carotene). In some aspects, the anchoring moiety comprises retinol. In some aspects, the anchoring moiety comprises a retinoid. Retinoids are a class of chemical compounds that are vitamers of vitamin A or are chemically related to it.

In some aspects, the anchoring moiety comprises a first generation retinoid (e.g., retinol, tretinoin, isotreatinoin, or alitretinoin), a second-generation retinoid (e.g., etretinate or acitretin), a third-generation retinoid (e.g., adapalene, bexarotene, or tazarotene), or any combination thereof.

II.G.3 Linker Combinations

In some aspects, a payload (e.g., ASO) (or any other moieties of interest described herein) is linked to an anchoring moiety disclosed herein via a linker combination. In certain aspects, the linker combination comprises multiple (e.g., two or more) cleavable linkers. In certain aspects, the linker combination comprises multiple (e.g., two or more) non-cleavable linkers. In some aspects, the linker combination comprises multiple (e.g., two or more) non-cleavable linkers and cleavable linkers.

Linkers can be susceptible to cleavage ("cleavable linker"), and thereby facilitating release of a biologically active molecule (e.g., payload). Thus, in some aspects, a linker combination disclosed herein can comprise a cleavable linker. Such cleavable linkers can be susceptible, for example, to acid-induced cleavage, photo-induced cleavage, peptidase-induced cleavage, esterase-induced cleavage, reactive oxygen species-induced cleavage, diselenide bond cleavage, and disulfide bond cleavage, at conditions under which the biologically active molecule (e.g., payload, e.g., ASO) remains active. Alternatively, linkers can be substantially resistant to cleavage ("non-cleavable linker"). In some aspects, the cleavable linker comprises a spacer. In some aspects the spacer is PEG.

In some aspects, a linker combination comprises at least 2, at least 3, at least 4, at least 5, or at least 6 or more different linkers disclosed herein. In some aspects, linkers in a linker combination can be linked by an ester linkage (e.g., phosphodiester or phosphorothioate ester).

In some aspects, the linker is a direct bond between an anchoring moiety and a payload (e.g., ASO).

II.G.3.a Non-Cleavable Linkers

In some aspects, the linker combination comprises a non-cleavable liker. "Non-cleavable linkers" are any chemical moiety capable of linking two or more components of a modified biologically active molecule of the present disclosure (e.g., a biologically active molecule and an anchoring moiety; a biologically active molecule and a cleavable linker; an anchoring moiety and a cleavable linker) in a stable, covalent manner and does not fall off under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage.

Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which a cyclic dinucleotide and/or the antibody does not lose its activity. In some aspects, the biologically active molecule is attached to the linker via another linker, e.g., a self-immolative linker.

In some aspects, the linker combination comprises a non-cleavable linker comprising, e.g., tetraethylene glycol (TEG), hexaethylene glycol (HEG), polyethylene glycol (PEG), succinimide, or any combination thereof. In some aspects, the non-cleavable linker comprises a spacer unit to link the biologically active molecule to the non-cleavable linker.

In some aspects, one or more non-cleavable linkers comprise smaller units (e.g., HEG, TEG, glycerol, $C_2$ to $C_{12}$ alkyl, and the like) linked together. In one aspect, the linkage is an ester linkage (e.g., phosphodiester or phosphorothioate ester) or other linkage.

II.G.3.a.1 Ethylene Glycols (HEG, TEG, PEG)

In some aspects, the linker combination comprises a non-cleavable linker, wherein the non-cleavable linker comprises a polyethylene glycol (PEG) characterized by a formula $R^3$—(O—$CH_2$—$CH_2$)$_n$— or $R^3$—(O—$CH_2$—$CH_2$)$_n$—O— with $R^3$ being hydrogen, methyl or ethyl and n having a value from 2 to 200. In some aspects, the linker comprises a spacer, wherein the spacer is PEG.

In some aspects, the PEG linker is an oligo-ethylene glycol, e.g., diethylene glycol, triethylene glycol, tetra ethylene glycol (TEG), pentaethylene glycol, or a hexaethylene glycol (HEG) linker.

In some aspects, n has a value of 2, 3, 4, 5, 6, 7, 8, 9, 10, 11, 12, 13, 14, 15, 16, 17,18,19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146,147,148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 189, 181, 182, 183, 184, 185, 186, 187, 188, 189, 190, 191, 192, 193, 194, 195, 196, 197, 198, 199, or 200.

In some aspects, n is between 2 and 10, between 10 and 20, between 20 and 30, between 30 and 40, between 40 and 50, between 50 and 60, between 60 and 70, between 70 and 80, between 80 and 90, between 90 and 100, between 100 and 110, between 110 and 120, between 120 and 130, between 130 and 140, between 140 and 150, between 150 and 160, between 160 and 170, between 170 and 180, between 180 and 190, or between 190 and 200.

In some specific aspects, n has a value from 3 to 200, from 3 to 20, from 10 to 30, or from 9 to 45.

In some aspects, the PEG is a branched PEG. Branched PEG has three to ten PEG chains emanating from a central core group.

In certain aspects, the PEG moiety is a monodisperse polyethylene glycol. In the context of the present disclosure, a monodisperse polyethylene glycol (mdPEG) is a PEG that has a single, defined chain length and molecular weight. mdPEG is typically generated by separation from the polymerization mixture by chromatography. In certain formulae, a monodisperse PEG moiety is assigned the abbreviation mdPEG.

In some aspects, the PEG is a Star PEG. Star PEG has 10 to 100 PEG chains emanating from a central core group.

In some aspects, the PEG is a Comb PEG. Comb PEG has multiple PEG chains normally grafted onto a polymer backbone.

In certain aspects, the PEG has a molar mass between 100 g/mol and 3000 g/mol, particularly between 100 g/mol and 2500 g/mol, more particularly of approx. 100 g/mol to 2000 g/mol. In certain aspects, the PEG has a molar mass between 200 g/mol and 3000 g/mol, particularly between 300 g/mol and 2500 g/mol, more particularly of approx. 400 g/mol to 2000 g/mol.

In some aspects, the PEG is $PEG_{100}$, $PEG_{200}$, $PEG_{300}$, $PEG_{400}$, $PEG_{500}$, $PEG_{600}$, $PEG_{700}$, $PEG_{800}$, $PEG_{900}$, $PEG_{1000}$, $PEG_{1100}$, $PEG_{1200}$, $PEG_{1300}$, $PEG_{1400}$, $PEG_{1500}$, $PEG_{1600}$, $PEG_{1700}$, $PEG_{1800}$, $PEG_{1900}$, $PEG_{2000}$, $PEG_{2100}$, $PEG_{2200}$, $PEG_{2300}$, $PEG_{2400}$, $PEG_{2500}$, $PEG_{1600}$, $PEG_{1700}$, $PEG_{1800}$, $PEG_{1900}$, $PEG_{2000}$, $PEG_{2100}$, $PEG_{2200}$, $PEG_{2300}$, $PEG_{2400}$, $PEG_{2500}$, $PEG_{2600}$, $PEG_{2700}$, $PEG_{2800}$, $PEG_{2900}$, or $PEG_{3000}$. In certain aspects, the PEG is $PEG_{400}$. In certain aspects, the PEG is $PEG_{2000}$.

In some aspects, a linker combination of the present disclosure can comprise several PEG linkers, e.g., a cleavable linker flanked by PEG, HEG, or TEG linkers.

In some aspects, the linker combination comprises (HEG)n and/or (TEG)n, wherein n is an integer between 1 and 50, and each unit is connected, e.g., via a phosphate ester linker, a phosphorothioate ester linkage, or a combination thereof.

II.G.3.a.2. Glycerol and Polyglycerols (PG)

In some aspects, the linker combination comprises a non-cleavable linker comprising a glycerol unit or a polyglycerol (PG) described by the formula ((R3-O—($CH_2$—CHOH—$CH_2$O)$_n$—) with R3 being hydrogen, methyl or ethyl, and n having a value from 3 to 200.

In some aspects, n has a value from 3 to 20. In some aspects, n has a value from 10 to 30.

In some aspects, the PG linker is a diglycerol, triglycerol, tetraglycerol (TG), pentaglycerol, or a hexaglycerol (IG) linker.

In some aspects, n has a value of 2, 3, 4, 5, 6, 7, 8, 9, 10, 11, 12, 13, 14, 15, 16, 17,18,19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95,96,97,98,99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144,145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 189, 181, 182, 183, 184, 185, 186, 187, 188, 189, 190, 191, 192, 193, 194, 195, 196, 197, 198, 199, or 200.

In some aspects, n is between 2 and 10, between 10 and 20, between 20 and 30, between 30 and 40, between 40 and 50, between 50 and 60, between 60 and 70, between 70 and 80, between 80 and 90, between 90 and 100, between 100 and 110, between 110 and 120, between 120 and 130, between 130 and 140, between 140 and 150, between 150 and 160, between 160 and 170, between 170 and 180, between 180 and 190, or between 190 and 200.

In some alternatives of these aspects, n has a value from 9 to 45. In some aspects, the heterologous moiety is a branched polyglycerol described by the formula ($R^3$—O—($CH_2$—$CHOR^5$—$CH_2$—O)$_n$—) with $R^5$ being hydrogen or a linear glycerol chain described by the formula ($R^3$—O—($CH_2$—CHOH—$CH_2$—O)$_n$—) and $R^3$ being hydrogen, methyl or ethyl. In some aspects, the heterologous moiety is a hyperbranched polyglycerol described by the formula ($R^3$—O—($CH_2$—$CHOR^5$—$CH_2$—O)$_n$—) with $R^5$ being hydrogen or a glycerol chain described by the formula ($R^3$—O($CH_2$—$CHOR^6$—$CH_2$—O)$_n$—), with $R^5$ being hydrogen or a glycerol chain described by the formula ($R^3$—O—($CH_2$—$CHOR^7$—$CH_2$—O)$_n$—), with $R^7$ being hydrogen or a linear glycerol chain described by the formula ($R^3$—O—($CH_2$—CHOH—$CH_2$—O)n-) and $R^3$ being hydrogen, methyl or ethyl. Hyperbranched glycerol and methods for its synthesis are described in Oudshorn et al.

(2006) Biomaterials 27:5471-5479; Wilms et al. (20100 Ace. Chem. Res. 43, 129-41, and references cited therein.

In certain aspects, the PG has a molar mass between 100 g/mol and 3000 g/mol, particularly between 100 g/mol and 2500 g/mol, more particularly of approx. 100 g/mol to 2000 g/mol. In certain aspects, the PG has a molar mass between 200 g/mol and 3000 g/mol, particularly between 300 g/mol and 2500 g/mol, more particularly of approx. 400 g/mol to 2000 g/mol.

In some aspects, the PG is $PG_{100}$, $PG_{200}$, $PG_{300}$, $PG_{400}$, $PG_{500}$, $PG_{600}$, $PG_{700}$, $PG_{800}$, $PG_{900}$, $PG_{1000}$, $PG_{1100}$, $PG_{1200}$, $PG_{1300}$, $PG_{1400}$, $PG_{1500}$, $PG_{1600}$, $PG_{1700}$, $PG_{1800}$, $PG_{1900}$, $PG_{2000}$, $PG_{2100}$, $PG_{2200}$, $PG_{2300}$, $PG_{2400}$, $PG_{2500}$, $PG_{1600}$, $PG_{1700}$, $PG_{1800}$, $PG_{1900}$, $PG_{2000}$, $PG_{2100}$, $PG_{2200}$, $PG_{2300}$, $PG_{2400}$, $PG_{2500}$, $PG_{2600}$, $PG_{2700}$, $PG_{2800}$, $PG_{2900}$, or $PG_{3000}$. In one particular aspect, the PG is $PG_{400}$. In another particular aspect, the PG is $PG_{2000}$.

In some aspects, the linker combination comprises (glycerol)n, and/or (HG)n and/or (TG)n, wherein n is an integer between 1 and 50, and each unit is connected, e.g., via a phosphate ester linker, a phosphorothioate ester linkage, or a combination thereof.

II.G.3.a.3. Aliphatic (Alkyl) Linkers

In some aspects, the linker combination comprises at least one aliphatic (alkyl) linker, e.g., propyl, butyl, hexyl, or C2-C12 alkyl, such as C2-C10 alkyl or C2-C6 alkyl.

In some aspects, the linker combination comprises an alkyl chain, e.g., an unsubstituted alkyl. In some aspects, the linker combination comprises an substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, Aryl, heteroaryl, heterocyclyl, cycloalkyl, cycloalkenyl, alkylarylalkyl, alkylarylalkenyl, alkylarylalkynyl, alkenylarylalkyl, alkenyl Reyl alkenyl, alkenyl aryl alkynyl, alkynyl aryl alkyl, alkynyl aryl alkenyl, alkynyl aryl alkynyl, alkyl heteroaryl alkyl, alkyl heteroaryl alkyl, alkyl heteroaryl alkenyl, alkyl heteroaryl alkynyl, alkenyl heteroaryl alkyl, alkenyl heteroaryl alkenyl, alkenyl heteroaryl alkynyl, alkynyl Heteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, or alkenylheterocyclylalkynyl.

Optionally these components are substituted. Substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, phosphoramidate, phosphorodithioate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, ether, sulfonyl halide, imidate ester, isocyanate, isothiocyanate, haloformate, carboduimide adduct, aldehydes, ketone, sulfhydryl, haloacetyl, alkyl halide, alkyl sulfonate, C(═O)CH═CHC(═O) (maleimide), thioether, cyano, sugar (such as mannose, galactose, and glucose), α,β-unsaturated carbonyl, alkyl mercurial, or α,β-unsaturated sulfone.

Examples of aliphatic linkers include the following structures:

O—CO—O—
NH—CO—O—
NH—CO—NH—
NH—$(CH_2)_{n1}$—
S—$(CH_2)_{n1}$—
—CO—$(CH_2)_{n1}$—CO—
—CO—$(CH_2)_{n1}$NH—
NH—$CH_2)_{n1}$—NH—
—CO—NH—$(CH_2)_{n1}$—NH—CO—
—C(═S)—NH$(CH_2)_{n1}$—NH—CO—
—C(═S)—NH—$(CH_2)_{n1}$—NH—C—(═S)—
—CO—O—$(CH_2)_{n1}$—O—CO—
—C(═S)—O$(CH_2)_{n1}$—OCO—
—C(═S)—O—(C H2)$_{n1}$—O—C—(═S)—
—CO—NH—$(CH_2)_{n1}$—O—CO—
—C(═S)—NH—$(CH_2)_{n1}$—O—CO—
—C(═S)—NH—$(CH_2)_{n1}$—O—C—(═S)—
—CO—NH—$(CH_2)_{n1}$—O—CO—
—C(═S)—NH—$(CH_2)_{n1}$—CO—
—C(═S)—O—$(CH_2)_{n1}$—NH—CO—
—C(═S)—NH—$(CH_2)_{n1}$—O—C—(═S)—
NH—$(CH_2CH_2O)_{n2}$—$CH(CH_2OH)$—
NH—$(CH_2CH_2O)_2$——$CH_2$—
NH—$(CH_2CH_2O)_{n2}$—$CH_2$—CO—
O—$(CH_2)_{n3}$—S—S—$(CH_2)_{n4}$—O—$P(═O)_2$—
—CO—$(CH_2)_{n3}$—O—CO—NH—$(CH_2)_{n4}$—
—CO—$(C_{12})_{n3}$—CO—NH—$(CH_2)_{n4}$—
$(CH_2)_{n1}$NH—
—C(O)$(CH_2)_{n1}$NH—
—C(O)—$(CH_2)_{n1}$—C(O)—
—C(O)—$(CH_2)_{n1}$—C(O)O—
—C(O)—O—
—C(O)—$(CH_2)_{n1}$—NH—C(O)—
—C(O)—$(CH_2)_{n1}$—
—C(O)—NH—
—C(O)—
(CH2)$_{n1}$—C(O)—
(CH2)$_{n1}$—C(O)O—
(CH2)$_{n1}$—
(CH2)$_{n1}$—NH—C(O)— n1 is an integer between 1 and 40 (e.g., 2 to 20, or 2 to 12); n2 is an integer between 1 and 20 (e.g., 1 to 10, or 1 to 6); n3 and n4 can be the same or different, and are an integer between 1 and 20 (e.g., 1 to 10, or 1 to 6).

In some aspects, the linker combination comprises (C3)n, (C4)n, (C5)n, (C6)n, (C7)n, or (C8)n, or a combination thereof, wherein n is an integer between 1 and 50, and each unit is connected, e.g., via a phosphate ester linker, a phosphorothioate ester linkage, or a combination thereof.

II.G.3.b. Cleavable Linkers

In some aspects, the linker combination comprises a cleavable linker. The term "cleavable linker" refers to a linker comprising at least one linkage or chemical bond that can be broken or cleaved. Cleavage can be mediated, e.g., by a nuclease, peptidase, protease, phosphatase, oxidase, esterase, or reductase, for example, or by specific physico-chemical conditions, e.g., redox environment, pH, presence of reactive oxygen species, or specific wavelengths of light.

In some aspects, the cleavable linker comprises a dinucleotide or trinucleotide or tetrapeptide linker, a disulfide, a diselenide, an imine, a beta-carboxylic amide, a thioketal, a val-cit dipeptide, a glutamic acid-valine-citrulline tripeptide, a glycine-histidine-leucine-glycine tetrapeptide, or any combination thereof. In some aspects, the cleavable linker comprises valine-alanine-p-aminobenzylcarbamate or valine-citrulline-p-aminobenzylcarbamate.

II.B.4. Specific Examples and Topologies

In specific aspects of the present disclosure, the linker combination consists of a linker of formula

[Alkyl linker]m-[PEG1]n-[PLG2]o wherein m, n, and o are 0 or 1, and at least one of m, n, or o is not zero. Exemplary linker combinations according to such formula are C6-TEG-HEG, C6-HEG, C6-TEG, C6, TEG-HEG, TEG, C8-TEG-HEG, C8-HEG, C8-TEG, and C8.

In some aspects, the linker combination comprises a non-cleavable linker (e.g., TEG or HEG) in combination with one or more cleavable linkers, e.g., an enzymatic cleavable linker and a self immolative linker.

In a specific aspect, the linker combination the linker combination comprises the linker combination TEG (non-cleavable linker)-Val-Cit(cleavable linker)-pAB(self-immolative linker), as shown below

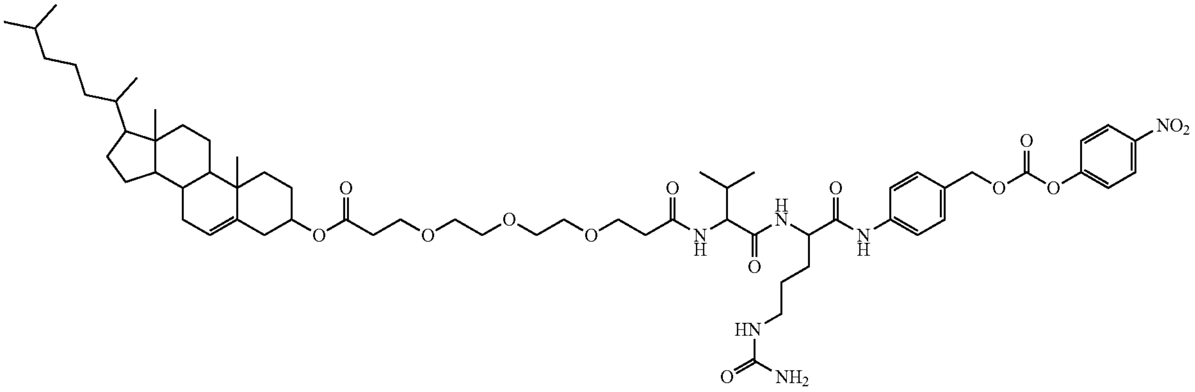 [SMILES: CC(C)CCCC(C)C1CCC2C3CC=C4CC(OC(=O)CCOCCOCCOCCC(=O)NC(C(=O)NC(CCCNC(N)=O)C(=O)Nc5ccc(COC(=O)Oc6ccc([N+](=O)[O-])cc6)cc5)C(C)C)CCC4(C)C3CCC12C]

Specific combinations of anchoring moieties and linker combinations are illustrated in the tables below.

TABLE 1

Anchoring Moieties and Linker Combinations

| Anchoring moiety | Linker combination 1st Linker | 2nd Linker | 3rd Linker |
|---|---|---|---|
| Cholesterol | C6 | TEG | HEG |
| Cholesterol | C6 | HEG | No |
| Cholesterol | C6 | TEG | No |
| Cholesterol | C6 | No | No |
| Cholesterol | TEG | HEG | No |
| Cholesterol | TEG | No | No |
| Tocopherol | C8 | TEG | HEG |
| Tocopherol | C8 | HEG | No |
| Tocopherol | C8 | TEG | No |
| Tocopherol | C8 | No | No |
| Tocopherol | TEG | HEG | No |
| Tocopherol | HEG | No | No |
| Tocopherol | TEG | No | No |
| Tocopherol | No | No | No |
| Palmitate | C6 | TEG | HEG |
| Palmitate | C6 | HEG | No |
| Palmitate | C6 | TEG | No |

TABLE 1-continued

Anchoring Moieties and Linker Combinations

| Anchoring moiety | Linker combination 1st Linker | 2nd Linker | 3rd Linker |
|---|---|---|---|
| Palmitate | C6 | No | No |
| Cholesterol | TEG | Glycerol | HEG |

TABLE 2

Exemplary Linker Combinations
Linker Combination

| Linker 1 | Cleavable Linker 2 | Linker 3 |
|---|---|---|
| C6 | Disulfide | C6 |
| None | Imine | None |
| TEG | Thioketal | TEG |
| HEG | Tri/Dinucleotide | HEG |
| TEG-HEG | Val-Cit | TEG-HEG |

Specific payloads (e.g., ASOs) useful for the present disclosure are exemplified below:

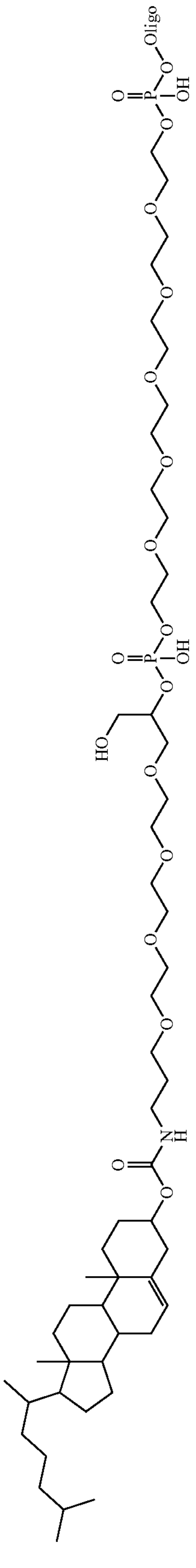
[Cholesterol]-[TEG]-[HEG]-[ASO]
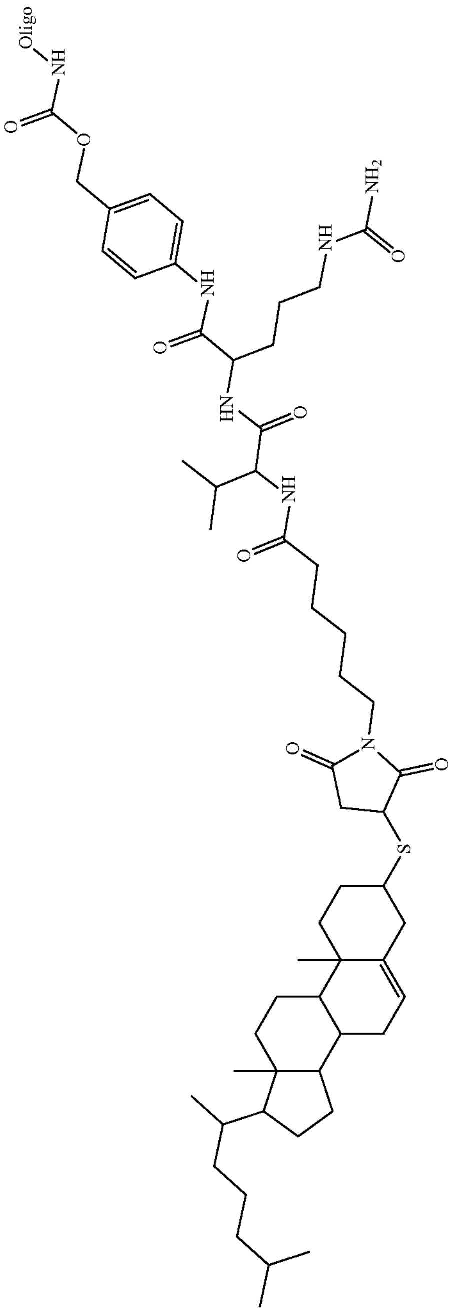
[Cholesterol]-[SMal]-[Val-Cit]-[pAB]-[ASO]

-continued
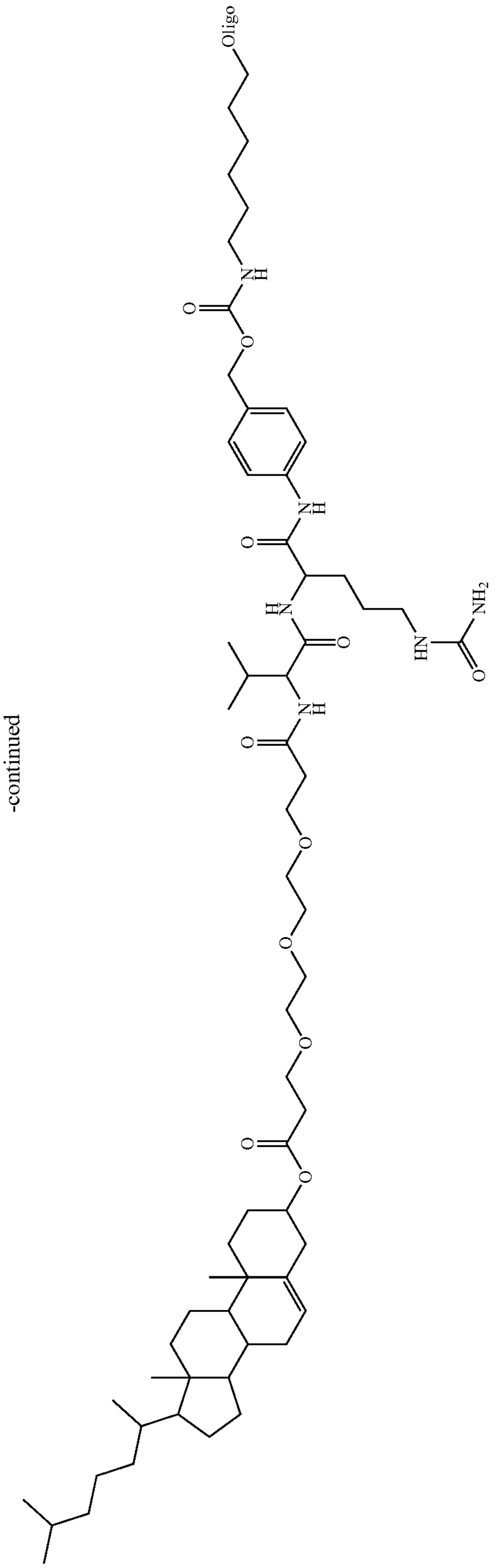
[Cholesterol]-[TEG]-[Val-Cit]-[C6]-[ASO]
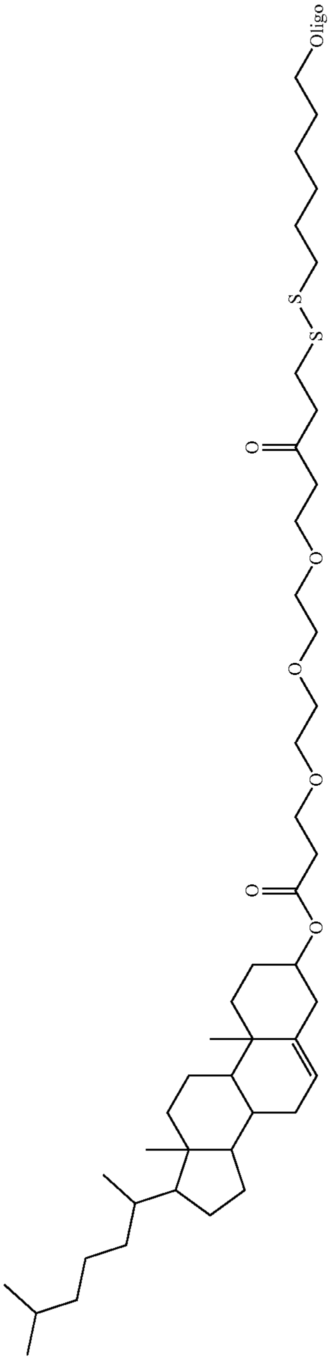
[Cholesterol]-[TEG]-[SS]-[C6]-[ASO]

wherein [Cholesterol] is a cholesterol anchoring moiety, [TEG] is a TEG non-cleavable linker, [HEG] is a HEG non-cleavable linker, [SS] is a disulfide redox cleavable linker, [C6] is an alkyl non-cleavable linker, [SMal] is S-maleimide, [Val-Cit] is a valine-citrulline cleavable linker, [pAB] is a pAB self-immolative linker. In some aspects, a payload (e.g., ASO) has a structure according to the exemplary structures provided above, in which one or more components has been replaced by a component in the same class as those depicted in the example. For example, the [cholesterol] anchoring moiety can be substituted by another anchoring moiety disclosed herein, a [TEG] can be substituted by another polymeric non-cleavable linker disclosed herein (e.g., HEG, PEG, PG), [Val-Cit] can be replaced by another peptidase cleavable linker, or [pAB] can be substituted by another self-immolative linker.

III. EVs

In some aspects, the present disclosure provides an EV which has been modified to comprise an increased amount of a moiety of interest (e.g., payload, e.g., antisense oligonucleotide). For instance, as further described elsewhere in the present disclosure, loading an EV with a payload (e.g., antisense oligonucleotide) at the loading conditions described herein (e.g., at the recited salt concentrations, loading temperature, loading duration, payload feed concentration, and/or EV feed concentration) can increase the loading of the payload in the EV. Accordingly, in some aspects, an EV described herein comprises a payload, wherein the amount of the payload that is associated with the exterior surface of the EV (e.g., payload concentration) is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold or more, compared to a reference EV (e.g., an EV that has not been modified using the loading methods described herein).

In some aspects, the EVs of the present disclosure comprises a payload on the exterior surface of the EV, wherein the number of payloads on the exterior surface of the EV is at least about 1,000, at least about 2,000, at least about 3,000, at least about 4,000, at least about 5,000, at least about 6,000, at least about 7,000, at least about 8,000, at least about 9,000, at least about 10,000, at least about 11,000, at least about 12,000, at least about 13,000, at least about 14,000, at least about 15,000, at least about 16,000, at least about 17,000, at least about 18,000, at least about 19,000, at least about 20,000, at least about 21,000, at least about 22,000, at least about 23,000, at least about 24,000, at least about 25,000, at least about 30,000, at least about 35,000, at least about 40,000, at least about 45,000, or at least about 50,000. In some aspects, the number of payloads on the exterior surface of the EV is between about 5,000 and about 20,000, between about 6,000 and about 20,000, between about 7,000 and about 20,000, between about 8,000 and about 20,000, between about 9,000 and about 20,000, between about 10,000 and about 20,000, between about 5,000 and about 18,000, between about 6,000 and about 18,000, between about 7,000 and about 18,000, between about 8,000 and about 18,000, between about 9,000 and about 18,000, between about 10,000 and about 18,000, between about 5,000 and about 15,000, between about 6,000 and about 15,000, between about 7,000 and about 15,000, between about 8,000 and about 15,000, between about 9,000 and about 15,000, or between about 10,000 and about 15,000. In some aspects, the number of payloads on the exterior surface of the EV is between about 10,000 and about 15,000.

In some aspects, each of the payloads on the exterior surface of the EV are the same. In some aspects, one or more of the payloads on the exterior surface of the EV are different. As described herein, in some aspects, an EV of the present disclosure can comprise one or more additional payloads. In certain aspects, the one or more additional payloads can be in the lumen of the EVs (i.e., encapsulated), associated with the exterior surface of the EVs, associated with the luminal surface of the EVs, or combinations thereof.

As described herein, EVs that are useful for the present disclosure can have a diameter between about 20-300 nm. In certain aspects, an EV of the present disclosure has a diameter between about 20-290 nm, 20-280 nm, 20-270 nm, 20-260 nm, 20-250 nm, 20-240 nm, 20-230 nm, 20-220 nm, 20-210 nm, 20-200 nm, 20-190 nm, 20-180 nm, 20-170 nm, 20-160 nm, 20-150 nm, 20-140 nm, 20-130 nm, 20-120 nm, 20-110 nm, 20-100 nm, 20-90 nm, 20-80 nm, 20-70 nm, 20-60 nm, 20-50 nm, 20-40 nm, 20-30 nm, 30-300 nm, 30-290 nm, 30-280 nm, 30-270 nm, 30-260 nm, 30-250 nm, 30-240 nm, 30-230 nm, 30-220 nm, 30-210 nm, 30-200 nm, 30-190 nm, 30-180 nm, 30-170 nm, 30-160 nm, 30-150 nm, 30-140 nm, 30-130 nm, 30-120 nm, 30-110 nm, 30-100 nm, 30-90 nm, 30-80 nm, 30-70 nm, 30-60 nm, 30-50 nm, 30-40 nm, 40-300 nm, 40-290 nm, 40-280 nm, 40-270 nm, 40-260 nm, 40-250 nm, 40-240 nm, 40-230 nm, 40-220 nm, 40-210 nm, 40-200 nm, 40-190 nm, 40-180 nm, 40-170 nm, 40-160 nm, 40-150 un, 40-140 nm, 40-130 nm, 40-120 nm, 40-110 nm, 40-100 nm, 40-90 nm, 40-80 nm, 40-70 nm, 40-60 nm, 40-50 nm, 50-300 nm, 50-290 nm, 50-280 nm, 50-270 nm, 50-260 nm, 50-250 nm, 50-240 nm, 50-230 nm, 50-220 nm, 50-210 nm, 50-200 nm, 50-190 urn, 50-180 nm, 50-170 nm, 50-160 nm, 50-150 nm, 50-140 nm, 50-130 nm, 50-120 nm, 50-110 nm, 50-100 nm, 50-90 nm, 50-80 nm, 50-70 nm, 50-60 nm, 60-300 nm, 60-290 nm, 60-280 nm, 60-270 nm, 60-260 nm, 60-250 nm, 60-240 nm, 60-230 nm, 60-220 nm, 60-210 nm, 60-200 nm, 60-190 nm, 60-180 nm, 60-170 nm, 60-160 nm, 60-150 nm, 60-140 nm, 60-130 un, 60-120 nm, 60-110 nm, 60-100 un, 60-90 nm, 60-80 nm, 60-70 nm, 70-300 nm, 70-290 nm, 70-280 nm, 70-270 nm, 70-260 nm, 70-250 nm, 70-240 nm, 70-230 nm, 70-220 nm, 70-210 nm, 70-200 nm, 70-190 nm, 70-180 nm, 70-170 nm, 70-160 nm, 70-150 nm, 70-140 nm, 70-130 un, 70-120 nm, 70-110 nm, 70-100 urn, 70-90 nm, 70-80 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 urn, 80-100 nm, 80-90 urn, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 un, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm. The size of the EV described herein can be measured according to methods known in the art.

In some aspects, an EV described herein comprises a bi-lipid membrane, comprising an interior (luminal) surface and an exterior surface. In certain aspects, the interior (luminal) surface faces the inner core (i.e., lumen) of the EV. In certain aspects, the exterior surface (also referred to herein as the "external surface") can be in contact with the endosome, the multivesicular bodies, or the membrane/cytoplasm of a producer cell or a target cell.

In some aspects, an EV membrane comprises lipids and fatty acids. In some aspects, the EV membrane comprises phospholipids, glycolipids, fatty acids, sphingolipids, phosphoglycerides, sterols, cholesterols, and phosphatidylserines.

In some aspects, the EV membrane comprises an inner leaflet and an outer leaflet. The composition of the inner and outer leaflet can be determined by transbilayer distribution assays known in the art, see, e.g., Kuypers et al., *Biohim Biophys Acta* 819:170 (1985). In some aspects, the composition of the outer leaflet is between approximately 70-90% choline phospholipids, between approximately 0-15% acidic phospholipids, and between approximately 5-30% phosphatidylethanolamine. In some aspects, the composition of the inner leaflet is between approximately 15-40% choline phospholipids, between approximately 10-50% acidic phospholipids, and between approximately 30-60% phosphatidylethanolamine.

In some aspects, the EV membrane comprises one or more polysaccharides, such as a glycan. Glycans on the surface of the EV can serve as an attachment to a maleimide moiety or a linker that connect the glycan and a maleimide moiety. The glycan can be present on one or more proteins on the surface of an EV, for example, a PTGFRN polypeptide, or on the lipid membrane of the EV.

III.A. EV Transmembrane Protein

In some aspects, the EVs useful for the present disclosure comprises one or more EV transmembrane proteins (also referred to herein as "exosomal protein" or "EV protein").

In certain aspects, the one or more transmembrane proteins are introduced into the EV (by transfection. In some aspects, the one or more transmembrane proteins can be introduced into the EV using synthetic macromolecules such as cationic lipids and polymers (Papapetrou et al., Gene Therapy 12: S 118-S130 (2005)). In certain aspects, chemicals such as calcium phosphate, cyclodextrin, or polybrene, can be used to introduce the one or more transmembrane proteins to the EV.

In some aspects, one or more transmembrane proteins can be CD47, CD55, CD49, CD40, CD133, CD59, glypican-1, CD9, CD63, CD81, integrins, selectins, lectins, cadherins, other similar polypeptides known to those of skill in the art, or any combination thereof.

In some aspects, one or more transmembrane proteins are expressed in the membrane of the EVs by recombinantly expressing the transmembrane proteins in the producer cells. The EVs obtained from the producer cells can be further modified to be conjugated to a maleimide moiety or to a linker.

Examples of transmembrane proteins include, but are not limited to, PTGFRN, BSG, IGSF2, IGSF3, IGSF8, ITGB1, ITGA4, SLC3A2, ATP transporter, or a fragment or a variant thereof). In some aspects, the transmembrane proteins can be CD9, CD63, CD81, PDGFR, GPI anchor proteins, lactadherin, LAMP2, or LAMP2B, or any combination thereof. Non-limiting examples of other transmembrane proteins that can be used with the present disclosure include: aminopeptidase N (CD13); Neprilysin, AKA membrane metalloendopeptidase (MME); ectonucleotide pyrophosphatase/phosphodiesterase family member 1 (ENPP1); Neuropilin-1 (NRP1); or any combination thereof.

In some aspects, further examples of the transmembrane proteins can be found in U.S. Pat. Nos. 10,195,290, issued Feb. 5, 2019 and U.S. Pat. No. 10,561,740, issued Feb. 18, 2020, and International Application No. PCT/US2018/048026, filed Aug. 24, 2018 (published as WO 2019/040920A1), which are incorporated herein by reference in their entireties.

In some aspects, EVs of the present disclosure comprise an internal space (i.e., lumen) that is different from that of the naturally occurring EVs. For example, the EV can be changed such that the composition on the luminal surface of the EV has the protein, lipid, or glycan content different from that of the naturally-occurring EVs.

In some aspects, engineered EVs can be produced from a cell transformed with an exogenous sequence encoding one or more exosomal proteins or a modification or a fragment of the exosomal proteins that changes the composition or content of the luminal surface of the exosome. Various modifications or fragments of the EV protein that can be expressed on the luminal surface of the EV can be used for the aspects of the present disclosure.

In some aspects, the EV proteins that can change the luminal surface of the EV include, but are not limited to the MARCKS protein, MARCKSL1 protein, BASP1 protein, or any combination thereof. In some aspects, the exosomal protein comprises Brain Acid Soluble Protein 1 (the BASP1 protein). The BASP1 protein is also known as 22 kDa neuronal tissue-enriched acidic protein or neuronal axonal membrane protein NAP-22. The full-length human BASP1 protein sequence (isomer 1) is shown below. Non limiting examples of exosome proteins include, but are not limited to, International Application No. PCT/US2018/061679, filed Nov. 16, 2018 (published as WO 2019/099942A1), and PCT/US2019/033629, filed May 22, 2019 (published as WO 2020/101740A1), which are incorporated herein by reference in their entireties.

IV. Methods of Producing EVs

In some aspects, a method of producing an EV useful for the present disclosure comprises modifying a producer cell with one or more moieties of interest (e.g., EV transmembrane protein).

In some aspects, the producer cell can be a mammalian cell line, a plant cell line, an insect cell line, a fungi cell line, or a prokaryotic cell line. In certain aspects, the producer cell is a mammalian cell line. Non-limiting examples of mammalian cell lines include: a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, a mesenchymal stem cell (MSC) cell line, and combinations thereof. In certain aspects, the mammalian cell line comprises HEK-293 cells, BJ human foreskin fibroblast cells, fHDF fibroblast cells, AGE.HN® neuronal precursor cells, CAP® amniocyte cells, adipose mesenchymal stem cells, RPTEC/TERT1 cells, or combinations thereof. In some aspects, the producer cell is a primary cell. In certain aspects, the primary cell can be a primary mammalian cell, a primary plant cell, a primary insect cell, a primary fungi cell, or a primary prokaryotic cell.

In some aspects, the producer cell is not an immune cell, such as an antigen presenting cell, a T cell, a B cell, a natural killer cell (NK cell), a macrophage, a T helper cell, or a regulatory T cell (Treg cell). In some aspects, the producer cell is not an antigen presenting cell (e.g., dendritic cells, macrophages, B cells, mast cells, neutrophils, Kupffer-Browicz cell, or a cell derived from any such cells). In some aspects, a producer cell is not a naturally-existing antigen-presenting cell (i.e., has been modified). In some aspects, a producer cell is not a naturally-existing dendritic cell, a B cell, a mast cell, a macrophage, a neutrophil, Kupffer-Browicz cell, cell derived from any of these cells, or any combination thereof.

In some aspects, the one or more moieties of interest (e.g., EV transmembrane protein) can be introduced into the producer cell methods that are known to the skilled in the art. See, e.g., WO 2020/191369 A1, which is incorporated herein by reference in its entirety.

IV.A. Isolating an EV

In some aspects, methods of producing EVs disclosed herein comprises isolating the EV from the producer cells. In certain aspects, the EVs are released by the producer cell into the cell culture medium. It is contemplated that all known manners of isolation of EVs are deemed suitable for use herein. For example, physical properties of EVs can be employed to separate them from a medium or other source material, including separation on the basis of electrical charge (e.g., electrophoretic separation), size (e.g., filtration, molecular sieving, etc.), density (e.g., regular or gradient centrifugation), Svedberg constant (e.g., sedimentation with or without external force, etc.). Alternatively, or additionally, isolation can be based on one or more biological properties, and include methods that can employ surface markers (e.g., for precipitation, reversible binding to solid phase, FACS separation, specific ligand binding, non-specific ligand binding, affinity purification etc.).

Isolation and enrichment can be done in a general and non-selective manner, typically including serial centrifugation. Alternatively, isolation and enrichment can be done in a more specific and selective manner, such as using EV or producer cell-specific surface markers.

For example, specific surface markers can be used in immunoprecipitation, FACS sorting, affinity purification, and magnetic separation with bead-bound ligands.

In some aspects, size exclusion chromatography can be utilized to isolate the EVs. Size exclusion chromatography techniques are known in the art. Exemplary, non-limiting techniques are provided herein. In some aspects, a void volume fraction is isolated and comprises the EVs of interest. Further, in some aspects, the EVs can be further isolated after chromatographic separation by centrifugation techniques (of one or more chromatography fractions), as is generally known in the art. In some aspects, for example, density gradient centrifugation can be utilized to further isolate the extracellular vesicles. In certain aspects, it can be desirable to further separate the producer cell-derived EVs from EVs of other origin. For example, the producer cell-derived EVs can be separated from non-producer cell-derived EVs by immunosorbent capture using an antigen antibody specific for the producer cell.

In some aspects, the isolation of EVs can involve combinations of methods that include, but are not limited to, differential centrifugation, size-based membrane filtration, immunoprecipitation, FACS sorting, and magnetic separation.

In addition to the increased loading efficiency described herein, adjusting one or more of the different loading parameters (e.g., salt concentration) can also greatly reduce dissociation of the moiety of interest (e.g., payload, e.g., ASO) from the EVs after loading and purification (e.g., chromatography purification). As demonstrated herein (see, e.g., Example 4), maintaining a high salt concentration (e.g., greater than about 100 mM) during the purification step can reduce dissociation of the moiety of interest from the EVs by at least about 5%, at least about 10%, at least about 20%, at least about 30%, at least about 40%, at least about 50%, at least about 60%, at least about 70%, at least about 80%, at least about 90%, or about 100%, compared to the dissociation observed when purifying the loaded EVs under low salt concentration (e.g., less than about 100 mM).

V. Therapeutic Uses

As described herein, the EVs described herein can be rapidly engineered to comprise various moieties of interest (e.g., payload, e.g., antisense oligonucleotide), which can be useful in treating a wide range of diseases and disorders. Accordingly, in some aspects, the present disclosure provides methods of treating a disease or condition in a subject in need thereof comprising administering a composition comprising EVs of the present disclosure to the subject.

In some aspects, a disease or disorder that can be treated with the present EVs comprises a cancer. Non-limiting examples of cancers that can be treated with the present disclosure include a colorectal cancer, lung cancer (e.g., non-small cell lung cancer (NSCLC)), pancreatic cancer (e.g., pancreatic ductal adenocarcinoma (PDAC)), leukemia, uterine cancer, ovarian cancer, bladder cancer, bile duct cancer, gastric cancer, or any combination thereof. In some aspects, the cancer is selected from colon adenocarcinoma, rectum adenocarcinoma, pancreatic adenocarcinoma, pancreatic ductal adenocarcinoma (PDAC), ovarian serous cystadenocarcinoma, acute myeloid leukemia, testicular germ cell tumors, lung adenocarcinoma, brain lower grade glioma, glioblastoma multiforme, uveal melanoma, thyroid carcinoma, uterine corpus endometrial carcinoma, uterine carcinosarcoma, pheochromocytoma, paraganglioma, and any combination thereof. In certain aspects, the cancer is a myeloid-rich cancer. In some aspects, the cancer comprises a liver cancer. In some aspects, the cancer comprises hepatocellular cancer (HCC). In some aspects, the cancer comprises pancreatic ductal adenocarcinoma (PDAC), in some aspects, the cancer comprises colorectal carcinoma (CRC). In some aspects, the cancer comprises ovarian cancer. In some aspects, the cancer comprises leptomeningeal cancer.

When administered to a subject with a cancer, in certain aspects, EVs of the present disclosure can up-regulate an immune response and enhance the tumor targeting of the subject's immune system. In some aspects, the cancer being treated is characterized by infiltration of leukocytes (T-cells, B-cells, macrophages, dendritic cells, monocytes) into the tumor microenvironment, or so-called "hot tumors" or "inflammatory tumors". In some aspects, the cancer being treated is characterized by low levels or undetectable levels of leukocyte infiltration into the tumor microenvironment, or so-called "cold tumors" or "non-inflammatory tumors". In some aspects, an EV is administered in an amount and for a time sufficient to convert a "cold tumor" into a "hot tumor", i.e., said administering results in the infiltration of leukocytes (such as T-cells) into the tumor microenvironment. In certain aspects, cancer comprises bladder cancer, cervical cancer, renal cell cancer, testicular cancer, colorectal cancer, lung cancer, head and neck cancer, and ovarian, lymphoma, liver cancer, glioblastoma, melanoma, myeloma, leukemia, pancreatic cancers, or combinations thereof. In other term, "distal tumor" or "distant tumor" refers to a tumor that has spread from the original (or primary) tumor to distant organs or distant tissues, e.g., lymph nodes. In some aspects, the EVs of the disclosure treats a tumor after the metastatic spread.

In some aspects, the EVs are administered intravenously to the circulatory system of the subject. In some aspects, the EVs are infused in suitable liquid and administered into a vein of the subject.

In some aspects, the EVs are administered intra-arterially to the circulatory system of the subject. In some aspects, the EVs are infused in suitable liquid and administered into an artery of the subject.

In some aspects, the EVs are administered to the subject by intrathecal administration In some aspects, the EVs are administered via an injection into the spinal canal, or into the subarachnoid space so that it reaches the cerebrospinal fluid (CSF).

In some aspects, the EVs are administered intratumorally into one or more tumors of the subject.

In some aspects, the EVs are administered to the subject by intranasal administration. In some aspects, the EVs can be insufflated through the nose in a form of either topical administration or systemic administration. In certain aspects, the EVs are administered as nasal spray.

In some aspects, the EVs are administered to the subject by intraperitoneal administration. In some aspects, the EVs are infused in suitable liquid and injected into the peritoneum of the subject. In some aspects, the intraperitoneal administration results in distribution of the EVs to the lymphatics. In some aspects, the intraperitoneal administration results in distribution of the EVs to the thymus, spleen, and/or bone marrow. In some aspects, the intraperitoneal administration results in distribution of the EVs to one or more lymph nodes. In some aspects, the intraperitoneal administration results in distribution of the EVs to one or more of the cervical lymph node, the inguinal lymph node, the mediastinal lymph node, or the sternal lymph node. In some aspects, the intraperitoneal administration results in distribution of the EVs to the pancreas.

In some aspects, the EVs are administered to the subject by periocular administration. In some aspects, the s are injected into the periocular tissues. Periocular drug administration includes the routes of subconjunctival, anterior sub-Tenon's, posterior sub-Tenon's, and retrobulbar administration.

Certain aspects of the present disclosure are directed to methods of treating a brain tumor in a subject in need thereof. In some aspects, the method comprises administering to the subject a therapeutically effective amount of an EV described herein. In some aspects, the EV is capable of targeted delivery of a payload (e.g., ASO) to the CNS to treat the brain tumor. In some aspects, the EV is capable of up-regulating an immune response in the subject, thereby enhancing the subject's immune response against the neuroimmunological disorder. In some aspects, the composition is administered intratumorally or intrathecally to the subject.

Also provided herein are methods of preventing metastasis of a brain tumor in a subject. The method comprises administering to the subject a therapeutically effective amount of the compositions disclosed herein, wherein the composition is capable of preventing a brain tumor at one location in the subject from promoting the growth of one or more tumors at another location in the subject. In some aspects, the composition is administered intratumorally or intrathecally in a first tumor in one location, and the composition administered in a first tumor prevents metastasis of one or more tumors at a second location.

VI. Pharmaceutical Compositions and Methods of Administration

The present disclosure also provides pharmaceutical compositions comprising EVs described herein that are suitable for administration to a subject. The pharmaceutical compositions generally comprise a plurality of EVs comprising a biologically active molecule covalently linked to the plurality of EVs via a maleimide moiety and a pharmaceutically-acceptable excipient or carrier in a form suitable for administration to a subject. Pharmaceutically acceptable excipients or carriers are determined in part by the particular composition being administered, as well as by the particular method used to administer the composition. Accordingly, there is a wide variety of suitable formulations of pharmaceutical compositions comprising a plurality of EVs. (See, e.g., Remington's Pharmaceutical Sciences, Mack Publishing Co., Easton, Pa. 18th ed. (1990)). The pharmaceutical compositions are generally formulated sterile and in full compliance with all Good Manufacturing Practice (GMP) regulations of the U.S. Food and Drug Administration. In some aspects, the pharmaceutical composition comprises one or more chemical compounds, such as for example, small molecules covalently linked to an EV described herein.

In some aspects, a pharmaceutical composition comprises one or more therapeutic agents and an EV described herein. In certain aspects, the EVs are co-administered with of one or more additional therapeutic agents, in a pharmaceutically acceptable carrier. In some aspects, the pharmaceutical composition comprising the EV is administered prior to administration of the additional therapeutic agents. In some aspects, the pharmaceutical composition comprising the EV is administered after the administration of the additional therapeutic agents. In further aspects, the pharmaceutical composition comprising the EV is administered concurrently with the additional therapeutic agents.

Provided herein are pharmaceutical compositions comprising an EV of the present disclosure having the desired degree of purity, and a pharmaceutically acceptable carrier or excipient, in a form suitable for administration to a subject. Pharmaceutically acceptable excipients or carriers can be determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

In some aspects, a pharmaceutical composition comprises one or more therapeutic agents and an EV described herein. In certain aspects, the EVs are co-administered with of one or more additional therapeutic agents, in a pharmaceutically acceptable carrier. In some aspects, the pharmaceutical composition comprising the EV is administered prior to administration of the additional therapeutic agents. In some aspects, the pharmaceutical composition comprising the EV is administered after the administration of the additional therapeutic agents. In further aspects, the pharmaceutical composition comprising the EV is administered concurrently with the additional therapeutic agents.

Acceptable carriers, excipients, or stabilizers are nontoxic to recipients (e.g., animals or humans) at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the extracellular vesicles described herein, use thereof in the compositions is contemplated. Supplementary therapeutic agents can also be incorporated into the compositions. Typically, a pharmaceutical composition is formulated to be compatible with its intended route of administration. The EVs of the present disclosure can be administered by parenteral, topical, intravenous, oral, subcutaneous, intra-arterial, intradermal, transdermal, rectal, intracranial, intraperitoneal, intranasal, intratumoral, intramuscular route or as inhalants. In certain aspects, the pharmaceutical composition comprising EVs is administered intravenously, e.g. by injection. The EVs can optionally be administered in combination with other therapeutic agents that are at least partly effective in treating the disease, disorder or condition for which the EVs are intended.

Solutions or suspensions can include the following components: a sterile diluent such as water, saline solution, fixed oils, polyethylene glycols, glycerin, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, and sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the EVs of the present disclosure in an effective amount and in an appropriate solvent with one or a combination of ingredients enumerated herein, as desired. Generally, dispersions are prepared by incorporating the EVs into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The EVs can be administered in the form of a depot injection or implant preparation which can be formulated in such a manner to permit a sustained or pulsatile release of the EVs.

Systemic administration of compositions comprising EVs of the present disclosure can also be by transmucosal means. For transmucosal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of, e.g., nasal sprays.

In certain aspects the pharmaceutical composition comprising EVs of the present disclosure is administered intravenously into a subject that would benefit from the pharmaceutical composition. In certain aspects, the composition is administered to the lymphatic system, e.g., by intralymphatic injection or by intranodal injection (see e.g., Senti et al., PNAS 105(46): 17908 (2008)), or by intramuscular injection, by subcutaneous administration, by intratumoral injection, by direct injection into the thymus, or into the liver.

In certain aspects, the pharmaceutical composition comprising EVs of the present disclosure is administered as a liquid suspension. In certain aspects, the pharmaceutical composition is administered as a formulation that is capable of forming a depot following administration. In certain preferred aspects, the depot slowly releases the EVs into circulation, or remains in depot form.

Typically, pharmaceutically-acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically-acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition can further include a lubricant, a wetting agent, a sweetener, a flavor enhancer, an emulsifying agent, a suspension agent, and/or a preservative.

The pharmaceutical compositions described herein comprise the EVs described herein and optionally a pharmaceutically active or therapeutic agent. The therapeutic agent can be a biological agent, a small molecule agent, or a nucleic acid agent.

Dosage forms are provided that comprise a pharmaceutical composition comprising the EVs described herein. In some aspects, the dosage form is formulated as a liquid suspension for intravenous injection. In some aspects, the dosage form is formulated as a liquid suspension for intratumoral injection.

The EVs of the present disclosure can be used concurrently with other drugs. To be specific, the EVs of the present disclosure can be used together with medicaments such as hormonal therapeutic agents, chemotherapeutic agents, immunotherapeutic agents, medicaments inhibiting the action of cell growth factors or cell growth factor receptors and the like.

VII. Kits

The present disclosure also provides kits, or products of manufacture comprising one or more EVs of the present disclosure and optionally instructions for use. In some aspects, the kit, or product of manufacture contains a pharmaceutical composition described herein which comprises at least one EV of the present disclosure, and instructions for use. In some aspects, the kit, or product of manufacture comprises at least one EV of the present disclosure or a pharmaceutical composition comprising the EVs in one or more containers. One skilled in the art will readily recognize that the EVs of the present disclosure, pharmaceutical composition comprising the EVs of the present disclosure, or combinations thereof can be readily incorporated into one of the established kit formats which are well known in the art.

In some aspects, the kit, or product of manufacture comprises EVs one or more biologically active molecules, reagents to covalently attach the one or more biologically active molecules to the EVs, or any combination thereof, and instructions to conduct the reaction to covalently attach the one or more biologically active molecules to the EVs.

In some aspects, the kit comprises reagents to conjugate a biologically active molecule to an EV, and instructions to conduct the conjugation.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooke, Antisense drug Technology: Principles, Strategies and Applications, 2nd Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1—Effect of Salt Concentration on EV Loading

To begin identifying the various loading parameters that are important in improving the payload loading efficiency, ASOs (e.g., targeting STAT6) were mixed with EVs in loading buffers comprising different NaCl (25 mM, 50 mM, 100 mM, or 150 mM) and sucrose concentrations (2.5%, 3.75%, or 5%). The ASO and the EVs were mixed at 37° C. for 24 hours. Then, the mixture was cooled to room temperature, and subsequently, filtered using 0.45 μm (PVDF) filtration. The filtrate was sampled and tested for AEX-UIIPLC (ASO content) and nanoparticle tracking analysis (NTA) (EV content) to determine the ASO loading efficiency prior to chromatography cleanup. Non-limiting examples of alternative methods for determining ASO content include (1) Quant-iT™ RiboGreen™ RNA Reagent (e.g., fluorescent dye for the quantitation of RNA in solution), (2) UV absorbance at 260 nm. Non-limiting examples of alternative methods for determining EV content include (1) intensity of dynamic light scattering and (2) UV absorbance at 405 nm. See, e.g., WO 2019/246591 A1, which is incorporated herein by reference in its entirety.

As shown in Table 3 below, increasing NaCl concentration resulted in greater loading of the ASOs onto the exterior surface of the exosomes. Among the different NaCl concentrations tested, the greatest ASO loading efficiency was observed with 150 mM, regardless of the sucrose concentration. These results suggest that modulating the salt concentration of the loading buffer can be useful in improving the loading efficiency of EVs.

TABLE 3

| Feed (250 μM ASO, | | Sucrose (%) | | |
|---|---|---|---|---|
| $1 \times 10^{13}$ EV particles) | | 5% | 3.75% | 2.5% |
| mM NaCl | 25 mM | 2030 | 1878 | 1949 |
| | 50 mM | 2360 | 2200 | 2299 |
| | 100 mM | 3080 | 3019 | 3136 |
| | 150 mM | 3924 | 4058 | 4079 |

Example 2—Effect of Time and Temperature on EV Loading

Next, to characterize the effects of loading time and loading temperature on ASO loading of EVs, EVs were mixed with ASOs at 5° C., 22° C., and 37° C. for up to 48 hours. Then, the mixture was cooled, filtered, and the filtrate analyzed for ASO and EV contents as described in Example 1.

As shown in FIG. 1A, loading time had no impact when the ASOs and EVs were mixed at 5° C. (diamond). In contrast, when the ASOs and EVs were mixed at either 22° C. or 37° C., increasing the loading time did have a positive effect on ASO loading efficiency (see square and triangle symbols, respectively, in FIG. 1A). At 22° C., a loading plateau (i.e., no further increase in ASO concentration of the EVs) was observed starting at around 24 hours. At 37° C., there was a continual increase in ASO concentration in the EVs with increased loading time.

The above results demonstrate that both loading time and temperature can have an effect on the loading efficiency of the EVs. By increasing both the loading time and temperature, the results suggest that it can be possible to produce more potent EVs (i.e., comprising greater amount of the loaded payload).

Example 3—Effect of Modulating Salt Concentration, Loading Time, EV Feed Concentration, and Payload Feed Concentration on EV Loading To further assess the effect that different loading parameters (e.g., those described herein) have on loading efficiency of EVs, the ASOs and EVs were mixed under one of the following two loading conditions: (i) Loading Buffer: 20 mM $PO_4$, 50 mM NaCl, 5.0% sucrose, pH 7.2, mixing temperature was room temperature, for 1 hour ("loading condition #1"); and (ii) Loading Buffer: 20 mM $PO_4$, 100 mM NaCl, 2.5% sucrose, pH 7.2, mixing temperature was room temperature, for 24 hours ("loading condition #2"). As a further variable, the EVs and ASOs were added to the mixture at various concentrations. In particular, the EVs were added at the following feed concentration: 1.4×10, $1.0\times10^{\prime 3}$, or $6.0\times10^{12}$. The ASOs were added at the following feed concentration: 800 μM, 600 μM, 400 μM, 200 μM, or 100 μM. Then, the ASO and EV contents were measured as described in the earlier Examples.

As shown in Tables 4 and 5 (below), the ASO loading efficiency was positively correlated with both increase in the EV feed concentration and increase in the ASO concentration. For instance, the highest loading efficiency (i.e., highest ASO concentration of the EVs) was observed when both the EV feed concentration and the ASO concentration were the greatest (i.e., $1.4\times10^{13}$ and 800 μM, respectively). As between the two loading conditions, there was approximately a four-fold increase in the ASO loading efficiency when the ASOs and EVs were mixed under loading condition #2.

The above results confirm the positive effect that increased salt concentration and loading time have on the loading efficiency of EVs. The results further demonstrate that both the EV feed concentration and ASO feed concentration can affect loading efficiency.

TABLE 4

ASO Concentration Per EV under Loading Condition #1

| | | Feed [EV] particles | | |
|---|---|---|---|---|
| | | $1.4 \times 10^{13}$ | $1.0 \times 10^{13}$ | $6.0 \times 10^{12}$ |
| Feed [ASO] (μM) | 800 | 6297 | 4731 | 3149 |
| | 600 | 4893 | 3885 | 2713 |
| | 400 | 5944 | 3117 | 1740 |
| | 200 | 3970 | 2587 | 1338 |
| | 100 | 5039 | 2209 | 1158 |

TABLE 5

ASO Concentration Per EV under Loading Condition #2

| | | Feed [EV] particles | | |
|---|---|---|---|---|
| | | $1.4 \times 10^{13}$ | $1.0 \times 10^{13}$ | $6.0 \times 10^{12}$ |
| Feed [ASO] (μM) | 800 | 18280 | 16521 | 10439 |
| | 600 | 16848 | 9012 | 5107 |
| | 400 | 17775 | 13913 | 6121 |
| | 200 | 16263 | 6263 | 3903 |
| | 100 | 8083 | 6555 | 2207 |

Example 4—Analysis of Loading Parameters on EV Potency

To further understand the effect that different loading parameters on EV loading efficiency, two different anti-STAT6 ASOs were used as payloads: one targeting human STAT6 ("human ASO") and the other targeting mouse STAT6 ("mouse ASO"). The mouse ASO contains a sequence complementary with the mouse STAT6 transcript, and the human ASO is complementary to the human STAT6 transcript. It will be apparent to those skilled in the arts that the mouse and human STAT6 transcripts differ in overall length. Similar to the methods provided in the earlier Examples, the mouse and human ASOs were independently mixed with EVs in a loading buffer comprising NaCl at a concentration of 150 mM. The mouse ASO was added at one of the following feed concentrations: 100 mM, 800 mM, or 950 mM. The human ASO was added at one of the following feed concentrations: 100 mM, 800 mM, or 1000 mM. The additional loading conditions were as follows: 37° C. for 24 hours at EV feed concentration of $1\times10^{13}$ p/mL. Then, the ASO and EV contents were measured as described in the earlier Examples.

As shown in Table 6 and in agreement with the earlier data (see, e.g., Example 3), increase in ASO feed concentration resulted in greater loading of the ASOs on a per EV basis. This was observed with both the mouse and human ASOs, indicating that loading methods provided herein can be used to increase loading efficiency for ASOs varying in sequence lengths. Similar results (at least as to the loading density) were observed with ASOs targeting other targets and conjugated to different lipid-linkers. For instance, as shown in FIG. 5, using the loading methods provided herein, on average, 10-14-fold increase in ASO loading was observed compared to the control loading condition.

TABLE 6

Human and Mouse ASO Concentration Per EV

| ASO | ASO Feed | Loading Buffer NaCl | ASO/EV |
|---|---|---|---|
| Mouse | 100 mM | 150 mM | 4279 |
| Mouse | 800 mM | 150 mM | 12855 |

TABLE 6-continued

| Human and Mouse ASO Concentration Per EV | | | |
|---|---|---|---|
| ASO | ASO Feed | Loading Buffer NaCl | ASO/ EV |
| Mouse | 950 mM | 150 mM | 14912 |
| Human | 100 mM | 150 mM | 4851 |
| Human | 800 mM | 150 mM | 14089 |
| Human | 1000 mM | 150 mM | 14811 |

Next, to confirm the potency of the resulting EVs, the EVs loaded with the mouse or human ASOs were used to knockdown STAT6 expression in liver cells. As shown in FIG. 4, when the total mass of ASO was dosed, there was no significant difference in the knockdown of STAT6 expression, demonstrating that the increased loading density of the ASOs allows the use of fewer EVs to achieve the same therapeutic effect.

The above results suggest that the loading methods provided herein allow for the generation of more potent EVs, which would allow a given batch of EVs produced to treat many more patients.

Example 5—Effect of Loading Temperature, Sodium Concentration, And Sucrose Concentration on ASO Concentration of EVs after Chromatography Purification To understand whether the different loading parameters described herein have an effect on ASO concentration of EVs after purification, the EVs and ASOs were mixed using loading buffers comprising either high salt and low sucrose (150 mM NaCl and 2.5% sucrose) or low salt and high sucrose (50 mM NaCl and 5% sucrose) concentrations. The loading temperature was either 24° C. (i.e., room temperature) or 37° C. The EVs were added to the mixture at a feed concentration of $1\times10^{13}$ p/mL. The ASOs were added at a feed concentration of 650 μM. Afterwards, the mixture of the EVs and the ASOs were filtered, and the loaded EVs cleaned up by chromatography with Capto Core 700 resin. The flow through were measured for EV loaded ASOs and free ASO by RiboGreen fluorescence.

As shown in Table 7 (below), the EVs had the highest ASO concentration when the EVs and ASOs were mixed using loading buffer with high salt concentration and at 37° C. loading temperature. The least amount of free ASOs were also observed under the same loading condition. With the low salt concentration loading buffer, there were less EVs loaded with the ASOs and more free ASO observed in the flow through at both of the loading temperatures tested. While the increase in loading temperature (37° C. v. 24° C.) did improve the loading efficiency observed with the low salt concentration loading buffer, it was still less than that observed with the high salt concentration at the 37° C. loading temperature.

TABLE 7

| | 24° C. | 37° C. | |
|---|---|---|---|
| Loading Buffer | 50 mM NaCl 5% Sucrose | 50 mM NaCl 5% Sucrose | 150 mM NaCl 2.5% Sucrose |
| CC700 Flow Throughs—ASO:EV | 13,200 | 17,500 | 23,200 |

TABLE 7-continued

| | 24° C. | 37° C. | |
|---|---|---|---|
| Loading Buffer | 50 mM NaCl 5% Sucrose | 50 mM NaCl 5% Sucrose | 150 mM NaCl 2.5% Sucrose |
| CC700 Flow Throughs—% Free ASO | 4% | 2% | 1% |

The above results further confirm the positive effects that increased salt concentration and loading temperature have on the loading efficiency of EVs. The results also demonstrate that Capto Core can clean up the free ASO independent of the loading temperature and salt concentration, indicating its robust cleanup capabilities.

Example 6—Effect of Different Loading Parameters on ASO Dissociation from EVs after Chromatography Purification Next, ASO dissociation after chromatography purification in EVs loaded with ASOs under different loading conditions was assessed. Briefly, the EVs and ASOs were mixed using one of the following two loading buffers: (i) CEF (20 mM $PO_4$, 50 mM NaCl, 5% sucrose); and (ii) Hi (20 mM $PO_4$, 150 mM NaCl, 2.5% sucrose). The EVs and ASOs were mixed at either room temperature (~24° C.) or 37° C. The ASO loaded EVs were then cleaned up by chromatography with Capto Core 700 resin. The effect of dilution factor, diluent, and hold time of diluted material on ASOs that dissociate from EVs after cleaning with Capto Core 700 was evaluated, and results are shown in Table 8.

TABLE 8

| | Loading Buffer | | | | | | | | |
|---|---|---|---|---|---|---|---|---|---|
| | CEF | | | Hi | | | | | |
| | Loading Temperature | | | | | | | | |
| | 22° C. | | | Room Temperature | | | 37° C. | | |
| | Diluent | | | | | | | | |
| | CEF | Hi | PBS | CEF | Hi | PBS | CEF | Hi | PBS |
| | % Free in Sup at Time 0 Hour | | | | | | | | |
| 1x | | 4% | | | 2% | | | 1% | |
| 5x | 14% | 2% | 5% | 11% | 3% | 2% | 6% | 1% | 1% |
| 10x | 14% | 2% | 2% | 15% | 2% | 3% | 10% | 1% | 1% |
| | % Free in Sup at Time 20 Hours | | | | | | | | |
| 1x | | 7% | | | 2% | | | 1% | |
| 5x | 17% | 2% | 2% | 14% | 2% | 2% | 7% | 1% | 1% |
| 10x | 29% | 1% | 1% | 23% | 2% | 3% | 15% | 1% | 1% |

The percent free indicated that when diluting loaded and cleaned up material in a loading buffer containing a lower salt concentration, more ASOs dissociate from the EVs. The dissociation became more drastic as the dilution factor increases. However, when diluting material in the higher salt containing loading buffer (150 mM NaCl), there was no dissociation of ASOs observed. When the diluted cleaned up material was held for 20 hours at room temperature, additional dissociation was observed only when the diluent contains lower salt concentrations (50 mM). For the higher salt containing diluents, no dissociation was observed when the diluted material was held for 20 hours at room temperature. This data indicates that the stability of the loaded exosomes can be optimized by maintaining a salt concentration.

Example 7—Scaling of ASO EV Loading Process

As is apparent from the above disclosures, the loading methods provided herein can be useful in producing EVs loaded with payloads on various scales. Table 9 (below) provides exemplary loading parameters for lab-scale, non-GMP, and GMP production.

TABLE 9

Exemplary Loading Parameters

| | Lab-Scale Development Lot | Non-GMP Manufacturing Lot | GMP Manufacturing Lot |
|---|---|---|---|
| Loading Buffer | 146 mM Sucrose, 150 mM Sodium Chloride, 15 mM Sodium Phosphate Dibasic, mm Potassium Phosphate Monobasic, pH 7.2 | | |
| ASO Feed Concentration (μM) | 636 | 601 | 638 |
| Exosome Feed Concentration (p/mL) | $7.0 \times 10^{12}$ | $7.0 \times 10^{12}$ | $6.5 \times 10^{12}$ |
| Loading Volume (mL) | 21 | 2488 | 1445 |
| Loading Temperature (° C.) | 37 | 37 | 37 |
| Loading Time (hr) | 20 | 20 | 20 |
| Final Loading Density (ASO:EV) | 18,176 | 20,608 | 18,484 |
| Free ASO (%) | 2.4 | 2.5 | 1.8 |

It is to be appreciated that the Detailed Description section, and not the Summary and Abstract sections, is intended to be used to interpret the claims. The Summary and Abstract sections can set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

The contents of all cited references (including literature references, patents, patent applications, and websites) that can be cited throughout this application are hereby expressly incorporated by reference in their entirety for any purpose, as are the references cited therein.

What is claimed is:

1. A method of loading a payload to an extracellular vesicle (EV) comprising mixing the payload with the extracellular vesicle in a loading buffer comprising a salt, wherein the salt comprises NaCl (sodium chloride) at a concentration of at least 140 mM to about 200 mM.

2. The method of claim 1, wherein the salt further comprises KCl (potassium chloride), $PO_4$ (phosphate salt), $CaCl_2$) (calcium chloride), $MgCl_2$ (magnesium chloride), $Mg_2SO_4$ (magnesium sulfate), $ZnCl_2$ (zinc chloride), $MnCl_2$ (manganese chloride), $MnSO_4$ (manganese sulfate), NaSCN (sodium thiocyanate), KSCN (potassium thiocyanate), LiCl (lithium chloride), $K_2HPO_4$ (dipotassium phosphate), $Na_2SO_4$ (sodium sulfate), NaPO4 (sodium phosphate), $K_2SO_4$ (potassium phosphate), sodium acetate, sodium bromide, sodium iodide, potassium bromide, lithium bromide, sodium fluoride, potassium fluoride, lithium fluoride, lithium iodide, potassium acetate, lithium acetate, potassium iodide, calcium sulfate, sodium sulfate, chromium trichloride, chromium sulfate, sodium citrate, iron (III) chloride, yttrium (III) chloride, potassium sulfate, ferrous chloride, calcium citrate, magnesium phosphate, ferric chloride, arginine-HCl, or any combination thereof.

3. The method of claim 1, wherein the loading buffer comprising the salt increases the loading of the payload to the EV by at least about 2 fold or more compared to a corresponding loading buffer without the salt or with a lower concentration of the salt.

4. The method of claim 1, comprising mixing the payload with the extracellular vesicle at a loading temperature between about 5° C. and about 50° C., and for a loading duration between one hour to about 48 hours.

5. The method of claim 1 for (i) increasing the stability of an extracellular vesicle (EV) loaded with a payload, or (ii) improving one or more properties of the EV, wherein the one or more properties comprise: inter-particle interaction, particle rigidity, particle size, or a combination thereof after loading with the payload.

6. The method of claim 1, wherein the loading buffer further comprises tris, sucrose, glucose, trehalose, mannose, sorbitol, mannitol, glycerol, histidine, arginine, methionine, tryptophan, tyrosine, sodium phosphate, potassium phosphate, polymers, surfactants, chelating agents, inorganic acids, or any combination thereof.

7. The method of claim 6, wherein the sucrose is at a concentration lower than about 10 00 w/v.

8. The method of claim 1, wherein the loading buffer is at a pH between about 6 and about 9.

9. The method of claim 1, wherein the payload comprises a peptide, a small molecule, an oligonucleotide, an antisense oligonucleotide (ASO), a PMO, an mRNA, an miRNA, an lcRNA, an antagomir, a tRNA, a siRNA, peptide nucleic acid, a cell penetrating peptide, an adjuvant, a protein, a carbohydrate, a sugar, an amino acid, or any combination thereof.

10. The method of claim 1, wherein the payload in the loading buffer is at a concentration between about 100 and about 1000 μM.

11. The method of claim 1, wherein the payload is conjugated to an anchoring moiety.

12. The method of claim 11, wherein the anchoring moiety further comprises a linker between the payload and the anchoring moiety.

13. The method of claim 12, which comprises (i) a payload comprising the nucleotide sequence set forth in any one of SEQ ID NOs: 41 to 112, and (ii) a linker.

14. The method of claim 13, wherein the payload comprises 5'GbsCbsAbsdAsdGsdAsdTs(5MdC)s(5MdC)s(5MdC)sdGsdGsdAsdTsdTs(5MdC)sdGsGbsTbs Cb3', wherein N is a nucleic acid base selected from adenine (A), guanine (G), cytosine (C), and thymine (T), Nb is an LNA base, dN is a DNA base, (5MdC) is 5-Methyl-dC, s is phosphorothioate, TEG is triethylene glycol, and HEG is hexaethylene glycol.

15. The method of claim 1, wherein the extracellular vesicle is at a concentration of at least about $1\times10^{11}$ particles/mL.

16. The method of claim 1, wherein the extracellular vesicle further comprises a protein in the membrane of the extracellular vesicle.

17. The method of claim 16, wherein the protein comprises prostaglandin F2 receptor negative regulator (the PTGFRN protein); basigin (the BSG protein); immunoglobulin superfamily member 2 (the IGSF2 protein); immunoglobulin superfamily member 3 (the IGSF3 protein); immunoglobulin superfamily member 8 (the IGSF8 protein); integrin beta-1 (the ITGB1 protein); integrin alpha-4 (the ITGA4 protein); 4F2 cell-surface antigen heavy chain (the SLC3A2 protein); a class of ATP transporter proteins; a functional fragment thereof; and any combination thereof.

18. An extracellular vesicle prepared by the method of claim 1.

19. A pharmaceutical composition comprising the extracellular vesicle of claim 18.

20. A method of treating a disease or condition in a subject in need thereof comprising administering the extracellular vesicle of claim 18 to the subject in need thereof.

* * * * *